US008063234B2

(12) United States Patent
Kolkhof et al.

(10) Patent No.: US 8,063,234 B2
(45) Date of Patent: Nov. 22, 2011

(54) SUBSTITUTED 7-SULFANYLMETHYL-, 7-SULFINYLMETHYL- AND 7-SULFONYLMETHYLINDOLES AND THE USE THEREOF

(75) Inventors: Peter Kolkhof, Wuppertal (DE); Astrid Brüns, Wuppertal (DE); Kai Thede, Berlin (DE); Karl-Heinz Schlemmer, Wuppertal (DE); Alexander Hillisch, Solingen (DE); Dieter Lang, Velbert (DE); Michael Gerisch, Wuppertal (DE); Andreas Goeller, Wuppertal (DE); Rolf Grosser, Leverkusen (DE); Carsten Schmeck, Mülheim (DE); Elisabeth Woltering, Hilden (DE); Olaf Prien, Berlin (DE); Holger Paulsen, Hilden (DE); Armin Kern, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 65 days.

(21) Appl. No.: 12/490,333

(22) Filed: Jun. 24, 2009

(65) Prior Publication Data

US 2010/0105744 A1    Apr. 29, 2010

(30) Foreign Application Priority Data

Jun. 25, 2008   (DE) .......................... 10 2008 030 207

(51) Int. Cl.
C07D 209/04    (2006.01)
(52) U.S. Cl. ........................ 548/509; 514/415
(58) Field of Classification Search .................. 548/509; 514/415
See application file for complete search history.

(56) References Cited

U.S. PATENT DOCUMENTS

| 2,752,358 A | 6/1956 | Ehrhart et al. |
| 2,765,320 A | 10/1956 | Bader et al. |
| 2,778,819 A | 1/1957 | Baumann et al. |
| 5,808,064 A | 9/1998 | Chen et al. |

FOREIGN PATENT DOCUMENTS

| WO | WO-90/05721 A1 | 5/1990 |
| WO | WO-97/43260 A1 | 11/1997 |
| WO | WO-98/06725 A1 | 2/1998 |
| WO | WO-00/06568 A1 | 2/2000 |
| WO | WO-00/06569 A1 | 2/2000 |
| WO | WO-01/19355 A2 | 3/2001 |
| WO | WO-01/19776 A2 | 3/2001 |
| WO | WO-01/19778 A1 | 3/2001 |
| WO | WO-01/19780 A2 | 3/2001 |
| WO | WO-02/42301 A1 | 5/2002 |
| WO | WO-02/070462 A1 | 9/2002 |
| WO | WO-02/070510 A2 | 9/2002 |
| WO | WO-03/095451 A1 | 11/2003 |
| WO | WO-2004/067529 A1 | 8/2004 |
| WO | WO-2005/092854 A1 | 10/2005 |
| WO | WO-2005/118539 A1 | 12/2005 |
| WO | WO-2007/040166 A1 | 4/2007 |
| WO | WO-2007/062994 A1 | 6/2007 |
| WO | WO-2007/070892 A2 | 6/2007 |
| WO | WO-2008/019357 A2 | 2/2008 |
| WO | WO-2008/157740 A2 | 12/2008 |

OTHER PUBLICATIONS

R. E. Booth et al.: "Aldosterone," Advances in Physiology Education, vol. 26, No. 1, Mar. 2002, pp. 8-20.
B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.
B. Pitt et al.: "The Effect of Spironolactone on Morbidity and Mortality in Patients with Severe Heart Failure," The New England Journal of Medicine, vol. 341, No. 10, pp. 709-717, (1999).
H. A. Kuhn et al.: Innere Medizin—Ein Lehrbuch fur Studierende der Medizin und Arzte Begrundet von Ludwig Heilmeyer, Springer-Verlag, Berlin, Heidelberg, New York, 1982.
M. A. Zaman et al.; "Drugs Targeting the Renin-Angiotension-Aldosterone System," Nature Reviews Drug Discovery, vol. 1, Aug. 2002, pp. 621-636.
L. Seiler et al.: "Der Aldosteron-Renin-Quotient bei Sekundarer Hypertonie," Herz, vol. 28, No. 8, 2003, 686-691.
J.W. Funder: "Mineralocorticoid Receptors and Cardiovascular Damage: It's Not Just Aldosterone", *Hypertension*, vol. 47 (2006) pp. 634-635.
L. Weihong et al., "Steroid receptor heterodimerization demonstrated in vitro and in vivo", *Proc. Natl. Acad. Sci. USA*, vol. 92, Dec. 1995, pp. 12480-12484.
M J Meyers et al., "Non-Steroidal mineralocorticoid receptor antagonists", *Expert Opin. Ther. Patents*, vol. 17, No. 1, 2007, pp. 17-23.
MG Bell et al., "(S)-N-{3-[1-Cyclopropyl-1-(2,4-difluoro-phenyl)-ethyl]-1H-indol-7-yl}-methanesulfonamide: A Potent, Nonsteroidal, Functional Antagonist of the Mineralocorticoid Receptor", *Journal of Medicinal Chemistry*, vol. 50, No. 26, 2007, pp. 6443-6445.
ML Kantam et al., "Friedel-Crafts alkylation of indoles with epoxides catalyzed by nanocrystalline titanium(IV) oxide", *Tetrahedron Letters* 47 (2006) pp. 6213-6216.

(Continued)

Primary Examiner — Yong Chu
Assistant Examiner — Valerie Rodriguez-Garcia
(74) Attorney, Agent, or Firm — Thomas C. Blankinship; Jonathan R Harris; Karen B King

(57) ABSTRACT

The present application relates to novel 7-sulfanylmethyl-, 7-sulfinylmethyl- and 7-sulfonylmethylindole derivatives, processes for the preparation thereof, the use thereof alone or in combinations for the treatment and/or prevention of diseases, and the use thereof for the manufacture of medicaments for the treatment and/or prevention of diseases, especially for the treatment and/or prevention of cardiovascular disorders.

26 Claims, No Drawings

OTHER PUBLICATIONS

Y. Oikawa et al., "Meldrum's Acid in Organic Synthesis. 1. A Convenient One-Pot Synthesis of Ethyl Indolepropionates", *Tetrahedron Letters* No. 20, (1978) pp. 1759-1762.

Z. Xu et al., "N-Fluorobis[(perfluoroalkyl)sulfonyl]imides. Efficient reagents for the fluorination of 1,3-dicarbonyl derivatives", *Journal of Fluorine Chemistry*, 58 (1992) pp. 71-79.

W.H. Bunnelle et al., "Difluorination of Esters. Preparation of $\alpha,\alpha$-Difluoro Ethers", *J. Org. Chem.* 55 (1990) pp. 768-770.

K.R. Gassen et al. "Fluorinated Cyclopropanecarboxylic Acids and Their Derivatives", *Journal of Fluorine Chemistry*, 49 (1990) pp. 127-139.

M.E. Rosenthale et al. "Determination of Antialdosterone Activity in Normal Dogs", *Proc. Soc. Exp. Biol. Med.*, vol. 118 (1965) pp. 806-809.

SUBSTITUTED 7-SULFANYLMETHYL-, 7-SULFINYLMETHYL- AND 7-SULFONYLMETHYLINDOLES AND THE USE THEREOF

The present application relates to novel 7-sulfanylmethyl-, 7-sulfinylmethyl- and 7-sulfonylmethylindole derivatives, processes for the preparation thereof, the use thereof alone or in combinations for the treatment and/or prevention of diseases, and the use thereof for the manufacture of medicaments for the treatment and/or prevention of diseases, especially for the treatment and/or prevention of cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

According to recent studies, a not inconsiderable number of patients suffering from essential hypertension are also found to have a so-called normokalemic variant of primary hyperaldosteronism [prevalence up to 11% of all hypertensives: L. Seiler and M. Reincke, *Der Aldosteron-Renin-Quotient bei sekundärer Hypertonie*, Herz 28, 686-691 (2003)]. The best diagnostic method for normokalemic hyperaldosteronism is the aldosterone/renin quotient of the corresponding plasma concentrations, so that relative elevations in aldosterone in relation to the renin plasma concentrations can also be diagnosed and eventually treated. For this reason, a hyperaldosteronism diagnosed in connection with essential hypertension is a starting point for a causal and prophylactically worthwhile therapy.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome, the leading symptoms of which are hypertension and hypokalemic alkalosis. The priority here too, besides surgical removal of the diseased tissue, is medical therapy with aldosterone antagonists [H. A. Kühn and J. Schirmeister (Editors), *Innere Medizin*, 4th edition, Springer Verlag, Berlin, 1982].

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

The effects of aldosterone are mediated by the mineralocorticoid receptor which has an intracellular location in the target cells. A receptor which is closely related to the mineralocorticoid receptor is the glucocorticoid receptor via which the activity of glucocorticoids (e.g. cortisone, cortisol or corticosterone) is mediated. The mineralocorticoid receptor binds not only aldosterone but also endogenous glucocorticoids [Funder J W. *Hypertension.* 47, 634-635 (2006)]. This interaction of the mineralocorticoid receptor with glucocorticoids appears likewise to play an important, but mostly unappreciated, role in the pathophysiology of cardiac disorders. In addition, there is suggested to be an interaction between mineralocorticoid and glucocorticoid receptors, e.g. in the form of heterodimer formation, which might be involved in the development of cardiovascular disorders [Liu W, Wang J, Sauter N K, Pearce D. *Proc Natl Acad Sci USA.* 92, 12480-12484 (1995)].

The aldosterone antagonists available to date have, like aldosterone itself, a basic steroid structure. The utility of such steroidal antagonists is limited by their interactions with the receptors of other steroid hormones, in particular of testosterone and progesterone, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The identification of potent, non-steroidal mineralocorticoid receptor antagonists, which show an improved selectivity in particular in relation to the androgen (testosterone) and progesterone receptors provides the possibility of achieving a distinct therapeutic advantage [cf. M. J. Meyers and X. Hu, *Expert Opin. Ther. Patents* 17 (1), 17-23 (2007)].

It is therefore an object of the present invention to provide novel compounds which act as potent mineralocorticoid receptor antagonists which are selective in relation to the androgen (testosterone) and progesterone receptors, and show an improved profile of side effects compared with compounds known in the prior art, and thus can be employed for the treatment of disorders, especially of cardiovascular disorders.

Indol-3-yl(phenyl)acetic acid derivatives are disclosed as endothelin receptor antagonists in WO 97/43260 and α-amino(indol-3-yl)acetic acid derivatives with an antidiabetic effect are disclosed in WO 90/05721. WO 2004/067529, WO 2005/092854 and M. G. Bell, *J. Med. Chem.* 2007, 50 (26), 6443-6445 describe various indole derivatives substituted in position 3 as modulators of steroid hormone receptors. WO 2007/062994 and WO 2005/118539 claim 3-(3-amino-1-arylpropyl)indoles for the treatment of depression and anxiety states. WO 2007/040166 claims fused pyrrole derivatives as glucocorticoid receptor modulators having anti-inflammatory and antidiabetic effects. WO 2007/070892 and WO 2008/019357 describe substituted indoles for the treatment of anxiety, pain, inflammatory disorders and cognitive impairments. WO 2008/157740 describes variously substituted indoles inter alia for the treatment of pain and inflammatory disorders. 3-(Indol-3-yl)-3-phenylpropionitrile derivatives are described inter alia in U.S. Pat. No. 2,752,358, U.S. Pat. No. 2,765,320 and U.S. Pat. No. 2,778,819. The preparation of 2-unsubstituted indoles is disclosed in WO 98/06725 and U.S. Pat. No. 5,808,064. The preparation of 2-(indol-3-yl)-2-phenylethanol derivatives is reported inter alia in M. L. Kantam et al., *Tetrahedron Lett.* 2006, 47 (35), 6213-6216.

The present invention relates to compounds of the general formula (I)

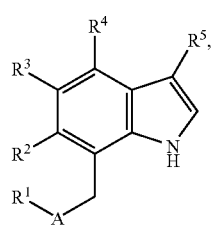

(I)

in which
A is —S—, —S(=O)— or —S(=O)$_2$—,
$R^1$ is (C$_1$-C$_4$)-alkyl or cyclopropyl,
$R^2$ is hydrogen, fluorine or chlorine,
$R^3$ is hydrogen, fluorine, chlorine or methyl,
$R^4$ is hydrogen or fluorine,
$R^5$ is a group of the formula

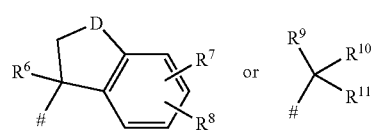

where
# is the point of attachment to the indole,
and
D is —CH$_2$—, —O—, —CH$_2$—CH$_2$— or —CH$_2$—O—,
$R^6$ is (C$_1$-C$_4$)-alkyl or (C$_3$-C$_6$)-cycloalkyl,
  in which (C$_1$-C$_4$)-alkyl may be substituted by 1 to 3 substituents independently of one another selected from the group of fluorine, trifluoromethyl, hydroxy and cyano,
  and
  in which (C$_3$-C$_6$)-cycloalkyl may be substituted by 1 to 3 substituents independently of one another selected from the group of fluorine, hydroxy and cyano,
$R^7$ is hydrogen, halogen, (C$_1$-C$_4$)-alkyl, trifluoromethyl or (C$_1$-C$_4$)-alkoxy,
$R^8$ is hydrogen, halogen, methyl or trifluoromethyl,
$R^9$ is phenyl, naphthyl or 5- to 10-membered heteroaryl,
  in which phenyl, naphthyl and 5- to 10-membered heteroaryl may be substituted by 1 to 3 substituents independently of one another selected from the group of halogen, cyano, (C$_1$-C$_4$)-alkyl, fluoromethyl, difluoromethyl, trifluoromethyl, (C$_1$-C$_4$)-alkoxy, fluoromethoxy, difluoromethoxy, trifluoromethoxy and trifluoromethylthio,
  or
  in which two substituents bonded on adjacent carbon atoms of a phenyl ring together form a group of the formula —O—CH$_2$—O—, —O—CHF—O—, —O—CF$_2$—O—, —O—CH$_2$—CH$_2$—O— or —O—CF$_2$—CF$_2$—O—,
$R^{10}$ is (C$_1$-C$_6$)-alkyl, (C$_3$-C$_7$)-cycloalkyl or phenyl,
  in which (C$_1$-C$_6$)-alkyl may be substituted by 1 to 3 substituents independently of one another selected from the group of fluorine, fluoromethyl, difluoromethyl, trifluoromethyl, hydroxy and cyano,
  and
  in which (C$_3$-C$_7$)-cycloalkyl may be substituted by 1 to 3 substituents independently of one another selected from the group of fluorine, hydroxy and cyano,
  and
  in which phenyl may be substituted by 1 to 3 substituents independently of one another selected from the group of halogen, cyano, (C$_1$-C$_4$)-alkyl, fluoromethyl, difluoromethyl, trifluoromethyl, (C$_1$-C$_4$)-alkoxy, fluoromethoxy, difluoromethoxy, trifluoromethoxy and trifluoromethylthio,
$R^{11}$ is hydrogen, methyl, ethyl, trifluoromethyl or cyclopropyl,
and the salts, solvates and solvates of the salts thereof.

Compounds of the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The present invention therefore relates to the enantiomers or diastereomers and respective mixtures thereof. The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:

Alkyl represents in the context of the invention a linear or branched alkyl radical having 1 to 6 or 1 to 4 carbon atoms. A linear or branched alkyl radical having 1 to 4 carbon atoms is preferred. Mention may be made by way of example and preferably of: methyl, ethyl, n-propyl, isopropyl, n-butyl, iso-butyl, sec-butyl, tert-butyl, 1-ethylpropyl, n-pentyl and n-hexyl.

Cycloalkyl represents in the context of the invention a saturated monocyclic carbocycle having 3 to 7 or 3 to 6 ring carbon atoms. Mention may be made by way of example and preferably of: cyclopropyl, cyclobutyl, cyclopentyl, cyclohexyl and cycloheptyl.

Alkoxy represents in the context of the invention a linear or branched alkoxy radical having 1 to 4 carbon atoms. Mention may be made by way of example and preferably of: methoxy, ethoxy, n-propoxy, isopropoxy, n-butoxy and tert-butoxy.

Heteroaryl represents in the context of the invention a monocyclic or, where appropriate, bicyclic aromatic heterocycle (heteroaromatic system) having a total of 5 to 10 ring atoms which comprises up to three identical or different ring heteroatoms from the series N, O and/or S and is linked via a ring carbon atom or, where appropriate, via a ring nitrogen atom. Mention may be made by way of example of: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, imidazo[1,2-a]pyridinyl and pyrazolo[3,4-b]pyridinyl.

Halogen includes in the context of the invention fluorine, chlorine, bromine and iodine. Fluorine, chlorine and bromine are preferred, and fluorine and chlorine are particularly preferred.

In the formulae of the group possible for $R^5$, $R^9$, $R^{10}$ and $R^{11}$, the end point of the line where there is a sign #, *, ## or ### does not represent a carbon atom or a $CH_2$ group but forms part of the bond to the atom which is designated in each case and to which $R^5$, $R^9$, $R^{10}$ and $R^{11}$, respectively, are bonded.

If radicals in the compounds of the invention are substituted, the radicals may be substituted one or more times, unless specified otherwise. In the context of the present invention, all radicals which occur more than once have a mutually independent meaning. Substitution by one or two identical or different substituents is preferred. Substitution by one substituent is very particularly preferred.

Preference is given in the context of the present invention to compounds of the formula (I) in which
A is —S—, —S(=O)— or —S(=O)$_2$—,
$R^1$ is ($C_1$-$C_4$)-alkyl or cyclopropyl,
$R^2$ is hydrogen, fluorine or chlorine,
$R^3$ is hydrogen, fluorine, chlorine or methyl,
$R^4$ is hydrogen or fluorine,
$R^5$ is a group of the formula

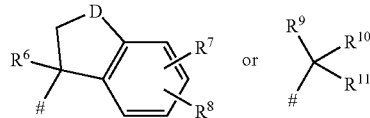

where
# is the point of attachment to the indole,
and
D is —$CH_2$—, —O—, —$CH_2$—$CH_2$— or —$CH_2$—O—,
$R^6$ is ($C_1$-$C_4$)-alkyl or ($C_3$-$C_6$)-cycloalkyl,
  in which ($C_1$-$C_4$)-alkyl may be substituted by 1 to 3 substituents independently of one another selected from the group of fluorine, trifluoromethyl, hydroxy and cyano,
  and
  in which ($C_3$-$C_6$)-cycloalkyl may be substituted by 1 to 3 substituents independently of one another selected from the group of fluorine, hydroxy and cyano,
$R^7$ is hydrogen, halogen, ($C_1$-$C_4$)-alkyl, trifluoromethyl or ($C_1$-$C_4$)-alkoxy,
$R^8$ is hydrogen, halogen, methyl or trifluoromethyl,
$R^9$ is phenyl, naphthyl or 5- to 10-membered heteroaryl,
  in which phenyl, naphthyl and 5- to 10-membered heteroaryl may be substituted by 1 to 3 substituents independently of one another selected from the group of halogen, cyano, ($C_1$-$C_4$)-alkyl, trifluoromethyl, ($C_1$-$C_4$)-alkoxy, trifluoromethoxy and trifluoromethylthio,
  or
  in which two substituents bonded to adjacent carbon atoms of a phenyl ring together form a group of the formula —O—CH₂—O—, —O—CHF—O—, —O—CF₂—O—, —O—CH₂—CH₂—O— or —O—CF₂—CF₂—O—, R¹⁰ is (C₁-C₆)-alkyl, (C₃-C₇)-cycloalkyl or phenyl,
in which (C₁-C₆)-alkyl may be substituted by 1 to 3 substituents independently of one another selected from the group of fluorine, trifluoromethyl, hydroxy and cyano,
and
in which (C₃-C₇)-cycloalkyl may be substituted by 1 to 3 substituents independently of one another selected from the group of fluorine, hydroxy and cyano, and
in which phenyl may be substituted by 1 to 3 substituents independently of one another selected from the group of halogen, cyano, (C₁-C₄)-alkyl, trifluoromethyl, (C₁-C₄)-alkoxy, trifluoromethoxy and trifluoromethylthio, R¹¹ is hydrogen, methyl, ethyl or trifluoromethyl,
and the salts, solvates and solvates of the salts thereof.

Preference is also given in the context of the present invention to compounds of the formula (I) in which
A is —S(=O)— or —S(=O)₂—,
R¹ is methyl or ethyl,
R² is hydrogen or fluorine,
R³ is hydrogen or fluorine,
R⁴ is hydrogen,
R⁵ is a group of the formula

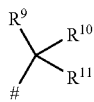

where
# is the point of attachment to the indole,
and
R⁹ is phenyl, naphthyl or benzothienyl,
in which phenyl, naphthyl and benzothienyl may be substituted by 1 to 3 substituents independently of one another selected from the group of fluorine, chlorine, cyano, methyl, ethyl, trifluoromethyl and methoxy,
or
in which two substituents bonded to adjacent carbon atoms of a phenyl ring together form a group of the formula —O—CH₂—O— or —O—CF₂—O—, R¹⁰ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl, 1-hydroxycycloprop-2-yl or phenyl,
in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl and 1-hydroxycycloprop-2-yl may be substituted by 1 or 2 fluorine substituents,
and
in which phenyl may be substituted by 1 or 2 substituents independently of one another selected from the group of fluorine, chlorine, cyano and methyl, R¹¹ is hydrogen,
and the salts, solvates and solvates of the salts thereof.

Preference is also given in the context of the present invention to compounds of the formula (I) in which
A is —S(=O)— or —S(=O)₂—,
R¹ is methyl or ethyl,
R² is hydrogen or fluorine,
R³ is hydrogen or fluorine,
R⁴ is hydrogen,
R⁵ is a group of the formula

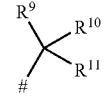

where
# is the point of attachment to the indole,
and
R⁹ is phenyl, naphthyl or benzothienyl,
in which phenyl, naphthyl and benzothienyl may be substituted by 1 to 3 substituents independently of one another selected from the group of fluorine, chlorine, cyano, methyl, ethyl and trifluoromethyl, R¹⁰ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl, 1-hydroxycycloprop-2-yl or phenyl,
in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl and 1-hydroxycycloprop-2-yl may be substituted by 1 or 2 fluorine substituents,
and
in which phenyl may be substituted by 1 or 2 substituents independently of one another selected from the group of fluorine, chlorine, cyano and methyl, R¹¹ is hydrogen,
and the salts, solvates and solvates of the salts thereof.

Preference is also given in the context of the present invention to compounds of the formula (I) in which
A is —S(=O)— or —S(=O)$_2$—,
R$^1$ is methyl or ethyl,
R$^2$ is hydrogen or fluorine,
R$^3$ is hydrogen or fluorine,
R$^4$ is hydrogen,
R$^5$ is a group of the formula

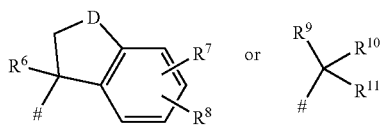

where
# is the point of attachment to the indole,
and
D is —CH$_2$— or —CH$_2$—O—,
R$^6$ is (C$_1$-C$_4$)-alkyl or (C$_3$-C$_6$)-cycloalkyl,
  in which (C$_1$-C$_4$)-alkyl and (C$_3$-C$_6$)-cycloalkyl may be substituted by 1 or 2 fluorine substituents,
  and
  in which (C$_1$-C$_4$)-alkyl may be substituted by a substituent selected from the group of hydroxy and cyano,
  and
  in which (C$_3$-C$_6$)-cycloalkyl may be substituted by a substituent selected from the group of hydroxy and cyano,
R$^7$ is hydrogen, fluorine, chlorine, methyl or trifluoromethyl,
R$^8$ is hydrogen, fluorine, chlorine, methyl or trifluoromethyl,
R$^9$ is phenyl, naphthyl or benzothienyl,
  in which phenyl, naphthyl and benzothienyl may be substituted by 1 to 3 substituents independently of one another selected from the group of fluorine, chlorine, cyano, methyl, ethyl, trifluoromethyl and methoxy,
  or
  in which two substituents bonded to adjacent carbon atoms of a phenyl ring together form a group of the formula —O—CH$_2$—O— or —O—CF$_2$—O—,
R$^{10}$ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, (C$_3$-C$_7$)-cycloalkyl or phenyl,
  in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dim-
ethylprop-3-yl and (C$_3$-C$_7$)-cycloalkyl may be substituted by 1 or 2 fluorine substituents,
  and
  in which (C$_3$-C$_7$)-cycloalkyl may be substituted by a substituent selected from the group of hydroxy and cyano,
  and
  in which phenyl may be substituted by 1 or 2 substituents independently of one another selected from the group of fluorine, chlorine, cyano and methyl,
R$^{11}$ is methyl or ethyl,
and the salts, solvates and solvates of the salts thereof.

Preference is also given in the context of the present invention to compounds of the formula (I) in which
A is —S(=O)— or —S(=O)$_2$—,
R$^1$ is methyl or ethyl,
R$^2$ is hydrogen or fluorine,
R$^3$ is hydrogen or fluorine,
R$^4$ is hydrogen,
R$^5$ is a group of the formula

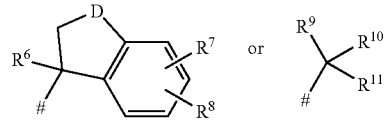

where
# is the point of attachment to the indole,
and
D is —CH$_2$— or —CH$_2$—O—,
R$^6$ is (C$_1$-C$_4$)-alkyl or (C$_3$-C$_6$)-cycloalkyl,
  in which (C$_1$-C$_4$)-alkyl and (C$_3$-C$_6$)-cycloalkyl may be substituted by 1 or 2 fluorine substituents,
  and
  in which (C$_1$-C$_4$)-alkyl may be substituted by a substituent selected from the group of hydroxy and cyano,
  and
  in which (C$_3$-C$_6$)-cycloalkyl may be substituted by a substituent selected from the group of hydroxy and cyano,
R$^7$ is hydrogen, fluorine, chlorine, methyl or trifluoromethyl,
R$^8$ is hydrogen, fluorine, chlorine, methyl or trifluoromethyl,
R$^9$ is phenyl, naphthyl or benzothienyl,
  in which phenyl, naphthyl and benzothienyl may be substituted by 1 to 3 substituents independently of one another selected from the group of fluorine, chlorine, cyano, methyl, ethyl and trifluoromethyl,
R$^{10}$ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, (C$_3$-C$_7$)-cycloalkyl or phenyl,
  in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl and $(C_3-C_7)$-cycloalkyl may be substituted by 1 or 2 fluorine substituents, and in which $(C_3-C_7)$-cycloalkyl may be substituted by a substituent selected from the group of hydroxy and cyano, and in which phenyl may be substituted by 1 or 2 substituents independently of one another selected from the group of fluorine, chlorine, cyano and methyl, $R^{11}$ is methyl or ethyl, and the salts, solvates and solvates of the salts thereof.

Particular preference is given in the context of the present invention to compounds of the formula (I) in which A is —S(=O)$_2$—,
$R^1$ is methyl,
$R^2$ is hydrogen or fluorine,
$R^3$ is hydrogen or fluorine,
$R^4$ is hydrogen,
$R^5$ is a group of the formula

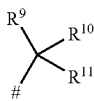

where
\# is the point of attachment to the indole,
and
$R^9$ is a group of the formula

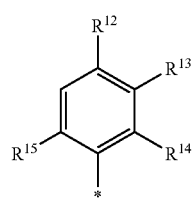

in which
* is the point of attachment to —CR$^{10}$R$^{11}$,
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is cyclopropyl,
in which cyclopropyl may be substituted by 1 or 2 fluorine substituents,
and
in which cyclopropyl may be substituted by a cyano substituent,
$R^{11}$ is methyl,
and the salts, solvates and solvates of the salts thereof.

Particular preference is also given in the context of the present invention to compounds of the formula (I) in which A is —S(=O)$_2$—,
$R^1$ is methyl or ethyl,
$R^2$ is hydrogen or fluorine,
$R^3$ is hydrogen or fluorine,
$R^4$ is hydrogen,
$R^5$ is a group of the formula

where
\# is the point of attachment to the indole,
and
$R^9$ is phenyl or benzothienyl,
in which phenyl and benzothienyl may be substituted by 1 or 2 substituents independently of one another selected from the group of fluorine, chlorine, methyl and trifluoromethyl,
$R^{10}$ is cyclopropyl,
in which cyclopropyl may be substituted by 1 or 2 fluorine substituents,
and
in which cyclopropyl may be substituted by a cyano substituent,
$R^{11}$ is methyl,
and the salts, solvates and solvates of the salts thereof.

Particular preference is also given in the context of the present invention to compounds of the formula (I) in which A is —S(=O)$_2$—,
$R^1$ is methyl or ethyl,
$R^2$ is hydrogen or fluorine,
$R^3$ is hydrogen or fluorine,
$R^4$ is hydrogen,
$R^5$ is a group of the formula

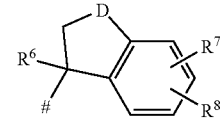

where
\# is the point of attachment to the indole,
and
D is —CH$_2$—,
$R^6$ is methyl, ethyl or cyclopropyl,
$R^7$ is hydrogen, fluorine, chlorine or methyl,
$R^8$ is hydrogen, fluorine or chlorine,
and the salts, solvates and solvates of the salts thereof.

Particular preference is also given in the context of the present invention to compounds of the formula (I) in which A is —S(=O)$_2$—,
$R^1$ is methyl,
$R^2$ is hydrogen or fluorine,
$R^3$ is hydrogen or fluorine,
$R^4$ is hydrogen,
$R^5$ is a group of the formula

where
# is the point of attachment to the indole,
and
$R^9$ is a group of the formula

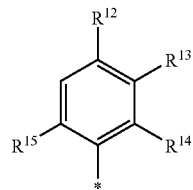

in which
* is the point of attachment to —$CR^{10}R^{11}$,
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is 1-cyanoeth-2-yl, 1-cyano-2-methyleth-2-yl or 1-cyanoprop-3-yl,
$R^{11}$ is methyl or ethyl,
and the salts, solvates and solvates of the salts thereof.

Particular preference is also given in the context of the present invention to compounds of the formula (I) in which
A is —$S(=O)_2$—,
$R^1$ is methyl,
$R^2$ is hydrogen or fluorine,
$R^3$ is hydrogen or fluorine,
$R^4$ is hydrogen,
$R^5$ is a group of the formula

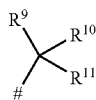

where
# is the point of attachment to the indole,
and
$R^9$ is a group of the formula

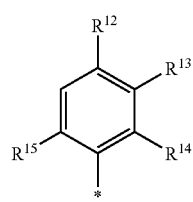

in which
* is the point of attachment to —$CR^{10}R^{11}$,
and
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is a group of the formula

in which
is the point of attachment to —$CR^9R^{11}$,
and
$R^{16}$ is fluorine or chlorine,
$R^{11}$ is hydrogen,
and the salts, solvates and solvates of the salts thereof.

Particular preference is also given in the context of the present invention to compounds of the formula (I) in which
A is —$S(=O)_2$—,
$R^1$ is methyl or ethyl,
$R^2$ is hydrogen or fluorine,
$R^3$ is hydrogen or fluorine,
$R^4$ is hydrogen,
$R^5$ is a group of the formula

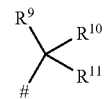

where
# is the point of attachment to the indole,
and
$R^9$ is phenyl or benzothienyl,
in which phenyl and benzothienyl may be substituted by 1 or 2 substituents independently of one another selected from the group of fluorine, chlorine, methyl and trifluoromethyl,
$R^{10}$ is phenyl,
in which phenyl may be substituted by a substituent selected from the group of fluorine and chlorine,
$R^{11}$ is hydrogen,
and the salts, solvates and solvates of the salts thereof.

Particular preference is also given in the context of the present invention to compounds of the formula (I) in which
A is —$S(=O)_2$—,
$R^1$ is methyl,
$R^2$ is hydrogen or fluorine,
$R^3$ is hydrogen or fluorine,
$R^4$ is hydrogen,
$R^5$ is a group of the formula

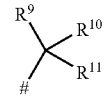

where
# is the point of attachment to the indole,
and
$R^9$ is phenyl or benzothienyl,
in which phenyl and benzothienyl may be substituted by 1 or 2 substituents independently of one another selected from the group of fluorine, chlorine, methyl and trifluoromethyl,
$R^{10}$ is 1-cyanoeth-2-yl, 1-cyano-2-methyleth-2-yl or 1-cyanoprop-3-yl,
$R^{11}$ is hydrogen,
and the salts, solvates and solvates of the salts thereof.

Particular preference is also given in the context of the present invention to compounds of the formula (I) in which
A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

where
\# is the point of attachment to the indole,
and
R$^9$ is a group of the formula

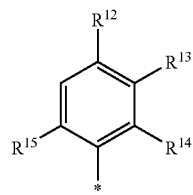

in which
\* is the point of attachment to —CR$^{10}$R$^{11}$,
R$^{12}$ is fluorine, chlorine, methyl and trifluoromethyl,
R$^{13}$ is hydrogen, fluorine or chlorine,
R$^{14}$ is hydrogen, fluorine or chlorine,
R$^{15}$ is hydrogen, fluorine or chlorine,
with the proviso that at least one of the radicals R$^{13}$, R$^{14}$ and R$^{15}$ is hydrogen,
R$^{10}$ is cyclopropyl,
in which cyclopropyl may be substituted by a cyano substituent,
or
in which cyclopropyl may be substituted by 1 or 2 fluorine substituents,
R$^{11}$ is hydrogen,
and the salts, solvates and solvates of the salts thereof.

Particular preference is also given in the context of the present invention to compounds of the formula (I) in which
A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

where
\# is the point of attachment to the indole,
and
R$^9$ is a group of the formula

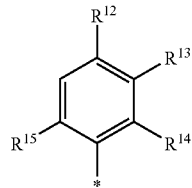

in which
\* is the point of attachment to —CR$^{10}$R$^{11}$,
R$^{12}$ is fluorine, chlorine, methyl and trifluoromethyl,
R$^{13}$ is hydrogen, fluorine or chlorine,
R$^{14}$ is hydrogen, fluorine or chlorine,
R$^{15}$ is hydrogen, fluorine or chlorine,
with the proviso that at least one of the radicals R$^{13}$, R$^{14}$ and R$^{15}$ is hydrogen,
R$^{10}$ is a group of the formula

in which
\#\#\# is the point of attachment to —CR$^9$R$^{11}$,
R$^{11}$ is hydrogen,
and the salts, solvates and solvates of the salts thereof.

Particular preference is also given in the context of the present invention to compounds of the formula (I) in which
A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

where
\# is the point of attachment to the indole,
and
R$^9$ is a group of the formula

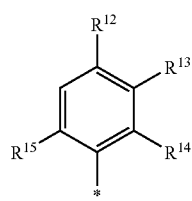

in which
* is the point of attachment to —$CR^{10}R^{11}$,
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is a group of the formula

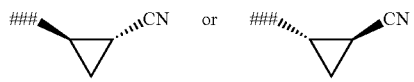

in which
is the point of attachment to —$CR^9R^{11}$,
$R^{11}$ is hydrogen,
and the salts, solvates and solvates of the salts thereof.

Preference is also given in the context of the present invention to compounds of the formula (I) in which A is S—, —S(=O)— or —S(=O)$_2$—.

Preference is also given in the context of the present invention to compounds of the formula (I) in which A is —S(=O)—.

Preference is also given in the context of the present invention to compounds of the formula (I) in which A is —S(=O)$_2$—.

Preference is also given in the context of the present invention to compounds of the formula (I) in which
$R^5$ is a group of the formula

where
# is the point of attachment to the indole,
and
$R^9$ is phenyl, naphthyl or 5- to 10-membered heteroaryl,
in which phenyl, naphthyl and 5- to 10-membered heteroaryl may be substituted by 1 to 3 substituents independently of one another selected from the group of halogen, cyano, (C$_1$-C$_4$)-alkyl, trifluoromethyl, (C$_1$-C$_4$)-alkoxy, trifluoromethoxy and trifluoromethylthio,
$R^{10}$ is 1-cyanoeth-2-yl, 1-cyano-2-methyleth-2-yl or 1-cyanoprop-3-yl,
$R^{11}$ is hydrogen.

Preference is also given in the context of the present invention to compounds of the formula (I) in which
$R^5$ is a group of the formula

where
# is the point of attachment to the indole,
and
$R^9$ is phenyl, naphthyl or benzothienyl,
in which phenyl, naphthyl and benzothienyl may be substituted by 1 to 3 substituents independently of one another selected from the group of fluorine, chlorine, cyano, methyl, ethyl and trifluoromethyl,
$R^{10}$ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl, 1-hydroxycycloprop-2-yl or phenyl,
in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl and 1-hydroxycycloprop-2-yl may be substituted by 1 or 2 fluorine substituents,
and
in which phenyl may be substituted by 1 or 2 substituents independently of one another selected from the group of fluorine, chlorine, cyano and methyl,
$R^{11}$ is hydrogen.

Preference is also given in the context of the present invention to compounds of the formula (I) in which
$R^5$ is a group of the formula

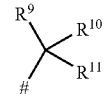

where
# is the point of attachment to the indole,
and
$R^9$ is phenyl, naphthyl or benzothienyl,
in which phenyl, naphthyl and benzothienyl may be substituted by 1 to 3 substituents independently of one another selected from the group of fluorine, chlorine, cyano, methyl, ethyl and trifluoromethyl,
$R^{10}$ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl, 1-hydroxycycloprop-2-yl or phenyl, in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl and 1-hydroxycycloprop-2-yl may be substituted by 1 or 2 fluorine substituents, and in which phenyl may be substituted by 1 or 2 substituents independently of one another selected from the group of fluorine, chlorine, cyano and methyl, $R^{11}$ is methyl.

Preference is also given in the context of the present invention to compounds of the formula (I) in which $R^{11}$ is hydrogen.

Preference is also given in the context of the present invention to compounds of the formula (I) in which $R^{11}$ is methyl.

Preference is also given in the context of the present invention to compounds of the formula (I) in which $R^{11}$ is methyl, ethyl or cyclopropyl.

Preference is also given in the context of the present invention to compounds of the formula (I) in which $R^{10}$ is cyclopropyl.

Preference is also given in the context of the present invention to compounds of the formula (I) in which $R^{10}$ is cyclopropyl, where cyclopropyl may be substituted by a cyano substituent, or where cyclopropyl may be substituted by 1 or 2 fluorine substituents.

Preference is also given in the context of the present invention to compounds of the formula (I) in which $R^{10}$ is a group of the formula

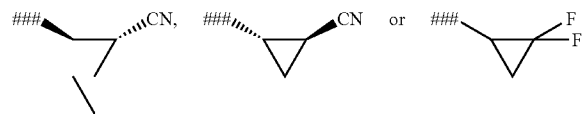

in which

\#\#\# is the point of attachment to —$CR^9R^{11}$.

Preference is also given in the context of the present invention to compounds of the formula (I) in which $R^{10}$ is phenyl, in which phenyl may be substituted by 1 or 2 substituents independently of one another selected from the group of fluorine, chlorine, cyano and methyl.

Preference is also given in the context of the present invention to compounds of the formula (I) in which $R^{10}$ is a group of the formula

in which

\#\# is the point of attachment to —$CR^9R^{11}$, $R^{16}$ is fluorine or chlorine.

Preference is also given in the context of the present invention to compounds of the formula (I) in which $R^9$ is a group of the formula

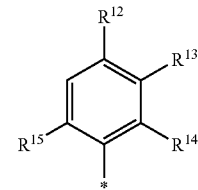

in which

* is the point of attachment to —$CR^{10}R^{11}$, $R^{12}$ is fluorine, chlorine, methyl and trifluoromethyl, $R^{13}$ is hydrogen, fluorine or chlorine, $R^{14}$ is hydrogen, fluorine or chlorine, $R^{15}$ is hydrogen, fluorine or chlorine, with the proviso that at least one of the radicals $R^{13}$, $R^{14}$ and $R^{15}$ is hydrogen.

Preference is also given in the context of the present invention to compounds of the formula (I) in which $R^9$ is phenyl, naphthyl or benzothienyl, in which phenyl, naphthyl and benzothienyl may be substituted by 1 to 3 substituents independently of one another selected from the group of fluorine, chlorine, cyano, methyl, ethyl and trifluoromethyl.

Preference is also given in the context of the present invention to compounds of the formula (I) in which $R^9$ is phenyl or benzothienyl, in which phenyl and benzothienyl may be substituted by 1 or 2 substituents independently of one another selected from the group of fluorine, chlorine, methyl and trifluoromethyl.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), characterized in that

[A] an indole derivative of the formula (I-1)

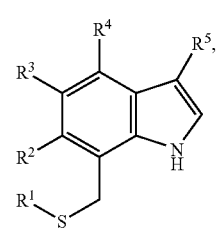

in which $R^1$, $R^2$, $R^3$, $R^4$ and $R^5$ have in each case the meanings indicated above, is reacted in an inert solvent with a suitable oxidizing agent, preferably meta-chloroperbenzoic acid, to give a compound of the formula (I-2)

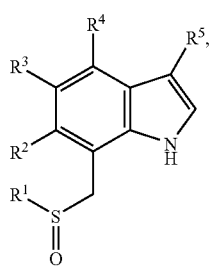
(I-2)

in which $R^1$, $R^2$, $R^3$, $R^4$ and $R^5$ have in each case the meanings indicated above, or

[B] an indole derivative of the formula (I-1)

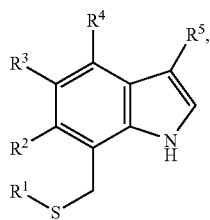
(I-1)

in which $R^1$, $R^2$, $R^3$, $R^4$ and $R^5$ have in each case the meanings indicated above, is reacted in an inert solvent with a suitable oxidizing agent, preferably meta-chloroperbenzoic acid, to give a compound of the formula (I-3)

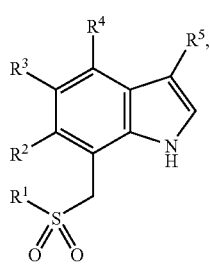
(I-3)

in which $R^1$, $R^2$, $R^3$, $R^4$ and $R^5$ have in each case the meanings indicated above, or

[C] an indole derivative of the formula (II)

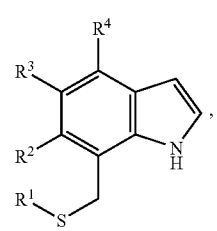
(II)

in which $R^1$, $R^2$, $R^3$ and $R^4$ have in each case the meanings indicated above, is oxidized in an inert solvent with a suitable oxidizing agent, preferably meta-chloroperbenzoic acid, to a compound of the formula (II-2)

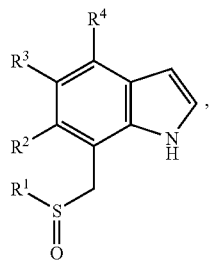
(II-2)

in which $R^1$, $R^2$, $R^3$ and $R^4$ have in each case the meanings indicated above, the latter is then reacted in an inert solvent in the presence of a suitable acid and/or Lewis acid with a compound of the formula (XI)

$$R^5\text{—OH,} \quad (XI)$$

in which $R^5$ has the meaning indicated above, to give a compound of the formula (I-2), or

[D] an indole derivative of the formula (II)

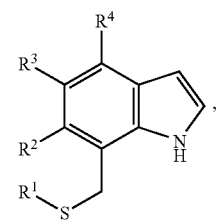
(II)

in which $R^1$, $R^2$, $R^3$ and $R^4$ have in each case the meanings indicated above, is oxidized in an inert solvent with a suitable oxidizing agent, preferably meta-chloroperbenzoic acid, to a compound of the formula (II-3)

(II-3)

in which $R^1$, $R^2$, $R^3$ and $R^4$ have in each case the meanings indicated above, the latter is then reacted in an inert solvent in the presence of a suitable acid and/or Lewis acid with a compound of the formula (XI)

$$R^5\text{—OH},\quad (XI)$$

in which $R^5$ has the meaning indicated above, to give a compound of the formula (I-3), and where appropriate the resulting compounds of the formula (I-2) or (I-3) are separated by methods known to a person skilled in the art into the enantiomers and/or diastereomers thereof, and/or converted with the appropriate (i) solvents and/or (ii) bases or acids into the solvates, salts and/or solvates of the salts thereof.

The compounds of the formulae (I-1), (I-2) and (I-3) together form the group of compounds of the invention of the formula (I).

Solvents suitable for the reactions (I-1)→(I-2) or (I-3) and (II)→(II-2) or (II-3) are all organic solvents which are inert under the reaction conditions. These include ketones such as acetone and methyl ethyl ketone, acyclic and cyclic ethers such as diethyl ether, methyl tert-butyl ether, 1,2-dimethoxyethane, tetrahydrofuran and dioxane, alcohols such as methanol, ethanol, isopropanol and tert-butanol, esters such as ethyl acetate or butyl acetate, hydrocarbons such as benzene, toluene, xylene, hexane and cyclohexane, chlorinated hydrocarbons such as dichloromethane, trichloromethane and chlorobenzene, or other solvents such as dimethylformamide (DMF), dimethyl sulfoxide (DMSO), N-methylpyrrolidinone (NMP), acetonitrile or pyridine. It is likewise possible to employ mixtures of the aforementioned solvents. Dichloromethane is preferably used.

Suitable oxidizing agents for the reactions (I-1)→(I-2) or (I-3) and (II)→(II-2) or (II-3) are organic oxidizing agents such as tert-butyl peroxide, meta-chloroperbenzoic acid, and inorganic oxidizing agents such as hydrogen peroxide, OXONE (CAS-RN 37222-66-5) or tetrabutylammonium perruthenate in conjunction with N-methylmorpholine oxide (TPAP/NMO). meta-Chloroperbenzoic acid is preferably used.

The oxidizing agent can be employed for the reaction (I-1)→(I-2) and (II)→(II-2) in an amount of from 1 to 1.2 mol, preferably from 1 to 1.05 mol, based on 1 mol of the compound of the formula (I-1) or (II).

The oxidizing agent can be employed for the reactions (I-1)→(I-3) and (II)→(II-3) in an amount of from 2 to 4 mol, preferably from 2 to 2.2 mol, based on 1 mol of the compound of the formula (I-1) or (II).

The reactions (I-1)→(I-2) or (I-3) and (II)→(II-2) or (II-3) generally take place in a temperature range from −78° C. to +50° C., preferably in the range from −20° C. to +50° C., in particular at 0° C. to +30° C. The reaction can be carried out under atmospheric, elevated or reduced pressure (e.g. in the range from 0.5 to 5 bar). It is generally carried out under atmospheric pressure.

Solvents suitable for process steps (II-2)+(XI)→(I-2) and (II-3)+(XI)→(I-3) are all organic solvents which are inert under the reaction conditions. These include acyclic and cyclic ethers such as diethyl ether, methyl tert-butyl ether, 1,2-dimethoxyethane, tetrahydrofuran and dioxane, primary alcohols such as methanol, ethanol, n-propanol and n-butanol, hydrocarbons such as benzene, toluene, xylene, hexane and cyclohexane, chlorinated hydrocarbons such as dichloromethane, trichloromethane, 1,2-dichloroethane and chlorobenzene, or dipolar aprotic solvents such as dimethylformamide (DMF), dimethyl sulfoxide (DMSO), N-methylpyrrolidinone (NMP) and acetonitrile. It is likewise possible to employ mixtures of the solvents mentioned. Dichloromethane, 1,2-dichloroethane and toluene are preferably used.

Acids suitable for process step (II-2)+(XI)→(I-2) and (II-3)+(XI)→(I-3) are acetic acid, trifluoroacetic acid, sulfuric acid, para-toluenesulfonic acid, camphorsulfonic acid, methanesulfonic acid or hydrochloric acid. Trifluoroacetic acid is preferably employed. The acid can be employed in this reaction in an amount of from 0.9 to 2.0 mol, preferably from 1 to 1.2 mol, based on 1 mol of the compound of the formula (II).

Lewis acids suitable for process step (II-2)+(XI)→(I-2) and (II-3)+(XI)→(I-3) are boron trifluoride-diethyl ether complex, cerium(IV) ammonium nitrate (CAN), tin(II) chloride, lithiumperchlorate, zinc(II) chloride, indium(III) chloride or indium(III) bromide. Indium(III) chloride is preferably used. The Lewis acid can be employed in this reaction in an amount of from 0.2 to 2.0 mol, preferably 0.7 to 1.2 mol, based on 1 mol of the compound of the formula (II).

The reactions (II-2)+(XI)→(I-2) and (II-3)+(XI)→(I-3) can where appropriate also be carried out using a mixture of acid and Lewis acid, with preference in this case for trifluoroacetic acid and indium(III) chloride. The acid and Lewis acid can be employed in a ratio of from 1:99 to 99:1, preferably 2:1 to 4:3.

The reaction takes place when acids are employed generally in a temperature range from −40° C. to +40° C., preferably at 0° C. to +30° C., and when Lewis acids are employed generally in a temperature range from +20° C. to +150° C., preferably at +40° C. to +100° C.

The process described is illustrated by means of the following schemes:

Scheme 1

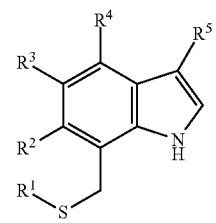

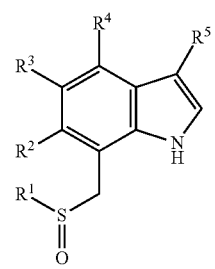 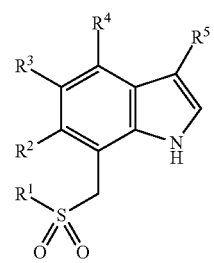

[a]: 1 eq. of meta-chlorperbenzoic acid, 0° C. → RT, $CH_2Cl_2$; b): 2.2 eq. of meta-chloroperbenzoic acid, 0° C. → RT, $CH_2Cl_2$].

Scheme 12

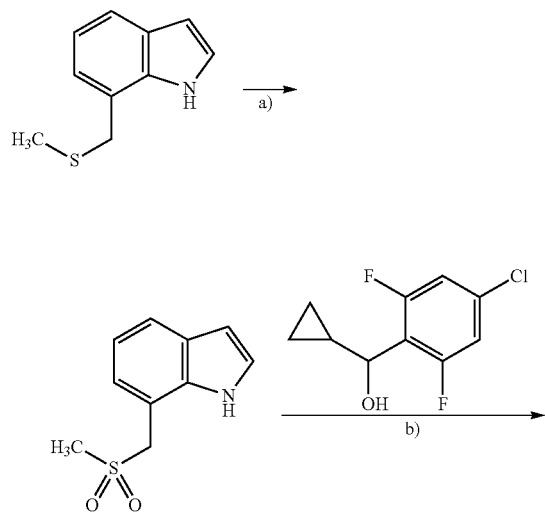

[a]: 1 eq. of meta-chlorperbenzoic acid, CH$_2$Cl$_2$, 0° C. → RT; b): trifluoroacetic acid, CH$_2$Cl$_2$, RT].

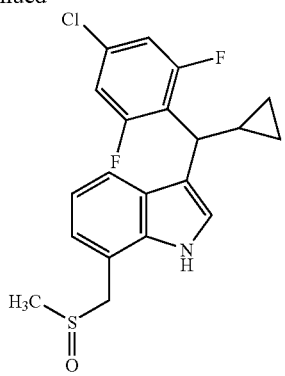

[a]: 2 eq. of meta-chlorperbenzoic acid, CH$_2$Cl$_2$, 0° C. → RT; b): trifluoroacetic acid, CH$_2$Cl$_2$, RT].

Scheme 13

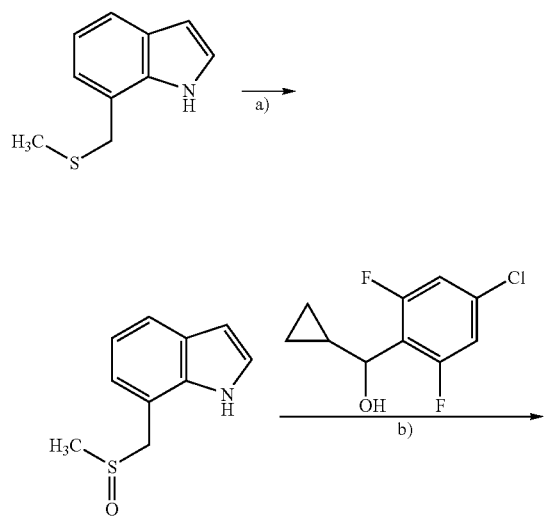

Alternatively, the reactions (II-2)→(I-2) and (II-3)→(I-3) can also be carried out using an acetate (XI-A)

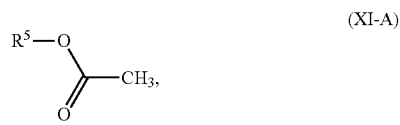

(XI-A)

in which R$^5$ has the meaning indicated above, (see Scheme 14).

Scheme 14

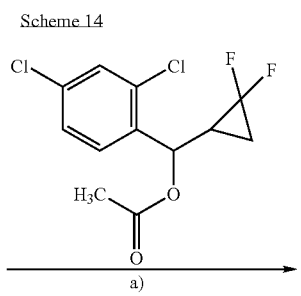

[a]: In(III)Cl$_3$, ClCH$_2$CH$_2$Cl, reflux].

The compounds of the invention of the formula (I-1) in which
R$^5$ is a group of the formula

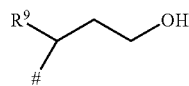

where # and R$^9$ each have the meanings indicated above,
can be prepared by initially condensing an indole derivative of the formula (II)

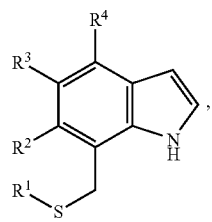

in which R$^1$, R$^2$, R$^3$ and R$^4$ have the meanings indicated above,
in an inert solvent, where appropriate in the presence of an acid and/or base, with a compound of the formula (III)

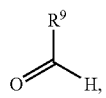

in which R$^9$ has the meaning indicated above,
and a malonic ester of the formula (IV)

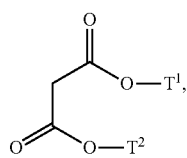

in which
T$^1$ and T$^2$ are identical or different and are (C$_1$-C$_4$)-alkyl or the two together form a >C(CH$_3$)$_2$ bridge,
to give a compound of the formula (V)

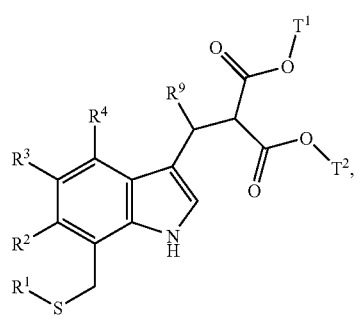

in which R$^1$, R$^2$, R$^3$, R$^4$, R$^9$, T$^1$ and T$^2$ each have the meanings indicated above, then cleaving the diester with decarboxylation to give a compound of the formula (VI)

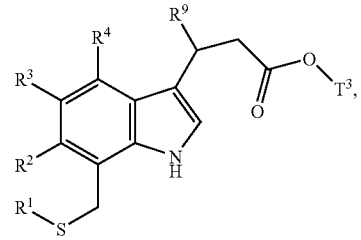

in which R$^1$, R$^2$, R$^3$, R$^4$ and R$^9$ each have the meanings indicated above,
and
T$^3$ is hydrogen or (C$_1$-C$_4$)-alkyl,
and then converting the latter in an inert solvent with a suitable reducing agent such as, for example, lithium aluminum hydride into a compound of the invention of the formula (I-1A)

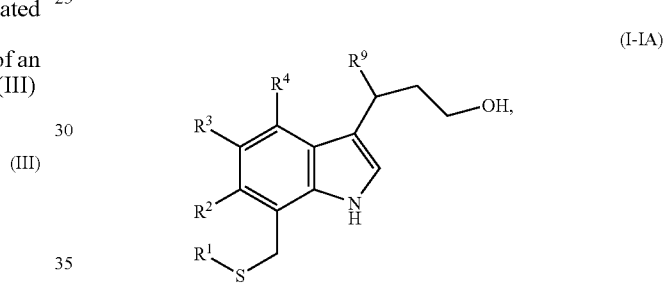

in which R$^1$, R$^2$, R$^3$, R$^4$ and R$^9$ each have the meanings indicated above.

Compounds of the invention of the formula (I-1) in which R$^5$ is a group of the formula

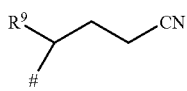

where # and R$^9$ each have the meanings indicated above,
can be prepared starting from a compound of the formula (I-1A) by reaction by standard methods to give a compound of the formula (VII)

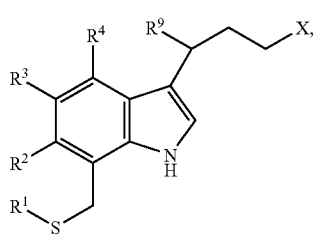

in which R$^1$, R$^2$, R$^3$, R$^4$ and R$^9$ each have the meanings indicated above, and X is a suitable leaving group such as, for example, halogen, mesylate, tosylate or triflate, and subsequent substitution reaction with an alkali metal cyanide to give a compound of the invention of the formula (I-1B)

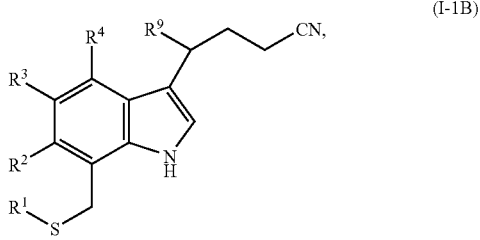

(I-1B)

in which $R^1$, $R^2$, $R^3$, $R^4$ and $R^9$ each have the meanings indicated above.

Process step (II)+(III)+(IV)→(V) can be carried out in one stage as 3-component reaction or else in two stages by initially condensing the aldehyde of the formula (III) with the malonic ester of the formula (IV) by standard methods to give a compound of the formula (VIII)

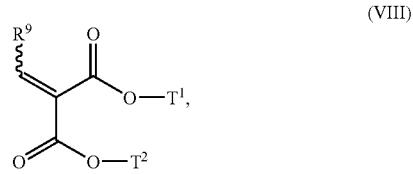

(VIII)

in which $R^9$, $T^1$ and $T^2$ each have the meanings indicated above, and then reacting the latter in a separate reaction step with an indole of the formula (II).

When the reaction (II)+(III)+(IV)→(V) is carried out in one stage, the malonic ester component (IV) preferably used is Meldrum's acid (cycl. isopropylidene malonate). The product of the formula (Va) resulting in this case

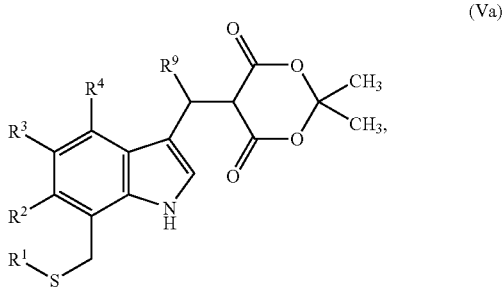

(Va)

in which $R^1$, $R^2$, $R^3$, $R^4$ and $R^9$ each have the meanings indicated above, is subsequently converted by solvolysis with methanol or ethanol in the presence of pyridine and copper powder into an ester of the formula (VI) [$T^3$=methyl or ethyl][cf. Y. Oikawa et al., *Tetrahedron Lett.*, 1759-1762 (1978)].

The one-stage process variant (II)+(III)+(IV)→(V) and—when the reaction is carried out in two stages—the condensation (III)+(IV)→(VIII) are preferably carried out in the presence of an acid/base catalyst such as, for example D,L-proline or piperidinium acetate. The reaction (VIII)+(II)→(V) can where appropriate take place advantageously with the aid of an amine base such as triethylamine or a Lewis acid such as copper(II) or ytterbium trifluoromethanesulfonate.

Solvents suitable for process steps (II)+(III)+(IV)→(V) and (VIII)+(II)→(V) are all organic solvents which are inert under the reaction conditions. These include acyclic and cyclic ethers such as diethyl ether, methyl tert-butyl ether, 1,2-dimethoxyethane, tetrahydrofuran and dioxane, hydrocarbons such as benzene, toluene, xylene, hexane and cyclohexane, chlorinated hydrocarbons such as dichloromethane, trichloromethane and chlorobenzene or dipolar aprotic solvents such as dimethylformamide (DMF), dimethyl sulfoxide (DMSO), N-methylpyrrolidinone (NMP) and acetonitrile. It is likewise possible to employ mixtures of the solvents mentioned. Acetonitrile is preferably used.

The reactions generally take place in a temperature range from 0° C. to +120° C., preferably at 0° C. to +60° C. The reactions can be carried out under atmospheric, elevated or reduced pressure (e.g. in the range from 0.5 to 5 bar). They are generally carried out under atmospheric pressure.

The reducing agent suitable in process step (VI)→(I-1A) is in particular lithium aluminum hydride or lithium borohydride. In the case of the carboxylic acid (VI) [$T^3$=H] it is also possible alternatively to use diborane or borane complexes. The reactions are preferably carried out in an ether such as diethyl ether or tetrahydrofuran as inert solvent in a temperature range from 0° C. to +80° C.

Inert solvents suitable in particular for process steps (VII)→(I-1B) are ethers such as diethyl ether, methyl tert-butyl ether, 1,2-dimethoxyethane, tetrahydrofuran and dioxane, or dipolar aprotic solvents such as dimethylformamide (DMF), dimethyl sulfoxide (DMSO), N-methylpyrrolidinone (NMP) and acetonitrile. It is likewise possible to employ mixtures of these solvents. Dimethylformamide is preferably used. The reactions generally take place in a temperature range from +20° C. to +150° C., preferably at +40° C. to +100° C.

The compounds of the formulae (III) and (IV) are commercially available, known from the literature or can be prepared in analogy to processes known from the literature.

The process described above is illustrated by the following synthesis scheme:

Scheme 2

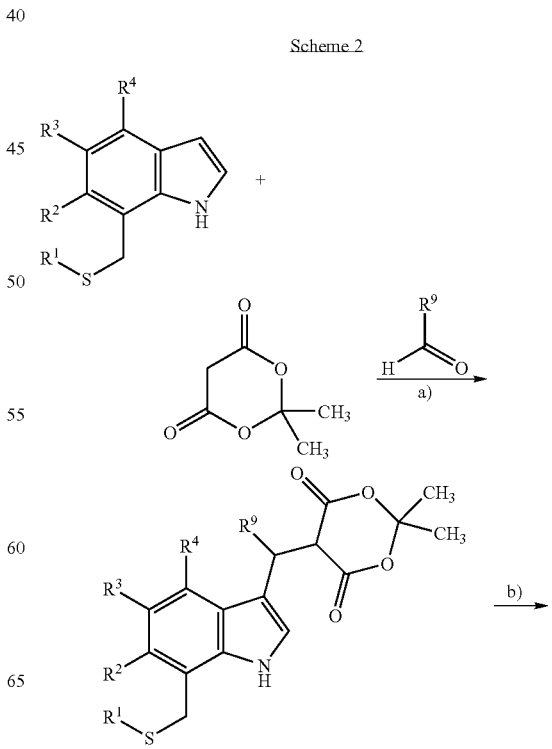

-continued

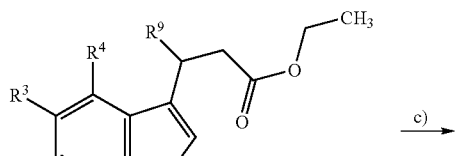

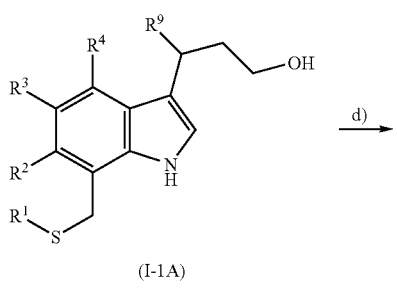

(I-1A)

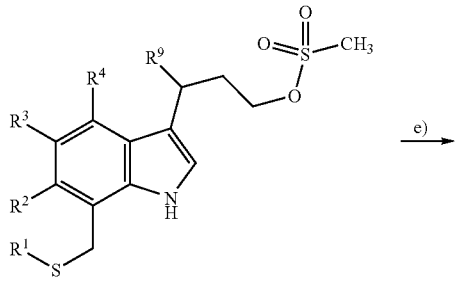

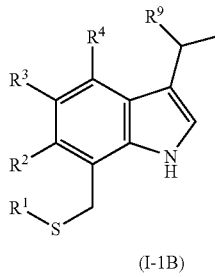

(I-1B)

[a): cat. D,L-proline, acetonitrile, RT; b): cat. Cu powder, EtOH/pyridine, reflux; c): LiAlH₄, Et₂O, 0° C. → RT: d) MsCl, Et₃N, DMAP, CH₂Cl₂, RT; e): KCN, DMF, 80° C.].

The indoles of the formula (II) can be prepared by reacting a 6-nitrobenzyl bromide derivative of the formula (IX)

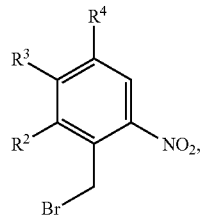

in which $R^2$, $R^3$ and $R^4$ each have the meanings indicated above, in an inert solvent with an alkali metal alkyl thiolate (X)

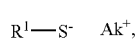

(X)

in which $R^1$ has the meaning indicated above, and
$Ak^+$ is an alkali metal ion, preferably sodium,
to give a compound of the formula (XI)

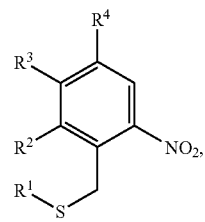

(XI)

in which $R^1$, $R^2$, $R^3$ and $R^4$ each have the meanings indicated above,
and then converting the latter in a Bartoli reaction with vinylmagnesium bromide into an indole of the formula (II)

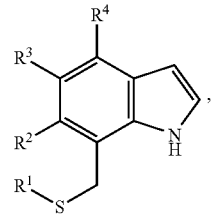

(II)

in which $R^1$, $R^2$, $R^3$ and $R^4$ each have the meanings indicated above.

Solvents suitable for process step (IX)+(X)→(XI) are all organic solvents which are inert under the reaction conditions. These include acyclic and cyclic ethers such as diethyl ether, methyl tert-butyl ether, 1,2-dimethoxyethane, tetrahydrofuran and dioxane, hydrocarbons such as benzene, toluene, xylene, hexane and cyclohexane, chlorinated hydrocarbons such as dichloromethane, trichloromethane and chlorobenzene, or dipolar aprotic solvents such as dimethylformamide (DMF), dimethyl sulfoxide (DMSO), N-methylpyrrolidinone (NMP) and acetonitrile. It is likewise possible to employ mixtures of the solvents mentioned. Tetrahydrofuran or DMF is preferably used.

The reaction generally takes place in a temperature range from −20° C. to +100° C., preferably at 0° C. to +60° C. The reactions can be carried out under atmospheric, elevated or reduced pressure (e.g. in the range from 0.5 to 5 bar). They are generally carried out under atmospheric pressure.

Solvents suitable for the Grignard reaction (XI)→(II) are all organic solvents which are inert under the reaction conditions. These include acyclic and cyclic ethers such as diethyl ether, methyl tert-butyl ether, 1,2-dimethoxyethane, tetrahydrofuran and dioxane, hydrocarbons such as benzene, toluene, xylene, hexane and cyclohexane, chlorinated hydrocarbons such as dichloromethane, trichloromethane and chlorobenzene, or dipolar aprotic solvents such as dimethylformamide (DMF), dimethyl sulfoxide (DMSO), N-methylpyrrolidinone (NMP) and acetonitrile. It is likewise possible to employ mixtures of the solvents mentioned. Tetrahydrofuran is preferably used.

The reaction generally takes place in a temperature range from −100° C. to +50° C., preferably at −78° C. to +25° C. The reactions can be carried out under atmospheric, elevated or reduced pressure (e.g. in the range from 0.5 to 5 bar). They are generally carried out under atmospheric pressure.

The compounds of the formulae (IX) are commercially available, known from the literature or can be prepared in analogy to processes known from the literature.

The process described above is illustrated by the following synthesis scheme:

Scheme 3

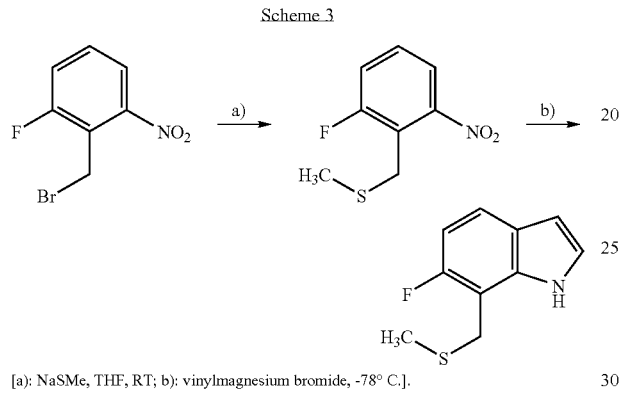

[a): NaSMe, THF, RT; b): vinylmagnesium bromide, -78° C.].

Alternatively, indoles of the formula (II) in which $R^2$, $R^3$ and $R^4$ are H can each be prepared starting from 7-methylindole, as illustrated by way of example in the synthesis scheme below:

Scheme 4

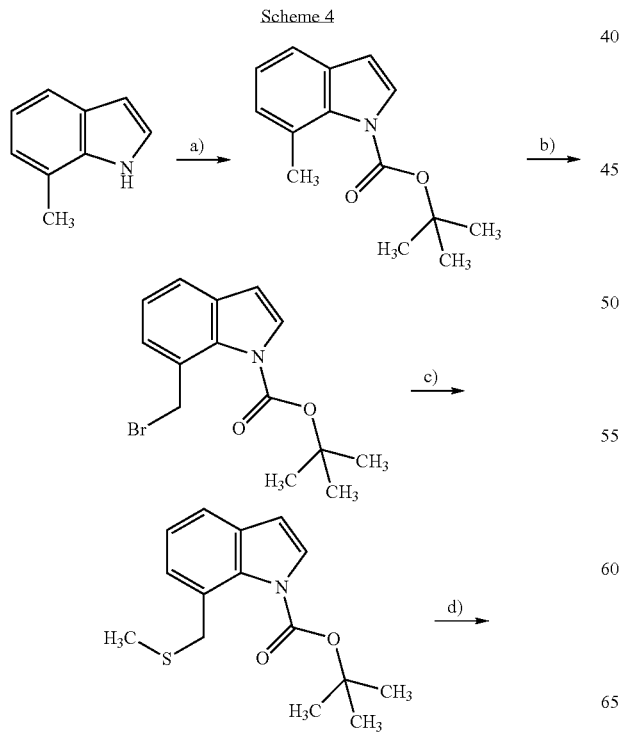

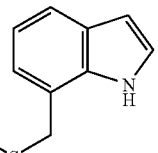

[a): NaH, THF, 0° C. → RT; di-tert-butyl dicarbonate, RT; b): N-bromosuccinimide, CCl$_4$, h • v, reflux; c): NaSMe, DMF, RT; d) NaOMe, MeOH, RT].

Further compounds of the invention of the formula (I-1) in which
$R^5$ is a group of the formula

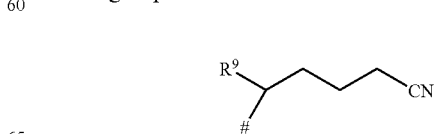

where # and $R^9$ each have the meanings indicated above, can be prepared by hydrolyzing a compound of the formula (I-1B) to a compound of the formula (XII)

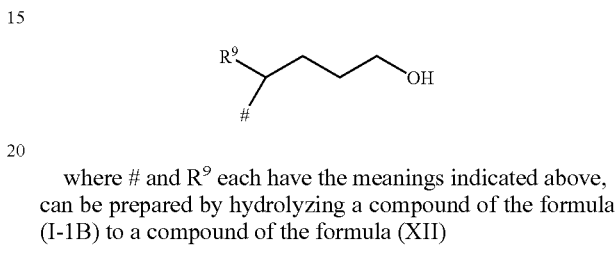

(XII)

in which $R^1$, $R^2$, $R^3$, $R^4$ and $R^9$ each have the meanings indicated above, and
$T^4$ is hydrogen or $(C_1-C_4)$-alkyl,
and subsequently reacting in an inert solvent with a suitable reducing agent such as, for example, lithium aluminum hydride to give a compound of the invention of the formula (I-1C)

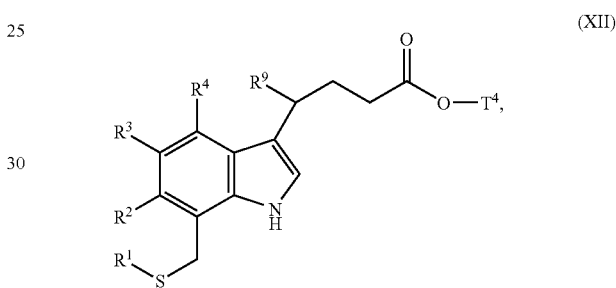

(I-1C)

in which $R^1$, $R^2$, $R^3$, $R^4$ and $R^9$ each have the meanings indicated above.

Further compounds of the invention of the formula (I-1) in which
$R^5$ is a group of the formula

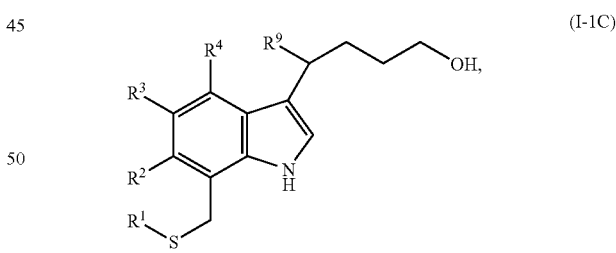

where # and $R^9$ each have the meanings indicated above, can be prepared by reacting a compound of the formula (I-1C), once again by standard methods via a compound of the formula (XIII)

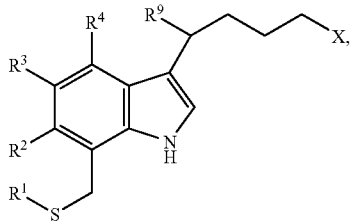
(XIII)

in which $R^1$, $R^2$, $R^3$, $R^4$ and $R^9$ each have the meanings indicated above,
and
X is a suitable leaving group such as, for example, halogen, mesylate, tosylate or triflate,
and a subsequent substitution reaction with an alkali metal cyanide to give a compound of the invention of the formula (I-1D)

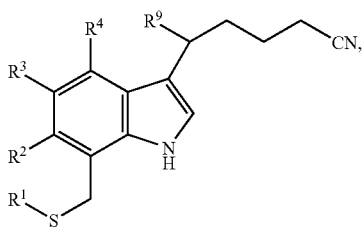
(I-1D)

in which $R^1$, $R^2$, $R^3$, $R^4$ and $R^9$ each have the meanings indicated above.

The hydrolysis of the nitriles (I-1B) to the carboxylic acids (XII) is preferably carried out with aqueous solutions of alkali metal or alkaline earth metal hydroxides such as lithium, sodium, potassium, calcium or barium hydroxide. Suitable cosolvents are alcohols such as methanol, ethanol, n-propanol, isopropanol, n-butanol or tert-butanol, ethers such as diethyl ether, tetrahydrofuran, dioxane or 1,2-dimethoxyethane, other solvents such as acetone, dimethylformamide (DMF) or dimethyl sulfoxide (DMSO), or mixtures of these solvents. The hydrolysis generally takes place in a temperature range from +50° C. to +150° C., preferably at +60° C. to +100° C.

For the synthesis sequence (I-1C)→(XII)→(I-1D) are carried out under the reaction conditions mentioned for the sequence (I-1A)→(VII)→(I-1B).

The preparation of the compounds of the invention can be illustrated by the following synthesis schemes:

Scheme 5

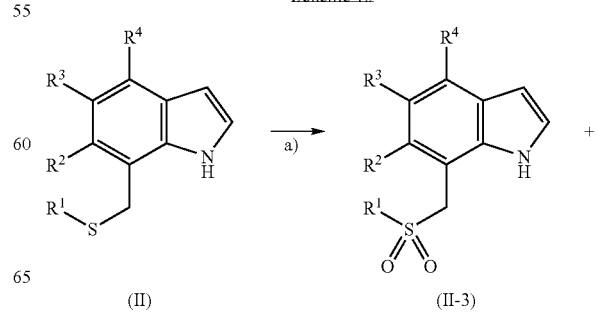

-continued

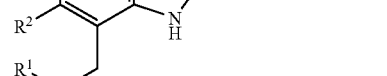

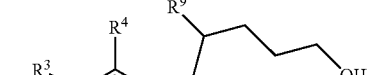

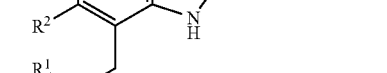

[a]: aq. KOH, EtOH, 80° C.; b): LiAlH$_4$, THF, 60° C.; c): MsCl, Et$_3$N, DMAP, CH$_2$Cl$_2$, RT; d): KCN, DMF, 80° C.].

The process (II)→(I-1A)→(I-1B)→(I-1C)→(I-1D) described above can alternatively also be carried out starting from compounds of the formula (II-2) or (II-3) to prepare the analogous compounds of the formula (I-2A), (I-3A), (I-2B), (I-3B) etc., as shown by way of example in the following synthesis scheme:

Scheme 15

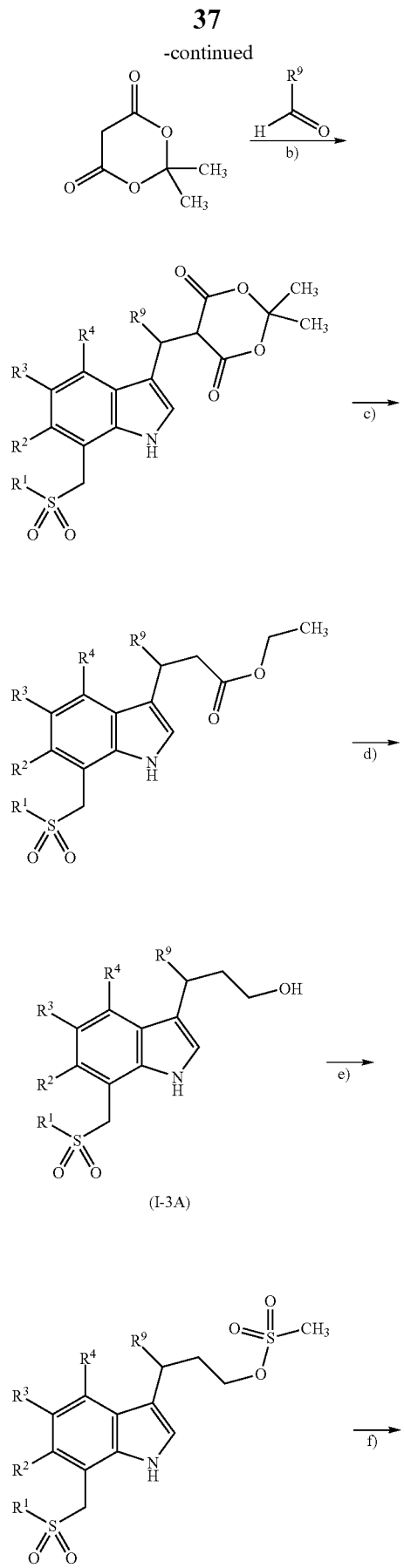
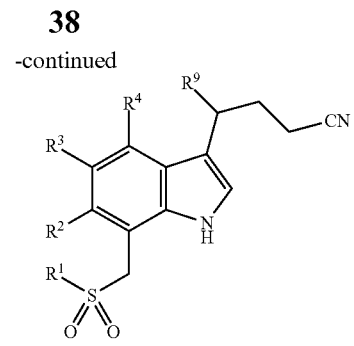

(I-3A)

(I-3B)

[a): 2 eq. m-CPBA, CH$_2$Cl$_2$, 0° C. → RT; b): cat. D,L-proline, acetonitrile, RT; c): cat. Cu powder, EtOH/pyridine, reflux; d): LiAlH$_4$, Et$_2$O, 0° C. → RT: e) MsCl, Et$_3$N, DMAP, CH$_2$Cl$_2$, RT; f): KCN, DMF, 80° C.].

Further compounds of the invention of the formula (I-1) in which

R$^5$ is a group of the formula

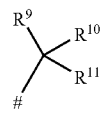

where # and R$^9$ each have the meanings indicated above, and

R$^{10}$ is (C$_4$-C$_6$)-alkyl,
in which (C$_4$-C$_6$)-alkyl is substituted by a substituent selected from the group of hydroxy and cyano, and R$^{11}$ is hydrogen, can be prepared starting from a compound of the formula (I-1D) by repeating process steps (I-1B)→(XII)→(I-1C)→(XIII)→(I-1D).

Compounds of the invention of the formula (I) in which

R$^5$ is a group of the formula

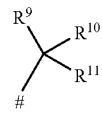

where # and R$^9$ each have the meanings indicated above, and

R$^{10}$ is 1-cyano-1-methyleth-2-yl, 1-cyano-2-methyleth-2-yl, 1-cyano-1,2-dimethyleth-2-yl, 1-cyano-2,2-dimethyleth-2-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxy-1-methylprop-3-yl, 1-hydroxy-2-methylprop-3-yl, 1-hydroxy-3-methylprop-3-yl or 1-hydroxy-2,3-dimethylprop-3-yl, R$^{11}$ is hydrogen, can be prepared by methods known to a person skilled in the art for the α-methylation or α-dimethylation of carbonyl compounds starting from the compounds of the formulae (VI) and (XII) described above [cf., for example, Scheme 6].

Scheme 6

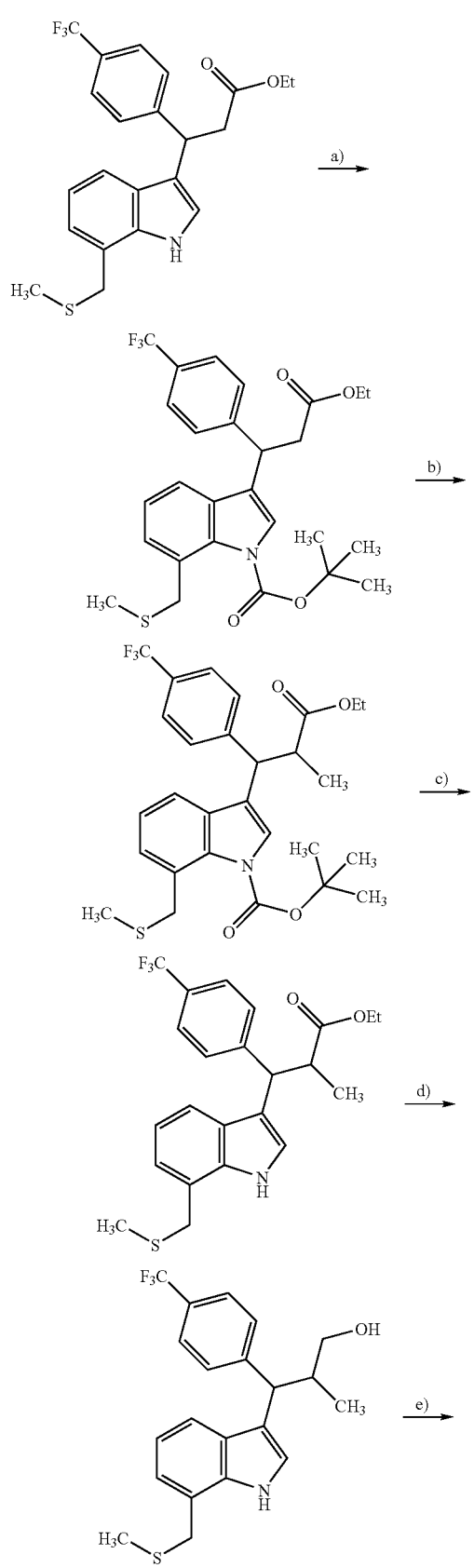

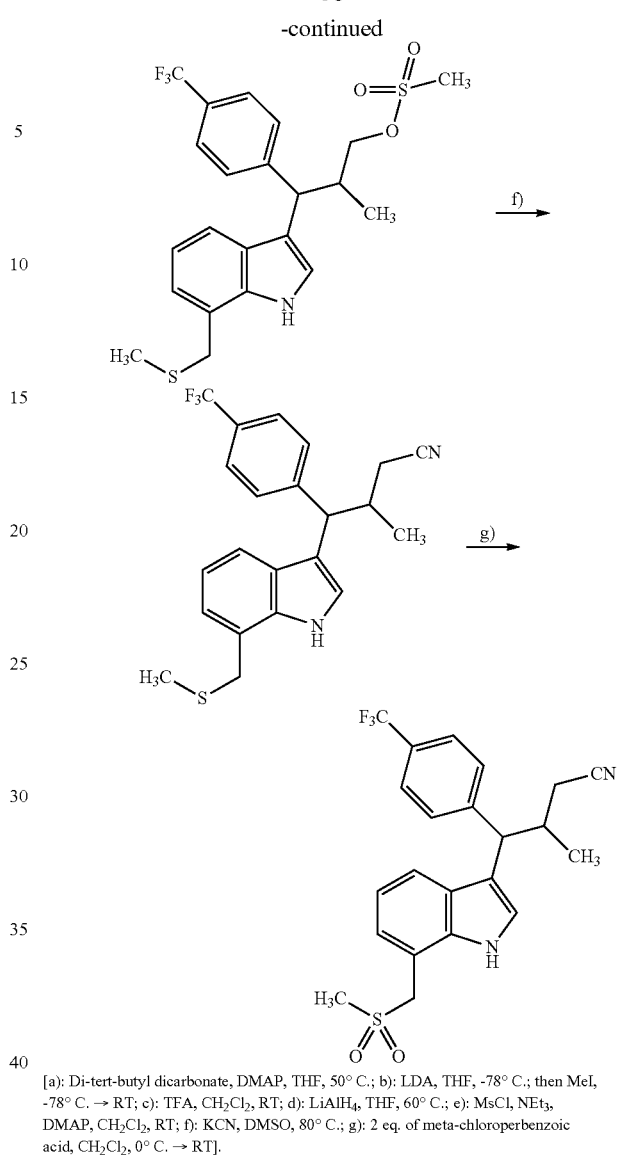

[a): Di-tert-butyl dicarbonate, DMAP, THF, 50° C.; b): LDA, THF, -78° C.; then MeI, -78° C. → RT; c): TFA, CH₂Cl₂, RT; d): LiAlH₄, THF, 60° C.; e): MsCl, NEt₃, DMAP, CH₂Cl₂, RT; f): KCN, DMSO, 80° C.; g): 2 eq. of meta-chloroperbenzoic acid, CH₂Cl₂, 0° C. → RT].

Compounds of the invention of the formula (I) in which $R^5$ is a group of the formula

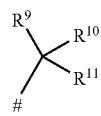

where # and $R^9$ each have the meanings indicated above, and
$R^{10}$ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl or 1-hydroxy-2,3-dimethylprop-3-yl, in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl and 1-hydroxy-2,3-dimethylprop-3-yl are substituted by 1 or 2 fluorine substituents, $R^{11}$ is hydrogen, can be prepared by known methods for fluorinating carbonyl compounds starting from the compounds of the formulae (VI), (XII), (I-1B) or (I-1D) described above [cf., for example, Z. Xu et al., *J. Fluorine Chem.* 1992, 58 (1), 71-79; W. H. Bunnelle, *J. Org. Chem.* 1990, 55, 768-770].

Compounds of the invention of the formula (I-1) in which $R^5$ is a group of the formula

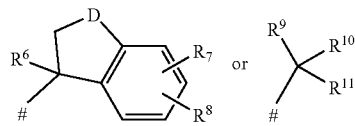

where #, D, $R^6$, $R^7$, $R^8$ and $R^9$ each have the meanings indicated above, and $R^{10}$ is $(C_1-C_6)$-alkyl, $(C_3-C_7)$-cycloalkyl or phenyl, in which $(C_3-C_7)$-cycloalkyl may be substituted by 1 or 2 substituents independently of one another selected from the group of fluorine, hydroxy and cyano, and in which phenyl may be substituted by 1 to 3 substituents independently of one another selected from the group of halogen, cyano, $(C_1-C_4)$-alkyl, trifluoromethyl, $(C_1-C_4)$-alkoxy, trifluoromethoxy and trifluoromethylthio, $R^{11}$ is hydrogen, methyl, ethyl or trifluoromethyl, can be prepared by reacting an indole of the formula (II) in an inert solvent in the presence of a suitable acid or Lewis acid with a compound of the formula (XI)

$R^5$—OH  (XI)

in which $R^5$ has the meaning indicated above.

Process step (II)+(XI)→(I-1) is carried out under the conditions mentioned for the reaction steps (II-2)+(XI)→(I-2) and (II-3)+(XI)→(I-3).

The process described above is illustrated by way of example by synthesis Schemes 7 and 8:

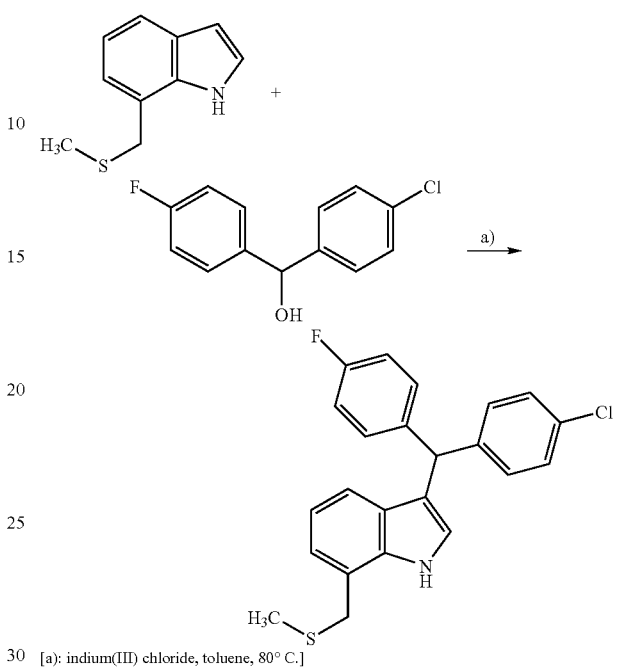

[a]: indium(III) chloride, toluene, 80° C.]

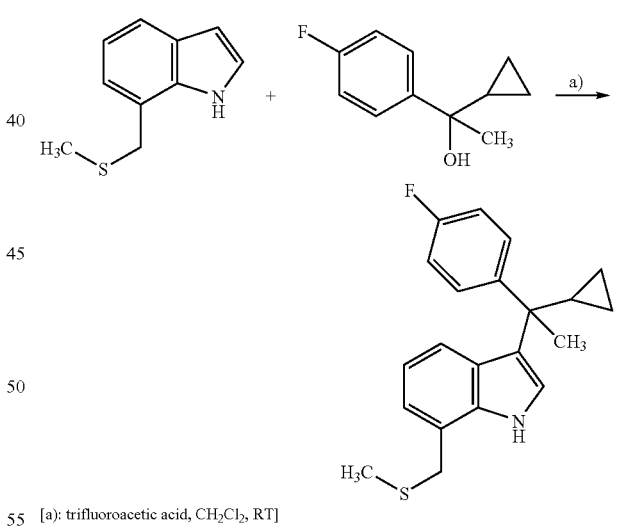

[a]: trifluoroacetic acid, CH$_2$Cl$_2$, RT]

Alternatively, compounds of the formula (I) in which $R^5$ is a group of the formula

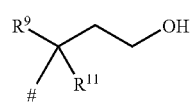

where #, $R^9$ and $R^{11}$ each have the meanings indicated above, can also be prepared by reacting a compound of the formula (XIV)

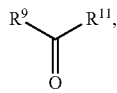
(XIV)

in which $R^9$ and $R^{11}$ each have the meanings indicated above, by methods known to a person skilled in the art with a compound of the formula (XV)

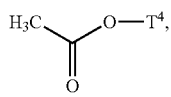
(XV)

in which $T^4$ is $(C_1-C_4)$-alkyl or benzyl, to give a compound of the formula (XVI)

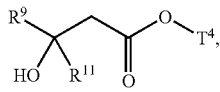
(XVI)

in which $R^9$, $R^{11}$ and $T^4$ each have the meanings indicated above, and then reacting the latter in an inert solvent in the presence of a Lewis acid or acid with a compound of the formula (II), (II-2) or (II-3) to give a compound of the formula (XVII), (XVII-2) or (XVII-3)

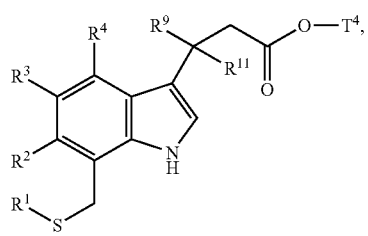
(XVII)

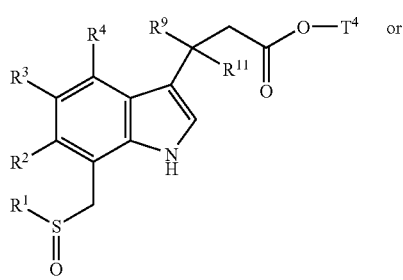
(XVII-2)

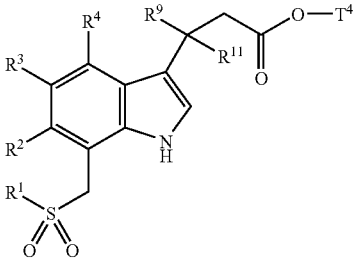
(XVII-3)

in which $R^1$, $R^2$, $R^3$, $R^4$, $R^9$, $R^{11}$ and $T^4$ each have the meanings indicated above, and then reducing the latter in an inert solvent with a suitable reducing agent to a compound of the formula (I-1A), (I-2A) or (I-3A), or alternatively reducing a compound of the formula (XVI) in an inert solvent with a suitable reducing agent to a compound of the formula (XVIII)

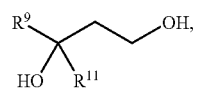
(XVIII)

in which $R^9$ and $R^{11}$ each have the meanings indicated above, and then reacting the latter under the conditions mentioned above with a compound of the formula (II), (II-2) or (II-3) to give a compound of the formula (I-1A), (I-2A) or (I-3A).

Inert solvents suitable for process steps (XVII)→(I-1A), (XVII-2)→(I-2A), (XVII-3)→(I-3A) and (XVI)→(XVIII) are in this case alcohols such as methanol, ethanol, n-propanol or isopropanol, or ethers such as diethyl ether, dioxane, tetrahydrofuran, glycol dimethyl ether or diethylene glycol dimethyl ether, or halohydrocarbons such as dichloromethane, trichloromethane, tetrachloromethane or 1,2-dichloroethane, or other solvents such as dimethylformamide. It is likewise possible to use mixtures of the solvents mentioned. Tetrahydrofuran is preferably used.

Reducing agents suitable for process steps (XVII)→(I-1A), (XVII-2)→(I-2A), (XVII-3)→(I-3A) and (XVI)→(XVIII) are borohydrides such as, for example, sodium borohydride, sodium triacetoxyborohydride, lithium borohydride or sodium cyanoborohydride, aluminum hydrides such as, for example, lithium aluminum hydride, sodiumbis(2-methoxyethoxy)aluminum hydride or diisobutylaluminium hydride or boron-tetrahydrofuran complex.

The reaction (IV-C)→(V-C) generally takes place in a temperature range from 0° C. to +60° C., preferably from 0° C. to +40° C.

The compounds of the formulae (XI), (XI-A), (XIV) and (XV) are commercially available, known from the literature or can be prepared in analogy to processes known from the literature, as illustrated by way of example by the following synthesis schemes:

Scheme 9
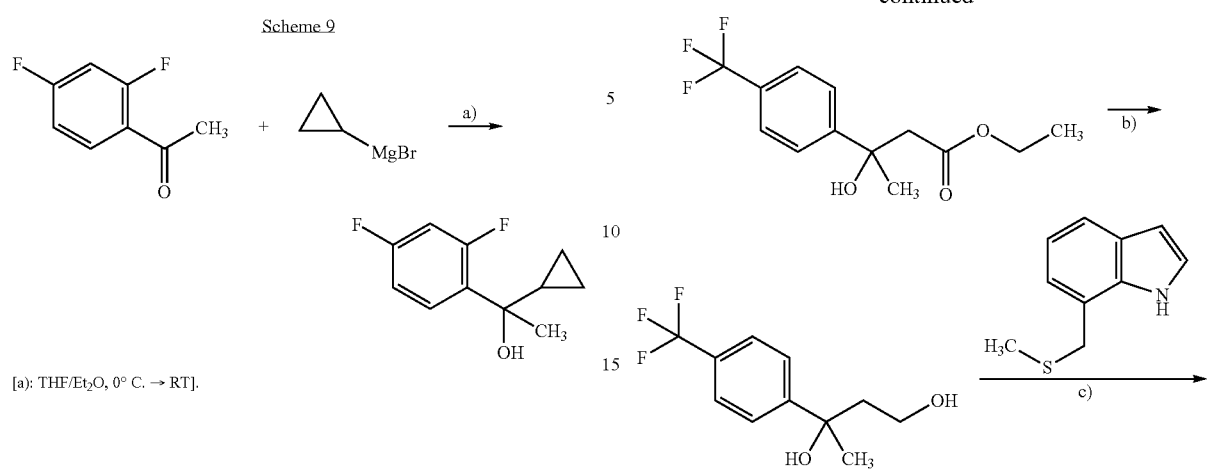
[a]: THF/Et₂O, 0° C. → RT].
[a]: LiHMDS, THF, -78° C.; then ethyl acetate, -78° C.; b): diisobutylaluminum hydride (1N in CH₂Cl₂), THF, RT; c): indium(III) chloride, toluene, 80° C.].
Scheme 10
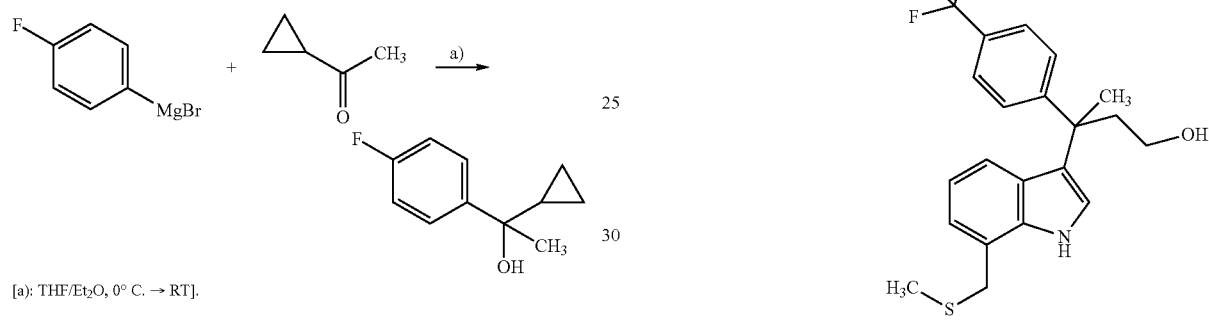
[a]: THF/Et₂O, 0° C. → RT].
Scheme 11
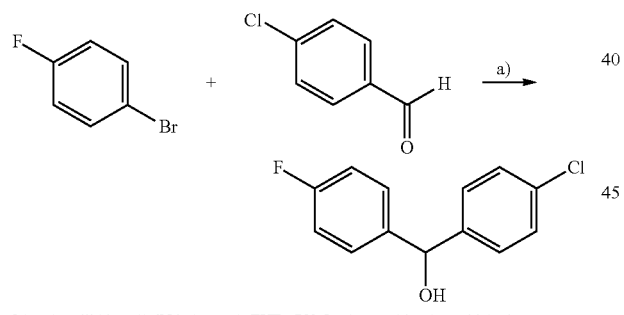
[a]: n-butyllithium (1.6N in hexane), THF, -78° C.; then p-chlorobenzaldehyde -78° C. → RT].
Scheme 17
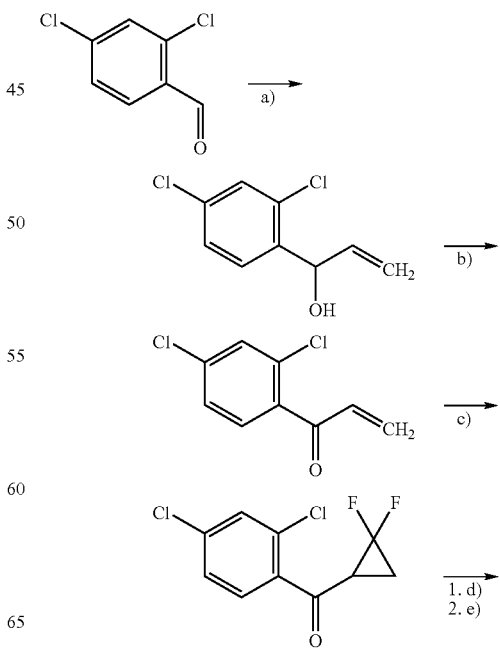
Scheme 16
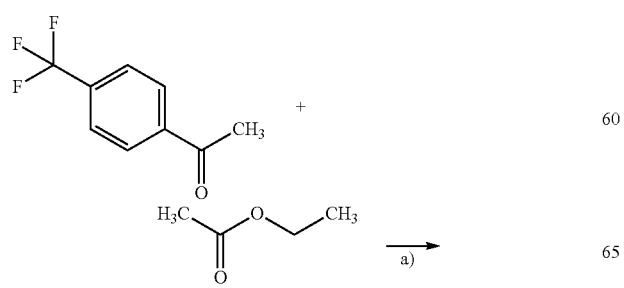

-continued

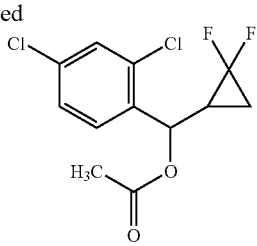

[a): vinylmagnesium bromide in THF, Et$_2$O, RT - reflux; b) MnO$_2$, CH$_2$Cl$_2$, reflux, then H$_2$SO$_4$, K$_2$Cr$_2$O$_7$, 15-20° C.; c) trimethylsilyl 2,2-difluoro-2-(fluorosulfonyl)acetate, NaF, 110° C.; d): NaBH$_4$, EtOH, ethyl acetate, 40° C.; e): (CH$_3$CO)$_2$O, pyridine, RT].

Scheme 18

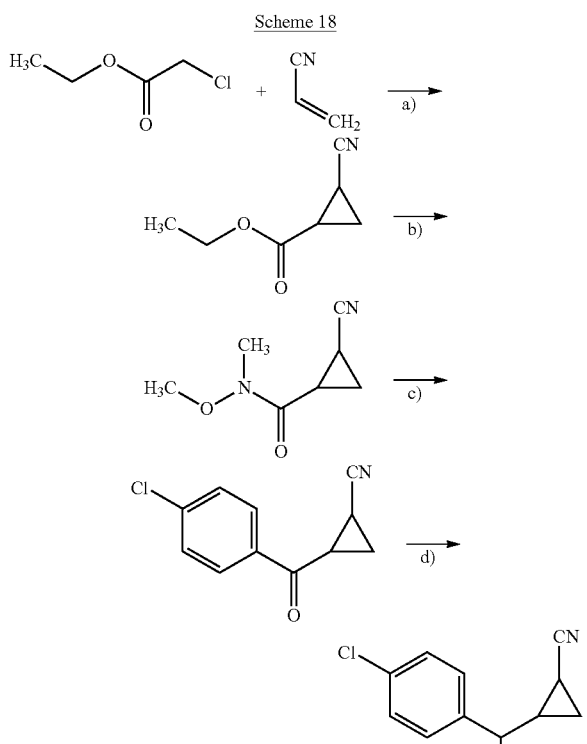

[a): benzyltriethylammonium chloride, K$_2$CO$_3$, DMF, RT; b): sodium hydroxide solution, MeOH, RT; hydrochloric acid; SOCl$_2$; N,O-dimethylhydroxylamine hydrochloride, Et$_3$N, CH$_2$Cl$_2$, RT; c): chlorophenylmagnesium bromide in Et$_2$O, THF, RT - reflux; d): NaBH$_4$, EtOH, ethyl acetate, 40° C.].

Further compounds of the invention can also be prepared where appropriate by conversions of functional groups of individual substituents, in particular those mentioned for A, $R^7$, $R^8$, $R^9$, $R^{10}$ and $R^{11}$, starting from compounds of the formula (I) obtained by the above processes. These conversions are carried out by conventional methods known to a person skilled in the art and include for example reactions such as nucleophilic, electrophilic or transition metal-catalyzed substitution reactions, oxidation, reduction, hydrogenation, alkylation, acylation, amination, esterification, ester cleavage, etherification, ether cleavage, formation of carbonamides and sulfonamides, and the introduction and removal of temporary protective groups.

The compounds of the invention are potent antagonists of the mineralocorticoid receptor which are selective in relation to the androgen (testosterone) and progesterone receptors and are distinguished by a valuable range of pharmacological effects which could not have been predicted, and an advantageous CYP inhibition profile by comparison with compounds disclosed in the prior art. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized either by an elevation of the plasma aldosterone concentration or by a change in the plasma aldosterone concentration relative to the plasma renin concentration, or are associated with these changes. Examples which may be mentioned are: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: primary and secondary hypertension, hypertensive heart disease with or without congestive heart failure, therapy-resistant hypertension, acute and chronic heart failure, coronary heart disease, stable and unstable angina pectoris, myocardial ischemia, myocardial infarction, dilated cardiomyopathies, congenital primary cardiomyopathies such as, for example, Brugada syndrome, cardiomyopathies induced by Chagas disease, shock, arteriosclerosis, atrial and ventricular arrhythmia, transient and ischemic attacks, stroke, inflammatory cardiovascular disorders, peripheral and cardiac vascular disorders, peripheral blood flow disturbances, arterial occlusive diseases such as intermittent claudication, asymptomatic left-ventricular dysfunction, myocarditis, hypertrophic alterations of the heart, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and coronary angioplasties (PTCA), heart transplants and bypass operations.

The compounds of the invention can additionally be employed for the prophylaxis and/or treatment of erectile dysfunction.

The compounds of the invention are further suitable for use as potassium-sparing diuretic and for electrolyte disturbances such as, for example, hypercalcemia, hypernatremia or hypokalemia, including genetically related forms such as Gitelman's or Barrter's syndrome.

The compounds of the invention are likewise suitable for the treatment of renal disorders such as acute and chronic renal failure, hypertensive kidney disease, arteriosclerotic nephritis (chronic and interstitial), nephrosclerosis, chronic renal failure and cystic renal disorders, for the prevention of kidney damage which may be caused for example by immunosuppressants such as cyclosporin A in association with organ transplants, and for renal cancer.

The compounds of the invention can additionally be employed for the prophylaxis and/or treatment of diabetes mellitus and diabetic sequelae such as, for example, neuropathy, nephropathy and cardiomyopathy.

The compounds of the invention can additionally be employed for the prophylaxis and/or treatment of eye disorders, especially forms based on angiogenesis and neovascularization, such as, for example, neonatal retinopathy, diabetic retinopathy, and age-related macular degeneration and glaucoma.

The compounds of the invention can further be used for the prophylaxis and/or treatment of microalbuminuria, for example caused by diabetes mellitus or high blood pressure, and of proteinuria.

The compounds of the invention are also suitable for the prophylaxis and/or treatment of disorders associated either with an increase in the plasma glucocorticoid concentration or with a local increase in the concentration of glucocorticoids in tissue (e.g. of the heart). Examples which may be mentioned are: adrenal dysfunctions leading to overproduction of glucocorticoids (Cushing's syndrome), adrenocortical tumors with resulting overproduction of glucocorticoids, and pituitary tumors which autonomously produce ACTH (adrenocorticotropic hormone) and thus lead to adrenal hyperplasias with resulting Cushing's disease.

The compounds of the invention can additionally be employed for the prophylaxis and/or treatment of obesity, of metabolic syndrome and of obstructive sleep apnea.

The compounds of the invention can further be used for the prophylaxis and/or treatment of inflammatory disorders caused for example by viruses, spirochetes, fungi, bacteria or mycobacteria, and of inflammatory disorders of unknown etiology, such as polyarthritis, lupus erythematosus, peri- or polyarteritis, dermatomyositis, scleroderma and sarcoidosis.

The compounds of the invention can further be employed for the treatment of central nervous disorders such as depressions, anxiety states and chronic pain, especially migraine, and for neurodegenerative disorders such as Alzheimer's disease and Parkinson's syndrome.

The compounds of the invention are also suitable for the prophylaxis and/or treatment of vascular damage, e.g. following procedures such as percutaneous transluminal coronary angioplasty (PTCA), implantations of stents, coronary angioscopy, reocclusion or restenosis following bypass operations, and for endothelial dysfunction, for Raynaud's disease, for thromboangitis obliterans (Buerger's syndrome) and for tinnitus syndrome.

The compounds of the invention are also suitable for the prophylaxis and/or treatment of gynaecological disorders such as endometriosis, leiomyomas of the uterus, dysfunctional bleeding and dysmenorrhoea.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The present invention further relates to the compounds of the invention for use in a method for the treatment and/or prophylaxis of aldosteronism, high blood pressure, acute and chronic heart failure, the sequence of the myocardial infarction, cirrhosis of the liver, renal failure and stroke.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients for combinations are by way of example and preferably:

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

agents having an antithrombotic effect, for example and preferably from the group of platelet aggregation inhibitors, of anticoagulants or of profibrinolytic substances;

active ingredients which alter lipid metabolism, for example and preferably from the group of thyroid receptor agonists, cholesterol synthesis inhibitors such as by way of example and preferably HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;

organic nitrates and NO donors such as, for example, sodium nitroprusside, nitroglycerin, isosorbide mononitrate, isosorbide dinitrate, molsidomine or SIN-1, and inhaled NO;

compounds having a positive inotropic effect, such as, for example, cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as aminone and milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

calcium sensitizers such as by way of example and preferably levosimendan;

NO- and heme-independent activators of guanylate cyclase, such as in particular cinaciguat and the compounds described in WO 01/19355, WO 01/19776, WO 01/19778, WO 01/19780, WO 02/070462 and WO 02/070510;

NO-independent but heme-dependent stimulators of guanylate cyclase such as in particular riociguat and the compounds described in WO 00/06568, WO 00/06569, WO 02/42301 and WO 03/095451;

modulators of adenosine receptors, especially adenosine A1 antagonists such as KW-3902, SLV-320 or BG-9928 (Adentri);

Vasopressin receptor antagonists such as, for example, conivaptan (Vaprisol), tolvaptan, satavaptan, lixivaptan, relcovaptan, RWJ-339489 or RWJ-351647.

inhibitors of human neutrophil elastase (HNE), such as, for example, sivelestat or DX-890 (reltran);

compounds which inhibit the signal transduction cascade, such as, for example, tyrosine kinase inhibitors, in particular sorafenib, imatinib, gefitinib and erlotinib; and/or compounds which influence the energy metabolism of the heart, such as by way of example and preferably etomoxir, dichloroacetate, ranolazine or trimetazidine.

In a preferred embodiment of the invention, the compounds of the invention are administered in combination with a diuretic such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, Rho kinase inhibitors, and diuretics.

In a preferred embodiment of the invention, the compounds of the invention are administered in combination with a calcium antagonist such as by way of example and preferably nifedipine, amlodipine, verapamil or diltiazem.

In a preferred embodiment of the invention, the compounds of the invention are administered in combination with an angiotensin AII antagonist such as by way of example and preferably losartan, candesartan, valsartan, telmisartan or embusartan.

In a preferred embodiment of the invention, the compounds of the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds of the invention are administered in combination with an endothelin antagonist such as by way of example and preferably bosentan, darusentan, ambrisentan or sitaxsentan.

In a preferred embodiment of the invention, the compounds of the invention are administered in combination with a renin inhibitor such as by way of example and preferably aliskiren, SPP-600, SPP-635, SPP-676, SPP-800 or SPP-1148.

In a preferred embodiment of the invention, the compounds of the invention are administered in combination with an alpha-1 receptor blocker such as by way of example and preferably prazosin.

In a preferred embodiment of the invention, the compounds of the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with a Rho kinase inhibitor such as by way of example and preferably fasudil, Y-27632, SLx-2119, BF-66851, BF-66852, BF-66853, KI-23095 or BA-1049.

Agents having an antithrombotic effect (antithrombotics) preferably mean compounds from the group of platelet aggregation inhibitors, of anticoagulants or of profibrinolytic substances.

In a preferred embodiment of the invention, the compounds of the invention are administered in combination with a platelet aggregation inhibitor such as by way of example and preferably aspirin, clopidogrel, ticlopidine or dipyridamole.

In a preferred embodiment of the invention, the compounds of the invention are administered in combination with a thrombin inhibitor such as by way of example and preferably ximelagatran, melagatran, bivalirudin or clexane.

In a preferred embodiment of the invention, the compounds of the invention are administered in combination with a GPIIb/IIIa antagonist such as by way of example and preferably tirofiban or abciximab.

In a preferred embodiment of the invention, the compounds of the invention are administered in combination with a factor Xa inhibitor such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or a low molecular weight (LMW) heparin derivative.

In a preferred embodiment of the invention, the compounds of the invention are administered in combination with a vitamin K antagonist such as by way of example and preferably coumarin.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds of the invention are administered in combination with a CETP inhibitor such as by way of example and preferably dalcetrapib, BAY 60-5521, anacetrapid or CETP vaccine (CETi-1).

In a preferred embodiment of the invention, the compounds of the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins such as by way of example and preferably lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor such as by way of example and preferably BMS-188494 or TAK-475.

In a preferred embodiment of the invention, the compounds of the invention are administered in combination with an ACAT inhibitor such as by way of example and preferably avasimibe, melinamide, pactimibe, eflucimibe or SMP-797.

In a preferred embodiment of the invention, the compounds of the invention are administered in combination with an MTP inhibitor such as by way of example and preferably implitapide, BMS-201038, R-103757 or JTT-130.

In a preferred embodiment of the invention, the compounds of the invention are administered in combination with a PPAR-gamma agonist such as by way of example and preferably pioglitazone or rosiglitazone.

In a preferred embodiment of the invention, the compounds of the invention are administered in combination with a PPAR-delta agonist such as by way of example and preferably GW-501516 or BAY 68-5042.

In a preferred embodiment of the invention, the compounds of the invention are administered in combination with a cholesterol absorption inhibitor such as by way of example and preferably ezetimibe, tiqueside or pamaqueside.

In a preferred embodiment of the invention, the compounds of the invention are administered in combination with a lipase inhibitor such as by way of example and preferably orlistat.

In a preferred embodiment of the invention, the compounds of the invention are administered in combination with a polymeric bile acid adsorbent such as by way of example and preferably cholestyramine, colestipol, colesolvam, Cholesta-Gel or colestimide.

In a preferred embodiment of the invention, the compounds of the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds of the invention are administered in combination with a lipoprotein(a) antagonist such as by way of example and preferably gemcabene calcium (CI-1027) or nicotinic acid.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated or coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

Abbreviations and Acronyms

Ac Acetyl
aq. Aqueous, aqueous solution
Bn Benzyl
Bu Butyl
cat. Catalytic
CI Chemical ionization (in MS)
conc. Concentrated
DAST Diethylaminosulfur trifluoride
dd Doublet of doublets (in NMR)
ddd Doublet of doublets of doublets (in NMR)
DMAP 4-N,N-Dimethylaminopyridine
DMF Dimethylformamide
DMSO Dimethyl sulfoxide
EI Electron impact ionization (in MS)
eq. equivalent(s)
ESI Electrospray ionization (in MS)
Et Ethyl
EtOAc Ethyl acetate
h Hour(s)
HPLC High pressure, high performance liquid chromatography
LC-MS Coupled liquid chromatography-mass spectrometry
Me Methyl min Minute(s)
Ms Methanesulfonyl (mesyl)
MS Mass spectrometry
NMR Nuclear magnetic resonance spectrometry
Ph Phenyl
RT Room temperature
$R_t$ Retention time (in HPLC)
SFC Superfluid chromatography
THF Tetrahydrofuran
UV Ultraviolet spectrometry
LC-MS and HPLC Methods:
Method 1 (HPLC):
Instrument: HP 1100 with DAD detection; column: Kromasil 100 RP-18, 60 mm×2.1 mm, 3.5 μm; eluent A: 5 ml $HClO_4$ (70%)/l water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.
Method 2 (HPLC):
Instrument: HP 1100 with DAD detection; column: Kromasil 100 RP-18, 60 mm×2.1 mm, 3.5 μm; eluent A: 5 ml $HClO_4$ (70%)/l water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.
Method 3 (LC-MS):
MS instrument type: Micromass ZQ; HPLC instrument type: Waters Alliance 2795; column: Phenomenex Synergi 2μ MAX-RP 100A Mercury 20 mm×4 mm; eluent A: 1 l water+0.5 ml 50% formic acid, eluent B: 1 l acetonitrile+0.5 ml 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
Method 4 (LC-MS):
Instrument: Micromass QuattroPremier with Waters HPLC Acquity; column: Thermo Hypersil GOLD 1.9μ 50 mm×1 mm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; flow rate: 0.33 ml/min; oven: 50° C.; UV detection: 210 nm.
Method 5 (LC-MS):
MS instrument type: Micromass ZQ; HPLC instrument type: HP 1100 Series; UV DAD; column: Phenomenex Gemini 3μ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 6 (LC-MS):
MS instrument type: Waters (Micromass) Quattro Micro; HPLC instrument type: Agilent 1100 Series; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A→4.01 min 100% A (Flow 2.5 ml)→5.0 min 100% A; flow rate: 2 ml/min; oven: 50° C.; UV detection: 210 nm.
Method 7 (GC-MS):
Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (hold for 3 min).
Method 8 (LC-MS):
MS instrument type: Waters ZQ; HPLC instrument type: Agilent 1100 Series; UV DAD; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A→4.1 min 100% flow rate: 2.5 ml/min, oven: 55° C.; flow rate: 2 ml/ml; UV detection: 210 nm.
Method 9 (LC-MS):
Instrument: Waters ACQUITY SQD UPLC System; column: Waters Acquity HPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A oven: 50° C.; flow rate: 0.40 ml/min; UV detection: 210-400 nm.

Starting Compounds and Intermediates

Example 1A 2-(Bromomethyl)-4-fluoro-1-nitrobenzene

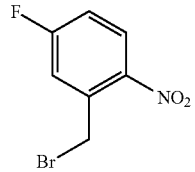

574 g (3.70 mol) of 5-fluoro-2-nitrotoluene and 659 g (3.70 mol) of N-bromosuccinimide were introduced into 3.7 l of chloroform, 30.0 g (183 mmol) of 2,2'-azobis-2-methylpropanenitrile were added, and the mixture was heated under reflux with irradiation by a UV lamp for 18 h. Cooling was followed by filtration with suction, and the filtrate was concentrated, the residue was taken up in diethyl ether and filtered with suction, and the filtrate was concentrated. The residue was dissolved in dichloromethane and petroleum ether and purified by flash chromatography (mobile phase: petroleum ether/ethyl acetate gradient) to result in 92.0 g (10% of theory) of the title compound.

$^1$H-NMR (400 MHz, $CDCl_3$): δ=4.83 (s, 2H), 7.14-7.21 (m, 1H), 7.32 (dd, 1H), 8.14 (dd, 1H).

Example 2A

1-Fluoro-2-[(methylsulfanyl)methyl]-3-nitrobenzene

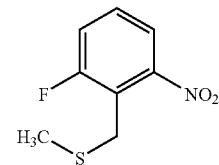

16.36 g (69.9 mmol) of 2-fluoro-6-nitrobenzyl bromide were introduced into 410 ml of THF, 5.88 g (83.9 mmol) of sodium methanethiolate were added in portions, and the mixture was stirred at RT for 24 h. The solid was filtered off and the filtrate was freed of solvent in a rotary evaporator. The residue was purified by flash chromatography (mobile phase: cyclohexane/ethyl acetate 10/1) to result in 11.43 g (81% of theory) of the title compound.

$^1$H-NMR (400 MHz, DMSO-$d_6$): δ=2.02 (d, 3H), 3.40 (d, 2H), 7.56-7.72 (m, 2H), 7.89 (d, 1H). GC-MS (Method 7): $R_t$=5.14 min; MS (EIpos): m/z=201 [M]$^+$.

Example 3A

1-[(Ethylsulfanyl)methyl]-2-nitrobenzene

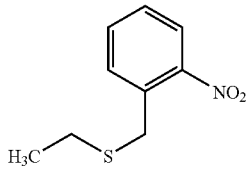

10.0 g (46.3 mmol) of 2-nitrobenzyl bromide were introduced into 100 ml of DMF at 0° C., 3.89 g (46.3 mmol) of sodium ethanethiolate were added in portions, and the mixture was stirred at RT for 4 h. It was diluted with water and extracted with ethyl acetate, and the organic phase was dried over magnesium sulfate, filtered and concentrated. The residue was purified by flash chromatography (mobile phase: cyclohexane/ethyl acetate 9/1) to result in 7.40 g (81% of theory) of the title compound.

$^1$H-NMR (400 MHz, DMSO-$d_6$): δ=1.12 (t, 3H), 2.39 (q, 2H), 4.05 (s, 2H), 7.50-7.56 (m, 1H), 7.57-7.61 (m, 1H), 7.68 (dt, 1H), 7.99 (dd, 1H).

Example 4A

4-Fluoro-2-[(methylsulfanyl)methyl]-1-nitrobenzene

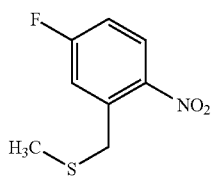

10.0 g (42.7 mmol) of the compound from Example 1A were introduced into 100 ml of tetrahydrofuran at RT, 3.29 g (47.0 mmol) of sodium methanethiolate were added, and the mixture was stirred at RT for 4 h. It was filtered with suction through kieselguhr and washed with tetrahydrofuran, and the filtrate was concentrated to result in 9.00 g (100% of theory) of the title compound which were reacted without further purification.

$^1$H-NMR (400 MHz, DMSO-$d_6$): δ=1.97 (s, 3H), 4.02 (s, 2H), 7.40 (ddd, 1H), 7.51 (dd, 1H), 8.15 (dd, 1H).

Example 5A 1-tert-Butoxycarbonyl-7-methyl-1H-indole

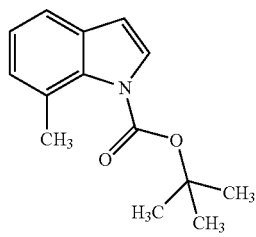

22.8 g (174 mmol) of 7-methyl-1H-indole were introduced into 800 ml of absolute tetrahydrofuran under argon at 0° C., 7.30 g (183 mmol) of a 60% strength suspension of sodium hydride in mineral oil were added, and the mixture was stirred at RT for 15 min. 39.8 g (183 mmol) of di-tert-butyl dicarbonate were added, and the mixture was stirred at RT for 1 h. Water was then added and concentrated. The residue was taken up in water and extracted with dichloromethane. The organic phase was dried over magnesium sulfate, filtered and concentrated. The residue was purified by flash chromatography (mobile phase: cyclohexane/ethyl acetate gradient) to result in 27.0 g (67% of theory) of the title compound.

$^1$H-NMR (400 MHz, DMSO-$d_6$): δ=2.53 (s, 3H), 1.60 (s, 9H), 6.66 (d, 1H), 7.09 (d, 1H), 7.15 (t, 1H), 7.44 (d, 1H), 7.63 (d, 1H).

Example 6A 7-(Bromomethyl)-1-tert-butoxycarbonyl-1H-indole

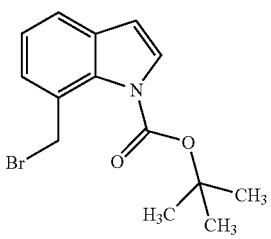

200 mg (865 µmol) of the compound from Example 5A were introduced into 10 ml of tetrachloromethane, 169 mg (951 µmol) of N-bromosuccinimide were added, and the mixture was heated under reflux while irradiating with a sun lamp for 4 h. The residue after concentration was purified by flash chromatography (mobile phase: cyclohexane/ethyl acetate gradient) to result in 168 mg (63% of theory) of the title compound.

$^1$H-NMR (400 MHz, DMSO-$d_6$): δ=1.64 (s, 9H), 5.28 (s, 2H), 6.76 (d, 1H), 7.23 (t, 1H), 7.40 (d, 1H), 7.66 (d, 1H), 7.73 (d, 1H).

Example 7A 1-tert-Butoxycarbonyl-7-[(methylsulfanyl)methyl]-1H-indole

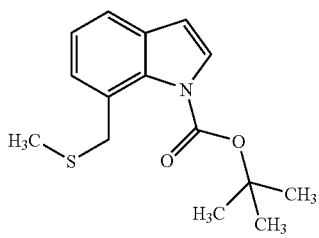

160 mg (516 μmmol) of the compound from Example 6A and 36.2 mg (516 μmol) of sodium methanethiolate were stirred in 5 ml of dimethylformamide at RT for three days. Water was then added, and the mixture was extracted with ethyl acetate. The organic phase was dried over magnesium sulfate, filtered and concentrated. The residue was purified by flash chromatography (mobile phase: cyclohexane/ethyl acetate gradient) to result in 64 mg (45% of theory) of the title compound.

$^1$H-NMR (400 MHz, DMSO-$d_6$): δ=1.61 (s, 9H), 1.68 (s, 3H), 4.21 (s, 2H), 6.70 (d, 1H), 7.15-7.18 (m, 2H), 7.53-7.58 (m, 1H), 7.66 (d, 1H).

MS (EIpos): m/z=277 [M]$^+$.

Example 8A

7-[(Methylsulfanyl)methyl]-1H-indole

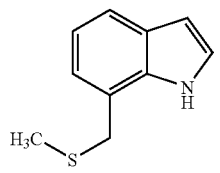

1.16 g (4.18 mmol) of the compound from Example 7A were introduced into 23 ml of methanol, 26 ml (113 mmol) of a 25% strength methanolic sodium methanolate solution were added, and the mixture was stirred at RT overnight. Then ice-water was added, and the mixture was extracted with dichloromethane. The organic phase was dried over magnesium sulfate, filtered and concentrated. The residue was purified by flash chromatography (mobile phase: cyclohexane/ethyl acetate gradient) to result in 549 mg (74% of theory) of the title compound.

$^1$H-NMR (400 MHz, DMSO-$d_6$): δ=1.95 (s, 3H), 3.96 (s, 2H), 6.44 (dd, 1H), 6.91-6.98 (m, 2H), 7.34 (t, 1H), 7.44 (d, 1H), 11.1 (s, 1H).

LC-MS (Method 4): $R_t$=1.13 min; MS (ESIpos): m/z=178 [M+H]$^+$.

Example 9A

6-Fluoro-7-[(methylsulfanyl)methyl]-1H-indole

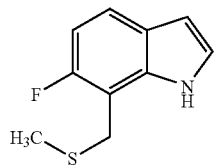

A solution of 11.42 g (56.7 mmol) of the compound from Example 2A in 127 ml of tetrahydrofuran was slowly added dropwise to 284 ml (283.7 mmol) of a 0.7N solution of vinylmagnesium bromide in tetrahydrofuran under argon at −78° C., and the solution was then stirred at −78° C. for 2 h. The reaction mixture was added to an ice-cold, saturated aqueous ammonium chloride solution, some ethyl acetate was added, the phases were separated, and the aqueous phase was extracted three times with ethyl acetate. Washing of the combined organic phases with saturated aqueous sodium chloride solution was followed by drying over sodium sulfate, filtration and removal of the solvents in vacuo. Purification of the residue by flash chromatography (mobile phase: cyclohexane/toluene/dichloromethane 10/10/1) afforded 6.31 g (57% of theory) of the title compound.

$^1$H-NMR (400 MHz, DMSO-$d_6$): δ=1.99 (s, 3H), 3.99 (s, 2H), 6.43-6.46 (m, 1H), 6.85 (dd, 1H), 7.34-7.37 (m, 1H), 7.43 (dd, 1H), 11.26 (s, 1H).

HPLC (Method 2): $R_t$=2.03 min; MS (ESIpos): m/z=194 [M−H]$^+$.

Example 10A

7-[(Ethylsulfanyl)methyl]-1H-indole

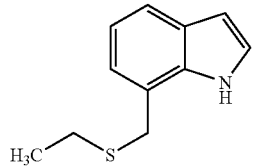

A solution of 7.40 g (37.5 mmol) of the compound from Example 3A in 195 ml of tetrahydrofuran was added dropwise to 134 ml (93.8 mmol) of a 0.7N solution of vinylmagnesium bromide in tetrahydrofuran under argon at −78° C., and the mixture was stirred at −78° C. for 2 h. The reaction mixture was then slowly added to an ice-cold, saturated aqueous ammonium chloride solution and extracted three times with ethyl acetate. The combined organic phases were washed with saturated aqueous sodium chloride solution, dried over sodium sulfate, filtered and concentrated. The residue was purified by flash chromatography (mobile phase: cyclohexane/ethyl acetate 9/1) to result in 4.98 g (69% of theory) of the title compound.

$^1$H-NMR (400 MHz, DMSO-$d_6$): δ=1.16 (t, 3H), 2.40 (q, 2H), 4.00 (s, 2H), 6.44 (dd, 1H), 6.93 (t, 1H), 6.97 (d, 1H), 7.33 (t, 1H), 7.44 (d, 1H), 11.1 (s, 1H).

LC-MS (Method 3): $R_t$=2.03 min; MS (ESIpos): m/z=192 [M+H]$^+$.

Example 11A

5-Fluoro-7-[(methylsulfanyl)methyl]-1H-indole

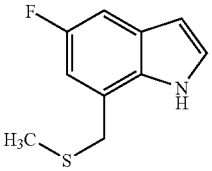

180 ml (180 mmol) of a 1N solution of vinylmagnesium bromide in tetrahydrofuran were added dropwise to a solution of 9.00 g (44.7 mmol) of the compound from Example 4A in 100 ml of tetrahydrofuran under argon at −40° C., and the mixture was stirred at −40° C. for 3 h. The reaction mixture was then added to saturated aqueous ammonium chloride solution and extracted with tert-butyl methyl ether. The combined organic phases were washed with saturated aqueous sodium chloride solution, dried over sodium sulfate, filtered and concentrated. The residue was purified by flash chromatography (mobile phase: petroleum ether/ethyl acetate 9/1) to result in 5.00 g (57% of theory) of the title compound.

$^1$H-NMR (400 MHz, DMSO-$d_6$): δ=1.96 (s, 3H), 3.96 (s, 2H), 6.43 (dd, 1H), 6.86 (dd, 1H), 7.20 (dd, 1H), 7.41 (t, 1H), 11.2 (s, 1H).

LC-MS (Method 6): $R_t$=2.18 min; MS (ESIpos): m/z=196 [M+H]$^+$.

Example 12A 2,2-Dimethyl-5-({7-[(methylsulfanyl)methyl]-1H-indol-3-yl}[4-(trifluoromethyl)phenyl]methyl)-1,3-dioxane-4,6-dione

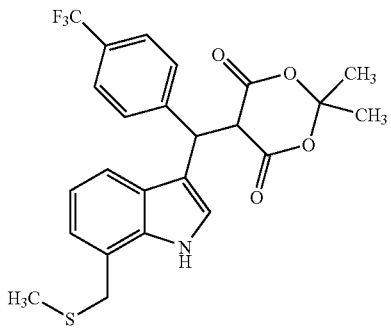

268 mg (1.54 mmol) of 4-(trifluoromethyl)benzaldehyde, 222 mg (1.54 mmol) of Meldrum's acid and 8.4 mg (0.07 mmol) of D,L-proline were added to a solution of 260 mg (1.47 mmol) of the compound from Example 8A in 12 ml of acetonitrile. The reaction mixture was stirred at RT overnight. It was concentrated, and the crude product was purified by preparative HPLC (RP18 column; mobile phase: acetonitrile/water gradient with addition of 0.1% formic acid) to result in 504 mg (72% of theory) of the title compound.

$^1$H-NMR (400 MHz, DMSO-$d_6$): δ=1.61 (s, 3H), 1.85 (s, 3H), 1.97 (s, 3H), 3.90-4.01 (m, 2H), 5.38 (d, 1H), 5.47 (d, 1H), 6.87 (t, 1H), 6.97 (d, 1H), 7.13 (d, 1H), 7.19 (d, 1H), 7.51-7.56 (m, 2H), 7.59-7.64 (m, 2H), 11.1 (s, 1H).

LC-MS (Method 5): Rt=2.91 min; MS (ESIpos): m/z=478 [M+H]$^+$.

Example 13A

5-[(4-Chlorophenyl){7-[(methylsulfanyl)methyl]-1H-indol-3-yl}methyl]-2,2-dimethyl-1,3-dioxane-4,6-dione

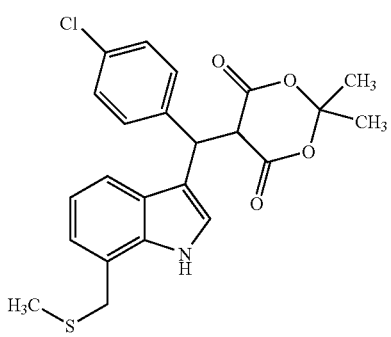

350 mg (2.49 mmol) of 4-chlorobenzaldehyde, 359 mg (2.49 mmol) of Meldrum's acid and 13.6 mg (0.12 mmol) of D,L-proline were added to a solution of 420 mg (2.40 mmol) of the compound from Example 8A in 20 ml of acetonitrile. The reaction mixture was stirred at RT overnight. It was concentrated, and the crude product was purified by preparative HPLC (RP18 column; mobile phase: acetonitrile/water gradient with addition of 0.1% formic acid) to result in 650 mg (62% of theory) of the title compound.

$^1$H-NMR (400 MHz, DMSO-$d_6$): δ=1.59 (s, 3H), 1.84 (s, 3H), 1.96 (s, 3H), 3.93-3.97 (m, 2H), 5.29 (d, 1H), 5.38 (d, 1H), 6.86 (t, 1H), 6.96 (d, 1H), 7.10 (d, 1H), 7.19 (d, 1H), 7.27-7.35 (m, 4H), 11.1 (s, 1H).

LC-MS (Method 4): $R_t$=1.42 min; MS (ESIneg): m/z=443 [M−H]$^-$.

Example 14A

5-[(4-Chlorophenyl){7-[(ethylsulfanyl)methyl]-1H-indol-3-yl}methyl]-2,2-dimethyl-1,3-dioxane-4,6-dione

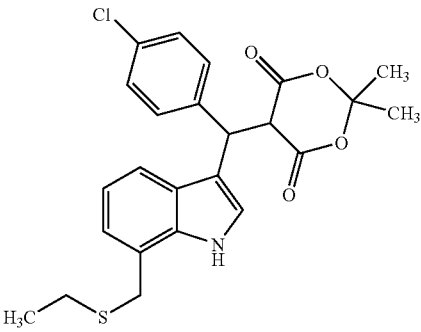

1.00 g (7.14 mmol) of 4-chlorobenzaldehyde, 1.03 g (7.14 mmol) of Meldrum's acid and 39.1 mg (0.34 mmol) of D,L-proline were added to a solution of 1.30 g (6.80 mmol) of the compound from Example 10A in 57 ml of acetonitrile. The reaction mixture was stirred at RT overnight. It was concentrated, and the crude product was stirred in diethyl ether and filtered, and the precipitate was dried under high vacuum to result in 1.38 g (44% of theory) of the title compound.

LC-MS (Method 5): $R_t$=2.90 min; MS (ESIpos): m/z=458 [M+H]$^+$.

Example 15A

5-[(4-Chloro-2-fluorophenyl){7-[(methylsulfanyl)methyl]-1H-indol-3-yl}methyl]-2,2-dimethyl-1,3-dioxane-4,6-dione

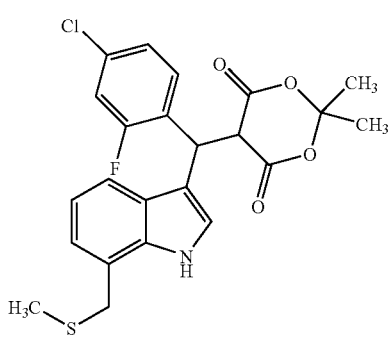

1.48 g (9.31 mmol) of 4-chloro-2-fluorobenzaldehyde, 1.34 g (9.31 mmol) of Meldrum's acid and 48.7 mg (0.42 mmol) of D,L-proline were added to a solution of 1.50 g (8.46 mmol) of the compound from Example 8A in 70 ml of acetonitrile. The reaction mixture was stirred at RT overnight. It was concentrated, and the residue was taken up in ethyl acetate, washed with saturated aqueous sodium bicarbonate solution, water and saturated aqueous sodium chloride solution, dried over magnesium sulfate, filtered and concentrated. 3.60 g of the title compound were obtained and were reacted without further purification.

LC-MS (Method 3): $R_t$=2.43 min; MS (ESIneg): m/z=460 [M−H]⁻.

Example 16A

5-[(4-Chloro-2-fluorophenyl){5-fluoro-7-[(methylsulfanyl)methyl]-1H-indol-3-yl}methyl]-2,2-dimethyl-1,3-dioxane-4,6-dione

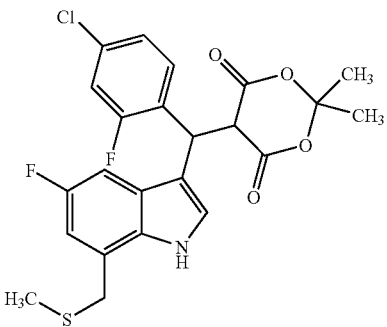

0.70 g (4.41 mmol) of 4-chloro-2-fluorobenzaldehyde, 0.64 g (4.41 mmol) of Meldrum's acid and 24 mg (0.21 mmol) of D,L-proline were added to a solution of 1.00 g of the compound of Example 11A with a purity of 82% (4.20 mmol) in 35 ml of acetonitrile. The reaction mixture was stirred at RT overnight. It was concentrated, and the residue was taken up in ethyl acetate, washed with 1N hydrochloric acid, saturated aqueous sodium bicarbonate solution and water, dried over magnesium sulfate, filtered and concentrated. 2.20 g of the title compound were obtained with a purity of 71% (78% of theory) and were reacted without further purification.

LC-MS (Method 5): $R_t$=2.94 min; MS (ESIpos): m/z=480 [M+H]⁺.

Example 17A

5-[(2,4-Dichlorophenyl){7-[(methylsulfanyl)methyl]-1H-indol-3-yl}methyl]-2,2-dimethyl-1,3-dioxane-4,6-dione

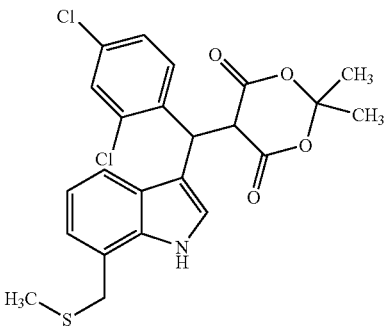

1.63 g (9.31 mmol) of 2,4-dichlorobenzaldehyde, 1.34 g (9.31 mmol) of Meldrum's acid and 48.7 mg (0.42 mmol) of D,L-proline were added to a solution of 1.50 g (8.46 mmol) of the compound from Example 8A in 70 ml of acetonitrile. The reaction mixture was stirred at RT overnight. It was concentrated, and the residue was taken up in ethyl acetate, washed with saturated aqueous sodium bicarbonate solution, water and saturated aqueous sodium chloride solution, dried over magnesium sulfate, filtered and concentrated. 3.99 g (98% of theory) of the title compound were obtained and were reacted without further purification.

LC-MS (Method 3): $R_t$=2.54 min; MS (ESIpos): m/z=478 [M+H]⁺.

Example 18A

5-[(2,4-Dichlorophenyl){5-fluoro-7-[(methylsulfanyl)methyl]-1H-indol-3-yl}methyl]-2,2-dimethyl-1,3-dioxane-4,6-dione

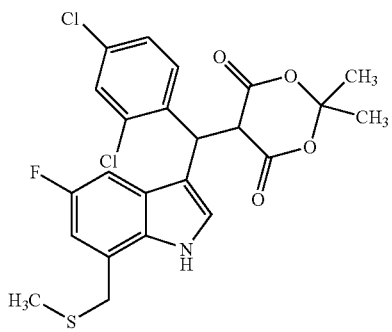

0.81 g (4.60 mmol) of 2,4-dichlorobenzaldehyde, 0.66 g (4.60 mmol) of Meldrum's acid and 25 mg (0.22 mmol) of D,L-proline were added to a solution of 0.95 g (4.38 mmol) of the compound from Example 11A in 36 ml of acetonitrile. The reaction mixture was stirred at RT overnight. It was concentrated to result in 3.10 g (97% of theory) of the title compound with a purity of 68% which were reacted without further purification.

LC-MS (Method 6): $R_t$=2.75 min; MS (ESIpos): m/z=496 [M+H]⁺.

Example 19A

5-[(4-Chlorophenyl){5-fluoro-7-[(methylsulfanyl)methyl]-1H-indol-3-yl}methyl]-2,2-dimethyl-1,3-dioxane-4,6-dione

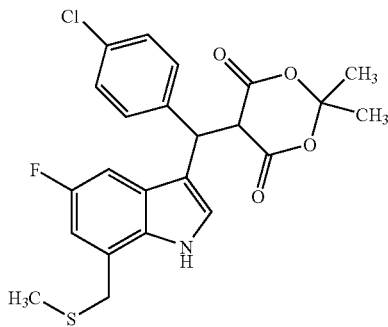

0.62 g (4.41 mmol) of 4-chlorobenzaldehyde, 0.64 g (4.41 mmol) of Meldrum's acid and 24 mg (0.21 mmol) of D,L-proline were added to a solution of 1.00 g (4.20 mmol) of the compound from Example 11A in 34 ml of acetonitrile. The reaction mixture was stirred at RT overnight. It was concentrated to result in 2.21 g (73% of theory) of the title compound with a purity of 64% which were reacted without further purification.

LC-MS (Method 5): $R_t$=2.87 min; MS (ESIpos): m/z=462 [M+H]$^+$.

Example 20A 2,2-Dimethyl-5-[{7-[(methylsulfanyl)methyl]-1H-indol-3-yl}(naphthalen-2-yl)methyl]-1,3-dioxane-4,6-dione

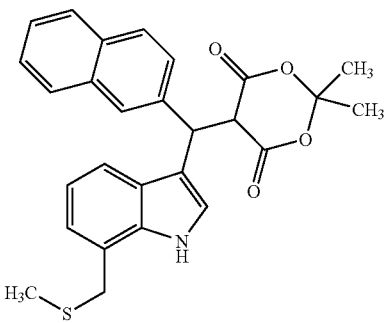

694 mg (4.44 mmol) of naphthalene-2-carbaldehyde, 640 mg (4.44 mmol) of Meldrum's acid and 24 mg (0.21 mmol) of D,L-proline were added to a solution of 750 mg (4.23 mmol) of the compound from Example 8A in 35 ml of acetonitrile. The reaction mixture was stirred at RT overnight. Then a further 35 ml of acetonitrile were added, and the mixture was stirred at RT for two days. It was concentrated, the residue was stirred in water, and the precipitate was filtered off with suction and dried in vacuo at 50° C. for 1 h. The crude product was stirred in acetonitrile, and the precipitate was filtered off with suction and dried under high vacuum to result in 882 mg (45% of theory) of the title compound which were reacted without further purification.

LC-MS (Method 5): $R_t$=2.80 min; MS (ESIpos): m/z=460 [M+H]$^+$.

Example 21A

5-[(4-Chlorophenyl){6-fluoro-7-[(methylsulfanyl)methyl]-1H-indol-3-yl}methyl]-2,2-dimethyl-1,3-dioxane-4,6-dione

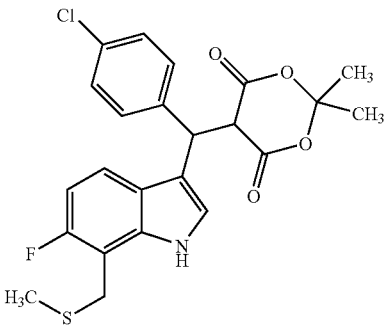

1.44 g (10.24 mmol) of 4-chlorobenzaldehyde, 1.48 g (10.24 mmol) of Meldrum's acid and 0.06 g (0.51 mmol) of D,L-proline were added to a solution of 2.00 g (10.24 mmol) of the compound from Example 9A in 15 ml of acetonitrile. The reaction mixture was stirred at RT overnight. The precipitated solid was filtered off with suction, washed with acetonitrile and dried under high vacuum. 3.32 g (67% of theory) of the title compound were obtained.

$^1$H-NMR (400 MHz, DMSO-d$_6$): δ=1.59 (s, 3H), 1.84 (s, 3H), 2.01 (s, 3H), 3.98 (s, 2H), 5.28-5.38 (m, 2H), 6.78 (dd, 1H), 7.07 (dd, 1H), 7.19-7.34 (m, 5H), 11.24 (s, 1H).

HPLC (Method 1): $R_t$=4.91 min; MS (ESIneg): m/z=460 [M–H]$^-$.

Example 22A 2,2-Dimethyl-5-({6-fluoro-7-[(methylsulfanyl)methyl]-1H-indol-3-yl}[4-(trifluoromethyl)phenyl]methyl)-1,3-dioxane-4,6-dione

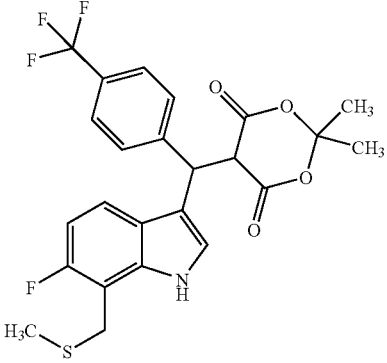

The title compound is prepared starting from 2.00 g (10.24 mmol) of the compound from Example 9A and 1.78 g (10.24 mmol) of 4-(trifluoromethyl)benzaldehyde in analogy to the synthesis of the compound from Example 21A. 3.83 g (75% of theory) of the title compound were obtained.

$^1$H-NMR (400 MHz, DMSO-d$_6$): δ=1.61 (s, 3H), 1.85 (s, 3H), 2.01 (s, 3H), 3.98 (s, 2H), 5.37-5.47 (m, 2H), 6.79 (dd, 1H), 7.12 (dd, 1H), 7.21 (d, 1H), 7.53 (d, 2H), 7.62 (d, 2H), 11.28 (s, 1H).

HPLC (Method 1): $R_t$=4.96 min; MS (ESIneg): m/z=494 [M–H]$^-$.

Example 23A

5-[(1-Benzothiophen-5-yl){7-[(methylsulfanyl)methyl]-1H-indol-3-yl}methyl]-2,2-dimethyl-1,3-dioxane-4,6-dione

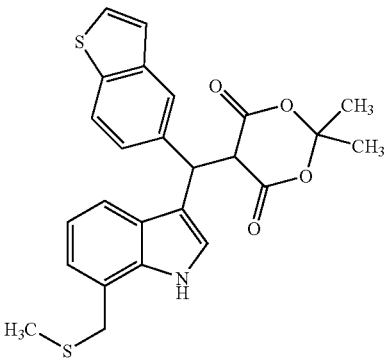

1.02 g (5.66 mmol) of 1-benzothiophene-5-carbaldehyde, 0.82 g (5.66 mmol) of Meldrum's acid and 0.03 g (0.28 mmol) of D,L-proline were added to a solution of 1.00 g (5.66 mmol) of the compound from Example 8A in 8 ml of acetonitrile. The reaction mixture was stirred at RT overnight and then the solvent was removed in vacuo. Purification of the residue by preparative HPLC (mobile phase: acetonitrile/water gradient) resulted in 1.73 g (71% purity, 47% of theory) of the title compound.

$^1$H-NMR (400 MHz, DMSO-$d_6$): δ=1.55 (s, 3H), 1.83 (s, 3H), 1.97 (s, 3H), 3.96 (dd, 2H), 5.31 (d, 1H), 5.53-5.56 (m, 1H), 6.82 (dd, 1H), 6.94 (dd, 1H), 7.09 (d, 1H), 7.27 (s, 1H), 7.37 (d, 2H), 7.69 (d, 1H), 7.77 (s, 1H), 7.85 (d, 1H), 11.08 (s, 1H).

HPLC (Method 1): $R_t$=4.84 min; MS (ESIneg): m/z=464 [M−H]$^-$.

Example 24A

5-[(2-Bromo-1,3-thiazol-5-yl){7-[(methylsulfanyl)methyl]-1H-indol-3-yl}methyl]-2,2-dimethyl-1,3-dioxane-4,6-dione

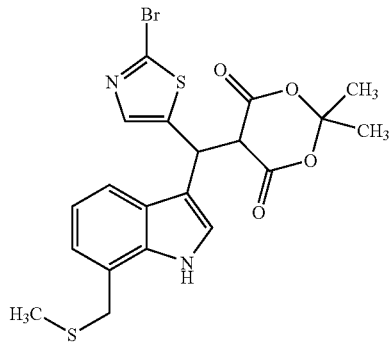

1.02 g (7.08 mmol) of Meldrum's acid, 0.04 g (0.34 mmol) of D,L-proline and 1.36 g (7.08 mmol) of 2-bromo-5-formylthiazole were successively added to a solution of 1.30 g (6.75 mmol) of the compound from Example 8A in 50 ml of acetonitrile. The reaction mixture was stirred at RT overnight and then the solvent was removed in vacuo. Purification of the residue by flash chromatography on silica gel (mobile phase: dichloromethane/methanol 95/5) resulted in 3.58 g (81% purity, 87% of theory) of the title compound.

LC-MS (Method 5): $R_t$=3.01 min; MS (ESIpos): m/z=495 [M+H]$^+$.

Example 25A

Ethyl 3-{7-[(methylsulfanyl)methyl]-1H-indol-3-yl}-3-[4-(trifluoromethyl)phenyl]propanoate

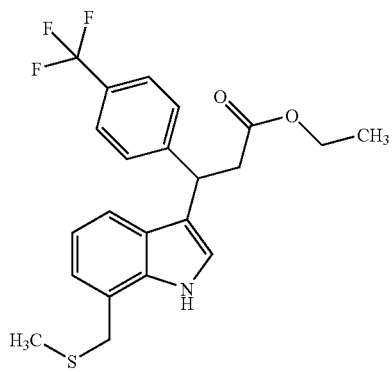

0.7 mg (0.01 mmol) of copper powder was added to 504 mg (1.06 mmol) of the compound from Example 12A in 8 ml of pyridine and 2 ml of ethanol. The reaction mixture was heated under reflux for 1 h. It was concentrated, and the crude product was purified by preparative HPLC (RP18 column; mobile phase: acetonitrile/water gradient with addition of 0.1% formic acid) to result in 241 mg (54% of theory) of the title compound.

$^1$H-NMR (400 MHz, DMSO-$d_6$): δ=1.04 (t, 3H), 1.93 (s, 3H), 3.13 (dd, 1H), 3.21 (dd, 1H), 3.90 (s, 2H), 3.96 (q, 2H), 4.73 (t, 1H), 6.85 (t, 1H), 6.92 (d, 1H), 7.29 (d, 1H), 7.39 (d, 1H), 7.57-7.63 (m, 4H), 11.0 (s, 1H).

LC-MS (Method 5): $R_t$=2.93 min; MS (ESIpos): m/z=422 [M+H]$^+$.

Example 26A tert-Butyl 3-{3-ethoxy-3-oxo-1-[4-(trifluoromethyl)phenyl]propyl}-7-[(methylsulfanyl)methyl]-1H-indole-1-carboxylate

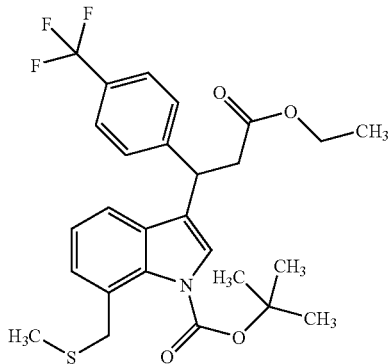

3.20 g (7.59 mmol) of the compound from Example 25A, 1.99 g (9.11 mmol) of di-tert-butyl dicarbonate and 0.09 g (0.76 mmol) of 4-N,N-dimethylaminopyridine were dissolved in 30 ml of tetrahydrofuran and stirred at 50° C. for 2 h. The reaction solution was mixed with water, the phases were separated, and the aqueous phase was extracted twice with dichloromethane. The combined organic phases were washed with saturated aqueous sodium bicarbonate solution and dried over sodium sulfate, the solid was filtered off, and the solvents were removed in vacuo. 3.91 g (96% of theory) of the title compound were obtained.

$^1$H-NMR (400 MHz, DMSO-$d_6$): δ=1.06 (t, 3H), 1.63 (s, 9H), 1.67 (s, 3H), 3.14-3.31 (m, 2H), 3.92-4.06 (m, 2H), 4.17 (dd, 2H), 4.73 (t, 1H), 7.05-7.16 (m, 2H), 7.39 (d, 1H), 7.61-7.68 (m, 4H), 7.75 (s, 1H).

LC-MS (Method 5): $R_t$=3.23 min; MS (ESIpos): m/z=522 [M+H]$^+$.

Example 27A tert-Butyl 3-{3-ethoxy-2-methyl-3-oxo-1-[4-(trifluoromethyl)phenyl]propyl}-7-[(methylsulfanyl)methyl]-1H-indole-1-carboxylate

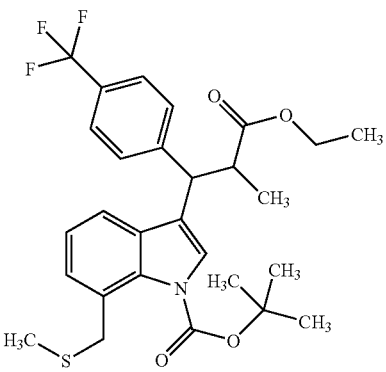

1.60 g (3.07 mmol) of the compound from Example 26A were dissolved in tetrahydrofuran at −78° C., and 3.2 ml (6.44 mmol) of a 2N solution of lithium diisopropylamide in tetrahydrofuran/n-heptane were slowly added dropwise. After 5 min, 0.40 ml (6.44 mmol) of iodomethane was added, and the mixture was stirred at −78° C. for 2 h and then warmed to RT over the course of a further 2 h. The reaction solution was mixed with water, the phases were separated, and the aqueous phase was extracted twice with ethyl acetate. The combined organic phases were dried over sodium sulfate, the solid was filtered off, and the solvents were removed in vacuo. The crude product was purified by preparative HPLC (mobile phase: acetonitrile-water gradient) to result in 1.20 g (73% of theory) of the title compound as mixture of diastereomers.

$^1$H-NMR (400 MHz, DMSO-$d_6$): δ=0.82-1.08 (m, 4H), 1.10-1.22 (m, 2H), 1.60-1.70 (m, 12H), 3.40-4.04 (m, 3H), 4.12-4.20 (m, 2H), 7.05-7.17 (m, 2H), 7.48-7.79 (m, 6H).

LC-MS (Method 5): $R_t$=3.26 min.

Example 28A

Ethyl 2-methyl-3-{7-[(methylsulfanyl)methyl]-1H-indol-3-yl}-3-[4-(trifluoromethyl)phenyl]propanoate

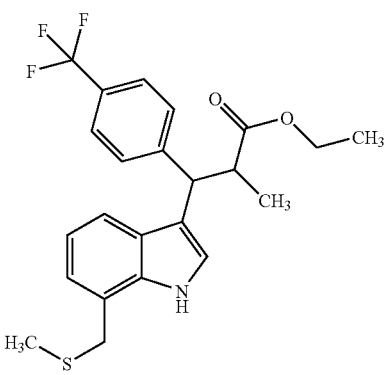

2.52 g (4.71 mmol) of the compound from Example 27A were dissolved in 70 ml of dichloromethane, and 14.5 ml (188.56 mmol) of trifluoroacetic acid were added. After stirring at RT for 3 h, the reaction solution was mixed with water, the phases were separated, and the aqueous phase was extracted twice with ethyl acetate. The combined organic phases were washed with saturated aqueous sodium bicarbonate solution and dried over sodium sulfate, the solid was filtered off and the solvents were removed in vacuo. Purification of the crude product by flash chromatography on silica gel (mobile phase: dichloromethane/methanol 95/5) and preparative HPLC (mobile phase: acetonitrile-water gradient) resulted in 1.01 g (48% of theory) of the title compound as mixture of diastereomers.

$^1$H-NMR (400 MHz, DMSO-$d_6$): δ=0.82-1.20 (m, 6H), 1.90-1.95 (m, 3H), 3.39-3.58 (m, 1H), 3.77-3.95 (m, 4H), 4.35-4.47 (m, 1H), 6.82-6.95 (m, 2H), 7.37-7.70 (m, 6H), 10.95-11.10 (m, 1H).

LC-MS (Method 6): $R_t$=2.74 min; MS (ESIpos): m/z=436 [M+H]$^+$.

Example 29A

Ethyl 3-(4-chlorophenyl)-3-{7-[(methylsulfanyl)methyl]-1H-indol-3-yl}propanoate

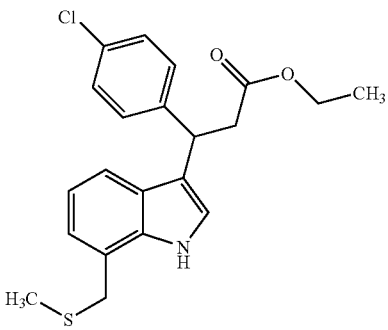

18 mg (0.28 mmol) of copper powder were added to 12.2 g (27.5 mmol) of the compound from Example 13A in 200 ml of pyridine and 55 ml of ethanol. The reaction mixture was heated under reflux for 4 h. It was concentrated, and the residue was taken up in dichloromethane, washed with water, 1N hydrochloric acid and saturated aqueous sodium chloride solution, dried over magnesium sulfate, filtered and concentrated. The residue was purified by flash chromatography on silica gel (mobile phase: toluene/ethyl acetate gradient). 6.68 g (56% of theory) of the target compound were obtained.

$^1$H-NMR (400 MHz, DMSO-$d_6$): δ=1.05 (t, 3H), 1.93 (s, 3H), 3.05 (dd, 1H), 3.16 (dd, 1H), 3.90 (s, 2H), 3.92-3.99 (m, 2H), 4.63 (t, 1H), 6.84 (t, 1H), 6.92 (d, 1H), 7.24-7.31 (m, 3H), 7.33-7.40 (m, 3H), 11.0 (s, 1H).

LC-MS (Method 4): $R_t$=1.50 min; MS (ESIpos): m/z=388 [M+H]$^+$.

Example 30A tert-Butyl 3-[1-(4-chlorophenyl)-3-ethoxy-3-oxopropyl]-7-[(methylsulfanyl)methyl]-1H-indole-1-carboxylate

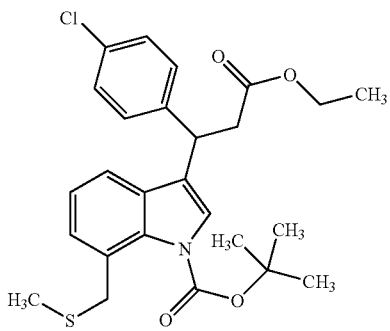

3.13 g (8.07 mmol) of the compound from Example 29A, 2.11 g (9.68 mmol) of di-tert-butyl dicarbonate and 0.10 g (0.81 mmol) of 4-N,N-dimethylaminopyridine were dissolved in 30 ml of tetrahydrofuran and stirred at 50° C. for 2 h. The reaction solution was mixed with water, the phases were separated, and the aqueous phase was extracted twice with dichloromethane. The combined organic phases were washed with saturated aqueous sodium bicarbonate solution and dried over sodium sulfate, the solid was filtered off and the solvents were removed in vacuo. The crude product was purified by preparative HPLC (mobile phase: acetonitrile-water gradient) to result in 4.10 g (91% purity, 95% of theory) of the title compound.

$^1$H-NMR (400 MHz, DMSO-$d_6$): δ=1.07 (t, 3H), 1.62 (s, 9H), 1.67 (s, 3H), 3.10 (dd, 1H), 3.20 (dd, 1H), 3.92-4.06 (m, 2H), 4.17 (dd, 2H), 4.62 (t, 1H), 7.05-7.15 (m, 2H), 7.29-7.46 (m, 5H), 7.70 (s, 1H).

LC-MS (Method 5): $R_t$=3.23 min; MS (ESIpos): m/z=488 [M+H]$^+$.

Example 31A tert-Butyl 3-[1-(4-chlorophenyl)-3-ethoxy-2-methyl-3-oxopropyl]-7-[(methylsulfanyl)methyl]-1H-indole-1-carboxylate

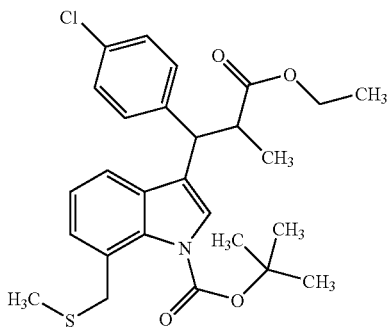

The title compound was prepared starting from 1.62 g (91% purity, 3.01 mmol) of the compound from Example 30A in analogy to the synthesis of the compound from Example 27A. 0.89 g (59% of theory) of the title compound was obtained as mixture of diastereomers.

$^1$H-NMR (400 MHz, DMSO-$d_6$): δ=0.89-1.19 (m, 6H), 1.59-1.69 (m, 12H), 3.33-3.62 (m, 1H), 3.81-4.37 (m, 5H), 7.06-7.16 (m, 2H), 7.27-7.35 (m, 2H), 7.43-7.60 (m, 2H), 7.71-7.90 (m, 1H).

LC-MS (Method 5): $R_t$=3.31 min.

Example 32A

Ethyl 3-(4-chlorophenyl)-2-methyl-3-{7-[(methylsulfanyl)methyl]-1H-indol-3-yl}propanoate

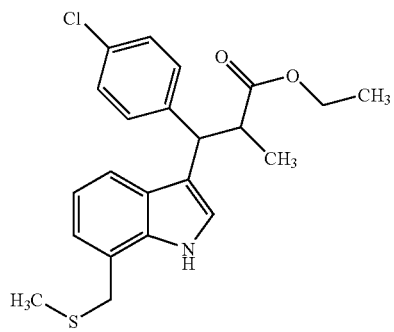

0.85 g (1.69 mmol) of the compound from Example 31A was dissolved in 10 ml of dichloromethane, and 2.61 ml (33.86 mmol) of trifluoroacetic acid were added. After stirring at RT for 2 h, the reaction solution was concentrated and the residue was purified twice by preparative HPLC (mobile phase: acetonitrile-water gradient). 0.42 g (61% of theory) of the title compound was obtained as mixture of diastereomers.

$^1$H-NMR (400 MHz, DMSO-$d_6$): δ=0.87-1.18 (m, 6H), 1.90-1.95 (m, 3H), 3.31-3.51 (m, 1H), 3.80-3.95 (m, 4H), 4.25-4.36 (m, 1H), 6.82-6.95 (m, 2H), 7.27-7.52 (m, 6H), 10.90-11.05 (m, 1H).

LC-MS (Method 6): $R_t$=2.77/2.82 min; MS (ESIneg): m/z=400 [M−H]$^-$.

Example 33A

Ethyl 3-(4-chlorophenyl)-3-{7-[(ethylsulfanyl)methyl]-1H-indol-3-yl}propanoate

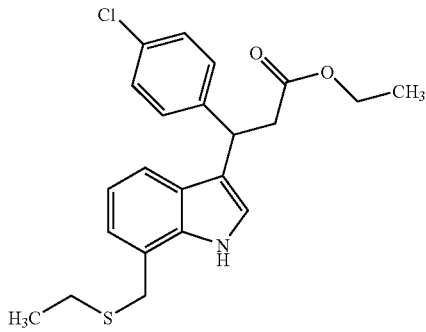

2 mg (0.03 mmol) of copper powder were added to 1.38 g (3.00 mmol) of the compound from Example 14A in 15 ml of pyridine and 5 ml of ethanol. The reaction mixture was heated under reflux for 1 h. It was concentrated, and the residue was taken up in ethyl acetate, washed with 1N hydrochloric acid, dried over magnesium sulfate, filtered through silica gel and concentrated. 1.13 g of the target compound with a purity of 84% (78% of theory) were obtained.

¹H-NMR (400 MHz, DMSO-d₆): δ=1.05 (t, 3H), 1.15 (t, 3H), 2.38 (q, 2H), 3.05 (dd, 1H), 3.16 (dd, 1H), 3.90-4.00 (m, 4H), 4.62 (t, 1H), 6.84 (t, 1H), 6.93 (d, 1H), 7.24-7.31 (m, 3H), 7.33-7.40 (m, 3H), 11.0 (s, 1H).

LC-MS (Method 3): $R_t$=2.63 min; MS (ESIpos): m/z=402 [M+H]⁺.

Example 34A

Ethyl 3-(4-chloro-2-fluorophenyl)-3-{7-[(methylsulfanyl)methyl]-1H-indol-3-yl}propanoate

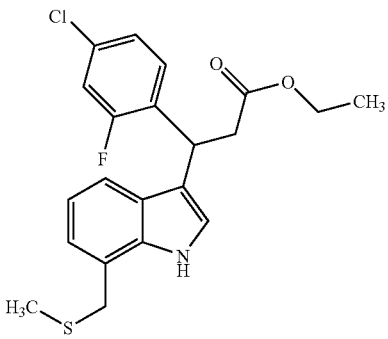

5.0 mg (0.08 mmol) of copper powder were added to 3.60 g (7.79 mmol) of the compound from Example 15A in 56 ml of pyridine and 14 ml of ethanol. The reaction mixture was heated under reflux for 1 h. It was concentrated, and the residue was taken up in ethyl acetate, washed with 1N hydrochloric acid, dried over magnesium sulfate, filtered through silica gel and concentrated. The crude product was purified by preparative HPLC (RP18 column; mobile phase: acetonitrile/water gradient with addition of 0.1% formic acid) to result in 2.23 g (70% of theory) of the title compound.

¹H-NMR (400 MHz, DMSO-d₆): δ=1.05 (t, 3H), 1.93 (s, 3H), 3.09-3.24 (m, 2H), 3.90 (s, 2H), 3.92-4.01 (m, 2H), 4.89 (t, 1H), 6.88 (t, 1H), 6.94 (d, 1H), 7.17 (dd, 1H), 7.26 (d, 1H), 7.32-7.38 (m, 2H), 7.41 (t, 1H), 11.0 (s, 1H).

LC-MS (Method 4): $R_t$=1.52 min; MS (ESIpos): m/z=406 [M+H]⁺.

The enantiomers were separated by preparative HPLC on a chiral phase [column with chiral selector poly(N-methacryloyl-L-leucine dicyclopropylmethylamide), 10 μm, 250 mm×30 mm; eluent: isohexane/ethyl acetate 82:18; flow rate: 45 ml/min; temperature: RT; UV detection: 260 nm]. The separated enantiomers were purified again by preparative HPLC on an achiral phase (RP18 column; mobile phase: acetonitrile/water gradient with addition of 0.1% formic acid):

Enantiomer 34A-1:
$R_t$=4.37 min [column with chiral selector poly(N-methacryloyl-L-leucine dicyclopropylmethylamide), 5 μm, 250 mm×4 mm; eluent: isohexane/ethyl acetate 4:1; flow rate: 1.5 ml/min; temperature: RT; UV detection: 260 nm];

Enantiomer 34A-2:
$R_t$=5.62 min [column with chiral selector poly(N-methacryloyl-L-leucine dicyclopropylmethylamide), 5 μm, 250 mm×4 mm; eluent: isohexane/ethyl acetate 4:1; flow rate: 1.5 ml/min; temperature: RT; UV detection: 260 nm].

Example 35A tert-Butyl 3-[1-(4-chloro-2-fluorophenyl)-3-ethoxy-3-oxopropyl]-7-[(methylsulfanyl)methyl]-1H-indole-1-carboxylate

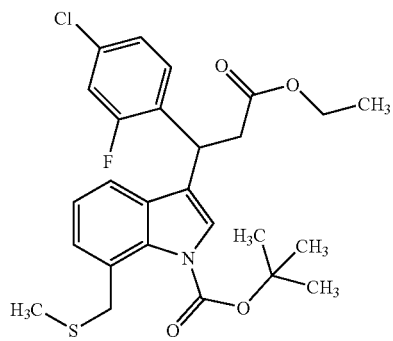

5.00 g (12.3 mmol) of the compound from Example 34A were introduced into 50 ml of absolute tetrahydrofuran under argon at 0° C., 0.52 g (12.9 mmol) of a 60% suspension of sodium hydride in mineral oil was added, and the mixture was stirred at RT for 15 min. 2.82 g (12.9 mmol) of di-tert-butyl dicarbonate were added, and the mixture was stirred at RT overnight. Water was then added, the mixture was extracted with dichloromethane, and the organic phase was dried over magnesium sulfate, filtered and concentrated. The residue was purified by flash chromatography (mobile phase: toluene/ethyl acetate gradient) to result in 6.1 g (98% of theory) of the title compound.

¹H-NMR (400 MHz, DMSO-d₆): δ=1.07 (t, 3H), 1.62 (s, 9H), 1.67 (s, 3H), 3.15-3.28 (m, 2H), 3.92-4.06 (m, 2H), 4.17 (q, 2H), 4.85 (t, 1H), 7.10-7.22 (m, 3H), 7.33 (dd, 1H), 7.40 (dd, 1H), 7.46 (t, 1H), 7.69 (s, 1H).

LC-MS (Method 5): $R_t$=3.26 min; MS (ESIpos): m/z=506 [M+H]⁺.

Example 36A tert-Butyl 3-[1-(4-chloro-2-fluorophenyl)-3-ethoxy-2-methyl-3-oxopropyl]-7-[(methylsulfanyl)methyl]-1H-indole-1-carboxylate

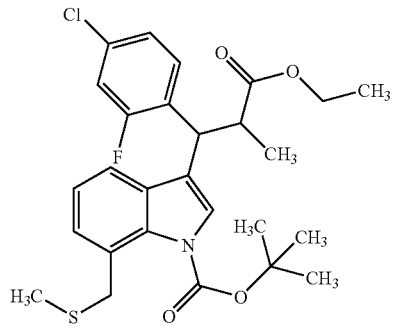

3.55 ml (7.10 mmol) of a 2N solution of lithium diisopropylamide in tetrahydrofuran were introduced into 40 ml of absolute tetrahydrofuran at −78° C., a solution of 3.00 g (5.93 mmol) of the compound from Example 35A in 20 ml of tetrahydrofuran was added, and the mixture was stirred for 1 h. 1.01 g (7.11 mmol) of methyl iodide were added at −78° C., and the reaction mixture was warmed to RT. It was then diluted with dichloromethane, the phases were separated, and the organic phase was washed with 1N hydrochloric acid, dried over magnesium sulfate, filtered and concentrated. The crude product was purified by preparative HPLC (RP18 column; mobile phase: acetonitrile/water gradient with addition of 0.1% formic acid) to result in 2.45 g (80% of theory) of the title compound as mixture of diastereomers.

$^1$H-NMR (400 MHz, DMSO-d$_6$): δ=0.93 (t, 1.5H), 0.97-1.04 (m, 3H), 1.18 (d, 1.5H), 1.63 (s, 9H), 1.67 (s, 1.5H), 1.67 (s, 1.5H), 3.41-3.51 (m, 0.5H), 3.63-3.73 (m, 0.5H), 3.88 (q, 1H), 3.92-4.06 (m, 1H), 4.11-4.21 (m, 2H), 4.56 (d, 0.5H), 4.60 (d, 0.5H), 7.10-7.24 (m, 3H), 7.30-7.36 (m, 1H), 7.42-7.47 (m, 0.5H), 7.50-7.57 (m, 1H), 7.63 (t, 0.5H), 7.73 (s, 0.5H), 7.87 (s, 0.5H).

LC-MS (Method 4): R$_t$=1.80 and 1.82 min; MS (ESIpos): m/z=520 [M+H]$^+$.

Example 37A

Ethyl 3-(4-chloro-2-fluorophenyl)-3-{5-fluoro-7-[(methylsulfanyl)methyl]-1H-indol-3-yl}propanoate

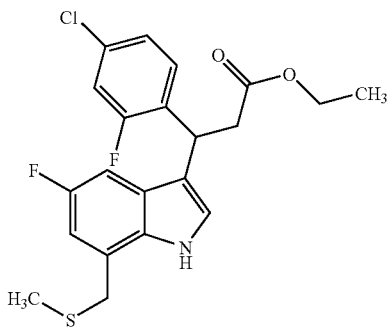

1.9 mg (0.03 mmol) of copper powder were added to 2.20 g of the compound from Example 16A with a purity of 71% (3.26 mmol) in 25 ml of pyridine and 6.7 ml of ethanol. The reaction mixture was heated under reflux for 1 h. It was concentrated, and the residue was purified by flash chromatography on silica gel (mobile phase: cyclohexane/ethyl acetate gradient) to result in 1.22 g (88% of theory) of the target compound.

$^1$H-NMR (400 MHz, DMSO-d$_6$): δ=1.05 (t, 3H), 1.94 (s, 3H), 3.10-3.24 (m, 2H), 3.90 (s, 2H), 3.93-4.00 (m, 2H), 4.83 (t, 1H), 6.84 (dd, 1H), 6.99 (dd, 1H), 7.19 (dd, 1H), 7.36 (dd, 1H), 7.40-7.48 (m, 2H), 11.1 (s, 1H).

LC-MS (Method 5): R$_t$=2.92 min; MS (ESIpos): m/z=424 [M+H]$^+$.

Example 38A

Ethyl 3-(2,4-dichlorophenyl)-3-{7-[(methylsulfanyl)methyl]-1H-indol-3-yl}propanoate

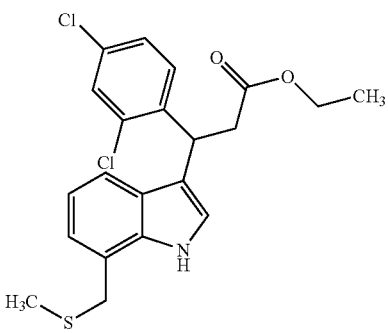

5.3 mg (0.08 mmol) of copper powder were added to 3.99 g (8.34 mmol) of the compound from Example 17A in 59 ml of pyridine and 15 ml of ethanol. The reaction mixture was heated under reflux for 1 h. It was concentrated, and the residue was taken up in ethyl acetate, washed with 1N hydrochloric acid, dried over magnesium sulfate, filtered through silica gel and concentrated. The crude product was purified by preparative HPLC (RP18 column; mobile phase: acetonitrile/water gradient with addition of 0.1% formic acid) to result in 2.34 g (67% of theory) of the title compound.

$^1$H-NMR (400 MHz, DMSO-d$_6$): δ=1.06 (t, 3H), 1.94 (s, 3H), 3.06 (dd, 1H), 3.17 (dd, 1H), 3.91 (s, 2H), 3.97 (q, 2H), 5.09 (t, 1H), 6.87 (t, 1H), 6.94 (d, 1H), 7.25 (d, 1H), 7.29-7.34 (m, 2H), 7.40 (d, 1H), 7.58 (d, 1H), 11.0 (s, 1H).

LC-MS (Method 4): R$_t$=1.59 min; MS (ESIpos): m/z=422 [M+H]$^+$.

Example 39A

Ethyl 3-(2,4-dichlorophenyl)-3-{5-fluoro-7-[(methylsulfanyl)methyl]-1H-indol-3-yl}propanoate

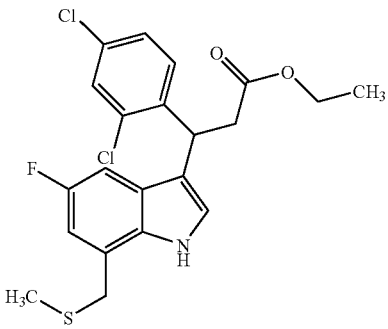

2.8 mg (0.05 mmol) of copper powder were added to 3.10 g of the compound from Example 18A with a purity of 68% (4.23 mmol) in 34 ml of pyridine and 8 ml of ethanol. The reaction mixture was heated under reflux for 1 h. It was concentrated, and the crude product was purified by preparative HPLC (RP18 column; mobile phase: acetonitrile/water gradient) to result in 1.52 g (82% of theory) of the title compound.

$^1$H-NMR (400 MHz, DMSO-d$_6$): δ=1.05 (t, 3H), 1.95 (s, 3H), 3.08 (dd, 1H), 3.18 (dd, 1H), 3.91 (s, 2H), 3.97 (q, 2H), 5.02 (t, 1H), 6.85 (dd, 1H), 6.97 (dd, 1H), 7.33 (dd, 1H), 7.41 (d, 1H), 7.44 (d, 1H), 7.58 (d, 1H), 11.2 (s, 1H).

LC-MS (Method 4): R$_t$=1.59 min; MS (ESIpos): m/z=440 [M+H]$^+$.

Example 40A

Ethyl 3-(4-chlorophenyl)-3-{5-fluoro-7-[(methylsulfanyl)methyl]-1H-indol-3-yl}propanoate

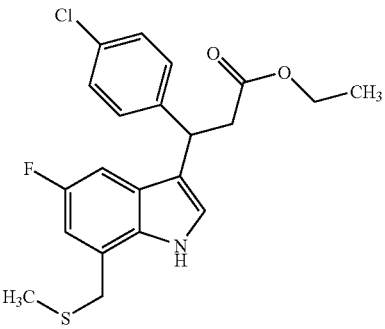

2.0 mg (0.03 mmol) of copper powder were added to 2.21 g (3.08 mmol) of the compound from Example 19A with a purity of 64% in 23 ml of pyridine and 6 ml of ethanol. The reaction mixture was heated under reflux for 1 h. It was concentrated, and the crude product was purified by preparative HPLC (RP18 column; mobile phase: acetonitrile/water gradient) to result in 1.29 g (82% of theory) of the title compound with a purity of 79%.

LC-MS (Method 3): R$_t$=2.54 min; MS (ESIpos): m/z=406 [M+H]$^+$.

Example 41A

Ethyl 3-(4-chloro-2-methylphenyl)-3-{7-[(ethylsulfanyl)methyl]-1H-indol-3-yl}propanoate

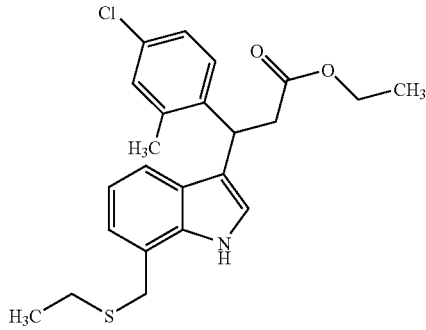

849 mg (5.49 mmol) of 4-chloro-2-methylbenzaldehyde, 791 mg (5.49 mmol) of Meldrum's acid and 30.1 mg (0.26 mmol) of D,L-proline were added to a solution of 1.00 g (5.23 mmol) of the compound from Example 10A in 44 ml of acetonitrile. The reaction mixture was stirred at RT overnight. It was concentrated, the residue was taken up in diethyl ether, and a precipitate was separated off and discarded. Concentration resulted in 2.70 g of a crude product, of which 2.40 g were introduced into 9.5 ml of pyridine and 2.5 ml of ethanol, and 0.9 mg (14 μmol) of copper powder was added. The reaction mixture was heated under reflux for 1 h. It was concentrated, and the residue was taken up in ethyl acetate, washed with 1N hydrochloric acid, dried over magnesium sulfate, filtered through silica gel and concentrated. 950 mg of a crude product were obtained and were introduced into 14.2 ml of pyridine and 3.7 ml of ethanol, and 1.3 mg (21 μmol) of copper powder were added. The reaction mixture was heated under reflux for 1 h. It was concentrated, and the residue was taken up in ethyl acetate, washed with 1N hydrochloric acid, dried over magnesium sulfate, filtered through silica gel and concentrated. The crude product was purified by preparative HPLC (RP18 column; mobile phase: acetonitrile/water gradient) to result in 620 mg of the title compound.

$^1$H-NMR (400 MHz, DMSO-d$_6$): δ=1.04 (t, 3H), 1.15 (t, 3H), 2.38 (q, 2H), 2.44 (s, 3H), 2.99 (dd, 1H), 3.11 (dd, 1H), 3.91-3.99 (m, 4H), 4.81 (t, 1H), 6.84 (t, 1H), 6.93 (d, 1H), 7.11-7.18 (m, 2H), 7.19-7.25 (m, 3H), 11.0 (s, 1H).

LC-MS (Method 3): R$_t$=2.73 min; MS (ESIpos): m/z=416 [M+H]$^+$.

Example 42A

Ethyl 3-(4-chloro-2-methylphenyl)-3-{7-[(methylsulfanyl)methyl]-1H-indol-3-yl}propanoate

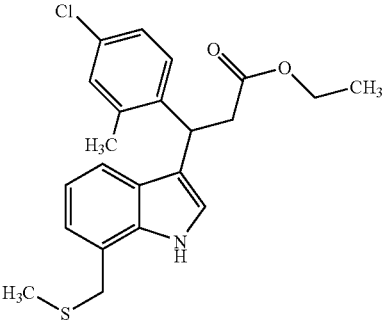

1.44 g (9.31 mmol) of 4-chloro-2-methylbenzaldehyde, 1.34 g (9.31 mmol) of Meldrum's acid and 48.7 mg (0.42 mmol) of D,L-proline were added to a solution of 1.50 g (8.46 mmol) of the compound from Example 8A in 70 ml of acetonitrile. The reaction mixture was stirred at RT overnight. It was concentrated, and the residue was taken up in ethyl acetate, washed with saturated aqueous sodium bicarbonate solution, water and saturated aqueous sodium chloride solution, dried over magnesium sulfate, filtered and concentrated. 3.43 g of a crude product were obtained and were introduced into 53 ml of pyridine and 14 ml of ethanol, and 4.8 mg (75 μmol) of copper powder were added. The reaction mixture was heated under reflux for 1 h. It was concentrated, and the residue was taken up in ethyl acetate, washed with 1N hydrochloric acid, dried over magnesium sulfate, filtered through silica gel and concentrated. The crude product was purified by preparative HPLC (RP18 column; mobile phase: acetonitrile/water gradient with addition of 0.1% formic acid) to result in 1.68 g (49% of theory) of the title compound.

$^1$H-NMR (400 MHz, DMSO-d$_6$): δ=1.04 (t, 3H), 1.94 (s, 3H), 2.44 (s, 3H), 2.99 (dd, 1H), 3.11 (dd, 1H), 3.87-4.00 (m, 4H), 4.81 (t, 1H), 6.85 (t, 1H), 6.93 (d, 1H), 7.11-7.18 (m, 2H), 7.19-7.26 (m, 3H), 11.0 (s, 1H).

LC-MS (Method 3): R$_t$=2.63 min; MS (ESIpos): m/z=402 [M+H]$^+$.

Example 43A

Ethyl 3-(4-fluoro-2-methylphenyl)-3-{7-[(methylsulfanyl)methyl]-1H-indol-3-yl}propanoate

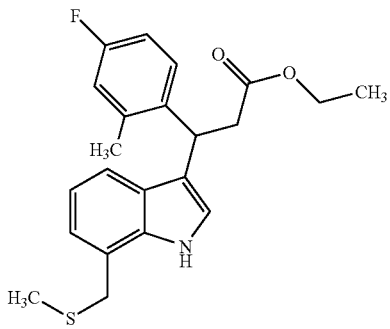

614 mg (4.44 mmol) of 4-fluoro-2-methylbenzaldehyde, 640 mg (4.44 mmol) of Meldrum's acid and 24.4 mg (0.21 mmol) of D,L-proline were added to a solution of 750 mg (4.23 mmol) of the compound from Example 8A in 35 ml of acetonitrile. The reaction mixture was stirred at RT overnight. A further 35 ml of acetonitrile were added, and the mixture was stirred at RT for two days. It was concentrated, and the crude product was purified by preparative HPLC (RP18 column; mobile phase: acetonitrile/water gradient with addition of 0.1% formic acid). 860 mg of a product were obtained and were introduced into 15 ml of pyridine and 5.2 ml of ethanol, and 1.2 mg (19 µmol) of copper powder were added. The reaction mixture was heated under reflux for 2 h. It was concentrated, and the crude product was purified by preparative HPLC (RP18 column; mobile phase: acetonitrile/water gradient with addition of 0.1% formic acid) to result in 607 mg (37% of theory) of the title compound.

$^1$H-NMR (400 MHz, DMSO-$d_6$): δ=1.04 (t, 3H), 1.94 (s, 3H), 2.45 (s, 3H), 2.98 (dd, 1H), 3.10 (dd, 1H), 3.91 (s, 2H), 3.96 (q, 2H), 4.81 (t, 1H), 6.85 (t, 1H), 6.88 (dd, 1H), 6.92 (d, 1H), 7.00 (dd, 1H), 7.16 (d, 1H), 7.19 (d, 1H), 7.24 (dd, 1H), 11.0 (s, 1H).

LC-MS (Method 5): $R_t$=2.80 min; MS (ESIpos): m/z=386 [M+H]$^+$.

Example 44A

Ethyl 3-[2-fluoro-4-(trifluoromethyl)phenyl]-3-{7-[(methylsulfanyl)methyl]-1H-indol-3-yl}propanoate

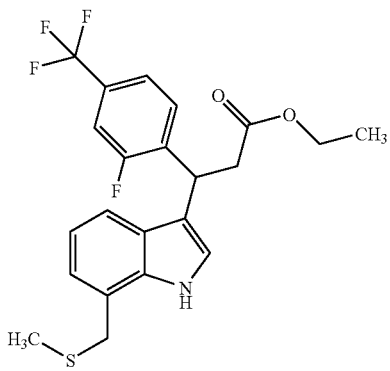

1.54 g (8.00 mmol) of 2-fluoro-4-(trifluoromethyl)benzaldehyde, 1.15 g (8.00 mmol) of Meldrum's acid and 44 mg (0.38 mmol) of D,L-proline were added to a solution of 1.50 g (7.62 mmol) of the compound from Example 8A in 62 ml of acetonitrile. The reaction mixture was stirred at RT overnight. It was concentrated to result in 4.47 g of a crude product which was introduced into 48 ml of pyridine and 12 ml of ethanol, and 4 mg (63 µmol) of copper powder were added. The reaction mixture was heated under reflux for 1 h. It was concentrated, and the crude product was purified by preparative HPLC (RP18 column; mobile phase: acetonitrile/water gradient with addition of 0.1% formic acid) to result in 2.74 g (82% of theory) of the title compound.

$^1$H-NMR (400 MHz, DMSO-$d_6$): δ=1.04 (t, 3H), 1.93 (s, 3H), 3.21-3.25 (m, 2H), 3.91 (s, 2H), 3.97 (q, 2H), 4.99 (t, 1H), 6.88 (t, 1H), 6.94 (d, 1H), 7.29 (d, 1H), 7.39 (d, 1H), 7.48 (d, 1H), 7.58-7.68 (m, 2H), 11.1 (s, 1H).

LC-MS (Method 5): $R_t$=2.89 min; MS (ESIpos): m/z=440 [M+H]$^+$.

Example 45A

Ethyl 3-{7-[(methylsulfanyl)methyl]-1H-indol-3-yl}-3-(naphthalen-2-yl)propanoate

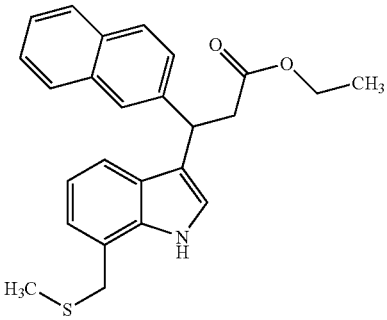

1.2 mg (0.02 mmol) of copper powder were added to 882 mg (1.92 mmol) of the compound from Example 20A in 15 ml of pyridine and 5 ml of ethanol. The reaction mixture was heated under reflux for 2 h. It was concentrated, and the crude product was purified by flash chromatography on silica gel (mobile phase: toluene/ethyl acetate gradient) and preparative HPLC (RP18 column; mobile phase: acetonitrile/water gradient) to result in 635 mg (82% of theory) of the title compound.

$^1$H-NMR (400 MHz, DMSO-$d_6$): δ=1.02 (t, 3H), 1.92 (s, 3H), 3.17 (dd, 1H), 3.26 (dd, 1H), 3.88-3.99 (m, 2H), 3.90 (s, 2H), 4.80 (t, 1H), 6.80 (t, 1H), 6.90 (d, 1H), 7.31 (d, 1H), 7.38-7.51 (m, 4H), 7.75-7.87 (m, 3H), 7.90 (s, 1H), 11.0 (s, 1H).

LC-MS (Method 4): $R_t$=1.52 min; MS (ESIpos): m/z=404 [M+H]$^+$.

Example 46A

Ethyl 4-(4-chlorophenyl)-4-{7-[(methylsulfanyl)methyl]-1H-indol-3-yl}butanoate

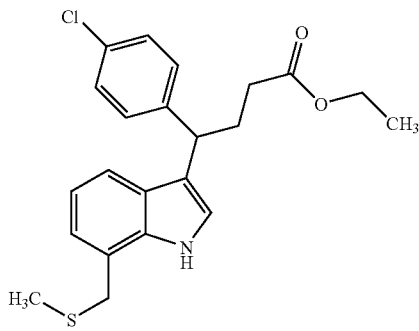

1.75 ml of concentrated sulfuric acid were added to 1.00 g (2.82 mmol) of the compound from Example 36 in 25 ml of ethanol. The reaction mixture was heated under reflux for 24 h. After cooling, the reaction mixture was added to saturated aqueous sodium bicarbonate solution, extracted with dichloromethane, dried over magnesium sulfate, filtered and concentrated. The residue was purified by preparative HPLC (RP18 column; mobile phase: acetonitrile-water gradient with addition of 0.1% formic acid). 0.45 g (39% of theory) of the target compound was obtained.

$^1$H-NMR (400 MHz, DMSO-$d_6$): δ=1.15 (t, 3H), 1.94 (s, 3H), 2.17-2.44 (m, 4H), 3.91 (s, 2H), 4.01 (q, 2H), 4.13-4.19 (m, 1H), 6.84 (t, 1H), 6.92 (d, 1H), 7.25 (d, 1H), 7.29-7.36 (m, 5H), 11.0 (s, 1H).

LC-MS (Method 5): $R_t$=2.93 min; MS (ESIpos): m/z=402 [M+H]$^+$.

Example 47A

Ethyl 3-(4-chlorophenyl)-3-{6-fluoro-7-[(methylsulfanyl)methyl]-1H-indol-3-yl}propanoate

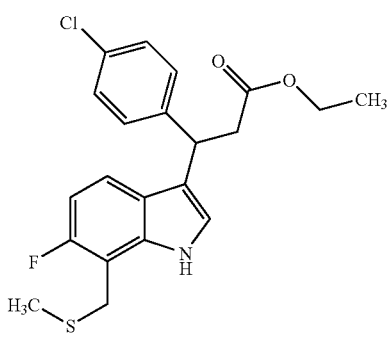

23 mg (0.36 mmol) of copper powder were added to 3.31 g (7.16 mmol) of the compound from Example 21A in 13 ml of pyridine and 3 ml of ethanol. The reaction mixture was heated under reflux for 4 h and then the pyridine was removed in vacuo. The residue was taken up in ethyl acetate, silica gel was added, and the mixture was concentrated. The crude product-silica gel mixture was initially prepurified by flash chromatography (mobile phase: cyclohexane/ethyl acetate 5/1→3/1), and the product was again purified by preparative HPLC (acetonitrile/water gradient). 2.38 g (82% of theory) of the title compound were obtained.

$^1$H-NMR (400 MHz, DMSO-$d_6$): δ=1.05 (t, 3H), 1.98 (s, 3H), 3.04 (dd, 1H), 3.15 (dd, 1H), 3.92-4.00 (m, 4H), 4.62 (t, 1H), 6.76 (dd, 1H), 7.24 (dd, 1H), 7.27-7.31 (m, 2H), 7.35-7.40 (m, 3H), 11.13 (s, 1H).

HPLC (Method 2): $R_t$=5.06 min; MS (ESIneg): m/z=404 [M−H]$^−$.

Example 48A

Ethyl 3-{6-fluoro-7-[(methylsulfanyl)methyl]-1H-indol-3-yl}-3-[4-(trifluoromethyl)phenyl]propanoate

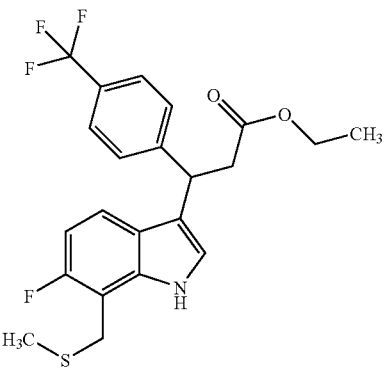

The title compound was prepared starting from 3.82 g (7.71 mmol) of the compound from Example 22A in analogy to the synthesis of the compound from Example 47A. 3.05 g (90% of theory) of the title compound were obtained.

$^1$H-NMR (400 MHz, DMSO-$d_6$): δ=1.03 (t, 3H), 1.98 (s, 3H), 3.08-3.24 (m, 2H), 3.91-4.00 (m, 4H), 4.72 (t, 1H), 6.77 (dd, 1H), 7.28 (dd, 1H), 7.42 (s, 1H), 7.57-7.63 (m, 4H), 11.17 (s, 1H).

HPLC (Method 2): $R_t$=5.11 min; MS (ESIneg): m/z=438 [M−H]$^−$.

Example 49A

Ethyl 3-(1-benzothiophen-5-yl)-3-{7-[(methylsulfanyl)methyl]-1H-indol-3-yl}propanoate

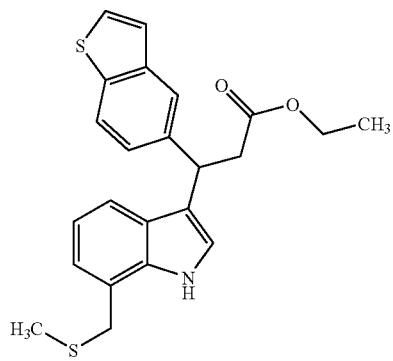

The title compound was prepared starting from 1.73 g (71% purity, 3.72 mmol) of the compound from Example 23A in analogy to the synthesis of the compound from Example 47A. 1.23 g (81% of theory) of the title compound were obtained.

$^1$H-NMR (400 MHz, DMSO-$d_6$): δ=1.03 (t, 3H), 1.92 (s, 3H), 3.11 (dd, 1H), 3.22 (dd, 1H), 3.90 (s, 2H), 3.91-4.00 (m, 2H), 4.75 (t, 1H), 6.81 (t, 1H), 6.90 (d, 1H), 7.27 (d, 1H), 7.34-7.39 (m, 3H), 7.69 (d, 1H), 7.82-7.86 (m, 2H), 10.96 (s, 1H).

HPLC (Method 2): $R_t$=5.02 min; MS (ESIpos): m/z=410 [M+H]$^+$.

Example 50A

Ethyl 3-(2-bromo-1,3-thiazol-5-yl)-3-{7-[(methyl-sulfanyl)methyl]-1H-indol-3-yl}propanoate

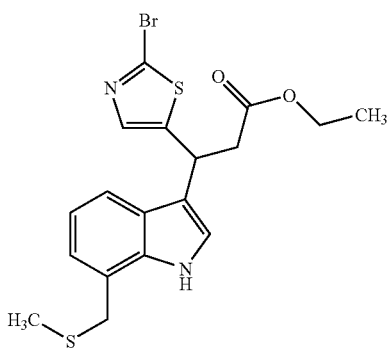

19 mg (0.29 mmol) of copper powder were added to 3.57 g (81% purity, 5.87 mmol) of the compound from Example 24A in 15 ml of pyridine and 8 ml of ethanol. The reaction mixture was heated under reflux for 5 h and then the copper was filtered off through kieselguhr. The filtrate was concentrated, the residue was stirred with diethyl ether/dichloromethane, and the precipitated solid was filtered off. The filtrate was concentrated and purified by preparative HPLC (acetonitrile/water gradient). 1.24 g (46% of theory) of the title compound were obtained.

$^1$H-NMR (400 MHz, DMSO-d$_6$): δ=1.08 (t, 3H), 1.95 (s, 3H), 3.20 (d, 2H), 3.92 (s, 2H), 4.01 (q, 2H), 4.97 (t, 1H), 6.89-6.99 (m, 2H), 7.35-7.40 (m, 2H), 7.61 (s, 1H), 11.09 (s, 1H).

LC-MS (Method 3): R$_t$=2.28 min; MS (ESIpos): m/z=439 [M+H]$^+$.

Example 51A

3-{7-[(Methylsulfanyl)methyl]-1H-indol-3-yl}-3-[4-(trifluoromethyl)phenyl]propyl methanesulfonate

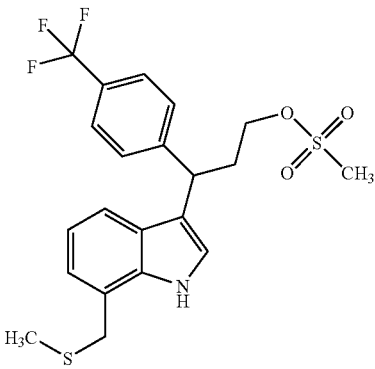

0.06 ml (0.45 mmol) of triethylamine and 3.3 mg (0.03 mmol) of 4-N,N-dimethylaminopyridine were added to 101 mg (0.27 mmol) of the compound from Example 1 in 5.5 ml of dichloromethane. The mixture was stirred at RT for 15 min and then 0.03 ml (0.40 mmol) of methanesulfonyl chloride was added. The reaction mixture was stirred at RT for 2 h and then diluted with dichloromethane, washed with 1N hydrochloric acid, water and saturated aqueous sodium chloride solution, dried over magnesium sulfate, filtered and concentrated. Purification by preparative HPLC (RP18 column; mobile phase: acetonitrile-water gradient with addition of 0.1% formic acid) resulted in 101 mg (83% of theory) of the title compound.

$^1$H-NMR (400 MHz, DMSO-d$_6$): δ=1.94 (s, 3H), 2.40-2.50 (m, 1H), 2.55-2.69 (m, 1H), 3.11 (s, 3H), 3.92 (s, 2H), 4.10-4.22 (m, 2H), 4.44 (t, 1H), 6.86 (t, 1H), 6.93 (d, 1H), 7.31 (d, 1H), 7.45 (d, 1H), 7.58-7.66 (m, 4H), 11.1 (s, 1H).

LC-MS (Method 3): R$_t$=2.35 min; MS (ESIpos): m/z=458 [M+H]$^+$.

Example 52A 3-(4-Chlorophenyl)-3-{7-[(methylsulfanyl)methyl]-1H-indol-3-yl}propyl methanesulfonate

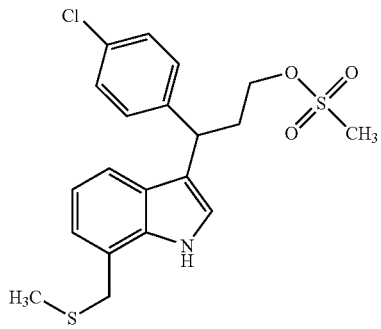

4.06 ml (29.1 mmol) of triethylamine and 209 mg (1.71 mmol) of 4-N,N-dimethylaminopyridine were added to 5.93 g (17.1 mmol) of the compound from Example 2 in 345 ml of dichloromethane. The mixture was stirred at RT for 15 min and then 2.0 ml (25.7 mmol) of methanesulfonyl chloride were added. The reaction mixture was stirred at RT for 2 h and then diluted with dichloromethane, washed with 1N hydrochloric acid, water and saturated aqueous sodium chloride solution, dried over magnesium sulfate, filtered and concentrated. 6.90 g (95% of theory) of the title compound were obtained and were reacted further without purification.

$^1$H-NMR (400 MHz, DMSO-d$_6$): δ=1.94 (s, 3H), 2.35-2.44 (m, 1H), 2.50-2.62 (m, 1H), 3.11 (s, 3H), 3.91 (s, 2H), 4.08-4.19 (m, 2H), 4.33 (t, 1H), 6.85 (t, 1H), 6.93 (d, 1H), 7.29 (d, 1H), 7.30-7.34 (m, 2H), 7.36-7.41 (m, 3H), 11.0 (s, 1H).

LC-MS (Method 5): R$_t$=2.70 min; MS (ESIpos): m/z=424 [M+H]$^+$.

Example 53A 3-(4-Chlorophenyl)-3-{7-[(ethylsulfanyl)methyl]-1H-indol-3-yl}propyl methanesulfonate

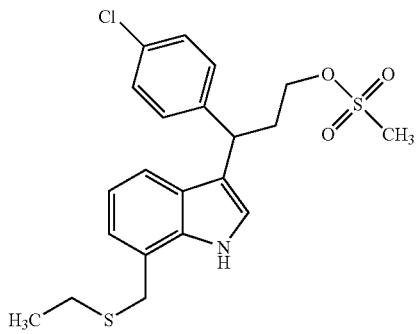

0.27 ml (1.96 mmol) of triethylamine and 14.1 mg (0.12 mmol) of 4-N,N-dimethylaminopyridine were added to 415 mg (1.15 mmol) of the compound from Example 3 in 23 ml of dichloromethane. The mixture was stirred at RT for 15 min and then 0.13 ml (1.73 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. Purification by preparative HPLC (RP18 column; mobile phase: acetonitrile-water gradient with addition of 0.1% formic acid) resulted in 520 mg (100% of theory) of the title compound.

LC-MS (Method 3): $R_t$=2.43 min; MS (ESIpos): m/z=438 [M+H]$^+$.

Example 54A 3-(4-Chloro-2-fluorophenyl)-3-{7-[(methylsulfanyl)methyl]-1H-indol-3-yl}propyl methanesulfonate

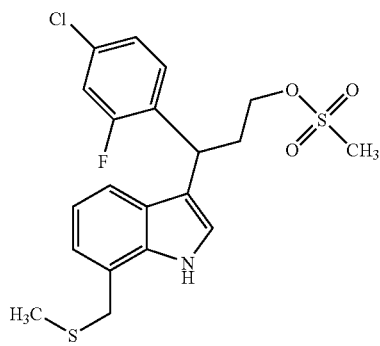

1.1 ml (7.77 mmol) of triethylamine and 55.8 mg (0.46 mmol) of 4-N,N-dimethylaminopyridine were added to 1.66 g (4.57 mmol) of the compound from Example 4 in 93 ml of dichloromethane. The mixture was stirred at RT for 15 min and then 0.5 ml (6.85 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. The crude product was purified by preparative HPLC (RP18 column; mobile phase: acetonitrile/water gradient with addition of 0.1% formic acid) to result in 1.94 g (96% of theory) of the title compound.

LC-MS (Method 3): $R_t$=2.35 min; MS (ESIpos): m/z=442 [M+H]$^+$.

Enantiomer 54A-1:

1.48 g (4.07 mmol) of enantiomer 4-1 were reacted in analogy to the synthesis of the compound from Example 54A. 1.88 g (100% of theory) of the corresponding enantiomer of the title compound were obtained as crude product which was reacted without purification.

Example 55A 3-(4-Chloro-2-fluorophenyl)-2-methyl-3-{7-[(methylsulfanyl)methyl]-1H-indol-3-yl}propyl methanesulfonate

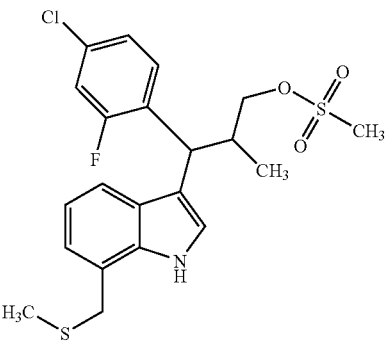

0.04 ml (0.27 mmol) of triethylamine and 1.9 mg (0.02 mmol) of 4-N,N-dimethylaminopyridine were added to 60 mg (0.16 mmol) of the compound from Example 5 in 4 ml of dichloromethane. The mixture was stirred at RT for 15 min and then 0.02 ml (0.24 mmol) of methanesulfonyl chloride was added. The reaction mixture was stirred at RT overnight and then diluted with dichloromethane, washed with saturated aqueous sodium bicarbonate solution and water, dried over magnesium sulfate, filtered and concentrated. 70 mg (97% of theory) of the title compound were obtained as a mixture of diastereomers which were reacted without further purification.

LC-MS (Method 5): $R_t$=2.73 and 2.81 min; MS (ESIpos): m/z=456 [M+H]$^+$.

Example 56A 3-(4-Chloro-2-fluorophenyl)-3-{5-fluoro-7-[(methylsulfanyl)methyl]-1H-indol-3-yl}propyl methanesulfonate

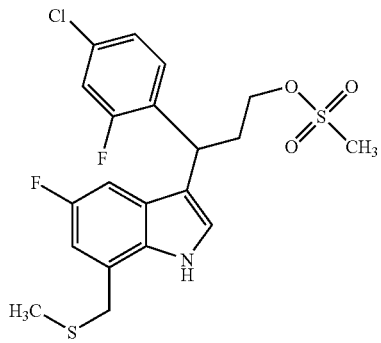

0.35 ml (2.54 mmol) of triethylamine and 18.2 mg (0.15 mmol) of 4-N,N-dimethylaminopyridine were added to 570 mg (1.49 mmol) of the compound from Example 6 in 40 ml of dichloromethane. The mixture was stirred at RT for 15 min and then 0.17 ml (2.24 mmol) of methanesulfonyl chloride was added. The reaction mixture was stirred at RT overnight and then diluted with dichloromethane, washed with saturated aqueous sodium bicarbonate solution and water, dried over magnesium sulfate, filtered and concentrated. 670 mg (98% of theory) of the title compound were obtained.

LC-MS (Method 3): $R_t$=2.37 min; MS (ESIpos): m/z=460 [M+H]$^+$.

Example 57A 3-(2,4-Dichlorophenyl)-3-{7-[(methylsulfanyl)methyl]-1H-indol-3-yl}propyl methanesulfonate

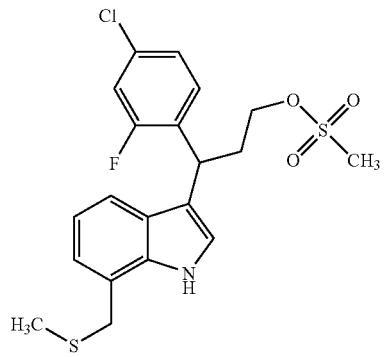

1.1 ml (7.93 mmol) of triethylamine and 57.0 mg (0.47 mmol) of 4-N,N-dimethylaminopyridine were added to 1.77 g (4.66 mmol) of the compound from Example 7 in 95 ml of dichloromethane. The mixture was stirred at RT for 15 min and then 0.5 ml (7.00 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. The crude product was purified by preparative HPLC (RP18 column; mobile phase: acetonitrile/water gradient with addition of 0.1% formic acid) to result in 1.98 g (93% of theory) of the title compound.

LC-MS (Method 3): $R_t$=2.45 min; MS (ESIpos): m/z=458 [M+H]$^+$.

Example 58A 3-(2,4-Dichlorophenyl)-3-{5-fluoro-7-[(methylsulfanyl)methyl]-1H-indol-3-yl}propyl methanesulfonate

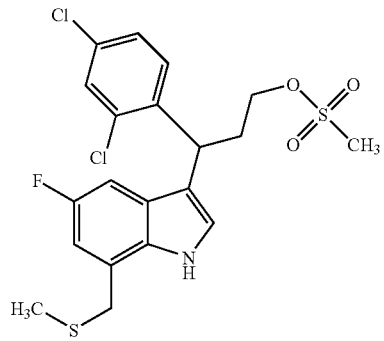

0.6 ml (4.48 mmol) of triethylamine and 32.2 mg (0.26 mmol) of 4-N,N-dimethylaminopyridine were added to 1.05 g (2.64 mmol) of the compound from Example 8 in 53 ml of dichloromethane. The mixture was stirred at RT for 15 min and then 0.3 ml (3.95 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. 1.36 g (97% of theory) of the title compound were obtained and were reacted without further purification.

LC-MS (Method 4): $R_t$=1.47 min; MS (ESIpos): m/z=476 [M+H]$^+$.

Example 59A 3-(4-Chlorophenyl)-3-{5-fluoro-7-[(methylsulfanyl)methyl]-1H-indol-3-yl}propyl methanesulfonate

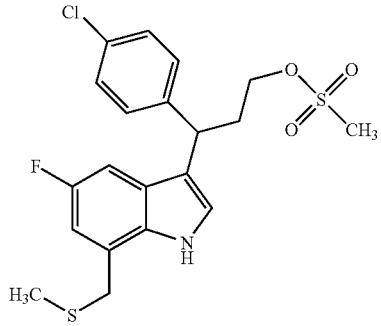

0.3 ml (2.28 mmol) of triethylamine and 16.4 mg (0.13 mmol) of 4-N,N-dimethylaminopyridine were added to 488 mg (1.34 mmol) of the compound from Example 9 in 27 ml of dichloromethane. The mixture was stirred at RT for 15 min and then 0.16 ml (2.01 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. 445 mg (71% of theory) of the title compound were obtained and were reacted without further purification.

LC-MS (Method 6): $R_t$=2.59 min; MS (ESIpos): m/z=442 [M+H]$^+$.

Example 60A 3-(4-Chloro-2-methylphenyl)-3-{7-[(ethylsulfanyl)methyl]-1H-indol-3-yl}propyl methanesulfonate

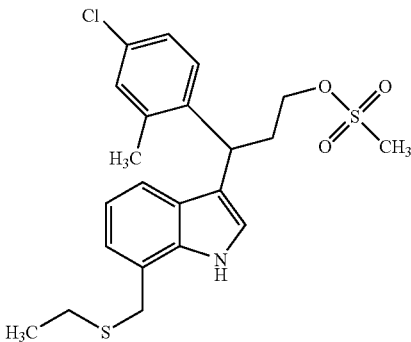

The title compound was prepared starting from 250 mg (0.67 mmol) of the compound from Example 10 in analogy to the synthesis of the compound from Example 54A. 308 mg (100% of theory) of the title compound were obtained.

$^1$H-NMR (400 MHz, DMSO-d$_6$): δ=1.15 (t, 3H), 2.25-2.42 (m, 2H), 2.39 (q, 2H), 2.42 (s, 3H), 3.11 (s, 3H), 3.92-4.01 (m, 2H), 4.10-4.24 (m, 2H), 4.51 (t, 1H), 6.86 (t, 1H), 6.94 (d, 1H), 7.16 (dd, 1H), 7.21 (d, 1H), 7.23-7.30 (m, 3H), 11.0 (s, 1H).

LC-MS (Method 3): R$_t$=2.51 min; MS (ESIpos): m/z=452 [M+H]$^+$.

Example 61A 3-(4-Chloro-2-methylphenyl)-3-{7-[(methylsulfanyl)methyl]-1H-indol-3-yl}propyl methanesulfonate

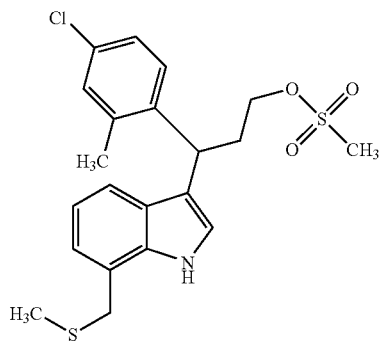

The title compound was prepared starting from 1.24 g (3.46 mmol) of the compound from Example 11 in analogy to the synthesis of the compound from Example 54A. 1.41 g (93% of theory) of the title compound were obtained.

LC-MS (Method 3): R$_t$=2.40 min; MS (ESIpos): m/z=438 [M+H]$^+$.

Example 62A 3-(4-Fluoro-2-methylphenyl)-3-{7-[(methylsulfanyl)methyl]-1H-indol-3-yl}propyl methanesulfonate

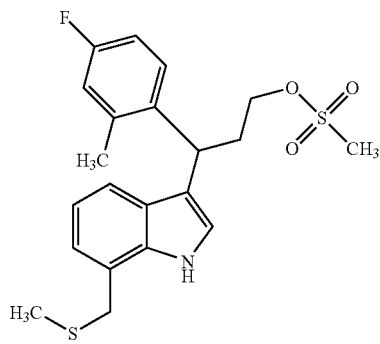

0.17 ml (1.24 mmol) of triethylamine and 8.9 mg (0.07 mmol) of 4-N,N-dimethylaminopyridine were added to 250 mg (0.73 mmol) of the compound from Example 12 in 15 ml of dichloromethane. The mixture was stirred at RT for 15 min and then 0.09 ml (1.09 mmol) of methanesulfonyl chloride was added. The reaction mixture was stirred at RT for 2 h and then diluted with dichloromethane, washed with 1N hydrochloric acid, water, saturated aqueous sodium bicarbonate solution and saturated aqueous sodium chloride solution, dried over magnesium sulfate, filtered and concentrated. 294 mg (96% of theory) of the title compound were obtained.

LC-MS (Method 3): R$_t$=2.28 min; MS (ESIpos): m/z=422 [M+H]$^+$.

Example 63A

3-[2-Fluoro-4-(trifluoromethyl)phenyl]-3-{7-[(methylsulfanyl)methyl]-1H-indol-3-yl}propyl methanesulfonate

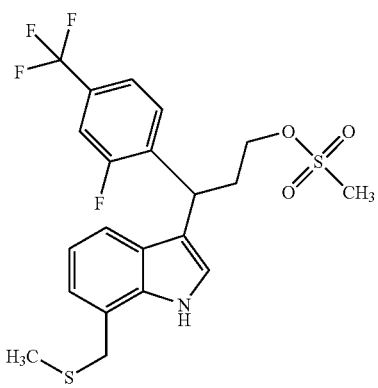

1.3 ml (9.41 mmol) of triethylamine and 67.6 mg (0.55 mmol) of 4-N,N-dimethylaminopyridine were added to 2.20 g (5.54 mmol) of the compound from Example 13 in 112 ml of dichloromethane. The mixture was stirred at RT for 15 min and then 0.64 ml (8.30 mmol) of methanesulfonyl chloride was added. The reaction mixture was stirred at RT for 4 h and then diluted with dichloromethane, washed with saturated aqueous sodium bicarbonate solution and water, dried over magnesium sulfate, filtered and concentrated. 2.66 g (94% of theory) of the title compound were obtained.

LC-MS (Method 4): R$_t$=1.44 min; MS (ESIpos): m/z=476 [M+H]$^+$.

Example 64A

3-{7-[(Methylsulfanyl)methyl]-1H-indol-3-yl}-3-(naphthalen-2-yl)propyl methanesulfonate

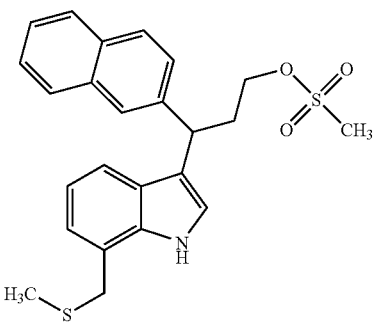

0.16 ml (1.18 mmol) of triethylamine and 8.5 mg (0.07 mmol) of 4-N,N-dimethylaminopyridine were added to 250 mg (0.69 mmol) of the compound from Example 14 in 15 ml of dichloromethane. The mixture was stirred at RT for 15 min and then 0.08 ml (1.04 mmol) of methanesulfonyl chloride was added. The reaction mixture was stirred at RT for 2 h and then diluted with dichloromethane, washed with 1N hydrochloric acid, water, saturated aqueous sodium bicarbonate solution and saturated aqueous sodium chloride solution, dried over magnesium sulfate, filtered and concentrated. 302 mg (99% of theory) of the title compound were obtained.

LC-MS (Method 3): $R_t$=2.35 min; MS (ESIpos): m/z=440 [M+H]$^+$.

Example 65A 4-(4-Chlorophenyl)-4-{7-[(methylsulfanyl)methyl]-1H-indol-3-yl}butyl methanesulfonate

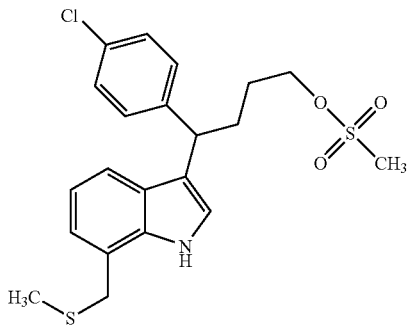

0.14 ml (1.00 mmol) of triethylamine and 7.2 mg (0.06 mmol) of 4-N,N-dimethylaminopyridine were added to 212 mg (0.59 mmol) of the compound from Example 15 in 12 ml of dichloromethane. The mixture was stirred at RT for 15 min and then 0.07 ml (0.88 mmol) of methanesulfonyl chloride was added. The reaction mixture was stirred at RT for 2 h and then diluted with dichloromethane, washed with saturated aqueous sodium bicarbonate solution, dried over magnesium sulfate, filtered and concentrated. 255 mg (98% of theory) of the title compound were obtained and were reacted further without purification.

LC-MS (Method 5): $R_t$=2.74 min; MS (ESIpos): m/z=438 [M+H]$^+$.

Example 66A 3-(4-Chlorophenyl)-3-{6-fluoro-7-[(methylsulfanyl)methyl]-1H-indol-3-yl}propyl methanesulfonate

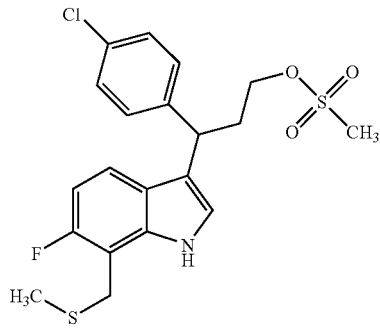

0.63 ml (4.53 mmol) of triethylamine, 0.04 g (0.35 mmol) of 4-N,N-dimethylaminopyridine and 0.3 ml (3.83 mmol) of methanesulfonyl chloride were added to 1.27 g (3.48 mmol) of the compound from Example 16 in 43 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 1.55 g of the title compound were obtained as crude product and were reacted further without purification.

LC-MS (Method 4): $R_t$=1.41 min; MS (ESIpos): m/z=442 [M+H]$^+$.

Example 67A

3-{6-Fluoro-7-[(methylsulfanyl)methyl]-1H-indol-3-yl}-3-[4-(trifluoromethyl)phenyl]propyl methanesulfonate

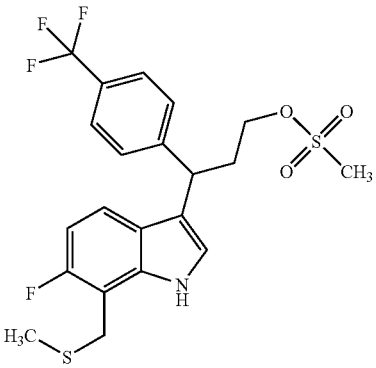

The title compound was prepared starting from 1.81 g (4.55 mmol) of the compound from Example 17 in analogy to the synthesis of the compound from Example 66A. 2.20 g of the title compound were obtained as crude product and were reacted further without purification.

LC-MS (Method 4): $R_t$=1.44 min; MS (ESIpos): m/z=476 [M+H]$^+$.

Example 68A 3-(1-Benzothiophen-5-yl)-3-{7-[(methylsulfanyl)methyl]-1H-indol-3-yl}propyl methanesulfonate

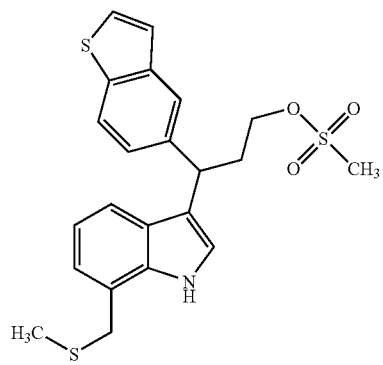

The title compound was prepared starting from 640 mg (1.74 mmol) of the compound from Example 18 in analogy to the synthesis of the compound from Example 66A. 768 mg of the title compound were obtained as crude product and were reacted further without purification.

LC-MS (Method 4): $R_t$=1.39 min; MS (ESIpos): m/z=446 [M+H]$^+$.

Example 69A 3-(2-Bromo-1,3-thiazol-5-yl)-3-{7-[(methylsulfanyl)methyl]-1H-indol-3-yl}propyl methanesulfonate

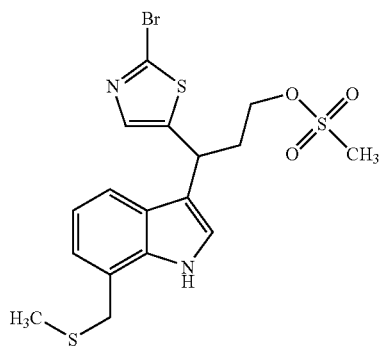

0.25 ml (1.77 mmol) of triethylamine, 15 mg (0.12 mmol) of 4-N,N-dimethylaminopyridine and 0.1 ml (1.30 mmol) of methanesulfonyl chloride were added to 470 mg (1.18 mmol) of the compound from Example 19 in 20 ml dichloromethane. The reaction mixture was stirred at RT for 1 h and then diluted with dichloromethane, washed with water and saturated aqueous sodium chloride solution, dried over sodium sulfate, filtered and concentrated. The crude product was purified by preparative HPLC (mobile phase: acetonitrile-water gradient) to result in 512 mg (91% of theory) of the title compound.

$^1$H-NMR (400 MHz, DMSO-d$_6$): δ=1.95 (s, 3H), 2.44-2.64 (m, 2H), 3.12 (s, 3H), 3.94 (s, 2H), 4.13-4.23 (m, 2H), 4.69 (t, 1H), 6.92 (t, 1H), 6.98 (d, 1H), 7.36-7.42 (m, 2H), 7.68 (s, 1H), 11.13 (s, 1H).

LC-MS (Method 4): $R_t$=1.26 min; MS (ESIpos): m/z=475 [M+H]$^+$.

Example 70A

2-Methyl-3-{7-[(methylsulfanyl)methyl]-1H-indol-3-yl}-3-[4-(trifluoromethyl)phenyl]propyl methanesulfonate

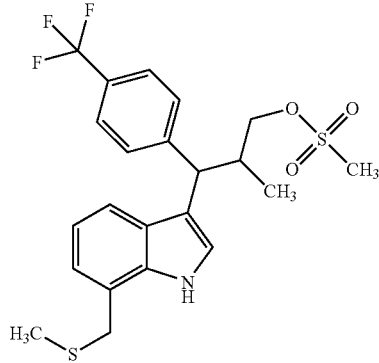

The title compound was prepared starting from 566 mg (1.44 mmol) of the compound from Example 20 in analogy to the synthesis of the compound from Example 69A. 622 mg (92% of theory) of the title compound were obtained as mixture of diastereomers.

LC-MS (Method 6): $R_t$=2.64/2.69 min; MS (ESIneg): m/z=470 [M-H]$^-$.

Example 71A 3-(4-Chlorophenyl)-2-methyl-3-{7-[(methylsulfanyl)methyl]-1H-indol-3-yl}propyl methanesulfonate

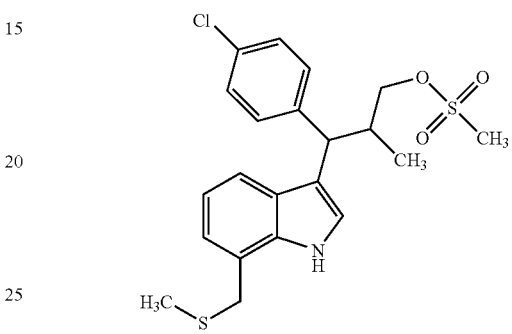

The title compound was prepared starting from 202 mg (0.56 mmol) of the compound from Example 21 in analogy to the synthesis of the compound from Example 69A. 221 mg (90% of theory) of the title compound were obtained as mixture of diastereomers.

LC-MS (Method 3): $R_t$=2.37/2.43 min; MS (ESIneg): m/z=436 [M-H]$^-$.

Example 72A

Ethyl 2-cyanocyclopropanecarboxylate [racemic trans-isomer]

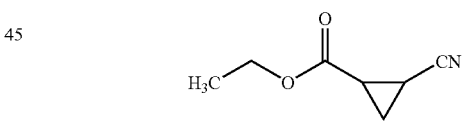

40.2 g (291 mmol) of potassium carbonate were introduced into 89 ml of DMF at RT, 9.6 ml (146 mmol) of acrylonitrile, 15.5 ml (146 mmol) of ethyl chloroacetate and 1.96 g (8.61 mmol) of benzyltriethylammonium chloride were added, and the mixture was stirred at RT for 3 days. Water was added, the mixture was extracted with diethyl ether, and the combined organic phases were dried over sodium sulfate, filtered and concentrated. The residue was purified by vacuum distillation. 6.50 g (30% of theory) of the title compound (boiling range: 63-66° C./0.9 mbar) and 1.41 g (7%) of the corresponding cis-isomer (boiling range: 85-89° C./0.9 mbar) were obtained.

$^1$H-NMR (400 MHz, DMSO-d$_6$): δ=1.21 (t, 3H), 1.39 (ddd, 1H), 1.57 (ddd, 1H), 2.20 (ddd, 1H), 2.41 (ddd, 1H), 4.11 (q, 2H).

GC-MS (Method 7): $R_t$=3.00 min; MS (EIpos): m/z=139 [M]$^+$.

Example 73A

2-Cyano-N-methoxy-N-methylcyclopropanecarboxamide [racemic trans-isomer]

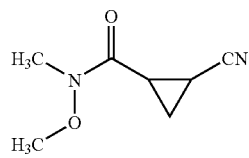

6.50 g (46.7 mmol) of the compound from Example 72A were introduced into 20 ml of methanol at RT, 46.7 ml (46.7 mmol) of a 1N aqueous sodium hydroxide solution were added, and the mixture was stirred at RT for 2 h. Concentrated hydrochloric acid was then added until the pH was 2, the mixture was extracted with diethyl ether, and the combined organic phases were dried over sodium sulfate, filtered and concentrated. The residue was taken up in 8.5 ml (117 mmol) of thionyl chloride and stirred at 65° C. for 4 h. Cooling was followed by concentration, and the residue was twice taken up in diethyl ether and again concentrated each time. The residue was introduced into 17 ml of dichloromethane, 3.43 g (35.1 mmol) of N,O-dimethylhydroxylamine hydrochloride and 9.8 ml (70.3 mmol) of triethylamine were added, and the mixture was stirred at RT overnight. Water was added, the phases were separated, two extractions with dichloromethane were carried out, and the combined organic phases were dried over sodium sulfate, filtered and concentrated. The crude product was purified by flash chromatography on silica gel (mobile phase: dichloromethane/methanol 9/1) to result in 1.72 g (24% of theory) of the title compound.

$^1$H-NMR (400 MHz, CDCl$_3$): δ=1.43 (ddd, 1H), 1.46-1.53 (m, 1H), 1.93 (ddd, 1H), 2.75-2.82 (m, 1H), 3.20 (s, 3H), 4.78 (s, 2H).

Example 74A

2-[(4-Chlorophenyl)carbonyl]cyclopropanecarbonitrile [racemic trans-isomer]

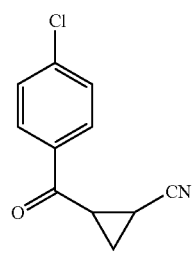

3.5 ml (3.50 mmol) of a 1N solution of chlorophenylmagnesium bromide in diethyl ether were introduced into 5 ml of THF at RT under argon, a solution of 490 mg (3.18 mmol) of the compound from Example 73A in 5 ml of tetrahydrofuran was added, and the mixture was heated under reflux for 2 h. Saturated aqueous ammonium chloride solution was added, two extractions with diethyl ether were carried out, and the combined organic phases were dried over sodium sulfate, filtered and concentrated. 714 mg of the title compound with a purity of 54% (59% of theory) were obtained and were reacted without further purification.

$^1$H-NMR (400 MHz, DMSO-d$_6$): δ=1.52 (ddd, 1H), 1.68 (ddd, 1H), 2.34 (ddd, 1H), 3.71 (ddd, 1H), 7.64-7.69 (m, 2H), 8.11-8.16 (m, 2H).

GC-MS (Method 7): R$_t$=6.16 min; MS (EIpos): m/z=205 [M]$^+$.

Example 75A

2-[1-(4-Chlorophenyl)-1-hydroxyethyl]cyclopropanecarbonitrile [trans-diastereomer mixture]

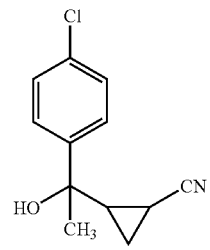

714 mg of the compound from Example 74A with a purity of 54% (1.89 mmol) were introduced into 7 ml of diethyl ether at RT, 0.94 ml (2.83 mmol) of a 3N solution of methylmagnesium bromide in diethyl ether was added, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by preparative HPLC (RP18 column; mobile phase: acetonitrile-water gradient) to result in 257 mg (55% of theory) of the title compound.

$^1$H-NMR (400 MHz, DMSO-d$_6$): δ=0.96-1.07 (m, 1H), 1.13-1.20 (m, 0.4H), 1.21-1.27 (m, 0.6H), 1.44 (s, 1.2H), 1.50-1.56 (m, 0.4H), 1.52 (s, 1.8H), 1.67-1.73 (m, 0.6H), 1.97-2.04 (ddd, 1H), 5.21 (s, 0.6H), 5.23 (s, 0.4H), 7.35-7.43 (m, 2.4H), 7.49-7.55 (m, 1.6H).

Example 76A

1-Cyclopropyl-5-fluoro-2,3-dihydro-1H-inden-1-ol

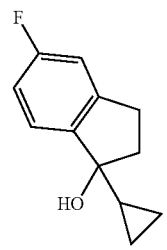

2.00 g (13.3 mmol) of 5-fluoro-1-indanone were introduced into 50 ml of diethyl ether at RT, 40 ml (20.0 mmol) of a 0.5N solution of cyclopropylmagnesium bromide in tetrahydrofuran were added, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient) to result in 2.22 g (87% of theory) of the title compound which were reacted without further purification.

$^1$H-NMR (400 MHz, DMSO-$d_6$): δ=0.24-0.36 (m, 4H), 1.00-1.09 (m, 1H), 1.97-2.05 (m, 1H), 2.08-2.16 (m, 1H), 2.70-2.80 (m, 1H), 2.83-2.92 (m, 1H), 4.79 (s, 1H), 6.94-7.07 (m, 2H), 7.28 (dd, 1H).

LC-MS (Method 3): $R_t$=1.69 min; MS (ESIpos): m/z=175 [M-OH]$^+$.

Example 77A

1-Cyclopropyl-1-(4-fluorophenyl)ethanol

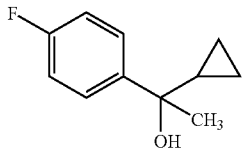

0.50 g (5.94 mmol) of acetylcyclopropane was dissolved at 0° C. in 5 ml of diethyl ether, and 8.9 ml (8.91 mmol) of a 1N solution of 4-fluorophenylmagnesium bromide in tetrahydrofuran were slowly added dropwise. Stirring at 0° C. for 1 h was followed by warming to RT, and the reaction solution was mixed with water and ethyl acetate, and the phases were separated. The organic phase was washed with saturated aqueous sodium chloride solution and dried over sodium sulfate, and the solvents were removed in vacuo. The crude product was purified by flash chromatography on silica gel (mobile phase: cyclohexane/ethyl acetate 10/1) to result in 0.99 g (93% of theory) of the title compound.

$^1$H-NMR (400 MHz, DMSO-$d_6$): δ=0.15-0.25 (m, 1H), 0.27-0.38 (m, 2H), 0.39-0.47 (m, 1H), 1.10-1.18 (m, 1H), 1.40 (s, 3H), 4.72 (s, 1H), 7.06-7.14 (m, 2H), 7.47-7.54 (m, 2H).

GC-MS (Method 7): $R_t$=3.96 min.

Example 78A

1-Cyclopropyl-1-(2,4-difluorophenyl)ethanol

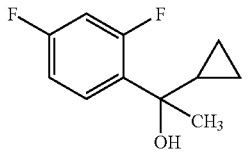

1.50 g (9.61 mmol) of 2',4'-difluoroacetophenone were dissolved at 0° C. in 8 ml of diethyl ether, and 38.4 ml (19.21 mmol) of a 0.5N solution of cyclopropylmagnesium bromide in tetrahydrofuran were slowly added dropwise. Stirring at 0° C. for 1 h was followed by warming to RT, and the reaction solution was mixed with water and ethyl acetate, and the phases were separated. The organic phase was washed with saturated aqueous sodium chloride solution and dried over sodium sulfate, and the solvents were removed in vacuo. The crude product was purified by preparative HPLC (mobile phase: acetonitrile-water gradient) to result in 0.63 g (33% of theory) of the title compound.

$^1$H-NMR (400 MHz, DMSO-$d_6$): δ=0.10-0.19 (m, 1H), 0.22-0.34 (m, 2H), 0.45-0.54 (m, 1H), 1.26-1.35 (m, 1H), 1.51 (s, 3H), 4.93 (s, 1H), 6.98-7.05 (m, 1H), 7.05-7.17 (m, 1H), 7.55-7.64 (m, 1H).

GC-MS (Method 7): $R_t$=3.61 min.

Example 79A 1-(4-Chloro-2-fluorophenyl)-1-cyclopropylethanol

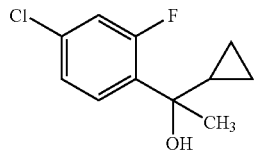

114.6 ml (57.31 mmol) of a 0.5N solution of cyclopropylmagnesium bromide in tetrahydrofuran were taken up at 0° C. in 23 ml of diethyl ether, and 4.95 g (28.65 mmol) of 4'-chloro-2'-fluoroacetophenone dissolved in 5 ml of diethyl ether were slowly added dropwise. Stirring at 0° C. for 1 h was followed by warming to RT, and the reaction solution was mixed with acetonitrile, water and a little kieselguhr, and the mixture was filtered through kieselguhr. The phases of the filtrate were separated and the aqueous phase was extracted twice with diethyl ether. The combined organic phases were washed with saturated aqueous sodium chloride solution and dried over sodium sulfate, and the solvents were removed in vacuo. The crude product was purified by preparative HPLC (mobile phase: acetonitrile-water gradient) to result in 4.30 g (70% of theory) of the title compound.

$^1$H-NMR (400 MHz, DMSO-$d_6$): δ=0.10-0.19 (m, 1H), 0.21-0.37 (m, 2H), 0.47-0.54 (m, 1H), 1.26-1.35 (m, 1H), 1.51 (d, 3H), 4.97 (s, 1H), 7.24 (dd, 1H), 7.32 (dd, 1H), 7.58 (t, 1H).

MS (ESIpos): m/z=197 [M-OH]$^+$.

Example 80A (4-Fluorophenyl)[4-(trifluoromethyl)phenyl]methanol

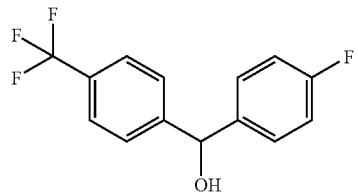

1.00 g (5.71 mmol) of 4-bromofluorobenzene were dissolved in 10 ml of tetrahydrofuran at −78° C. Addition of 2.2 ml (6.86 mmol) of a 1.6N solution of n-butyllithium in hexane was followed by stirring for 15 min, and then 1.26 g (6.86 mmol) of trifluoro-p-tolualdehyde dissolved in 10 ml of tetrahydrofuran were added dropwise. The mixture was stirred at −78° C. for 1 h and then at RT for 1 h. The reaction solution was mixed with water and dichloromethane, and the phases were separated. The aqueous phase was extracted with dichloromethane, and the combined organic phases were washed with saturated aqueous sodium chloride solution, dried over sodium sulfate and filtered, and the solvents were removed in vacuo. The crude product was purified by preparative HPLC (mobile phase: acetonitrile-water gradient). 1.02 g (66% of theory) of the title compound were obtained.

$^1$H-NMR (400 MHz, DMSO-$d_6$): δ=5.82 (d, 1H), 6.15 (d, 1H), 7.14 (t, 2H), 7.41 (dd, 2H), 7.59 (d, 2H), 7.67 (d, 2H).

LC-MS (Method 5): $R_t$=2.41 min; MS (ESIpos): m/z=271 [M+H]$^+$.

Example 81A (4-Chlorophenyl)(4-fluorophenyl)methanol

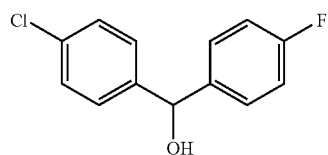

The title compound was prepared starting from 6.00 g (34.29 mmol) of 4-bromofluorobenzene and 5.78 g (41.14 mmol) of 4-chlorobenzaldehyde in analogy to the synthesis of the compound from Example 80A. 7.14 g (88% of theory) of the title compound were obtained.

$^1$H-NMR (400 MHz, DMSO-$d_6$): δ=5.72 (d, 1H), 6.03 (d, 1H), 7.08-7.16 (m, 2H), 7.33-7.41 (m, 6H).

LC-MS (Method 5): $R_t$=2.31 min; MS (ESIpos): m/z=219 [M-OH]$^+$.

Example 82A (4-Fluoro-2-methylphenyl)(4-fluorophenyl)methanol

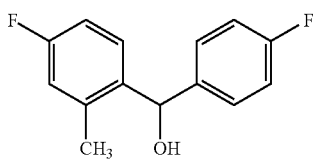

1.00 g (5.29 mmol) of 2-bromo-5-fluorotoluene were dissolved in 10 ml of tetrahydrofuran at −78° C. Addition of 4.0 ml (6.35 mmol) of a 1.6N solution of n-butyllithium in hexane was followed by stirring for 15 min, and then 0.79 g (6.35 mmol) of p-fluorobenzaldehyde dissolved in 10 ml of tetrahydrofuran was added dropwise. The mixture was warmed to RT and stirred for 1 h. The reaction solution was mixed with water and ethyl acetate, and the phases were separated. The aqueous phase was extracted three times with ethyl acetate, and the combined organic phases were washed with saturated aqueous sodium chloride solution. The solvents were removed in vacuo, and the crude product was purified by preparative HPLC (mobile phase: acetonitrile-water gradient). 0.56 g (43% of theory) of the title compound was obtained.

$^1$H-NMR (400 MHz, DMSO-$d_6$): δ=2.19 (s, 3H), 5.81 (d, 1H), 5.86 (d, 1H), 6.94-7.04 (m, 2H), 7.09-7.16 (m, 2H), 7.25-7.32 (m, 2H), 7.43 (dd, 1H).

LC-MS (Method 3): $R_t$=1.98 min; MS (ESIpos): m/z=217 [M-OH]$^+$.

Example 83A (4-Chloro-2-methylphenyl)(4-fluorophenyl)methanol

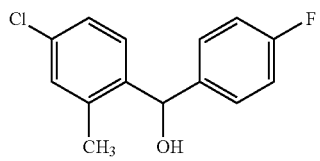

The title compound was prepared starting from 1.00 g (4.87 mmol) of 2-bromo-5-chlorotoluene and 0.72 g (5.84 mmol) of 4-fluorobenzaldehyde in analogy to the synthesis of the compound from Example 80A. 0.64 g (52% of theory) of the title compound was obtained.

$^1$H-NMR (400 MHz, DMSO-$d_6$): δ=2.17 (s, 3H), 5.81 (d, 1H), 5.91 (d, 1H), 7.09-7.16 (m, 2H), 7.19-7.22 (m, 1H), 7.24-7.31 (m, 3H), 7.46 (d, 1H).

LC-MS (Method 3): $R_t$=2.15 min; MS (ESIpos): m/z=233 [M-OH]$^+$.

Example 84A (2,4-Difluorophenyl)(4-fluorophenyl)methanol

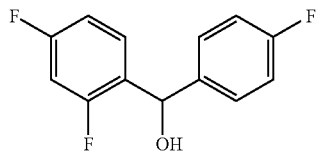

The title compound was prepared starting from 1.00 g (5.71 mmol) of 4-bromofluorobenzene and 0.97 g (6.86 mmol) of 2,4-difluorobenzaldehyde in analogy to the synthesis of the compound from Example 80A. 0.53 g (38% of theory) of the title compound was obtained.

$^1$H-NMR (400 MHz, DMSO-$d_6$): δ=5.90 (d, 1H), 6.10 (d, 1H), 7.05-7.19 (m, 4H), 7.31-7.38 (m, 2H), 7.53-7.60 (m, 1H).

LC-MS (Method 4): $R_t$=1.18 min; MS (ESIpos): m/z=221 [M-OH]$^+$.

Example 85A (4-Chloro-2-fluorophenyl)(4-fluorophenyl)methanol

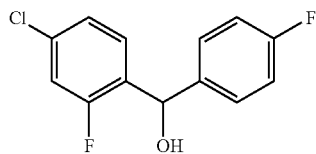

The title compound was prepared starting from 4.60 g (26.28 mmol) of 4-bromofluorobenzene and 5.00 g (31.53 mmol) of 4-chloro-2-fluorobenzaldehyde in analogy to the synthesis of the compound from Example 80A. 4.45 g (66% of theory) of the title compound were obtained.

$^1$H-NMR (400 MHz, DMSO-d$_6$): δ=5.90 (d, 1H), 6.15 (d, 1H), 7.10-7.17 (m, 2H), 7.28-7.38 (m, 4H), 7.57 (t, 1H).

LC-MS (Method 5): R$_t$=2.41 min; MS (ESIpos): m/z=237 [M-OH]$^+$.

Example 86A

7-[(Methylsulfonyl)methyl]-1H-indole

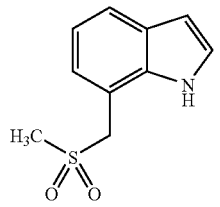

36.7 g (149 mmol) of 70% pure meta-chloroperbenzoic acid were added to 12.0 g (67.7 mmol) of the compound from Example 8A in 800 ml of tetrahydrofuran at 0° C., and the mixture was stirred at RT for 15 min. Addition of 100 ml of a saturated aqueous sodium sulfite solution was followed by extraction with ethyl acetate several times. The combined organic phases were washed five times with saturated aqueous sodium bicarbonate solution, dried over magnesium sulfate, filtered and concentrated. 11.0 g (75% of theory) of the title compound were obtained.

$^1$H-NMR (400 MHz, DMSO-d$_6$) δ=11.2 (s, 1H), 7.57 (d, 1H), 7.41 (t, 1H), 7.14 (d, 1H), 7.03 (t, 1H), 6.48 (dd, 1H), 4.76 (s, 2H), 2.88 (s, 3H).

LC-MS (Method 9): R$_t$=0.74 min; MS (ESIpos): m/z=210 [M+H]$^+$.

Example 87A

5-Fluoro-7-[(methylsulfonyl)methyl]-1H-indole

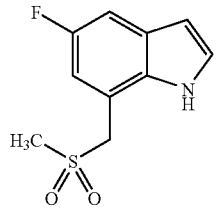

35.4 g (143 mmol) of 70% pure meta-chloroperbenzoic acid were added in 5 portions to 14.0 g (71.7 mmol) of the compound from Example 11A in 700 ml of tetrahydrofuran at 0° C., and the mixture was stirred at RT for 30 min. The reaction mixture was added to saturated aqueous sodium bicarbonate solution, the aqueous phase was extracted four times with dichloromethane, and the combined organic phases were washed with water and saturated aqueous sodium chloride solution, dried over sodium sulfate, filtered and concentrated. 15.7 g (84% of theory) of the title compound were obtained.

$^1$H-NMR (400 MHz, DMSO-d$_6$) δ=11.3 (s, 1H), 7.50 (t, 1H), 7.35 (dd, 1H), 7.02 (dd, 1H), 6.48 (dd, 1H), 4.78 (s, 2H), 2.91 (s, 3H).

LC-MS (Method 6): R$_t$=1.59 min; MS (ESIneg): m/z=226 [M-H]$^-$.

Example 88A

Ethyl 3-hydroxy-3-[4-(trifluoromethyl)phenyl]butanoate

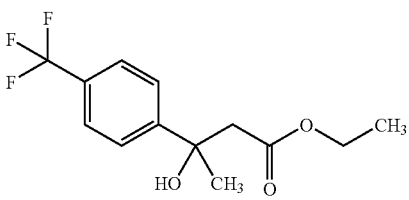

19.9 ml (31.89 mmol) of a 1.6N solution of n-butyllithium in hexane were added dropwise to a solution of 6.7 ml (31.89 mmol) of hexamethyldisilazane in 50 ml of tetrahydrofuran at 0° C., and the mixture was stirred for 15 min and then cooled to −78° C. 3.12 ml (31.89 mmol) of ethyl acetate were added, the mixture was stirred for 1 h and, after addition of 5.00 g (26.57 mmol) of 4-trifluoromethylacetophenone, dissolved in 20 ml of tetrahydrofuran, stirred at −78° C. for a further hour. 1N hydrochloric acid was added to the reaction solution, and the phases were separated. The aqueous phase was extracted with ethyl acetate, and the combined organic phases were dried over sodium sulfate, filtered and concentrated. The crude product was purified by flash chromatography on silica gel (mobile phase: cyclohexane/ethyl acetate 8/2) to result in 7.14 g (97% of theory) of the title compound.

$^1$H-NMR (400 MHz, DMSO-d$_6$) δ=7.62-7.70 (m, 4H), 5.49 (s, 1H), 3.90 (q, 2H), 2.78 (q, 2H), 1.55 (s, 3H), 1.00 (t, 3H).

Example 89A

3-[4-(Trifluoromethyl)phenyl]butane-1,3-diol

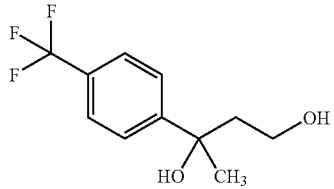

7.00 g (25.34 mmol) of the compound from Example 88A, dissolved in 150 ml of tetrahydrofuran, were added dropwise to 76.0 ml (76.0 mmol) of a 1N solution of diisobutylaluminum hydride in dichloromethane in 250 ml of tetrahydrofuran, and the reaction mixture was stirred at room temperature for 3 h. After addition of 1N hydrochloric acid, the phases were separated, the aqueous phase was extracted with dichloromethane, and the combined organic phases were washed with saturated aqueous sodium chloride solution. Drying over sodium sulfate and filtration was followed by removal of the solvents in a rotary evaporator. The crude product was purified by flash chromatography on silica gel (mobile phase: dichloromethane/methanol gradient) to result in 5.55 g (91% purity, 85% of theory) of the title compound.

¹H-NMR (400 MHz, DMSO-d₆) δ=7.61-7.69 (m, 4H), 5.22 (s, 1H), 4.36-4.41 (m, 1H), 3.37-3.47 (m, 1H), 3.17-3.26 (m, 1H), 1.93 (t, 2H), 1.44 (s, 3H).

Example 90A

Ethyl 3-(4-chlorophenyl)-3-cyclopropyl-3-hydroxypropanoate

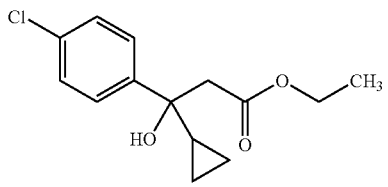

13.8 ml (22.14 mmol) of a 1.6N solution of n-butyllithium in hexane were added dropwise to a solution of 4.7 ml (22.14 mmol) of hexamethyldisilazane in 17 ml of tetrahydrofuran at −20° C., and the mixture was stirred at 0° C. for 30 min and then cooled again to −78° C. 2.17 ml (22.14 mmol) of ethyl acetate were added, and the mixture was stirred for 30 min and, after addition of 2.00 g (11.07 mmol) of 4-chlorophenyl cyclopropyl ketone, dissolved in 17 ml of tetrahydrofuran, stirred at −78° C. for a further hour. The reaction solution was mixed with 1N hydrochloric acid and ethyl acetate, and the phases were separated. The organic phase was washed successively with 0.5N hydrochloric acid, water and saturated aqueous sodium chloride solution, dried over sodium sulfate, filtered and concentrated. After purification of the crude product by preparative HPLC (mobile phase: acetonitrile/water gradient) the acetonitrile was removed in a rotary evaporator, and the aqueous phase was extracted several times with diethyl ether. The combined organic phases were washed with saturated aqueous sodium chloride solution, dried over sodium sulfate, filtered and concentrated. 2.54 g (99% of theory) of the title compound were obtained.

¹H-NMR (400 MHz, DMSO-d₆) δ=7.50 (d, 2H), 7.34 (d, 2H), 4.90 (s, 1H), 3.88 (q, 2H), 2.92 (d, 1H), 2.78 (d, 1H), 1.34-1.43 (m, 1H), 1.00 (t, 3H), 0.48-0.56 (m, 1H), 0.13-0.39 (m, 3H).

Example 91A

Ethyl 3-(2,3-dihydro-1,4-benzodioxin-6-yl)-3-hydroxybutanoate

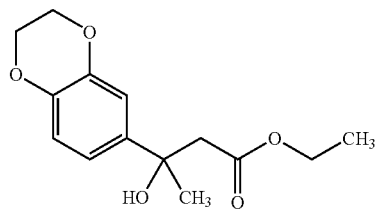

The title compound was prepared starting from 2.00 g (11.22 mmol) of 1,4-benzodioxan-6-yl methyl ketone and 4.74 ml (22.45 mmol) of ethyl acetate in analogy to the synthesis of the compound from Example 90A. 2.52 g (84% of theory) of the title compound were obtained.

¹H-NMR (400 MHz, DMSO-d₆) δ=6.91 (d, 1H), 6.85 (dd, 1H), 6.74 (d, 1H), 5.12 (s, 1H), 4.20 (s, 4H), 3.94 (q, 2H), 2.65 (s, 2H), 1.48 (s, 3H), 1.06 (t, 3H).

Example 92A

5-[(4-Chloro-2-methylphenyl){5-fluoro-7-[(methylsulfanyl)methyl]-1H-indol-3-yl}methyl]-2,2-dimethyl-1,3-dioxane-4,6-dione

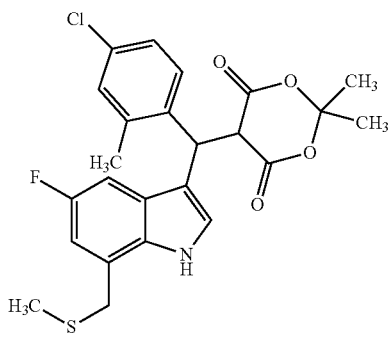

0.68 g (4.41 mmol) of 4-chloro-2-methylbenzaldehyde, 0.64 g (4.41 mmol) of Meldrum's acid and 24.0 mg (0.21 mmol) of D,L-proline were added to a solution of 1.00 g of the compound from Example 11A with a purity of 82% (4.20 mmol) in 35 ml of acetonitrile. The reaction mixture was stirred at RT overnight. It was concentrated, and the residue was taken up in ethyl acetate, washed with 1N hydrochloric acid, saturated aqueous sodium bicarbonate solution and water, dried over magnesium sulfate, filtered and concentrated. 2.40 g of the title compound were obtained and were reacted without further purification.

LC-MS (Method 5): R_t=3.03 min; MS (ESIneg): m/z=474 [M−H]⁻.

Example 93A 5-([2-Chloro-4-(trifluoromethyl)phenyl]{7-[(methylsulfanyl)methyl]-1H-indol-3-yl}methyl)-2,2-dimethyl-1,3-dioxane-4,6-dione

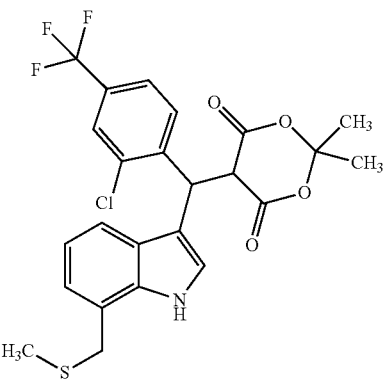

1.50 g (7.19 mmol) of 2-chloro-4-(trifluoromethyl)benzaldehyde, 1.04 g (7.19 mmol) of Meldrum's acid and 39.4 mg (0.34 mmol) of D,L-proline were added to a solution of 1.21 g (6.85 mmol) of the compound from Example 8A in 57 ml of acetonitrile. The reaction mixture was stirred at RT overnight. It was concentrated, and the residue was taken up in diethyl ether and again concentrated. 3.64 g (75% of theory, 72% purity) of the title compound were obtained and were reacted without further purification.

LC-MS (Method 4): $R_t$=1.50 min; MS (ESIneg): m/z=510 [M−H]⁻.

Example 94A 2,2-Dimethyl-5-[(4-methylphenyl){7-[(methylsulfanyl)methyl]-1H-indol-3-yl}methyl]-1,3-dioxane-4,6-dione

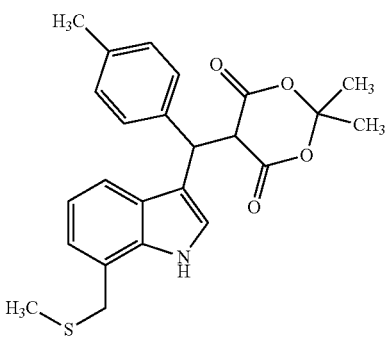

1.28 g (10.7 mmol) of 4-methylbenzaldehyde, 1.54 g (10.7 mmol) of Meldrum's acid and 58.0 mg (0.51 mmol) of D,L-proline were added to a solution of 2.00 g (10.2 mmol) of the compound from Example 8A in 80 ml of acetonitrile. The reaction mixture was stirred at RT overnight. It was concentrated, and the residue was taken up in ethyl acetate, washed with 1N hydrochloric acid, saturated aqueous sodium bicarbonate solution and water, dried over magnesium sulfate, filtered and concentrated. 4.34 g of the title compound were obtained and were reacted without further purification.

LC-MS (Method 5): $R_t$=2.70 min; MS (ESIneg): m/z=422 [M−H]⁻.

Example 95A

5-[(4-Chloro-3-fluorophenyl){7-[(methylsulfanyl)methyl]-1H-indol-3-yl}methyl]-2,2-dimethyl-1,3-dioxane-4,6-dione

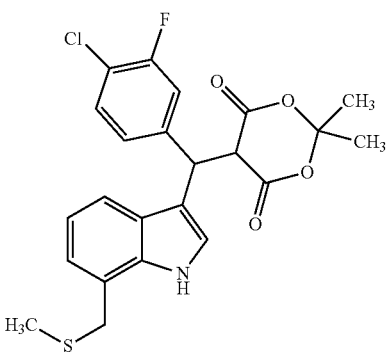

1.34 g (8.46 mmol) of 4-chloro-3-fluorobenzaldehyde, 1.22 g (8.46 mmol) of Meldrum's acid and 0.05 g (0.42 mmol) of D,L-proline were added to a solution of 1.50 g (8.46 mmol) of the compound from Example 8A in 12 ml of acetonitrile. The reaction mixture was stirred at RT overnight. The precipitated solid was filtered off with suction, washed with acetonitrile and dried under high vacuum. 2.42 g (98% of theory) of the title compound were obtained.

¹H-NMR (400 MHz, DMSO-d₆): δ=1.62 (s, 3H), 1.85 (s, 3H), 1.96 (s, 3H), 3.95 (q, 2H), 5.31-5.42 (m, 2H), 6.88 (t, 1H), 6.97 (d, 1H), 7.12-7.19 (m, 3H), 7.33 (d, 1H), 7.45 (t, 1H), 11.1 (s, 1H).

HPLC (Method 2): $R_t$=4.99 min; MS (ESIneg): m/z=460 [M−H]⁻.

Example 96A

5-[(4-Chloro-2,6-difluorophenyl){7-[(methylsulfanyl)methyl]-1H-indol-3-yl}methyl]-2,2-dimethyl-1,3-dioxane-4,6-dione

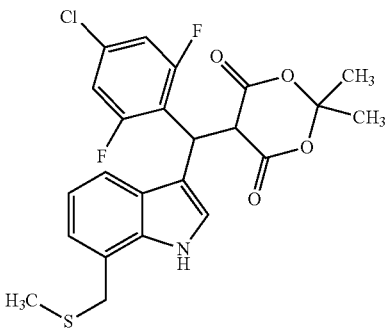

1.64 g (9.31 mmol) of 4-chloro-2,4-difluorobenzaldehyde, 1.22 g (8.46 mmol) of Meldrum's acid and 0.05 g (0.42 mmol) of D,L-proline were added to a solution of 1.50 g (8.46 mmol) of the compound from Example 8A in 12 ml of acetonitrile. The reaction mixture was stirred at RT overnight. The crude product was purified by preparative HPLC (mobile phase: acetonitrile/water gradient) to afford 1.61 g (36% of theory) of the title compound.

¹H-NMR (400 MHz, DMSO-d₆): δ=1.71 (s, 3H), 1.89 (s, 3H), 1.95 (s, 3H), 3.92 (s, 2H), 5.03 (d, 1H), 5.33 (d, 1H), 6.88-6.98 (m, 2H), 7.23-7.32 (m, 4H), 11.0 (s, 1H).

HPLC (Method 2): $R_t$=4.77 min; MS (ESIneg): m/z=478 [M−H]⁻.

Example 97A

5-[(2,2-Difluoro-1,3-benzodioxol-5-yl){7-[(methylsulfanyl)methyl]-1H-indol-3-yl}methyl]-2,2-dimethyl-1,3-dioxane-4,6-dione

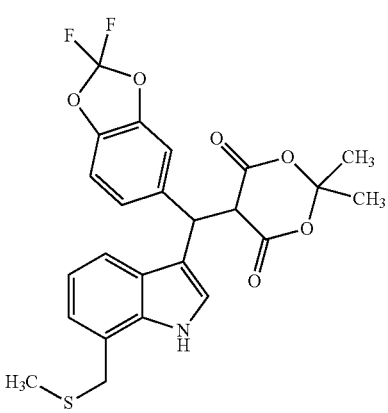

1.57 g (8.46 mmol) of 2,2-difluoro-1,3-benzodioxole-5-carbaldehyde, 1.22 g (8.46 mmol) of Meldrum's acid and 0.05 g (0.42 mmol) of D,L-proline were added to a solution of 1.50 g (8.46 mmol) of the compound from Example 8A in 12 ml of acetonitrile. The reaction mixture was stirred at RT overnight. The precipitated solid was filtered off with suction, washed with acetonitrile and dried under high vacuum. 2.67 g (91% of theory) of the title compound were obtained.

$^1$H-NMR (400 MHz, DMSO-$d_6$): δ=1.61 (s, 3H), 1.85 (s, 3H), 1.96 (s, 3H), 3.95 (q, 2H), 5.29 (d, 1H), 5.39-5.44 (m, 1H), 6.87 (t, 1H), 6.97 (d, 1H), 7.11-7.35 (m, 5H), 11.1 (s, 1H).

HPLC (Method 1): $R_t$=4.99 min; MS (ESIneg): m/z=488 [M−H]⁻.

Example 98A

Ethyl 3-(4-chloro-2-methylphenyl)-3-{5-fluoro-7-[(methylsulfanyl)methyl]-1H-indol-3-yl}propanoate

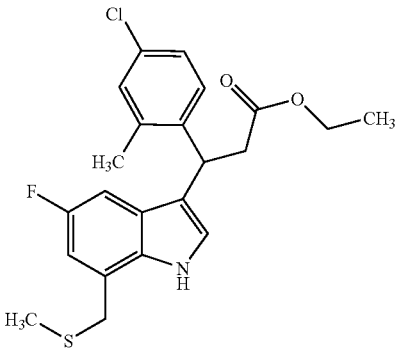

2.1 mg (34 μmol) of copper powder were added to a solution of 2.48 g of the compound from Example 92A in 28 ml of pyridine and 8 ml of ethanol. The reaction mixture was heated under reflux for 1 h. It was concentrated, and the crude product was purified by flash chromatography on silica gel (mobile phase: cyclohexane/ethyl acetate gradient) to result in 0.69 g of the title compound.

$^1$H-NMR (400 MHz, DMSO-$d_6$) δ=11.1 (s, 1H), 7.22-7.29 (m, 3H), 7.15 (dd, 1H), 6.80-6.89 (m, 2H), 4.75 (t, 1H), 3.96 (q, 2H), 3.91 (s, 2H), 3.11 (dd, 1H), 2.99 (dd, 1H), 2.42 (s, 3H), 1.95 (s, 3H), 1.04 (t, 3H).

LC-MS (Method 3): $R_t$=2.65 min; MS (ESIneg): m/z=418 [M−H]⁻.

Example 99A

Ethyl 3-[2-chloro-4-(trifluoromethyl)phenyl]-3-{7-[(methylsulfanyl)methyl]-1H-indol-3-yl}propanoate

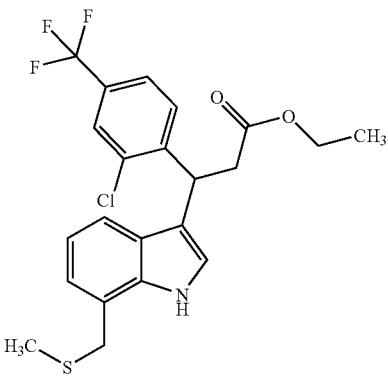

2.8 mg (45 μmol) of copper powder were added to a solution of 3.64 g (approx. 5.12 mmol, 72% purity) of the compound from Example 93A in 41 ml of pyridine and 10 ml of ethanol. The reaction mixture was heated under reflux overnight. It was concentrated, and the crude product was purified by preparative HPLC (RP18 column; mobile phase: acetonitrile/water gradient) to result in 1.34 g (57% of theory) of the title compound.

$^1$H-NMR (400 MHz, DMSO-$d_6$) δ=11.1 (s, 1H), 7.84 (s, 1H), 7.58-7.66 (m, 2H), 7.37 (d, 1H), 7.28 (d, 1H), 6.95 (d, 1H), 6.88 (t, 1H), 5.19 (t, 1H), 3.98 (q, 2H), 3.91 (s, 2H), 3.21 (dd, 1H), 3.13 (dd, 1H), 1.94 (s, 3H), 1.05 (t, 3H).

LC-MS (Method 4): $R_t$=1.62 min; MS (ESIpos): m/z=456 [M+H]⁺.

Example 100A

Ethyl 3-(4-methylphenyl)-3-{7-[(methylsulfanyl)methyl]-1H-indol-3-yl}propanoate

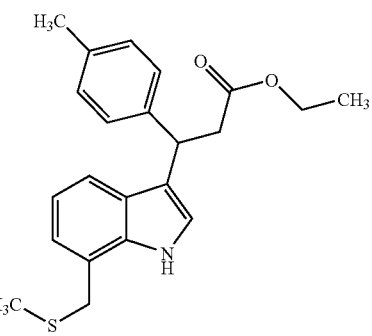

6.5 mg (102 μmol) of copper powder were added to a solution of 4.34 g of the compound from Example 94A in 75 ml of pyridine and 20 ml of ethanol. The reaction mixture was heated under reflux for 1 h. It was concentrated, and the crude product was purified by flash chromatography on silica gel (mobile phase: toluene/ethyl acetate gradient) to result in 2.55 g of the title compound.

$^1$H-NMR (400 MHz, DMSO-$d_6$) δ=10.9 (s, 1H), 7.29 (d, 1H), 7.19-7.27 (m, 3H), 7.01-7.06 (m, 2H), 6.90 (d, 1H), 6.80-6.85 (m, 1H), 4.57 (t, 1H), 3.90-4.00 (m, 2H), 3.90 (s, 2H), 3.13 (dd, 1H), 3.00 (dd, 1H), 2.21 (s, 3H), 1.93 (s, 3H), 1.05 (t, 3H).

LC-MS (Method 3): $R_t$=2.49 min; MS (ESIneg): m/z=366 [M−H]⁻.

Example 101A

Ethyl 3-(4-chloro-3-fluorophenyl)-3-{7-[(methylsulfanyl)methyl]-1H-indol-3-yl}propanoate

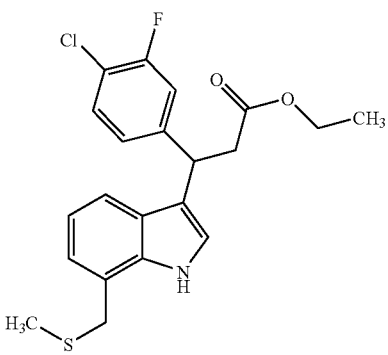

17 mg (262 µmol) of copper powder were added to a solution of 2.42 g (5.24 mmol) of the compound from Example 95A in 10 ml of pyridine and 2 ml of ethanol. The reaction mixture was heated under reflux for 4 h. It was concentrated, and the crude product was purified by preparative HPLC (mobile phase: acetonitrile/water gradient) to result in 1.82 g (85% of theory) of the title compound.

$^1$H-NMR (400 MHz, DMSO-$d_6$): δ=1.05 (t, 3H), 1.93 (s, 3H), 3.06-3.22 (m, 2H), 3.90 (s, 2H), 3.97 (q, 2H), 4.66 (t, 1H), 6.86 (t, 1H), 6.93 (d, 1H), 7.25 (dd, 1H), 7.33 (d, 1H), 7.36-7.46 (m, 3H), 11.0 (s, 1H).

HPLC (Method 1): $R_t$=5.11 min; MS (ESIpos): m/z=406 [M+H]$^+$.

Example 102A

Ethyl 3-(4-chloro-2,6-difluorophenyl)-3-{7-[(methylsulfanyl)methyl]-1H-indol-3-yl}propanoate

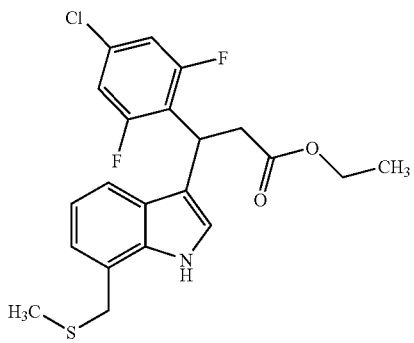

11 mg (166 µmol) of copper powder were added to a solution of 1.60 g (3.33 mmol) of the compound from Example 96A in 6 ml of pyridine and 1.3 ml of ethanol. The reaction mixture was heated under reflux for 4 h. It was concentrated, and the crude product was purified firstly by flash chromatography on silica gel (mobile phase: cyclohexane/ethyl acetate 5/1) and then by preparative HPLC (mobile phase: acetonitrile/water gradient). 1.15 g (81% of theory) of the title compound were obtained.

$^1$H-NMR (400 MHz, DMSO-$d_6$): δ=1.06 (t, 3H), 1.93 (s, 3H), 3.25-3.34 (m, 2H), 3.91 (s, 2H), 3.99 (q, 2H), 4.97 (t, 1H), 6.87-6.97 (m, 2H), 7.22-7.34 (m, 4H), 11.1 (s, 1H).

HPLC (Method 1): $R_t$=4.97 min; MS (ESIpos): m/z=424 [M+H]$^+$.

Example 103A

Ethyl 3-(2,2-difluoro-1,3-benzodioxol-5-yl)-3-{7-[(methylsulfanyl)methyl]-1H-indol-3-yl}propanoate

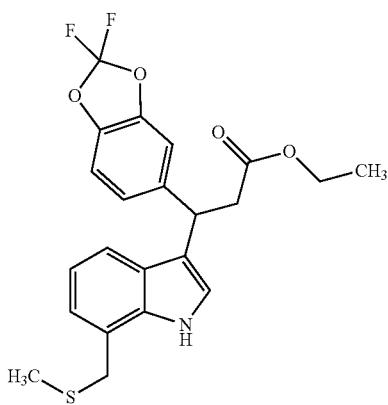

17 mg (271 µmol) of copper powder were added to a solution of 2.66 g (5.43 mmol) of the compound from Example 97A in 10 ml of pyridine and 2 ml of ethanol. The reaction mixture was heated under reflux for 4 h. It was concentrated, and the crude product was purified firstly by flash chromatography on silica gel (mobile phase: cyclohexane/ethyl acetate gradient) and then by preparative HPLC (mobile phase: acetonitrile/water gradient). 1.73 g (74% of theory) of the title compound were obtained.

$^1$H-NMR (400 MHz, DMSO-$d_6$): δ=1.04 (t, 3H), 1.93 (s, 3H), 3.05-3.22 (m, 2H), 3.90 (s, 2H), 3.96 (q, 2H), 4.67 (t, 1H), 6.86 (t, 1H), 6.93 (d, 1H), 7.21-7.28 (m, 2H), 7.32-7.39 (m, 2H), 7.44 (d, 1H), 11.1 (s, 1H).

HPLC (Method 1): $R_t$=5.09 min; MS (ESIpos): m/z=434 [M+H]$^+$.

Example 104A

Ethyl 3-(4-chlorophenyl)-3-{7-[(methylsulfanyl)methyl]-1H-indol-3-yl}butanoate

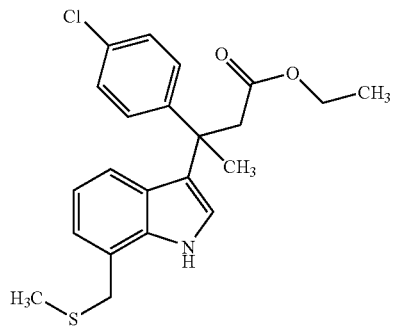

3.42 g (14.10 mmol) of ethyl 3-(4-chlorophenyl)-3-hydroxybutanoate (preparation in analogy to the synthesis of Example 88A starting from 4-chloroacetophenone and ethyl acetate) and 3.12 g (14.10 mmol) of indium(III) chloride were added to 2.50 g (14.10 mmol) of the compound from Example 8A in 100 ml of toluene. The reaction mixture was stirred at 80° C. for 5 h. After cooling to RT, the reaction solution was mixed with water and ethyl acetate, and the solid was filtered off. The phases of the filtrate were separated, and the aqueous phase was extracted with ethyl acetate. The combined organic phases were dried over sodium sulfate, filtered and concentrated. Purification of the crude product by flash chromatography on silica gel (mobile phase: dichloromethane/methanol 95/5) and then by preparative HPLC (mobile phase: acetonitrile/water gradient) resulted in 0.98 g (17% of theory) of the title compound.

$^1$H-NMR (400 MHz, DMSO-$d_6$): δ=0.84 (t, 3H), 1.84 (s, 3H), 1.95 (s, 3H), 3.16 (s, 2H), 3.72-3.85 (m, 2H), 3.91 (s, 2H), 6.67-6.75 (m, 2H), 6.87 (dd, 1H), 7.26-7.31 (m, 5H), 11.0 (s, 1H).

LC-MS (Method 3): $R_t$=2.60 min; MS (ESIpos): m/z=400 [M−H]$^-$.

Example 105A

Ethyl 3-(4-chlorophenyl)-3-cyclopropyl-3-{7-[(methylsulfanyl)methyl]-1H-indol-3-yl}propanoate

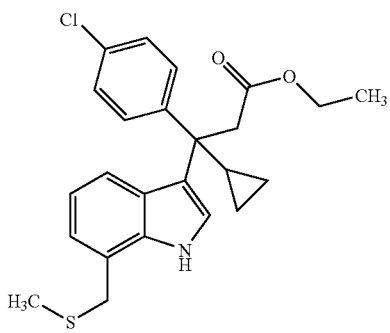

700 mg (2.61 mmol) of the compound from Example 90A and 576 mg (2.61 mmol) of indium(III) chloride were added to 462 mg (2.61 mmol) of the compound from Example 8A in 11 ml of toluene. The reaction mixture was stirred at 80° C. for 5 h. After cooling to RT, the solid was filtered off through silica gel, and the solvents were removed in a rotary evaporator. Purification of the crude product by preparative HPLC (mobile phase: acetonitrile/water gradient) resulted in 69 mg (6% of theory) of the title compound.

$^1$H-NMR (400 MHz, DMSO-$d_6$): δ=−0.16-−0.10 (m, 2H), 0.40-0.49 (m, 2H), 0.78 (t, 3H), 1.96 (s, 3H), 2.01-2.10 (m, 1H), 3.19 (m, 1H), 3.28-3.33 (m, 1H), 3.69-3.79 (m, 2H), 3.90 (q, 2H), 6.37 (d, 1H), 6.61 (t, 1H), 6.82 (d, 1H), 7.27-7.41 (m, 5H), 11.0 (s, 1H).

HPLC (Method 1): $R_t$=5.11 min; MS (ESIpos): m/z=428 [M+H]$^+$.

Example 106A

Ethyl 3-(2,3-dihydro-1,4-benzodioxin-6-yl)-3-{7-[(methylsulfanyl)methyl]-1H-indol-3-yl}butanoate

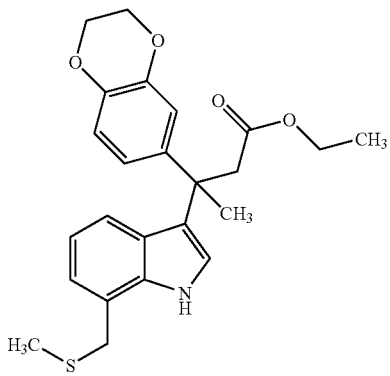

600 mg (2.25 mmol) of the compound from Example 91A and 0.21 ml (2.70 mmol) of trifluoroacetic acid were added to 399 mg (2.25 mmol) of the compound from Example 8A in 4 ml of dichloromethane. The reaction mixture was stirred at RT for 30 min. Purification of the crude product by preparative HPLC (mobile phase: acetonitrile/water gradient) resulted in 576 mg (60% of theory) of the title compound.

$^1$H-NMR (400 MHz, DMSO-$d_6$): δ=0.83 (t, 3H), 1.80 (s, 3H), 1.96 (s, 3H), 309 (q, 2H), 3.71-3.84 (m, 2H), 3.92 (s, 2H), 4.16 (s, 4H), 6.67-6.74 (m, 4H), 6.82 (d, 1H), 6.87 (d, 1H), 7.24 (d, 1H), 10.9 (s, 1H).

HPLC (Method 2): $R_t$=4.69 min; MS (ESIpos): m/z=426 [M+H]$^+$.

Example 107A 3-(4-Chloro-2-methylphenyl)-3-{5-fluoro-7-[(methylsulfanyl)methyl]-1H-indol-3-yl}propyl methanesulfonate

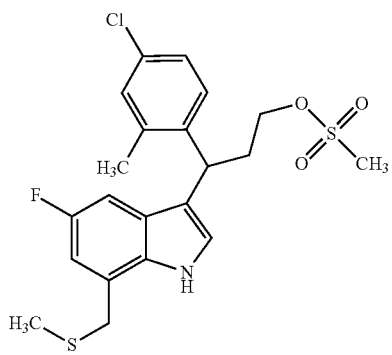

512 mg (1.36 mmol) of the compound from Example 132 in 25 ml of dichloromethane were mixed with 0.32 ml (2.30 mmol) of triethylamine and 16.6 mg (0.13 mmol) of 4-N,N-dimethylaminopyridine and stirred at RT for 15 min. Then 0.16 ml (2.03 mmol) of methanesulfonyl chloride was added, and the mixture was stirred at RT for 4 h. It was diluted with dichloromethane, washed with saturated aqueous sodium bicarbonate solution and water, dried over magnesium sulfate, filtered and concentrated. 608 mg (98% of theory) of the title compound were obtained and were reacted further directly without further purification.

LC-MS (Method 4): $R_t$=1.45 min; MS (ESIpos): m/z=456 [M+H]$^+$.

Example 108A

3-[2-Chloro-4-(trifluoromethyl)phenyl]-3-{7-[(methylsulfanyl)methyl]-1H-indol-3-yl}propyl methanesulfonate

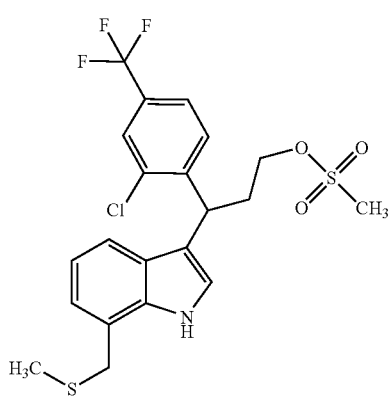

560 mg (1.35 mmol) of the compound from Example 133 in 22 ml of dichloromethane were mixed with 0.32 ml (2.30 mmol) of triethylamine and 16.5 mg (0.14 mmol) of 4-N,N-dimethylaminopyridine and stirred at RT for 15 min. Then 0.16 ml (2.03 mmol) of methanesulfonyl chloride was added, and the mixture was stirred at RT for 4 h. It was diluted with dichloromethane, washed with 1N hydrochloric acid, water and saturated aqueous sodium chloride solution, dried over magnesium sulfate, filtered and concentrated. 664 mg (100% of theory) of the title compound were obtained and were reacted further directly without further purification.

LC-MS (Method 5): $R_t$=2.84 min; MS (ESIpos): m/z=492 [M+H]$^+$.

Example 109A 3-(4-Methylphenyl)-3-{7-[(methylsulfanyl)methyl]-1H-indol-3-yl}propyl methanesulfonate

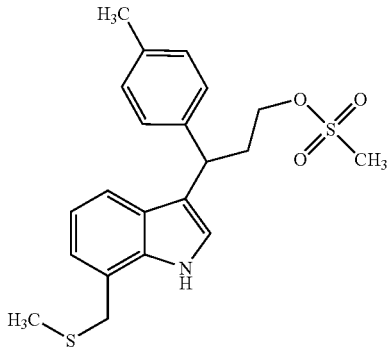

1.77 g (5.44 mmol) of the compound from Example 134 in 100 ml of dichloromethane were mixed with 1.3 ml (9.25 mmol) of triethylamine and 66.4 mg (0.54 mmol) of 4-N,N-dimethylaminopyridine and stirred at RT for 15 min. Then 0.63 ml (8.16 mmol) of methanesulfonyl chloride was added, and the mixture was stirred at RT for 4 h. It was diluted with dichloromethane, washed with saturated aqueous sodium bicarbonate solution and water, dried over magnesium sulfate, filtered and concentrated. 2.08 g (95% of theory) of the title compound were obtained and were reacted further directly without further purification.

$^1$H-NMR (400 MHz, DMSO-d$_6$) δ=11.0 (s, 1H), 7.34 (d, 1H), 7.28 (d, 1H), 7.21-7.26 (m, 2H), 7.04-7.10 (m, 2H), 6.91 (d, 1H), 6.83 (t, 1H), 4.26 (t, 1H), 4.07-4.19 (m, 2H), 3.91 (s, 2H), 3.10 (s, 3H), 2.48-2.60 (m, 1H), 2.31-2.44 (m, 1H), 2.22 (s, 3H), 1.93 (s, 3H).

LC-MS (Method 3): $R_t$=2.29 min; MS (ESIpos): m/z=404 [M+H]$^+$.

Example 110A 3-(4-Chloro-3-fluorophenyl)-3-{7-[(methylsulfanyl)methyl]-1H-indol-3-yl}propyl methanesulfonate

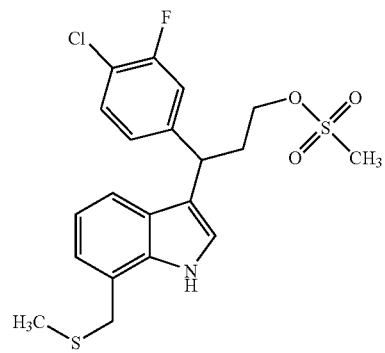

0.52 ml (3.70 mmol) of triethylamine, 0.04 g (0.28 mmol) of 4-N,N-dimethylaminopyridine and 0.24 ml (3.13 mmol) of methanesulfonyl chloride were added to 1.03 g (2.84 mmol) of the compound from Example 135 in 35 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 1.30 g of the title compound were obtained as crude product and were reacted further without purification.

LC-MS (Method 5): $R_t$=2.68 min; MS (ESIneg): m/z=440 [M-H]$^-$.

Example 111A 3-(4-Chloro-2,6-difluorophenyl)-3-{7-[(methylsulfanyl)methyl]-1H-indol-3-yl}propyl methanesulfonate

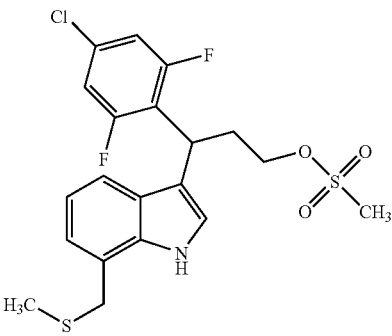

0.40 ml (2.89 mmol) of triethylamine, 0.03 g (0.22 mmol) of 4-N,N-dimethylaminopyridine and 0.194 ml (2.45 mmol) of methanesulfonyl chloride were added to 0.85 g (2.23 mmol) of the compound from Example 136 in 28 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 1.05 g of the title compound were obtained as crude product and were reacted further without purification.

LC-MS (Method 9): $R_t$=1.24 min; MS (ESIneg): m/z=458 [M-H]$^-$.

Example 112A 3-(2,2-Difluoro-1,3-benzodioxol-5-yl)-3-{7-[(methylsulfanyl)methyl]-1H-indol-3-yl}propyl methanesulfonate

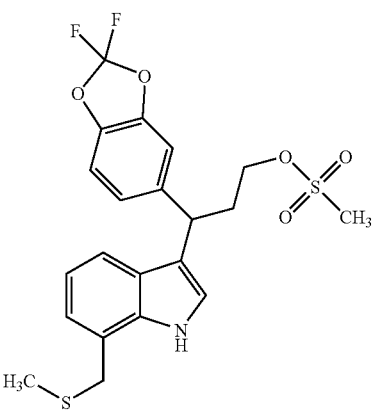

0.49 ml (3.52 mmol) of triethylamine, 0.03 g (0.27 mmol) of 4-N,N-dimethylaminopyridine and 0.23 ml (2.98 mmol) of methanesulfonyl chloride were added to 1.06 g (2.71 mmol) of the compound from Example 137 in 33 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 1.35 g of the title compound were obtained as crude product and were reacted further without purification.

LC-MS (Method 3): $R_t$=2.38 min; MS (ESIneg): m/z=468 [M−H]⁻.

Example 113A

3-{7-[(Methylsulfanyl)methyl]-1H-indol-3-yl}-3-[4-(trifluoromethyl)phenyl]butyl methanesulfonate

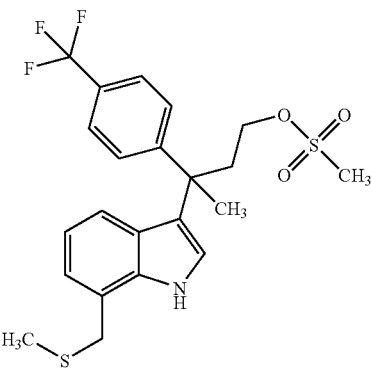

0.07 ml (0.52 mmol) of triethylamine, 4 mg (0.03 mmol) of 4-N,N-dimethylaminopyridine and 0.03 ml (0.38 mmol) of methanesulfonyl chloride were added to 135 mg (0.34 mmol) of the compound from Example 138 in 10 ml of dichloromethane. The reaction mixture was stirred at RT for 1 h, water was added, and the solvents were removed in a rotary evaporator. The crude product was purified by preparative HPLC (mobile phase: acetonitrile/water gradient) to result in 118 mg (73% of theory) of the title compound.

LC-MS (Method 4): $R_t$=1.48 min; MS (ESIneg): m/z=470 [M−H]⁻.

Example 114A 3-(4-Chlorophenyl)-3-{7-[(methylsulfanyl)methyl]-1H-indol-3-yl}butyl methanesulfonate

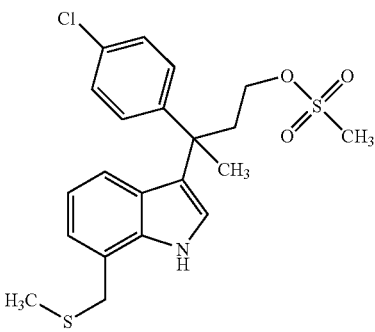

0.23 ml (1.65 mmol) of triethylamine, 13 mg (0.11 mmol) of 4-N,N-dimethylaminopyridine and 0.09 ml (1.21 mmol) of methanesulfonyl chloride were added to 395 mg (1.10 mmol) of the compound from Example 139 in 30 ml of dichloromethane. The reaction mixture was stirred at RT for 1 h, water was added, and the solvents were removed in a rotary evaporator. The crude product was purified by preparative HPLC (mobile phase: acetonitrile/water gradient) to result in 439 mg (73% of theory) of the title compound.

¹H-NMR (400 MHz, DMSO-$d_6$): δ=1.70 (s, 3H), 1.97 (s, 3H), 2.50-2.72 (m, 2H), 3.04 (s, 2H), 3.88-4.08 (m, 4H), 6.69-6.77 (m, 2H), 6.89 (dd, 1H), 7.26-7.37 (m, 5H), 11.0 (s, 1H).

LC-MS (Method 4): $R_t$=1.44 min; MS (ESIneg): m/z=436 [M−H]⁻.

Example 115A 3-(4-Chlorophenyl)-3-{7-[(methylsulfanyl)methyl]-1H-indol-3-yl}pentyl methanesulfonate

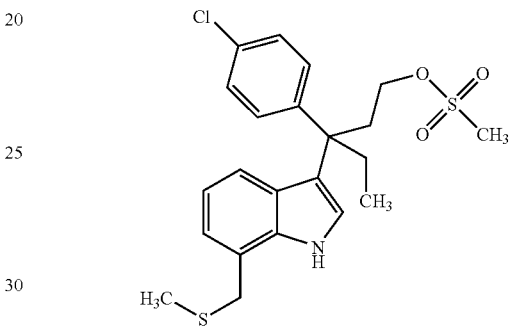

0.39 ml (2.81 mmol) of triethylamine, 23 mg (0.23 mmol) of 4-N,N-dimethylaminopyridine and 0.16 ml (2.06 mmol) of methanesulfonyl chloride were added to 700 mg (1.10 mmol) of the compound from Example 140 in 50 ml of dichloromethane. The reaction mixture was stirred at RT for 1 h, water was added, and the solvents were removed in a rotary evaporator. The crude product was purified by preparative HPLC (mobile phase: acetonitrile/water gradient) to result in 782 mg (92% of theory) of the title compound.

¹H-NMR (400 MHz, DMSO-$d_6$): δ=0.63 (t, 3H), 1.97 (s, 3H), 2.04-2.17 (m, 1H), 2.18-2.30 (m, 1H), 2.46-2.64 (m, 2H), 3.03 (s, 3H), 3.77-3.87 (m, 1H), 3.91-4.02 (m, 1H), 3.93 (s, 2H), 6.59-6.71 (m, 2H), 6.87 (d, 1H), 7.24-7.34 (m, 4H), 7.40 (d, 1H), 11.0 (s, 1H).

LC-MS (Method 4): $R_t$=1.49 min; MS (ESIneg): m/z=450 [M−H]⁻.

Example 116A 3-(4-Chlorophenyl)-3-cyclopropyl-3-{7-[(methylsulfanyl)methyl]-1H-indol-3-yl}propyl methanesulfonate

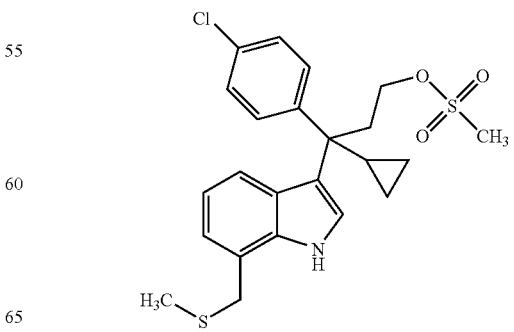

0.02 ml (0.02 mmol) of triethylamine, 2 mg (0.01 mmol) of 4-N,N-dimethylaminopyridine and 0.01 ml (0.14 mmol) of methanesulfonyl chloride were added to 47 mg (0.12 mmol) of the compound from Example 141 in 1.5 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 57 mg of the title compound were obtained as crude product and were reacted further without purification.

LC-MS (Method 9): $R_t$=1.32 min; MS (ESIneg): m/z=462 [M−H]⁻.

Example 117A 3-(2,3-Dihydro-1,4-benzodioxin-6-yl)-3-{7-[(methylsulfanyl)methyl]-1H-indol-3-yl}butyl methanesulfonate

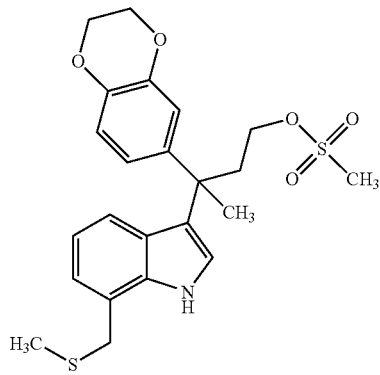

0.21 ml (1.50 mmol) of triethylamine, 14 mg (0.12 mmol) of 4-N,N-dimethylaminopyridine and 0.10 ml (1.27 mmol) of methanesulfonyl chloride were added to 443 mg (1.15 mmol) of the compound from Example 142 in 14 ml of dichloromethane. The reaction mixture was stirred at RT for 2 h and then diluted with ethyl acetate, washed with 1N hydrochloric acid, water and saturated aqueous sodium chloride solution, dried over sodium sulfate, filtered and concentrated. 532 mg of the title compound were obtained as crude product and were reacted further without purification.

LC-MS (Method 6): $R_t$=2.37 min; MS (ESIneg): m/z=460 [M−H]⁻.

Example 118A

5-Chloro-1-cyclopropyl-2,3-dihydro-1H-inden-1-ol

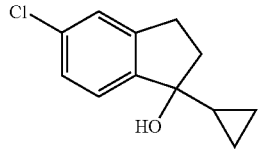

45 ml (22.5 mmol) of a 0.5N solution of cyclopropylmagnesium bromide in tetrahydrofuran were added to 2.50 g (15.0 mmol) of a mixture of 5-chloro-2,3-dihydro-1H-inden-1-one and 6-chloro-2,3-dihydro-1H-inden-1-one in 56 ml of diethyl ether at RT, and the mixture was stirred at RT overnight. The reaction mixture was added to ice-water, the phases were separated, the aqueous phase was extracted with dichloromethane, and the combined organic phases were dried over magnesium sulfate, filtered and concentrated. The crude product was purified by flash chromatography on silica gel (mobile phase: toluene/ethyl acetate gradient) and preparative HPLC (mobile phase: acetonitrile/water gradient) to result in 71.0 mg (2% of theory) of a mixture of 5-chloro-1-cyclopropyl-2,3-dihydro-1H-inden-1-ol and 6-chloro-1-cyclopropyl-2,3-dihydro-1H-inden-1-ol.

¹H-NMR (400 MHz, DMSO-d₆) =7.20-7.30 (m, 3H), 4.91 (s, 0.3H), 4.86 (s, 0.7H), 2.81-2.93 (m, 1H), 2.69-2.81 (m, 1H), 2.07-2.15 (m, 1H), 1.95-2.05 (m, 1H), 1.00-1.10 (m, 1H), 0.23-0.44 (m, 4H).

LC-MS (Method 4): $R_t$=1.19 min; MS (ESIpos): m/z=191 [M-OH]⁺.

Example 119A

6-Chloro-1-cyclopropyl-2,3-dihydro-1H-inden-1-ol

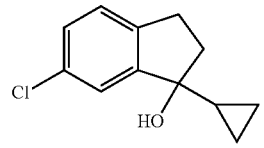

45 ml (22.5 mmol) of a 0.5N solution of cyclopropylmagnesium bromide in tetrahydrofuran were added to 2.50 g (15.0 mmol) of a mixture of 5-chloro-2,3-dihydro-1H-inden-1-one and 6-chloro-2,3-dihydro-1H-inden-1-one in 56 ml of diethyl ether at RT, and the mixture was stirred at RT overnight. The reaction mixture was added to ice-water, the phases were separated, the aqueous phase was extracted with dichloromethane, and the combined organic phases were dried over magnesium sulfate, filtered and concentrated. The crude product was purified by flash chromatography on silica gel (mobile phase: toluene/ethyl acetate gradient) and preparative HPLC (mobile phase: acetonitrile/water gradient) to result in 152 mg (5% of theory) of the title compound.

¹H-NMR (400 MHz, DMSO-d₆): =7.21-7.27 (m, 3H), 4.91 (s, 1H), 2.81-2.91 (m, 1H), 2.69-2.79 (m, 1H), 2.07-2.16 (m, 1H), 1.96-2.05 (m, 1H), 1.00-1.10 (m, 1H), 0.26-0.43 (m, 4H).

LC-MS (Method 4): $R_t$=1.19 min; MS (ESIpos): m/z=191 [M-OH]⁺.

Example 120A 2,2-Difluoro-N-methoxy-N-methylcyclopropanecarboxamide

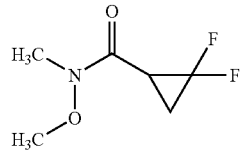

7.00 g (49.8 mmol) of 2,2-difluorocyclopropanecarbonyl chloride (described in the *Journal of Fluorine Chemistry*

1990, 49, 127-139) in 100 ml of dichloromethane were mixed with 6.32 g (64.8 mmol) of N,O-dimethylhydroxylamine hydrochloride and 18.1 ml (130 mmol) of triethylamine and stirred at RT overnight. Water was added to the reaction mixture, the phases were separated, and the aqueous phase was extracted twice with dichloromethane. The combined organic phases were dried over sodium sulfate and concentrated. 5.73 g (70% of theory) of the title compound were obtained and were reacted without further purification.

$^1$H-NMR (400 MHz, DMSO-d$_6$) δ=3.72 (s, 3H), 3.16 (s, 3H), 3.05-3.19 (m, 1H), 1.85-1.99 (m, 2H).

GC-MS (Method 7): R$_t$=2.32 min; MS (EIpos): m/z=165 [M]$^+$.

Example 121A

2-Chloro-N-methoxy-N,4-dimethylbenzamide

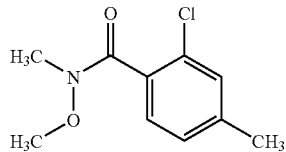

1.25 g (6.61 mmol) of 2-chloro-4-methylbenzoyl chloride in 4 ml of dichloromethane were mixed with 0.84 g (8.60 mmol) of N,O-dimethylhydroxylamine hydrochloride and 2.4 ml (17.2 mmol) of triethylamine and stirred for 24 h. Water and 1N hydrochloric acid were added to the reaction mixture, the phases were separated, and the aqueous phase was extracted twice with dichloromethane. The combined organic phases were dried over sodium sulfate, filtered and concentrated. The crude product was purified by preparative HPLC (RP18 column; mobile phase: acetonitrile/water gradient) to result in 1.10 g (78% of theory) of the title compound.

$^1$H-NMR (400 MHz, DMSO-d$_6$) δ=7.35-7.41 (m, 1H), 7.22-7.28 (m, 2H), 3.44 (s, 3H), 3.27 (s, 3H), 2.31 (s, 3H).

LC-MS (Method 9): R$_t$=0.87 min; MS (ESIpos): m/z=214 [M+H]$^+$.

Example 122A

2-[4-(Trifluoromethyl)benzoyl]cyclopropanecarbonitrile [racemic trans-isomer]

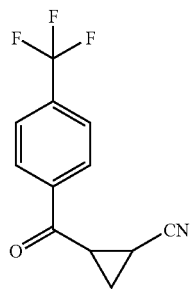

Under argon, a few drops of dibromoethane and a solution of 4.00 g (14.7 mmol) of 1-iodo-4-(trifluoromethyl)benzene in 10 ml of dry diethyl ether were added to 375 mg (15.4 mmol) of magnesium in 40 ml of dry diethyl ether, and the mixture was heated under reflux for 2 h. After cooling, the supernatant reaction solution was added dropwise under argon to 2.00 g (13.0 mmol) of the compound from Example 73A in 50 ml of THF, and the mixture was stirred at RT overnight. The reaction solution was then added to saturated aqueous ammonium chloride solution, the phases were separated, and the aqueous phase was extracted with dichloromethane. The combined organic phases were dried over magnesium sulfate, filtered and concentrated. Purification of the residue by flash chromatography on silica gel (mobile phase: toluene/ethyl acetate gradient) resulted in 1.42 g (46% of theory) of the title compound.

$^1$H-NMR (400 MHz, DMSO-d$_6$) δ=8.28-8.33 (m, 2H), 7.94-7.99 (m, 2H), 3.76 (ddd, 1H), 2.39 (ddd, 1H), 1.73 (ddd, 1H), 1.57 (ddd, 1H).

GC-MS (Method 7): R$_t$=5.08 min; MS (EIpos): m/z=239 [M]$^+$.

Example 123A 2-(2,4-Difluorobenzoyl)cyclopropanecarbonitrile [racemic trans-isomer]

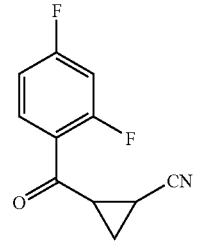

Under argon, a few drops of dibromoethane and then 5.00 g (25.9 mmol) of 2,4-difluorobromobenzene, dissolved in 50 ml of diethyl ether, were added to 661 mg (27.2 mmol) of magnesium in 100 ml of dry diethyl ether. The mixture was heated under reflux for 2 h. After cooling, the supernatant reaction solution was added dropwise under argon to a solution of 3.63 g (23.5 mmol) of the compound from Example 73A in 80 ml of THF, and the mixture was stirred at RT overnight. The reaction solution was then added to saturated aqueous ammonium chloride solution and extracted with dichloromethane. The organic phase was dried over magnesium sulfate, filtered and concentrated. Purification of the residue by flash chromatography on silica gel (mobile phase: toluene/ethyl acetate gradient) resulted in 2.15 g (44% of theory) of the title compound.

$^1$H-NMR (400 MHz, DMSO-d$_6$) δ=7.95 (dt, 1H), 7.50 (ddd, 1H), 7.28 (dt, 1H), 3.30-3.39 (m, 1H), 2.37 (ddd, 1H), 1.72 (ddd, 1H), 1.55-1.63 (m, 1H).

LC-MS (Method 4): R$_t$=1.03 min; MS (ESIpos): m/z=208 [M+H]$^+$.

Example 124A (4-Chlorophenyl)(2,2-difluorocyclopropyl)methanone

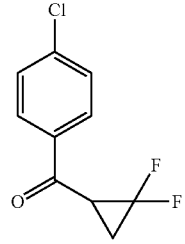

A solution of 2.00 g (12.1 mmol) of the compound from Example 120A in 20 ml of THF was added under argon to 2.87 g (13.3 mmol) of a 1N chlorophenylmagnesium bromide solution in diethyl ether in 20 ml of THF at RT, and the mixture was heated under reflux for 2 h. The reaction mixture was added to saturated aqueous ammonium chloride solution and extracted twice with diethyl ether, and the combined organic phases were dried over magnesium sulfate and concentrated. 2.47 g (94% of theory) of the title compound were obtained and were reacted without further purification.

$^1$H-NMR (400 MHz, DMSO-$d_6$) δ=8.06-8.10 (m, 2H), 7.65-7.70 (m, 2H), 4.03 (ddd, 1H), 2.20-2.30 (m, 1H), 2.03-2.14 (m, 1H).

GC-MS (Method 7): $R_t$=4.41 min; MS (EIpos): m/z=216 [M]$^+$.

Example 125A (2-Chloro-4-methylphenyl)(cyclopropyl)methanone

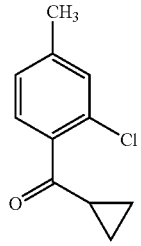

7.7 ml (7.65 mmol) of a 1N cyclopropylmagnesium bromide solution in THF were added to 1.09 g (5.10 mmol) of the compound from Example 121A in 19 ml of diethyl ether, and the mixture was stirred at RT overnight. A further 7.7 ml (7.65 mmol) of a 1N cyclopropylmagnesium bromide solution in THF were added, and the mixture was stirred at RT overnight. The reaction mixture was added to ice-water and extracted with dichloromethane, the organic phase was dried over magnesium sulfate, filtered and concentrated, and the crude product was purified by preparative HPLC (RP18 column; mobile phase: acetonitrile/water gradient) to result in 326 mg (33% of theory) of the title compound.

$^1$H-NMR (400 MHz, DMSO-$d_6$) δ=7.39-7.45 (m, 2H), 7.34 (dd, 1H), 2.44-2.50 (m, 1H), 2.34 (s, 3H), 1.05-1.15 (m, 4H).

LC-MS (Method 9): $R_t$=1.11 min; MS (ESIpos): m/z=195 [M+H]$^+$.

Example 126A 2-(4-Methylbenzoyl)cyclopropanecarbonitrile [racemic trans-isomer]

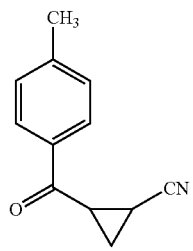

A solution of 4.00 g (26.0 mmol) of the compound from Example 73A in 10 ml of THF was added under argon to 29 ml (28.5 mmol) of a 1N para-toluenemagnesium bromide solution in THF in 70 ml of THF at RT, and the mixture was heated under reflux for 2 h. The reaction mixture was added to saturated aqueous ammonium chloride solution and extracted with ethyl acetate, and the organic phase was dried over magnesium sulfate and concentrated. The residue was purified by flash chromatography on silica gel (mobile phase: toluene/ethyl acetate 95/5). 2.60 g (54% of theory) of the title compound were obtained.

$^1$H-NMR (400 MHz, DMSO-$d_6$) δ=8.00-8.05 (m, 2H), 7.37-7.42 (m, 2H), 3.68 (ddd, 1H), 2.41 (s, 3H), 2.30 (ddd, 1H), 1.65 (ddd, 1H), 1.50 (d, 1H).

GC-MS (Method 7): $R_t$=5.84 min; MS (EIpos): m/z=185 [M]$^+$.

Example 127A 2-(2-Chloro-4-fluorobenzoyl)cyclopropanecarbonitrile [racemic trans-isomer]

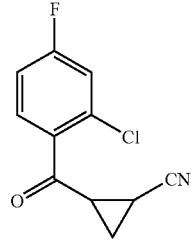

A solution of 24.0 g (115 mmol) of 2-chloro-4-fluorobromobenzene in 20 ml of diethyl ether was added dropwise to 2.92 g (120 mmol) of magnesium turnings in 780 ml of diethyl ether, activated by adding a few drops of dibromoethane, and the reaction mixture was heated under reflux overnight. The reaction solution was added dropwise under argon to a solution of 17.7 g (68.8 mmol) of the compound from Example 73A in 300 ml of THF, and the reaction mixture was stirred initially at RT overnight and then under reflux for 8 h. It was concentrated and taken up in ethyl acetate and saturated aqueous ammonium chloride solution, the phases were separated, and the organic phase was washed with water and saturated aqueous sodium bicarbonate solution, dried over magnesium sulfate, filtered and concentrated. The residue was purified by flash chromatography on silica gel (mobile phase: toluene/ethyl acetate gradient) to result in 2.20 g (14% of theory) of the title compound.

$^1$H-NMR (400 MHz, DMSO-$d_6$) δ=7.86 (dd, 1H), 7.65 (dd, 1H), 7.42 (dt, 1H), 3.29-3.35 (m, 1H), 2.40 (ddd, 1H), 1.76 (ddd, 1H), 1.60 (ddd, 1H).

GC-MS (Method 7): $R_t$=5.68 min; MS (EIpos): m/z=223 [M]$^+$.

Example 128A 2-(4-Chloro-2-methoxybenzoyl)cyclopropanecarbonitrile [racemic trans-isomer]

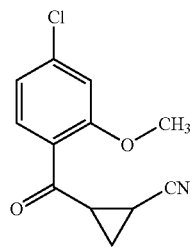

A solution of 500 mg (2.26 mmol) of 2-bromo-4-chloroanisole in 5 ml of diethyl ether was added dropwise to 57.6 mg (2.37 mmol) of magnesium turnings in 10 ml of diethyl ether, activated by adding a few drops of dibromoethane, and the reaction mixture was heated under reflux overnight. The reaction solution was added dropwise under argon to a solution of 316 mg (2.05 mmol) of the compound from Example 73A in 10 ml of THF, and the reaction mixture was heated under reflux for 2 h. It was diluted with ethyl acetate, and the organic phase was washed with water and saturated aqueous sodium bicarbonate solution, dried over magnesium sulfate, filtered and concentrated. The residue was purified by flash chromatography on silica gel (mobile phase: toluene/ethyl acetate 9/1) to result in 278 mg (58% of theory) of the title compound.

$^1$H-NMR (400 MHz, DMSO-d$_6$) δ=7.55 (d, 1H), 7.35 (d, 1H), 7.14 (dd, 1H), 3.35 (ddd, 1H), 2.26 (ddd, 1H), 1.66 (ddd, 1H), 1.56 (ddd, 1H).

GC-MS (Method 7): R$_t$=6.73 min; MS (EIpos): m/z=235 [M]$^+$.

Example 129A

2-[2-Fluoro-4-(trifluoromethyl)benzoyl]cyclopropanecarbonitrile [racemic trans-isomer]

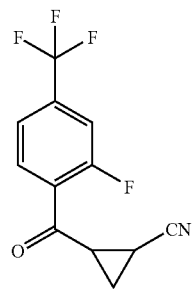

2.6 ml (4.12 mmol) of a 1.6N solution of n-butyllithium in hexane were added dropwise to a solution of 1.00 g (4.12 mmol) of 1-bromo-2-fluoro-4-(trifluoromethyl)benzene in 8 ml of THF at −78° C., and the mixture was stirred for 0.5 h. Then, at −78° C., a solution of 423 mg (2.74 mmol) of the compound from Example 73A in 2 ml of THF was added, and the mixture was allowed to warm to RT and was stirred at RT for 2 h. It was diluted with dichloromethane, and the organic phase was washed with water and saturated aqueous sodium bicarbonate solution, dried over magnesium sulfate, filtered and concentrated. The residue was purified by flash chromatography on silica gel (mobile phase: toluene/ethyl acetate gradient) to result in 206 mg (29% of theory) of the title compound.

$^1$H-NMR (400 MHz, DMSO-d$_6$) δ=8.02 (t, 1H), 7.95 (d, 1H), 7.77 (d, 1H), 3.36-3.43 (m, 1H), 2.43 (ddd, 1H), 1.78 (ddd, 1H), 1.64 (ddd, 1H).

GC-MS (Method 7): R$_t$=4.66 min; MS (EIpos): m/z=257 [M]$^+$.

Example 130A 2-(4-Chloro-2-fluorobenzoyl)cyclopropanecarbonitrile [racemic trans-isomer]

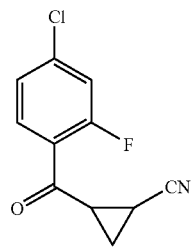

5.67 g (134 mmol) of lithium chloride and 0.7 ml of a 0.1N solution of diisobutylaluminum hydride in THF were added to 6.50 g (268 mmol) of magnesium turnings in 30 ml of THF. The mixture was stirred for five minutes and cooled to 0° C., 22.4 g (107 mmol) of 1-bromo-4-chloro-2-fluorobenzene were added, and the mixture was allowed to warm to RT and was stirred at RT overnight. The reaction solution was added dropwise under argon to a solution of 15.0 g (97.3 mmol) of the compound from Example 73A in 10 ml of THF, and the reaction mixture was heated under reflux for 2 h. The reaction mixture was added to saturated aqueous ammonium chloride solution and extracted with dichloromethane, and the organic phase was washed with water, dried over magnesium sulfate, filtered and concentrated. The residue was purified by flash chromatography on silica gel (mobile phase: toluene/ethyl acetate 95/5) to result in 5.40 g (25% of theory) of the title compound.

$^1$H-NMR (400 MHz, DMSO-d$_6$) δ=7.86 (t, 1H), 7.70 (dd, 1H), 7.48 (dd, 1H), 3.32-3.38 (m, 1H), 2.38 (ddd, 1H), 1.73 (ddd, 1H), 1.60 (ddd, 1H).

LC-MS (Method 9): R$_t$=1.01 min; MS (ESIneg): m/z=222 [MH]$^-$.

Example 131A 2-(2-Fluoro-4-methylbenzoyl)cyclopropanecarbonitrile [racemic trans-isomer]

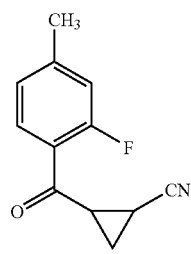

16.5 ml (26.5 mmol) of a 1.6N solution of n-butyllithium in hexane were added dropwise to a solution of 5.00 g (26.5 mmol) of 4-bromo-3-fluorotoluene in 40 ml of THF at −78° C., and the mixture was stirred for 0.5 h. Then, at −78° C., a solution of 2.72 g (17.6 mmol) of the compound from Example 73A in 10 ml of THF was added, and the mixture was allowed to warm to RT and was stirred at RT for 2 h. Water was added, the mixture was concentrated, and the crude product was purified by preparative HPLC (RP18 column; mobile phase: acetonitrile/water gradient with addition of 0.1% formic acid). 300 mg (9% of theory) of the title compound were obtained.

$^1$H-NMR (400 MHz, DMSO-$d_6$) δ=7.40 (t, 1H), 7.26 (d, 1H), 7.20 (d, 1H), 3.29-3.37 (m, 1H), 2.40 (s, 3H), 2.35 (ddd, 1H), 1.70 (ddd, 1H), 1.57 (ddd, 1H).

GC-MS (Method 7): $R_t$=5.68 min; MS (EIpos): m/z=203 [M]$^+$.

Example 132A

2-{1-Hydroxy-1-[4-(trifluoromethyl)phenyl]ethyl}cyclopropanecarbonitrile [trans-diastereomer mixture]

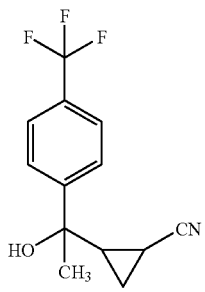

3.0 ml (9.09 mmol) of a 3N solution of methylmagnesium bromide in diethyl ether were added to 1.45 g (6.06 mmol) of the compound from Example 122A in 25 ml of diethyl ether at RT, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient) to result in 1.40 g (90% of theory) of a mixture of the diastereomers of the title compound.

$^1$H-NMR (400 MHz, DMSO-$d_6$) δ=7.67-7.77 (m, 4H), 5.37 (s, 0.4H), 5.35 (s, 0.6H), 2.03-2.11 (m, 1H), 1.75 (dt, 0.6H), 1.57 (s, 1.8H), 1.52-1.59 (m, 0.4H), 1.48 (s, 1.2H) 1.28 (ddd, 0.4H), 1.19 (dt, 0.4H), 1.05 (ddd, 0.6H), 1.00 (dt, 0.6H).

Example 133A

2-[1-(2,4-Difluorophenyl)-1-hydroxyethyl]cyclopropanecarbonitrile [trans-diastereomer mixture]

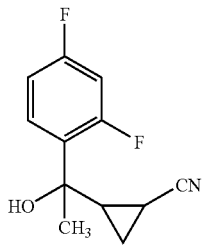

5.2 ml (15.6 mmol) of a 3N solution of methylmagnesium bromide in diethyl ether were added to 2.15 g (10.4 mmol) of the compound from Example 123A in 50 ml of diethyl ether at RT, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient) to result in 2.16 g (93% of theory) of a mixture of the diastereomers of the title compound.

$^1$H-NMR (400 MHz, DMSO-$d_6$): δ=7.51-7.62 (m, 1H), 7.16-7.28 (m, 1H), 7.02-7.13 (m, 1H), 5.48 (s, 0.5H), 5.47 (s, 0.5H), 1.99-2.09 (m, 1H), 1.72-1.78 (m, 0.5H), 1.59 (s, 1.5H), 1.51 (s, 1.5H), 1.46-1.53 (m, 0.5H), 1.16-1.31 (m, 1H), 0.96-1.05 (m, 1H).

LC-MS (Method 9): $R_t$=0.92, 0.93 min; MS (ESIneg): m/z=222 [M−H]$^-$.

Example 134A 1-(4-Chlorophenyl)-1-(2,2-difluorocyclopropyl)ethanol

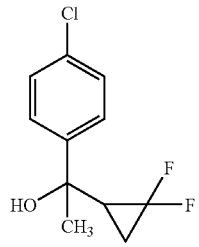

5.7 ml (17.1 mmol) of a 3N solution of methylmagnesium bromide in diethyl ether were added to 2.47 g (11.4 mmol) of the compound from Example 124A in 40 ml of diethyl ether at RT, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient) to result in 2.09 g (78% of theory) of a mixture of the diastereomers of the title compound.

$^1$H-NMR (400 MHz, DMSO-$d_6$): δ=7.49-7.56 (m, 2H), 7.36-7.42 (m, 1.8H), 7.11-7.28 (m, 0.2H), 5.38 (s, 0.1H), 5.36 (s, 0.9H), 2.14 (ddd, 0.9H), 2.01 (ddd, 0.1H), 1.58-1.69 (m, 1H), 1.43-1.56 (m, 4H).

Example 135A

1-Ethyl-5-fluoroindan-1-ol

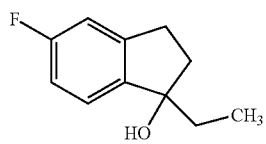

292 ml (876 mmol) of a 3N solution of ethylmagnesium bromide in diethyl ether were added to 5.00 g (33.3 mmol) of 5-fluoroindan-1-one in 150 ml of diethyl ether at RT, and the mixture was stirred at RT overnight. The reaction mixture was added to a saturated, ice-cold aqueous ammonium chloride solution, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient) to result in 5.70 g (94% of theory) of the title compound.

$^1$H-NMR (400 MHz, DMSO-$d_6$): δ=7.24 (dd, 1H), 6.94-7.03 (m, 2H), 4.89 (s, 1H), 2.82-2.93 (m, 1H), 2.66-2.76 (m, 1H), 2.07-2.17 (m, 1H), 1.92-2.02 (m, 1H), 1.67-1.78 (m, 1H), 1.54-1.64 (m, 1H), 0.82 (t, 3H).

Example 136A

1-Cyclopropyl-1-[2-fluoro-4-(trifluoromethyl)phenyl]ethanol

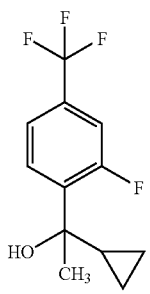

A few drops of dibromoethane and then 6.30 g (52.1 mmol) of cyclopropyl bromide, dissolved in 20 ml of diethyl ether, were added under argon to 1.33 g (54.7 mmol) of magnesium in 90 ml of dry diethyl ether. The mixture was heated under reflux for 2 h. After cooling, 21 ml (9.94 mmol) of the supernatant reaction solution were added dropwise under argon to a solution of 850 mg (4.12 mmol) of 1-[2-fluoro-4-(trifluoromethyl)phenyl]ethanone in 17 ml of diethyl ether, and the mixture was stirred at RT overnight. The reaction mixture was added to ice-water, the phases were separated, the aqueous phase was extracted with dichloromethane, and the combined organic phases were dried over magnesium sulfate, filtered and concentrated. The residue was purified by flash chromatography on silica gel (mobile phase: toluene/ethyl acetate gradient with addition of 0.1% triethylamine) to result in 157 mg (15% of theory) of a mixture of the diastereomers of the title compound.

$^1$H-NMR (400 MHz, DMSO-$d_6$) δ=7.80 (t, 1H), 7.53-7.61 (m, 2H), 5.11 (s, 1H), 1.55 (s, 1.5H), 1.54 (s, 1.5H), 1.30-1.40 (m, 1H), 0.51-0.59 (m, 1H), 0.32-0.40 (m, 1H), 0.23-0.31 (m, 1H), 0.11-0.20 (m, 1H).

Example 137A

1-Cyclopropyl-1-(4-methylphenyl)ethanol

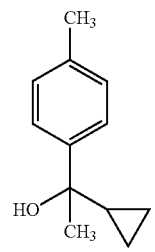

27 ml (26.8 mmol) of 1N cyclopropylmagnesium bromide solution in THF were added to 3.00 g (22.4 mmol) of 1-(4-methylphenyl)ethanone in 60 ml of diethyl ether at RT, and the mixture was stirred at RT overnight. Then a further 11 ml (11.2 mmol) of 1N cyclopropylmagnesium bromide solution in THF were added, and the mixture was stirred at RT overnight. The reaction mixture was added to ice-water, the phases were separated, the aqueous phase was extracted with dichloromethane, and the combined organic phases were dried over magnesium sulfate, filtered and concentrated. The residue was purified by flash chromatography on silica gel (mobile phase: cyclohexane/ethyl acetate gradient with addition of 0.1% triethylamine) to result in 491 mg (13% of theory) of the title compound.

$^1$H-NMR (400 MHz, DMSO-$d_6$) δ=7.33-7.38 (m, 2H), 7.05-7.12 (m, 2H), 4.56 (s, 1H), 2.26 (s, 3H), 1.38 (s, 3H), 1.07-1.16 (m, 1H), 0.36-0.44 (m, 1H), 0.26-0.33 (m, 2H), 0.14-0.22 (m, 1H).

Example 138A

1-Cyclopropyl-1-(4-chlorophenyl)ethanol

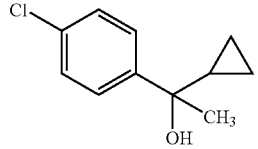

1.50 g (9.70 mmol) of 4-chloroacetophenone were dissolved in 8 ml of diethyl ether at 0° C., and 38.8 ml (19.41 mmol) of a 0.5N solution of cyclopropylmagnesium bromide in tetrahydrofuran were slowly added dropwise. Stirring at 0° C. for 1 h was followed by warming to RT, addition of water and acetonitrile to the reaction solution, and filtration of the mixture through kieselguhr. The organic solvents were removed in a rotary evaporator, and the aqueous phase was extracted twice with diethyl ether. The combined organic phases were washed with saturated aqueous sodium chloride solution, and the solvents were removed in vacuo. The crude product was purified twice by preparative HPLC (mobile phase: acetonitrile/water gradient). The acetonitrile was removed from the combined product phases in a rotary evaporator, and the aqueous phase was extracted twice with diethyl ether. The combined organic phases were again washed with saturated aqueous sodium chloride solution, dried over sodium sulfate and filtered, and the solvents were removed in vacuo. 1.37 g (72% of theory) of the title compound were obtained.

$^1$H-NMR (400 MHz, DMSO-$d_6$): δ=0.15-0.25 (m, 1H), 0.27-0.39 (m, 2H), 0.40-0.49 (m, 1H), 1.08-1.18 (m, 1H), 1.39 (s, 3H), 4.78 (s, 1H), 7.35 (d, 2H), 7.50 (d, 2H).

GC-MS (Method 7): $R_t$=4.96 min; DCI-MS (ESIpos): m/z=179 [M−H$_2$O+H]$^+$.

Example 139A

1-Cyclopropyl-1-[4-(trifluoromethyl)phenyl]ethanol

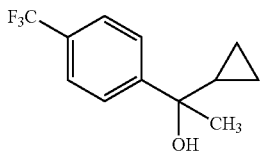

The title compound was prepared starting from 1.50 g (7.97 mmol) of 4'-(trifluoromethyl)acetophenone and 31.9 ml (15.95 mmol) of a 0.5N solution of cyclopropylmagnesium bromide in tetrahydrofuran in analogy to the synthesis of the compound from Example 138A. 1.27 g (69% of theory) of the title compound were obtained.

$^1$H-NMR (400 MHz, DMSO-$d_6$): δ=0.16-0.25 (m, 1H), 0.30-0.40 (m, 2H), 0.45-0.54 (m, 1H), 1.13-1.22 (m, 1H), 1.45 (s, 3H), 4.91 (s, 1H), 7.65 (d, 2H), 7.71 (d, 2H).

GC-MS (Method 7): $R_t$=3.88 min; DCI-MS (ESIpos): m/z=213 [M−H$_2$O+H]$^+$.

Example 140A

1-Cyclopropyl-1-(3-fluoro-4-methoxyphenyl)ethanol

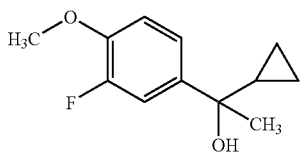

The title compound was prepared starting from 1.50 g (8.92 mmol) of 3-fluoro-4-methoxyacetophenone and 35.7 ml (17.8 mmol) of a 0.5N solution of cyclopropylmagnesium bromide in tetrahydrofuran in analogy to the synthesis of the compound from Example 138A. 1.38 g (74% of theory) of the title compound were obtained.

$^1$H-NMR (400 MHz, DMSO-$d_6$): δ=0.15-0.24 (m, 1H), 0.26-0.37 (m, 2H), 0.37-0.46 (m, 1H), 1.07-1.17 (m, 1H), 1.38 (s, 3H), 3.81 (s, 3H), 4.69 (s, 1H), 7.07 (t, 1H), 7.19-7.29 (m, 2H).

GC-MS (Method 7): $R_t$=5.27 min; MS (EIpos): m/z=210 [M]$^+$.

Example 141A 1-(1-Benzothiophen-5-yl)-1-cyclopropylethanol

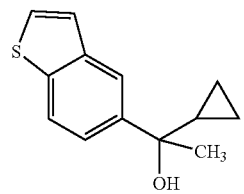

0.60 g (24.64 mmol) of magnesium turnings were dried by heating under argon and, after cooling to RT, 30 ml of tetrahydrofuran were added. 5.00 g (23.46 mmol) of 5-bromo-1-benzothiophene in 30 ml of tetrahydrofuran, and traces of iodine, were added to the mixture, which was stirred at RT for 30 min. Addition of 2.17 g (25.81 mmol) of acetylcyclopropane in 30 ml of tetrahydrofuran was followed by stirring for 2 h. The reaction solution was mixed with water and acetonitrile, and the mixture was filtered through kieselguhr. The organic solvents were removed in a rotary evaporator, and the aqueous phase was extracted twice with diethyl ether. The combined organic phases were washed with saturated aqueous sodium chloride solution, dried over sodium sulfate and filtered, and the solvents were removed in vacuo. The crude product was purified by preparative HPLC (mobile phase: acetonitrile/water gradient). The acetonitrile was removed from the combined product phases in a rotary evaporator, and the aqueous phase was extracted twice with diethyl ether. The combined organic phases were again washed with saturated aqueous sodium chloride solution, dried over sodium sulfate and filtered, and the solvents were removed in vacuo. 2.39 g (46% of theory) of the title compound were obtained.

$^1$H-NMR (400 MHz, DMSO-$d_6$): δ=0.15-0.26 (m, 1H), 0.31-0.41 (m, 2H), 0.43-0.52 (m, 1H), 1.17-1.27 (m, 1H), 1.47 (s, 3H), 4.75 (s, 1H), 7.43 (d, 1H), 7.52 (dd, 1H), 7.70 (d, 1H), 7.90 (d, 1H), 7.98 (d, 1H).

GC-MS (Method 7): $R_t$=6.64 min; DCI-MS (ESIpos): m/z=201 [M−H$_2$O+H]$^+$.

Example 142A

1-Cyclopropyl-1-(2,3-dihydro-1,4-benzodioxin-6-yl)ethanol

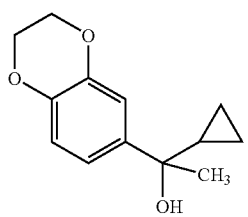

The title compound was prepared starting from 1.50 g (8.42 mmol) of 1,4-benzodioxan-6-yl methyl ketone and 33.7 ml (16.84 mmol) of a 0.5N solution of cyclopropylmagnesium bromide in tetrahydrofuran in analogy to the synthesis of the compound from Example 138A. 1.12 g (59% of theory) of the title compound were obtained.

$^1$H-NMR (400 MHz, DMSO-d$_6$): δ=0.13-0.23 (m, 1H), 0.26-0.35 (m, 2H), 0.35-0.43 (m, 1H), 1.05-1.14 (m, 1H), 1.34 (s, 3H), 4.20 (s, 4H), 4.53 (s, 1H), 6.75 (d, 1H), 6.89-6.96 (m, 2H).

GC-MS (Method 7): R$_t$=6.46 min; MS (EIpos): m/z=220 [M]$^+$.

Example 143A 1-(1,3-Benzodioxol-5-yl)-1-cyclopropylethanol

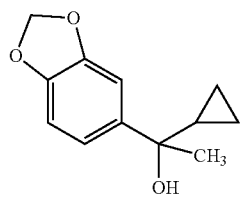

The title compound was prepared starting from 1.50 g (9.14 mmol) of 3,4-(methylenedioxy)acetophenone and 36.5 ml (18.28 mmol) of a 0.5N solution of cyclopropylmagnesium bromide in tetrahydrofuran in analogy to the synthesis of the compound from Example 138A. 1.32 g (70% of theory) of the title compound were obtained.

$^1$H-NMR (400 MHz, DMSO-d$_6$): δ=0.14-0.23 (m, 1H), 0.27-0.36 (m, 2H), 0.36-0.45 (m, 1H), 1.07-1.15 (m, 1H), 1.36 (s, 3H), 4.60 (s, 1H), 5.96 (s, 2H), 6.81 (d, 1H), 6.98 (dd, 1H), 7.02 (d, 1H).

HPLC (Method 1): R$_t$=3.84 min.

Example 144A

1-Cyclopropyl-1-(2,2-difluoro-1,3-benzodioxol-5-yl)ethanol

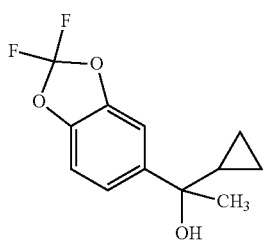

The title compound was prepared starting from 0.75 g (3.75 mmol) of 1-(2,2-difluoro-1,3-benzodioxol-5-yl)ethanone and 15.0 ml (7.50 mmol) of a 0.5N solution of cyclopropylmagnesium bromide in tetrahydrofuran in analogy to the synthesis of the compound from Example 138A. 0.67 g (74% of theory) of the title compound was obtained.

$^1$H-NMR (400 MHz, DMSO-d$_6$): δ=0.15-0.24 (m, 1H), 0.28-0.40 (m, 2H), 0.42-0.50 (m, 1H), 1.11-1.20 (m, 1H), 1.41 (s, 3H), 4.86 (s, 1H), 7.27-7.35 (m, 2H), 7.47 (d, 1H).

HPLC (Method 1): R$_t$=4.50 min; DCI-MS (ESIpos): m/z=225 [M-OH]$^+$.

Example 145A

1-Cyclopropyl-1-(4-chlorophenyl)propanol

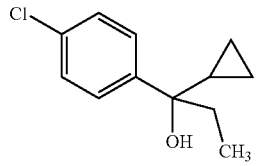

The title compound was prepared starting from 1.50 g (8.90 mmol) of 1-(4-chlorophenyl)propan-1-one and 35.6 ml (17.79 mmol) of a 0.5N solution of cyclopropylmagnesium bromide in tetrahydrofuran in analogy to the synthesis of the compound from Example 138A. 1.42 g (76% of theory) of the title compound were obtained.

$^1$H-NMR (400 MHz, DMSO-d$_6$): δ=0.08-0.24 (m, 2H), 0.28-0.38 (m, 1H), 0.45-0.53 (m, 1H), 0.67 (t, 3H), 1.16-1.25 (m, 1H), 1.69-1.88 (m, 2H), 4.43 (s, 1H), 7.34 (d, 2H), 7.45 (d, 2H).

GC-MS (Method 7): R$_t$=5.24 min; MS (EIpos): m/z=210 [M]$^+$.

Example 146A 3-(4-Chloro-2-fluorophenyl)pentan-3-ol

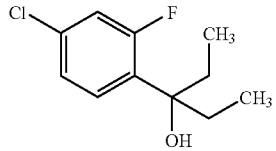

The title compound was prepared starting from 2.00 g (10.61 mmol) of methyl 4-chloro-2-fluorobenzoate and 31.8 ml (31.82 mmol) of a 1N solution of ethylmagnesium bromide in tetrahydrofuran in analogy to the synthesis of the compound from Example 138A. 1.27 g (55% of theory) of the title compound were obtained.

$^1$H-NMR (400 MHz, DMSO-d$_6$): δ=0.64 (t, 6H), 1.65-1.75 (m, 1H), 1.81-1.93 (m, 1H), 4.85 (s, 1H), 7.23-7.32 (m, 2H), 7.58 (t, 1H).

HPLC (Method 1): R$_t$=4.72 min; DCI-MS (EIpos): m/z=210 [M+NH$_4$]$^+$.

Example 147A

Cyclopropyl(2,4-dichlorophenyl)methanol

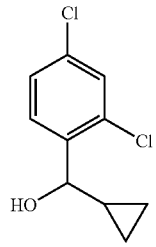

17 ml (8.57 mmol) of 0.5N cyclopropylmagnesium bromide solution in THF were added to 1.00 g (5.71 mmol) of 2,4-dichlorobenzaldehyde in 20 ml of diethyl ether at 0° C., and the mixture was warmed to RT and stirred at RT overnight. The reaction mixture was added to water and ethyl acetate, the phases were separated, the aqueous phase was extracted twice with ethyl acetate, and the combined organic phases were washed with saturated aqueous sodium chloride solution, dried over sodium sulfate, filtered and concentrated. The crude product was purified by preparative HPLC (RP18 column; mobile phase: acetonitrile/water) to result in 925 mg (74% of theory) of the title compound.

$^1$H-NMR (400 MHz, DMSO-$d_6$) δ=7.59 (d, 1H), 7.54 (d, 1H), 7.44 (dd, 1H), 5.41 (d, 1H), 4.57-4.63 (m, 1H), 1.04-1.14 (m, 1H), 0.33-0.41 (m, 4H).

Example 148A

Cyclopropyl[2-fluoro-4-(trifluoromethyl)phenyl]methanol

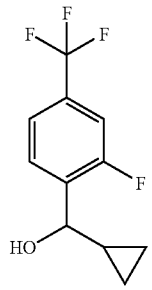

31 ml (15.6 mmol) of 0.5N cyclopropylmagnesium bromide solution in THF were added to 2.00 g (10.4 mmol) of 2-fluoro-4-(trifluoromethyl)benzaldehyde in 40 ml of diethyl ether at 0° C., and the mixture was warmed to RT and stirred at RT overnight. The reaction mixture was added to water and ethyl acetate, the phases were separated, the aqueous phase was extracted twice with ethyl acetate, and the combined organic phases were washed with saturated aqueous sodium chloride solution, dried over sodium sulfate, filtered and concentrated. The crude product was purified by flash chromatography on silica gel (mobile phase: toluene/ethyl acetate 95/5) to result in 1.68 g (69% of theory) of the title compound.

$^1$H-NMR (400 MHz, DMSO-$d_6$) δ=7.77 (t, 1H), 7.57-7.63 (m, 2H), 5.52 (d, 1H), 4.41 (dd, 1H), 1.05-1.15 (m, 1H), 0.29-0.50 (m, 4H).

GC-MS (Method 7): $R_t$=3.53 min; MS (EIpos): m/z=234 [M]$^+$.

Example 149A

Cyclopropyl[4-(trifluoromethyl)phenyl]methanol

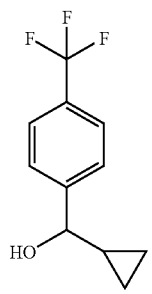

34 ml (17.2 mmol) of 0.5N cyclopropylmagnesium bromide solution in THF were added to 2.00 g (11.5 mmol) of 4-(trifluoromethyl)benzaldehyde in 44 ml of diethyl ether at 0° C., and the mixture was warmed to RT and stirred at RT overnight. The reaction mixture was added to water and ethyl acetate, the phases were separated, the aqueous phase was extracted twice with ethyl acetate, and the combined organic phases were washed with saturated aqueous sodium chloride solution, dried over sodium sulfate, filtered and concentrated. The crude product was purified by flash chromatography on silica gel (mobile phase: toluene/ethyl acetate 95/5) to result in 1.77 g (71% of theory) of the title compound.

$^1$H-NMR (400 MHz, DMSO-$d_6$) δ=7.65-7.70 (m, 2H), 7.58-7.62 (m, 2H), 5.38 (d, 1H), 4.07 (dd, 1H), 0.97-1.07 (m, 1H), 0.36-0.50 (m, 4H).

GC-MS (Method 7): $R_t$=3.87 min; MS (EIpos): m/z=216 [M]$^+$.

Example 150A

[2-Chloro-4-(trifluoromethyl)phenyl](cyclopropyl)methanol

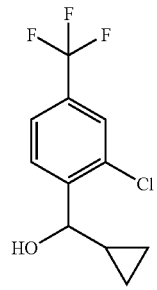

84 ml (41.9 mmol) of 0.5N cyclopropylmagnesium bromide solution in THF were added to 5.83 g (30.0 mmol) of 2-chloro-4-(trifluoromethyl)benzaldehyde in 117 ml of diethyl ether at 0° C., and the mixture was warmed to RT and stirred at RT overnight. The reaction mixture was added to water and ethyl acetate, the phases were separated, the aqueous phase was extracted three times with ethyl acetate, and the combined organic phases were washed with saturated aqueous sodium chloride solution, dried over sodium sulfate, filtered and concentrated. The crude product was purified by flash chromatography on silica gel (mobile phase: toluene/ethyl acetate 95/5) to result in 5.00 g (61% of theory) of the title compound.

$^1$H-NMR (400 MHz, DMSO-$d_6$) δ=7.81 (d, 1H), 7.69 (s, 1H), 7.56 (d, 1H), 5.53 (d, 1H), 4.09 (dd, 1H), 0.97-1.07 (m, 1H), 0.36-0.50 (m, 4H).

Example 151A (4-Chloro-2-fluorophenyl)(cyclopropyl)methanol

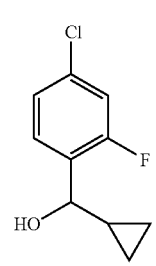

1.00 g (6.31 mmol) of 4-chloro-2-fluorobenzaldehyde were introduced into 20 ml of diethyl ether at 0° C., 19 ml (9.46 mmol) of 0.5N cyclopropylmagnesium bromide solution in THF were added, and the mixture was stirred at RT overnight. The reaction mixture was added to water, the phases were separated, the aqueous phase was extracted twice with ethyl acetate, and the combined organic phases were dried over magnesium sulfate, filtered and concentrated. The crude product was purified by preparative HPLC (RP18 column; mobile phase: acetonitrile/water) to result in 730 mg (58% of theory) of the title compound.

$^1$H-NMR (400 MHz, DMSO-$d_6$) δ=7.55 (t, 1H), 7.34 (dd, 1H), 7.28 (dd, 1H), 5.38 (d, 1H), 4.31 (dd, 1H), 1.03-1.13 (m, 1H), 0.24-0.49 (m, 4H).

LC-MS (Method 9): $R_t$=1.08 min; MS (ESIpos): m/z=183 [M-OH]$^+$.

Example 152A (2-Chloro-4-methylphenyl)(cyclopropyl)methanol

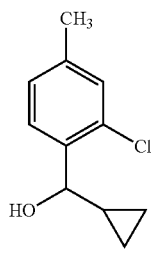

51.3 mg (1.36 mmol) of sodium borohydride were added to 320 mg (1.23 mmol) of the compound from Example 125A in 5 ml of ethanol and 1 ml of ethyl acetate under argon, and the mixture was stirred at 40° C. for 2 h. Then a further 46.6 mg (1.23 mmol) of sodium borohydride were added, and the mixture was stirred at 40° C. overnight. The reaction mixture was added to saturated aqueous ammonium chloride solution and diethyl ether, the phases were separated, the aqueous phase was extracted twice with diethyl ether, and the combined organic phases were washed with saturated aqueous sodium chloride solution, dried over sodium sulfate, filtered and concentrated. 307 mg of the title compound were obtained and were reacted without further purification.

$^1$H-NMR (400 MHz, DMSO-$d_6$) δ=7.39 (d, 1H), 7.24 (d, 1H), 7.06 (dd, 1H), 5.26 (d, 1H), 4.58 (dd, 1H), 2.30 (s, 3H), 1.05-1.15 (m, 1H), 0.30-0.40 (m, 4H).

LC-MS (Method 9): $R_t$=1.11 min; MS (ESIpos): m/z=179 [M-OH]$^+$.

Example 153A

Cyclopropyl-(4-chlorophenyl)methanol

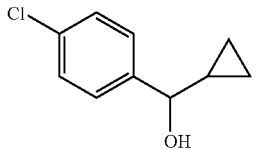

1.50 g (10.67 mmol) of 4-chlorobenzaldehyde were dissolved in 20 ml of diethyl ether at 0° C., and 32.0 ml (16.00 mmol) of a 0.5N solution of cyclopropylmagnesium bromide in tetrahydrofuran were slowly added dropwise. Stirring at 0° C. for 1 h was followed by warming to RT, addition of water and ethyl acetate to the reaction solution, and separation of the phases. The organic phase was dried over sodium sulfate, the solid was filtered off, and the solvents were removed in vacuo. The crude product was purified by preparative HPLC (mobile phase: acetonitrile/water gradient) to result in 1.21 g (62% of theory) of the title compound.

$^1$H-NMR (400 MHz, DMSO-$d_6$): δ=0.29-0.49 (m, 4H), 0.94-1.04 (m, 1H), 3.97 (dd, 1H), 5.25 (d, 1H), 7.36 (d, 2H), 7.40 (d, 2H).

LC-MS (Method 9): $R_t$=0.95 min; MS (ESIpos): m/z=165 [M-OH]$^+$.

Example 154A

Cyclopropyl-(2,4-difluorophenyl)methanol

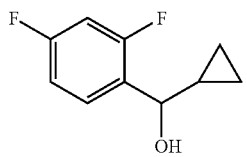

The title compound was prepared starting from 1.50 g (10.55 mmol) of 2,4-difluorobenzaldehyde and 31.7 ml (15.83 mmol) of a 0.5N solution of cyclopropylmagnesium bromide in tetrahydrofuran in analogy to the synthesis of the compound from Example 153A. 0.33 g (17% of theory) of the title compound was obtained.

$^1$H-NMR (400 MHz, DMSO-$d_6$): δ=0.22-0.49 (m, 4H), 1.03-1.14 (m, 1H), 4.29 (dd, 1H), 5.33 (d, 1H), 7.03-7.18 (m, 2H), 7.56 (dd, 1H).

LC-MS (Method 9): $R_t$=0.90 min; MS (ESIpos): m/z=167 [M-OH]$^+$.

Example 155A

Cyclopropyl-(2-chloro-4-fluorophenyl)methanol

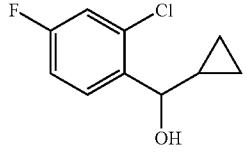

The title compound was prepared starting from 1.50 g (9.46 mmol) of 2-chloro-4-fluorobenzaldehyde and 28.4 ml (14.19 mmol) of a 0.5N solution of cyclopropylmagnesium bromide in tetrahydrofuran in analogy to the synthesis of the compound from Example 153A. 1.51 g (80% of theory) of the title compound were obtained.

$^1$H-NMR (400 MHz, DMSO-$d_6$): δ=0.33-0.40 (m, 4H), 1.05-1.15 (m, 1H), 4.59 (t, 1H), 5.36 (d, 1H), 7.23 (dt, 1H), 7.35 (dd, 1H), 7.61 (dd, 1H).

LC-MS (Method 9): $R_t$=0.99 min; MS (ESIpos): m/z=183 [M-OH]$^+$.

Example 156A (4-Chloro-2,6-difluorophenyl)(cyclopropyl)methanol

2.00 g (11.33 mmol) of 4-chloro-2,6-difluorobenzaldehyde were dissolved in 15 ml of diethyl ether at 0° C., and 34.0 ml (16.99 mmol) of a 0.5N solution of cyclopropylmagnesium bromide in tetrahydrofuran were slowly added dropwise. After stirring at RT for 2 h, the reaction solution was mixed with 1N hydrochloric acid and ethyl acetate, and the phases were separated. The aqueous phase was extracted three times with diethyl ether. The combined organic phases were washed with saturated aqueous sodium chloride solution, and the solvents were removed in vacuo. The crude product was purified by preparative HPLC (mobile phase: acetonitrile/water gradient). 1.20 g (48% of theory) of the title compound were obtained.

$^1$H-NMR (400 MHz, DMSO-d$_6$): δ=0.04-0.12 (m, 1H), 0.33-0.48 (m, 2H), 0.53-0.62 (m, 1H), 1.31-1.42 (m, 1H), 4.06 (dd, 1H), 5.51 (d, 1H), 7.27-7.34 (m, 2H).

LC-MS (Method 6): R$_t$=1.97 min; MS (ESIpos): m/z=201 [M-OH]$^+$.

Example 157A

Cyclopropyl(2,2-difluoro-1,3-benzodioxol-5-yl)methanol

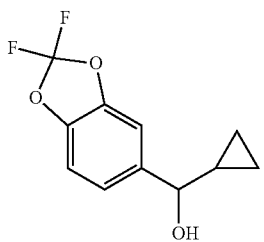

The title compound was prepared starting from 3.50 g (18.81 mmol) of 2,2-difluoro-5-formylbenzodioxolane and 56.4 ml (28.21 mmol) of a 0.5N solution of cyclopropylmagnesium bromide in tetrahydrofuran in analogy to the synthesis of the compound from Example 156A. 1.59 (37% of theory) of the title compound were obtained.

$^1$H-NMR (400 MHz, DMSO-d$_6$): δ=0.31-0.49 (m, 4H), 3.99 (dd, 1H), 5.33 (d, 1H), 7.20 (dd, 1H), 7.32 (d, 1H), 7.38 (d, 1H).

LC-MS (Method 9): R$_t$=1.00 min; MS (ESIpos): m/z=211 [M-OH]$^+$.

Example 158A

2-[Hydroxy(4-methylphenyl)methyl]cyclopropanecarbonitrile [trans-diastereomer mixture]

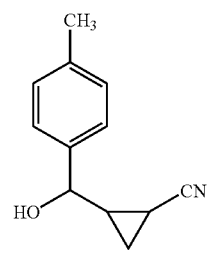

607 mg (16.0 mmol) of sodium borohydride were added to 2.70 g (14.6 mmol) of the compound from Example 126A in 60 ml of ethanol and 16 ml of ethyl acetate under argon, and the mixture was stirred at 40° C. for 2 h. The reaction mixture was added to water and extracted with dichloromethane, and the organic phase was washed with water, dried over magnesium sulfate, filtered and concentrated. The crude product was purified by flash chromatography on silica gel (mobile phase: toluene/ethyl acetate gradient) to result in 2.56 g (94% of theory) of a mixture of the diastereomers of the title compound.

$^1$H-NMR (400 MHz, DMSO-d$_6$) δ=7.24-7.29 (m, 2H), 7.12-7.17 (m, 2H), 5.48 (d, 0.5H), 5.43 (d, 0.5H), 4.37 (t, 0.5H), 4.18 (t, 0.5H), 2.29 (s, 3H), 1.66-1.77 (m, 2H), 1.09-1.18 (m, 2H).

Example 159A (4-Chlorophenyl)(2,2-difluorocyclopropyl)methanol

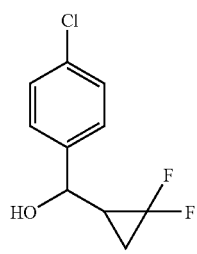

336 mg (8.89 mmol) of sodium borohydride were added to 1.75 g (8.08 mmol) of the compound from Example 124A in 33 ml of ethanol and 9 ml of ethyl acetate under argon, and the mixture was stirred at 40° C. for 1 h. The reaction mixture was added to saturated aqueous ammonium chloride solution and diethyl ether, the phases were separated, the aqueous phase was extracted twice with diethyl ether, and the combined organic phases were washed with saturated aqueous sodium chloride solution, dried over magnesium sulfate, filtered and concentrated. 1.44 g (82% of theory) of a mixture of the diastereomers of the title compound were obtained.

¹H-NMR (400 MHz, DMSO-d₆) δ=7.44-7.49 (m, 2H), 7.37-7.42 (m, 2H), 5.75 (d, 1H), 4.28 (dd, 1H), 1.90-2.03 (m, 1H), 1.33-1.54 (m, 2H).

Example 160A

2-{Hydroxy[4-(trifluoromethyl)phenyl]methyl}cyclopropanecarbonitrile [trans-diastereomer mixture]

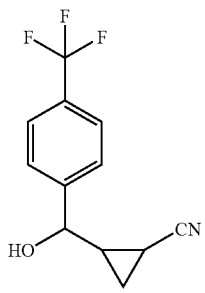

298 mg (7.88 mmol) of sodium borohydride were added to 1.71 g (7.17 mmol) of the compound from Example 122A in 30 ml of ethanol and 7 ml of ethyl acetate under argon, and the mixture was stirred at 40° C. for 1 h. The reaction mixture was added to saturated aqueous ammonium chloride solution and ethyl acetate, the phases were separated, the aqueous phase was extracted twice with ethyl acetate, and the combined organic phases were dried over magnesium sulfate, filtered and concentrated. The crude product was purified by flash chromatography on silica gel (mobile phase: toluene/ethyl acetate gradient) to result in 1.64 g (95% of theory) of a mixture of the diastereomers of the title compound.

¹H-NMR (400 MHz, DMSO-d₆) δ=7.70-7.75 (m, 2H), 7.60-7.65 (m, 2H), 5.79 (d, 0.5H), 5.74 (d, 0.5H), 4.54 (t, 0.5H), 4.34 (t, 0.5H), 1.73-1.85 (m, 2H), 1.13-1.26 (m, 2H).

Example 161A

2-[(2-Chloro-4-fluorophenyl)(hydroxy)methyl]cyclopropanecarbonitrile [trans-diastereomer mixture]

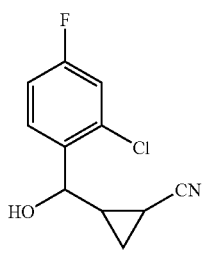

409 mg (10.8 mmol) of sodium borohydride were added to 2.20 g (9.84 mmol) of the compound from Example 127A in 180 ml of ethanol and 60 ml of ethyl acetate under argon, and the mixture was stirred at 40° C. for 2 h. The reaction mixture was added to dichloromethane, the phases were separated, and the organic phase was washed with water, dried over magnesium sulfate, filtered and concentrated. The crude product was purified by flash chromatography on silica gel (mobile phase: toluene/ethyl acetate gradient) to result in 1.52 g (69% of theory) of a mixture of the diastereomers of the title compound.

¹H-NMR (400 MHz, DMSO-d₆) δ=7.65 (d, 0.5H), 7.57 (d, 0.5H), 7.44 (t, 0.5H), 7.41 (t, 0.5H), 7.22-7.31 (m, 1H), 5.80 (d, 0.5H), 5.76 (d, 0.5H), 4.96 (t, 0.5H), 4.73 (t, 0.5H), 1.77-1.88 (m, 1.5H), 1.66-1.73 (m, 0.5H), 1.08-1.23 (m, 2H).

LC-MS (Method 4): R_t=1.01 min; MS (ESIpos): m/z=208 [M-OH]⁺.

Example 162A

2-[(2,4-Difluorophenyl)(hydroxy)methyl]cyclopropanecarbonitrile [trans-diastereomer mixture]

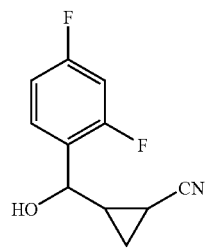

342 mg (9.03 mmol) of sodium borohydride were added to 1.70 g (8.21 mmol) of the compound from Example 123A in 35 ml of ethanol and 15 ml of ethyl acetate under argon, and the mixture was stirred at 40° C. for 1 h. The reaction mixture was added to saturated aqueous ammonium chloride solution and ethyl acetate, the phases were separated, the aqueous phase was extracted twice with ethyl acetate, and the combined organic phases were dried over magnesium sulfate, filtered and concentrated. The crude product was purified by flash chromatography on silica gel (mobile phase: toluene/ethyl acetate 9/1) to result in 1.50 g (87% of theory) of a mixture of the diastereomers of the title compound.

¹H-NMR (400 MHz, DMSO-d₆) δ=7.49-7.61 (m, 1H), 7.18-7.26 (m, 1H), 7.07-7.15 (m, 1H), 5.75 (d, 0.5H), 5.70 (d, 0.5H), 4.71 (t, 0.5H), 4.48 (t, 0.5H), 1.77-1.87 (m, 1.5H), 1.62-1.69 (m, 0.5H), 1.12-1.22 (m, 1.5H), 1.04-1.11 (m, 0.5H).

Example 163A

2-[(4-Chloro-2-methoxyphenyl)(hydroxy)methyl]cyclopropanecarbonitrile [trans-diastereomer mixture]

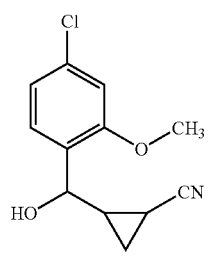

49.1 mg (1.30 mmol) of sodium borohydride were added to 278 mg (1.18 mmol) of the compound from Example 128A in 23 ml of ethanol and 10 ml of ethyl acetate under argon, and the mixture was stirred at 40° C. for 1 h. The reaction mixture was added to saturated aqueous ammonium chloride solution and ethyl acetate, the phases were separated, the aqueous phase was extracted twice with ethyl acetate, and the combined organic phases were dried over magnesium sulfate, filtered and concentrated. 190 mg (68% of theory) of a mixture of the diastereomerse of the title compound were obtained.

$^1$H-NMR (400 MHz, DMSO-$d_6$) δ=7.40 (d, 0.5H), 7.35 (d, 0.5H), 6.99-7.08 (m, 2H), 5.48 (d, 0.5H), 5.45 (d, 0.5H), 4.85 (t, 0.5H), 4.65 (t, 0.5H), 3.84 (s, 1.5H), 3.82 (s, 1.5H), 1.71-1.82 (m, 1H), 1.58-1.70 (m, 1H), 1.08-1.17 (m, 1H), 1.01-1.07 (m, 1H).

Example 164A

2-{[2-Fluoro-4-(trifluoromethyl)phenyl](hydroxy)methyl}cyclopropanecarbonitrile [trans-diastereomer mixture]

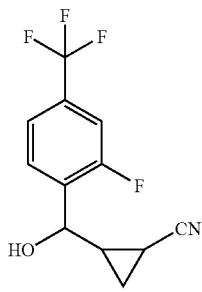

351 mg (9.28 mmol) of sodium borohydride were added to 2.17 g (8.44 mmol) of the compound from Example 129A in 38 ml of ethanol and 16 ml of ethyl acetate under argon, and the mixture was stirred at 40° C. for 1 h. The reaction mixture was added to saturated aqueous ammonium chloride solution and ethyl acetate, the phases were separated, the aqueous phase was extracted twice with ethyl acetate, and the combined organic phases were dried over magnesium sulfate, filtered and concentrated. The crude product was purified by flash chromatography on silica gel (mobile phase: toluene/ethyl acetate 9/1) to result in 1.59 g (73% of theory) of a mixture of the diastereomers of the title compound.

$^1$H-NMR (400 MHz, DMSO-$d_6$) δ=7.70-7.81 (m, 1H), 7.60-7.70 (m, 2H), 5.93 (d, 0.5H), 5.88 (d, 0.5H), 4.83 (t, 0.5H), 4.60 (t, 0.5H), 1.80-1.90 (m, 1.5H), 1.69-1.76 (m, 0.5H), 1.10-1.26 (m, 2H).

Example 165A

2-[(4-Chloro-2-fluorophenyl)(hydroxy)methyl]cyclopropanecarbonitrile [trans-diastereomer mixture]

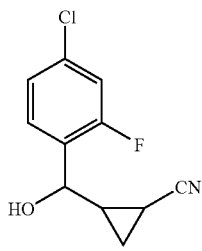

1.01 g (26.6 mmol) of sodium borohydride were added to 5.40 g (24.1 mmol) of the compound from Example 130A in 99 ml of ethanol and 25 ml of ethyl acetate under argon, and the mixture was stirred at 40° C. for 45 minutes. The reaction mixture was added to saturated aqueous ammonium chloride solution and diethyl ether, the phases were separated, the aqueous phase was extracted twice with diethyl ether, and the combined organic phases were washed with saturated aqueous sodium chloride solution, dried over sodium sulfate, filtered and concentrated. 5.25 g (96% of theory) of a mixture of the diastereomers of the title compound were obtained.

$^1$H-NMR (400 MHz, DMSO-$d_6$) δ=7.56 (t, 0.5H), 7.51 (t, 0.5H), 7.43 (dd, 0.5H), 7.40 (dd, 0.5H), 7.33 (dd, 0.5H), 7.31 (dd, 0.5H), 5.80 (d, 0.5H), 5.74 (d, 0.5H), 4.73 (t, 0.5H), 4.50 (t, 0.5H), 1.76-1.87 (m, 1.5H), 1.63-1.70 (m, 0.5H), 1.05-1.22 (m, 2H).

Example 166A

2-[(2-Fluoro-4-methylphenyl)(hydroxy)methyl]cyclopropanecarbonitrile [trans-diastereomer mixture]

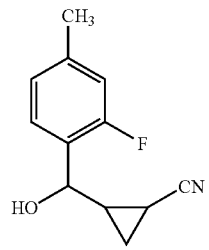

61.0 mg (1.62 mmol) of sodium borohydride were added to 300 mg (1.48 mmol) of the compound from Example 131A in 30 ml of ethanol and 13 ml of ethyl acetate under argon, and the mixture was stirred at 40° C. for 1 h. The reaction mixture was added to saturated aqueous ammonium chloride solution and ethyl acetate, the phases were separated, the aqueous phase was extracted twice with ethyl acetate, and the combined organic phases were dried over magnesium sulfate, filtered and concentrated. 280 mg (92% of theory) of a mixture of the diastereomers of the title compound were obtained.

$^1$H-NMR (400 MHz, DMSO-$d_6$) δ=7.40 (t, 0.5H), 7.36 (t, 0.5H), 6.96-7.05 (m, 2H), 5.62 (d, 0.5H), 5.58 (d, 0.5H), 4.70 (t, 0.5H), 4.48 (t, 0.5H), 1.74-1.84 (m, 1.5H), 1.58-1.65 (m, 0.5H), 1.10-1.20 (m, 1.5H), 1.03-1.10 (m, 0.5H).

Example 167A

2-[(4-Chlorophenyl)(hydroxy)methyl]cyclopropanecarbonitrile [trans-diastereomer mixture]

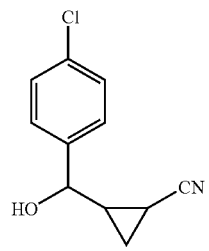

736 mg (19.5 mmol) of sodium borohydride were added to 4.85 g (17.7 mmol) of the compound from Example 74A in 73 ml of ethanol and 18 ml of ethyl acetate under argon, and the mixture was stirred at 40° C. for 2 h. The reaction mixture was added to saturated aqueous ammonium chloride solution and diethyl ether, the phases were separated, the aqueous phase was extracted twice with diethyl ether, and the combined organic phases were washed with saturated aqueous sodium chloride solution, dried over sodium sulfate, filtered and concentrated. The crude product was purified by flash chromatography on silica gel (mobile phase: toluene/ethanol 9/1) to result in 2.79 g (76% of theory) of a mixture of the diastereomers of the title compound.

$^1$H-NMR (400 MHz, DMSO-d$_6$) δ=7.38-7.44 (m, 4H), 5.66 (d, 0.5H), 5.61 (d, 0.5H), 4.43 (t, 0.5H), 4.23 (t, 0.5H), 1.70-1.80 (m, 2H), 1.10-1.20 (m, 2H).

Example 168A 3-(3,5-Difluorophenoxy)propan-1-ol

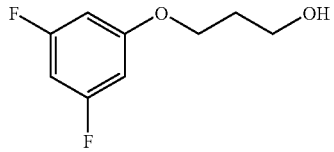

2.77 g (69.18 mmol) of sodium hydride (60% in mineral oil) were dissolved in 80 ml of DMF. At 0° C., 7.50 g (57.65 mmol) of 3,5-difluorophenol in 15 ml of DMF were added dropwise and, after the gas evolution subsided, the mixture was stirred at RT for 30 min. The solution was cooled to 0° C., 5.45 g (57.65 mmol) of 3-chloro-1-propanol in 15 ml of DMF were added, and the mixture was then stirred at 60° C. for 2 h and at 75° C. for 16 h. The precipitated salts were filtered off, and DMF was removed in a rotary evaporator. The residue was taken up in water and extracted twice with diethyl ether. The combined organic phases were washed successively with water, 1N aqueous sodium hydroxide solution and saturated aqueous sodium chloride solution, dried over sodium sulfate and filtered, and the solvents were removed in vacuo. The crude product was purified by column chromatography on silica gel (mobile phase: cyclohexane/ethyl acetate gradient) to result in 8.15 g (75% of theory) of the title compound.

$^1$H-NMR (400 MHz, DMSO-d$_6$): δ=1.84 (quint, 2H), 3.54 (dd, 2H), 4.06 (t, 2H), 4.57 (t, 1H), 6.66-6.79 (m, 3H).

LC-MS (Method 4): R$_t$=0.98 min.

Example 169A 3-(3,5-Difluorophenoxy)propanoic acid

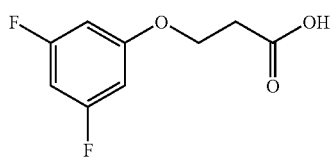

At about −20° C., 17.22 g (172.18 mmol) of chromium(VI) oxide were taken up in 1.2 l of acetone and 38 ml of water, and 19 ml of conc. sulfuric acid were slowly added to the mixture.

The mixture was stirred for 10 min and then 8.10 g (43.05 mmol) of the compound from Example 168A in 400 ml of acetone were added dropwise over the course of 1 h. The mixture was stirred at 0° C. for 1.5 h. After addition of 90 ml of propan-2-ol, the reaction mixture was filtered through kieselguhr, the solvents were removed from the filtrate in vacuo, and the residue was taken up in 500 ml of diethyl ether. The solution was washed twice with saturated aqueous sodium chloride solution and dried over sodium sulfate, and the solvents were removed in vacuo. 11.36 g of the title compound were obtained and were reacted further in the next stage without further purification.

$^1$H-NMR (400 MHz, DMSO-d$_6$): δ=2.69 (t, 2H), 4.19 (t, 2H), 6.68-6.81 (m, 3H), 12.4 (s, 1H).

LC-MS (Method 6): R$_t$=1.76 min; MS (ESIneg): m/z=201 [M-OH]$^+$.

Example 170A 5,7-Difluoro-2,3-dihydro-4H-chromen-4-one

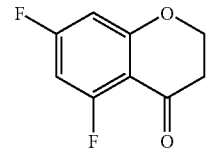

0.5 ml of DMF and 7.35 ml (84.29 mmol) of oxalyl chloride were slowly added dropwise to a solution of 11.36 g (42.15 mmol) of the compound from Example 169A in 400 ml of dichloromethane at RT. After stirring at RT for 3 h, the solvents were removed in a rotary evaporator, and the residue was again taken up in 200 ml of dichloromethane. 6.74 g (50.57 mmol) of aluminum trichloride were added in portions to the reaction mixture, and the mixture was stirred for 1 h. 150 ml of 2N hydrochloric acid and 200 ml of dichloromethane were added, the phases were separated, and the aqueous phase was extracted twice with dichloromethane. The combined organic phases were dried over sodium sulfate and filtered, and the solvents were removed in vacuo. The crude product was purified by flash chromatography on silica gel (mobile phase: dichloromethane). 6.46 g (80% of theory) of the title compound were obtained.

$^1$H-NMR (400 MHz, DMSO-d$_6$): δ=2.77 (t, 2H), 4.57 (t, 2H), 6.81-6.95 (m, 2H).

GC-MS (Method 7): R$_t$=4.45 min; MS (EIpos): m/z=184 [M]$^+$.

Example 171A 5,7-Difluoro-4-methyl-3,4-dihydro-2H-chromen-4-ol

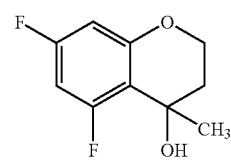

2.00 g (10.86 mmol) of the compound from Example 170A were dissolved in 40 ml of diethyl ether at 0° C., and 5.4 ml (16.29 mmol) of a 3N solution of methylmagnesium bromide in diethyl ether were slowly added dropwise. Stirring at 0° C. for 1 h was followed by warming to RT, addition of water and diethyl ether to the reaction solution and separation of the phases. The aqueous phase was extracted with diethyl ether, and the combined organic phases were dried over sodium sulfate and filtered, and the solvents were removed in vacuo. The crude product was purified by flash chromatography on silica gel (mobile phase: dichloromethane). 2.03 g (93% of theory) of the title compound were obtained.

$^1$H-NMR (400 MHz, DMSO-$d_6$): δ=1.56 (d, 3H), 1.92-1.96 (m, 2H), 4.12-4.22 (m, 2H), 5.25 (s, 1H), 6.51 (dt, 1H), 6.64-6.72 (m, 1H).

GC-MS (Method 7): $R_t$=3.88 min; MS (EIpos): m/z=200 [M]$^+$.

Example 172A

4-Cyclopropyl-5,7-difluoro-3,4-dihydro-2H-chromen-4-ol

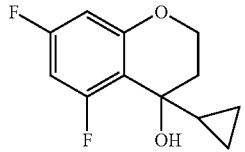

2.00 g (10.86 mmol) of the compound from Example 170A were dissolved in 40 ml of diethyl ether at 0° C., and 32.6 ml (16.29 mmol) of a 0.5N solution of cyclopropylmagnesium bromide in tetrahydrofuran were slowly added dropwise. Stirring at 0° C. for 1 h was followed by warming to RT, addition of water and diethyl ether to the reaction solution and separation of the phases. The aqueous phase was extracted with diethyl ether, and the combined organic phases were dried over sodium sulfate and filtered, and the solvents were removed in vacuo. The crude product was purified by preparative HPLC (mobile phase: acetonitrile/water gradient). The acetonitrile was removed from the combined product phases in a rotary evaporator, and the aqueous phase was extracted with dichloromethane. The combined organic phases were dried over sodium sulfate and filtered, and the solvents were removed in vacuo. 0.66 g (27% of theory) of the title compound was obtained.

$^1$H-NMR (400 MHz, DMSO-$d_6$): δ=0.24-0.33 (m, 2H), 0.45-0.51 (m, 1H), 0.74-0.84 (m, 1H), 1.15-1.25 (m, 1H), 1.82-1.95 (m, 2H), 4.14-4.29 (m, 2H), 5.02 (s, 1H), 6.51 (d, 1H), 6.62-6.70 (m, 1H).

Example 173A

4-[(4-Fluorophenyl)(hydroxy)methyl]benzonitrile

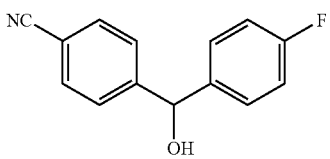

5.00 g (28.57 mmol) of 4-fluorobromobenzene were dissolved in 100 ml tetrahydrofuran at −78° C. Addition of 21.4 ml (34.29 mmol) of a 1.6N solution of n-butyllithium in hexane was followed by stirring for 15 min and then dropwise addition of 4.50 g (34.29 mmol) of 4-cyanobenzaldehyde dissolved in 30 ml of tetrahydrofuran. The mixture was stirred at −78° C. for 1 h, warmed to RT and then stirred for 1 h. The reaction solution was mixed with water and ethyl acetate and the phases were separated. The aqueous phase was extracted three times with ethyl acetate, and the combined organic phases were washed with saturated aqueous sodium chloride solution and dried over sodium sulfate, and the solid was filtered. The solvents were removed in vacuo and the crude product was purified by preparative HPLC (mobile phase: acetonitrile/water gradient). Acetonitrile was removed from the product-containing fractions in a rotary evaporator, and the aqueous residue was extracted with dichloromethane. Removal of the solvent resulted in 2.37 g (36% of theory) of the title compound.

$^1$H-NMR (400 MHz, DMSO-$d_6$): δ=5.81 (d, 1H), 6.19 (d, 1H), 7.10-7.17 (m, 2H), 7.37-7.44 (m, 2H), 7.57 (d, 2H), 7.78 (d, 2H).

LC-MS (Method 9): $R_t$=0.94 min; MS (ESIpos): m/z=210 [M-OH]$^+$.

Example 174A

4-[(4-Chlorophenyl)(hydroxy)methyl]benzonitrile

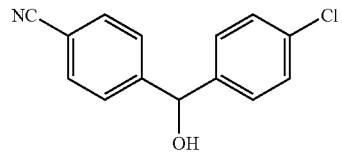

0.67 g (27.42 mmol) of magnesium turnings were dried by heating under argon and, after cooling to RT, 30 ml of tetrahydrofuran and 2 ml of dibromoethane were added. At 0° C., 5.00 g (26.12 mmol) of 4-chlorobromobenzene in 30 ml of tetrahydrofuran were slowly added to the mixture, and the mixture was stirred at RT for 30 min. Addition of 3.77 g (28.73 mmol) of 4-cyanobenzaldehyde in 30 ml of tetrahydrofuran was followed by stirring for 3 h. The THF was removed from the reaction solution in a rotary evaporator, and the residue was taken up in dichloromethane. It was washed with 1N hydrochloric acid, dried over sodium sulfate and filtered, and the solvents were removed in vacuo. The precipitate which separated out of the oily residue was filtered off, washed with diethyl ether and then purified by preparative HPLC (mobile phase: acetonitrile/water gradient). Acetonitrile was removed from the product-containing fractions in a rotary evaporator, and the aqueous residue was extracted with dichloromethane. Removal of the solvent resulted in 1.43 g (23% of theory) of the title compound.

$^1$H-NMR (400 MHz, DMSO-$d_6$): δ=5.81 (d, 1H), 6.23 (d, 1H), 7.35-7.42 (m, 4H), 7.57 (d, 2H), 7.78 (d, 2H).

LC-MS (Method 5): $R_t$=2.20 min; MS (ESIpos): m/z=226 [M-OH]$^+$.

Example 175A (4-Chlorophenyl)(4-methoxyphenyl)methanol

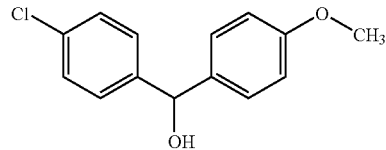

5.00 g (26.12 mmol) of 4-chlorobromobenzene were dissolved in 100 ml of tetrahydrofuran at −78° C. Addition of 19.6 ml (31.34 mmol) of a 1.6N solution of n-butyllithium in hexane was followed by stirring for 15 min and then dropwise addition of 4.27 g (31.34 mmol) of 4-methoxybenzaldehyde dissolved in 30 ml of tetrahydrofuran. The mixture was stirred at −78° C. for 1 h, warmed to RT and then stirred for 1 h. The reaction solution was mixed with water and ethyl acetate and the phases were separated. The aqueous phase was extracted three times with ethyl acetate and the combined organic phases were washed with saturated aqueous sodium chloride solution and dried over sodium sulfate, and the solid was filtered. The solvents were removed in vacuo and the crude product was purified by preparative HPLC (mobile phase: acetonitrile/water gradient). Acetonitrile was removed from the product-containing fractions in a rotary evaporator, and the aqueous residue was extracted with dichloromethane. Removal of the solvent resulted in 4.20 g (65% of theory) of the title compound.

$^1$H-NMR (400 MHz, DMSO-$d_6$): δ=3.71 (s, 3H), 5.64 (d, 1H), 5.86 (d, 1H), 6.83-6.88 (m, 2H), 7.22-7.26 (m, 2H), 7.35 (s, 4H).

LC-MS (Method 3): $R_t$=1.92 min; MS (ESIpos): m/z=231 [M-OH]$^+$.

Example 176A (4-Chloro-3-fluorophenyl)(4-fluorophenyl)methanol

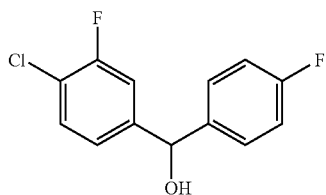

The title compound was prepared starting from 5.00 g (28.57 mmol) of 4-fluorobromobenzene and 5.44 g (34.29 mmol) of 3-fluoro-4-chlorobenzaldehyde in analogy to the synthesis of the compound from Example 175A. 5.01 g (69% of theory) of the title compound were obtained.

$^1$H-NMR (400 MHz, DMSO-$d_6$): δ=5.74 (s, 1H), 6.16 (d, 1H), 7.10-7.17 (m, 2H), 7.20 (dd, 1H), 7.36-7.44 (m, 3H), 7.51 (t, 1H).

LC-MS (Method 9): $R_t$=1.11 min; DCI-MS (ESIpos): m/z=237 [M−H$_2$O+H]$^+$.

Example 177A (3-Chloro-4-fluorophenyl)(4-chlorophenyl)methanol

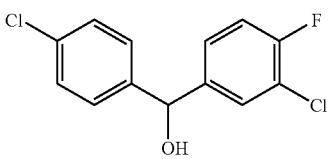

The title compound was prepared starting from 5.00 g (26.12 mmol) of 4-chlorobromobenzene and 4.97 g (31.34 mmol) of 4-fluoro-3-chlorobenzaldehyde in analogy to the synthesis of the compound from Example 175A. 5.57 g (77% of theory) of the title compound were obtained.

$^1$H-NMR (400 MHz, DMSO-$d_6$): δ=5.74 (d, 1H), 6.17 (d, 1H), 7.31-7.42 (m, 6H), 7.55 (d, 1H).

LC-MS (Method 4): $R_t$=1.34 min; MS (ESIpos): m/z=253 [M-OH]$^+$.

Example 178A (4-Chloro-2,6-difluorophenyl)(4-fluorophenyl)methanol

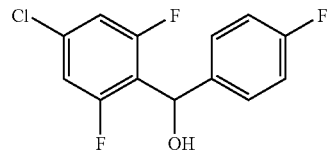

5.00 g (21.98 mmol) of 2-bromo-5-chloro-1,3-dibromobenzene were dissolved in 100 ml of tetrahydrofuran at −78° C. Addition of 16.5 ml (26.38 mmol) of a 1.6N solution of n-butyllithium in hexane was followed by stirring for 15 min and then dropwise addition of 3.27 g (26.38 mmol) of 4-fluorobenzaldehyde dissolved in 30 ml of tetrahydrofuran. The mixture was stirred at −78° C. for 1 h, warmed to RT and then stirred for 1 h. The reaction solution was mixed with water and ethyl acetate and the phases were separated. The aqueous phase was extracted three times with ethyl acetate, and the combined organic phases were washed with saturated aqueous sodium chloride solution and dried over sodium sulfate, and the solid was filtered. The solvents were removed in vacuo and the crude product was purified twice by preparative HPLC (mobile phase: acetonitrile/water gradient) and once by flash chromatography on silica gel (mobile phase: cyclohexane/ethyl acetate 4/1). The solvent was removed from the product-containing fractions in a rotary evaporator, and the aqueous residue was extracted with dichloromethane. Removal of the solvent resulted in 0.80 g (13% of theory) of the title compound.

$^1$H-NMR (400 MHz, DMSO-$d_6$): δ=6.03 (d, 1H), 6.28 (d, 1H), 7.11-7.18 (m, 2H), 7.29-7.41 (m, 4H).

LC-MS (Method 4): $R_t$=1.28 min; MS (ESIpos): m/z=255 [M-OH]$^+$.

Example 179A

Bis(4-chloro-2-fluorophenyl)methanol

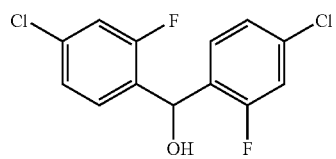

The title compound was prepared starting from 5.00 g (23.87 mmol) of 4-chloro-2-fluorobromobenzene and 4.54 g (28.65 mmol) of 4-chloro-2-fluorobenzaldehyde in analogy to the synthesis of the compound from Example 175A. A difference was that a preliminary separation by column chromatography on silica gel (mobile phase: cyclohexane/ethyl acetate gradient) was carried out before the purification of the crude product by preparative HPLC. 1.79 g (26% of theory) of the title compound were obtained.

$^1$H-NMR (400 MHz, DMSO-$d_6$): δ=6.09 (s, 1H), 6.31 (d, 1H), 7.30 (dd, 2H), 7.34-7.40 (m, 2H), 7.45-7.53 (m, 2H).

LC-MS (Method 4): $R_t$=1.38 min; MS (ESIpos): m/z=271 [M-OH]$^+$.

Example 180A (4-Chloro-2-fluorophenyl)(4-fluoro-2-methylphenyl)methanol

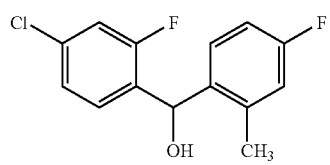

The title compound was prepared starting from 5.00 g (26.45 mmol) of 2-bromo-5-fluorotoluene and 5.03 g (31.74 mmol) of 4-chloro-2-fluorobenzaldehyde in analogy to the synthesis of the compound from Example 175A. A difference was that the crude product was purified twice by preparative HPLC. 4.84 g (65% of theory) of the title compound were obtained.

$^1$H-NMR (400 MHz, DMSO-d$_6$): δ=2.23 (s, 3H), 6.01 (s, 2H), 6.96-7.03 (m, 2H), 7.26-7.43 (m, 4H).

LC-MS (Method 4): R$_t$=1.33 min; MS (ESIpos): m/z=251 [M-OH]$^+$.

Example 181A (4-Chloro-2-fluorophenyl)(2,4-difluorophenyl)methanol

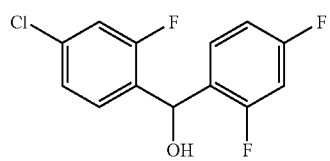

The title compound was prepared starting from 5.00 g (25.91 mmol) of 2,4-difluorobromobenzene and 4.93 g (31.09 mmol) of 4-chloro-2-fluorobenzaldehyde in analogy to the synthesis of the compound from Example 175A. 3.34 g (47% of theory) of the title compound were obtained.

$^1$H-NMR (400 MHz, DMSO-d$_6$): δ=6.19 (d, 1H), 6.38 (d, 1H), 6.99-7.07 (m, 2H), 7.30 (dd, 1H), 7.33-7.42 (m, 2H), 7.82 (d, 1H).

LC-MS (Method 4): R$_t$=1.26 min; MS (ESIpos): m/z=255 [M-OH]$^+$.

Example 182A 1-(4-Chlorophenyl)-1-(4-fluorophenyl)ethanol

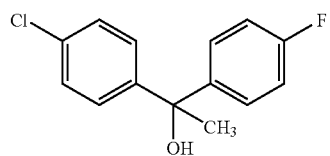

The title compound was prepared starting from 5.00 g (28.57 mmol) of 4-bromofluorobenzene and 4.86 g (31.43 mmol) of 4-chloroacetophenone in analogy to the synthesis of the compound from Example 176A. A difference was that a preliminary separation by column chromatography on silica gel (mobile phase: cyclohexane/ethyl acetate 9/1) was carried out before the purification of the crude product by preparative HPLC. 5.23 g (73% of theory) of the title compound were obtained.

$^1$H-NMR (400 MHz, DMSO-d$_6$): δ=1.81 (s, 3H), 5.86 (s, 1H), 7.06-7.13 (m, 2H), 7.31-7.36 (m, 2H), 7.39-7.45 (m, 4H).

LC-MS (Method 3): R$_t$=2.12 min; MS (ESIpos): m/z=233 [M-OH]$^+$.

Example 183A 1-(4-Chloro-2-fluorophenyl)-1-(4-fluorophenyl)ethanol

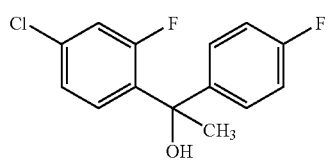

The title compound was prepared starting from 4.22 g (24.14 mmol) of 4-bromofluorobenzene and 5.00 g (28.97 mmol) of 4-chloro-2-fluoroacetophenone in analogy to the synthesis of the compound from Example 176A. A difference was that the crude product was purified by column chromatography on silica gel (mobile phase: cyclohexane/ethyl acetate 9/1). 5.23 g (73% of theory) of the title compound were obtained.

$^1$H-NMR (400 MHz, DMSO-d$_6$): δ=1.84 (s, 3H), 5.98 (s, 1H), 7.06-7.13 (m, 2H), 7.25 (dd, 1H), 7.29-7.38 (m, 3H), 7.77 (t, 1H).

LC-MS (Method 4): R$_t$=1.32 min; MS (ESIpos): m/z=251 [M-OH]$^+$.

Example 184A

1-[4-(Trifluoromethyl)phenyl]prop-2-en-1-ol

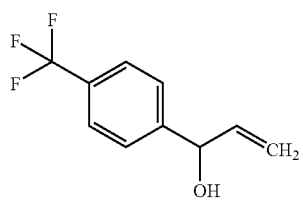

A solution of 75.0 g (431 mmol) of 4-(trifluoromethyl)benzaldehyde in 750 ml of diethyl ether was slowly added dropwise to 517 ml (517 mmol) of a 1N solution of vinylmagnesium bromide in tetrahydrofuran at RT under argon. After heating under reflux for 1 h, the reaction mixture was added to saturated aqueous ammonium chloride solution and extracted with tert-butyl methyl ether. The organic phase was dried, filtered and concentrated. The crude product was purified by column chromatography on silica gel (mobile phase: petroleum ether/ethyl acetate 9/1) to result in 87.0 g (100% of theory) of the title compound.

$^1$H-NMR (400 MHz, DMSO-d$_6$): δ=7.67-7.71 (m, 2H), 7.54-7.58 (m, 2H), 5.95 (ddd, 1H), 5.74 (d, 1H), 5.30 (d, 1H), 5.18 (t, 1H), 5.10 (d, 1H).

GC-MS (Method 7): R$_t$=3.10 min; MS (EIpos): m/z=202 [M]$^+$.

Example 185A 1-(2,4-Dichlorophenyl)prop-2-en-1-ol

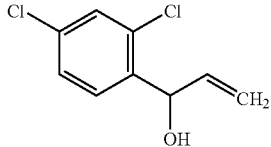

A solution of 20.0 g (114 mmol) of 2,4-dichlorobenzaldehyde in 200 ml of diethyl ether was slowly added dropwise to 137 ml (137 mmol) of a 1N solution of vinylmagnesium bromide in tetrahydrofuran at RT under argon. After heating under reflux for 1 h, the reaction mixture was added to saturated aqueous ammonium chloride solution and diluted with diethyl ether and water. The phases were separated, and the organic phase was washed twice with saturated aqueous sodium bicarbonate solution, dried over sodium sulfate, filtered and concentrated. The crude product was purified by column chromatography on silica gel (mobile phase: cyclohexane/ethyl acetate 5/1) to result in 18.8 g (81% of theory) of the title compound.

$^1$H-NMR (400 MHz, DMSO-d$_6$): δ=7.52-7.57 (m, 2H), 7.44 (dd, 1H), 5.91 (ddd, 1H), 5.80 (d, 1H), 5.37 (t, 1H), 5.24 (dt, 1H), 5.10 (dt, 1H).

Example 186A

1-[4-(Trifluoromethyl)phenyl]prop-2-en-1-one

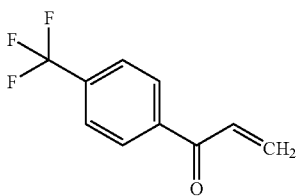

A solution of 18.0 g (89.0 mmol) of the compound from Example 184A in 360 ml of dichloromethane was added dropwise to a solution of 45.3 g (107 mmol) of 1,1,1-triacetoxy-1,1-dihydro-1,2-benziodoxol-3(1H)-one in 360 ml of dichloromethane at RT. After stirring at RT for 1 h, the reaction mixture was added to a mixture of saturated aqueous sodium bicarbonate solution and sodium thiosulfate and extracted three times with dichloromethane. The organic phase was dried, filtered and concentrated. 17.5 g (98% of theory) of the title compound were obtained.

$^1$H-NMR (400 MHz, DMSO-d$_6$): δ=8.16-8.20 (m, 2H), 7.90-7.95 (m, 2H), 7.40 (dd, 1H), 6.40 (dd, 1H), 6.10 (dd, 1H).

GC-MS (Method 7): R$_t$=2.88 min; MS (EIpos): m/z=200 [M]$^+$.

Example 187A 1-(2,4-Dichlorophenyl)prop-2-en-1-one

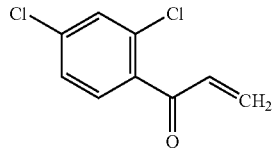

73.5 g (362 mmol) of the compound from Example 185A in 2.21 of dichloromethane were mixed with 105 g (1.21 mol) of activated manganese dioxide and heated under reflux for 20 h. A further 105 g (1.21 mol) of activated manganese dioxide was added in each case after 2 and 4 h. Filtration with suction through kieselguhr, washing with dichloromethane and concentration resulted in 57.0 g of a mixture of the title compound and the compound from Example 185A. 47.7 g (162 mmol) of potassium dichromate were added to 47.0 g of this mixture in 329 ml of 10% strength sulfuric acid, occasionally cooling at 15-20° C., and the mixture was stirred for 1.5 h. This was followed by addition of 400 ml of ethyl acetate, neutralization by adding sodium bicarbonate, filtration through kieselguhr, washing with ethyl acetate, separation of the phases, drying of the organic phase and concentration. The crude product was purified by column chromatography on silica gel (mobile phase: cyclohexane/ethyl acetate 6/1) to result in 17.8 g (55%) of the title compound.

$^1$H-NMR (400 MHz, DMSO-d$_6$): δ=7.77 (d, 1H), 7.52-7.59 (m, 2H), 6.75 (dd, 1H), 6.23 (d, 1H), 6.06 (d, 1H).

GC-MS (Method 7): R$_t$=4.55 min; MS (EIpos): m/z=200 [M]$^+$.

Example 188A 2,2-Difluorocyclopropyl)[4-(trifluoromethyl)phenyl]methanone

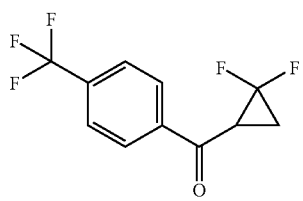

10.0 g (50.0 mmol) of the compound from Example 186A were stirred with 210 mg (5.00 mmol) of sodium fluoride at 110° C. under argon for 5 minutes, 25.0 g (99.9 mmol) of trimethylsilyl 2,2-difluoro-2-(fluorosulfonyl)acetate were slowly added in small portions, and the mixture was stirred at 110° C. for 20 minutes. The reaction mixture was then mixed with saturated aqueous sodium bicarbonate solution and ethyl acetate, the phases were separated, and the organic phase was dried and concentrated. The crude product was purified by column chromatography on silica gel (mobile phase: cyclohexane/ethyl acetate 4/1) to result in 6.80 g (54% of theory) of the title compound.

$^1$H-NMR (400 MHz, DMSO-d$_6$): δ=8.22-8.27 (m, 2H), 7.93-7.98 (m, 2H), 4.08 (ddd, 1H), 2.24-2.34 (m, 1H), 2.07-2.18 (m, 1H).

GC-MS (Method 7): R$_t$=3.15 min; MS (EIpos): m/z=250 [M]$^+$.

Example 189A (2,4-Dichlorophenyl)(2,2-difluorocyclopropyl)methanone

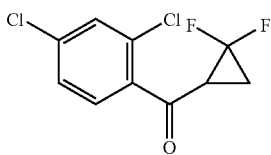

The title compound was prepared starting from 20.0 g (99.5 mmol) of the compound from Example 187A in analogy to the synthesis of the compound from Example 188A. 13.4 g (54% of theory) of the title compound were obtained.

$^1$H-NMR (400 MHz, DMSO-d$_6$): δ=7.81 (d, 1H), 7.72 (d, 1H), 7.62 (dd, 1H), 3.70 (ddd, 1H), 2.24-2.34 (m, 1H), 2.08-2.19 (m, 1H).

GC-MS (Method 7): R$_t$=4.83 min; MS (EIpos): m/z=250 [M]$^+$.

Example 190A (2,2-Difluorocyclopropyl)[4-(trifluoromethyl)phenyl]methanol

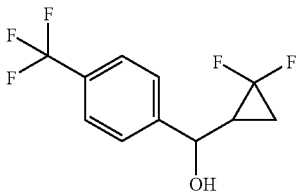

1.13 g (29.9 mmol) of sodium borohydride were added to a solution of 6.80 g (27.2 mmol) of the compound from Example 188A in 111 ml of ethanol and 29 ml of ethyl acetate under argon, and the mixture was stirred at 40° C. for 1 h. The reaction mixture was then added to ethyl acetate and saturated aqueous ammonium chloride solution and stirred for 10 minutes. The phases were separated, and the organic phase was washed with saturated aqueous sodium chloride solution, dried and concentrated. The crude product was purified by column chromatography on silica gel (mobile phase: cyclohexane/ethyl acetate 4/1) to result in 2.50 g (37% of theory) of the title compound as mixture of diastereomers.

$^1$H-NMR (400 MHz, DMSO-d$_6$): δ=7.65-7.74 (m, 3.4H), 7.61-7.65 (m, 0.3H), 7.50-7.54 (m, 0.3H), 5.89 (d, 0.85H), 5.55 (d, 0.15H), 4.55 (dd, 0.15H), 4.39 (dd, 0.85H), 1.96-2.06 (m, 1H), 1.43-1.55 (m, 2H).

Example 191A (2,4-Dichlorophenyl)(2,2-difluorocyclopropyl)methanol

The title compound was prepared starting from 9.00 g (35.8 mmol) of the compound from Example 189A in analogy to the synthesis of the compound from Example 190A. 7.30 g (80% of theory) of diastereomer 1 and 1.10 g (12% of theory) of diastereomer 2 of the title compound were obtained.

Diastereomer 191A-1:

$^1$H-NMR (400 MHz, DMSO-d$_6$): δ=7.69 (d, 1H), 7.59 (d, 1H), 7.49 (dd, 1H), 5.95 (d, 1H), 4.74 (dd, 1H), 2.07-2.19 (m, 1H), 1.48-1.58 (m, 1H), 1.28-1.38 (m, 1H).

Diastereomer 191A-2:

$^1$H-NMR (400 MHz, DMSO-d$_6$): δ=7.65 (d, 1H), 7.59 (d, 1H), 7.48 (dd, 1H), 5.83 (d, 1H), 4.74-4.80 (m, 1H), 2.04-2.16 (m, 1H), 1.61-1.71 (m, 1H), 1.50-1.60 (m, 1H).

Example 192A (2,2-Difluorocyclopropyl)[4-(trifluoromethyl)phenyl]methyl acetate

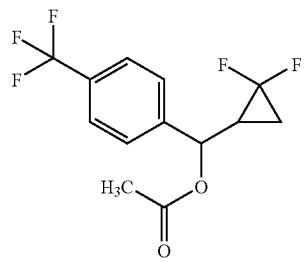

0.23 ml (2.86 mmol) of pyridine was added dropwise to 2.40 g (9.52 mmol) of the compound from Example 190A and 1.94 g (19.0 mmol) of acetic anhydride, and the mixture was stirred at RT overnight. The reaction mixture was then added to ethyl acetate and saturated aqueous sodium bicarbonate solution. The phases were separated, and the organic phase was concentrated, and the crude product was purified by column chromatography on silica gel (mobile phase: cyclohexane/ethyl acetate 6/1). 2.66 g (95% of theory) of the title compound were obtained as mixture of diastereomers.

$^1$H-NMR (400 MHz, DMSO-d$_6$): δ=7.74-7.80 (m, 2H), 7.68-7.73 (m, 1.8H), 7.57-7.61 (m, 0.2H), 5.57 (d, 0.1H), 5.53 (d, 0.9H), 2.33-2.46 (m, 1H), 2.09 (s, 3H), 1.74-1.84 (m, 1H), 1.60-1.71 (m, 1H).

Example 193A (2,4-Dichlorophenyl)(2,2-difluorocyclopropyl)methyl acetate

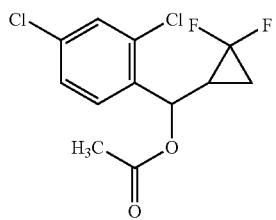

The title compound was prepared starting from 8.20 g (32.4 mmol) of a mixture of the two diastereomers of the compound from Example 191A in analogy to the synthesis of the compound from Example 192A. 7.70 g (81% of theory) of the title compound were obtained.

$^1$H-NMR (400 MHz, DMSO-d$_6$): δ=7.64-7.68 (m, 2H), 7.51 (dd, 1H), 5.75 (d, 1H), 2.41-2.50 (m, 1H), 2.07 (s, 3H), 1.67-1.79 (m, 1H), 1.47-1.57 (m, 1H).

EXEMPLARY EMBODIMENTS

Example 1

3-{7-[(Methylsulfanyl)methyl]-1H-indol-3-yl}-3-[4-(trifluoromethyl)phenyl]propan-1-ol

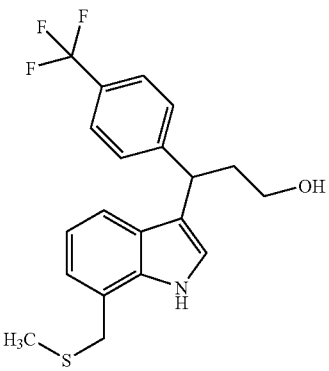

A solution of 215 mg (0.51 mmol) of the compound from Example 25A was added dropwise to 1.8 ml (1.80 mmol) of a 1N solution of lithium aluminum hydride in tetrahydrofuran under argon in 10 ml of tetrahydrofuran at RT. The mixture was stirred at RT for 15 min and then, while cooling in ice, 1N hydrochloric acid was added. The mixture was extracted with ethyl acetate, and the organic phase was dried over magnesium sulfate, filtered and concentrated. Purification by preparative HPLC (RP18 column; mobile phase: acetonitrile-water gradient) resulted in 169 mg (87% of theory) of the title compound.

$^1$H-NMR (400 MHz, DMSO-d$_6$): δ=1.94 (s, 3H), 2.10-2.20 (m, 1H), 2.28-2.38 (m, 1H), 3.30-3.42 (m, 2H), 3.91 (s, 2H), 4.43 (t, 1H), 4.50 (t, 1H), 6.83 (t, 1H), 6.91 (d, 1H), 7.27 (d, 1H), 7.35 (d, 1H), 7.52-7.57 (m, 2H), 7.58-7.62 (m, 2H), 11.0 (s, 1H).

LC-MS (Method 4): R$_t$=1.33 min; MS (ESIpos): m/z=380 [M+H]$^+$.

Example 2

3-(4-Chlorophenyl)-3-{7-[(methylsulfanyl)methyl]-1H-indol-3-yl}propan-1-ol

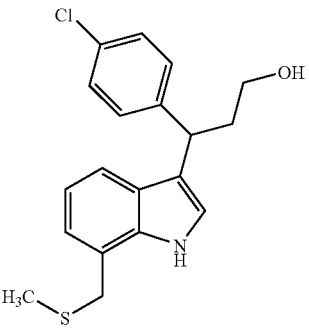

A solution of 6.68 g (17.2 mmol) of the compound from Example 29A in 100 ml of tetrahydrofuran was added dropwise to 60 ml (60 mmol) of a 1N solution of lithium aluminum hydride in tetrahydrofuran under argon in 300 ml of tetrahydrofuran at RT. The mixture was stirred at RT for 15 min and then, while cooling in ice, 1N hydrochloric acid was added. The mixture was extracted with ethyl acetate, and the organic phase was dried over magnesium sulfate, filtered and concentrated. The residue was purified by flash chromatography on silica gel (mobile phase: toluene/ethyl acetate gradient). 5.93 g (99% of theory) of the target compound were obtained.

$^1$H-NMR (400 MHz, DMSO-d$_6$): δ=1.94 (s, 3H), 2.04-2.14 (m, 1H), 2.24-2.34 (m, 1H), 3.30-3.41 (m, 2H), 3.91 (s, 2H), 4.31 (t, 1H), 6.83 (t, 1H), 6.91 (d, 1H), 7.25 (d, 1H), 7.27-7.30 (m, 3H), 7.31-7.36 (m, 2H), 10.9 (s, 1H).

LC-MS (Method 5): R$_t$=2.48 min; MS (ESIpos): m/z=346 [M+H]$^+$.

Example 3

3-(4-Chlorophenyl)-3-{7-[(ethylsulfanyl)methyl]-1H-indol-3-yl}propan-1-ol

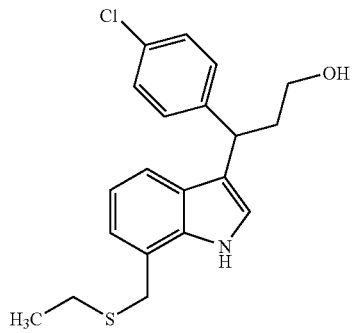

A solution of 1.05 g of the compound from Example 33A with a purity of 84% (2.19 mmol) in 20 ml of tetrahydrofuran was added dropwise to 9.1 ml (9.1 mmol) of a 1N solution of lithium aluminum hydride in tetrahydrofuran under argon in 50 ml of tetrahydrofuran at RT. The mixture was stirred at RT for 15 min and then, while cooling in ice, 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 0.95 g (94% of theory) of the title compound.

$^1$H-NMR (400 MHz, DMSO-d$_6$): δ=1.15 (t, 3H), 2.04-2.14 (m, 1H), 2.24-2.34 (m, 1H), 2.38 (q, 2H), 3.29-3.42 (m, 2H), 3.91-3.99 (m, 2H), 4.31 (t, 1H), 4.48 (t, 1H), 6.83 (t, 1H), 6.92 (d, 1H), 7.23-7.36 (m, 6H), 10.9 (s, 1H).

LC-MS (Method 4): R$_t$=1.36 min; MS (ESIpos): m/z=360 [M+H]$^+$.

Example 4

3-(4-Chloro-2-fluorophenyl)-3-{7-[(methylsulfanyl)methyl]-1H-indol-3-yl}propan-1-ol

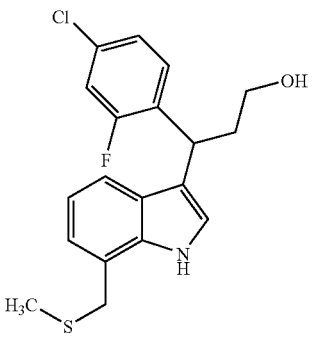

A solution of 2.23 g (5.49 mmol) of the compound from Example 34A in 20 ml of tetrahydrofuran was added dropwise to 19.2 ml (19.2 mmol) of a 1N solution of lithium aluminum hydride in tetrahydrofuran in 50 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 1.89 g (95% of theory) of the title compound.

$^1$H-NMR (400 MHz, DMSO-$d_6$): δ=1.94 (s, 3H), 2.08-2.19 (m, 1H), 2.26-2.35 (m, 1H), 3.34-3.41 (m, 2H), 3.91 (s, 2H), 4.50 (t, 1H), 4.61 (t, 1H), 6.86 (t, 1H), 6.93 (d, 1H), 7.17 (dd, 1H), 7.24-7.30 (m, 2H), 7.33 (dd, 1H), 7.37 (t, 1H), 11.0 (s, 1H).

LC-MS (Method 5): $R_t$=2.47 min; MS (ESIpos): m/z=364 [M+H]$^+$.

Enantiomer 4-1:

2.20 g with a purity of 90% (4.88 mmol) of the enantiomer 34A-2 were reacted in analogy to the synthesis of the compound from Example 4. 1.50 g (85% of theory) of the enantiomer of the title compound were obtained.

[α]$_D^{20}$=+53.0°, c=0.204, chloroform

Example 5

3-(4-Chloro-2-fluorophenyl)-2-methyl-3-{7-[(methylsulfanyl)methyl]-1H-indol-3-yl}propan-1-ol

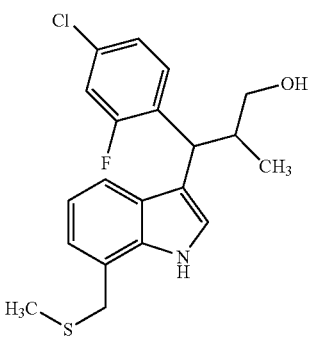

A solution of 200 mg of the compound from Example 36A with a purity of 90% (0.35 mmol) in 4 ml of tetrahydrofuran was added dropwise to 1.2 ml (1.2 mmol) of a 1N solution of lithium aluminum hydride in tetrahydrofuran in 2 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 66 mg (51% of theory) of the title compound as mixture of diastereomers.

$^1$H-NMR (400 MHz, DMSO-$d_6$): δ=0.83 (d, 1.8H), 0.97 (d, 1.2H), 1.94 (s, 3H), 2.46-2.60 (m, 1H), 3.06-3.14 (m, 0.4H), 3.22-3.28 (m, 0.6H), 3.28-3.35 (m, 0.4H), 3.45-3.51 (m, 0.6H), 3.86-3.95 (m, 2H), 4.26-4.34 (m, 1H), 4.42-4.47 (m, 1H), 6.85-6.94 (m, 2H), 7.14-7.18 (m, 1H), 7.26-7.40 (m, 3H), 7.46 (t, 0.6H), 7.52 (t, 0.4H), 11.0 (s, 1H).

LC-MS (Method 3): $R_t$=2.21 and 2.28 min; MS (ESIpos): m/z=378 [M+H]$^+$.

Example 6

3-(4-Chloro-2-fluorophenyl)-3-{5-fluoro-7-[(methylsulfanyl)methyl]-1H-indol-3-yl}propan-1-ol

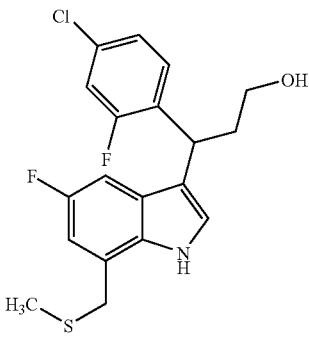

A solution of 1.1 g (2.57 mmol) of the compound from Example 37A in 20 ml of tetrahydrofuran was added dropwise to 9.0 ml (9.0 mmol) of a 1N solution of lithium aluminum hydride in tetrahydrofuran in 50 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 715 mg (73% of theory) of the title compound.

$^1$H-NMR (400 MHz, DMSO-$d_6$): δ=1.95 (s, 3H), 2.09-2.19 (m, 1H), 2.25-2.35 (m, 1H), 3.33-3.42 (m, 2H), 3.91 (s, 2H), 4.50 (t, 1H), 4.55 (t, 1H), 6.83 (dd, 1H), 6.98 (dd, 1H), 7.19 (dd, 1H), 7.31-7.37 (m, 2H), 7.41 (t, 1H), 11.1 (s, 1H).

LC-MS (Method 3): $R_t$=2.19 min; MS (ESIpos): m/z=382 [M+H]$^+$.

Example 7

3-(2,4-Dichlorophenyl)-3-{7-[(methylsulfanyl)methyl]-1H-indol-3-yl}propan-1-ol

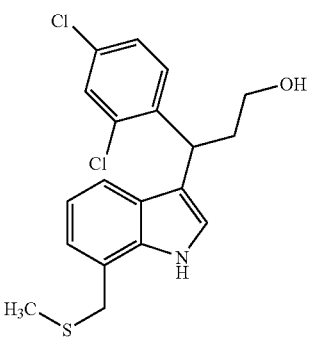

A solution of 2.34 g (5.54 mmol) of the compound from Example 38A in 20 ml of tetrahydrofuran was added dropwise to 19.4 ml (19.4 mmol) of a 1N solution of lithium aluminum hydride in tetrahydrofuran in 50 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 2.00 g (95% of theory) of the title compound.

$^1$H-NMR (400 MHz, DMSO-$d_6$): δ=1.94 (s, 3H), 2.04-2.15 (m, 1H), 2.23-2.35 (m, 1H), 3.34-3.46 (m, 2H), 3.87-3.96 (m, 2H), 4.50 (t, 1H), 4.76 (t, 1H), 6.85 (t, 1H), 6.93 (d, 1H), 7.24 (d, 1H), 7.28-7.32 (m, 2H), 7.36 (d, 1H), 7.55 (d, 1H), 11.0 (s, 1H).

LC-MS (Method 4): $R_t$=1.38 min; MS (ESIpos): m/z=380 [M+H]$^+$.

Example 8

3-(2,4-Dichlorophenyl)-3-{5-fluoro-7-[(methylsulfanyl)methyl]-1H-indol-3-yl}propan-1-ol

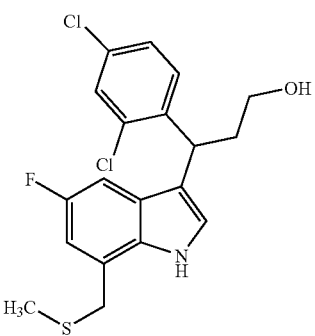

A solution of 1.48 g (3.36 mmol) of the compound from Example 39A in 20 ml of tetrahydrofuran was added dropwise to 11.8 ml (11.8 mmol) of a 1N solution of lithium aluminum hydride in tetrahydrofuran in 50 ml of tetrahydrofuran at RT under argon. The mixture was stirred at RT for 15 min and then 1N hydrochloric acid was added. The mixture was extracted with ethyl acetate, and the organic phase was dried over magnesium sulfate, filtered and concentrated. 1.32 g (99% of theory) of the title compound were obtained.

$^1$H-NMR (400 MHz, DMSO-$d_6$): δ=1.96 (s, 3H), 2.05-2.15 (m, 1H), 2.24-2.35 (m, 1H), 3.34-3.45 (m, 2H), 3.87-3.96 (m, 2H), 4.51 (t, 1H), 4.71 (t, 1H), 6.83 (dd, 1H), 6.95 (dd, 1H), 7.32 (dd, 1H), 7.37-7.41 (m, 2H), 7.56 (d, 1H), 11.1 (s, 1H).

LC-MS (Method 4): $R_t$=1.39 min; MS (ESIpos): m/z=398 [M+H]$^+$.

Example 9

3-(4-Chlorophenyl)-3-{5-fluoro-7-[(methylsulfanyl)methyl]-1H-indol-3-yl}propan-1-ol

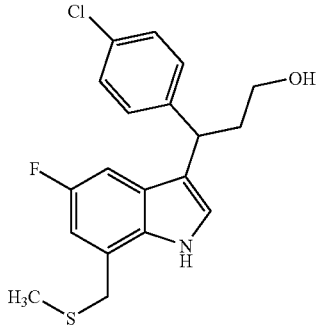

A solution of 1.29 g of the compound from Example 40A with a purity of 79% (2.52 mmol) in 30 ml of tetrahydrofuran was added dropwise to 11.1 ml (11.1 mmol) of a 1N solution of lithium aluminum hydride in tetrahydrofuran in 70 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 0.68 g (74% of theory) of the title compound.

$^1$H-NMR (400 MHz, DMSO-$d_6$): δ=1.95 (s, 3H), 2.03-2.14 (m, 1H), 2.21-2.32 (m, 1H), 3.28-3.41 (m, 2H), 3.91 (s, 2H), 4.27 (t, 1H), 4.47 (t, 1H), 6.81 (dd, 1H), 6.99 (dd, 1H), 7.28-7.37 (m, 4H), 7.38 (d, 1H), 11.1 (s, 1H).

LC-MS (Method 6): $R_t$=2.40 min; MS (ESIpos): m/z=364 [M+H]$^+$.

Example 10

3-(4-Chloro-2-methylphenyl)-3-{7-[(ethylsulfanyl)methyl]-1H-indol-3-yl}propan-1-ol

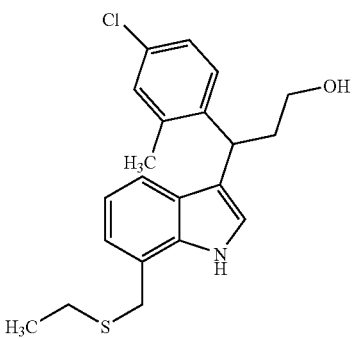

A solution of 2.23 g (5.49 mmol) of the compound from Example 41A in 20 ml of tetrahydrofuran was added dropwise to 5.7 ml (5.7 mmol) of a 1N solution of lithium aluminum hydride in tetrahydrofuran in 50 ml of tetrahydrofuran at RT under argon. The mixture was stirred at RT for 15 min and then 1N hydrochloric acid was added. The mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 458 mg (76% of theory) of the title compound.

$^1$H-NMR (400 MHz, DMSO-$d_6$): δ=1.15 (t, 3H), 1.96-2.06 (m, 1H), 2.21-2.32 (m, 1H), 2.39 (q, 2H), 2.42 (s, 3H), 3.32-3.46 (m, 2H), 3.92-4.00 (m, 2H), 4.48-4.54 (m, 2H), 6.83 (t, 1H), 6.92 (d, 1H), 7.11 (dd, 1H), 7.15-7.22 (m, 4H), 10.9 (s, 1H).

LC-MS (Method 5): $R_t$=2.64 min; MS (ESIpos): m/z=374 [M+H]$^+$.

Example 11

3-(4-Chloro-2-methylphenyl)-3-{7-[(methylsulfanyl)methyl]-1H-indol-3-yl}propan-1-ol

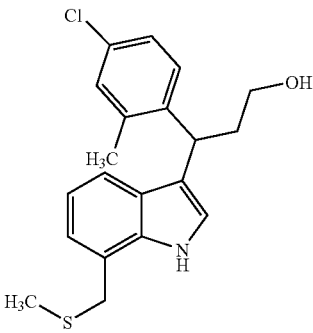

The title compound was prepared starting from 1.62 g (4.03 mmol) of the compound from Example 42A in analogy to the synthesis of the compound from Example 4. 1.4 g (97% of theory) of the title compound were obtained.

$^1$H-NMR (400 MHz, DMSO-$d_6$): δ=1.94 (s, 3H), 1.96-2.06 (m, 1H), 2.21-2.32 (m, 1H), 2.42 (s, 3H), 3.30-3.46 (m, 2H), 3.87-3.96 (m, 2H), 4.48-4.55 (m, 2H), 6.83 (t, 1H), 6.91 (d, 1H), 7.11 (dd, 1H), 7.15-7.22 (m, 4H), 10.9 (s, 1H).

LC-MS (Method 4): $R_t$=1.35 min; MS (ESIpos): m/z=360 [M+H]$^+$.

Example 12

3-(4-Fluoro-2-methylphenyl)-3-{7-[(methylsulfanyl)methyl]-1H-indol-3-yl}propan-1-ol

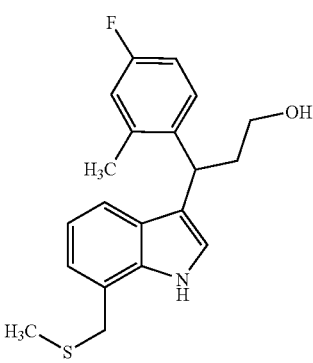

A solution of 585 mg (1.52 mmol) of the compound from Example 43A in 15 ml of tetrahydrofuran was added dropwise to 5.3 ml (5.31 mmol) of a 1N solution of lithium aluminum hydride in tetrahydrofuran in 30 ml of tetrahydrofuran at RT under argon. The mixture was stirred at RT for 15 min and then, while cooling in ice, 1N hydrochloric acid was added. The mixture was extracted with ethyl acetate, and the organic phase was dried over magnesium sulfate, filtered and concentrated. The crude product was purified by preparative HPLC (RP18 column; mobile phase: acetonitrile/water gradient with addition of 0.1% formic acid) to result in 369 mg (71% of theory) of the title compound.

$^1$H-NMR (400 MHz, DMSO-$d_6$): δ=1.94 (s, 3H), 1.96-2.07 (m, 1H), 2.21-2.32 (m, 1H), 2.43 (s, 3H), 3.29-3.46 (m, 2H), 3.88-3.96 (m, 2H), 4.46-4.54 (m, 2H), 6.83 (t, 1H), 6.86 (dd, 1H), 6.91 (d, 1H), 6.97 (dd, 1H), 7.17-7.23 (m, 3H), 10.9 (s, 1H).

LC-MS (Method 4): $R_t$=1.28 min; MS (ESIpos): m/z=344 [M+H]$^+$.

Example 13

3-[2-Fluoro-4-(trifluoromethyl)phenyl]-3-{7-[(methylsulfanyl)methyl]-1H-indol-3-yl}propan-1-ol

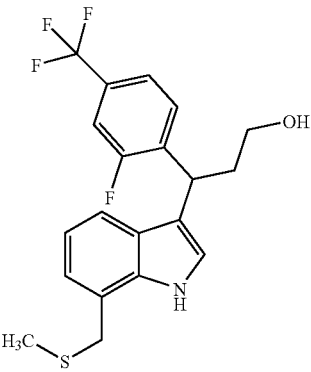

A solution of 2.74 g (6.13 mmol) of the compound from Example 44A in 20 ml of tetrahydrofuran was added dropwise to 21.5 ml (21.5 mmol) of a 1N solution of lithium aluminum hydride in tetrahydrofuran in 50 ml of tetrahydrofuran at RT under argon. Stirring at RT for 15 min was followed by addition of 1N hydrochloric acid, extraction with dichloromethane, drying of the organic phase over magnesium sulfate, filtration and concentration. 2.47 g (99% of theory) of the title compound were obtained.

$^1$H-NMR (400 MHz, DMSO-$d_6$): δ=1.94 (s, 3H), 2.14-2.24 (m, 1H), 2.31-2.41 (m, 1H), 3.33-3.46 (m, 2H), 3.92 (s, 2H), 4.50-4.56 (m, 1H), 4.72 (t, 1H), 6.87 (t, 1H), 6.93 (d, 1H), 7.29 (d, 1H), 7.34 (d, 1H), 7.47 (d, 1H), 7.56-7.63 (m, 2H), 11.0 (s, 1H).

LC-MS (Method 4): $R_t$=1.36 min; MS (ESIpos): m/z=398 [M+H]$^+$.

Example 14

3-{7-[(Methylsulfanyl)methyl]-1H-indol-3-yl}-3-(naphthalen-2-yl)propan-1-ol

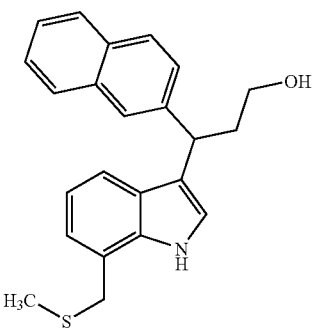

A solution of 600 mg (1.49 mmol) of the compound from Example 45A in 15 ml of tetrahydrofuran was added dropwise to 5.2 ml (5.2 mmol) of a 1N solution of lithium aluminum hydride in tetrahydrofuran in 30 ml of tetrahydrofuran at RT under argon. Stirring at RT for 15 min was followed by addition, while cooling in ice, of 1N hydrochloric acid, extraction with ethyl acetate, drying of the organic phase over magnesium sulfate, filtration and concentration. 486 mg (90% of theory) of the title compound were obtained.

$^1$H-NMR (400 MHz, DMSO-$d_6$): δ=1.92 (s, 3H), 2.19-2.29 (m, 1H), 2.33-2.44 (m, 1H), 3.35-3.45 (m, 2H), 3.87-3.95 (m, 2H), 4.45-4.50 (m, 2H), 6.79 (t, 1H), 6.88 (d, 1H), 7.31 (d, 1H), 7.35 (d, 1H), 7.39-7.48 (m, 3H), 7.75-7.87 (m, 4H), 10.9 (s, 1H).

LC-MS (Method 5): $R_t$=2.48 min; MS (ESIpos): m/z=362 [M+H]$^+$.

Example 15

4-(4-Chlorophenyl)-4-{7-[(methylsulfanyl)methyl]-1H-indol-3-yl}butan-1-ol

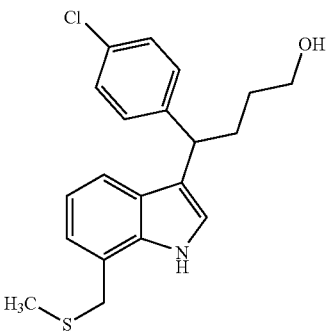

A solution of 420 mg (1.05 mmol) of the compound from Example 46A in 10 ml of tetrahydrofuran was added dropwise to 3.7 ml (3.7 mmol) of a 1N solution of lithium aluminum hydride in tetrahydrofuran under argon in 20 ml of tetrahydrofuran at RT. The mixture was stirred at RT for 15 min and then, while cooling in ice, 1N hydrochloric acid was added. The mixture was extracted with ethyl acetate, and the organic phase was dried over magnesium sulfate, filtered and concentrated. The residue was purified by preparative HPLC (RP18 column; mobile phase: acetonitrile/water gradient with addition of 0.1% formic acid). 243 mg (65% of theory) of the target compound were obtained.

$^1$H-NMR (400 MHz, DMSO-$d_6$): δ=1.28-1.50 (m, 2H), 1.92-2.03 (m, 1H), 1.94 (s, 3H), 2.07-2.19 (m, 1H), 3.38-3.44 (m, 2H), 3.91 (s, 2H), 4.12 (t, 1H), 4.36 (t, 1H), 6.83 (t, 1H), 6.90 (d, 1H), 7.25-7.31 (m, 4H), 7.32-7.36 (m, 2H), 10.9 (s, 1H).

LC-MS (Method 4): $R_t$=1.36 min; MS (ESIpos): m/z=360 [M+H]$^+$.

Example 16

3-(4-Chlorophenyl)-3-{6-fluoro-7-[(methylsulfanyl)methyl]-1H-indol-3-yl}propan-1-ol

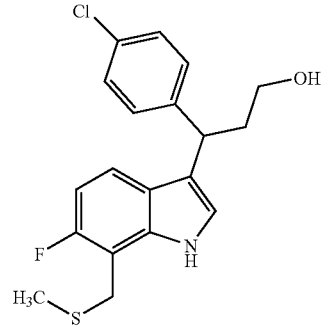

A solution of 2.33 g (5.7 mmol) of the compound from Example 47A in 18 ml of tetrahydrofuran was added dropwise to 20.1 ml (60.1 mmol) of a 1N solution of lithium aluminum hydride in tetrahydrofuran and 20 ml of tetrahydrofuran at RT. The mixture was stirred at 60° C. for 1 h, acetonitrile was added, and water was added to the solution while cooling in ice. The solid was filtered off with suction from the suspension, the filtrate was concentrated, and the residue was purified by preparative HPLC (mobile phase: acetonitrile/water gradient). 1.72 g (82% of theory) of the title compound were obtained.

$^1$H-NMR (400 MHz, DMSO-$d_6$): δ=1.98 (s, 3H), 2.02-2.13 (m, 1H), 2.22-2.32 (m, 1H), 3.29-3.41 (m, 2H), 3.94 (s, 2H), 4.30 (t, 1H), 4.48 (t, 1H), 6.75 (dd, 1H), 7.22 (dd, 1H), 7.26-7.37 (m, 5H), 11.09 (s, 1H).

LC-MS (Method 3): $R_t$=2.16 min; MS (ESIpos): m/z=364 [M+H]$^+$.

Example 17

3-{6-Fluoro-7-[(methylsulfanyl)methyl]-1H-indol-3-yl}-3-[4-(trifluoromethyl)phenyl]propan-1-ol

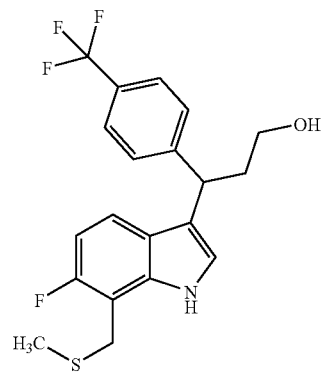

The title compound was prepared starting from 2.98 g (6.78 mmol) of the compound from Example 48A in analogy to the synthesis of the compound from Example 16. 2.47 g (92% of theory) of the title compound were obtained.

¹H-NMR (400 MHz, DMSO-d₆): δ=1.98 (s, 3H), 2.07-2.18 (m, 1H), 2.26-2.38 (m, 1H), 3.29-3.43 (m, 2H), 3.95 (s, 2H), 4.42 (t, 1H), 4.51 (t, 1H), 6.76 (t, 1H), 7.24 (dd, 1H), 7.37 (s, 1H), 7.54 (d, 2H), 7.61 (d, 2H), 11.13 (s, 1H).

LC-MS (Method 3): $R_t$=2.23 min; MS (ESIpos): m/z=398 [M+H]⁺.

Example 18

3-(1-Benzothiophen-5-yl)-3-{7-[(methylsulfanyl)methyl]-1H-indol-3-yl}propan-1-ol

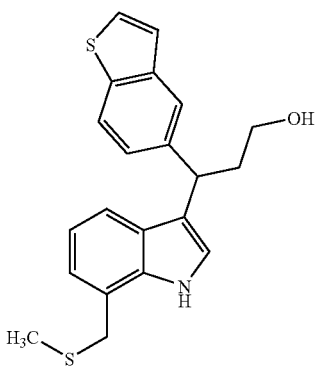

The title compound was prepared starting from 1.17 g (2.87 mmol) of the compound from Example 49A in analogy to the synthesis of the compound from Example 16. 0.93 g (88% of theory) of the title compound were obtained.

¹H-NMR (400 MHz, DMSO-d₆): δ=1.93 (s, 3H), 2.13-2.24 (m, 1H), 2.31-2.41 (m, 1H), 3.34-3.44 (m, 2H), 3.91 (s, 2H), 4.39-4.49 (m, 2H), 6.80 (t, 1H), 6.89 (d, 1H), 7.26-7.40 (m, 4H), 7.68 (d, 1H), 7.80-7.86 (m, 2H), 10.91 (s, 1H).

LC-MS (Method 4): $R_t$=1.29 min; MS (ESIpos): m/z=368 [M+H]⁺.

Example 19

3-(2-Bromo-1,3-thiazol-5-yl)-3-{7-[(methylsulfanyl)methyl]-1H-indol-3-yl}propan-1-ol

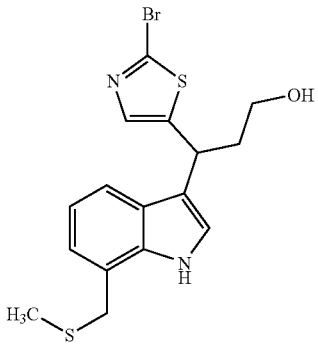

A solution of 1.19 g (2.71 mmol) of the compound from Example 50A in 25 ml of tetrahydrofuran was added dropwise to 8.13 ml (8.13 mmol) of a 1N solution of diisobutylaluminum hydride in heptane/tetrahydrofuran and 25 ml of tetrahydrofuran at RT. The mixture was stirred at RT for 1 h, and the solution was mixed with ethyl acetate, water and 1N hydrochloric acid. The phases were separated, the aqueous phase was extracted three times with ethyl acetate, and the combined organic phases were washed with saturated aqueous sodium chloride solution. This was followed by drying over sodium sulfate, removal of the solid by filtration and removal of the solvents from the crude product in vacuo. Purification of the residue by preparative HPLC (mobile phase: acetonitrile/water gradient) resulted in 0.73 g (68% of theory) of the title compound.

¹H-NMR (400 MHz, DMSO-d₆): δ=1.95 (s, 3H), 2.12-2.35 (m, 2H), 3.35-3.45 (m, 2H), 3.93 (s, 2H), 4.57 (t, 1H), 4.68 (t, 1H), 6.90 (t, 1H), 6.96 (d, 1H), 7.31 (d, 1H), 7.36 (d, 1H), 7.59 (s, 1H), 11.05 (s, 1H).

LC-MS (Method 5): $R_t$=2.16 min; MS (ESIpos): m/z=397 [M+H]⁺.

Example 20

2-Methyl-3-{7-[(methylsulfanyl)methyl]-1H-indol-3-yl}-3-[4-(trifluoromethyl)phenyl]propan-1-ol

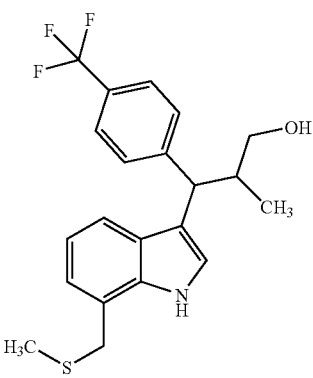

The title compound was prepared starting from 0.97 g (2.23 mmol) of the compound from Example 28A in analogy to the synthesis of the compound from Example 19. 0.66 g (75% of theory) of the title compound was obtained as mixture of diastereomers.

¹H-NMR (400 MHz, DMSO-d₆): δ=0.76-1.01 (m, 3H), 1.94 (s, 3H), 2.47-2.57 (m, 1H), 3.01-3.50 (m, 2H), 3.90 (s, 2H), 4.10-4.17 (m, 1H), 4.40-4.49 (m, 1H), 6.81-6.94 (m, 2H), 7.34-7.45 (m, 2H), 7.55-7.63 (m, 4H), 10.97 (s, 1H).

LC-MS (Method 4): $R_t$=1.37/1.39 min; MS (ESIpos): m/z=394 [M+H]⁺.

Example 21

3-(4-Chlorophenyl)-2-methyl-3-{7-[(methylsulfanyl)methyl]-1H-indol-3-yl}propan-1-ol

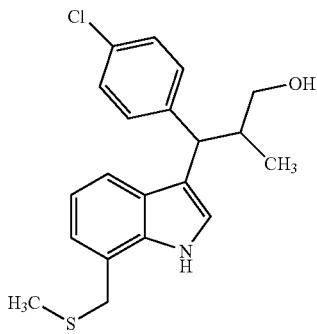

The title compound was prepared starting from 395 mg (0.98 mmol) of the compound from Example 32A in analogy to the synthesis of the compound from Example 19. 222 mg (63% of theory) of the title compound were obtained as mixture of diastereomers.

$^1$H-NMR (400 MHz, DMSO-d$_6$): δ=0.76-0.99 (m, 3H), 1.94 (s, 3H), 2.40-3.48 (m, 3H), 3.90 (s, 2H), 4.00-4.06 (m, 1H), 4.37-4.46 (m, 1H), 6.81-6.93 (m, 2H), 7.23-7.42 (m, 6H), 10.93 (s, 1H).

LC-MS (Method 6): R$_t$=2.40/2.45 min; MS (ESIpos): m/z=360 [M+H]$^+$.

Example 22

3-(4-Chloro-2-fluorophenyl)-3-{5-fluoro-7-[(methylsulfonyl)methyl]-1H-indol-3-yl}propan-1-ol

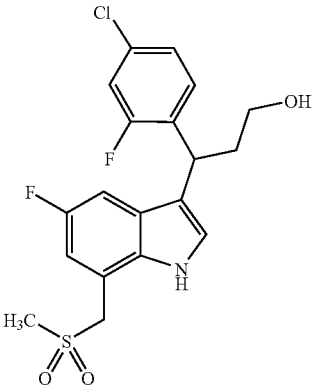

60 mg (0.16 mmol) of the compound from Example 6 were introduced into 2 ml of dichloromethane at 0° C., 79.4 mg (0.32 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 27 mg (42% of theory) of the title compound.

$^1$H-NMR (400 MHz, DMSO-d$_6$): δ=2.10-2.20 (m, 1H), 2.25-2.35 (m, 1H), 2.91 (s, 3H), 3.32-3.42 (m, 2H), 4.51 (t, 1H), 4.57 (t, 1H), 4.70-4.78 (m, 2H), 6.99 (dd, 1H), 7.12 (dd, 1H), 7.20 (dd, 1H), 7.34 (dd, 1H), 7.39-7.45 (m, 2H), 11.2 (s, 1H).

LC-MS (Method 3): R$_t$=1.78 min; MS (ESIpos): m/z=414 [M+H]$^+$.

Example 23

3-(2,4-Dichlorophenyl)-3-{7-[(methylsulfonyl)methyl]-1H-indol-3-yl}propan-1-ol

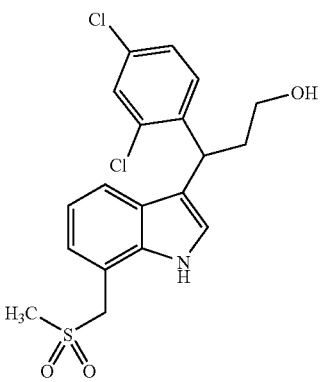

100 mg (0.26 mmol) of the compound from Example 7 were introduced into 15 ml of dichloromethane at 0° C., 130 mg (0.53 mmol) of 70% pure meta-chloroperbenzoic acid were added, and the mixture was stirred at RT overnight. 2 ml of methanol were added, the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 50 mg (46% of theory) of the title compound.

$^1$H-NMR (400 MHz, DMSO-d$_6$): δ=2.05-2.15 (m, 1H), 2.25-2.35 (m, 1H), 2.88 (s, 3H), 3.35-3.45 (m, 2H), 4.51 (t, 1H), 4.67-4.76 (m, 2H), 4.78 (t, 1H), 6.95 (t, 1H), 7.10 (d, 1H), 7.30 (dd, 1H), 7.33-7.40 (m, 3H), 7.56 (d, 1H), 11.1 (s, 1H).

LC-MS (Method 5): R$_t$=2.17 min; MS (ESIpos): m/z=412 [M+H]$^+$.

Example 24

3-(2,4-Dichlorophenyl)-3-{5-fluoro-7-[(methylsulfonyl)methyl]-1H-indol-3-yl}propan-1-ol

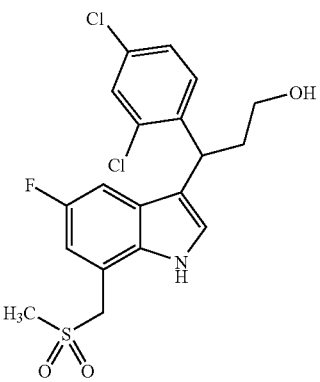

100 mg (0.25 mmol) of the compound from Example 8 were introduced into 15 ml of dichloromethane at 0° C., 124 mg (0.50 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 51 mg (47% of theory) of the title compound.

$^1$H-NMR (400 MHz, DMSO-d$_6$): δ=2.05-2.16 (m, 1H), 2.24-2.34 (m, 1H), 2.91 (s, 3H), 3.33-3.43 (m, 2H), 4.52 (t, 1H), 4.69-4.79 (m, 3H), 6.99 (dd, 1H), 7.08 (dd, 1H), 7.33 (dd, 1H), 7.40 (d, 1H), 7.46 (s, 1H), 7.57 (d, 1H), 11.2 (s, 1H).

LC-MS (Method 3): R$_t$=1.89 min; MS (ESIpos): m/z=430 [M+H]$^+$.

Example 25

3-(4-Chlorophenyl)-3-{5-fluoro-7-[(methylsulfonyl)methyl]-1H-indol-3-yl}propan-1-ol

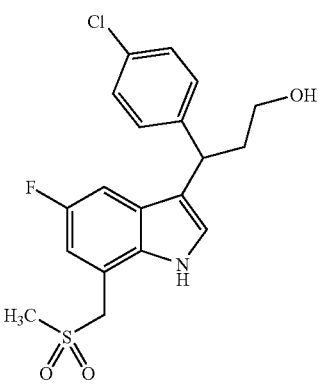

75.0 mg (0.21 mmol) of the compound from Example 9 were introduced into 12 ml of dichloromethane at 0° C., 102 mg (0.41 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 42 mg (52% of theory) of the title compound.

$^1$H-NMR (400 MHz, DMSO-d$_6$): δ=2.04-2.14 (m, 1H), 2.22-2.32 (m, 1H), 2.90 (s, 3H), 3.28-3.41 (m, 2H), 4.29 (t, 1H), 4.48 (t, 1H), 4.69-4.78 (m, 2H), 6.97 (dd, 1H), 7.13 (dd, 1H), 7.28-7.37 (m, 4H), 7.47 (d, 1H), 11.2 (s, 1H).

LC-MS (Method 6): R$_t$=2.06 min; MS (ESIpos): m/z=396 [M+H]$^+$.

Example 26

3-(4-Chloro-2-methylphenyl)-3-{7-[(methylsulfonyl)methyl]-1H-indol-3-yl}propan-1-ol

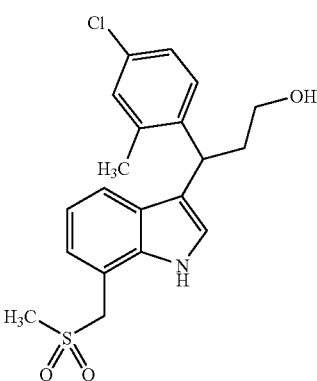

100 mg (0.28 mmol) of the compound from Example 11 were introduced into 15 ml of dichloromethane at 0° C., 137 mg (0.56 mmol) of 70% pure meta-chloroperbenzoic acid were added, and the mixture was stirred at RT overnight. 2 ml of methanol were added, the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 40 mg (37% of theory) of the title compound.

$^1$H-NMR (400 MHz, DMSO-d$_6$): δ=1.96-2.06 (m, 1H), 2.21-2.31 (m, 1H), 2.42 (s, 3H), 2.87 (s, 3H), 3.28-3.46 (m, 2H), 4.50-4.56 (m, 2H), 4.66-4.76 (m, 2H), 6.93 (t, 1H), 7.07-7.14 (m, 2H), 7.17-7.23 (m, 2H), 7.26-7.30 (m, 2H), 11.0 (s, 1H).

LC-MS (Method 5): R$_t$=2.13 min; MS (ESIpos): m/z=392 [M+H]$^+$.

Example 27

4-(4-Chlorophenyl)-4-{7-[(methylsulfonyl)methyl]-1H-indol-3-yl}butan-1-ol

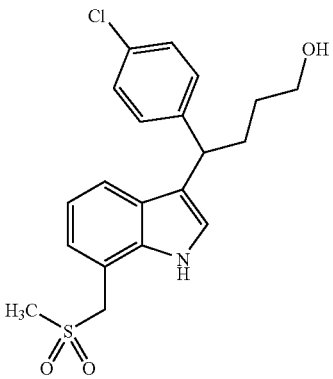

40 mg (0.11 mmol) of the compound from Example 15 were introduced into 7 ml of dichloromethane at 0° C., 54.8 mg (0.22 mmol) of 70% pure meta-chloroperbenzoic acid were added, and the mixture was stirred at RT overnight and then under reflux for 15 minutes. 2 ml of methanol were added, the mixture was concentrated, the residue was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 20 mg (46% of theory) of the title compound.

$^1$H-NMR (400 MHz, DMSO-d$_6$): δ=1.28-1.50 (m, 2H), 1.92-2.03 (m, 1H), 2.08-2.19 (m, 1H), 2.87 (s, 3H), 3.41 (t, 2H), 4.14 (t, 1H), 4.36 (s, 1H), 4.66-4.75 (m, 2H), 6.92 (t, 1H), 7.08 (d, 1H), 7.27-7.31 (m, 2H), 7.32-7.40 (m, 4H), 11.0 (s, 1H).

LC-MS (Method 8): R$_t$=2.09 min; MS (ESIneg): m/z=390 [M−H]$^−$.

Example 28

3-(1-Benzothiophen-5-yl)-3-{7-[(methylsulfonyl)methyl]-1H-indol-3-yl}propan-1-ol

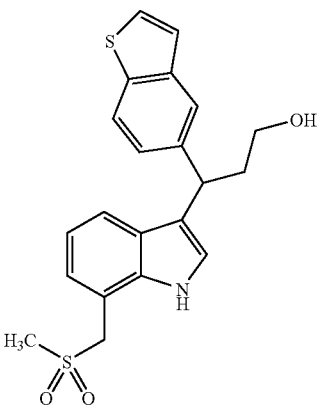

100 mg (0.27 mmol) of the compound from Example 18 were introduced into 19 ml of dichloromethane at 0° C., 134 mg (0.54 mmol) of 70% pure meta-chloroperbenzoic acid were added, and the mixture was stirred at RT for 2 h. 2 ml of methanol were added and then the solvents were removed in vacuo. The crude product was purified by preparative HPLC (mobile phase: acetonitrile/water gradient) three times to result in 23 mg (21% of theory) of the title compound.

$^1$H-NMR (400 MHz, DMSO-$d_6$): δ=2.13-2.24 (m, 1H), 2.31-2.41 (m, 1H), 2.86 (s, 3H), 3.33-3.43 (m, 2H), 4.40-4.50 (m, 2H), 4.71 (s, 2H), 6.89 (t, 1H), 7.07 (d, 1H), 7.31-7.42 (m, 4H), 7.69 (d, 1H), 7.81-7.86 (m, 2H), 11.01 (s, 1H).

HPLC (Method 2): $R_t$=4.16 min; MS (ESIpos): m/z=400 [M+H]$^+$.

Example 29

3-(4-Chlorophenyl)-2-methyl-3-{7-[(methylsulfonyl)methyl]-1H-indol-3-yl}propan-1-ol

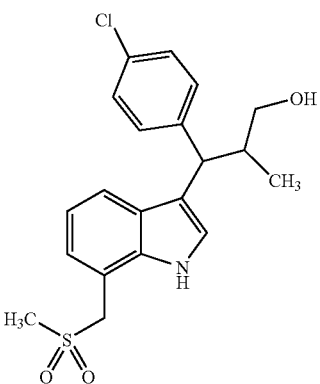

The title compound was prepared starting from 57 mg (0.15 mmol) of the compound from Example 21 in analogy to the synthesis of the compound from Example 28. 46 mg (77% of theory) of the title compound were obtained as mixture of diastereomers.

$^1$H-NMR (400 MHz, DMSO-$d_6$): δ=0.76-0.99 (m, 3H), 2.40-3.46 (m, 3H), 2.87 (s, 3H), 4.01-4.09 (m, 1H), 4.37-4.47 (m, 1H), 4.70 (s, 2H), 6.95 (t, 1H), 7.09 (d, 1H), 7.24-7.29 (m, 2H), 7.33-7.54 (m, 4H), 11.02 (s, 1H).

LC-MS (Method 4): $R_t$=1.10/1.15 min; MS (ESIpos): m/z=392 [M+H]$^+$.

Example 30

3-(4-Chloro-2-fluorophenyl)-3-{5-fluoro-7-[(methylsulfinyl)methyl]-1H-indol-3-yl}propan-1-ol

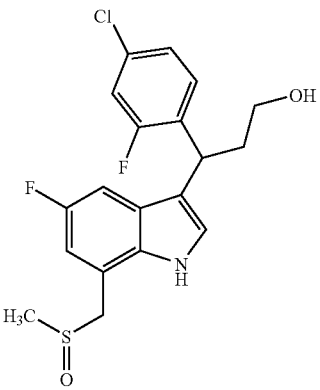

60 mg (0.16 mmol) of the compound from Example 6 were introduced into 2 ml of dichloromethane at 0° C., 40.7 mg (0.17 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 29 mg (46% of theory) of the title compound as mixture of diastereomers.

$^1$H-NMR (400 MHz, DMSO-$d_6$): δ=2.09-2.20 (m, 1H), 2.25-2.35 (m, 1H), 2.52-2.54 (m, 3H), 3.32-3.42 (m, 2H), 4.18-4.25 (m, 1H), 4.33-4.39 (m, 1H), 4.51 (t, 1H), 4.56 (t, 1H), 6.89 (dd, 1H), 7.07 (d, 1H), 7.20 (dd, 1H), 7.34 (dd, 1H), 7.38-7.44 (m, 2H), 11.2 (s, 1H).

LC-MS (Method 5): $R_t$=2.02 min; MS (ESIpos): m/z=398 [M+H]$^+$.

Example 31

3-(2,4-Dichlorophenyl)-3-{7-[(methylsulfinyl)methyl]-1H-indol-3-yl}propan-1-ol

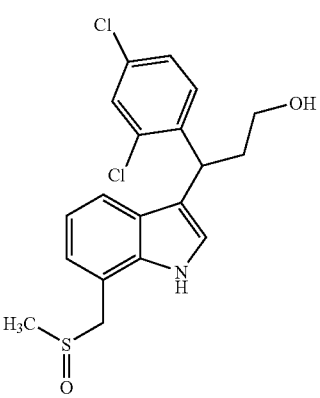

75.9 mg (0.20 mmol) of the compound from Example 7 were introduced into 11 ml of dichloromethane at 0° C., 49.2 mg (0.20 mmol) of 70% pure meta-chloroperbenzoic acid were added, and the mixture was stirred at RT overnight. 2 ml of methanol were added, the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 50 mg (63% of theory) of the title compound as mixture of diastereomers.

$^1$H-NMR (400 MHz, DMSO-$d_6$): δ=2.04-2.15 (m, 1H), 2.25-2.35 (m, 1H), 2.52 (s, 3H), 3.33-3.46 (m, 2H), 4.18-4.25 (m, 1H), 4.31-4.38 (m, 1H), 4.51 (t, 1H), 4.77 (t, 1H), 6.91 (t, 1H), 7.00 (d, 1H), 7.27-7.39 (m, 4H), 7.55 (d, 1H), 11.1 (s, 1H).

LC-MS (Method 5): $R_t$=2.06 min; MS (ESIpos): m/z=396 [M+H]$^+$.

Example 32

3-(2,4-Dichlorophenyl)-3-{5-fluoro-7-[(methylsulfinyl)methyl]-1H-indol-3-yl}propan-1-ol

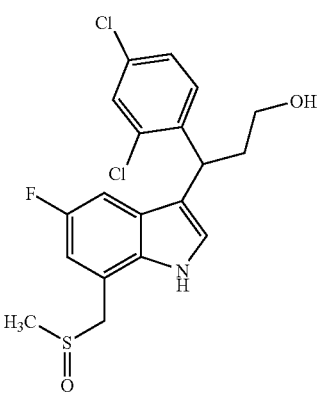

100 mg (0.25 mmol) of the compound from Example 8 were introduced into 15 ml of dichloromethane at 0° C., 61.9 mg (0.25 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 91 mg (88% of theory) of the title compound as mixture of diastereomers.

$^1$H-NMR (400 MHz, DMSO-$d_6$): δ=2.05-2.15 (m, 1H), 2.24-2.34 (m, 1H), 2.53-2.54 (m, 3H), 3.34-3.45 (m, 2H), 4.18-4.26 (m, 1H), 4.33-4.40 (m, 1H), 4.52 (t, 1H), 4.72 (t, 1H), 6.89 (d, 1H), 7.03 (d, 1H), 7.33 (dd, 1H), 7.39 (d, 1H), 7.44 (s, 1H), 7.56 (d, 1H), 11.2 (s, 1H).

LC-MS (Method 3): $R_t$=1.76 min; MS (ESIpos): m/z=414 [M+H]$^+$.

Example 33

3-(4-Chlorophenyl)-3-{5-fluoro-7-[(methylsulfinyl)methyl]-1H-indol-3-yl}propan-1-ol

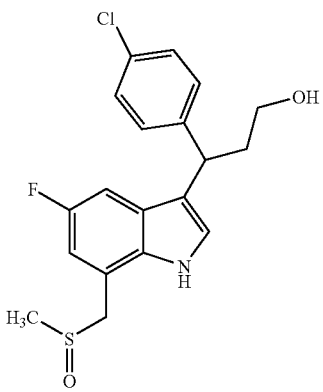

75.0 mg (0.21 mmol) of the compound from Example 9 were introduced into 12 ml of dichloromethane at 0° C., 50.8 mg (0.21 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 25 mg (30% of theory) of the title compound which are contaminated with meta-chlorobenzoic acid. It was taken up in ethyl acetate, washed with saturated aqueous sodium bicarbonate solution, dried over sodium sulfate, filtered and concentrated to result in 23 mg (29% of theory) of the title compound as mixture of diastereomers.

$^1$H-NMR (400 MHz, DMSO-$d_6$): δ=2.03-2.14 (m, 1H), 2.22-2.32 (m, 1H), 2.52-2.53 (m, 3H), 3.28-3.40 (m, 2H), 4.18-4.25 (m, 1H), 4.28 (t, 1H), 4.32-4.39 (m, 1H), 4.49 (s, 1H), 6.86 (dd, 1H), 7.05-7.09 (m, 1H), 7.28-7.37 (m, 4H), 7.45 (s, 1H), 11.2 (s, 1H).

LC-MS (Method 3): $R_t$=1.61 min; MS (ESIpos): m/z=380 [M+H]$^+$.

Example 34

4-(4-Chlorophenyl)-4-{7-[(methylsulfinyl)methyl]-1H-indol-3-yl}butan-1-ol

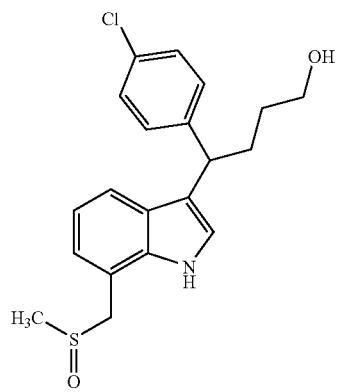

40 mg (0.11 mmol) of the compound from Example 15 were introduced into 7 ml of dichloromethane at 0° C., 27.4 mg (0.11 mmol) of 70% pure meta-chloroperbenzoic acid were added, and the mixture was stirred at RT overnight. 2 ml of methanol were added, the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 33 mg (79% of theory) of the title compound as mixture of diastereomers.

$^1$H-NMR (400 MHz, DMSO-d$_6$): δ=1.28-1.50 (m, 2H), 1.92-2.03 (m, 1H), 2.09-2.19 (m, 1H), 2.51 (s, 3H), 3.38-3.44 (m, 2H), 4.14 (t, 1H), 4.19-4.24 (m, 1H), 4.29-4.38 (m, 2H), 6.88 (t, 1H), 6.98 (d, 1H), 7.25-7.31 (m, 2H), 7.32-7.36 (m, 4H), 11.1 (s, 1H).

LC-MS (Method 6): R$_t$=1.97 min; MS (ESIpos): m/z=376 [M+H]$^+$.

Example 35

4-{7-[(Methylsulfanyl)methyl]-1H-indol-3-yl}-4-[4-(trifluoromethyl)phenyl]butanonitrile

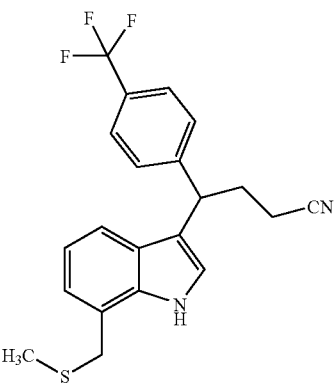

28.5 g (0.44 mmol) of potassium cyanide were added to 100 mg (0.22 mmol) of the compound from Example 51A in 5 ml of DMF. The mixture was stirred at 80° C. for 2 h and then concentrated, and the residue was taken up in ethyl acetate, washed with saturated aqueous sodium bicarbonate solution, water and saturated aqueous sodium chloride solution, dried over magnesium sulfate, filtered and concentrated. Purification by preparative HPLC (RP18 column; mobile phase: acetonitrile-water gradient with addition of 0.1% formic acid) resulted in 77 mg (91% of theory) of the title compound.

$^1$H-NMR (400 MHz, DMSO-d$_6$): δ=1.94 (s, 3H), 2.31-2.39 (m, 1H), 2.41-2.46 (m, 2H), 2.47-2.55 (m, 1H), 3.92 (s, 2H), 4.35 (t, 1H), 6.86 (t, 1H), 6.94 (d, 1H), 7.30 (d, 1H), 7.44 (d, 1H), 7.57-7.61 (m, 2H), 7.62-7.65 (m, 2H), 11.1 (s, 1H).

LC-MS (Method 4): R$_t$=1.43 min; MS (ESIpos): m/z=389 [M+H]$^+$.

Example 36

4-(4-Chlorophenyl)-4-{7-[(methylsulfanyl)methyl]-1H-indol-3-yl}butanonitrile

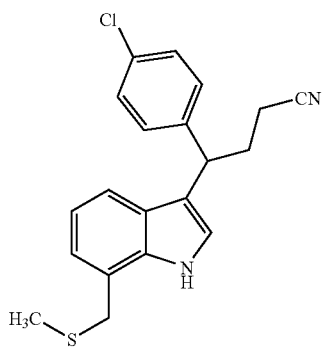

2.12 g (32.5 mmol) of potassium cyanide were added to 6.90 g (16.3 mmol) of the compound from Example 52A in 345 ml of DMF. The mixture was stirred at 80° C. for 4 h and then concentrated, and the residue was taken up in ethyl acetate, washed with saturated aqueous sodium bicarbonate solution, water and saturated aqueous sodium chloride solution, dried over magnesium sulfate, filtered and concentrated. The residue was purified by flash chromatography on silica gel (mobile phase: toluene/ethyl acetate gradient). 5.05 g (87% of theory) of the target compound were obtained.

$^1$H-NMR (400 MHz, DMSO-d$_6$): δ=1.94 (s, 3H), 2.25-2.34 (m, 1H), 2.38-2.48 (m, 3H), 3.91 (s, 2H), 4.20-4.26 (m, 1H), 6.85 (t, 1H), 6.93 (d, 1H), 7.28 (d, 1H), 7.30-7.34 (m, 2H), 7.35-7.41 (m, 3H), 11.0 (s, 1H).

LC-MS (Method 3): R$_t$=2.31 min; MS (ESIpos): m/z=355 [M+H]$^+$.

Example 37

4-(4-Chlorophenyl)-4-{7-[(ethylsulfanyl)methyl]-1H-indol-3-yl}butanonitrile

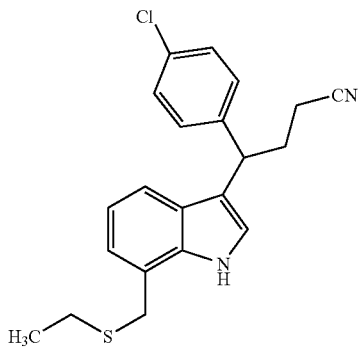

152 mg (2.33 mmol) of potassium cyanide were added to 510 mg (1.16 mmol) of the compound from Example 53A in 7 ml of DMF. The mixture was stirred at 80° C. for 2 h and, after cooling, water was added, the mixture was extracted with ethyl acetate, and the combined organic phases were washed with saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid). 222 mg (52% of theory) of the target compound were obtained.

$^1$H-NMR (400 MHz, DMSO-$d_6$): δ=1.15 (t, 3H), 2.25-2.34 (m, 1H), 2.35-2.48 (m, 5H), 3.96 (s, 2H), 4.20-4.26 (m, 1H), 6.85 (t, 1H), 6.94 (d, 1H), 7.28 (d, 1H), 7.30-7.35 (m, 2H), 7.36-7.40 (m, 3H), 11.0 (s, 1H).

LC-MS (Method 4): $R_t$=1.48 min; MS (ESIpos): m/z=369 [M+H]$^+$.

Example 38

4-(4-Chloro-2-fluorophenyl)-4-{7-[(methylsulfanyl)methyl]-1H-indol-3-yl}butanonitrile

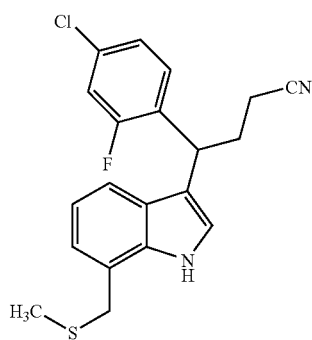

572 mg (8.78 mmol) of potassium cyanide were added to 1.94 g (4.39 mmol) of the compound from Example 54A in 26 ml of DMF. The mixture was stirred at 80° C. for 2 h and then concentrated, and the crude product was purified by preparative HPLC (RP18 column; mobile phase: acetonitrile/water gradient with addition of 0.1% formic acid) to result in 1.30 g (79% of theory) of the title compound.

$^1$H-NMR (400 MHz, DMSO-$d_6$): δ=1.94 (s, 3H), 2.24-2.38 (m, 1H), 2.45-2.51 (m, 3H), 3.92 (s, 2H), 4.51-4.57 (m, 1H), 6.89 (t, 1H), 6.95 (d, 1H), 7.20 (dd, 1H), 7.28 (d, 1H), 7.36-7.43 (m, 3H), 11.1 (s, 1H).

LC-MS (Method 5): $R_t$=2.70 min; MS (ESIpos): m/z=373 [M+H]$^+$.

Enantiomer 38-1:

554 mg (8.51 mmol) of potassium cyanide were added to 1.88 g (4.25 mmol) of enantiomer 54A-1 in 95 ml of DMF. The mixture was stirred at 80° C. for 2 h and then concentrated, and the residue was taken up in ethyl acetate, washed with saturated aqueous sodium bicarbonate solution, water and saturated aqueous sodium chloride solution, dried over magnesium sulfate, filtered and concentrated. The residue was purified by preparative HPLC (RP18 column; mobile phase: acetonitrile/water gradient with addition of 0.1% formic acid). 727 mg (46% of theory) of the corresponding enantiomer of the title compound were obtained.

Example 39

4-(4-Chloro-2-fluorophenyl)-3-methyl-4-{7-[(methylsulfanyl)methyl]-1H-indol-3-yl}butanonitrile

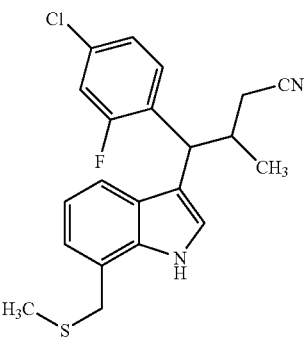

16.2 mg (0.25 mmol) of potassium cyanide were added to 70 mg (0.12 mmol) of the compound from Example 55A in 3 ml of DMSO. The mixture was stirred at 80° C. for 4 h and then concentrated, and the residue was taken up in ethyl acetate, washed with saturated aqueous sodium bicarbonate solution, water and saturated aqueous sodium chloride solution, dried over magnesium sulfate, filtered and concentrated. The residue was purified by preparative HPLC (RP18 column; mobile phase: acetonitrile/water gradient with addition of 0.1% formic acid). 33.4 mg (69% of theory) of the title compound were obtained as a mixture of diastereomers.

$^1$H-NMR (400 MHz, DMSO-$d_6$): δ=0.97 (d, 1.8H), 1.09 (d, 1.2H), 1.93-1.95 (m, 3H), 2.31 (dd, 0.4H), 2.46-2.55 (m, 1H), 2.65 (dd, 0.6H), 2.86-2.97 (m, 1H), 3.87-3.95 (m, 2H), 4.25-4.33 (m, 1H), 6.89-6.97 (m, 2H), 7.18-7.24 (m, 1H), 7.32-7.37 (m, 1H), 7.39-7.45 (m, 1.4H), 7.50-7.63 (m, 1.6H), 11.0 (s, 0.4H), 11.0 (s, 0.6H).

LC-MS (Method 3): $R_t$=2.46 and 2.51 min; MS (ESIpos): m/z=387 [M+H]$^+$.

$[α]_D^{20}$=+48.0°, c=0.196, chloroform

Example 40

4-(4-Chloro-2-fluorophenyl)-4-{5-fluoro-7-[(methylsulfanyl)methyl]-1H-indol-3-yl}butanonitrile

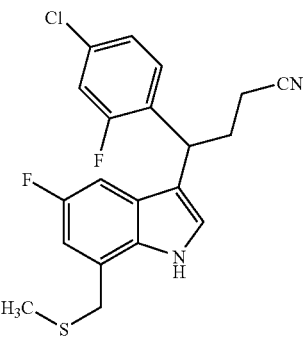

190 mg (2.91 mmol) of potassium cyanide and 8.9 mg (0.07 mmol) of 4-N,N-dimethylaminopyridine were added to 670 mg (1.46 mmol) of the compound from Example 56A in 40 ml of DMSO. The mixture was stirred at 80° C. for 2 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 522 mg (92% of theory) of the title compound.

$^1$H-NMR (400 MHz, DMSO-$d_6$): δ=1.95 (s, 3H), 2.25-2.37 (m, 1H), 2.44-2.52 (m, 3H), 3.92 (s, 2H), 4.44-4.50 (m, 1H), 6.85 (dd, 1H), 7.01 (dd, 1H), 7.22 (dd, 1H), 7.39 (dd, 1H), 7.41-7.47 (m, 2H), 11.2 (s, 1H).

LC-MS (Method 5): $R_t$=2.76 min; MS (ESIpos): m/z=391 [M+H]$^+$.

Example 41

4-(2,4-Dichlorophenyl)-4-{7-[(methylsulfanyl)methyl]-1H-indol-3-yl}butanonitrile

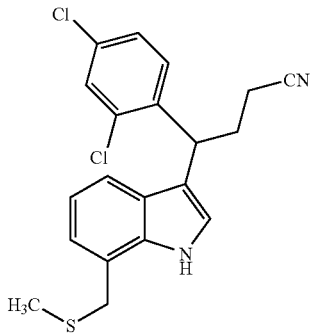

563 mg (8.64 mmol) of potassium cyanide were added to 1.98 g (4.32 mmol) of the compound from Example 57A in 26 ml of DMF. The mixture was stirred at 80° C. for 2 h and then concentrated, and the crude product was purified by preparative HPLC (RP18 column; mobile phase: acetonitrile/water gradient with addition of 0.1% formic acid) to result in 1.42 g (84% of theory) of the title compound.

$^1$H-NMR (400 MHz, DMSO-$d_6$): δ=1.95 (s, 3H), 2.21-2.31 (m, 1H), 2.41-2.58 (m, 3H), 3.88-3.96 (m, 2H), 4.67-4.76 (m, 1H), 6.88 (t, 1H), 6.95 (d, 1H), 7.25 (d, 1H), 7.33 (dd, 1H), 7.38 (d, 1H), 7.42 (s, 1H), 7.60 (d, 1H), 11.1 (s, 1H).

LC-MS (Method 3): $R_t$=2.51 min; MS (ESIpos): m/z=389 [M+H]$^+$.

Example 42

4-(2,4-Dichlorophenyl)-4-{5-fluoro-7-[(methylsulfanyl)methyl]-1H-indol-3-yl}butanonitrile

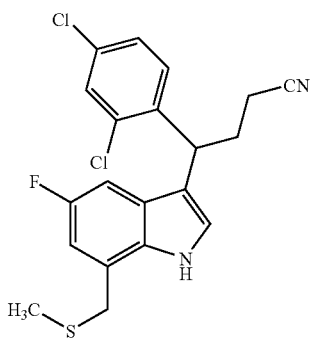

1.36 g (2.86 mmol) of the compound from Example 58A and 372 mg (5.71 mmol) of potassium cyanide were dissolved in 65 ml of DMSO and stirred at 120° C. overnight. The mixture was concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 790 mg (68% of theory) of the title compound.

$^1$H-NMR (400 MHz, DMSO-$d_6$): δ=1.96 (s, 3H), 2.20-2.33 (m, 1H), 2.41-2.53 (m, 3H), 3.88-3.96 (m, 2H), 4.66 (t, 1H), 6.86 (dd, 1H), 6.97 (dd, 1H), 7.35 (dd, 1H), 7.43 (d, 1H), 7.49 (d, 1H), 7.61 (d, 1H), 11.2 (s, 1H).

LC-MS (Method 5): $R_t$=2.87 min; MS (ESIpos): m/z=407 [M+H]$^+$.

Example 43

4-(4-Chlorophenyl)-4-{5-fluoro-7-[(methylsulfanyl)methyl]-1H-indol-3-yl}butanonitrile

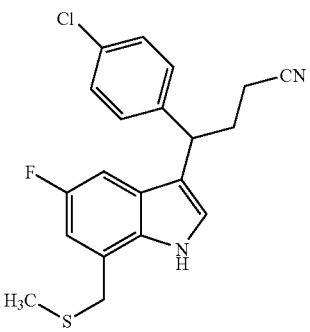

445 mg (1.01 mmol) of the compound from Example 59A and 131 mg (2.01 mmol) of potassium cyanide were dissolved in 23 ml of DMF and stirred at 80° C. for three days. The mixture was concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 102 mg (27% of theory) of the title compound. Also obtained were 180 mg (0.47 mmol) of 3-[3-chloro-1-(4-chlorophenyl)propyl]-5-fluoro-7-[(methylsulfanyl)methyl]-1H-indole.

LC-MS (Method 4): $R_t$=1.59 min; MS (ESIpos): m/z=382 [M+H]$^+$.

180 mg (0.47 mmol) of 3-[3-chloro-1-(4-chlorophenyl)propyl]-5-fluoro-7-[(methylsulfanyl)methyl]-1H-indole and 61.3 mg (0.94 mmol) of potassium cyanide were dissolved in 11 ml of DMSO and stirred at 120° C. overnight. The mixture was concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in a further 140 mg (80% of theory) of the title compound and thus in an overall yield of the title compound of 242 mg (64% of theory).

¹H-NMR (400 MHz, DMSO-d₆): δ=1.95 (s, 3H), 2.24-2.34 (m, 1H), 2.36-2.49 (m, 3H), 3.91 (s, 2H), 4.19 (t, 1H), 6.83 (dd, 1H), 7.04 (dd, 1H), 7.31-7.41 (m, 4H), 7.48 (d, 1H), 11.2 (s, 1H).

LC-MS (Method 4): $R_t$=1.42 min; MS (ESIpos): m/z=373 [M+H]⁺.

Example 44

4-(4-Chloro-2-methylphenyl)-4-{7-[(ethylsulfanyl)methyl]-1H-indol-3-yl}butanonitrile

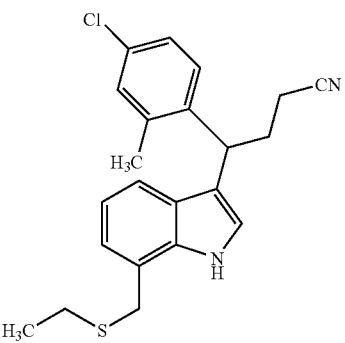

86.4 mg (1.33 mmol) of potassium cyanide were added to 300 mg (0.66 mmol) of the compound from Example 60A in 4 ml of DMF. Stirring at 80° C. for 2 h was followed by addition of water, extraction with ethyl acetate, washing of the combined organic phases with saturated aqueous sodium bicarbonate solution, drying over magnesium sulfate, filtration and concentration. The crude product was purified by preparative HPLC (RP18 column; mobile phase: acetonitrile/water gradient with addition of 0.1% formic acid) to result in 207 mg (81% of theory) of the title compound.

¹H-NMR (400 MHz, DMSO-d₆): δ=1.16 (t, 3H), 2.14-2.27 (m, 1H), 2.39 (q, 2H), 2.42 (s, 3H), 2.43-2.52 (m, 3H), 3.92-4.01 (m, 2H), 4.44 (t, 1H), 6.87 (t, 1H), 6.95 (d, 1H), 7.16 (dd, 1H), 7.20-7.29 (m, 4H), 11.0 (s, 1H).

LC-MS (Method 4): $R_t$=1.52 min; MS (ESIpos): m/z=383 [M+H]⁺.

Example 45

4-(4-Chloro-2-methylphenyl)-4-{7-[(methylsulfanyl)methyl]-1H-indol-3-yl}butanonitrile

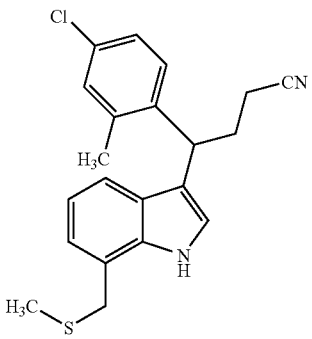

419 mg (6.44 mmol) of potassium cyanide were added to 1.41 g (3.22 mmol) of the compound from Example 61A in 20 ml of DMF. The mixture was stirred at 80° C. for 2 h and then concentrated, and the crude product was purified by preparative HPLC (RP18 column; mobile phase: acetonitrile/water gradient with addition of 0.1% formic acid) to result in 987 mg (83% of theory) of the title compound.

¹H-NMR (400 MHz, DMSO-d₆): δ=1.94 (s, 3H), 2.14-2.27 (m, 1H), 2.36-2.52 (m, 3H), 2.43 (s, 3H), 3.88-3.96 (m, 2H), 4.44 (t, 1H), 6.87 (t, 1H), 6.94 (d, 1H), 7.16 (dd, 1H), 7.21-7.29 (m, 4H), 11.0 (s, 1H).

LC-MS (Method 3): $R_t$=2.45 min; MS (ESIpos): m/z=369 [M+H]⁺.

Example 46

4-(4-Fluoro-2-methylphenyl)-4-{7-[(methylsulfanyl)methyl]-1H-indol-3-yl}butanonitrile

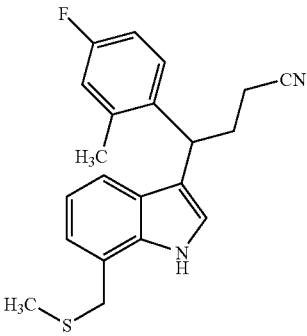

90.8 mg (1.40 mmol) of potassium cyanide were added to 294 mg (0.70 mmol) of the compound from Example 62A in 15 ml of DMF. The mixture was stirred at 80° C. for 4 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 188 mg (77% of theory) of the title compound.

¹H-NMR (400 MHz, DMSO-d₆): δ=1.95 (s, 3H), 2.15-2.25 (m, 1H), 2.36-2.48 (m, 3H), 2.43 (s, 3H), 3.88-3.96 (m, 2H), 4.41-4.46 (m, 1H), 6.87 (t, 1H), 6.89-6.96 (m, 2H), 7.01 (dd, 1H), 7.22-7.30 (m, 3H), 11.0 (s, 1H).

LC-MS (Method 4): $R_t$=1.40 min; MS (ESIpos): m/z=353 [M+H]⁺.

Example 47

4-[2-Fluoro-4-(trifluoromethyl)phenyl]-4-{7-[(methylsulfanyl)methyl]-1H-indol-3-yl}butanonitrile

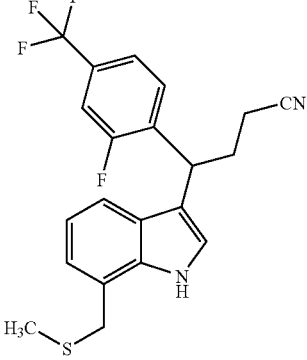

726 mg (11.1 mmol) of potassium cyanide were added to 2.65 g (5.57 mmol) of the compound from Example 63A in 128 ml of DMF. The mixture was stirred at 80° C. for 2 h and then concentrated, and the residue was taken up in ethyl acetate, washed with saturated aqueous sodium bicarbonate solution, water and saturated aqueous sodium chloride solution, dried over magnesium sulfate, filtered and concentrated. 1.46 g of the title compound were obtained with a purity of 85% (55% of theory).

$^1$H-NMR (400 MHz, DMSO-$d_6$): δ=1.94 (s, 3H), 2.32-2.41 (m, 1H), 2.43-2.60 (m, 3H), 3.92 (s, 2H), 4.61-4.67 (m, 1H), 6.90 (t, 1H), 6.95 (d, 1H), 7.30 (d, 1H), 7.44 (d, 1H), 7.51 (d, 1H), 7.60-7.66 (m, 2H), 11.1 (s, 1H).

LC-MS (Method 3): $R_t$=2.45 min; MS (ESIpos): m/z=407 [M+H]$^+$.

Example 48

4-{7-[(Methylsulfanyl)methyl]-1H-indol-3-yl}-4-(naphthalen-2-yl)butanonitrile

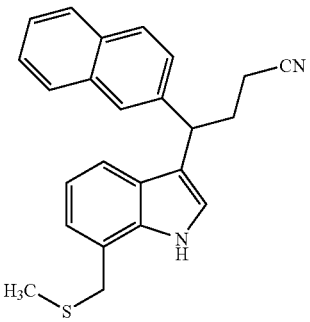

97.5 mg (1.50 mmol) of potassium cyanide were added to 329 mg (0.75 mmol) of the compound from Example 64A in 15 ml of DMF. The mixture was stirred at 80° C. for 4 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 181 mg (65% of theory) of the title compound.

$^1$H-NMR (400 MHz, DMSO-$d_6$): δ=1.92 (s, 3H), 2.39-2.59 (m, 4H), 3.87-3.95 (m, 2H), 4.37-4.42 (m, 1H), 6.82 (t, 1H), 6.91 (d, 1H), 7.34 (d, 1H), 7.41-7.50 (m, 4H), 7.79-7.85 (m, 2H), 7.88 (d, 1H), 7.92 (s, 1H), 11.0 (s, 1H).

LC-MS (Method 3): $R_t$=2.39 min; MS (ESIpos): m/z=371 [M+H]$^+$.

Example 49

5-(4-Chlorophenyl)-5-{7-[(methylsulfanyl)methyl]-1H-indol-3-yl}pentanonitrile

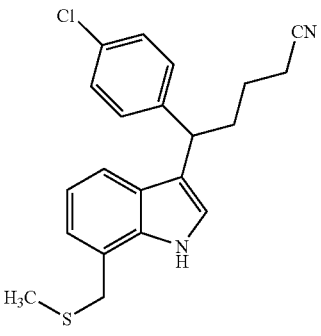

91.9 mg (1.41 mmol) of potassium cyanide were added to 309 mg (0.71 mmol) of the compound from Example 65A in 5 ml of DMF. The mixture was stirred at 80° C. for 2 h and then concentrated, and the residue was purified by preparative HPLC (RP18 column; mobile phase: acetonitrile/water gradient with addition of 0.1% formic acid). DMF was removed by taking the crude product up in dichloromethane, washing twice with water and saturated aqueous sodium chloride solution, drying over magnesium sulfate, filtering and concentrating. 134 mg (52% of theory) of the target compound were obtained.

$^1$H-NMR (400 MHz, DMSO-$d_6$): δ=1.41-1.63 (m, 2H), 1.94 (s, 3H), 2.00-2.11 (m, 1H), 2.16-2.27 (m, 1H), 2.50-2.56 (m, 2H), 3.91 (s, 2H), 4.20 (t, 1H), 6.84 (t, 1H), 6.92 (d, 1H), 7.26-7.33 (m, 4H), 7.34-7.38 (m, 2H), 11.0 (s, 1H).

LC-MS (Method 5): $R_t$=2.78 min; MS (ESIpos): m/z=369 [M+H]$^+$.

Example 50

4-(4-Chlorophenyl)-4-{6-fluoro-7-[(methylsulfanyl)methyl]-1H-indol-3-yl}butanonitrile

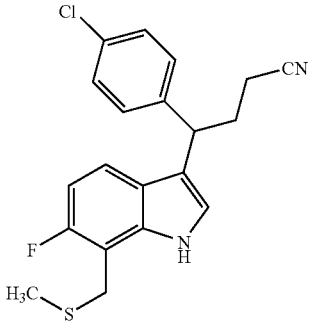

0.46 g (7.01 mmol) of potassium cyanide were added to 1.55 g (3.50 mmol) of the compound from Example 66A in 32 ml of DMF. The mixture was stirred at 80° C. for 3 h, ethyl acetate was added to the reaction solution, and the mixture was washed twice with water and once with saturated aqueous sodium chloride solution. The combined organic phases were dried over sodium sulfate, the solid was filtered off, and the solvents were removed. The crude product was purified by preparative HPLC (mobile phase: acetonitrile/water gradient). 1.00 g (77% of theory) of the target compound was obtained.

$^1$H-NMR (400 MHz, DMSO-$d_6$): δ=1.98 (s, 3H), 2.21-2.49 (m, 4H), 3.95 (s, 2H), 4.19-4.25 (m, 1H), 6.78 (dd, 1H), 7.25 (dd, 1H), 7.29-7.46 (m, 5H), 11.19 (s, 1H).

HPLC (Method 1): $R_t$=5.03 min; MS (ESIneg): m/z=371 [M−H]$^−$.

Example 51

4-{6-Fluoro-7-[(methylsulfanyl)methyl]-1H-indol-3-yl}-4-[4-(trifluoromethyl)phenyl]butanonitrile

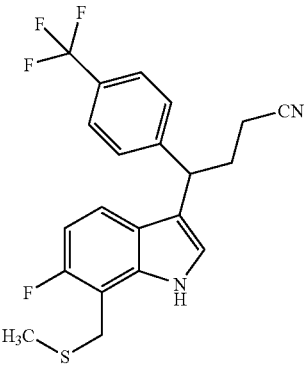

The title compound was prepared starting from 2.20 g (4.62 mmol) of the compound from Example 67A in analogy to the synthesis of the compound from Example 50. 1.66 g (88% of theory) of the target compound were obtained.

¹H-NMR (400 MHz, DMSO-d₆): δ=1.98 (s, 3H), 2.28-2.48 (m, 4H), 3.95 (s, 2H), 4.33 (t, 1H), 6.78 (dd, 1H), 7.28 (dd, 1H), 7.48 (s, 1H), 7.59 (d, 2H), 7.64 (d, 2H), 11.23 (s, 1H).

HPLC (Method 1): R$_t$=5.06 min; MS (ESIneg): m/z=405 [M–H]⁻.

Example 52

4-(1-Benzothiophen-5-yl)-4-{7-[(methylsulfanyl)methyl]-1H-indol-3-yl}butanonitrile

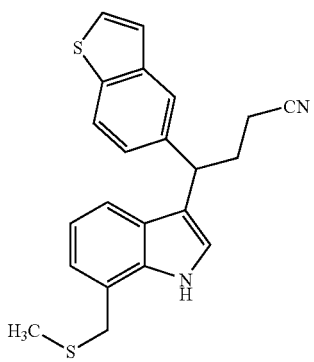

The title compound was prepared starting from 768 mg (1.72 mmol) of the compound from Example 68A in analogy to the synthesis of the compound from Example 50. 494 mg (76% of theory) of the target compound were obtained.

¹H-NMR (400 MHz, DMSO-d₆): δ=1.93 (s, 3H), 2.32-2.56 (m, 4H), 3.91 (s, 2H), 4.34 (t, 1H), 6.83 (t, 1H), 6.91 (d, 1H), 7.28-7.44 (m, 4H), 7.71 (d, 1H), 7.85-7.90 (m, 2H), 11.02 (s, 1H).

HPLC (Method 1): R$_t$=4.97 min; MS (ESIneg): m/z=375 [M–H]⁻.

Example 53

4-(2-Bromo-1,3-thiazol-5-yl)-4-{7-[(methylsulfanyl)methyl]-1H-indol-3-yl}butanonitrile

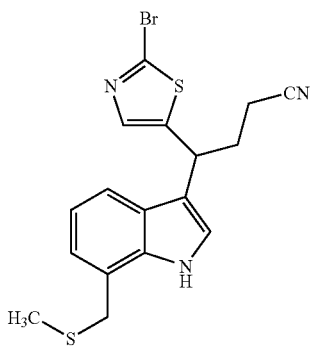

14 mg (0.21 mmol) of potassium cyanide were added to 50 mg (0.11 mmol) of the compound from Example 69A in 1 ml of DMF. The mixture was stirred at 80° C. for 5 h, water was added to the reaction solution, and the aqueous phase was extracted twice with dichloromethane. The combined organic phases were dried over sodium sulfate, the solid was filtered off, and the solvents were removed. The crude product was purified by preparative HPLC (mobile phase: acetonitrile/water gradient). 38 mg (89% of theory) of the target compound were obtained.

¹H-NMR (400 MHz, DMSO-d₆): δ=1.96 (s, 3H), 2.32-2.53 (m, 4H), 3.93 (s, 2H), 4.60 (t, 1H), 6.92 (t, 1H), 6.98 (d, 1H), 7.36-7.42 (m, 2H), 7.68 (s, 1H), 11.15 (s, 1H).

LC-MS (Method 5): R$_t$=2.40 min; MS (ESIpos): m/z=406 [M+H]⁺.

Example 54

3-Methyl-4-{7-[(methylsulfanyl)methyl]-1H-indol-3-yl}-4-[4-(trifluoromethyl)phenyl]butanonitrile

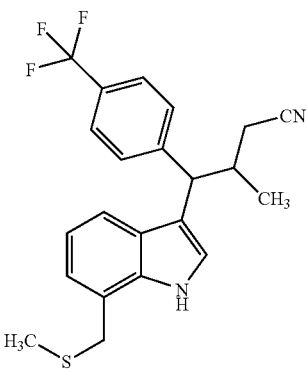

The title compound was prepared starting from 620 mg (1.32 mmol) of the compound from Example 70A in analogy to the synthesis of the compound from Example 53 but with dimethyl sulfoxide as solvent. 492 mg (93% of theory) of the target compound were obtained as mixture of diastereomers.

¹H-NMR (400 MHz, DMSO-d₆): δ=0.91-1.13 (m, 3H), 1.95 (s, 3H), 2.17-2.70 (m, 2H), 2.87-2.99 (m, 1H), 3.90 (s, 2H), 4.06-4.12 (m, 1H), 6.86-6.96 (m, 2H), 7.44-7.70 (m, 6H), 11.04-11.11 (s, 1H).

LC-MS (Method 6): R$_t$=2.68 min; MS (ESIpos): m/z=403 [M+H]⁺.

Example 55

4-(4-Chlorophenyl)-3-methyl-4-{7-[(methylsulfanyl)methyl]-1H-indol-3-yl}butanonitrile

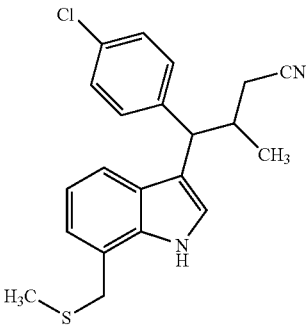

The title compound was prepared starting from 215 mg (0.49 mmol) of the compound from Example 71A in analogy to the synthesis of the compound from Example 53, but with dimethyl sulfoxide as solvent. 177 mg (98% of theory) of the target compound were obtained as mixture of diastereomers.

$^1$H-NMR (400 MHz, DMSO-d$_6$): δ=0.91-1.11 (m, 3H), 1.93 (s, 3H), 2.16-2.69 (m, 2H), 2.79-2.91 (m, 1H), 3.90 (s, 2H), 3.95-4.01 (m, 1H), 6.86-6.95 (m, 2H), 7.27-7.34 (m, 2H), 7.42-7.52 (m, 4H), 11.00-11.07 (s, 1H).

LC-MS (Method 4): R$_t$=1.44/1.46 min; MS (ESIneg): m/z=367 [M−H]$^-$.

Example 56

4-{7-[(Methylsulfonyl)methyl]-1H-indol-3-yl}-4-[4-(trifluoromethyl)phenyl]butanonitrile

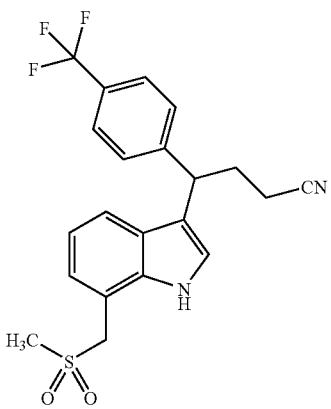

100 mg (0.26 mmol) of the compound from Example 35 were introduced into 20 ml of dichloromethane at 0° C., 159 mg (0.64 mmol) of 70% pure meta-chloroperbenzoic acid were added, and the mixture was stirred at RT overnight. It was concentrated, and the residue was purified by preparative HPLC (RP18 column; mobile phase: acetonitrile-water gradient with addition of 0.1% formic acid) to result in 51 mg (47% of theory) of the title compound.

$^1$H-NMR (400 MHz, DMSO-d$_6$): δ=2.29-2.48 (m, 4H), 2.88 (s, 3H), 4.36 (t, 1H), 4.72 (s, 2H), 6.96 (t, 1H), 7.11 (d, 1H), 7.42 (d, 1H), 7.53 (d, 1H), 7.57-7.61 (m, 2H), 7.62-7.66 (m, 2H), 11.2 (s, 1H).

LC-MS (Method 5): R$_t$=2.40 min; MS (ESIpos): m/z=421 [M+H]$^+$.

The enantiomers were separated by preparative HPLC on a chiral phase [column: Daicel Chiralpak AD-H, 5 μm, 250 mm×20 mm; eluent: isohexane/isopropanol 6:4; flow rate: 20 ml/min; temperature: 22° C.; UV detection: 230 nm]. The separated enantiomers were purified again by preparative HPLC on achiraler phase (RP18 column; mobile phase: acetonitrile/water gradient with addition of 0.1% formic acid):

Enantiomer 56-1:

R$_t$=6.86 min [column: Daicel AD-H, 5 μm, 250 mm×4.6 mm; eluent: isohexane/isopropanol 6:4; flow rate: 1.0 ml/min; temperature: 23° C.; UV detection: 230 nm];

Yield: 7.1 mg

Enantiomer 56-2:

R$_t$=7.71 min [column: Daicel AD-H, 5 μm, 250 mm×4.6 mm; eluent: isohexane/isopropanol 6:4; flow rate: 1.0 ml/min; temperature: 22° C.; UV detection: 230 nm].

Yield: 9.6 mg

Example 57

4-(4-Chlorophenyl)-4-{7-[(methylsulfonyl)methyl]-1H-indol-3-yl}butanonitrile

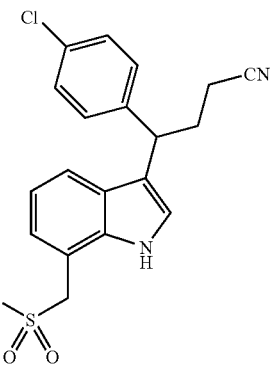

3.00 g (8.45 mmol) of the compound from Example 36 were introduced into 600 ml of dichloromethane at 0° C., 2.08 g (8.45 mmol) of 70% pure meta-chloroperbenzoic acid were added, and the mixture was stirred at RT overnight. 20 ml of methanol were added, the mixture was extracted with water and saturated aqueous sodium bicarbonate solution, and the organic phase was dried over magnesium sulfate, filtered and concentrated. The residue was purified by preparative HPLC (RP18 column; mobile phase: acetonitrile/water gradient with addition of 0.1% formic acid) to result in 205 mg (6% of theory) of the title compound.

$^1$H-NMR (400 MHz, DMSO-d$_6$): δ=2.25-2.35 (m, 1H), 2.38-2.48 (m, 3H), 2.87 (s, 3H), 4.22-4.28 (m, 1H), 4.71 (s, 2H), 6.95 (t, 1H), 7.11 (d, 1H), 7.31-7.35 (m, 2H), 7.36-7.42 (m, 3H), 7.47 (d, 1H), 11.1 (s, 1H).

LC-MS (Method 4): R$_t$=1.21 min; MS (ESIpos): m/z=387 [M+H]$^+$.

The enantiomers were separated by preparative HPLC on a chiral phase [column: Daicel Chiralpak AD-H, 5 μm, 250 mm×20 mm; eluent: isohexane/isopropanol 3:7; flow rate: 25 ml/min; temperature: 26° C.; UV detection: 230 nm]. The separated enantiomers were purified again by preparative HPLC on achiral phase (RP18 column; mobile phase: acetonitrile/water gradient with addition of 0.1% formic acid):

Enantiomer 57-1:

R$_t$=6.93 min [column: Daicel AD-H, 5 μm, 250 mm×4 mm; eluent: isohexane/isopropanol 1:1; flow rate: 1.0 ml/min; temperature: RT; UV detection: 230 nm];

Yield: 50 mg

Enantiomer 57-2:

R$_t$=7.82 min [column: Daicel AD-H, 5 μm, 250 mm×4 mm; eluent: isohexane/isopropanol 1:1; flow rate: 1.0 ml/min; temperature: RT; UV detection: 230 nm];

Yield: 54 mg

Example 58

4-(4-Chlorophenyl)-4-{7-[(ethylsulfonyl)methyl]-1H-indol-3-yl}butanonitrile

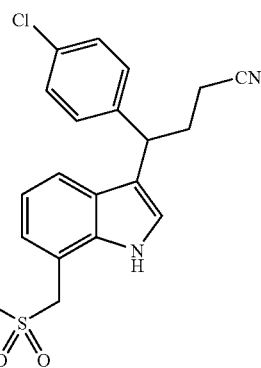

83.0 mg (0.23 mmol) of the compound from Example 37 were introduced into 13 ml of dichloromethane at 0° C., 111 mg (0.45 mmol) of 70% pure meta-chloroperbenzoic acid were added, and the mixture was stirred at RT overnight. It was concentrated and the residue was purified by preparative HPLC (RP18 column; mobile phase: acetonitrile/water gradient with addition of 0.1% formic acid) to result in 43.5 mg (48% of theory) of the title compound.

$^1$H-NMR (400 MHz, DMSO-d$_6$): δ=1.19 (t, 3H), 2.25-2.35 (m, 1H), 2.36-2.48 (m, 3H), 3.02 (q, 2H), 4.22-4.28 (m, 1H), 4.66-4.75 (m, 2H), 6.94 (t, 1H), 7.10 (d, 1H), 7.31-7.35 (m, 2H), 7.36-7.41 (m, 3H), 7.47 (d, 1H), 11.1 (s, 1H).

LC-MS (Method 3): R$_t$=2.03 min; MS (ESIpos): m/z=401 [M+H]$^+$.

Example 59

4-(4-Chloro-2-fluorophenyl)-4-{7-[(methylsulfonyl)methyl]-1H-indol-3-yl}butanonitrile

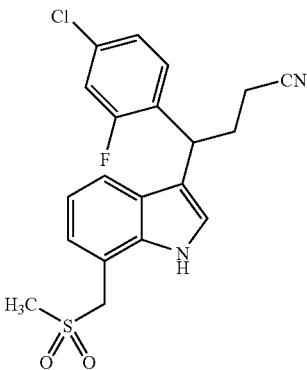

660 mg (1.77 mmol) of the compound from Example 38 were introduced into 99 ml of dichloromethane at 0° C., 873 mg (3.54 mmol) of 70% pure meta-chloroperbenzoic acid were added, and the mixture was stirred at RT overnight. 20 ml of methanol were added, and the residue after concentration was taken up in dichloromethane and washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 620 mg (87% of theory) of the title compound.

$^1$H-NMR (400 MHz, DMSO-d$_6$): δ=2.25-2.39 (m, 1H), 2.45-2.51 (m, 3H), 2.88 (s, 3H), 4.52-4.58 (m, 1H), 4.72 (s, 2H), 6.98 (t, 1H), 7.13 (d, 1H), 7.21 (dd, 1H), 7.36-7.43 (m, 3H), 7.45-7.48 (m, 1H), 11.2 (s, 1H).

LC-MS (Method 5): R$_t$=2.31 min; MS (ESIpos): m/z=405 [M+H]$^+$.

Enantiomer 59-1:

600 mg (1.61 mmol) of enantiomer 38-1 were introduced into 20 ml of dichloromethane at 0° C., 813 mg (3.30 mmol) of 70% pure meta-chloroperbenzoic acid were added, and the mixture was stirred at RT overnight. The residue after concentration was purified by preparative HPLC (RP18 column; mobile phase: acetonitrile/water gradient with addition of 0.1% formic acid) to result in 450 mg (69% of theory) of the corresponding enantiomer of the title compound.

$[α]_D^{20}$=+45.9°, c=0.505, chloroform

Example 60

4-(4-Chloro-2-fluorophenyl)-3-methyl-4-{7-[(methylsulfonyl)methyl]-1H-indol-3-yl}butanonitrile

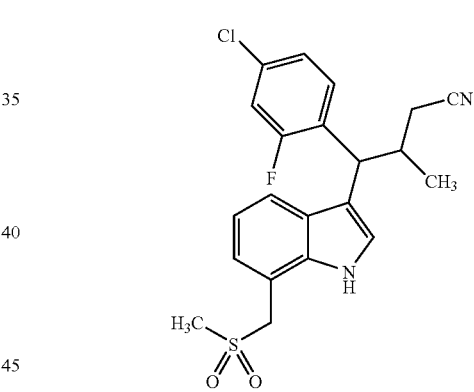

30.0 mg (0.08 mmol) of the compound from Example 39 were introduced into 2 ml of dichloromethane at RT, 39.2 mg (0.16 mmol) of 70% pure meta-chloroperbenzoic acid were added, and the mixture was stirred at RT overnight. 1 ml of methanol was added, and the residue after concentration was purified by preparative HPLC (RP18 column; mobile phase: acetonitrile/water gradient with addition of 0.1% formic acid) to result in 9 mg (28% of theory) of diastereomer 60-1 and 16.1 mg (50% of theory) of diastereomer 60-2 of the title compound.

Diastereomer 60-1:

$^1$H-NMR (400 MHz, DMSO-d$_6$): δ=1.08 (d, 3H), 2.32 (dd, 1H), 2.48-2.55 (m, 1H), 2.87 (s, 3H), 2.86-2.98 (m, 1H), 4.29 (d, 1H), 4.71 (s, 2H), 7.01 (t, 1H), 7.12 (d, 1H), 7.22 (dd, 1H), 7.35 (dd, 1H), 7.51-7.56 (m, 2H), 7.60 (t, 1H), 11.2 (s, 1H).

LC-MS (Method 3): R$_t$=2.02 min; MS (ESIpos): m/z=419 [M+H]$^+$.

Diastereomer 60-2:

$^1$H-NMR (400 MHz, DMSO-d$_6$): δ=0.97 (d, 3H), 2.45-2.54 (m, 1H), 2.64 (dd, 1H), 2.87 (s, 3H), 2.84-2.95 (m, 1H), 4.31 (d, 1H), 4.71 (s, 2H), 7.01 (t, 1H), 7.13 (d, 1H), 7.21 (dd, 1H), 7.35 (dd, 1H), 7.50-7.60 (m, 3H), 11.2 (s, 1H).

LC-MS (Method 3): $R_t$=2.10 min; MS (ESIpos): m/z=419 [M+H]$^+$.

Example 61

4-(4-Chloro-2-fluorophenyl)-4-{5-fluoro-7-[(methylsulfonyl)methyl]-1H-indol-3-yl}butanonitrile

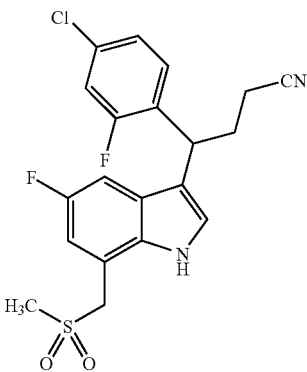

80.0 mg (0.21 mmol) of the compound from Example 40 were introduced into 5 ml of dichloromethane at 0° C., 103 mg (0.42 mmol) of 70% pure meta-chloroperbenzoic acid were added, and the mixture was stirred at RT overnight. Methanol was added, and the residue after concentration was purified by preparative HPLC (RP18 column; mobile phase: acetonitrile/water gradient with addition of 0.1% formic acid) to result in 46 mg (53% of theory) of the title compound.

$^1$H-NMR (400 MHz, DMSO-d$_6$): δ=2.26-2.38 (m, 1H), 2.44-2.52 (m, 3H), 2.91 (s, 3H), 4.45-4.51 (m, 1H), 4.75 (s, 2H), 7.01 (dd, 1H), 7.15 (dd, 1H), 7.23 (dd, 1H), 7.39 (dd, 1H), 7.45 (t, 1H), 7.54 (d, 1H), 11.3 (s, 1H).

LC-MS (Method 5): $R_t$=2.38 min; MS (ESIpos): m/z=423 [M+H]$^+$.

Example 62

4-(2,4-Dichlorophenyl)-4-{7-[(methylsulfonyl)methyl]-1H-indol-3-yl}butanonitrile

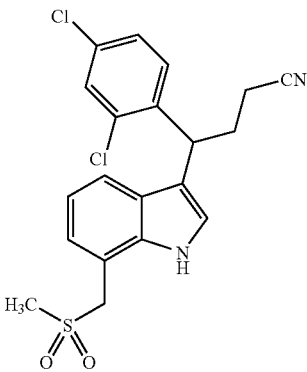

200 mg (0.51 mmol) of the compound from Example 41 were introduced into 30 ml of dichloromethane at 0° C., 253 mg (1.03 mmol) of 70% pure meta-chloroperbenzoic acid were added, and the mixture was stirred at RT overnight. 2 ml of methanol were added, and the residue after concentration was taken up in dichloromethane and saturated aqueous sodium bicarbonate solution, and the phases were separated. The organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 136 mg (63% of theory) of the title compound.

$^1$H-NMR (400 MHz, DMSO-d$_6$): δ=2.20-2.32 (m, 1H), 2.41-2.56 (m, 3H), 2.88 (s, 3H), 4.68-4.77 (m, 3H), 6.98 (t, 1H), 7.13 (d, 1H), 7.31-7.40 (m, 3H), 7.50 (s, 1H), 7.61 (d, 1H), 11.2 (s, 1H).

LC-MS (Method 4): $R_t$=1.28 min; MS (ESIpos): m/z=421 [M+H]$^+$.

The enantiomers were separated by preparative HPLC on a chiral phase [column: Daicel Chiralpak AD-H, 5 μm, 250 mm×20 mm; eluent: isohexane/isopropanol 7:3; flow rate: 20 ml/min; temperature: RT; UV detection: 230 nm]. The separated enantiomers were purified again by preparative HPLC on achiral phase (RP18 column; mobile phase: acetonitrile/water gradient with addition of 0.1% formic acid):

Enantiomer 62-1:

$R_t$=18.55 min [column: Daicel AD-H, 5 μm, 250 mm×4 mm; eluent: isohexane/isopropanol 4:1; flow rate: 1.0 ml/min; temperature: RT; UV detection: 230 nm];

Enantiomer 62-2:

$R_t$=20.07 min [column: Daicel AD-H, 5 μm, 250 mm×4 mm; eluent: isohexane/isopropanol 4:1; flow rate: 1.0 ml/min; temperature: RT; UV detection: 230 nm].

Example 63

4-(2,4-Dichlorophenyl)-4-{5-fluoro-7-[(methylsulfonyl)methyl]-1H-indol-3-yl}butanonitrile

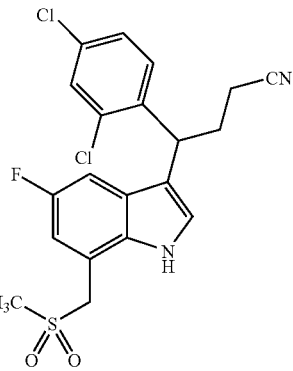

590 mg (1.45 mmol) of the compound from Example 42 were introduced into 85 ml of dichloromethane at 0° C., 714 mg (2.90 mmol) of 70% pure meta-chloroperbenzoic acid were added, and the mixture was stirred at RT overnight. It was concentrated and the residue was purified by preparative HPLC (RP18 column; mobile phase: acetonitrile/water gradient with addition of 0.1% formic acid) to result in 520 mg (82% of theory) of the title compound.

¹H-NMR (400 MHz, DMSO-d₆): δ=2.22-2.35 (m, 1H), 2.40-2.53 (m, 3H), 2.92 (s, 3H), 4.67 (t, 1H), 4.71-4.80 (m, 2H), 7.02 (dd, 1H), 7.12 (dd, 1H), 7.36 (dd, 1H), 7.44 (d, 1H), 7.56 (d, 1H), 7.61 (d, 1H), 11.3 (s, 1H).

LC-MS (Method 5): $R_t$=2.48 min; MS (ESIpos): m/z=439 [M+H]⁺.

Example 64

4-(4-Chlorophenyl)-4-{5-fluoro-7-[(methylsulfonyl)methyl]-1H-indol-3-yl}butanonitrile

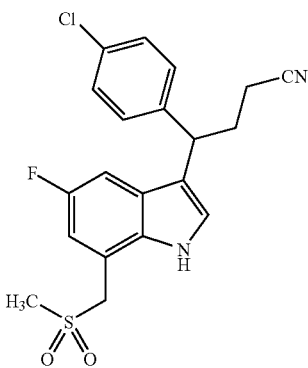

140 mg (0.38 mmol) of the compound from Example 43 were introduced into 22 ml of dichloromethane at 0° C., 185 mg (0.75 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 122 mg (80% of theory) of the title compound.

¹H-NMR (400 MHz, DMSO-d₆): δ=2.24-2.35 (m, 1H), 2.36-2.49 (m, 3H), 2.90 (s, 3H), 4.21 (t, 1H), 4.69-4.78 (m, 2H), 6.99 (dd, 1H), 7.19 (dd, 1H), 7.31-7.42 (m, 4H), 7.57 (d, 1H), 11.3 (s, 1H).

LC-MS (Method 5): $R_t$=2.34 min; MS (ESIpos): m/z=405 [M+H]⁺.

Example 65

4-(4-Chloro-2-methylphenyl)-4-{7-[(ethylsulfonyl)methyl]-1H-indol-3-yl}butanonitrile

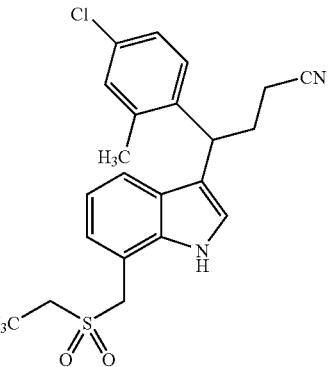

73.0 mg (0.19 mmol) of the compound from Example 44 were introduced into 11 ml of dichloromethane at 0° C., 94.0 mg (0.38 mmol) of 70% pure meta-chloroperbenzoic acid were added, and the mixture was stirred at RT overnight. Methanol was added, and the residue after concentration was purified by preparative HPLC (RP18 column; mobile phase: acetonitrile/water gradient with addition of 0.1% formic acid) to result in 38.0 mg (48% of theory) of the title compound.

¹H-NMR (400 MHz, DMSO-d₆): δ=1.19 (t, 3H), 2.15-2.27 (m, 1H), 2.38-2.50 (m, 3H), 2.42 (s, 3H), 3.02 (q, 2H), 4.45 (t, 1H), 4.67-4.76 (m, 2H), 6.96 (t, 1H), 7.11 (d, 1H), 7.17 (dd, 1H), 7.25 (s, 1H), 7.26 (d, 1H), 7.32-7.37 (m, 2H), 11.1 (s, 1H).

LC-MS (Method 3): $R_t$=2.12 min; MS (ESIpos): m/z=415 [M+H]⁺.

Example 66

4-(4-Chloro-2-methylphenyl)-4-{7-[(methylsulfonyl)methyl]-1H-indol-3-yl}butanonitrile

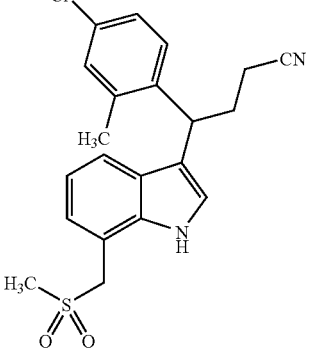

200 mg (0.54 mmol) of the compound from Example 45 were introduced into 30 ml of dichloromethane at 0° C., 267 mg (1.08 mmol) of 70% pure meta-chloroperbenzoic acid were added, and the mixture was stirred at RT overnight. 2 ml of methanol were added, and the residue after concentration was taken up in dichloromethane, washed twice with saturated aqueous sodium bicarbonate solution, water, and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 87 mg (40% of theory) of the title compound.

¹H-NMR (400 MHz, DMSO-d₆): δ=2.15-2.28 (m, 1H), 2.39-2.54 (m, 3H), 2.42 (s, 3H), 2.88 (s, 3H), 4.45 (t, 1H), 4.68-4.77 (m, 2H), 6.97 (t, 1H), 7.12 (d, 1H), 7.17 (dd, 1H), 7.25 (s, 1H), 7.26 (d, 1H), 7.33-7.37 (m, 2H), 11.1 (s, 1H).

LC-MS (Method 4): $R_t$=1.26 min; MS (ESIpos): m/z=401 [M+H]⁺.

The enantiomers were separated by preparative HPLC on a chiral phase [column: Daicel Chiralpak AD-H, 5 μm, 250 mm×20 mm; eluent: isohexane/isopropanol 4:1; flow rate: 20 ml/min; temperature: RT; UV detection: 230 nm]. The separated enantiomers were purified again by preparative HPLC on achiral phase (RP18 column; mobile phase: acetonitrile/water gradient with addition of 0.1% formic acid):

Enantiomer 66-1:
$R_t$=6.92 min [column: Daicel AD-H, 5 μm, 250 mm×4 mm; eluent: isohexane/isopropanol 3:2; flow rate: 1.0 ml/min; temperature: RT; UV detection: 230 nm];

Enantiomer 66-2:
$R_t$=7.52 min [column: Daicel AD-H, 5 μm, 250 mm×4 mm; eluent: isohexane/isopropanol 3:2; flow rate: 1.0 ml/min; temperature: RT; UV detection: 230 nm].

Example 67

4-(4-Fluoro-2-methylphenyl)-4-{7-[(methylsulfonyl)methyl]-1H-indol-3-yl}butanonitrile

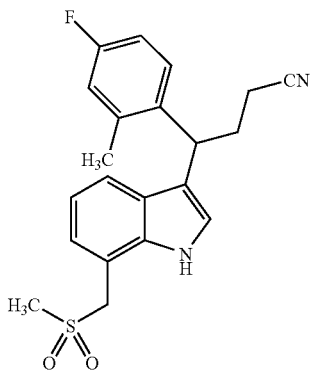

50 mg (0.14 mmol) of the compound from Example 46 were introduced into 10 ml of dichloromethane at 0° C., 69.9 mg (0.28 mmol) of 70% pure meta-chloroperbenzoic acid were added, and the mixture was stirred at RT for 4 h and then under reflux for 15 minutes. 2 ml of methanol were added, and the residue after concentration was taken up in dichloromethane and saturated aqueous sodium bicarbonate solution, and the phases were separated. The organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 24.6 mg (45% of theory) of the title compound.

$^1$H-NMR (400 MHz, DMSO-d$_6$): δ=2.16-2.28 (m, 1H), 2.37-2.49 (m, 3H), 2.43 (s, 3H), 2.88 (s, 3H), 4.42-4.48 (m, 1H), 4.67-4.76 (m, 2H), 6.90-6.99 (m, 2H), 7.02 (dd, 1H), 7.11 (d, 1H), 7.27 (dd, 1H), 7.33-7.37 (m, 2H), 11.1 (s, 1H).

LC-MS (Method 5): R$_t$=2.24 min; MS (ESIpos): m/z=385 [M+H]$^+$.

Example 68

4-[2-Fluoro-4-(trifluoromethyl)phenyl]-4-{7-[(methylsulfonyl)methyl]-1H-indol-3-yl}butanonitrile

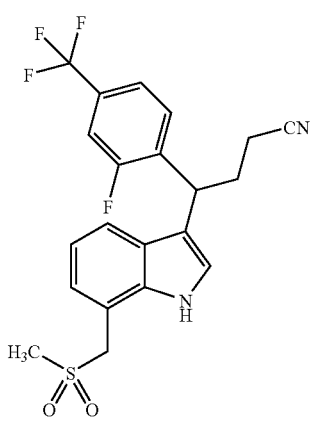

100 mg of the compound from Example 47 with a purity of 85% (0.21 mmol) were introduced into 14 ml of dichloromethane at 0° C., 118 mg (0.48 mmol) of 70% pure meta-chloroperbenzoic acid were added, and the mixture was stirred at RT overnight. The residue after concentration was purified by preparative HPLC (RP18 column; mobile phase: acetonitrile/water gradient with addition of 0.1% formic acid) to result in 65 mg (71% of theory) of the title compound.

$^1$H-NMR (400 MHz, DMSO-d$_6$): δ=2.32-2.42 (m, 1H), 2.45-2.60 (m, 3H), 2.88 (s, 3H), 4.62-4.68 (m, 1H), 4.73 (s, 2H), 6.99 (t, 1H), 7.13 (d, 1H), 7.42 (d, 1H), 7.49-7.54 (m, 2H), 7.61-7.66 (m, 2H), 11.2 (s, 1H).

LC-MS (Method 4): R$_t$=1.26 min; MS (ESIpos): m/z=439 [M+H]$^+$.

Example 69

4-{7-[(Methylsulfonyl)methyl]-1H-indol-3-yl}-4-(naphthalen-2-yl)butanonitrile

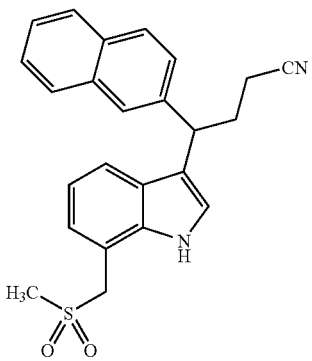

50 mg (0.14 mmol) of the compound from Example 48 were introduced into 10 ml of dichloromethane at 0° C., 66.5 mg (0.27 mmol) of 70% pure meta-chloroperbenzoic acid were added, and the mixture was stirred at RT for 4 h and then under reflux for 15 minutes. 2 ml of methanol were added, and the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 30 mg (55% of theory) of the title compound.

$^1$H-NMR (400 MHz, DMSO-d$_6$): δ=2.40-2.60 (m, 4H), 2.86 (s, 3H), 4.38-4.44 (m, 1H), 4.67-4.75 (m, 2H), 6.92 (t, 1H), 7.09 (d, 1H), 7.42-7.54 (m, 5H), 7.79-7.85 (m, 2H), 7.88 (d, 1H), 7.93 (s, 1H), 11.1 (s, 1H).

LC-MS (Method 5): R$_t$=2.34 min; MS (ESIpos): m/z=403 [M+H]$^+$.

Example 70

5-(4-Chlorophenyl)-5-{7-[(methylsulfonyl)methyl]-1H-indol-3-yl}pentanonitrile

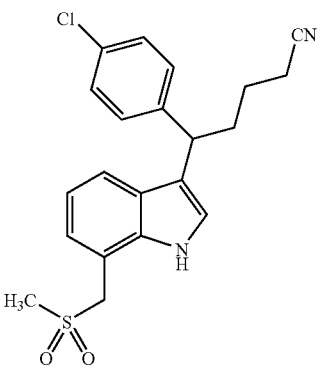

50 mg (0.14 mmol) of the compound from Example 49 were introduced into 9 ml of dichloromethane at 0° C., 66.8 mg (0.27 mmol) of 70% pure meta-chloroperbenzoic acid were added, and the mixture was stirred at RT overnight and then under reflux for 15 minutes. 2 ml of methanol were added, and the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 30 mg (55% of theory) of the title compound.

$^1$H-NMR (400 MHz, DMSO-$d_6$): δ=1.41-1.63 (m, 2H), 2.00-2.11 (m, 1H), 2.16-2.26 (m, 1H), 2.50-2.57 (m, 2H), 2.87 (s, 3H), 4.22 (t, 1H), 4.67-4.76 (m, 2H), 6.84 (t, 1H), 7.10 (d, 1H), 7.29-7.34 (m, 2H), 7.34-7.41 (m, 4H), 11.1 (s, 1H).

LC-MS (Method 5): $R_t$=2.36 min; MS (ESIpos): m/z=401 [M+H]$^+$.

Example 71

4-(4-Chlorophenyl)-4-{6-fluoro-7-[(methylsulfonyl)methyl]-1H-indol-3-yl}butanonitrile

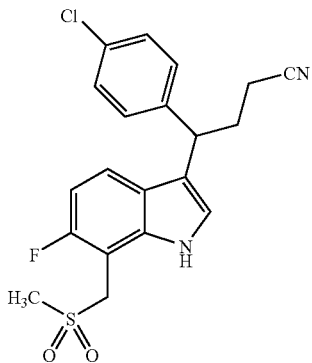

0.66 g (1.77 mmol) of the compound from Example 50 was introduced into 120 ml of dichloromethane at 0° C., 1.09 g (4.43 mmol) of 70% pure meta-chloroperbenzoic acid were added, and the mixture was stirred at RT for 3 h. 2 ml of methanol were added, and the mixture was extracted with water and saturated aqueous sodium bicarbonate solution. The phases were separated, the combined organic phases were dried over sodium sulfate and filtered, and the solvents were removed from the residue in vacuo. The crude product was purified initially by preparative HPLC (mobile phase: acetonitrile/water gradient) and then by flash chromatography of the resulting, slightly impure product on silica gel (mobile phase: cyclohexane/ethyl acetate 3/2). 317 mg (44% of theory) of the title compound were obtained.

$^1$H-NMR (400 MHz, DMSO-$d_6$): δ=2.21-2.49 (m, 4H), 2.95 (s, 3H), 4.21-4.28 (m, 1H), 4.73 (s, 2H), 6.86 (dd, 1H), 7.31-42 (m, 5H), 7.41 (m, 1H), 11.24 (s, 1H).

HPLC (Method 2): $R_t$=4.52 min; MS (ESIneg): m/z=422 [M−H]$^−$.

Example 72

4-{6-Fluoro-7-[(methylsulfonyl)methyl]-1H-indol-3-yl}-4-[4-(trifluoromethyl)phenyl]butanonitrile

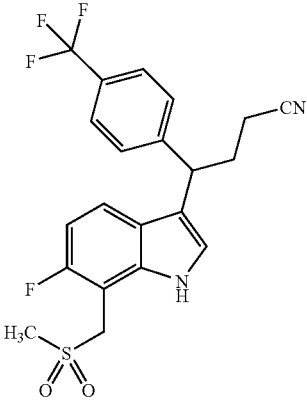

0.95 g (2.35 mmol) of the compound from Example 51 was introduced into 160 ml of dichloromethane at 0° C., 1.45 g (5.88 mmol) of 70% pure meta-chloroperbenzoic acid were added, and the mixture was stirred at RT for 3 h. 2 ml of methanol were added, and the mixture was extracted with water, saturated aqueous sodium bicarbonate solution and saturated aqueous sodium chloride solution. The phases were separated, and the solvents were removed from the organic phase in vacuo. The crude product was purified initially by preparative HPLC (mobile phase: acetonitrile/water gradient) and then by flash chromatography of the resulting, slightly impure product on silica gel (mobile phase: cyclohexane/ethyl acetate 1/1). 483 mg (47% of theory) of the title compound were obtained.

$^1$H-NMR (400 MHz, DMSO-$d_6$): δ=2.29-2.48 (m, 4H), 2.95 (s, 3H), 4.36 (t, 1H), 4.73 (s, 2H), 6.87 (dd, 1H), 7.42 (dd, 1H), 7.55 (s, 1H), 7.59 (d, 2H), 7.65 (d, 2H), 11.29 (s, 1H).

HPLC (Method 2): $R_t$=4.58 min; MS (ESIpos): m/z=439 [M+H]$^+$.

Example 73

4-(1-Benzothiophen-5-yl)-4-{7-[(methylsulfonyl)methyl]-1H-indol-3-yl}butanonitrile

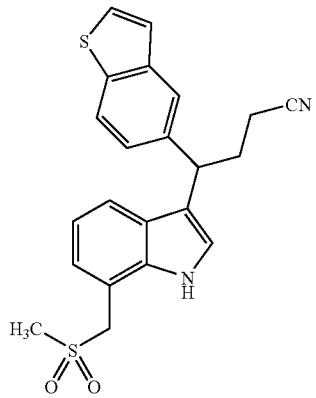

The title compound was prepared starting from 284 mg (0.75 mmol) of the compound from Example 52 in analogy to the synthesis of the compound from Example 72. 409 mg (54% of theory) of the target compound were obtained.

$^1$H-NMR (400 MHz, DMSO-d$_6$): δ=2.23-2.52 (m, 4H), 2.86 (s, 3H), 4.36 (t, 1H), 4.71 (s, 2H), 6.92 (dd, 1H), 7.09 (d, 1H), 7.33-7.44 (m, 3H), 7.49-7.52 (m, 1H), 7.72 (d, 1H), 7.85-7.91 (m, 2H), 11.11 (s, 1H).

HPLC (Method 2): R$_t$=4.46 min; DCI-MS (ESIpos): m/z=409 [M+H]$^+$.

Example 74

4-(2-Bromo-1,3-thiazol-5-yl)-4-{7-[(methylsulfonyl)methyl]-1H-indol-3-yl}butanonitrile

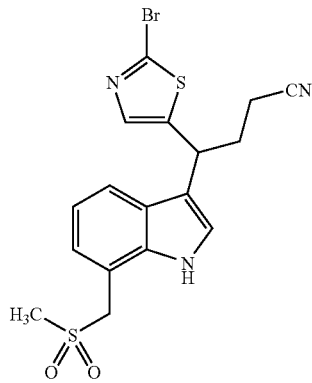

125 mg (0.31 mmol) of the compound from Example 53 were introduced into 15 ml of dichloromethane at 0° C., 152 mg (0.62 mmol) of 70% pure meta-chloroperbenzoic acid were added, and the mixture was stirred at RT for 2 h. 2 ml of methanol were added, and the solution was concentrated. The residue was purified initially by preparative HPLC (mobile phase: acetonitrile/water gradient) and then by flash chromatography of the resulting, slightly impure product on silica gel (mobile phase: cyclohexane/ethyl acetate 1/1). 119 mg (85% of theory) of the title compound were obtained.

$^1$H-NMR (400 MHz, DMSO-d$_6$): δ=2.31-2.53 (m, 4H), 2.89 (s, 3H), 4.62 (t, 1H), 4.74 (s, 2H), 7.02 (t, 1H), 7.16 (d, 1H), 7.46-7.53 (m, 2H), 7.69 (s, 1H), 11.24 (s, 1H).

LC-MS (Method 3): R$_t$=1.61 min; MS (ESIneg): m/z=436 [MH]$^-$.

Example 75

3-Methyl-4-{7-[(methylsulfonyl)methyl]-1H-indol-3-yl}-4-[4-(trifluoromethyl)phenyl]butanonitrile

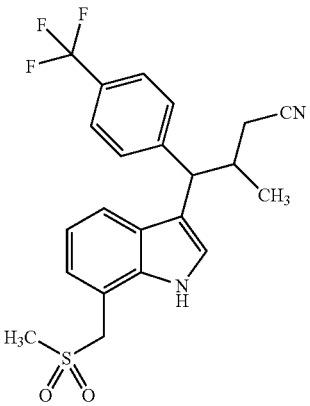

335 mg (0.83 mmol) of the compound from Example 54 were introduced into 40 ml of dichloromethane at 0° C., 410 mg (1.67 mmol) of 70% pure meta-chloroperbenzoic acid were added, and the mixture was stirred at RT for 2 h. 2 ml of methanol were added, and the solution was concentrated. The residue was taken up in a little acetonitrile. The product-containing solid was filtered off, and the filtrate was purified by preparative HPLC (mobile phase: acetonitrile/water gradient). The product-containing fractions were combined, taken up in dichloromethane and washed with saturated aqueous sodium bicarbonate solution and saturated aqueous sodium chloride solution. Drying of the organic phase over sodium sulfate, filtering-off of the solid and removal of the solvent resulted in 336 mg (93% of theory) of the title compound as mixture of diastereomers.

$^1$H-NMR (400 MHz, DMSO-d$_6$): δ=0.91-1.13 (m, 3H), 2.18-2.69 (m, 2H), 2.87 (s, 2H), 2.87-2.96 (m, 2H), 4.08-4.15 (m, 1H), 4.70 (s, 2H), 6.99 (t, 1H), 7.12 (d, 1H), 7.57-7.70 (m, 6H), 11.14-11.20 (s, 1H).

LC-MS (Method 4): R$_t$=1.26/1.29 min; MS (ESIpos): m/z=435 [M+H]$^+$.

Example 76

4-(4-Chlorophenyl)-3-methyl-4-{7-[(methylsulfonyl)methyl]-1H-indol-3-yl}butanonitrile

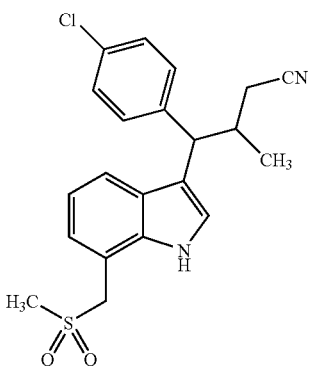

The title compound was prepared starting from 160 mg (0.43 mmol) of the compound from Example 55 in analogy to the synthesis of the compound from Example 74. 160 mg (92% of theory) of the target compound were obtained as mixture of diastereomers.

¹H-NMR (400 MHz, DMSO-$d_6$): δ=0.91-1.11 (m, 3H), 2.17-2.68 (m, 2H), 2.79-2.90 (m, 4H), 3.97-4.06 (m, 1H), 4.70 (s, 2H), 6.98 (t, 1H), 7.11 (d, 1H), 7.31 (t, 2H), 7.45 (d, 2H), 7.53-7.61 (m, 2H), 11.10-11.16 (s, 1H).

LC-MS (Method 5): $R_t$=2.33/2.40 min; MS (ESIneg): m/z=399 [M−H]⁻.

Example 77

4-{7-[(Methylsulfinyl)methyl]-1H-indol-3-yl}-4-[4-(trifluoromethyl)phenyl]butanonitrile

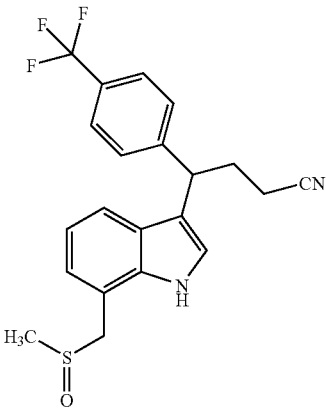

25 mg (64 µmol) of the compound from Example 35 were introduced into 5 ml of dichloromethane at 0° C., 16 mg (64 µmol) of 70% pure meta-chloroperbenzoic acid were added, and the mixture was stirred at RT overnight. The residue after concentration was purified by preparative HPLC (RP18 column; mobile phase: acetonitrile-water gradient with addition to 0.1% formic acid) to result in 24 mg (92% of theory) of the title compound as mixture of diastereomers.

¹H-NMR (400 MHz, DMSO-$d_6$): δ=2.30-2.40 (m, 1H), 2.41-2.47 (m, 2H), 2.48-2.52 (m, 1H), 2.52 (s, 3H), 4.19-4.25 (m, 1H), 4.32-4.39 (m, 2H), 6.92 (t, 1H), 7.01 (d, 1H), 7.35-7.40 (m, 1H), 7.51 (s, 1H), 7.56-7.61 (m, 2H), 7.62-7.66 (m, 2H), 11.2 (s, 1H).

LC-MS (Method 4): $R_t$=1.18 min; MS (ESIpos): m/z=405 [M+H]⁺.

Example 78

4-(4-Chlorophenyl)-4-{7-[(methylsulfinyl)methyl]-1H-indol-3-yl}butanonitrile

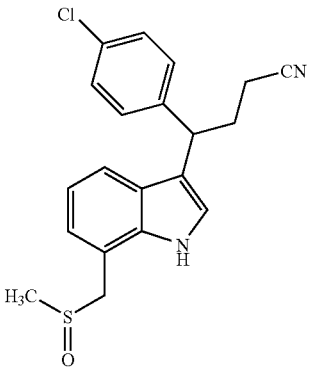

The title compound was prepared starting from 85.0 mg (0.24 mmol) of the compound from Example 36 in analogy to the synthesis of the compound from Example 77. Purification by preparative HPLC (RP18 column; mobile phase: acetonitrile-water gradient with addition of 0.1% formic acid) resulted in 86 mg (97% of theory) of the title compound as mixture of diastereomers.

¹H-NMR (400 MHz, DMSO-$d_6$): δ=2.25-2.35 (m, 1H), 2.38-2.48 (m, 3H), 2.51 (s, 3H), 4.19-4.28 (m, 2H), 4.34 (dd, 1H), 6.91 (t, 1H), 7.00 (d, 1H), 7.30-7.40 (m, 5H), 7.46 (s, 1H), 11.2 (s, 1H).

LC-MS (Method 5): $R_t$=2.20 min; MS (ESIpos): m/z=371 [M+H]⁺.

The diastereomers were separated by preparative HPLC on a chiral phase [column: Daicel Chiralpak AD-H, 5 µm, 250 mm×20 mm; eluent: isohexane/isopropanol 1:1; flow rate: 15 ml/min; temperature: 30° C.; UV detection: 220 nm]:

Diastereomer 78-1:
$R_t$=14.17 min [column: Daicel Chiralpak AD-H, 5 µm, 250 mm×4.6 mm; eluent: isohexane/ethanol 1:1; flow rate: 1.0 ml/min; temperature: 30° C.; UV detection: 220 nm];

Diastereomer 78-2:
$R_t$=15.40 min [column: Daicel Chiralpak AD-H, 5 µm, 250 mm×4.6 mm; eluent: isohexane/ethanol 1:1; flow rate: 1.0 ml/min; temperature: 30° C.; UV detection: 220 nm];

Diastereomer 78-3:
$R_t$=16.85 min [column: Daicel Chiralpak AD-H, 5 µm, 250 mm×4.6 mm; eluent: isohexane/ethanol 1:1; flow rate: 1.0 ml/min; temperature: 30° C.; UV detection: 220 nm];

Diastereomer 78-4:
$R_t$=20.10 min [column: Daicel Chiralpak AD-H, 5 µm, 250 mm×4.6 mm; eluent: isohexane/ethanol 1:1; flow rate: 1.0 ml/min; temperature: 30° C.; UV detection: 220 nm].

Example 79

4-(4-Chloro-2-fluorophenyl)-4-{7-[(methylsulfinyl)methyl]-1H-indol-3-yl}butanonitrile

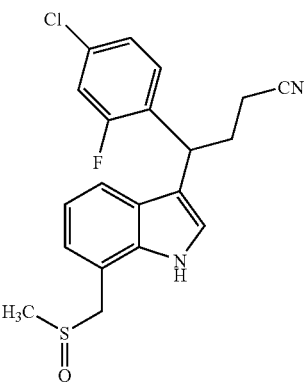

200 mg (0.54 mmol) of the compound from Example 38 were introduced into 30 ml of dichloromethane at 0° C., 132 mg (0.54 mmol) of 70% pure meta-chloroperbenzoic acid were added, and the mixture was stirred at RT overnight. 2 ml of methanol were added, and the residue after concentration was taken up in dichloromethane, washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 107 mg (51% of theory) of the title compound as mixture of diastereomers.

$^1$H-NMR (400 MHz, DMSO-$d_6$): δ=2.25-2.37 (m, 1H), 2.45-2.51 (m, 3H), 2.52 (s, 3H), 4.19-4.26 (m, 1H), 4.32-4.39 (m, 1H), 4.51-4.57 (m, 1H), 6.94 (t, 1H), 7.02 (d, 1H), 7.20 (d, 1H), 7.32-7.42 (m, 3H), 7.45 (d, 1H), 11.2 (s, 1H).

LC-MS (Method 4): $R_t$=1.17 min; MS (ESIpos): m/z=389 [M+H]$^+$.

Example 80

4-(4-Chloro-2-fluorophenyl)-4-{5-fluoro-7-[(methylsulfinyl)methyl]-1H-indol-3-yl}butanonitrile

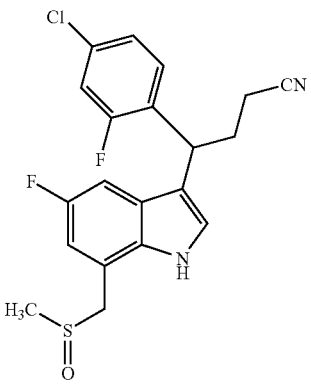

80.0 mg (0.21 mmol) of the compound from Example 40 were introduced into 5 ml of dichloromethane at 0° C., 53.0 mg (0.22 mmol) of 70% pure meta-chloroperbenzoic acid were added, and the mixture was stirred at RT overnight. Methanol was added, and the residue after concentration was purified by preparative HPLC (RP18 column; mobile phase: acetonitrile/water gradient with addition of 0.1% formic acid) to result in 58.8 mg (71% of theory) of the title compound as mixture of diastereomers.

$^1$H-NMR (400 MHz, DMSO-$d_6$): δ=2.25-2.39 (m, 1H), 2.44-2.52 (m, 3H), 2.52-2.54 (m, 3H), 4.19-4.25 (m, 1H), 4.34-4.40 (m, 1H), 4.45-4.51 (m, 1H), 6.91 (dd, 1H), 7.10 (d, 1H), 7.23 (dd, 1H), 7.39 (dd, 1H), 7.41-7.47 (m, 1H), 7.51-7.54 (m, 1H), 11.3 (s, 1H).

LC-MS (Method 6): $R_t$=2.20 min; MS (ESIpos): m/z=407 [M+H]$^+$.

Example 81

4-(2,4-Dichlorophenyl)-4-{7-[(methylsulfinyl)methyl]-1H-indol-3-yl}butanonitrile

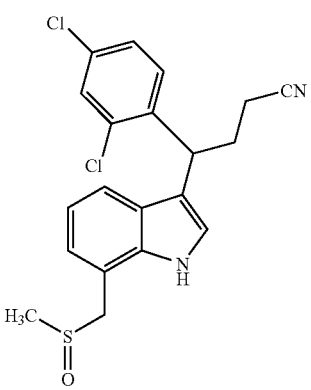

200 mg (0.51 mmol) of the compound from Example 41 were introduced into 30 ml of dichloromethane at 0° C., 127 mg (0.51 mmol) of 70% pure meta-chloroperbenzoic acid were added, and the mixture was stirred at RT overnight. 2 ml of methanol were added, and the residue after concentration was taken up in dichloromethane, washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 99 mg (48% of theory) of the title compound as mixture of diastereomers.

$^1$H-NMR (400 MHz, DMSO-$d_6$): δ=2.20-2.32 (m, 1H), 2.41-2.58 (m, 3H), 2.52 (s, 3H), 4.19-4.26 (m, 1H), 4.32-4.39 (m, 1H), 4.69-4.76 (m, 1H), 6.94 (t, 1H), 7.02 (d, 1H), 7.30-7.35 (m, 2H), 7.35-7.39 (m, 1H), 7.48 (d, 1H), 7.60 (d, 1H), 11.2 (s, 1H).

LC-MS (Method 4): $R_t$=1.24 min; MS (ESIpos): m/z=405 [M+H]$^+$.

Example 82

4-(2,4-Dichlorophenyl)-4-{5-fluoro-7-[(methylsulfinyl)methyl]-1H-indol-3-yl}butanonitrile

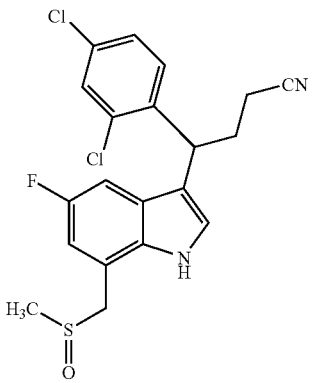

100 mg (0.25 mmol) of the compound from Example 42 were introduced into 14 ml of dichloromethane at 0° C., 60.5 mg (0.25 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 80 mg (76% of theory) of the title compound as mixture of diastereomers.

$^1$H-NMR (400 MHz, DMSO-$d_6$): δ=2.21-2.34 (m, 1H), 2.42-2.55 (m, 3H), 2.53 (s, 3H), 4.19-4.26 (m, 1H), 4.34-4.40 (m, 1H), 4.66 (t, 1H), 6.91 (dd, 1H), 7.03-7.08 (m, 1H), 7.36 (dd, 1H), 7.42 (dd, 1H), 7.55 (d, 1H), 7.61 (d, 1H), 11.3 (s, 1H).

LC-MS (Method 5): $R_t$=2.35 min; MS (ESIpos): m/z=423 [M+H]$^+$.

Example 83

4-(4-Chlorophenyl)-4-{5-fluoro-7-[(methylsulfinyl)methyl]-1H-indol-3-yl}butanonitrile

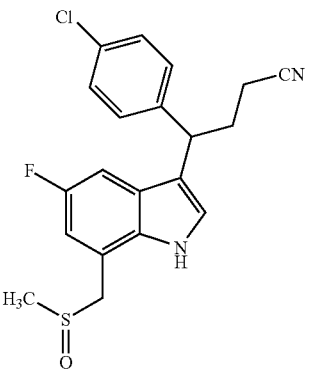

64.0 mg (0.17 mmol) of the compound from Example 43 were introduced into 10 ml of dichloromethane at 0° C., 42.3 mg (0.17 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 54 mg (79% of theory) of the title compound as mixture of diastereomers.

$^1$H-NMR (400 MHz, DMSO-$d_6$): δ=2.24-2.34 (m, 1H), 2.36-2.49 (m, 3H), 2.52-2.53 (m, 3H), 4.18-4.25 (m, 2H), 4.32-4.39 (m, 1H), 6.88 (dd, 1H), 7.10-7.15 (m, 1H), 7.31-7.41 (m, 4H), 7.55 (d, 1H), 11.3 (s, 1H).

LC-MS (Method 5): $R_t$=2.22 min; MS (ESIpos): m/z=389 [M+H]$^+$.

Example 84

4-(4-Chloro-2-methylphenyl)-4-{7-[methylsulfinyl)methyl]-1H-indol-3-yl}butanonitrile

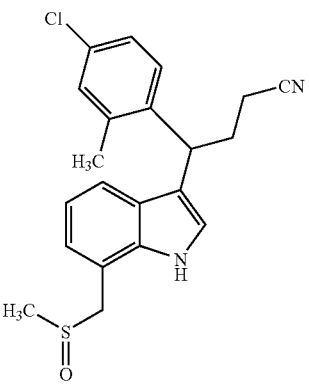

The title compound was prepared starting from 200 mg (0.54 mmol) of the compound from Example 45 in analogy to the synthesis of the compound from Example 79. 146 mg (70% of theory) of the title compound were obtained as mixture of diastereomers.

$^1$H-NMR (400 MHz, DMSO-$d_6$): δ=2.15-2.27 (m, 1H), 2.38-2.52 (m, 3H), 2.42 (s, 3H), 2.52 (s, 3H), 4.19-4.26 (m, 1H), 4.31-4.39 (m, 1H), 4.45 (t, 1H), 6.93 (t, 1H), 7.01 (d, 1H), 7.16 (dd, 1H), 7.23-7.27 (m, 2H), 7.30 (d, 1H), 7.33-7.36 (m, 1H), 11.2 (s, 1H).

LC-MS (Method 4): $R_t$=1.21 min; MS (ESIpos): m/z=385 [M+H]$^+$.

Example 85

4-(4-Fluoro-2-methylphenyl)-4-{7-[(methylsulfinyl)methyl]-1H-indol-3-yl}butanonitrile

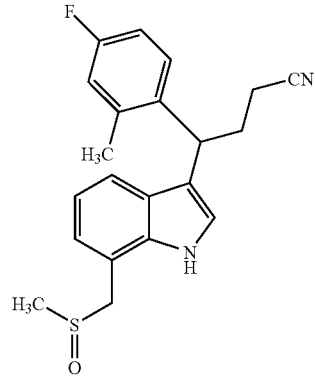

50 mg (0.14 mmol) of the compound from Example 46 were introduced into 10 ml of dichloromethane at RT, 35.0 mg (0.14 mmol) of 70% pure meta-chloroperbenzoic acid were added, and the mixture was stirred at RT for 4 h. 2 ml of methanol were added, and the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 24.6 mg (47% of theory) of the title compound as mixture of diastereomers.

$^1$H-NMR (400 MHz, DMSO-$d_6$): δ=2.15-2.25 (m, 1H), 2.36-2.49 (m, 3H), 2.43 (s, 3H), 2.52 (s, 3H), 4.18-4.26 (m, 1H), 4.31-4.38 (m, 1H), 4.44 (t, 1H), 6.89-6.96 (m, 2H), 6.99-7.04 (m, 2H), 7.23-7.35 (m, 3H), 11.1 (s, 1H).

LC-MS (Method 3): $R_t$=1.76 min; MS (ESIpos): m/z=369 [M+H]$^+$.

Example 86

4-[2-Fluoro-4-(trifluoromethyl)phenyl]-4-{7-[(methylsulfinyl)methyl]-1H-indol-3-yl}butanonitrile

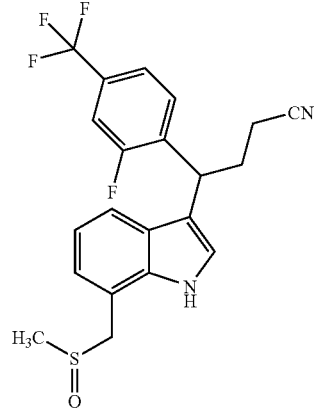

100 mg of the compound from Example 47 with a purity of 85% (0.21 mmol) were introduced into 14 ml of dichloromethane at 0° C., 59.1 mg (0.24 mmol) of 70% pure meta-chloroperbenzoic acid were added, and the mixture was stirred at RT overnight. It was concentrated, and the residue was purified by preparative HPLC (RP18 column; mobile phase: acetonitrile/water gradient with addition of 0.1% formic acid) to result in 62 mg (71% of theory) of the title compound as mixture of diastereomers.

$^1$H-NMR (400 MHz, DMSO-$d_6$): δ=2.32-2.42 (m, 1H), 2.43-2.60 (m, 3H), 2.52 (s, 3H), 4.20-4.26 (m, 1H), 4.32-4.38 (m, 1H), 4.62-4.67 (m, 1H), 6.95 (t, 1H), 7.03 (d, 1H), 7.37 (d, 1H), 7.49-7.53 (m, 2H), 7.59-7.66 (m, 2H), 11.2 (s, 1H).

LC-MS (Method 4): $R_t$=1.21 min; MS (ESIpos): m/z=423 [M+H]$^+$.

Example 87

5-(4-Chlorophenyl)-5-{7-[(methylsulfinyl)methyl]-1H-indol-3-yl}pentanonitrile

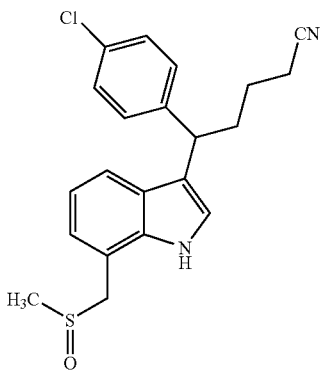

50 mg (0.14 mmol) of the compound from Example 49 were introduced into 9 ml of dichloromethane while cooling in ice, 33.4 mg (0.14 mmol) of 70% pure meta-chloroperbenzoic acid were added, and the mixture was stirred at RT overnight. 2 ml of methanol were added, and the residue after concentration was taken up in dichloromethane and saturated aqueous sodium bicarbonate solution, the phases were separated, the organic phase was washed twice with saturated aqueous sodium bicarbonate solution, water and saturated aqueous sodium chloride solution, and the organic phase was dried over magnesium sulfate, filtered and concentrated. The residue was purified by preparative HPLC (RP18 column; mobile phase: acetonitrile/water gradient with addition of 0.1% formic acid) to result in 33 mg (63% of theory) of the title compound as mixture of diastereomers.

$^1$H-NMR (400 MHz, DMSO-$d_6$): δ=1.41-1.63 (m, 2H), 2.00-2.11 (m, 1H), 2.16-2.26 (m, 1H), 2.50-2.56 (m, 2H), 2.51 (s, 3H), 4.19-4.25 (m, 2H), 4.31-4.37 (m, 1H), 6.89 (t, 1H), 6.99 (d, 1H), 7.29-7.33 (m, 2H), 7.33-7.40 (m, 4H), 11.1 (s, 1H).

LC-MS (Method 6): $R_t$=2.17 min; MS (ESIpos): m/z=385 [M+H]$^+$.

Example 88

4-(4-Chlorophenyl)-4-{6-fluoro-7-[(methylsulfinyl)methyl]-1H-indol-3-yl}butanonitrile

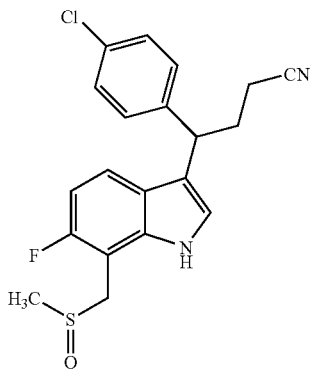

300 mg (0.80 mmol) of the compound from Example 50 were introduced into 55 ml of dichloromethane at 0° C., 198 mg (0.80 mmol) of 70% pure meta-chloroperbenzoic acid were added, and the mixture was stirred at RT for 2 h. 2 ml of methanol were added, and the mixture was extracted with water, saturated aqueous sodium bicarbonate solution and saturated aqueous sodium chloride solution. The phases were separated, and the solvents were removed from the organic phase in vacuo. The crude product was purified initially by preparative HPLC (mobile phase: acetonitrile/water gradient) and then by flash chromatography of the resulting, slightly impure product on silica gel (mobile phase: ethyl acetate). 197 mg (63% of theory) of the title compound were obtained as mixture of diastereomers.

$^1$H-NMR (400 MHz, DMSO-$d_6$): δ=2.21-2.48 (m, 4H), 2.55 (s, 3H), 4.20-4.36 (m, 3H), 6.84 (dd, 1H), 7.30-7.40 (m, 5H), 7.47 (s, 1H), 11.28 (s, 1H).

HPLC (Method 2): $R_t$=4.52 min; MS (ESIpos): m/z=389 [M+H]$^+$.

Example 89

4-{6-Fluoro-7-[(methylsulfinyl)methyl]-1H-indol-3-yl}-4-[4-(trifluoromethyl)phenyl]butanonitrile

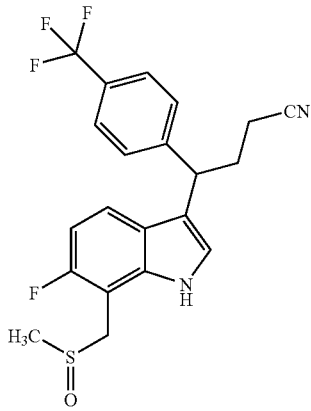

The title compound was prepared starting from 557 mg (1.37 mmol) of the compound from Example 51 in analogy to the synthesis of the compound from Example 88. 412 mg (71% of theory) of the target compound were obtained as mixture of diastereomers.

$^1$H-NMR (400 MHz, DMSO-$d_6$): δ=2.28-2.49 (m, 4H), 2.58 (s, 3H), 4.27-4.38 (m, 3H), 6.85 (dd, 1H), 7.36 (dd, 1H), 7.53 (s, 1H), 7.58 (d, 2H), 7.64 (d, 2H), 11.32 (s, 1H).

HPLC (Method 2): $R_t$=4.47 min; MS (ESIpos): m/z=423 [M+H]$^+$.

Example 90

4-(1-Benzothiophen-5-yl)-4-{7-[(methylsulfinyl)methyl]-1H-indol-3-yl}butanonitrile

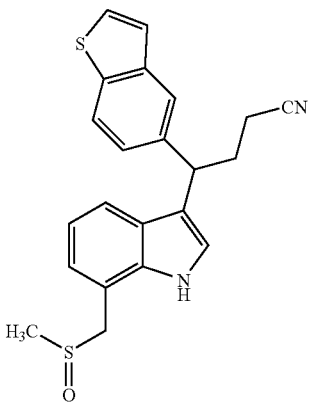

157 mg (0.42 mmol) of the compound from Example 52 were introduced into 28 ml of dichloromethane at 0° C., 102 mg (0.42 mmol) of 70% pure meta-chloroperbenzoic acid were added, and the mixture was stirred at RT for 2 h. 2 ml of methanol and a little ethyl acetate were added, and the mixture was extracted with water, saturated aqueous sodium bicarbonate solution and saturated aqueous sodium chloride solution. The phases were separated, and the solvents were removed from the organic phase in vacuo. The crude product was purified by preparative HPLC (mobile phase: acetonitrile/water gradient) and afforded 141 mg (86% of theory) of the title compound as mixture of diastereomers.

$^1$H-NMR (400 MHz, DMSO-$d_6$): δ=2.31-2.53 (m, 7H), 4.19-4.26 (dd, 1H), 4.30-4.39 (m, 2H), 6.88 (t, 1H), 6.98 (d, 1H), 7.33-7.42 (m, 3H), 7.49 (s, 1H), 7.71 (d, 1H), 7.84-7.91 (m, 2H), 11.14 (s, 1H).

HPLC (Method 2): $R_t$=4.32 min; MS (ESIpos): m/z=393 [M+H]$^+$.

Example 91

3-Methyl-4-{7-[(methylsulfinyl)methyl]-1H-indol-3-yl}-4-[4-(trifluoromethyl)phenyl]butanonitrile

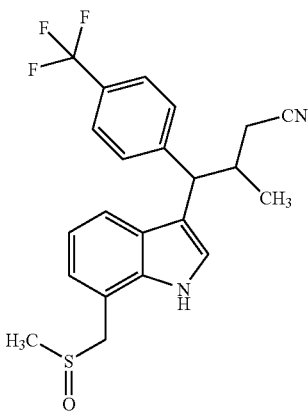

150 mg (0.37 mmol) of the compound from Example 54 were introduced into 20 ml of dichloromethane at 0° C., 92 mg (0.37 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 150 mg (96% of theory) of the title compound were obtained as mixture of diastereomers.

$^1$H-NMR (400 MHz, DMSO-$d_6$): δ=0.91-1.13 (m, 3H), 2.18-2.70 (m, 5H), 2.86-2.98 (m, 1H), 4.08-4.14 (m, 1H), 4.18-4.38 (m, 2H), 6.93-7.03 (m, 2H), 7.53-7.69 (m, 6H), 11.16-11.23 (s, 1H).

LC-MS (Method 4): $R_t$=1.21/1.24 min; MS (ESIpos): m/z=419 [M+H]$^+$.

Example 92

2-[1-(4-Chlorophenyl)-1-{7-[(methylsulfanyl)methyl]-1H-indol-3-yl}ethyl]cyclopropanecarbonitrile [trans-diastereomer mixture]

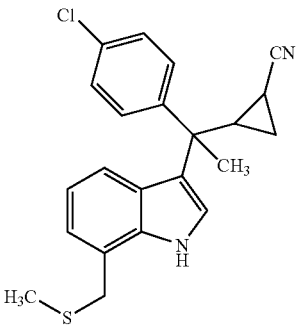

150 mg (0.68 mmol) of the compound from Example 75A and 120 mg (0.68 mmol) of the compound from Example 8A were introduced into 4 ml of dichloromethane at 0° C., 157 mg (0.71 mmol) of indium(III) chloride were added, and the mixture was stirred at RT for 1 h and under reflux for 0.5 h. After cooling, 0.05 ml (0.68 mmol) of trifluoroacetic acid was added, and the mixture was stirred under reflux for 5 min. It was diluted with dichloromethane, washed with saturated aqueous sodium bicarbonate solution, water and saturated aqueous sodium chloride solution, dried over magnesium sulfate, filtered and concentrated. The residue was purified by preparative HPLC (RP18 column; mobile phase: acetonitrile/water gradient with addition of 0.1% formic acid) to result in 117 mg (45% of theory) of the title compound as mixture of diastereomers.

$^1$H-NMR (400 MHz, DMSO-$d_6$): 0.84 (ddd, 0.6H), 0.97 (ddd, 0.4H), 1.26-1.36 (m, 1H), 1.37-1.43 (m, 0.4H), 1.49-1.56 (m, 0.6H), 1.54 (s, 1.2H), 1.55 (s, 1.8H), 1.97 (s, 1.8H), 1.98 (s, 1.2H), 2.28-2.36 (m, 1H), 3.88-3.99 (m, 2H), 6.53 (d, 0.6H), 6.60 (d, 0.4H), 6.65-6.73 (m, 1H), 6.85-6.91 (m, 1H), 7.25-7.39 (m, 5H), 11.1 (s, 1H).

LC-MS (Method 3): $R_t$=2.52 min; MS (ESIneg): m/z=379 [M−H]$^-$.

Example 93

3-(1-Cyclopropyl-5-fluoro-2,3-dihydro-1H-inden-1-yl)-7-[(methylsulfanyl)methyl]-1H-indole

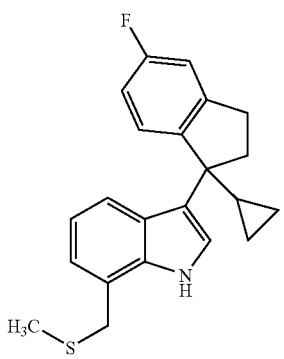

200 mg (0.78 mmol) of the compound from Example 76A with a purity of 75% and 152 mg (0.86 mmol) of the compound from Example 8A were introduced into 3.8 ml of dichloromethane at 0° C., 0.07 ml (0.94 mmol) of trifluoroacetic acid was added, and the mixture was stirred at 0° C. for 4 h. It was diluted with dichloromethane and added to saturated aqueous ammonium chloride solution, the phases were separated, the aqueous phase was extracted with dichloromethane, and the combined organic phases were dried over magnesium sulfate, filtered and concentrated. The residue was purified by preparative HPLC (RP18 column; mobile phase: acetonitrile/water gradient with addition of 0.1% formic acid) to result in 175 mg (64% of theory) of the title compound.

$^1$H-NMR (400 MHz, DMSO-$d_6$): δ=−0.26−−0.19 (m, 1H), −0.01-0.09 (m, 1H), 0.41-0.52 (m, 2H), 1.46-1.55 (m, 1H), 1.96 (s, 3H), 2.14 (ddd, 1H), 2.54-2.62 (m, 1H), 2.87-3.04 (m, 2H), 3.87-3.97 (m, 2H), 6.67-6.74 (m, 3H), 6.79-6.90 (m, 2H), 7.11 (dd, 1H), 7.28 (d, 1H), 10.9 (s, 1H).

LC-MS (Method 4): $R_t$=1.63 min; MS (ESIneg): m/z=350 [M−H]$^−$.

Example 94

3-(1-Cyclopropyl-5-fluoro-2,3-dihydro-1H-inden-1-yl)-5-fluoro-7-[(methylsulfanyl)methyl]-1H-indole

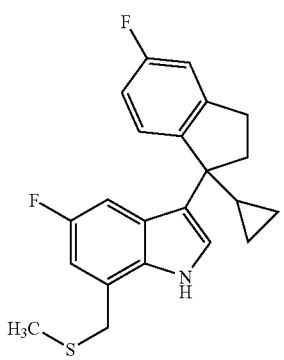

633 mg (2.47 mmol) of the compound from Example 76A with a purity of 75% and 530 mg (2.71 mmol) of the compound from Example 11A were introduced into 12 ml of dichloromethane at 0° C., 0.23 ml (2.96 mmol) of trifluoroacetic acid was added, and the mixture was stirred at 0° C. for 4 h. It was diluted with dichloromethane and added to saturated aqueous ammonium chloride solution, the phases were separated, the aqueous phase was extracted with dichloromethane, and the combined organic phases were dried over magnesium sulfate, filtered and concentrated. The residue was purified by preparative HPLC (RP18 column; mobile phase: acetonitrile/water gradient with addition of 0.1% formic acid) to result in 570 mg (63% of theory) of the title compound.

$^1$H-NMR (400 MHz, DMSO-$d_6$): δ=−0.26−−0.19 (m, 1H), 0.00-0.06 (m, 1H), 0.41-0.52 (m, 2H), 1.46-1.54 (m, 1H), 1.97 (s, 3H), 2.09-2.18 (m, 1H), 2.42-2.54 (m, 1H), 2.88-3.01 (m, 2H), 3.88-3.97 (m, 2H), 6.30 (dd, 1H), 6.71 (dd, 1H), 6.78 (dd, 1H), 6.82-6.88 (m, 1H), 7.13 (dd, 1H), 7.36-7.38 (m, 1H), 11.0 (s, 1H).

LC-MS (Method 3): $R_t$=2.76 min; MS (ESIneg): m/z=368 [M−H]$^−$.

Example 95

3-[1-Cyclopropyl-1-(4-fluorophenyl)ethyl]-7-[(methylsulfanyl)methyl]-1H-indole

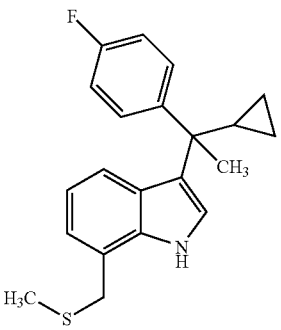

559 mg (3.10 mmol) of the compound from Example 77A and 0.26 ml (3.39 mmol) of trifluoroacetic acid were added to 500 mg (2.82 mmol) of the compound from Example 8A in 12 ml of dichloromethane. The reaction mixture was stirred at RT for 30 min and then diluted with dichloromethane, washed with saturated aqueous sodium bicarbonate solution and saturated aqueous sodium chloride solution, dried over sodium sulfate, filtered and concentrated. Purification of the crude product by preparative HPLC (mobile phase: acetonitrile/water gradient) resulted in 361 mg (38% of theory) of the title compound.

$^1$H-NMR (400 MHz, DMSO-$d_6$): δ=0.04-0.13 (m, 1H), 0.15-0.26 (m, 1H), 0.36-0.55 (m, 2H), 1.50 (s, 3H), 1.52-1.62 (m, 1H), 1.98 (s, 3H), 3.87-3.98 (m, 2H), 6.56-6.68 (m, 2H), 6.84 (d, 1H), 7.04 (t, 2H), 7.27-7.37 (m, 3H), 10.93 (s, 1H).

LC-MS (Method 3): $R_t$=2.68 min; MS (ESIneg): m/z=338 [M−H]$^−$.

Example 96

3-[1-Cyclopropyl-1-(2,4-difluorophenyl)ethyl]-7-[(methylsulfanyl)methyl]-1H-indole

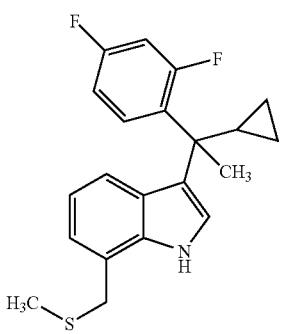

The title compound was prepared starting from 500 mg (2.82 mmol) of the compound from Example 8 and 615 mg (3.10 mmol) of the compound from Example 78A in analogy to the synthesis of the compound from Example 95. 227 mg (94% purity, 21% of theory) of the target compound were obtained.

$^1$H-NMR (400 MHz, DMSO-$d_6$): δ=0.12-0.19 (m, 2H), 0.44-0.53 (m, 2H), 1.58 (s, 3H), 1.57-1.67 (m, 1H), 1.97 (s, 3H), 3.91 (s, 2H), 6.53 (d, 1H), 6.64 (t, 1H), 6.83 (d, 1H), 6.93-7.01 (m, 1H), 7.06-7.13 (m, 1H), 7.24 (d, 1H), 7.75-7.84 (m, 1H), 10.91 (s, 1H).

HPLC (Method 2): $R_t$=5.31 min; MS (ESIneg): m/z=356 [M−H]$^-$.

Example 97

3-[1-(4-Chloro-2-fluorophenyl)-1-cyclopropylethyl]-7-[(methylsulfanyl)methyl]-1H-indole

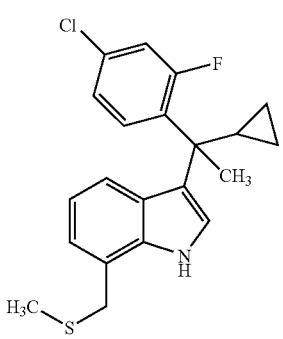

The title compound was prepared starting from 3.00 g (16.92 mmol) of the compound from Example 8 and 4.00 g (18.62 mmol) of the compound from Example 79A in analogy to the synthesis of the compound from Example 95. As a difference, the reaction mixture was stirred at 0° C. for 2 h and then warmed to RT. 1.54 g (24% of theory) of the target compound were obtained.

$^1$H-NMR (400 MHz, DMSO-$d_6$): δ=0.14-0.19 (m, 2H), 0.45-0.52 (m, 2H), 1.57 (s, 3H), 1.59-1.67 (m, 1H), 1.97 (s, 3H), 3.91 (s, 2H), 6.55 (d, 1H), 6.65 (t, 1H), 6.84 (d, 1H), 7.16 (dd, 1H), 7.25 (s, 1H), 7.31 (dd, 1H), 7.78 (t, 1H), 10.93 (s, 1H).

HPLC (Method 1): $R_t$=5.59 min; MS (ESIneg): m/z=374 [M−H]$^-$.

Example 98

3-[1-(4-Chloro-2-fluorophenyl)-1-cyclopropylethyl]-5-fluoro-7-[(methylsulfanyl)methyl]-1H-indole

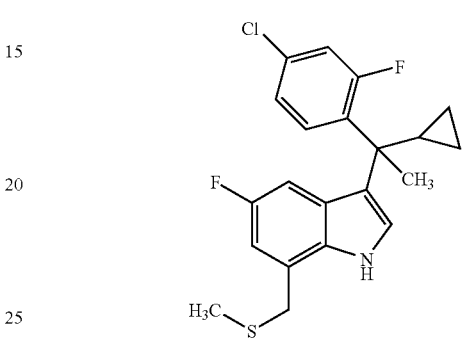

The title compound was prepared starting from 500 mg (2.56 mmol) of the compound from Example 8 and 605 mg (2.82 mmol) of the compound from Example 79A in analogy to the synthesis of the compound from Example 95. As a difference, the reaction mixture was stirred at 0° C. for 2 h and then warmed to RT. 67 mg (7% of theory) of the target compound were obtained.

$^1$H-NMR (400 MHz, DMSO-$d_6$): δ=0.09-0.20 (m, 2H), 0.44-0.54 (m, 2H), 1.56 (s, 3H), 1.56-1.66 (m, 1H), 1.98 (s, 3H), 3.91 (s, 2H), 6.17 (dd, 1H), 6.75 (dd, 1H), 7.20 (dd, 1H), 7.31-7.38 (m, 2H), 7.80 (t, 1H), 11.08 (s, 1H).

HPLC (Method 1): $R_t$=5.48 min; MS (ESIneg): m/z=390 [M−H]$^-$.

Example 99

3-{(4-Fluorophenyl)[4-(trifluoromethyl)phenyl]methyl}-7-[(methylsulfanyl)methyl]-1H-indole

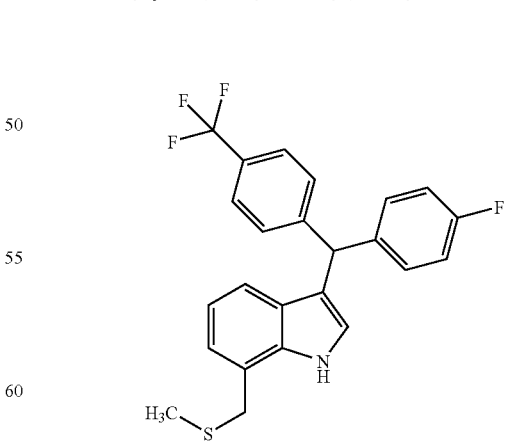

503 mg (1.86 mmol) of the compound from Example 80A and 75 mg (0.34 mmol) of indium(III) chloride were added to 300 mg (1.69 mmol) of the compound from Example 8 in 15 ml of toluene. The reaction mixture was stirred at 80° C. for 5

Example 100

3-[(4-Chlorophenyl)(4-fluorophenyl)methyl]-7-[(methylsulfanyl)methyl]-1H-indole

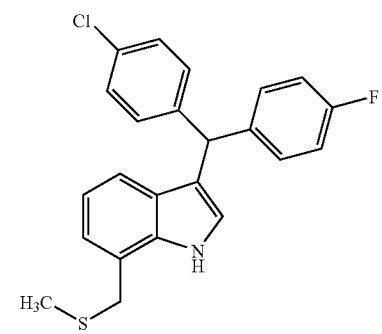

2.94 g (12.41 mmol) of the compound from Example 81A and 2.50 g (11.28 mmol) of indium(III) chloride were added to 2.00 g (11.28 mmol) of the compound from Example 8 in 100 ml of toluene. The reaction mixture was stirred at 80° C. for 3 h. After cooling to RT, the reaction solution was mixed with water and ethyl acetate and the solid was filtered off. The phases of the filtrate were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 0.83 g (19% of theory) of the title compound.

$^1$H-NMR (400 MHz, DMSO-$d_6$): δ=1.96 (s, 3H), 3.94 (s, 2H), 5.72 (s, 1H), 6.70 (s, 1H), 6.83 (t, 1H), 6.95 (d, 1H), 7.01 (d, 1H), 7.09-7.16 (m, 2H), 7.21-7.29 (m, 4H), 7.33-7.38 (m, 2H), 11.00 (s, 1H).

LC-MS (Method 4): $R_t$=1.65 min; MS (ESIneg): m/z=394 [M−H]$^-$.

h, a further 187 mg (0.85 mmol) of indium(III) chloride were added, and the mixture was again stirred for 5 h. After cooling to RT, the reaction solution was mixed with water and ethyl acetate, and the solid was filtered off. The phases of the filtrate were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 107 mg (15% of theory) of the title compound.

$^1$H-NMR (400 MHz, DMSO-$d_6$): δ=1.96 (s, 3H), 3.94 (s, 2H), 5.84 (s, 1H), 6.74 (s, 1H), 6.84 (t, 1H), 6.96 (d, 1H), 7.03 (d, 1H), 7.10-7.18 (m, 2H), 7.24-7.31 (m, 2H), 7.45 (d, 2H), 7.67 (d, 2H), 11.04 (s, 1H).

LC-MS (Method 5): $R_t$=3.11 min; MS (ESIpos): m/z=430 [M+H]$^+$.

Example 101

3-[(4-Fluoro-2-methylphenyl)(4-fluorophenyl)methyl]-7-[(methylsulfanyl)methyl]-1H-indole

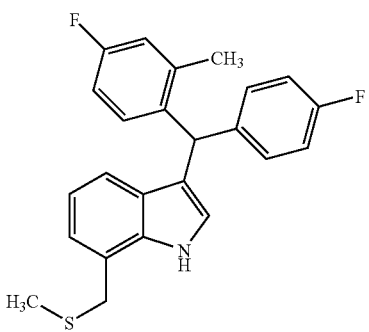

509 mg (2.17 mmol) of the compound from Example 82A and 437 mg (1.97 mmol) of indium(III) chloride were added to 350 mg (1.97 mmol) of the compound from Example 8 in 15 ml of toluene. The reaction mixture was stirred at 80° C. for 5 h. After cooling to RT, the reaction solution was mixed with water and ethyl acetate, and the solid was filtered off. The phases of the filtrate were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 174 mg (22% of theory) of the title compound.

$^1$H-NMR (400 MHz, DMSO-$d_6$): δ=1.97 (s, 3H), 2.26 (s, 3H), 3.94 (d, 2H), 5.78 (s, 1H), 6.54 (s, 1H), 6.80-6.93 (m, 3H), 6.95 (d, 1H), 7.00 (d, 1H), 7.05 (dd, 1H), 7.09-7.22 (m, 4H), 10.96 (s, 1H).

LC-MS (Method 5): $R_t$=3.06 min; MS (ESIneg): m/z=392 [M−H]$^-$.

Example 102

3-[(4-Chloro-2-methylphenyl)(4-fluorophenyl)methyl]-7-[(methylsulfanyl)methyl]-1H-indole

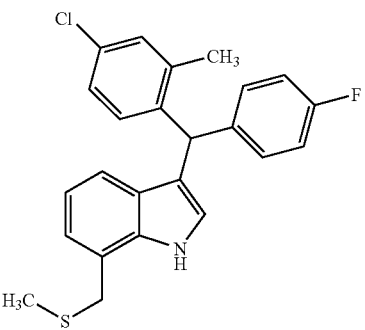

The title compound was prepared starting from 380 mg (2.14 mmol) of the compound from Example 8 and 591 mg (2.36 mmol) of the compound from Example 83A in analogy to the synthesis of the compound from Example 101. 307 mg (35% of theory) of the target compound were obtained.

¹H-NMR (400 MHz, DMSO-d₆): δ=1.97 (s, 3H), 2.26 (s, 3H), 3.94 (d, 2H), 5.79 (s, 1H), 6.53-6.56 (m, 1H), 6.80-6.88 (m, 2H), 6.96 (d, 1H), 7.00 (d, 1H), 7.09-7.22 (m, 5H), 7.28 (d, 1H), 10.98 (s, 1H).

LC-MS (Method 3): R$_t$=2.89 min; MS (ESIneg): m/z=408 [M−H]⁻.

Example 103

3-[(2,4-Difluorophenyl)(4-fluorophenyl)methyl]-7-[(methylsulfanyl)methyl]-1H-indole

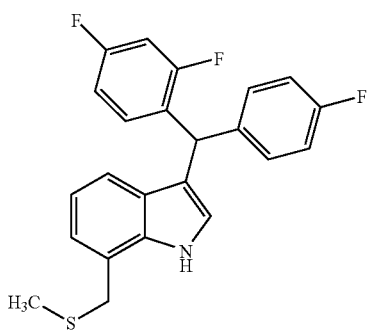

The title compound was prepared starting from 350 mg (1.97 mmol) of the compound from Example 8 and 470 mg (1.97 mmol) of the compound from Example 84A in analogy to the synthesis of the compound from Example 101. 191 mg (24% of theory) of the target compound were obtained.

¹H-NMR (400 MHz, DMSO-d₆): δ=1.96 (s, 3H), 3.94 (s, 2H), 5.88 (s, 1H), 6.69 (s, 1H), 6.85 (t, 1H), 6.94-7.17 (m, 6H), 7.19-7.28 (m, 3H), 11.04 (s, 1H).

LC-MS (Method 5): R$_t$=3.00 min; MS (ESIneg): m/z=396 [M−H]⁻.

Example 104

3-[(4-Chloro-2-fluorophenyl)(4-fluorophenyl)methyl]-7-[(methylsulfanyl)methyl]-1H-indole

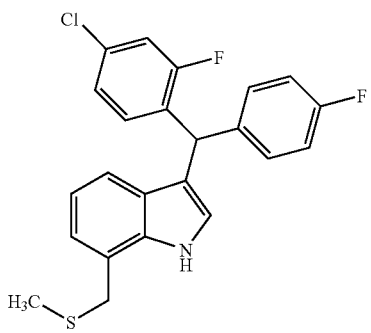

The title compound was prepared starting from 1.50 g (8.46 mmol) of the compound from Example 8 and 2.15 g (8.46 mmol) of the compound from Example 85A in analogy to the synthesis of the compound from Example 101. A difference was, however, that stirring was at 80° C. for 3 h. 0.66 g (19% of theory) of the target compound was obtained.

¹H-NMR (400 MHz, DMSO-d₆): δ=1.96 (s, 3H), 3.94 (s, 2H), 5.89 (s, 1H), 6.70 (d, 1H), 6.82-6.88 (m, 1H), 6.97 (d, 1H), 7.00-7.09 (m, 2H), 7.11-7.18 (m, 2H), 7.20-7.27 (m, 3H), 7.42 (dd, 1H), 11.04 (s, 1H).

LC-MS (Method 6): R$_t$=2.99 min; MS (ESIneg): m/z=412 [M−H]⁻.

Example 105

3-[(4-Chloro-2-fluorophenyl)(4-fluorophenyl)methyl]-5-fluoro-7-[(methylsulfanyl)methyl]-1H-indole

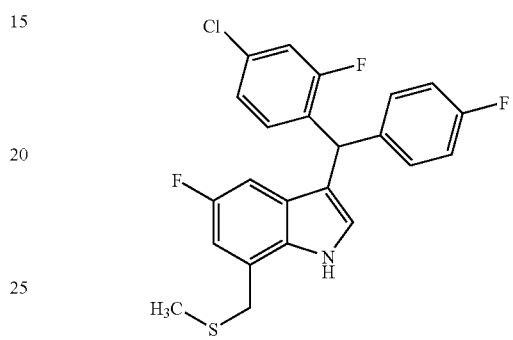

The title compound was prepared starting from 500 mg (2.56 mmol) of the compound from Example 9 and 652 mg (2.56 mmol) of the compound from Example 85A in analogy to the synthesis of the compound from Example 101. 197 mg (18% of theory) of the target compound were obtained.

¹H-NMR (400 MHz, DMSO-d₆): δ=1.97 (s, 3H), 3.94 (s, 2H), 5.87 (s, 1H), 6.74 (dd, 1H), 6.81 (d, 1H), 6.85-6.89 (m, 1H), 7.05 (t, 1H), 7.11-7.18 (m, 2H), 7.20-7.26 (m, 3H), 7.42 (dd, 1H), 11.19 (s, 1H).

LC-MS (Method 3): R$_t$=2.85 min; MS (ESIneg): m/z=430 [M−H]⁻.

Example 106

2-[1-(4-Chlorophenyl)-1-{7-[(methylsulfonyl)methyl]-1H-indol-3-yl}ethyl]cyclopropanecarbonitrile [trans-diastereomer mixture]

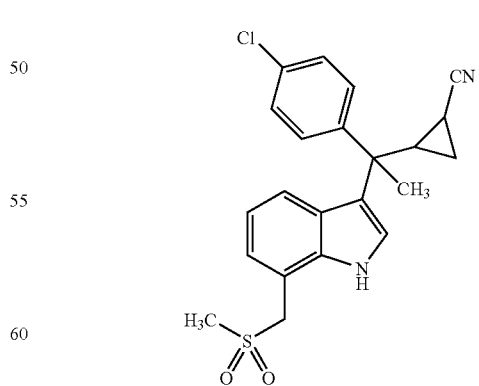

112 mg (0.29 mmol) of the compound from Example 92 were introduced into 20 ml of dichloromethane at 0° C., 145 mg (0.59 mmol) of 70% pure meta-chloroperbenzoic acid were added, and the mixture was stirred at RT overnight.

Methanol was added, and the residue after concentration was purified by preparative HPLC (RP18 column; mobile phase: acetonitrile/water gradient with addition of 0.1% formic acid) to result in 62 mg (51% of theory) of the title compound as mixture of diastereomers.

$^1$H-NMR (400 MHz, DMSO-d$_6$): 0.85 (ddd, 0.6H), 0.97 (ddd, 0.4H), 1.27-1.42 (m, 1.4H), 1.52-1.58 (m, 0.6H), 1.55 (s, 1.8H), 1.56 (s, 1.2H), 2.29-2.39 (m, 1H), 2.91 (s, 3H), 4.68-4.78 (m, 2H), 6.65 (d, 0.6H), 6.71 (d, 0.4H), 6.75-6.83 (m, 1H), 7.03-7.08 (m, 1H), 7.25-7.29 (m, 0.8H), 7.30-7.37 (m, 3.2H), 7.45-7.48 (m, 1H), 11.2 (s, 1H).

LC-MS (Method 4): R$_t$=1.27 min; MS (ESIneg): m/z=411 [M–H]$^-$.

Example 107

3-(1-Cyclopropyl-5-fluoro-2,3-dihydro-1H-inden-1-yl)-7-[(methylsulfonyl)methyl]-1H-indole

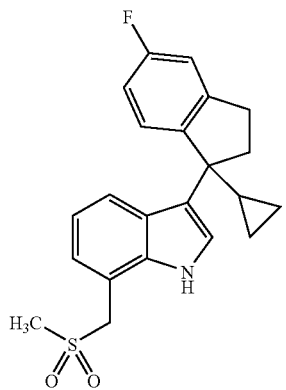

240 mg (0.68 mmol) of the compound from Example 93 were introduced into 40 ml of dichloromethane at 0° C., 354 mg (1.43 mmol) of 70% pure meta-chloroperbenzoic acid were added, and the mixture was stirred at RT overnight. 2 ml of methanol were added, and the residue after concentration was purified by preparative HPLC (RP18 column; mobile phase: acetonitrile/water gradient with addition of 0.1% formic acid) to result in 92 mg (35% of theory) of the title compound.

$^1$H-NMR (400 MHz, DMSO-d$_6$): δ=–0.27--–0.19 (m, 1H), 0.00-0.07 (m, 1H), 0.42-0.52 (m, 2H), 1.47-1.55 (m, 1H), 2.16 (ddd, 1H), 2.55-2.62 (m, 1H), 2.90 (s, 3H), 2.87-3.07 (m, 2H), 4.68-4.77 (m, 2H), 6.70 (dd, 1H), 6.77-6.86 (m, 3H), 7.02-7.08 (m, 1H), 7.12 (dd, 1H), 7.36-7.38 (m, 1H), 11.0 (s, 1H).

LC-MS (Method 4): R$_t$=1.41 min; MS (ESIneg): m/z=382 [M–H]$^-$.

The enantiomers were separated by preparative HPLC on a chiral phase [column: Daicel Chiralpak AD-H, 5 μm, 250 mm×20 mm; eluent: isohexane/isopropanol 4:1; flow rate: 20 ml/min; temperature: RT; UV detection: 230 nm]. The separated enantiomers were purified again by preparative HPLC on achiral phase (RP18 column; mobile phase: acetonitrile/water gradient with addition of 0.1% formic acid):

Enantiomer 107-1:
R$_t$=4.63 min [column: Daicel AD-H, 5 μm, 250 mm×4 mm; eluent: isohexane/isopropanol 3:2; flow rate: 1.0 ml/min; temperature: RT; UV detection: 230 nm];
Yield: 28.7 mg Enantiomer 107-2:
R$_t$=4.95 min [column: Daicel AD-H, 5 μm, 250 mm×4 mm; eluent: isohexane/isopropanol 3:2; flow rate: 1.0 ml/min; temperature: RT; UV detection: 230 nm];
Yield: 25.0 mg Example 108

3-(1-Cyclopropyl-5-fluoro-2,3-dihydro-1H-inden-1-yl)-5-fluoro-7-[(methylsulfonyl)methyl]-1H-indole

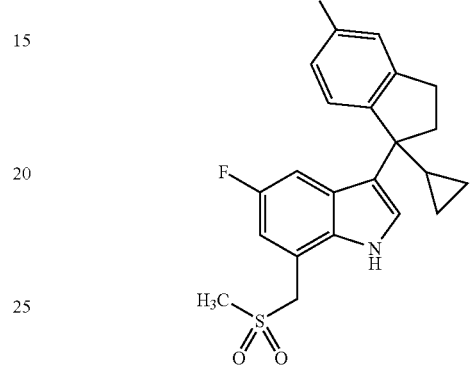

80.0 mg (0.22 mmol) of the compound from Example 94 were introduced into 6 ml of dichloromethane at 0° C., 109 mg (0.44 mmol) of 70% pure meta-chloroperbenzoic acid were added, and the mixture was stirred at RT overnight. Methanol was added, and the residue after concentration was purified by preparative HPLC (RP18 column; mobile phase: acetonitrile/water gradient with addition of 0.1% formic acid) to result in 36.1 mg (42% of theory) of the title compound.

$^1$H-NMR (400 MHz, DMSO-d$_6$): δ=–0.26--–0.19 (m, 1H), –0.01-0.06 (m, 1H), 0.42-0.53 (m, 2H), 1.45-1.55 (m, 1H), 2.11-2.19 (m, 1H), 2.44-2.54 (m, 1H), 2.93 (s, 3H), 2.90-3.00 (m, 2H), 4.71-4.80 (m, 2H), 6.42 (dd, 1H), 6.70 (dd, 1H), 6.82-6.88 (m, 1H), 6.94 (dd, 1H), 7.14 (dd, 1H), 7.47 (d, 1H), 11.1 (s, 1H).

LC-MS (Method 3): R$_t$=2.36 min; MS (ESIneg): m/z=400 [M–H]$^-$.

Example 109

3-[1-Cyclopropyl-1-(4-fluorophenyl)ethyl]-7-[(methylsulfonyl)methyl]-1H-indole

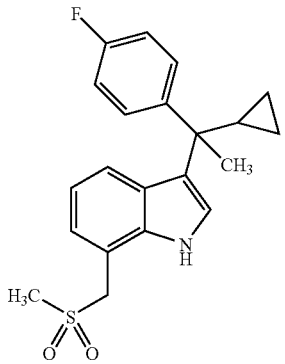

107 mg (0.31 mmol) of the compound from Example 95 were introduced into 21 ml of dichloromethane at 0° C., 155 mg (0.63 mmol) of 70% pure meta-chloroperbenzoic acid were added, and the mixture was stirred at RT for 2 h. 2 ml of methanol were added, and the solution was concentrated. The residue was dissolved in acetonitrile and purified by preparative HPLC (mobile phase: acetonitrile/water gradient). 106 mg (91% of theory) of the title compound were obtained.

$^1$H-NMR (400 MHz, DMSO-$d_6$): δ=0.04-0.25 (m, 2H), 0.36-0.56 (m, 2H), 1.51 (s, 3H), 1.52-1.63 (m, 1H), 2.91 (s, 3H), 4.72 (s, 2H), 6.66-6.79 (m, 2H), 6.98-7.10 (m, 3H), 7.23-7.35 (m, 2H), 7.44 (d, 1H), 11.02 (s, 1H).

HPLC (Method 2): $R_t$=4.81 min; MS (ESIpos): m/z=372 [M+H]$^+$.

The enantiomers were separated by preparative HPLC on a chiral phase [column: Daicel Chiralpak AD-H, 5 μm, 250 mm×20 mm; eluent: isohexane/isopropanol 7:3; flow rate: 25 ml/min; temperature: 24° C.; UV detection: 230 nm]. The separated enantiomers were purified again by preparative HPLC on achiral phase (mobile phase: acetonitrile/water gradient):

Enantiomer 109-1:
$R_t$=4.42 min [column: Daicel Chiralpak AD-H, 5 μm, 250 mm×4 mm; eluent: isohexane/isopropanol 1:1; flow rate: 1 ml/min; temperature: 24° C.; UV detection: 230 nm];
Yield: 25.8 mg Enantiomer 109-2:
$R_t$=4.96 min [column: Daicel Chiralpak AD-H, 5 μm, 250 mm×4 mm; eluent: isohexane/isopropanol 1:1; flow rate: 1 ml/min; temperature: 24° C.; UV detection: 230 nm];
Yield: 23.7 mg Example 110

3-[1-Cyclopropyl-1-(2,4-difluorophenyl)ethyl]-7-[(methylsulfonyl)methyl]-1H-indole

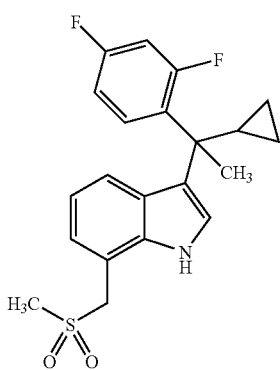

The title compound was prepared starting from 91 mg (0.26 mmol) of the compound from Example 96 in analogy to the synthesis of the compound from Example 109. 71 mg (72% of theory) of the target compound were obtained.

$^1$H-NMR (400 MHz, DMSO-$d_6$): δ=0.12-0.21 (m, 2H), 0.44-0.53 (m, 2H), 1.58 (s, 3H), 1.60-1.68 (m, 1H), 2.89 (s, 3H), 4.71 (s, 2H), 6.64 (d, 1H), 6.73 (t, 1H), 6.92-7.04 (m, 2H), 7.12 (dt, 1H), 7.34 (s, 1H), 7.75-7.84 (m, 1H), 11.01 (s, 1H).

HPLC (Method 2): $R_t$=5.31 min; MS (ESIneg): m/z=388 [M-H]$^-$.

Example 111

3-[1-(4-Chloro-2-fluorophenyl)-1-cyclopropylethyl]-7-[(methylsulfonyl)methyl]-1H-indole

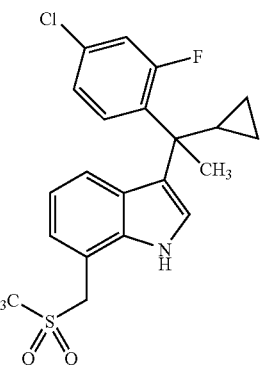

1.42 g (3.80 mmol) of the compound from Example 97 were introduced into 260 ml of dichloromethane at 0° C., 1.87 g (7.60 mmol) of 70% pure meta-chloroperbenzoic acid were added, and the mixture was stirred at RT for 2 h. 10 ml of methanol were added, and the solvents were removed in vacuo. The residue was taken up in ethyl acetate and washed with water, saturated aqueous sodium bicarbonate solution and saturated aqueous sodium chloride solution. The solvents were removed in vacuo. The crude product was purified by preparative HPLC (mobile phase: acetonitrile/water gradient) to result in 1.23 g (80% of theory) of the title compound.

$^1$H-NMR (400 MHz, DMSO-$d_6$): δ=0.13-0.21 (m, 2H), 0.45-0.53 (m, 2H), 1.57 (s, 3H), 1.59-1.68 (m, 1H), 2.89 (s, 3H), 4.71 (s, 2H), 6.67 (d, 1H), 6.75 (t, 1H), 7.02 (d, 1H), 7.17 (dd, 1H), 7.27-7.37 (m, 2H), 7.78 (t, 1H), 11.03 (s, 1H).

HPLC (Method 2): $R_t$=4.99 min; DCI-MS (ESIpos): m/z=406 [M+H]$^+$.

The enantiomers were separated by preparative HPLC on a chiral phase [column: Daicel Chiralpak IA, 5 μm, 250 mm×20 mm; eluent: isohexane/isopropanol 7:3; flow rate: 20 ml/min; temperature: 24° C.; UV detection: 260 nm]. The separated enantiomers were purified again by preparative HPLC on achiral phase (mobile phase: acetonitrile/water gradient):

Enantiomer 111-1:
$R_t$=5.42 min [column: Daicel Chiralpak IA, 5 μm, 250 mm×4 mm; eluent: isohexane/isopropanol 1:1; flow rate: 1 ml/min; temperature: 24° C.; UV detection: 230 nm];
Yield: 540.4 mg Enantiomer 111-2:
$R_t$=5.90 min [column: Daicel Chiralpak IA, 5 μm, 250 mm×4 mm; eluent: isohexane/isopropanol 1:1; flow rate: 1 ml/min; temperature: 24° C.; UV detection: 230 nm];
Yield: 534.7 mg

Example 112

3-[1-(4-Chloro-2-fluorophenyl)-1-cyclopropylethyl]-5-fluoro-7-[(methylsulfonyl)methyl]-1H-indole

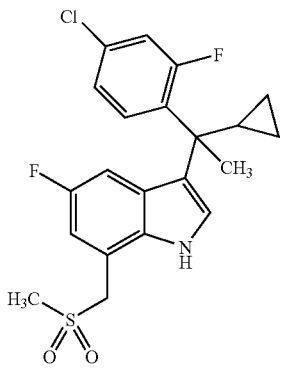

The title compound was prepared starting from 58 mg (0.15 mmol) of the compound from Example 98 in analogy to the synthesis of the compound from Example 111. 57 mg (86% of theory) of the target compound were obtained.

$^1$H-NMR (400 MHz, DMSO-d$_6$): δ=0.10-0.20 (m, 2H), 0.45-0.55 (m, 2H), 1.56 (s, 3H), 1.58-1.67 (m, 1H), 2.92 (s, 3H), 4.74 (s, 2H), 6.31 (dd, 1H), 6.91 (dd, 1H), 7.20 (dd, 1H), 7.35 (dd, 1H), 7.44 (d, 1H), 7.80 (t, 1H), 11.18 (s, 1H).

HPLC (Method 1): R$_t$=5.00 min; MS (ESIneg): m/z=422 [M−H]$^−$.

Example 113

3-{(4-Fluorophenyl) [4-(trifluoromethyl)phenyl]methyl}-7-[(methylsulfonyl)methyl]-1H-indole

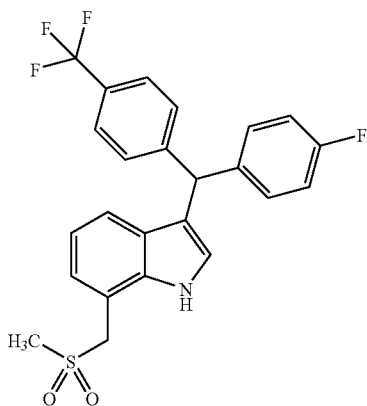

52 mg (0.12 mmol) of the compound from Example 99 were introduced into 12 ml of dichloromethane at 0° C., 60 mg (0.24 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 38 mg (68% of theory) of the title compound were obtained.

$^1$H-NMR (400 MHz, DMSO-d$_6$): δ=2.89 (s, 3H), 4.75 (s, 2H), 5.87 (s, 1H), 6.82 (s, 1H), 6.94 (t, 1H), 7.10-7.18 (m, 4H), 7.24-7.31 (m, 2H), 7.45 (d, 2H), 7.68 (d, 2H), 11.13 (s, 1H).

LC-MS (Method 4): R$_t$=1.47 min; MS (ESIpos): m/z=462 [M+H]$^+$.

Example 114

3-[(4-Chlorophenyl)(4-fluorophenyl)methyl]-7-[(methylsulfonyl)methyl]-1H-indole

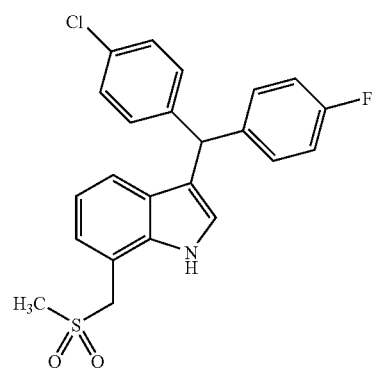

0.83 g (2.10 mmol) of the compound from Example 100 was introduced into 150 ml of dichloromethane at 0° C., 1.03 g (4.19 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 0.70 g (78% of theory) of the title compound was obtained.

$^1$H-NMR (400 MHz, DMSO-d$_6$): δ=2.89 (s, 3H), 4.74 (s, 2H), 5.75 (s, 1H), 6.78 (s, 1H), 6.93 (t, 1H), 7.09-7.16 (m, 4H), 7.22-7.28 (m, 4H), 7.34-7.38 (m, 2H), 11.09 (s, 1H).

LC-MS (Method 3): R$_t$=2.39 min; MS (ESIneg): m/z=426 [M−H]$^−$.

The enantiomers were separated by preparative HPLC on a chiral phase [column: Daicel Chiralpak AD-H, 5 μm, 250 mm×20 mm; eluent: isohexane/ethanol 7:3; flow rate: 20 ml/min; temperature: 24° C.; UV detection: 230 nm]. The separated enantiomers were purified again by preparative HPLC on achiral phase (mobile phase: acetonitrile/water gradient):

Enantiomer 114-1:

R$_t$=12.89 min [column: Daicel Chiralpak AD-H, 5 μm, 250 mm×4 mm; eluent: isohexane/ethanol 7:3; flow rate: 1 ml/min; temperature: 24° C.; UV detection: 230 nm];

Yield: 217.0 mg

Enantiomer 114-2:

R$_t$=13.91 min [column: Daicel Chiralpak AD-H, 5 μm, 250 mm×4 mm; eluent: isohexane/ethanol 7:3; flow rate: 1 ml/min; temperature: 24° C.; UV detection: 230 nm];

Yield: 186.0 mg

Example 115

3-[(4-Fluoro-2-methylphenyl)(4-fluorophenyl)methyl]-7-[(methylsulfonyl)methyl]-1H-indole

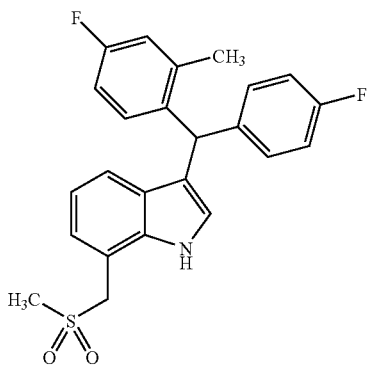

65 mg (0.17 mmol) of the compound from Example 101 were introduced into 8 ml of dichloromethane at 0° C., 81 mg (0.33 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 63 mg (88% of theory) of the title compound were obtained.

$^1$H-NMR (400 MHz, DMSO-$d_6$): δ=2.27 (s, 3H), 2.89 (s, 3H), 4.74 (s, 2H), 5.80 (s, 1H), 6.63 (s, 1H), 6.82-6.95 (m, 3H), 7.05 (dd, 1H), 7.09-7.22 (m, 6H), 11.05 (s, 1H).

LC-MS (Method 3): $R_t$=2.37 min; MS (ESIneg): m/z=424 [M−H]$^-$.

The enantiomers were separated by preparative HPLC on a chiral phase [column: Daicel Chiralpak IA, 5 μm, 250 mm×20 mm; eluent: isohexane/ethanol 6:4; flow rate: 20 ml/min; temperature: 24° C.; UV detection: 230 nm]. The separated enantiomers were purified again by preparative HPLC on achiral phase (mobile phase: acetonitrile/water gradient):

Enantiomer 115-1:

$R_t$=5.09 min [column: Daicel Chiralpak AD-H, 5 μm, 250 mm×4 mm; eluent: isohexane/ethanol 5:5; flow rate: 1 ml/min; temperature: 24° C.; UV detection: 230 nm];

Yield: 15 mg

Enantiomer 115-2:

$R_t$=5.62 min [column: Daicel Chiralpak AD-H, 5 μm, 250 mm×4 mm; eluent: isohexane/ethanol 5:5; flow rate: 1 ml/min; temperature: 24° C.; UV detection: 230 nm];

Yield: 15 mg

Example 116

3-[(4-Chloro-2-methylphenyl)(4-fluorophenyl)methyl]-7-[(methylsulfonyl)methyl]-1H-indole

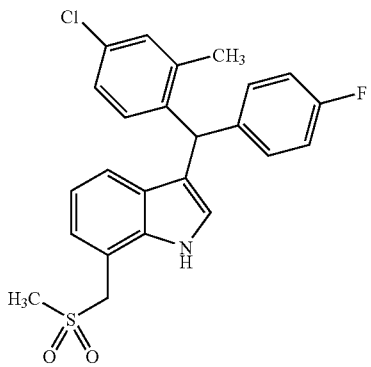

130 mg (0.32 mmol) of the compound from Example 102 were introduced into 15 ml of dichloromethane at 0° C., 156 mg (0.63 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 106 mg (76% of theory) of the title compound were obtained.

$^1$H-NMR (400 MHz, DMSO-$d_6$): δ=2.26 (s, 3H), 2.89 (s, 3H), 4.74 (s, 2H), 5.81 (s, 1H), 6.64 (s, 1H), 6.85 (d, 1H), 6.93 (t, 1H), 7.10-7.22 (m, 7H), 7.28 (d, 1H), 11.07 (s, 1H).

LC-MS (Method 3): $R_t$=2.50 min; MS (ESIneg): m/z=440 [M−H]$^-$.

The enantiomers were separated by preparative HPLC on a chiral phase [column: Daicel Chiralpak IA, 5 μm, 250 mm×20 mm; eluent: isohexane/ethanol 6:4; flow rate: 20 ml/min; temperature: 24° C.; UV detection: 230 nm]. The separated enantiomers were purified again by preparative HPLC on achiral phase (mobile phase: acetonitrile/water gradient):

Enantiomer 116-1:

$R_t$=5.38 min [column: Daicel Chiralpak AD-H, 5 μm, 250 mm×4 mm; eluent: isohexane/ethanol 5:5; flow rate: 1 ml/min; temperature: 24° C.; UV detection: 230 nm];

Yield: 48.0 mg

Enantiomer 116-2:

$R_t$=6.15 min [column: Daicel Chiralpak AD-H, 5 μm, 250 mm×4 mm; eluent: isohexane/ethanol 5:5; flow rate: 1 ml/min; temperature: 24° C.; UV detection: 230 nm];

Yield: 39.0 mg

Example 117

3-[(2,4-Difluorophenyl)(4-fluorophenyl)methyl]-7-[(methylsulfonyl)methyl]-1H-indole

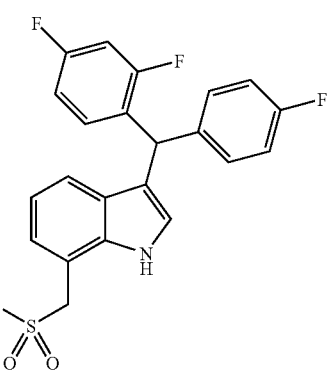

75 mg (0.19 mmol) of the compound from Example 103 were introduced into 14 ml of dichloromethane at 0° C., 93 mg (0.34 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 49 mg (60% of theory) of the title compound were obtained.

Example 118

3-[(4-Chloro-2-fluorophenyl)(4-fluorophenyl)methyl]-7-[(methylsulfonyl)methyl]-1H-indole

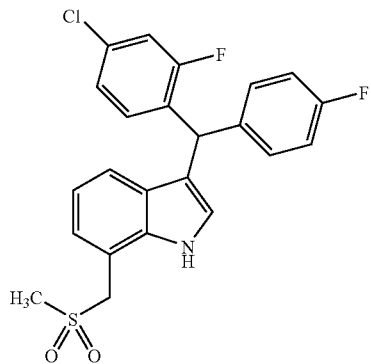

335 mg (0.81 mmol) of the compound from Example 104 were introduced into 25 ml of dichloromethane at 0° C., 93 mg (0.34 mmol) of 70% pure meta-chloroperbenzoic acid were added, and the mixture was stirred at RT for 2 h. 2 ml of methanol were added, and the solution was concentrated. The residue was taken up in acetonitrile, the remaining solid was filtered off, and the filtrate was purified by preparative HPLC (mobile phase: acetonitrile/water gradient). 286 mg (79% of theory) of the title compound were obtained.

$^1$H-NMR (400 MHz, DMSO-d$_6$): δ=2.90 (s, 3H), 4.75 (s, 2H), 5.91 (s, 1H), 6.79 (d, 1H), 6.95 (t, 1H), 7.04 (t, 1H), 7.11-7.18 (m, 4H), 7.20-7.27 (m, 3H), 7.42 (dd, 1H), 11.14 (s, 1H).

LC-MS (Method 4): R$_t$=1.46 min; MS (ESIneg): m/z=444 [M−H]$^−$.

The enantiomers were separated by preparative HPLC on a chiral phase [column: Daicel Chiralpak AD-H, 5 μm, 250 mm×20 mm; eluent: isohexane/ethanol 6:4; flow rate: 20 ml/min; temperature: 24° C.; UV detection: 230 nm]. The separated enantiomers were purified again by preparative HPLC on achiral phase (mobile phase: acetonitrile/water gradient):

Enantiomer 118-1:

R$_t$=6.20 min [column: Daicel Chiralpak AD-H, 5 μm, 250 mm×4 mm; eluent: isohexane/ethanol 5:5; flow rate: 1 ml/min; temperature: 24° C.; UV detection: 230 nm];

Enantiomer 118-2:

R$_t$=6.96 min [column: Daicel Chiralpak AD-H, 5 μm, 250 mm×4 mm; eluent: isohexane/ethanol 5:5; flow rate: 1 ml/min; temperature: 24° C.; UV detection: 230 nm].

Example 119

3-[(4-Chloro-2-fluorophenyl)(4-fluorophenyl)methyl]-5-fluoro-7-[(methylsulfonyl)methyl]-1H-indole

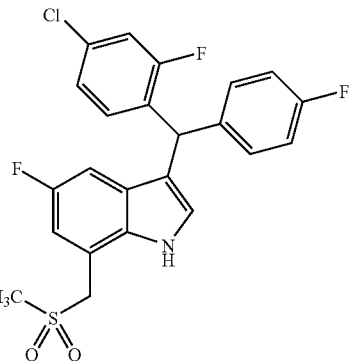

110 mg (0.26 mmol) of the compound from Example 105 were introduced into 12 ml of dichloromethane at 0° C., 126 mg (0.51 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 96 mg (81% of theory) of the title compound were obtained.

$^1$H-NMR (400 MHz, DMSO-d$_6$): δ=2.93 (s, 3H), 4.78 (s, 2H), 5.89 (s, 1H), 6.87-6.92 (m, 2H), 7.00-7.07 (m, 2H), 7.12-7.19 (m, 2H), 7.20-7.26 (m, 3H), 7.42 (dd, 1H), 11.27 (s, 1H).

LC-MS (Method 5): R$_t$=2.82 min; MS (ESIneg): m/z=462 [M−H]$^−$.

Example 120

3-(1-Cyclopropyl-5-fluoro-2,3-dihydro-1H-inden-1-yl)-7-[(methylsulfinyl)methyl]-1H-indole

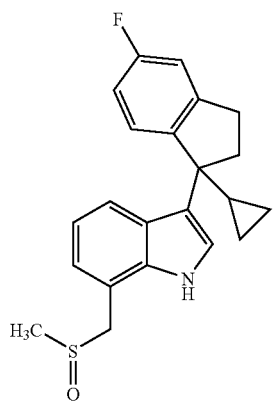

62.0 mg (0.18 mmol) of the compound from Example 93 were introduced into 10 ml of dichloromethane at 0° C., 43.5 mg (0.18 mmol) of 70% pure meta-chloroperbenzoic acid were added, and the mixture was stirred at RT overnight. 2 ml of methanol were added, and the residue after concentration was purified by preparative HPLC (RP18 column; mobile phase: acetonitrile/water gradient with addition of 0.1% formic acid) to result in 48 mg (74% of theory) of the title compound as mixture of diastereomers.

$^1$H-NMR (400 MHz, DMSO-d$_6$): δ=−0.26-−0.20 (m, 1H), −0.01-0.06 (m, 1H), 0.42-0.52 (m, 2H), 1.47-1.55 (m, 1H), 2.12-2.19 (m, 1H), 2.53-2.54 (m, 3H), 2.52-2.61 (m, 1H), 2.88-3.05 (m, 2H), 4.18-4.27 (m, 1H), 4.31-4.39 (m, 1H), 6.70 (dd, 1H), 6.73-6.77 (m, 2H), 6.78-6.85 (m, 1H), 6.91-6.96 (m, 1H), 7.12 (dd, 1H), 7.35-7.37 (m, 1H), 11.0-11.1 (m, 1H).

LC-MS (Method 4): $R_t$=1.35 min; MS (ESIneg): m/z=366 [M−H]$^−$.

Example 121

3-(1-Cyclopropyl-5-fluoro-2,3-dihydro-1H-inden-1-yl)-5-fluoro-7-[(methylsulfinyl)methyl]-1H-indole

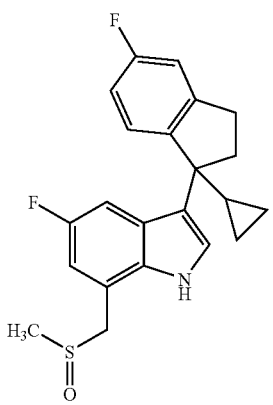

80.0 mg (0.22 mmol) of the compound from Example 94 were introduced into 6 ml of dichloromethane at 0° C., 56.1 mg (0.23 mmol) of 70% pure meta-chloroperbenzoic acid were added, and the mixture was stirred at RT overnight. Methanol was added, and the residue after concentration was purified by preparative HPLC (RP18 column; mobile phase: acetonitrile/water gradient with addition of 0.1% formic acid) to result in 43.6 mg (52% of theory) of the title compound as mixture of diastereomers.

$^1$H-NMR (400 MHz, DMSO-d$_6$): δ=−0.26-−0.19 (m, 1H), −0.01-0.06 (m, 1H), 0.42-0.53 (m, 2H), 1.46-1.55 (m, 1H), 2.10-2.19 (m, 1H), 2.44-2.54 (m, 1H), 2.54-2.56 (m, 3H), 2.90-3.04 (m, 2H), 4.18-4.27 (m, 1H), 4.33-4.42 (m, 1H), 6.34-6.39 (m, 1H), 6.71 (dd, 1H), 6.81-6.88 (m, 2H), 7.14 (dd, 1H), 7.45 (d, 1H), 11.1 (d, 1H).

LC-MS (Method 4): $R_t$=1.36 min; MS (ESIneg): m/z=384 [M−H]$^−$.

Example 122

3-[1-Cyclopropyl-1-(4-fluorophenyl)ethyl]-7-[(methylsulfinyl)methyl]-1H-indole

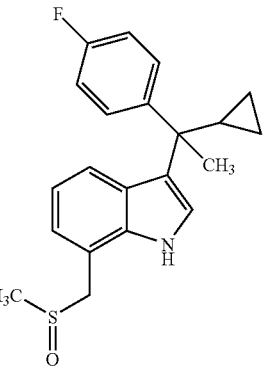

The title compound was prepared starting from 273 mg (0.81 mmol) of the compound from Example 95 in analogy to the synthesis of the compound from Example 91. 213 mg (73% of theory) of the target compound were obtained as mixture of diastereomers.

$^1$H-NMR (400 MHz, DMSO-d$_6$): δ=0.04-0.13 (m, 1H), 0.16-0.25 (m, 1H), 0.36-0.56 (m, 2H), 1.50 (s, 3H), 1.53-1.63 (m, 1H), 2.55 (s, 3H), 4.21 (dd, 1H), 4.35 (dd, 1H), 6.65 (d, 1H), 6.71 (t, 1H), 6.91 (d, 1H), 7.05 (t, 2H), 7.28-7.35 (m, 2H), 7.42 (d, 1H), 11.05 (s, 1H).

HPLC (Method 2): $R_t$=4.67 min; MS (ESIneg): m/z=354 [M−H]$^−$.

The diastereomers and enantiomers were separated by preparative HPLC on chiral phases [1$^{st}$ column: Daicel Chiralcel OJ-H, 5 μm, 250 mm×20 mm; eluent: isohexane/isopropanol 93:7; flow rate: 25 ml/min; temperature: 24° C.; UV detection: 230 nm1. 2$^{nd}$ column: Daicel Chiralpak AD-H, 5 μm, 250 mm×20 mm; eluent: Milli-Q water/ethanol 93:7; flow rate: 25 ml/min; temperature: 24° C.; UV detection: 230 nm]. The separated enantiomers were purified again by preparative HPLC on an achiral phase (mobile phase: acetonitrile/water gradient):

Isomer 122-1:
$R_t$=9.84 min [column: Daicel Chiralpak AD-H, 5 μm, 250 mm×4 mm; eluent: isohexane/ethanol 9:1; flow rate: 1 ml/min; temperature: 24° C.; UV detection: 260 nm];

$^1$H-NMR (400 MHz, DMSO-d$_6$): δ=0.03-0.13 (m, 1H), 0.15-0.25 (m, 1H), 0.36-0.57 (m, 2H), 1.51 (s, 3H), 1.53-1.63 (m, 1H), 2.55 (s, 3H), 4.23 (d, 1H), 4.34 (d, 1H), 6.61-6.75 (m, 2H), 6.92 (d, 1H), 7.04 (t, 2H), 7.31 (dd, 2H), 7.42 (d, 1H), 11.05 (s, 1H).

Isomer 122-2:
$R_t$=8.31 min [column: Daicel Chiralpak AD-H, 5 μm, 250 mm×4 mm; eluent: isohexane/ethanol 9:1; flow rate: 1 ml/min; temperature: 24° C.; UV detection: 260 nm].

$^1$H-NMR (400 MHz, DMSO-d$_6$): δ=0.04-0.13 (m, 1H), 0.16-0.25 (m, 1H), 0.37-0.55 (m, 2H), 1.50 (s, 3H), 1.53-1.62 (m, 1H), 2.55 (s, 3H), 4.12 (d, 1H), 4.37 (d, 1H), 6.65 (d, 1H), 6.71 (t, 1H), 6.91 (d, 1H), 7.05 (t, 2H), 7.28-7.35 (m, 2H), 7.42 (d, 1H), 11.04 (s, 1H).

Isomer 122-3:
$R_t$=8.86 min [column: Daicel Chiralpak AD-H, 5 μm, 250 mm×4 mm; eluent: isohexane/ethanol 9:1; flow rate: 1 ml/min; temperature: 24° C.; UV detection: 260 nm].

$^1$H-NMR (400 MHz, DMSO-d$_6$): δ=0.03-0.13 (m, 1H), 0.15-0.25 (m, 1H), 0.36-0.57 (m, 2H), 1.51 (s, 3H), 1.53-1.63 (m, 1H), 2.55 (s, 3H), 4.23 (d, 1H), 4.34 (d, 1H), 6.61-6.75 (m, 2H), 6.92 (d, 1H), 7.04 (t, 2H), 7.31 (dd, 2H), 7.42 (d, 1H), 11.05 (s, 1H).

Isomer 122-4:

$R_t$=10.30 min [column: Daicel Chiralpak AD-H, 5 µm, 250 mm×4 mm; eluent: isohexane/ethanol 9:1; flow rate: 1 ml/min; temperature: 24° C.; UV detection: 260 nm].

$^1$H-NMR (400 MHz, DMSO-d$_6$): δ=0.04-0.13 (m, 1H), 0.16-0.25 (m, 1H), 0.37-0.55 (m, 2H), 1.50 (s, 3H), 1.53-1.62 (m, 1H), 2.55 (s, 3H), 4.12 (d, 1H), 4.37 (d, 1H), 6.65 (d, 1H), 6.71 (t, 1H), 6.91 (d, 1H), 7.05 (t, 2H), 7.28-7.35 (m, 2H), 7.42 (d, 1H), 11.04 (s, 1H).

Example 123

3-[1-Cyclopropyl-1-(2,4-difluorophenyl)ethyl]-7-[(methylsulfinyl)methyl]-1H-indole

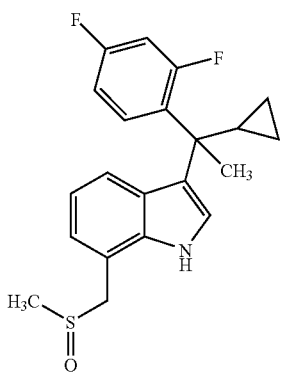

The title compound was prepared starting from 217 mg (94% purity, 0.61 mmol) of the compound from Example 96 in analogy to the synthesis of the compound from Example 91. 212 mg (99% of theory) of the target compound were obtained as mixture of diastereomers.

$^1$H-NMR (400 MHz, DMSO-d$_6$): δ=0.12-0.20 (m, 2H), 0.45-0.52 (m, 2H), 1.58 (s, 3H), 1.59-1.68 (m, 1H), 2.54 (s, 3H), 4.20 (dd, 1H), 4.34 (dd, 1H), 6.59 (d, 1H), 6.69 (t, 1H), 6.90 (d, 1H), 6.93-7.01 (m, 1H), 7.10 (dt, 1H), 7.32 (s, 1H), 7.76-7.85 (m, 1H), 11.04 (s, 1H).

HPLC (Method 1): $R_t$=4.64 min; DCI-MS (ESIpos): m/z=374 [M+H]$^+$.

Example 124

3-[1-(4-Chloro-2-fluorophenyl)-1-cyclopropylethyl]-7-[(methylsulfinyl)methyl]-1H-indole

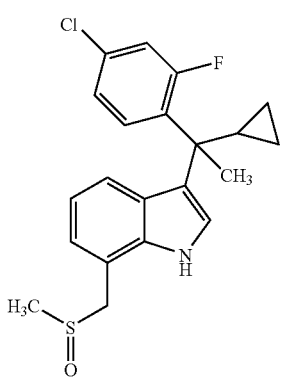

100 mg (0.27 mmol) of the compound from Example 97 were introduced into 18 ml of dichloromethane at 0° C., 66 mg (0.27 mmol) of 70% pure meta-chloroperbenzoic acid were added, and the mixture was stirred at RT for 2 h. 2 ml of methanol were added, and the solvents were removed in vacuo. The residue was taken up in ethyl acetate and washed with water, saturated aqueous sodium bicarbonate solution and saturated aqueous sodium chloride solution. The solvents were removed in vacuo. The crude product was purified by preparative HPLC (mobile phase: acetonitrile/water gradient) to result in 86 mg (83% of theory) of the title compound as mixture of diastereomers.

$^1$H-NMR (400 MHz, DMSO-d$_6$): δ=0.13-0.20 (m, 2H), 0.45-0.53 (m, 2H), 1.58 (s, 3H), 1.59-1.68 (m, 1H), 2.55 (s, 3H), 4.20 (dd, 1H), 4.34 (dd, 1H), 6.62 (d, 1H), 6.71 (t, 1H), 6.91 (d, 1H), 7.16 (dt, 1H), 7.29-7.35 (m, 2H), 7.78 (dt, 1H), 11.05 (s, 1H).

HPLC (Method 2): $R_t$=4.85 min; MS (ESIneg): m/z=388 [M−H]$^-$.

Example 125

3-{(4-Fluorophenyl) [4-(trifluoromethyl)phenyl]methyl}-7-[(methylsulfinyl)methyl]-1H-indole

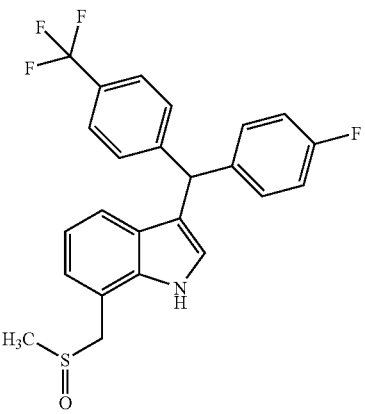

75 mg (0.18 mmol) of the compound from Example 99 were introduced into 25 ml of dichloromethane at 0° C., 43 mg (0.18 mmol) of 70% pure meta-chloroperbenzoic acid were added, and the mixture was stirred at RT for 2 h. 2 ml of methanol were added, and the solution was concentrated. The residue was purified twice by preparative HPLC (mobile phase: acetonitrile/water gradient). 65 mg (84% of theory) of the title compound were obtained as mixture of diastereomers.

$^1$H-NMR (400 MHz, DMSO-d$_6$): δ=2.54 (s, 3H), 4.24 (d, 1H), 4.37 (d, 1H), 5.86 (s, 1H), 6.81 (s, 1H), 6.90 (t, 1H), 7.03 (d, 1H), 7.08-7.18 (m, 3H), 7.24-7.31 (m, 2H), 7.45 (d, 2H), 7.67 (d, 2H), 11.15 (s, 1H).

LC-MS (Method 4): $R_t$=1.42 min; MS (ESIneg): m/z=444 [M−H]$^-$.

Example 126

3-[(4-Chlorophenyl)(4-fluorophenyl)methyl]-7-[(methylsulfinyl)methyl]-1H-indole

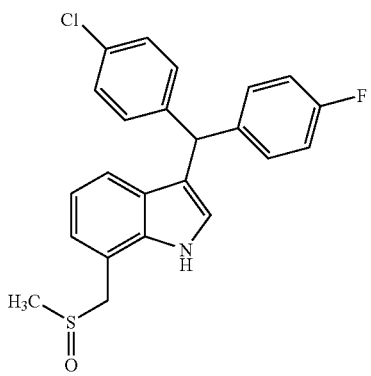

110 mg (0.28 mmol) of the compound from Example 100 were introduced into 20 ml of dichloromethane at 0° C., 68 mg (0.28 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 93 mg (81% of theory) of the title compound were obtained as mixture of diastereomers.

$^1$H-NMR (400 MHz, DMSO-$d_6$): δ=2.54 (s, 3H), 4.23 (d, 1H), 4.37 (d, 1H), 5.74 (s, 1H), 6.77 (s, 1H), 6.89 (t, 1H), 7.02 (d, 1H), 7.06-7.16 (m, 3H), 7.21-7.28 (m, 4H), 7.34-7.38 (m, 2H), 11.11 (s, 1H).

LC-MS (Method 3): $R_t$=2.28 min; MS (ESIneg): m/z=410 [M–H]$^-$.

Example 127

3-[(4-Fluoro-2-methylphenyl)(4-fluorophenyl)methyl]-7-[(methylsulfinyl)methyl]-1H-indole

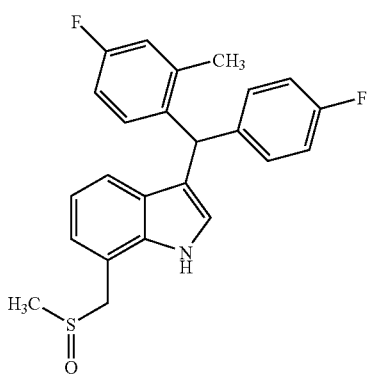

65 mg (0.17 mmol) of the compound from Example 101 were introduced into 8 ml of dichloromethane at 0° C., 41 mg (0.17 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 67 mg (99% of theory) of the title compound were obtained as mixture of diastereomers.

$^1$H-NMR (400 MHz, DMSO-$d_6$): δ=2.26 (s, 3H), 2.54 (s, 3H), 4.23 (dd, 1H), 4.37 (dd, 1H), 5.80 (s, 1H), 6.62 (s, 1H), 6.82-6.94 (m, 3H), 6.98-7.23 (m, 7H), 11.07 (s, 1H).

LC-MS (Method 4): $R_t$=1.38 min; MS (ESIneg): m/z=408 [M–H]$^-$.

Example 128

3-[(4-Chloro-2-methylphenyl)(4-fluorophenyl)methyl]-7-[(methylsulfinyl)methyl]-1H-indole

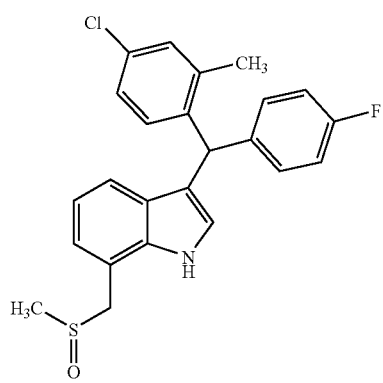

130 mg (0.32 mmol) of the compound from Example 102 were introduced into 15 ml of dichloromethane at 0° C., 78 mg (0.32 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 129 mg (96% of theory) of the title compound were obtained as mixture of diastereomers.

$^1$H-NMR (400 MHz, DMSO-$d_6$): δ=2.26 (s, 3H), 2.53 (s, 3H), 4.24 (dd, 1H), 4.37 (dd, 1H), 5.81 (s, 1H), 6.63 (s, 1H), 6.85 (d, 1H), 6.89 (t, 1H), 7.02 (d, 1H), 7.08 (d, 1H), 7.10-7.22 (m, 5H), 7.28 (d, 1H), 11.09 (s, 1H).

LC-MS (Method 3): $R_t$=2.38 min; MS (ESIneg): m/z=424 [M–H]$^-$.

Example 129

3-[(2,4-Difluorophenyl)(4-fluorophenyl)methyl]-7-[(methylsulfinyl)methyl]-1H-indole

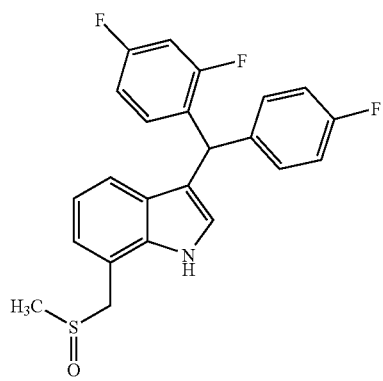

75 mg (0.19 mmol) of the compound from Example 103 were introduced into 14 ml of dichloromethane at 0° C., 47 mg (0.19 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 74 mg (95% of theory) of the title compound were obtained as mixture of diastereomers.

$^1$H-NMR (400 MHz, DMSO-$d_6$): δ=2.54 (s, 3H), 4.24 (dd, 1H), 4.38 (dd, 1H), 5.89 (s, 1H), 6.77 (s, 1H), 6.90 (t, 1H), 6.97-7.17 (m, 6H), 7.20-7.27 (m, 3H), 11.15 (s, 1H).

LC-MS (Method 3): $R_t$=2.17 min; MS (ESIneg): m/z=412 [M−H]$^-$.

Example 130

3-[(4-Chloro-2-fluorophenyl)(4-fluorophenyl)methyl]-7-[(methylsulfinyl)methyl]-1H-indole

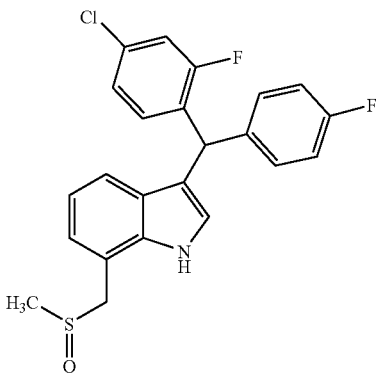

70 mg (0.17 mmol) of the compound from Example 104 were introduced into 10 ml of dichloromethane at 0° C., 42 mg (0.17 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 76 mg (99% of theory) of the title compound were obtained as mixture of diastereomers.

$^1$H-NMR (400 MHz, DMSO-$d_6$): δ=2.54 (s, 3H), 4.24 (dd, 1H), 4.38 (dd, 1H), 5.90 (s, 1H), 6.78 (s, 1H), 6.90 (t, 1H), 7.01-7.18 (m, 3H), 7.19-7.20 (m, 5H), 7.42 (dd, 1H), 11.14 (s, 1H).

LC-MS (Method 3): $R_t$=2.31 min; MS (ESIneg): m/z=428 [M−H]$^-$.

Example 131

3-[(4-Chloro-2-fluorophenyl)(4-fluorophenyl)methyl]-5-fluoro-7-[(methylsulfinyl)methyl]-1H-indole

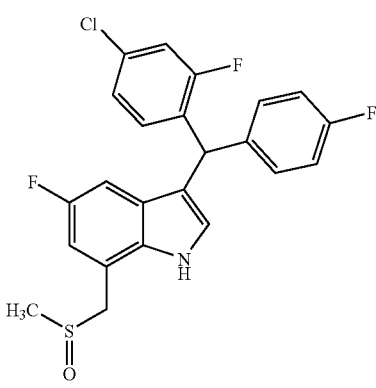

50 mg (0.12 mmol) of the compound from Example 105 were introduced into 6 ml of dichloromethane at 0° C., 29 mg (0.12 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient). 45 mg (87% of theory) of the title compound were obtained as mixture of diastereomers.

$^1$H-NMR (400 MHz, DMSO-$d_6$): δ=2.53 (s, 3H), 4.24 (dd, 1H), 4.40 (dd, 1H), 5.88 (s, 1H), 6.81-6.95 (m, 3H), 7.04 (dt, 1H), 7.11-7.18 (m, 2H), 7.20-7.26 (m, 3H), 7.42 (dd, 1H), 11.28 (s, 1H).

LC-MS (Method 5): $R_t$=2.70 min; MS (ESIneg): m/z=446 [M−H]$^-$.

Example 132

3-(4-Chloro-2-methylphenyl)-3-{5-fluoro-7-[(methylsulfanyl)methyl]-1H-indol-3-yl}propan-1-ol

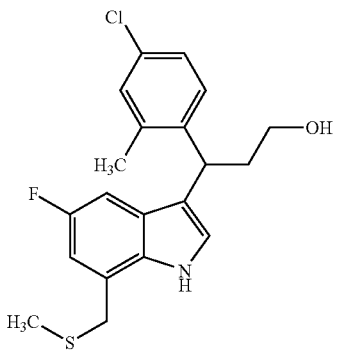

A solution of 690 mg (1.64 mmol) of the compound from Example 98A in 10 ml of THF was added dropwise to 5.8 ml (5.75 mmol) of a 1N lithium aluminum hydride solution in THF under argon in 20 ml of THF at RT. 1N hydrochloric acid was then added, the mixture was extracted with ethyl acetate, and the organic phase was dried over magnesium sulfate, filtered and concentrated. The crude product was purified by preparative HPLC (RP18 column; mobile phase: acetonitrile/water gradient with addition of 0.1% formic acid) to result in 0.60 g (97% of theory) of the title compound.

$^1$H-NMR (400 MHz, DMSO-$d_6$): δ=11.1 (s, 1H), 7.18-7.28 (m, 3H), 7.13 (dd, 1H), 6.87 (dd, 1H), 6.82 (dd, 1H), 4.50 (t, 1H), 4.46 (t, 1H), 3.87-3.96 (m, 2H), 3.32-3.45 (m, 2H), 2.39 (s, 3H), 2.19-2.29 (m, 1H), 1.06-2.05 (m, 1H), 1.96 (s, 3H).

LC-MS (Method 5): $R_t$=2.59 min; MS (ESIpos): m/z=378 [M+H]$^+$.

Example 133

3-[2-Chloro-4-(trifluoromethyl)phenyl]-3-{7-[(methylsulfanyl)methyl]-1H-indol-3-yl}propan-1-ol

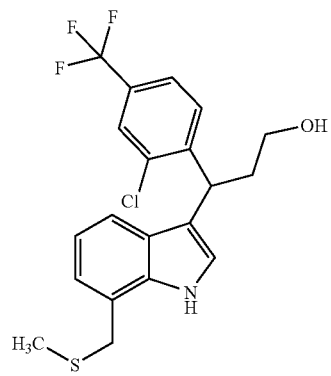

A solution of 1.30 g (2.85 mmol) of the compound from Example 99A in 20 ml of THF was added dropwise to 10 ml (9.98 mmol) of a 1N lithium aluminum hydride solution in THF under argon in 80 ml of THF at RT. 1N hydrochloric acid was then added, the mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 0.73 g (61% of theory) of the title compound.

$^1$H-NMR (400 MHz, DMSO-d$_6$): δ=11.0 (s, 1H), 7.81 (s, 1H), 7.56-7.62 (m, 2H), 7.36 (d, 1H), 7.25 (d, 1H), 6.93 (d, 1H), 6.86 (t, 1H), 4.88 (t, 1H), 4.53 (t, 1H), 3.88-3.96 (s, 2H), 3.35-3.49 (m, 2H), 2.29-2.40 (m, 1H), 2.08-2.20 (m, 1H), 1.94 (s, 3H).

LC-MS (Method 4): R$_t$=1.43 min; MS (ESIpos): m/z=414 [M+H]$^+$.

Example 134

3-(4-Methylphenyl)-3-{7-[(methylsulfanyl)methyl]-1H-indol-3-yl}propan-1-ol

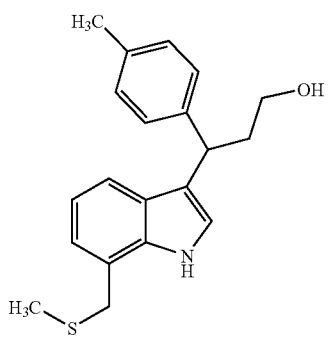

A solution of 2.41 g (6.57 mmol) of the compound from Example 100A in 20 ml of THF was added dropwise to 23 ml (23.0 mmol) of a 1N lithium aluminum hydride solution in THF under argon in 80 ml of THF at RT. 1N hydrochloric acid was then added, the mixture was extracted with dichloromethane, and the organic phase was dried over magnesium sulfate, filtered and concentrated. The crude product was purified by preparative HPLC (RP18 column; mobile phase: acetonitrile/water gradient with addition of 0.1% formic acid) to result in 1.77 g (83% of theory) of the title compound.

$^1$H-NMR (400 MHz, DMSO-d$_6$): δ=10.9 (s, 1H), 7.22-7.28 (m, 2H), 7.16-7.21 (m, 2H), 7.01-7.06 (m, 2H), 6.89 (d, 1H), 6.81 (t, 1H), 4.42 (t, 1H), 4.23 (t, 1H), 3.91 (s, 2H), 3.32-3.39 (m, 2H), 2.22-2.32 (m, 1H), 2.21 (s, 3H), 2.03-2.14 (m, 1H), 1.93 (s, 3H).

LC-MS (Method 4): R$_t$=1.29 min; MS (ESIpos): m/z=326 [M+H]$^+$.

Example 135

3-(4-Chloro-3-fluorophenyl)-3-{7-[(methylsulfanyl)methyl]-1H-indol-3-yl}propan-1-ol

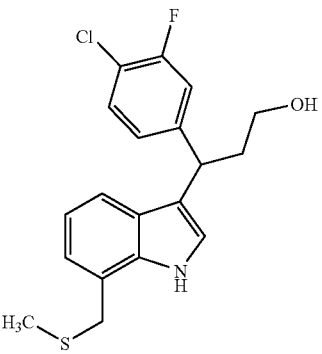

A solution of 1.74 g (4.28 mmol) of the compound from Example 101A in 7 ml of tetrahydrofuran was added dropwise to 15.0 ml (15.05 mmol) of a 1N solution of lithium aluminum hydride in tetrahydrofuran in 20 ml of tetrahydrofuran at RT under argon. The mixture was stirred at 60° C. for 1 h and then water and acetonitrile were added, and the suspension was filtered through kieselguhr. The solvents were removed in a rotary evaporator, and the residue was purified by preparative HPLC (mobile phase: acetonitrile/water gradient). 1.36 g (87% of theory) of the title compound were obtained.

$^1$H-NMR (400 MHz, DMSO-d$_6$): δ=1.94 (s, 3H), 2.08-2.17 (m, 1H), 2.23-2.34 (m, 1H), 3.27-3.42 (m, 2H), 3.91 (s, 2H), 4.35 (t, 1H), 4.49 (t, 1H), 6.85 (t, 1H), 6.92 (d, 1H), 7.20 (dd, 1H), 7.27-7.38 (m, 3H), 11.0 (s, 1H).

HPLC (Method 1): R$_t$=4.63 min; MS (ESIneg): m/z=462 [M−H]$^-$.

Example 136

3-(4-Chloro-2,6-difluorophenyl)-3-{7-[(methylsulfanyl)methyl]-1H-indol-3-yl}propan-1-ol

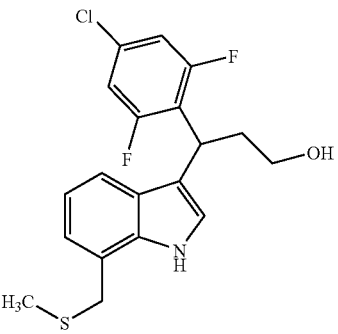

A solution of 1.09 g (2.56 mmol) of the compound from Example 102A in 6 ml of tetrahydrofuran was added dropwise to 9.0 ml (9.0 mmol) of a 1N solution of lithium aluminum hydride in tetrahydrofuran in 12 ml of tetrahydrofuran at RT under argon. The mixture was stirred at 60° C. for 1 h and then water and acetonitrile were added, and the suspension was filtered through kieselguhr. The solvents were removed in a rotary evaporator, and the residue was purified by preparative HPLC (mobile phase: acetonitrile/water gradient). 0.88 g (90% of theory) of the title compound was obtained.

$^1$H-NMR (400 MHz, DMSO-$d_6$): δ=1.93 (s, 3H), 2.22-2.46 (m, 2H), 3.33-3.51 (m, 2H), 3.91 (s, 2H), 4.53 (t, 1H), 4.74 (t, 1H), 6.85-6.96 (m, 2H), 7.22-7.32 (m, 4H), 11.0 (s, 1H).

HPLC (Method 1): $R_t$=4.55 min; MS (ESIneg): m/z=380 [M−H]$^−$.

Example 137

3-(2,2-Difluoro-1,3-benzodioxol-5-yl)-3-{7-[(methylsulfanyl)methyl]-1H-indol-3-yl}propan-1-ol

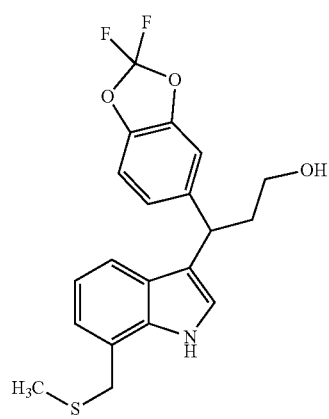

A solution of 1.67 g (3.86 mmol) of the compound from Example 103A in 8 ml of tetrahydrofuran was added dropwise to 13.5 ml (13.5 mmol) of a 1N solution of lithium aluminum hydride in tetrahydrofuran in 16 ml of tetrahydrofuran at RT under argon. The mixture was stirred at 60° C. for 1 h and then water and acetonitrile were added, and the suspension was filtered through kieselguhr. The solvents were removed in a rotary evaporator, and the residue was purified by preparative HPLC (mobile phase: acetonitrile/water gradient). 1.39 g (92% of theory) of the title compound were obtained.

$^1$H-NMR (400 MHz, DMSO-$d_6$): δ=1.94 (s, 3H), 2.07-2.17 (m, 1H), 2.24-2.35 (m, 1H), 3.28-3.42 (m, 2H), 3.91 (s, 2H), 4.36 (t, 1H), 4.48 (t, 1H), 6.84 (t, 1H), 6.92 (d, 1H), 7.18 (dd, 1H), 7.25 (d, 1H), 7.29-7.36 (m, 3H), 11.0 (s, 1H).

HPLC (Method 2): $R_t$=4.65 min; MS (ESIneg): m/z=390 [M−H]$^−$.

Example 138

3-{7-[(Methylsulfanyl)methyl]-1H-indol-3-yl}-3-[4-(trifluoromethyl)phenyl]butan-1-ol

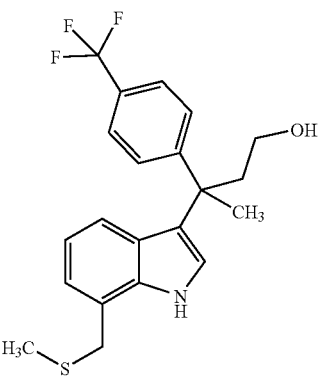

1.59 g (91% purity, approx. 6.77 mmol) of the compound from Example 89A and 1.50 g (6.77 mmol) of indium(III) chloride were added to 1.20 g (6.77 mmol) of the compound from Example 8A in 29 ml of toluene. The reaction mixture was stirred at 80° C. for 5 h. After cooling to RT, the reaction solution was mixed with water and ethyl acetate, and the solid was filtered off. The phases of the filtrate were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 0.14 g (5% of theory) of the title compound.

$^1$H-NMR (400 MHz, DMSO-$d_6$): δ=1.69 (s, 3H), 1.97 (s, 3H), 2.26-2.53 (m, 2H), 3.10-3.21 (m, 1H), 3.21-3.29 (m, 1H), 3.93 (s, 2H), 4.33 (t, 1H), 6.66-6.73 (m, 2H), 6.87 (dd, 1H), 7.33 (d, 1H), 7.47 (d, 2H), 7.60 (d, 2H), 11.0 (s, 1H).

LC-MS (Method 9): $R_t$=1.20 min; MS (ESIpos): m/z=392 [M+H]$^+$.

Example 139

3-(4-Chlorophenyl)-3-{7-[(methylsulfanyl)methyl]-1H-indol-3-yl}butan-1-ol

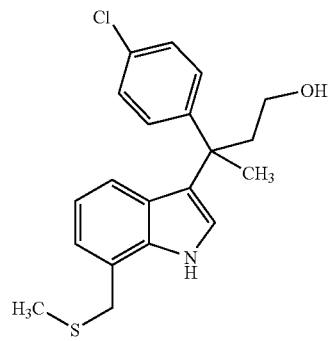

A solution of 740 mg (1.84 mmol) of the compound from Example 104A in 20 ml of tetrahydrofuran was added dropwise to 5.5 ml (5.5 mmol) of a 1N solution of diisobutylaluminum hydride in dichloromethane in 20 ml of tetrahydrofuran at RT under argon. The mixture was stirred at RT for 2 h and then water and dichloromethane were added, and the phases were separated. The aqueous phase was extracted with dichloromethane. The combined organic phases were washed with saturated aqueous sodium chloride solution, dried over sodium sulfate, filtered and concentrated. The residue was purified by preparative HPLC (mobile phase: acetonitrile/water gradient). 437 mg (66% of theory) of the title compound were obtained.

$^1$H-NMR (400 MHz, DMSO-$d_6$): δ=1.64 (s, 3H), 1.97 (s, 3H), 2.20-2.44 (m, 2H), 3.10-3.30 (m, 2H), 3.92 (s, 2H), 4.30 (t, 1H), 6.66-6.74 (m, 2H), 6.87 (d, 1H), 7.23-7.30 (m, 5H), 10.9 (s, 1H).

LC-MS (Method 5): $R_t$=2.52 min; MS (ESIpos): m/z=360 [M+H]$^+$.

Example 140

3-(4-Chlorophenyl)-3-{7-[(methylsulfanyl)methyl]-1H-indol-3-yl}pentan-1-ol

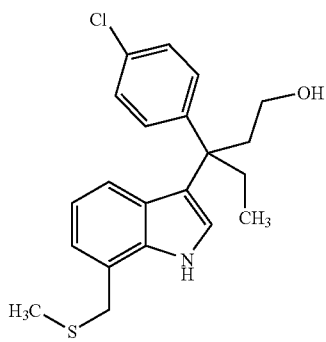

3.04 g (14.10 mmol) of 3-(4-chlorophenyl)pentane-1,3-diol (preparation in analogy to the synthesis of Example 88A and 89A starting from 1-(4-chloropenyl)propan-1-one and ethyl acetate) and 3.12 g (14.10 mmol) of indium(III) chloride were added to 2.50 g (14.10 mmol) of the compound from Example 8A in 60 ml of toluene. The reaction mixture was stirred at 80° C. for 5 h. After cooling to RT, the reaction solution was mixed with water and ethyl acetate, and the solid was filtered off through kieselguhr. The phases of the filtrate were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 2.13 g (40% of theory) of the title compound.

$^1$H-NMR (400 MHz, DMSO-$d_6$): δ=0.61 (t, 3H), 1.97 (s, 3H), 1.98-2.38 (m, 4H), 2.98-3.09 (m, 1H), 3.12-3.22 (m, 1H), 3.92 (s, 2H), 4.27 (t, 1H), 6.59-6.68 (m, 2H), 6.85 (dd, 1H), 7.22-7.34 (m, 5H), 10.9 (s, 1H).

LC-MS (Method 4): $R_t$=1.38 min; MS (ESIneg): m/z=372 [M−H]$^-$.

Example 141

3-(4-Chlorophenyl)-3-cyclopropyl-3-{7-[(methylsulfanyl)methyl]-1H-indol-3-yl}propan-1-ol

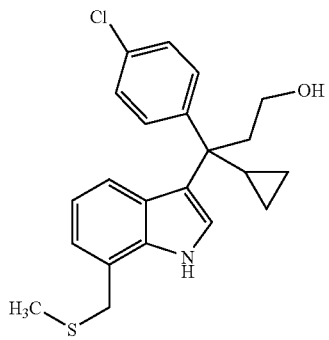

A solution of 62 mg (0.15 mmol) of the compound from Example 105A in 0.5 ml of tetrahydrofuran was added dropwise to 0.51 ml (0.51 mmol) of a 1N solution of lithium aluminum hydride in tetrahydrofuran in 1 ml of tetrahydrofuran at RT under argon. The mixture was stirred at 60° C. for 1 h and then mixed with water and acetonitrile, and the suspension was filtered through kieselguhr. The solvents were removed in a rotary evaporator, and the residue was purified by preparative HPLC (mobile phase: acetonitrile/water gradient). 52 mg (93% of theory) of the title compound were obtained.

$^1$H-NMR (400 MHz, DMSO-$d_6$): δ=−0.20−−0.10 (m, 2H), 0.34-0.49 (m, 2H), 1.63-1.72 (m, 1H), 1.98 (s, 3H), 2.27-2.50 (m, 2H), 3.13-3.23 (m, 1H), 3.23-3.32 (m, 1H), 3.94 (q, 2H), 4.30 (t, 1H), 6.44 (d, 1H), 6.64 (t, 1H), 6.85 (d, 1H), 7.23 (d, 2H), 7.29 (d, 2H), 7.38 (d, 1H), 11.0 (s, 1H).

LC-MS (Method 4): $R_t$=1.42 min; MS (ESIneg): m/z=384 [M−H]$^-$.

Example 142

3-(2,3-Dihydro-1,4-benzodioxin-6-yl)-3-{7-[(methylsulfanyl)methyl]-1H-indol-3-yl}butan-1-ol

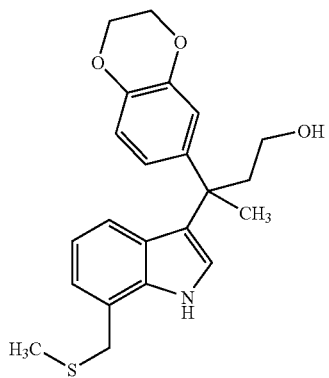

A solution of 625 mg (1.47 mmol) of the compound from Example 106A in 3 ml of tetrahydrofuran was added dropwise to 5.14 ml (5.14 mmol) of a 1N solution of lithium aluminum hydride in tetrahydrofuran in 6 ml of tetrahydrofuran at RT under argon. The mixture was stirred at 60° C. for 1 h and then mixed with water and acetonitrile, and the suspension was filtered through kieselguhr. The solvents were removed in a rotary evaporator, and the residue was purified by preparative HPLC (mobile phase: acetonitrile/water gradient). 491 mg (87% of theory) of the title compound were obtained.

$^1$H-NMR (400 MHz, DMSO-$d_6$): δ=1.60 (s, 3H), 1.97 (s, 3H), 2.15-2.25 (m, 1H), 2.29-2.40 (m, 1H), 3.09-3.29 (m, 2H), 3.92 (s, 2H), 4.16 (s, 4H), 4.25 (t, 1H), 6.63-6.73 (m, 4H), 6.83 (d, 1H), 6.87 (d, 1H), 7.21 (d, 1H), 10.9 (s, 1H).

HPLC (Method 1): $R_t$=4.28 min; DCI-MS (ESIpos): m/z=383 [M−H$_2$O+NH$_4$]$^+$.

Example 143

3-(4-Chlorophenyl)-3-{7-[(methylsulfinyl)methyl]-1H-indol-3-yl}pentan-1-ol

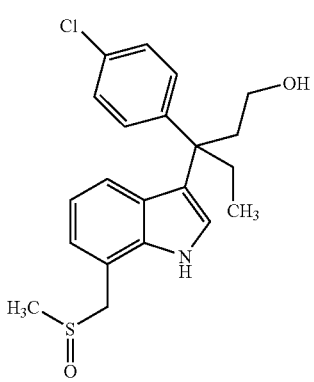

60 mg (0.16 mmol) of the compound from Example 140 were introduced into 6 ml of dichloromethane at 0° C., 40 mg (0.16 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 62 mg (99% of theory) of the title compound as mixture of diastereomers.

$^1$H-NMR (400 MHz, DMSO-$d_6$): δ=0.61 (t, 3H), 1.99-2.11 (m, 1H), 2.13-2.27 (m, 2H), 2.29-2.39 (m, 1H), 2.50 (s, 3H), 2.99-3.09 (m, 1H), 3.11-3.22 (m, 1H), 4.22 (dd, 1H), 4.27 (t, 1H), 4.35 (dd, 1H), 6.65-6.73 (m, 2H), 6.91 (dd, 1H), 7.24 (d, 2H), 7.29 (d, 2H), 7.40 (d, 1H), 11.1 (s, 1H).

LC-MS (Method 3): $R_t$=1.73 min; MS (ESIneg): m/z=388 [M−H]$^-$.

Example 144

3-(4-Chloro-2-fluorophenyl)-3-{7-[(methylsulfonyl)methyl]-1H-indol-3-yl}propan-1-ol

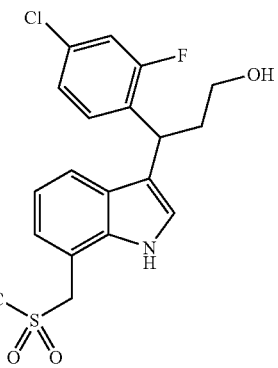

33.2 mg (ft 12 mmol) of 60% pure meta-chloroperbenzoic acid were added to 40.0 mg (0.11 mmol) of the compound from Example 4 in 5 ml of dichloromethane, and the mixture was stirred at RT overnight. It was concentrated, and the residue was purified by preparative HPLC (RP18 column; mobile phase: acetonitrile/water gradient with addition of 0.1% formic acid) to result in 16.2 mg (37% of theory) of the title compound.

$^1$H-NMR (400 MHz, DMSO-$d_6$): δ=11.1 (s, 1H), 7.31-7.40 (m, 4H), 7.18 (dd, 1H), 7.11 (d, 1H), 6.96 (t, 1H), 4.67-4.76 (m, 2H), 4.62 (t, 1H), 4.51 (t, 1H), 3.34-3.43 (m, 2H), 2.88 (s, 3H), 2.27-2.38 (m, 1H), 2.09-2.20 (m, 1H).

LC-MS (Method 3): $R_t$=1.73 min; MS (ESIpos): m/z=396 [M+H]$^+$.

Example 145

3-(4-Chloro-2-methylphenyl)-3-{7-[(ethylsulfonyl)methyl]-1H-indol-3-yl}propan-1-ol

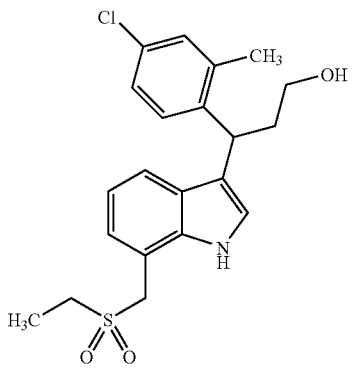

106 mg (0.43 mmol) of 70% pure meta-chloroperbenzoic acid were added to 80.0 mg (0.21 mmol) of the compound from Example 10 in 12 ml of dichloromethane, and the mixture was stirred at RT overnight. It was concentrated, and the residue was purified by preparative HPLC (RP18 column; mobile phase: acetonitrile/water gradient with addition of 0.1% formic acid) to result in 45 mg (51% of theory) of the title compound.

¹H-NMR (400 MHz, DMSO-d₆): δ=11.0 (s, 1H), 7.26-7.30 (m, 2H), 7.22 (d, 1H), 7.19 (d, 1H), 7.12 (dd, 1H), 7.08 (d, 1H), 6.92 (t, 1H), 4.66-4.76 (m, 2H), 4.49-4.56 (m, 2H), 3.32-3.46 (m, 2H), 3.02 (q, 2H), 2.42 (s, 3H), 2.21-2.32 (m, 1H), 1.96-2.07 (m, 1H), 1.19 (t, 3H).

LC-MS (Method 3): $R_t$=1.87 min; MS (ESIpos): m/z=406 [M+H]⁺.

Example 146

3-(2,2-Difluoro-1,3-benzodioxol-5-yl)-3-{7-[(methylsulfonyl)methyl]-1H-indol-3-yl}propan-1-ol

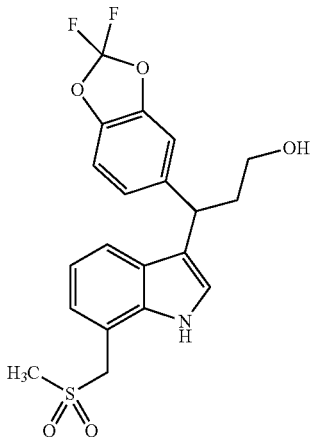

140 mg (0.36 mmol) of the compound from Example 137 were introduced into 24 ml of dichloromethane at 0° C., 176 mg (0.72 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 43 mg (28% of theory) of the title compound.

¹H-NMR (400 MHz, DMSO-d₆): δ=2.07-2.18 (m, 1H), 2.24-2.35 (m, 1H), 2.87 (s, 3H), 3.27-3.42 (m, 2H), 4.38 (t, 1H), 4.49 (t, 1H), 4.71 (s, 2H), 6.94 (t, 1H), 7.10 (d, 1H), 7.18 (d, 1H), 7.26 (d, 1H), 7.34-7.46 (m, 3H), 11.0 (s, 1H).

HPLC (Method 1): $R_t$=4.19 min; DCI-MS (ESIpos): m/z=424 [M+H]⁺.

Example 147

3-(4-Chlorophenyl)-3-{7-[(methylsulfonyl)methyl]-1H-indol-3-yl}pentan-1-ol

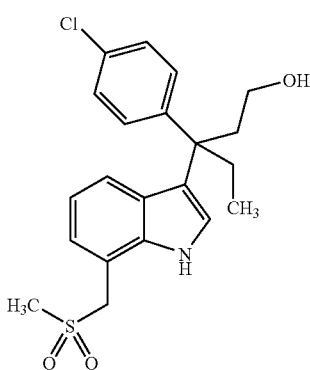

2.12 g (5.67 mmol) of the compound from Example 140 were introduced into 150 ml of dichloromethane at 0° C., 2.80 g (11.34 mmol) of 70% pure meta-chloroperbenzoic acid were added, and the mixture was stirred at RT for 2 h. 15 ml of methanol were added, and the solution was concentrated. The crude product was purified by preparative HPLC (mobile phase: acetonitrile/water gradient) to result in 1.76 g (77% of theory) of the title compound.

¹H-NMR (400 MHz, DMSO-d₆): δ=0.61 (t, 3H), 1.99-2.11 (m, 1H), 2.13-2.27 (m, 2H), 2.29-2.39 (m, 1H), 2.89 (s, 3H), 2.99-3.09 (m, 1H), 3.11-3.22 (m, 1H), 4.28 (t, 1H), 4.72 (s, 2H), 6.69-6.77 (m, 2H), 7.02 (dd, 1H), 7.24 (d, 2H), 7.29 (d, 2H), 7.42 (d, 1H), 11.0 (s, 1H).

LC-MS (Method 3): $R_t$=1.86 min; MS (ESIneg): m/z=404 [M−H]⁻.

Example 148

3-(4-Chloro-2-methylphenyl)-3-{5-fluoro-7-[(methylsulfonyl)methyl]-1H-indol-3-yl}propan-1-ol

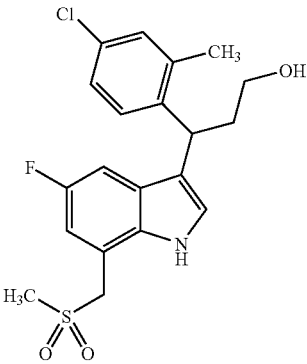

53.5 mg (0.22 mmol) of 70% pure meta-chloroperbenzoic acid were added to 40.0 mg (0.11 mmol) of the compound from Example 132 in 3 ml of dichloromethane at 0° C., and the mixture was stirred at RT overnight. 2 ml of methanol were added, and the residue after concentration was purified by preparative HPLC (RP18 column; mobile phase: acetonitrile/water gradient with addition of 0.1% formic acid) to result in 24.0 mg (55% of theory) of the title compound.

¹H-NMR (400 MHz, DMSO-d₆): δ=11.2 (s, 1H), 7.33-7.35 (m, 1H), 7.19-7.24 (m, 2H), 7.14 (dd, 1H), 6.95-7.03 (m, 2H), 4.70-4.80 (m, 2H), 4.48 (t, 1H), 3.30-3.44 (m, 3H), 2.91 (s, 3H), 2.39 (s, 3H), 2.17-2.30 (m, 1H), 1.96-2.07 (m, 1H).

LC-MS (Method 6): $R_t$=2.15 min; MS (ESIpos): m/z=410 [M+H]⁺.

Example 149

4-(4-Chloro-2-methylphenyl)-4-{5-fluoro-7-[(methylsulfanyl)methyl]-1H-indol-3-yl}butanonitrile

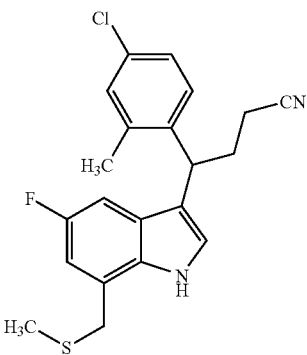

174 mg (2.67 mmol) of potassium cyanide and 8.1 mg (0.07 mmol) of 4-N,N-dimethylaminopyridine were added to 608 mg (1.33 mmol) of the compound from Example 107A in 30 ml of DMSO. The mixture was stirred at 120° C. for 2 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 154 mg (30% of theory) of the title compound.

$^1$H-NMR (400 MHz, DMSO-$d_6$): δ=11.2 (s, 1H), 7.34-7.36 (m, 1H), 7.24-7.30 (m, 2H), 7.18 (dd, 1H), 6.95 (dd, 1H), 6.84 (dd, 1H), 4.38 (t, 1H), 3.87-3.97 (m, 2H), 2.37-2.48 (m, 3H), 2.40 (s, 3H), 2.13-2.26 (m, 1H), 1.96 (s, 3H).

LC-MS (Method 3): $R_t$=2.47 min; MS (ESIpos): m/z=387 [M+H]$^+$.

Example 150

4-[2-Chloro-4-(trifluoromethyl)phenyl]-4-{7-[(methylsulfanyl)methyl]-1H-indol-3-yl}butanonitrile

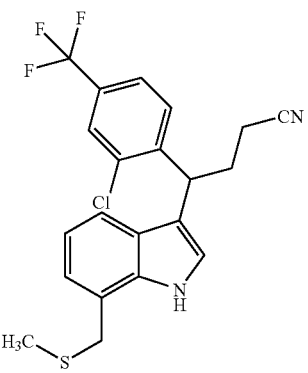

176 mg (2.70 mmol) of potassium cyanide and 8.2 mg (0.07 mmol) of 4-N,N-dimethylaminopyridine were added to 664 mg (1.35 mmol) of the compound from Example 108A in 29 ml of DMSO. The mixture was stirred at 120° C. for 1 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 460 mg (81% of theory) of the title compound.

$^1$H-NMR (400 MHz, DMSO-$d_6$): δ=11.2 (s, 1H), 7.86 (s, 1H), 7.58-7.65 (m, 2H), 7.47 (d, 1H), 7.27 (d, 1H), 6.96 (d, 1H), 6.89 (t, 1H), 4.85 (t, 1H), 3.89-3.97 (m, 2H), 2.43-2.62 (m, 3H), 2.24-2.38 (m, 1H), 1.95 (s, 3H).

LC-MS (Method 9): $R_t$=1.33 min; MS (ESIpos): m/z=423 [M+H]$^+$.

Example 151

4-(4-Methylphenyl)-4-{7-[(methylsulfanyl)methyl]-1H-indol-3-yl}butanonitrile

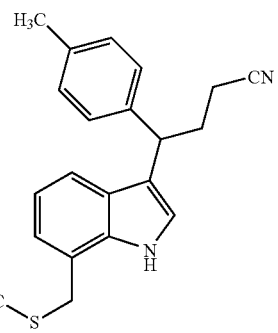

671 mg (10.3 mmol) of potassium cyanide and 31.5 mg (0.26 mmol) of 4-N,N-dimethylaminopyridine were added to 2.08 g (5.15 mmol) of the compound from Example 109A in 112 ml of DMSO. The mixture was stirred at 120° C. for 1 h and then concentrated, and the residue was taken up in ethyl acetate, washed with saturated aqueous sodium bicarbonate solution, water and saturated aqueous sodium chloride solution, dried over magnesium sulfate, filtered and concentrated. The crude product was purified by preparative HPLC (RP18 column; mobile phase: acetonitrile/water gradient with addition of 0.1% formic acid) to result in 1.92 g (99% of theory) of the title compound.

LC-MS (Method 3): $R_t$=2.34 min; MS (ESIpos): m/z=335 [M+H]$^+$.

Example 152

4-(4-Chloro-3-fluorophenyl)-4-{7-[(methylsulfanyl)methyl]-1H-indol-3-yl}butanonitrile

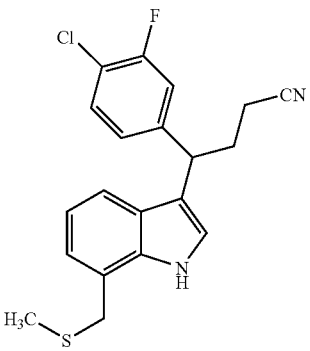

0.38 g (5.90 mmol) of potassium cyanide was added to 1.30 g (2.95 mmol) of the compound from Example 110A in 27 ml of DMSO. The mixture was stirred at 80° C. for 3 h, ethyl acetate was added to the reaction solution, and the mixture was washed twice with water and once with saturated aqueous sodium chloride solution. The combined organic phases were freed of solvent, and the crude product was purified by preparative HPLC (mobile phase: acetonitrile/water gradient). 0.95 g (86% of theory) of the target compound was obtained.

¹H-NMR (400 MHz, DMSO-d₆): δ=1.94 (s, 3H), 2.28-2.51 (m, 4H), 3.92 (s, 2H), 4.24-4.30 (m, 1H), 6.87 (t, 1H), 6.94 (d, 1H), 7.24 (dd, 1H), 7.34 (d, 1H), 7.42 (dt, 2H), 7.47 (t, 1H), 11.1 (s, 1H).

HPLC (Method 1): R_t=4.91 min; DCI-MS (ESIpos): m/z=373 [M+H]⁺.

Example 153

4-(4-Chloro-2,6-difluorophenyl)-4-{7-[(methylsulfanyl)methyl]-1H-indol-3-yl}butanonitrile

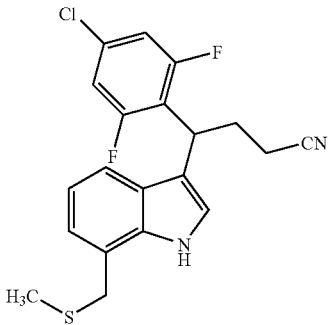

0.30 g (4.57 mmol) of potassium cyanide was added to 1.05 g (2.28 mmol) of the compound from Example 111A in 21 ml of DMSO. The mixture was stirred at 80° C. for 3 h, ethyl acetate was added to the reaction solution, and the mixture was washed twice with water and once with saturated aqueous sodium chloride solution. The combined organic phases were freed of solvent, and the crude product was purified by preparative HPLC (mobile phase: acetonitrile/water gradient). 0.74 g (83% of theory) of the target compound was obtained.

¹H-NMR (400 MHz, DMSO-d₆): δ=1.94 (s, 3H), 2.40-2.63 (m, 4H), 3.92 (s, 2H), 4.59-4.66 (m, 1H), 6.91 (t, 1H), 6.95 (d, 1H), 7.26 (d, 1H), 7.28-7.37 (m, 3H), 11.1 (s, 1H).

HPLC (Method 2): R_t=4.78 min; DCI-MS (ESIpos): m/z=391 [M+H]⁺.

Example 154

4-(2,2-Difluoro-1,3-benzodioxol-5-yl)-4-{7-[(methylsulfanyl)methyl]-1H-indol-3-yl}butanonitrile

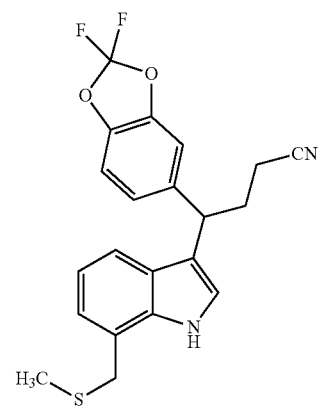

0.37 g (5.76 mmol) of potassium cyanide was added to 1.35 g (2.88 mmol) of the compound from Example 112A in 26 ml of DMSO. The mixture was stirred at 80° C. for 3 h, ethyl acetate was added to the reaction solution, and the mixture was washed twice with water and once with saturated aqueous sodium chloride solution. The combined organic phases were freed of solvent, and the crude product was purified by preparative HPLC (mobile phase: acetonitrile/water gradient). 0.90 g (78% of theory) of the target compound was obtained.

¹H-NMR (400 MHz, DMSO-d₆): δ=1.94 (s, 3H), 2.29-2.51 (m, 4H), 3.92 (s, 2H), 4.24-4.31 (m, 1H), 6.87 (t, 1H), 6.94 (d, 1H), 7.22 (dd, 1H), 7.29 (d, 1H), 7.35 (d, 1H), 7.42 (s, 2H), 11.1 (s, 1H).

HPLC (Method 1): R_t=4.89 min; DCI-MS (ESIpos): m/z=401 [M+H]⁺.

Example 155

4-{7-[(Methylsulfanyl)methyl]-1H-indol-3-yl}-4-[4-(trifluoromethyl)phenyl]pentanonitrile

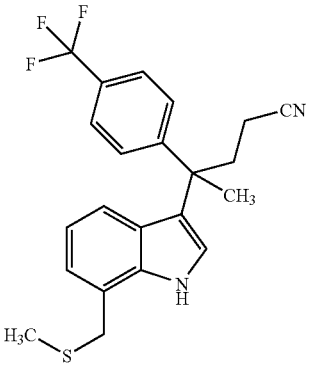

33 mg (0.50 mmol) of potassium cyanide were added to 118 mg (0.25 mmol) of the compound from Example 113A in 1.5 ml of DMSO. The mixture was stirred at 80° C. for 4 h, water and dichloromethane were added to the reaction solution, and the phases were separated. The organic phase was extracted with dichloromethane, and the combined organic phases were freed of solvent. The crude product was purified by preparative HPLC (mobile phase: acetonitrile/water gradient). 62 mg (62% of theory) of the target compound were obtained.

¹H-NMR (400 MHz, DMSO-d₆): δ=1.68 (s, 3H), 1.97 (s, 3H), 2.07-2.18 (m, 1H), 2.20-2.31 (m, 1H), 2.47-2.64 (m, 2H), 3.94 (q, 2H), 6.72 (d, 2H), 6.90 (t, 1H), 7.40 (d, 1H), 7.49 (d, 2H), 7.62 (d, 2H), 11.1 (s, 1H).

LC-MS (Method 9): R_t=1.29 min; MS (ESIneg): m/z=401 [M−H]⁻.

Example 156

4-(4-Chlorophenyl)-4-{7-[(methylsulfanyl)methyl]-1H-indol-3-yl}pentanonitrile

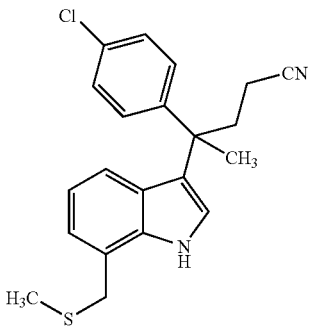

128 mg (1.96 mmol) of potassium cyanide were added to 430 mg (0.98 mmol) of the compound from Example 114A in 8 ml of DMSO. The mixture was stirred at 80° C. for 8 h, water and dichloromethane were added to the reaction solution, and the phases were separated. The organic phase was extracted with dichloromethane, and the combined organic phases were freed of solvent. The crude product was purified by preparative HPLC (mobile phase: acetonitrile/water gradient). 280 mg (77% of theory) of the target compound were obtained.

$^1$H-NMR (400 MHz, DMSO-$d_6$): δ=1.64 (s, 3H), 1.97 (s, 3H), 2.07-2.29 (m, 2H), 2.43-2.59 (m, 2H), 3.93 (q, 2H), 6.69-6.75 (m, 2H), 6.89 (dd, 1H), 7.25-7.36 (m, 5H), 11.1 (s, 1H).

LC-MS (Method 3): $R_t$=2.46 min; MS (ESIneg): m/z=367 [M−H]$^−$.

Example 157

4-(4-Chlorophenyl)-4-{7-[(methylsulfanyl)methyl]-1H-indol-3-yl}hexanonitrile

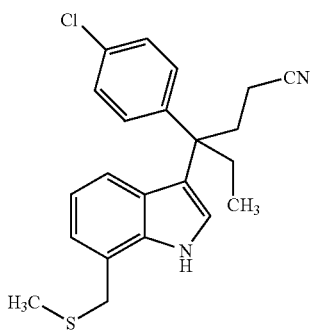

223 mg (3.43 mmol) of potassium cyanide were added to 775 mg (1.71 mmol) of the compound from Example 115A in 12 ml of DMSO. The mixture was stirred at 80° C. for 12 h, water and dichloromethane were added to the reaction solution, and the phases were separated. The organic phase was extracted with dichloromethane, and the combined organic phases were freed of solvent. The crude product was purified by preparative HPLC (mobile phase: acetonitrile/water gradient). 551 mg (84% of theory) of the target compound were obtained.

$^1$H-NMR (400 MHz, DMSO-$d_6$): δ=0.59 (t, 3H), 1.97 (s, 3H), 1.96-2.23 (m, 2H), 2.43-2.53 (m, 2H), 3.93 (s, 2H), 6.60 (d, 1H), 6.67 (t, 1H), 6.87 (d, 1H), 7.24-7.33 (m, 4H), 7.40 (d, 1H), 11.1 (s, 1H).

LC-MS (Method 4): $R_t$=1.51 min; MS (ESIneg): m/z=381 [M−H]$^−$.

Example 158

4-(4-Chlorophenyl)-4-cyclopropyl-4-{7-[(methylsulfanyl)methyl]-1H-indol-3-yl}butanonitrile

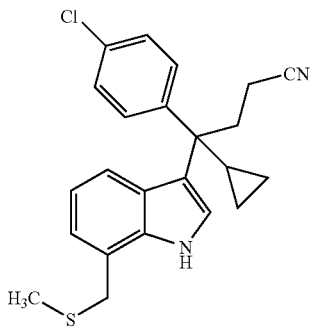

16 mg (0.25 mmol) of potassium cyanide were added to 57 mg (0.12 mmol) of the compound from Example 116A in 1 ml of DMSO. The mixture was stirred at 80° C. for 16 h, water was added to the reaction solution, and the crude product was purified directly by preparative HPLC (mobile phase: acetonitrile/water gradient). 29 mg (60% of theory) of the target compound were obtained.

$^1$H-NMR (400 MHz, DMSO-$d_6$): δ=−0.20−−0.12 (m, 2H), 0.38-0.51 (m, 2H), 1.62-1.71 (m, 1H), 1.97 (s, 3H), 2.12-2.34 (m, 2H), 2.49-2.64 (m, 2H), 3.93 (s, 2H), 6.40 (d, 1H), 6.65 (t, 2H), 6.86 (d, 1H), 7.25 (d, 2H), 7.31 (d, 2H), 7.47 (d, 1H), 11.1 (s, 1H).

LC-MS (Method 4): $R_t$=1.55 min; MS (ESIneg): m/z=393 [M−H]$^−$.

Example 159

4-(2,3-Dihydro-1,4-benzodioxin-6-yl)-4-{7-[(methylsulfanyl)methyl]-1H-indol-3-yl}pentanonitrile

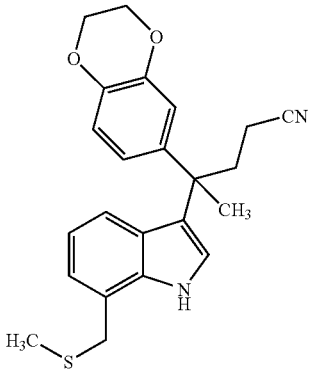

150 mg (2.30 mmol) of potassium cyanide were added to 530 mg (1.15 mmol) of the compound from Example 117A in 10 ml of DMSO. The mixture was stirred at 80° C. for 16 h, ethyl acetate was added to the reaction solution, and the mixture was washed twice with water and once with saturated aqueous sodium chloride solution. The combined organic phases were freed of solvent, and the crude product was purified by preparative HPLC (mobile phase: acetonitrile/water gradient). 328 mg (73% of theory) of the target compound were obtained.

$^1$H-NMR (400 MHz, DMSO-$d_6$): δ=1.59 (s, 3H), 1.97 (s, 3H), 2.05-2.25 (m, 2H), 2.36-2.52 (m, 2H), 3.93 (q, 2H), 4.17 (s, 4H), 6.66-6.75 (m, 4H), 6.82 (d, 1H), 6.89 (d, 1H), 7.29 (d, 1H), 11.0 (s, 1H).

HPLC (Method 2): $R_t$=4.55 min; DCI-MS (ESIpos): m/z=393 [M+H]$^+$.

Example 160

4-(4-Chloro-3-fluorophenyl)-4-{7-[(methylsulfinyl)methyl]-1H-indol-3-yl}butanonitrile

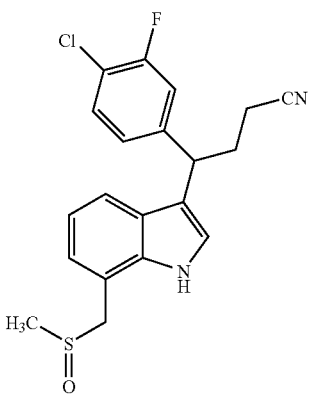

300 mg (0.81 mmol) of the compound from Example 152 were introduced into 55 ml of dichloromethane at 0° C., 198 mg (0.81 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 266 mg (85% of theory) of the title compound as mixture of diastereomers.

$^1$H-NMR (400 MHz, DMSO-$d_6$): δ=2.29-2.56 (m, 7H), 4.18-4.39 (m, 3H), 6.93 (t, 1H), 7.01 (d, 1H), 7.24 (d, 1H), 7.38-7.52 (m, 4H), 11.2 (s, 1H).

HPLC (Method 1): $R_t$=4.31 min; DCI-MS (ESIpos): m/z=389 [M+H]$^+$.

Example 161

4-(4-Chloro-2,6-difluorophenyl)-4-{7-[(methylsulfinyl)methyl]-1H-indol-3-yl}butanonitrile

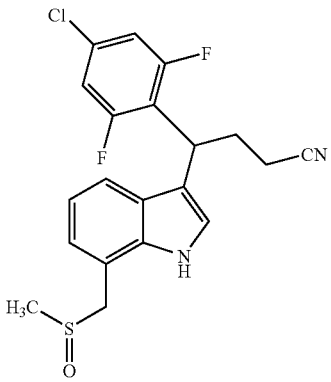

231 mg (0.59 mmol) of the compound from Example 153 were introduced into 40 ml of dichloromethane at 0° C., 198 mg (0.81 mmol) of 70% pure meta-chloroperbenzoic acid were added, and the mixture was stirred at 0° C. for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 171 mg (71% of theory) of the title compound as mixture of diastereomers.

$^1$H-NMR (400 MHz, DMSO-$d_6$): δ=2.40-2.64 (m, 7H), 4.22 (d, 1H), 4.35 (d, 1H), 4.60-4.67 (m, 1H), 6.97 (t, 1H), 7.02 (d, 1H), 7.32 (d, 3H), 7.43 (s, 1H), 11.2 (s, 1H).

HPLC (Method 1): $R_t$=4.25 min; DCI-MS (ESIpos): m/z=407 [M+H]$^+$.

Example 162

4-(2,2-Difluoro-1,3-benzodioxol-5-yl)-4-{7-[methylsulfinyl)methyl]-1H-indol-3-yl}butanonitrile

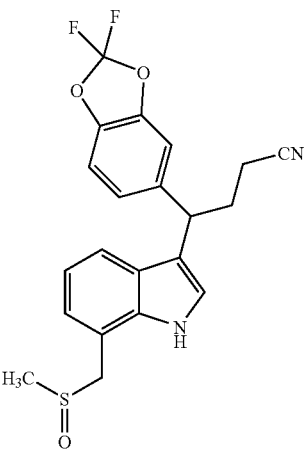

272 mg (0.68 mmol) of the compound from Example 154 were introduced into 46 ml of dichloromethane at 0° C., 167 mg (0.68 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 236 mg (81% of theory) of the title compound as mixture of diastereomers.

$^1$H-NMR (400 MHz, DMSO-$d_6$): δ=2.27-2.57 (m, 7H), 4.18-4.38 (m, 3H), 6.93 (t, 1H), 7.01 (d, 1H), 7.22 (d, 1H), 7.29 (d, 1H), 7.38-7.50 (m, 3H), 11.2 (s, 1H).

HPLC (Method 2): $R_t$=4.44 min; DCI-MS (ESIpos): m/z=417 [M+H]$^+$.

Example 163

4-(4-Chlorophenyl)-4-{7-[(methylsulfinyl)methyl]-1H-indol-3-yl}hexanonitrile

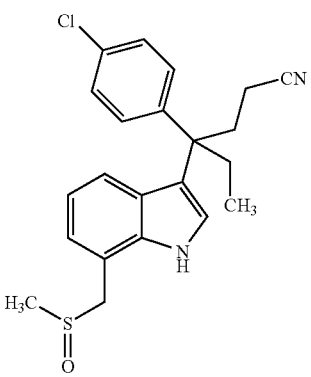

120 mg (0.31 mmol) of the compound from Example 157 were introduced into 12 ml of dichloromethane at 0° C., 77 mg (0.31 mmol) of 70% pure meta-chloroperbenzoic acid were added, and the mixture was stirred at RT for 2 h. 2 ml of methanol were added and the solution was concentrated. The crude product was purified by preparative HPLC (mobile phase: acetonitrile/water gradient) to result in 120 mg (96% of theory) of the title compound as mixture of diastereomers.

$^1$H-NMR (400 MHz, DMSO-d$_6$): δ=0.59 (t, 3H), 1.96-2.24 (m, 4H), 2.41-2.58 (m, 5H), 4.16-4.25 (m, 1H), 4.36 (d, 1H), 6.66 (d, 1H), 6.72 (t, 1H), 6.94 (d, 1H), 7.26 (d, 2H), 7.31 (d, 2H), 7.48 (d, 1H), 11.2 (s, 1H).

LC-MS (Method 4): R$_t$=1.24 min; MS (ESIneg): m/z=397 [M−H]$^-$.

Example 164

4-(4-Chloro-2-methylphenyl)-4-{5-fluoro-7-[(methylsulfonyl)methyl]-1H-indol-3-yl}butanonitrile

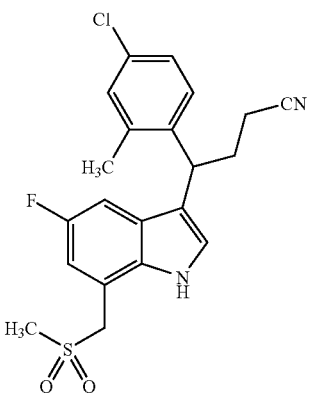

87.5 mg (0.36 mmol) of 70% pure meta-chloroperbenzoic acid were added to 67.0 mg (0.17 mmol) of the compound from Example 149 in 5 ml of dichloromethane at 0° C., and the mixture was stirred at RT overnight. Methanol was added, and the residue after concentration was purified by preparative HPLC (RP18 column; mobile phase: acetonitrile/water gradient with addition of 0.1% formic acid) to result in 36.6 mg (51% of theory) of the title compound.

$^1$H-NMR (400 MHz, DMSO-d$_6$): δ=11.3 (s, 1H), 7.43 (d, 1H), 7.29 (d, 1H), 7.26 (d, 1H), 7.19 (dd, 1H), 7.10 (dd, 1H), 7.00 (dd, 1H), 4.70-4.80 (m, 2H), 4.39 (t, 1H), 2.91 (s, 3H), 2.36-2.48 (m, 3H), 2.39 (s, 3H), 2.15-2.28 (m, 1H).

LC-MS (Method 5): R$_t$=2.43 min; MS (ESIpos): m/z=419 [M+H]$^+$.

Example 165

4-[2-Chloro-4-(trifluoromethyl)phenyl]-4-{7-[(methylsulfonyl)methyl]-1H-indol-3-yl}butanonitrile

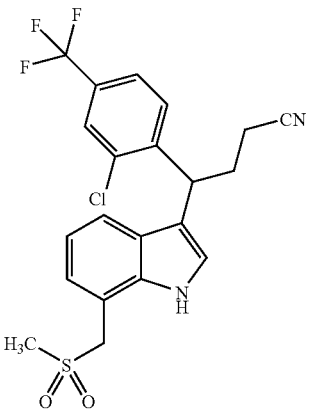

406 mg (1.65 mmol) of 70% pure meta-chloroperbenzoic acid were added to 348 mg (0.82 mmol) of the compound from Example 150 in 6 ml of dichloromethane at 0° C., and the mixture was stirred at RT overnight. It was diluted with dichloromethane, washed with saturated aqueous sodium bicarbonate solution and concentrated, and the residue was purified by preparative HPLC (RP18 column; mobile phase: acetonitrile/water gradient with addition of 0.1% formic acid) to result in 200 mg (53% of theory) of the title compound.

$^1$H-NMR (400 MHz, DMSO-d$_6$): δ=11.2 (s, 1H), 7.87 (s, 1H), 7.59-7.66 (m, 2H), 7.55 (d, 1H), 7.39 (d, 1H), 7.14 (d, 1H), 6.99 (t, 1H), 4.84 (t, 1H), 4.69-4.78 (m, 2H), 2.89 (s, 3H), 2.44-2.60 (m, 3H), 2.26-2.38 (m, 1H).

LC-MS (Method 4): R$_t$=1.33 min; MS (ESIpos): m/z=455 [M+H]$^+$.

Example 166

4-(4-Methylphenyl)-4-{7-[(methylsulfonyl)methyl]-1H-indol-3-yl}butanonitrile

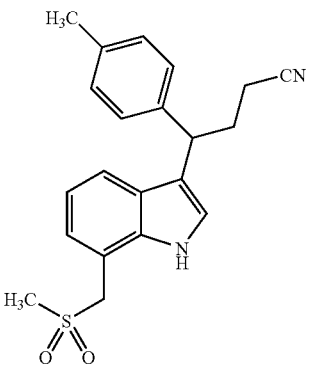

251 mg (1.02 mmol) of 70% pure meta-chloroperbenzoic acid were added to 200 mg (0.60 mmol) of the compound from Example 151 in 10 ml of dichloromethane, and the mixture was stirred at RT overnight. 2 ml of methanol were added, and the residue after concentration was taken up in dichloromethane, washed with saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 48.0 mg (22% of theory) of the title compound.

$^1$H-NMR (400 MHz, DMSO-$d_6$): δ=11.1 (s, 1H), 7.42 (d, 1H), 7.39 (d, 1H), 7.20-7.25 (m, 2H), 7.06-7.11 (m, 3H), 6.94 (t, 1H), 4.71 (s, 2H), 4.18 (t, 1H), 2.86 (s, 3H), 2.35-2.48 (m, 3H), 2.23-2.32 (m, 1H), 2.23 (s, 3H).

LC-MS (Method 4): $R_t$=1.21 min; MS (ESIpos): m/z=367 [M+H]$^+$.

Example 167

4-(4-Chloro-3-fluorophenyl)-4-{7-[(methylsulfonyl)methyl]-1H-indol-3-yl}butanonitrile

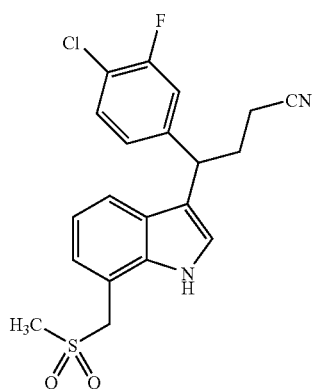

300 mg (0.81 mmol) of the compound from Example 152 were introduced into 55 ml of dichloromethane at 0° C., 198 mg (0.81 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 266 mg (85% of theory) of the title compound.

$^1$H-NMR (400 MHz, DMSO-$d_6$): δ=2.29-2.49 (m, 4H), 2.88 (s, 3H), 4.26-4.32 (m, 1H), 4.72 (s, 2H), 6.97 (t, 1H), 7.12 (d, 1H), 7.24 (dd, 1H), 7.41-7.52 (m, 4H), 11.2 (s, 1H).

HPLC (Method 1): $R_t$=4.42 min; MS (ESIpos): m/z=405 [M+H]$^+$.

Example 168

4-(4-Chloro-2,6-difluorophenyl)-4-{7-[(methylsulfonyl)methyl]-1H-indol-3-yl}butanonitrile

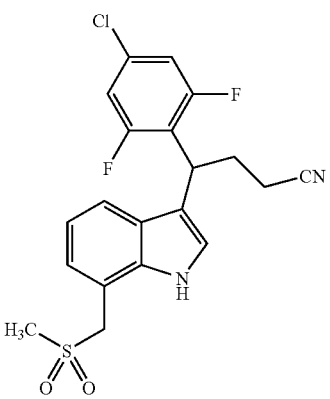

461 mg (1.18 mmol) of the compound from Example 153 were introduced into 80 ml of dichloromethane at 0° C., 581 mg (2.36 mmol) of 70% pure meta-chloroperbenzoic acid were added, and the mixture was stirred at 0° C. for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 342 mg (68% of theory) of the title compound.

$^1$H-NMR (400 MHz, DMSO-$d_6$): δ=2.40-2.64 (m, 4H), 2.88 (s, 3H), 4.61-4.67 (m, 1H), 4.73 (s, 2H), 7.01 (t, 1H), 7.13 (d, 1H), 7.29-7.39 (m, 3H), 7.45 (s, 1H), 11.2 (s, 1H).

HPLC (Method 1): $R_t$=4.33 min; DCI-MS (ESIpos): m/z=440 [M+NH$_4$]$^+$.

Example 169

4-(2,2-Difluoro-1,3-benzodioxol-5-yl)-4-{7-[(methylsulfonyl)methyl]-1H-indol-3-yl}butanonitrile

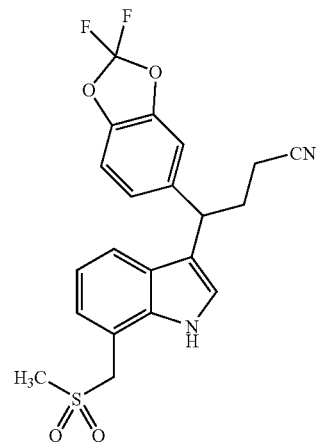

544 mg (1.36 mmol) of the compound from Example 154 were introduced into 93 ml of dichloromethane at 0° C., 670 mg (2.72 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 352 mg (60% of theory) of the title compound.

$^1$H-NMR (400 MHz, DMSO-$d_6$): δ=2.29-2.49 (m, 3H), 2.88 (s, 3H), 4.26-4.32 (m, 1H), 4.72 (s, 2H), 6.97 (t, 1H), 7.12 (d, 1H), 7.23 (dd, 1H), 7.29 (d, 1H), 7.43 (d, 1H), 7.45-7.51 (m, 2H), 11.1 (s, 1H).

HPLC (Method 2): $R_t$=4.34 min; DCI-MS (ESIpos): m/z=450 [M+NH$_4$]$^+$.

The enantiomers were separated by preparative HPLC on a chiral phase [column: Daicel Chiralpak AD-H, 5 μm, 250 mm×20 mm; eluent: isohexane/isopropanol 1:1; flow rate: 20 ml/min; temperature: 24° C.; UV detection: 230 nm]. The separated enantiomers were purified again by preparative HPLC on achiral phase (mobile phase: acetonitrile/water gradient):
Enantiomer 169-1:
  $R_t$=5.86 min [column: Daicel Chiralpak AD-H, 5 μm, 250 mm×4 mm; eluent: isohexane/isopropanol 1:1; flow rate: 1 ml/min; temperature: 24° C.; UV detection: 230 nm];
Enantiomer 169-2:
  $R_t$=6.85 min [column: Daicel Chiralpak AD-H, 5 μm, 250 mm×4 mm; eluent: isohexane/isopropanol 1:1; flow rate: 1 ml/min; temperature: 24° C.; UV detection: 230 nm].

Example 170

4-{7-[(Methylsulfonyl)methyl]-1H-indol-3-yl}-4-[4-(trifluoromethyl)phenyl]pentanonitrile

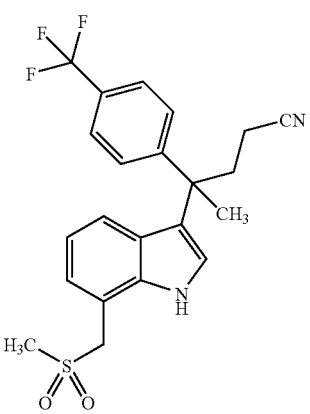

45 mg (0.11 mmol) of the compound from Example 155 were introduced into 5 ml of dichloromethane at 0° C., 55 mg (0.22 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 43 mg (89% of theory) of the title compound.

$^1$H-NMR (400 MHz, DMSO-$d_6$): δ=1.68 (s, 3H), 2.08-2.35 (m, 2H), 2.46-2.63 (m, 2H), 2.90 (s, 3H), 4.73 (s, 2H), 6.78-6.84 (m, 2H), 7.07 (dd, 1H), 7.46-7.52 (m, 3H), 7.63 (d, 2H), 11.2 (s, 1H).

LC-MS (Method 4): $R_t$=1.28 min; MS (ESIpos): m/z=435 [M+H]$^+$.

Example 171

4-(4-Chlorophenyl)-4-{7-[(methylsulfonyl)methyl]-1H-indol-3-yl}-pentanonitrile

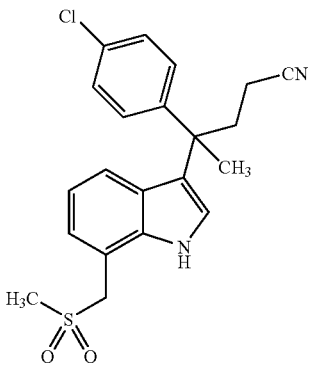

180 mg (0.49 mmol) of the compound from Example 156 were introduced into 20 ml of dichloromethane at 0° C., 241 mg (0.98 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 185 mg (95% of theory) of the title compound.

$^1$H-NMR (400 MHz, DMSO-$d_6$): δ=1.64 (s, 3H), 2.06-2.29 (m, 2H), 2.43-2.60 (m, 2H), 2.89 (s, 3H), 4.73 (s, 2H), 6.77-6.85 (m, 2H), 7.07 (dd, 1H), 7.24-7.33 (m, 4H), 7.44 (d, 1H), 11.2 (s, 1H).

LC-MS (Method 5): $R_t$=2.40 min; MS (ESIneg): m/z=399 [M−H]$^-$.

The enantiomers were separated by preparative HPLC on a chiral phase [column: chiral silica gel phase based on the selector poly-(N-methacryloyl-L-leucine dicyclopropylmethylamide), 5 μm, 250 mm×20 mm; eluent: isohexane/ethyl acetate 4:6; flow rate: 20 ml/min; temperature: 24° C.; UV detection: 260 nm]. The separated enantiomers were purified again by preparative HPLC on an achiral phase (mobile phase: acetonitrile/water gradient):
Enantiomer 171-1:
  $R_t$=4.06 min [column: chiral silica gel phase based on the selector poly-(N-methacryloyl-L-leucine dicyclopropylmethylamide), 5 μm, 250 mm×4 mm; eluent: isohexane/ethyl acetate 3:7; flow rate: 1.5 ml/min; temperature: 24° C.; UV detection: 260 nm];
  Yield: 54.0 mg
Enantiomer 171-2:
  $R_t$=4.83 min [column: chiral silica gel phase based on the selector poly-(N-methacryloyl-L-leucine dicyclopropylmethylamide), 5 μm, 250 mm×4 mm; eluent: isohexane/ethyl acetate 3:7; flow rate: 1.5 ml/min; temperature: 24° C.; UV detection: 260 nm];
  Yield: 55.0 mg

Example 172

4-(4-Chlorophenyl)-4-{7-[(methylsulfonyl)methyl]-1H-indol-3-yl}hexanonitrile

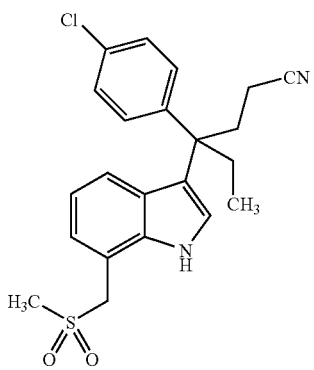

380 mg (0.99 mmol) of the compound from Example 157 were introduced into 40 ml of dichloromethane at 0° C., 489 mg (1.99 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 377 mg (92% of theory) of the title compound.

$^1$H-NMR (400 MHz, DMSO-$d_6$): δ=0.59 (t, 3H), 1.97-2.24 (m, 4H), 2.42-2.56 (m, 2H), 2.88 (s, 3H), 4.72 (q, 2H), 6.70 (d, 1H), 6.76 (t, 1H), 7.04 (d, 1H), 7.26 (d, 2H), 7.32 (d, 2H), 7.50 (d, 1H), 11.2 (s, 1H).

LC-MS (Method 4): $R_t$=1.29 min; MS (ESIneg): m/z=413 [M–H]$^-$.

The enantiomers were separated by preparative HPLC on a chiral phase [column: chiral silica gel phase based on the selector poly-(N-methacryloyl-L-isoleucine 3-pentylamide), 5 µm, 250 mm×20 mm; eluent: isohexane/ethyl acetate 4:6; flow rate: 20 ml/min; temperature: 24° C.; UV detection: 260 nm]. The separated enantiomers were purified again by preparative HPLC on an achiral phase (mobile phase: acetonitrile/water gradient):

Enantiomer 172-1:

$R_t$=3.70 min [column: chiral silica gel phase based on the selector poly-(N-methacryloyl-L-isoleucine 3-pentylamide), 5 µm, 250 mm×4 mm; eluent: isohexane/ethyl acetate 3:7; flow rate: 1.5 ml/min; temperature: 24° C.; UV detection: 260 nm];

Yield: 102 mg

Enantiomer 172-2:

$R_t$=4.86 min [column: chiral silica gel phase based on the selector poly-(N-methacryloyl-L-isoleucine 3-pentylamide), 5 µm, 250 mm×4 mm; eluent: isohexane/ethyl acetate 3:7; flow rate: 1.5 ml/min; temperature: 24° C.; UV detection: 260 nm];

Yield: 95 mg

Example 173

4-(4-Chlorophenyl)-4-cyclopropyl-4-{7-[(methylsulfonyl)methyl]-1H-indol-3-yl}butanonitrile

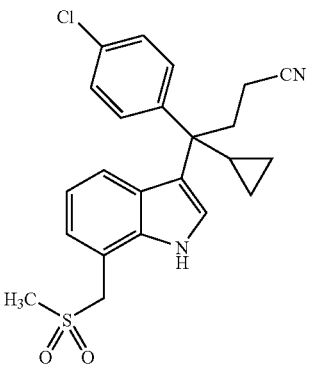

23 mg (0.06 mmol) of the compound from Example 158 were introduced into 4 ml of dichloromethane at 0° C., 29 mg (0.12 mmol) of 70% pure meta-chloroperbenzoic acid were added, and the mixture was stirred at 0° C. for 2 h. 1 ml of methanol was added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 21 mg (82% of theory) of the title compound.

$^1$H-NMR (400 MHz, DMSO-$d_6$): δ=–0.22--–0.12 (m, 2H), 0.38-0.53 (m, 2H), 1.63-1.73 (m, 1H), 2.12-2.34 (m, 2H), 2.49-2.65 (m, 2H), 2.89 (s, 3H), 4.72 (q, 2H), 6.51 (d, 1H), 6.74 (t, 1H), 7.03 (d, 1H), 7.24 (d, 2H), 7.31 (d, 2H), 7.57 (s, 1H), 11.2 (s, 1H).

HPLC (Method 1): $R_t$=4.52 min; DCI-MS (ESIpos): m/z=427 [M+H]$^+$.

Example 174

4-(2,3-Dihydro-1,4-benzodioxin-6-yl)-4-{7-[(methylsulfonyl)methyl]-1H-indol-3-yl}pentanonitrile

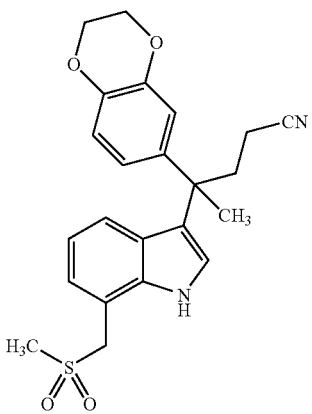

185 mg (0.47 mmol) of the compound from Example 159 were introduced into 32 ml of dichloromethane at 0° C., 232 mg (0.94 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 128 mg (64% of theory) of the title compound.

$^1$H-NMR (400 MHz, DMSO-$d_6$): δ=1.60 (s, 3H), 2.08-2.25 (m, 2H), 2.36-2.53 (m, 2H), 2.89 (s, 3H), 4.17 (s, 4H), 4.72 (s, 2H), 6.65-6.75 (m, 3H), 6.82 (t, 1H), 6.92 (d, 1H), 7.06 (d, 1H), 7.38 (d, 1H), 11.1 (s, 1H).

HPLC (Method 2): $R_t$=4.13 min; MS (ESIpos): m/z=425 [M+H]$^+$.

Example 175

3-(5-Chloro-1-cyclopropyl-2,3-dihydro-1H-inden-1-yl)-7-[(methylsulfanyl)methyl]-1H-indole

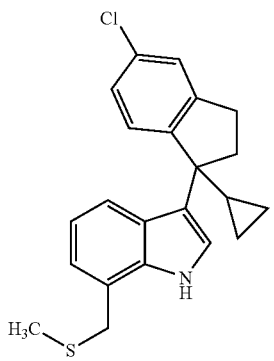

0.03 ml (0.40 mmol) of trifluoroacetic acid was added to 70.0 mg (0.34 mmol) of the compound from Example 118A and 65.4 mg (0.37 mmol) of the compound from Example 8A in 1.6 ml of dichloromethane at 0° C., and the mixture was stirred at 0° C. for 4 h. It was diluted with dichloromethane and added to saturated aqueous ammonium chloride solution, the phases were separated, the aqueous phase was extracted with dichloromethane, and the combined organic phases were dried over magnesium sulfate, filtered and concentrated. The residue was purified by preparative HPLC (RP18 column; mobile phase: acetonitrile/water gradient with addition of 0.1% formic acid) to result in 48.8 mg (40% of theory) of the title compound.

$^1$H-NMR (400 MHz, DMSO-$d_6$): δ=10.9 (s, 1H), 7.35 (d, 1H), 7.29 (d, 1H), 7.07 (dd, 1H), 6.88 (dd, 1H), 6.68-6.74 (m, 3H), 3.87-3.97 (m, 2H), 2.88-3.04 (m, 2H), 2.52-2.60 (m, 1H), 2.08-2.16 (m, 1H), 1.96 (s, 3H), 1.46-1.56 (m, 1H), 0.41-0.53 (m, 2H), 0.00-0.07 (m, 1H), −0.24-−0.17 (m, 1H).

LC-MS (Method 9): $R_t$=1.49 min; MS (ESIneg): m/z=366 [M−H]$^-$.

Example 176

3-(6-Chloro-1-cyclopropyl-2,3-dihydro-1H-inden-1-yl)-7-[(methylsulfanyl)methyl]-1H-indole

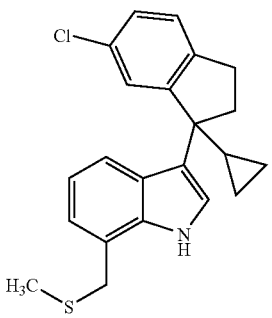

0.03 ml (0.40 mmol) of trifluoroacetic acid was added to 70.0 mg (0.34 mmol) of the compound from Example 119A and 65.4 mg (0.37 mmol) of the compound from Example 8A in 1.6 ml of dichloromethane at 0° C., and the mixture was stirred at 0° C. for 4 h. It was diluted with dichloromethane and added to saturated aqueous ammonium chloride solution, the phases were separated, the aqueous phase was extracted with dichloromethane, and the combined organic phases were dried over magnesium sulfate, filtered and concentrated. The residue was purified by preparative HPLC (RP18 column; mobile phase: acetonitrile/water gradient with addition of 0.1% formic acid) to result in 52.4 mg (42% of theory) of the title compound.

$^1$H-NMR (400 MHz, DMSO-$d_6$): δ=10.9 (s, 1H), 7.32 (d, 1H), 7.28 (d, 1H), 7.22 (dd, 1H), 6.89 (dd, 1H), 6.68-6.76 (m, 3H), 3.87-3.99 (m, 2H), 2.86-3.01 (m, 2H), 2.50-2.59 (m, 1H), 2.05-2.14 (m, 1H), 1.97 (s, 3H), 1.47-1.56 (m, 1H), 0.43-0.56 (m, 2H), 0.03-0.11 (m, 1H), −0.18-−0.11 (m, 1H).

LC-MS (Method 4): $R_t$=1.68 min; MS (ESIneg): m/z=366 [M−H]$^-$.

Example 177

2-(1-{7-[(Methylsulfanyl)methyl]-1H-indol-3-yl}-1-[4-(trifluoromethyl)phenyl]ethyl)cyclopropanecarbonitrile [trans-diastereomer mixture]

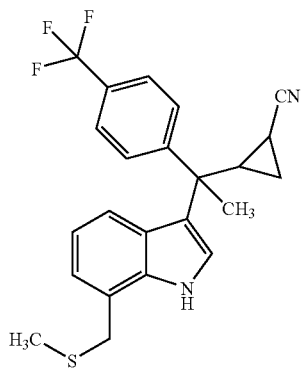

0.02 ml (0.24 mmol) of trifluoroacetic acid and 43.3 mg (0.20 mmol) of indium(III) chloride were added to 50.0 mg (0.20 mmol) of the compound from Example 132A and 69.5 mg (0.39 mmol) of the compound from Example 8A in 2 ml of dichloromethane at RT, and the mixture was heated under reflux overnight. It was concentrated and the residue was purified by preparative HPLC (RP18 column; mobile phase: acetonitrile/water gradient with addition of 0.1% formic acid) to result in 9.0 mg (11% of theory) of the title compound as mixture of diastereomers.

$^1$H-NMR (400 MHz, DMSO-$d_6$): δ=11.1 (s, 1H), 7.62-7.69 (m, 2H), 7.48-7.56 (m, 2H), 7.39-7.44 (m, 1H), 6.85-6.91 (m, 1H), 6.70 (t, 1H), 6.67 (t, 1H), 6.58 (d, 1H), 6.50 (d, 1H), 3.88-4.00 (m, 2H), 2.31-2.44 (m, 0.5H), 1.92-2.00 (m, 3.5H), 1.52-1.62 (m, 3.5H), 1.44-1.52 (m, 0.5H), 1.29-1.39 (m, 1H), 1.00-1.07 (m, 0.5H), 0.85-0.95 (m, 0.5H).

LC-MS (Method 9): $R_t$=1.31 min; MS (ESIneg): m/z=413 [M−H]$^−$.

Example 178

2-[1-(2,4-Difluorophenyl)-1-{7-[(methylsulfanyl)methyl]-1H-indol-3-yl}ethyl]cyclopropane-carbonitrile [trans-diastereomer mixture]

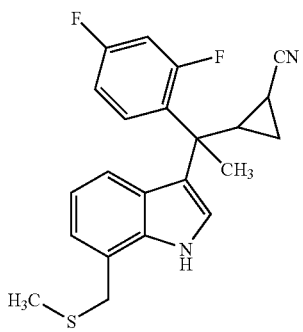

0.08 ml (1.08 mmol) of trifluoroacetic acid and 218 mg (0.99 mmol) of indium(III) chloride were added to 200 mg (0.90 mmol) of the compound from Example 133A and 318 mg (1.79 mmol) of the compound from Example 8A in 8 ml of dichloromethane at RT, and the mixture was heated under reflux overnight. It was concentrated and the residue was purified by preparative HPLC (RP18 column; mobile phase: acetonitrile/water gradient with addition of 0.1% formic acid) to result in 128 mg (37% of theory) of the title compound as mixture of diastereomers.

$^1$H-NMR (400 MHz, DMSO-$d_6$): δ=11.1 (s, 1H), 7.66-7.74 (m, 0.5H), 7.58-7.66 (m, 0.5H), 7.32 (d, 0.5H), 7.27 (d, 0.5H), 7.11-7.19 (m, 1H), 7.01-7.10 (m, 1H), 6.84-6.91 (m, 1H), 6.63-6.73 (m, 1H), 6.54 (d, 0.5H), 6.46 (d, 0.5H), 3.87-3.97 (m, 2H), 2.35-2.45 (m, 1H), 1.97 (s, 1.5H), 1.96 (s, 1.5H), 1.65 (s, 1.5H), 1.60 (s, 1.5H), 1.38-1.50 (m, 1H), 1.30-1.37 (m, 1H), 0.91-0.98 (m, 0.5H), 0.78-0.85 (m, 0.5H).

LC-MS (Method 4): $R_t$=1.42 min; MS (ESIneg): m/z=381 [M−H]$^−$.

Example 179

2-[1-(4-Chlorophenyl)-1-{5-fluoro-7-[(methylsulfanyl)methyl]-1H-indol-3-yl}ethyl]cyclopropanecarbonitrile [trans-diastereomer mixture]

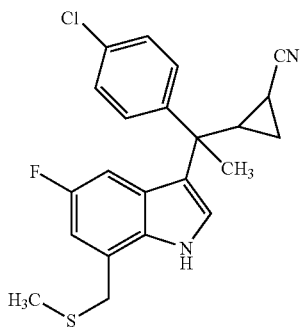

367 mg (1.66 mmol) of indium(III) chloride and 0.12 ml (1.58 mmol) of trifluoroacetic acid were added to 350 mg (1.58 mmol) of the compound from Example 75A and 308 mg (1.58 mmol) of the compound from Example 11A in 9 ml of dichloromethane at RT, and the mixture was heated under reflux for 15 min. It was diluted with dichloromethane, washed with saturated aqueous sodium bicarbonate solution, water and saturated aqueous sodium chloride solution, dried over magnesium sulfate, filtered and concentrated. The residue was purified by preparative HPLC (RP18 column; mobile phase: acetonitrile/water gradient with addition of 0.1% formic acid) to result in 32.5 mg (5% of theory) of the title compound as mixture of diastereomers.

$^1$H-NMR (400 MHz, DMSO-$d_6$): δ=11.2 (s, 1H), 7.44-7.48 (m, 1H), 7.25-7.40 (m, 4H), 6.76-6.83 (m, 1H), 6.26 (dd, 0.2H), 6.17 (dd, 0.8H), 3.87-3.99 (m, 2H), 2.28-2.39 (m, 1H), 1.99 (s, 0.6H), 1.98 (s, 2.4H), 1.50-1.57 (m, 3.8H), 1.27-1.43 (m, 1.2H), 0.95-1.03 (m, 0.2H), 0.78-0.86 (m, 0.8H).

LC-MS (Method 3): $R_t$=2.50 min; MS (ESIneg): m/z=397 [M−H]$^−$.

Example 180

3-[1-(4-Chlorophenyl)-1-(2,2-difluorocyclopropyl)ethyl]-7-[(methylsulfanyl)methyl]-2,3-dihydro-1H-indole

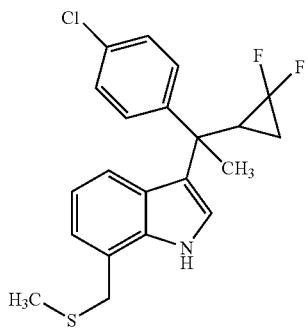

76.2 mg (0.43 mmol) of the compound from Example 8A, dissolved in 1 ml of toluene, were added to 190 mg (0.86 mmol) of indium(III) chloride and 100 mg (0.43 mmol) of the compound from Example 134A in 1 ml of toluene at RT, and the mixture was stirred at 80° C. for 2 h. Then a further 1.90 g (8.60 mmol) of indium(III) chloride were added, and the mixture was stirred at 80° C. for 1 h. It was diluted with toluene and washed with water, and the organic phase was dried over magnesium sulfate, filtered and concentrated. The residue was purified by preparative HPLC (RP18 column; mobile phase: acetonitrile/water gradient with addition of 0.1% formic acid) to result in 16.0 mg (10% of theory) of the title compound as mixture of diastereomers.

$^1$H-NMR (400 MHz, DMSO-d$_6$): δ=11.1 (s, 1H), 7.33-7.38 (m, 3H), 7.26-7.31 (m, 2H), 6.89 (d, 1H), 6.64-6.75 (m, 2H), 3.89-3.97 (m, 2H), 2.39-2.54 (m, 1H), 1.98 (s, 3H), 1.55-1.68 (m, 4H), 1.41-1.53 (m, 1H).

LC-MS (Method 5): R$_t$=3.06 min; MS (ESIneg): m/z=390 [M−H]$^−$.

Example 181

3-(1-Ethyl-5-fluoro-2,3-dihydro-1H-inden-1-yl)-7-[(methylsulfanyl)methyl]-1H-indole

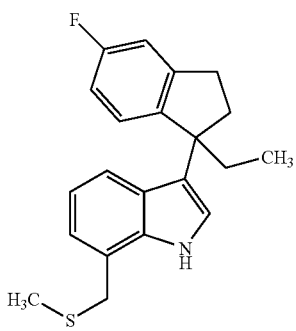

515 mg (2.33 mmol) of indium(III) chloride and 0.17 ml (2.22 mmol) of trifluoroacetic acid were added to 400 mg (2.22 mmol) of the compound from Example 135A and 393 mg (2.22 mmol) of the compound from Example 8A in 12 ml of dichloromethane at 0° C., and the mixture was stirred at RT for 1 h. It was diluted with dichloromethane, washed with water, dried over magnesium sulfate, filtered and concentrated. The residue was purified by preparative HPLC (RP18 column; mobile phase: acetonitrile/water gradient with addition of 0.1% formic acid) to result in 33 mg (4% of theory) of the title compound as mixture of diastereomers.

$^1$H-NMR (400 MHz, DMSO-d$_6$): δ=10.8 (s, 1H), 7.09 (dd, 1H), 6.98-7.06 (m, 3H), 6.87-6.95 (m, 2H), 6.78 (t, 1H), 3.86-3.96 (m, 2H), 2.88-3.03 (m, 2H), 2.46-2.55 (m, 1H), 2.15-2.27 (m, 2H), 1.98-2.10 (m, 1H), 1.95 (s, 3H), 0.78 (t, 3H).

LC-MS (Method 4): R$_t$=1.62 min; MS (ESIneg): m/z=338 [M−H]$^−$.

Example 182

3-{1-Cyclopropyl-1-[2-fluoro-4-(trifluoromethyl)phenyl]ethyl}-7-[(methylsulfanyl)methyl]-1H-indole

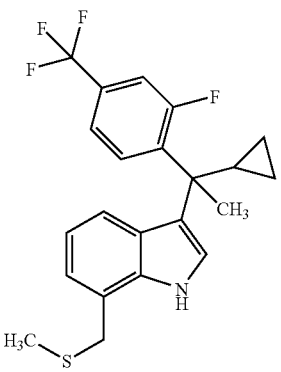

0.02 ml (0.24 mmol) of trifluoroacetic acid was added to 50.0 mg (0.20 mmol) of the compound from Example 136A and 35.7 mg (0.20 mmol) of the compound from Example 8A in 4 ml of dichloromethane, and the mixture was stirred at RT overnight. It was concentrated, and the residue was purified by preparative HPLC (RP18 column; mobile phase: acetonitrile/water gradient with addition of 0.1% formic acid) to result in 10.0 mg (12% of theory) of the title compound as mixture of diastereomers.

$^1$H-NMR (400 MHz, DMSO-d$_6$): δ=11.0 (s, 1H), 8.01 (t, 1H), 7.63 (d, 1H), 7.42 (d, 1H), 7.27-7.30 (m, 1H), 6.84 (d, 1H), 6.64 (t, 1H), 6.53 (d, 1H), 3.87-3.96 (m, 2H), 1.97 (s, 3H), 1.64-1.73 (m, 1H), 1.60 (s, 3H), 0.46-0.50 (m, 2H), 0.16-0.25 (m, 2H).

LC-MS (Method 9): R$_t$=1.44 min; MS (ESIneg): m/z=406 [M−H]$^−$.

Example 183

3-[1-Cyclopropyl-1-(4-methylphenyl)ethyl]-7-[(methylsulfanyl)methyl]-1H-indole

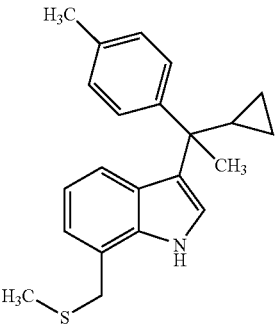

0.23 ml (3.00 mmol) of trifluoroacetic acid was added to 885 mg (4.99 mmol) of the compound from Example 8A and 440 mg (2.50 mmol) of the compound from Example 137A in 44 ml of dichloromethane, and the mixture was stirred at RT overnight. The reaction mixture was concentrated in a rotary evaporator. The residue was purified by preparative HPLC (RP18 column; mobile phase: acetonitrile/water gradient with addition of 0.1% formic acid) to result in 87.4 mg (10% of theory) of the title compound as mixture of diastereomers.

$^1$H-NMR (400 MHz, DMSO-d$_6$): δ=10.9 (s, 1H), 7.33 (d, 1H), 7.12-7.20 (m, 2H), 6.99-7.05 (m, 2H), 6.80-6.86 (m, 1H), 6.60-6.66 (m, 2H), 3.87-3.97 (m, 2H), 2.24 (s, 3H), 1.97 (s, 3H), 1.51-1.60 (m, 1H), 1.49 (s, 3H), 0.43-0.51 (m, 1H), 0.34-0.42 (m, 1H), 0.14-0.21 (m, 1H), 0.02-0.10 (m, 1H).

LC-MS (Method 9): R$_t$=1.44 min; MS (ESIneg): m/z=334 [M−H]⁻.

Example 184

3-[1-(4-Chlorophenyl)-1-cyclopropylethyl]-7-[(methylsulfanyl)methyl]-1H-indole

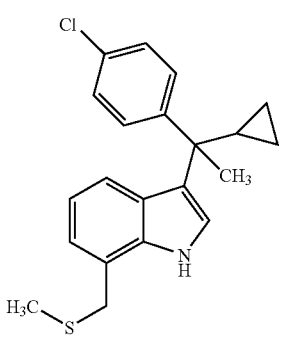

600 mg (3.05 mmol) of the compound from Example 138A and 0.28 ml (3.66 mmol) of trifluoroacetic acid were added to 541 mg (3.05 mmol) of the compound from Example 8A in 4 ml of dichloromethane. The reaction mixture was stirred at RT for 30 min, and the crude product was then purified three times by preparative HPLC (mobile phase: acetonitrile/water gradient) and once by flash chromatography on silica gel (mobile phase: cyclohexane/ethyl acetate 10/1). 441 mg (41% of theory) of the title compound were obtained.

$^1$H-NMR (400 MHz, DMSO-d$_6$): δ=0.05-0.15 (m, 1H), 0.17-0.25 (m, 1H), 0.37-0.54 (m, 2H), 1.49 (s, 3H), 1.52-1.61 (m, 1H), 1.98 (s, 3H), 3.92 (q, 2H), 6.60 (d, 1H), 6.66 (t, 1H), 6.85 (d, 1H), 7.26-7.37 (m, 5H), 10.9 (s, 1H).

HPLC (Method 1): R$_t$=5.35 min; DCI-MS (ESIpos): m/z=356 [M+H]⁺.

Example 185

3-{1-Cyclopropyl-1-[4-(trifluoromethyl)phenyl]ethyl}-7-[(methylsulfanyl)methyl]-1H-indole

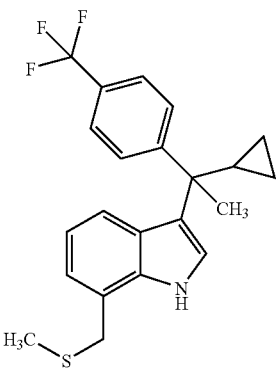

The title compound was prepared starting from 462 mg (2.61 mmol) of the compound from Example 8A and 600 mg (2.61 mmol) of the compound from Example 139A in analogy to the synthesis of the compound from Example 184. 273 mg (27% of theory) of the target compound were obtained.

$^1$H-NMR (400 MHz, DMSO-d$_6$): δ=0.11-0.19 (m, 1H), 0.22-0.30 (m, 1H), 0.41-0.57 (m, 2H), 1.51 (s, 3H), 1.57-1.67 (m, 1H), 1.98 (s, 3H), 3.93 (q, 2H), 6.58 (d, 1H), 6.65 (t, 1H), 6.85 (d, 1H), 7.40 (d, 1H), 7.53 (d, 2H), 7.61 (d, 2H), 11.0 (s, 1H).

HPLC (Method 1): R$_t$=5.35 min; DCI-MS (ESIpos): m/z=390 [M+H]⁺.

Example 186

3-[1-Cyclopropyl-1-(3-fluoro-4-methoxyphenyl)ethyl]-7-[(methylsulfanyl)methyl]-1H-indole

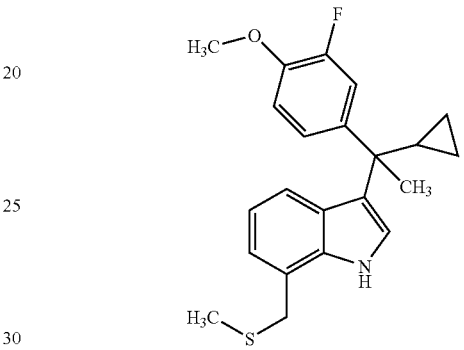

100 mg (0.48 mmol) of the compound from Example 140A and 0.04 ml (0.57 mmol) of trifluoroacetic acid were added to 84 mg (0.48 mmol) of the compound from Example 8A in 2.5 ml of dichloromethane. The reaction mixture was stirred at RT for 30 min, and the crude product was then purified directly by preparative HPLC (mobile phase: acetonitrile/water gradient). 63 mg (361% of theory) of the title compound were obtained.

$^1$H-NMR (400 MHz, DMSO-d$_6$): δ=0.05-0.13 (m, 1H), 0.16-0.24 (m, 1H), 0.36-0.53 (m, 2H), 1.48 (s, 3H), 1.51-1.59 (m, 1H), 1.97 (s, 3H), 3.78 (s, 3H), 3.92 (q, 2H), 6.61-6.70 (m, 2H), 6.85 (dd, 1H), 6.98-7.07 (m, 3H), 7.33 (d, 1H), 10.9 (s, 1H).

LC-MS (Method 5): R$_t$=2.94 min; MS (ESIneg): m/z=368 [M−H]⁻.

Example 187

3-[1-(1-Benzothiophen-5-yl)-1-cyclopropylethyl]-7-[(methylsulfanyl)methyl]-1H-indole

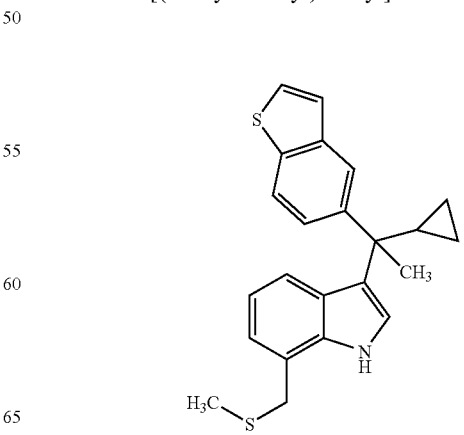

600 mg (2.75 mmol) of the compound from Example 141A and 0.25 ml (3.30 mmol) of trifluoroacetic acid were added to 487 mg (2.75 mmol) of the compound from Example 8A in 4 ml of dichloromethane. The reaction mixture was stirred at RT for 30 min, and the crude product was then purified twice by preparative HPLC (mobile phase: acetonitrile/water gradient) and once by flash chromatography on silica gel (mobile phase: cyclohexane/ethyl acetate 10/1). 404 mg (39% of theory) of the title compound were obtained.

$^1$H-NMR (400 MHz, DMSO-$d_6$): δ=0.08-0.17 (m, 1H), 0.21-0.29 (m, 1H), 0.39-0.56 (m, 2H), 1.57 (s, 3H), 1.61-1.71 (m, 1H), 1.98 (s, 3H), 3.93 (q, 2H), 6.55-6.60 (m, 2H), 6.79-6.85 (m, 1H), 7.24 (dd, 1H), 7.37-7.42 (m, 2H), 7.67 (d, 1H), 7.79 (d, 1H), 7.91 (d, 1H), 11.0 (s, 1H).

LC-MS (Method 3): $R_t$=2.76 min; MS (ESIneg): m/z=376 [M–H]$^-$.

Example 188

3-[1-Cyclopropyl-1-(2,3-dihydro-1,4-benzodioxin-6-yl)ethyl]-7-[(methylsulfanyl)methyl]-1H-indole

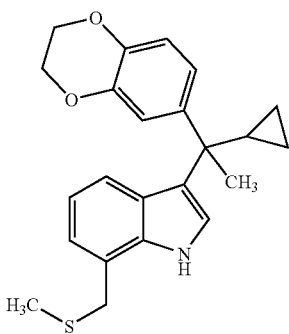

400 mg (1.82 mmol) of the compound from Example 142A and 0.17 ml (2.18 mmol) of trifluoroacetic acid were added to 322 mg (1.82 mmol) of the compound from Example 8A in 3 ml of dichloromethane. The reaction mixture was stirred at RT for 30 min, and the crude product was then purified twice by preparative HPLC (mobile phase: acetonitrile/water gradient) and by recrystallization from acetonitrile. 184 mg (27% of theory) of the title compound were obtained.

$^1$H-NMR (400 MHz, DMSO-$d_6$): δ=0.03-0.12 (m, 1H), 0.16-0.24 (m, 1H), 0.33-0.52 (m, 2H), 1.45 (s, 3H), 1.48-1.57 (m, 1H), 1.98 (s, 3H), 3.92 (q, 2H), 4.17 (s, 4H), 6.64-6.76 (m, 5H), 6.85 (d, 1H), 7.30 (s, 1H), 10.9 (s, 1H).

HPLC (Method 1): $R_t$=4.98 min; MS (EIpos): m/z=379 [M]$^+$.

Example 189

3-[1-(1,3-Benzodioxol-5-yl)-1-cyclopropylethyl]-7-[(methylsulfanyl)methyl]-1H-indole

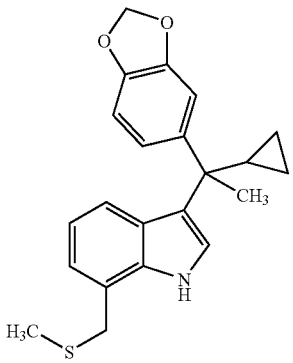

600 mg (2.91 mmol) of the compound from Example 143A and 0.27 ml (3.49 mmol) of trifluoroacetic acid were added to 516 mg (2.91 mmol) of the compound from Example 8A in 4 ml of dichloromethane. The reaction mixture was stirred at RT for 30 min, and the crude product was then purified twice by preparative HPLC (mobile phase: acetonitrile/water gradient). 377 mg (35% of theory) of the title compound were obtained.

$^1$H-NMR (400 MHz, DMSO-$d_6$): δ=0.05-0.13 (m, 1H), 0.17-0.28 (m, 1H), 0.34-0.52 (m, 2H), 1.46 (s, 3H), 1.49-1.59 (m, 1H), 1.98 (s, 3H), 3.93 (q, 2H), 5.93 (s, 2H), 6.64-6.87 (m, 6H), 7.31 (d, 1H), 10.9 (s, 1H).

HPLC (Method 1): $R_t$=4.91 min; DCI-MS (ESIpos): m/z=365 [M+H]$^+$.

Example 190

3-[1-Cyclopropyl-1-(2,2-difluoro-1,3-benzodioxol-5-yl)ethyl]-7-[(methylsulfanyl)methyl]-1H-indole

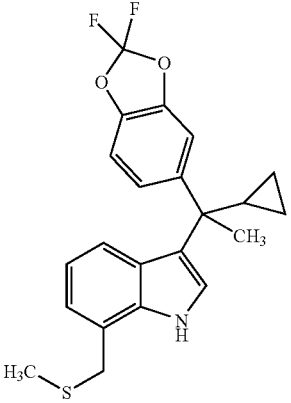

The title compound was prepared starting from 32 mg (0.18 mmol) of the compound from Example 8A and 43 mg (0.18 mmol) of the compound from Example 144A in analogy to the synthesis of the compound from Example 186. 38 mg (53% of theory) of the target compound were obtained.

$^1$H-NMR (400 MHz, DMSO-$d_6$): δ=0.10-0.18 (m, 1H), 0.21-0.30 (m, 1H), 0.39-0.55 (m, 2H), 1.48 (s, 3H), 1.53-1.63 (m, 1H), 1.98 (s, 3H), 3.93 (q, 2H), 6.61-6.71 (m, 2H), 6.86 (d, 1H), 7.14 (dd, 1H), 7.25 (d, 1H), 7.28 (d, 1H), 7.35 (d, 1H), 11.0 (s, 1H).

HPLC (Method 1): $R_t$=5.39 min; DCI-MS (ESIpos): m/z=402 [M+H]$^+$.

Example 191

3-[1-(4-Chlorophenyl)-1-cyclopropylpropyl]-7-[(methylsulfanyl)methyl]-1H-indole

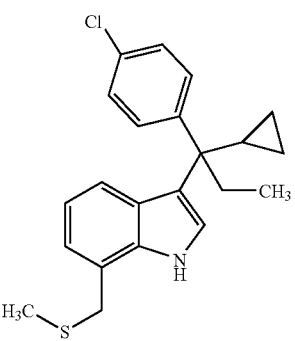

The title compound was prepared starting from 84 mg (0.48 mmol) of the compound from Example 8A and 100 mg (0.48 mmol) of the compound from Example 145A in analogy to the synthesis of the compound from Example 186. 38 mg (21% of theory) of the target compound were obtained.

$^1$H-NMR (400 MHz, DMSO-$d_6$): δ=−0.22−−0.13 (m, 2H), 0.34-0.47 (m, 2H), 0.68 (t, 3H), 1.61-1.71 (m, 1H), 1.97 (s, 3H), 2.11-2.32 (m, 2H), 3.92 (q, 2H), 6.41 (d, 1H), 6.61 (t, 1H), 6.83 (d, 1H), 7.23-7.31 (m, 4H), 7.37 (d, 1H), 11.0 (s, 1H).

HPLC (Method 1): $R_t$=5.54 min; DCI-MS (ESIpos): m/z=370 [M+H]$^+$.

Example 192

3-[3-(4-Chloro-2-fluorophenyl)pentan-3-yl]-7-[(methylsulfanyl)methyl]-1H-indole

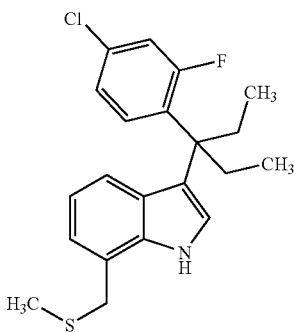

600 mg (2.77 mmol) of the compound from Example 146A, 585 mg (2.64 mmol) of indium(III) chloride and 301 mg (2.64 mmol) of trifluoroacetic acid were added to 446 mg (2.52 mmol) of the compound from Example 8A in 15 ml of dichloromethane. The reaction mixture was stirred at 80° C. for 1 h. After cooling to RT, the reaction solution was mixed with dichloromethane and silica gel, and the solvent was removed in a rotary evaporator. The residue was purified twice by flash chromatography on silica gel (mobile phase: cyclohexane/ethyl acetate gradient) and twice by preparative HPLC (mobile phase: acetonitrile/water gradient). 208 mg (22% of theory) of the title compound were obtained.

$^1$H-NMR (400 MHz, DMSO-$d_6$): δ=0.59 (t, 6H), 1.97 (s, 3H), 2.11-2.26 (m, 4H), 3.92 (s, 2H), 6.62-6.68 (m, 2H), 6.84 (dd, 1H), 7.13 (dd, 1H), 7.24-7.30 (m, 2H), 7.55 (t, 1H), 10.9 (s, 1H).

HPLC (Method 2): $R_t$=5.49 min; DCI-MS (ESIpos): m/z=376 [M+H]$^+$.

Example 193

3-(5,7-Difluoro-4-methyl-3,4-dihydro-2H-chromen-4-yl)-7-[(methylsulfanyl)methyl]-1H-indole

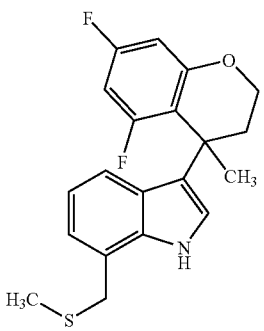

565 mg (2.82 mmol) of the compound from Example 171A and 0.26 ml (3.39 mmol) of trifluoroacetic acid were added to 500 mg (2.82 mmol) of the compound from Example 8A in 20 ml of dichloromethane. The reaction mixture was stirred at RT for 30 min, the solvent was removed in vacuo, and the crude product was then purified by preparative HPLC (mobile phase: acetonitrile/water gradient) and subsequent flash chromatography on silica gel (mobile phase: dichloromethane). 632 mg (62% of theory) of the title compound were obtained.

$^1$H-NMR (400 MHz, DMSO-$d_6$): δ=1.82-1.93 (m, 4H), 1.97 (s, 3H), 2.36-2.46 (m, 1H), 3.92 (q, 2H), 4.09-4.23 (m, 2H), 6.52-6.60 (m, 1H), 6.63-6.68 (m, 1H), 6.76 (t, 1H), 6.84 (d, 1H), 6.90 (d, 1H), 7.07 (d, 1H), 10.9 (s, 1H).

LC-MS (Method 9): $R_t$=1.32 min; MS (ESIneg): m/z=358 [M−H]$^-$.

Example 194

3-(4-Cyclopropyl-5,7-difluoro-3,4-dihydro-2H-chromen-4-yl)-7-[(methylsulfanyl)methyl]-1H-indole

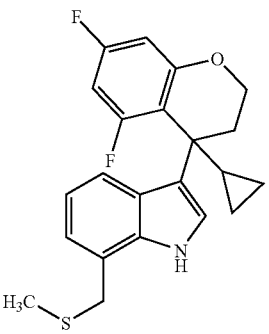

The title compound was prepared starting from 450 mg (2.54 mmol) of the compound from Example 8A and 574 mg (2.54 mmol) of the compound from Example 172A in analogy to the synthesis of the compound from Example 193. 80 mg (8% of theory) of the target compound were obtained.

$^1$H-NMR (400 MHz, DMSO-$d_6$): δ=0.09-0.18 (m, 1H), 0.44-0.59 (m, 2H), 0.68-0.78 (m, 1H), 1.65-1.75 (m, 1H), 1.97 (s, 3H), 2.13-2.23 (m, 1H), 3.93 (q, 2H), 3.96-4.06 (m, 1H), 4.28-4.36 (m, 1H), 6.53-6.64 (m, 2H), 6.81 (t, 1H), 6.92 (d, 1H), 7.04 (d, 1H), 7.09 (d, 1H), 10.9 (s, 1H).

LC-MS (Method 9): $R_t$=1.36 min; MS (ESIneg): m/z=384 [M−H]$^-$.

Example 195

2-[1-(2,4-Difluorophenyl)-1-{5-fluoro-7-[(methylsulfanyl)methyl]-1H-indol-3-yl}ethyl]cyclopropanecarbonitrile [trans-diastereomer mixture]

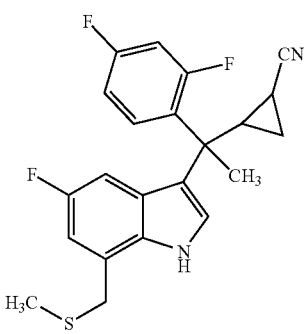

273 mg (1.23 mmol) of indium(III) chloride and 0.1 ml (1.34 mmol) of trifluoroacetic acid were added to 250 mg (1.12 mmol) of the compound from Example 11A and 437 mg (2.24 mmol) of the compound from Example 133A were introduced into 44 ml of dichloromethane, and the mixture was stirred at RT overnight. The reaction mixture was concentrated in a rotary evaporator. The residue was purified by preparative HPLC (RP18 column; mobile phase: acetonitrile/water gradient with addition of 0.1% formic acid) to result in 313 mg (69% of theory) of the title compound as mixture of diastereomers.

$^1$H-NMR (400 MHz, DMSO-d$_6$): δ=11.2 (s, 1H), 7.68-7.76 (m, 0.6H), 7.59-7.67 (m, 0.4H), 7.41 (d, 0.6H), 7.35 (d, 0.4H), 7.14-7.21 (m, 1H), 7.05-7.13 (m, 1H), 6.75-6.82 (m, 1H), 6.19 (d, 0.4H), 6.08 (d, 0.6H), 3.87-3.97 (m, 2H), 2.36-2.46 (m, 1H), 1.98 (s, 1.2H), 1.97 (s, 1.8H), 1.63 (s, 1.8H), 1.57 (s, 1.2H), 1.39-1.51 (m, 1H), 1.31-1.38 (m, 1H), 0.93-1.01 (m, 0.4H), 0.75-0.82 (m, 0.6H).

LC-MS (Method 4): R$_t$=1.42 min; MS (ESIneg): m/z=399 [M–H]$^-$.

Example 196

3-[1-(4-Chlorophenyl)-1-cyclopropylethyl]-7-[(methylsulfinyl)methyl]-1H-indole

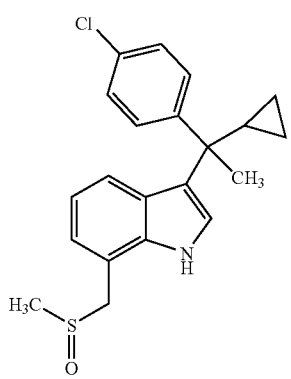

131 mg (0.37 mmol) of the compound from Example 184 were introduced into 25 ml of dichloromethane at 0° C., 91 mg (0.37 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 113 mg (83% of theory) of the title compound as mixture of diastereomers.

$^1$H-NMR (400 MHz, DMSO-d$_6$): δ=0.05-0.14 (m, 1H), 0.17-0.26 (m, 1H), 0.38-0.55 (m, 2H), 1.49 (s, 3H), 1.52-1.62 (m, 1H), 2.55 (d, 3H), 4.21 (t, 1H), 4.35 (t, 1H), 6.65-6.74 (m, 2H), 6.92 (d, 1H), 7.26-7.33 (m, 4H), 7.43 (s, 1H), 11.1 (s, 1H).

HPLC (Method 2): R$_t$=4.77 min; MS (ESIpos): m/z=372 [M+H]$^+$.

Example 197

3-{1-Cyclopropyl-1-[4-(trifluoromethyl)phenyl]ethyl}-7-[(methylsulfinyl)methyl]-1H-indole

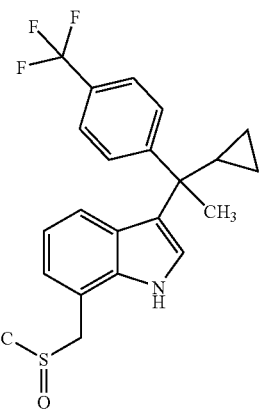

The title compound was prepared starting from 76 mg (0.20 mmol) of the compound from Example 185 in analogy to the synthesis of the compound from Example 196. 42 mg (53% of theory) of the target compound were obtained as mixture of diastereomers.

$^1$H-NMR (400 MHz, DMSO-d$_6$): δ=0.10-0.19 (m, 1H), 0.22-0.31 (m, 1H), 0.41-0.58 (m, 2H), 1.51 (s, 3H), 1.57-1.68 (m, 1H), 2.55 (s, 3H), 4.22 (t, 1H), 4.36 (dd, 1H), 6.64 (d, 1H), 6.71 (t, 1H), 6.92 (d, 1H), 7.47 (s, 1H), 7.53 (d, 2H), 7.61 (d, 2H), 11.1 (s, 1H).

HPLC (Method 2): R$_t$=4.79 min; MS (ESIneg): m/z=404 [M–H]$^-$.

Example 198

3-[1-(4-Chlorophenyl)-1-cyclopropylpropyl]-7-[(methylsulfinyl)methyl]-1H-indole

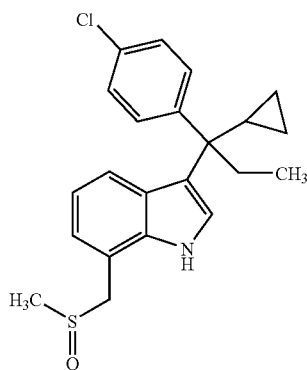

The title compound was prepared starting from 58 mg (0.16 mmol) of the compound from Example 191 in analogy to the synthesis of the compound from Example 196. 50 mg (82% of theory) of the target compound were obtained as mixture of diastereomers.

¹H-NMR (400 MHz, DMSO-d₆): δ=−0.23--−0.13 (m, 2H), 0.35-0.47 (m, 2H), 0.69 (t, 3H), 1.62-1.71 (m, 1H), 2.11-2.34 (m, 2H), 2.54 (s, 3H), 4.20 (t, 1H), 4.34 (dd, 1H), 6.47 (dd, 1H), 6.67 (d, 1H), 6.89 (d, 1H), 7.23-7.31 (m, 4H), 7.45 (d, 1H), 11.1 (s, 1H).

HPLC (Method 1): R$_t$=4.94 min; MS (ESIneg): m/z=384 [M−H]⁻.

Example 199

3-(5,7-Difluoro-4-methyl-3,4-dihydro-2H-chromen-4-yl)-7-[(methylsulfinyl)methyl]-1H-indole

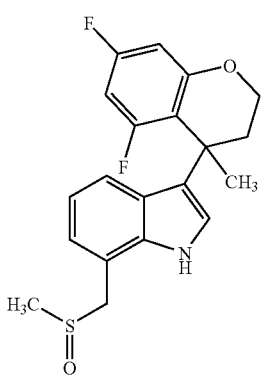

75 mg (0.21 mmol) of the compound from Example 193 were introduced into 10 ml of dichloromethane at 0° C., 51 mg (0.21 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient).

¹H-NMR (400 MHz, DMSO-d₆): δ=1.81-1.93 (m, 4H), 2.36-2.46 (m, 1H), 2.54 (s, 3H), 4.10-4.26 (m, 3H), 4.35 (dd, 1H), 6.51-6.59 (m, 1H), 6.63-6.69 (m, 1H), 6.82 (t, 1H), 6.88 (d, 1H), 6.96 (dd, 1H), 7.16 (d, 1H), 11.0 (s, 1H).

LC-MS (Method 9): R$_t$=1.08 min; MS (ESIneg): m/z=374 [M−H]⁻.

Example 200

3-[5-Chloro-1-cyclopropyl-2,3-dihydro-1H-inden-1-yl]-7-[(methylsulfonyl)methyl]-1H-indole

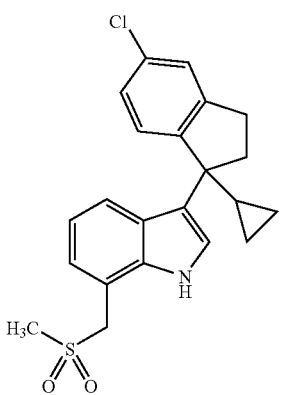

64.0 mg (0.26 mmol) of 70% pure meta-chloroperbenzoic acid were added to 46.6 mg (0.13 mmol) of the compound from Example 175 in 10 ml of dichloromethane at 0° C., and the mixture was stirred at RT overnight. It was concentrated and the residue was purified by preparative HPLC (RP18 column; mobile phase: acetonitrile/water gradient with addition of 0.1% formic acid) to result in 18 mg (35.5% of theory) of the title compound as mixture of diastereomers.

¹H-NMR (400 MHz, DMSO-d₆): δ=11.0 (s, 1H), 7.35-7.39 (m, 2H), 7.03-7.09 (m, 2H), 6.78-6.84 (m, 2H), 6.71 (d, 1H), 4.68-4.77 (m, 2H), 2.92-3.08 (m, 2H), 2.90 (s, 3H), 2.51-2.60 (m, 1H), 2.10-2.18 (m, 1H), 1.47-1.56 (m, 1H), 0.42-0.54 (m, 2H), 0.00-0.07 (m, 1H), −0.24--−0.17 (m, 1H).

LC-MS (Method 4): R$_t$=1.49 min; MS (ESIneg): m/z=398 [M−H]⁻.

Example 201

3-(6-Chloro-1-cyclopropyl-2,3-dihydro-1H-inden-1-yl)-7-[(methylsulfonyl)methyl]-1H-indole

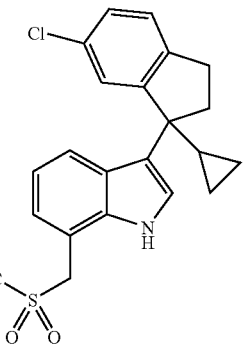

64.0 mg (0.26 mmol) of 70% pure meta-chloroperbenzoic acid were added to 46.6 mg (0.13 mmol) of the compound from Example 176 in 10 ml of dichloromethane at 0° C., and the mixture was stirred at RT overnight. It was concentrated and the residue was purified by preparative HPLC (RP18 column; mobile phase: acetonitrile/water gradient with addition of 0.1% formic acid) to result in 24.0 mg (47% of theory) of the title compound as mixture of diastereomers.

¹H-NMR (400 MHz, DMSO-d₆): δ=11.0 (s, 1H), 7.37 (d, 1H), 7.33 (d, 1H), 7.22 (dd, 1H), 7.07 (dd, 1H), 6.79-6.85 (m, 2H), 6.69 (d, 1H), 4.68-4.79 (m, 2H), 2.91-3.01 (m, 2H), 2.90 (s, 3H), 2.51-2.60 (m, 1H), 2.07-2.15 (m, 1H), 1.48-1.57 (m, 1H), 0.44-0.58 (m, 2H), 0.03-0.10 (m, 1H), −0.18--−0.10 (m, 1H).

LC-MS (Method 9): R$_t$=1.27 min; MS (ESIneg): m/z=398 [M−H]⁻.

Example 202

2-(1-{7-[(Methylsulfonyl)methyl]-1H-indol-3-yl}-1-[4-(trifluoromethyl)phenyl]ethyl)cyclopropanecarbonitrile [trans-diastereomer mixture]

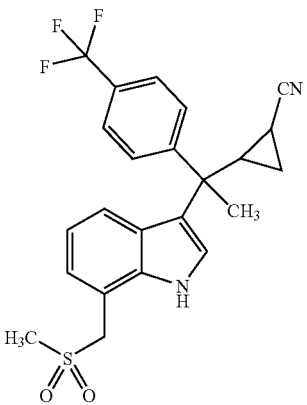

8.5 mg (0.04 mmol) of 70% pure meta-chloroperbenzoic acid were added to 7.0 mg (0.02 mmol) of the compound from Example 177 in 1 ml of dichloromethane at 0° C., and the mixture was stirred at RT for 1 h. It was concentrated and the residue was purified by preparative HPLC (RP18 column; mobile phase: acetonitrile/water gradient with addition of 0.1% formic acid) to result in 4.8 mg (64% of theory) of the title compound as mixture of diastereomers.

$^1$H-NMR (400 MHz, DMSO-d$_6$): δ=11.2 (s, 1H), 7.63-7.70 (m, 2H), 7.47-7.56 (m, 3H), 7.06 (t, 1H), 6.74-6.83 (m, 1H), 6.70 (d, 0.5H), 6.62 (d, 0.5H), 4.68-4.79 (m, 2H), 2.91 (s, 3H), 2.34-2.45 (m, 1H), 1.55-1.65 (m, 3.5H), 1.43-1.50 (m, 0.5H), 1.29-1.40 (m, 1H), 1.00-1.07 (m, 0.5H), 0.80-0.95 (m, 0.5H).

LC-MS (Method 9): R$_t$=1.13 min; MS (ESIneg): m/z=445 [M−H]$^−$.

Example 203

2-[1-(2,4-Difluorophenyl)-1-{7-[(methylsulfonyl)methyl]-1H-indol-3-yl}ethyl]cyclopropane-carbonitrile [trans-diastereomer mixture]

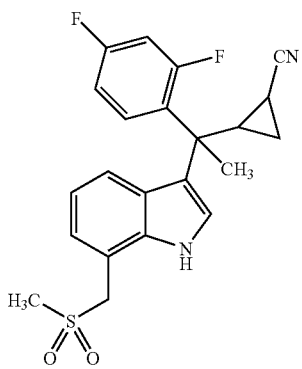

135 mg (0.55 mmol) of 70% pure meta-chloroperbenzoic acid were added to 100 mg (0.26 mmol) of the compound from Example 178 in 6 ml of dichloromethane at 0° C., and the mixture was stirred at RT for 1 h. It was concentrated and the residue was purified by preparative HPLC (RP18 column; mobile phase: acetonitrile/water gradient with addition of 0.1% formic acid) to result in 80.5 mg (74% of theory) of the title compound as mixture of diastereomers.

$^1$H-NMR (400 MHz, DMSO-d$_6$): δ=11.2 (s, 1H), 7.66-7.74 (m, 0.5H), 7.58-7.66 (m, 0.5H), 7.40 (d, 0.5H), 7.36 (d, 0.5H), 7.12-7.19 (m, 2H), 7.01-7.10 (m, 1H), 6.73-6.82 (m, 1H), 6.66 (d, 0.5H), 6.58 (d, 0.5H), 4.66-4.77 (m, 2H), 2.89 (s, 3H), 2.36-2.46 (m, 1H), 1.64 (s, 1.5H), 1.61 (s, 1.5H), 1.45-1.52 (m, 0.5H), 1.38-1.44 (m, 0.5H), 1.31-1.38 (m, 1H), 0.91-0.99 (m, 0.5H), 0.79-0.87 (m, 0.5H).

LC-MS (Method 9): R$_t$=1.06 min; MS (ESIneg): m/z=413 [M−H]$^−$.

In a batch carried out analogously, a further 25.0 mg of the title compound were obtained as mixture of diastereomers which were combined with the first fraction.

The diastereomers and enantiomers were separated by preparative HPLC on a chiral phase [column: Daicel Chiralpak AD-H, 5 μm, 250 mm×20 mm; eluent: isohexane/(isopropanol/methanol (1:1)) 75:25; flow rate: 20 ml/min; temperature: 24° C.; UV detection: 230 nm]. The separated enantiomers were purified again by preparative HPLC on an achiral phase (mobile phase: acetonitrile/water gradient):

Enantiomer 203-1:

R$_t$=14.37 min [column: Daicel Chiralpak AD-H, 5 μm, 250 mm×4 mm; eluent: isopropanol/methanol (1:1)/isohexane 25:75; flow rate: 1 ml/min; temperature: 24° C.; UV detection: 230 nm].

$^1$H-NMR (400 MHz, DMSO-d$_6$) δ=11.2 (s, 1H), 7.66-7.74 (m, 1H), 7.40 (d, 1H), 7.15 (t, 1H), 7.01-7.10 (m, 2H), 6.76 (t, 1H), 6.58 (d, 1H), 4.66-4.76 (m, 2H), 2.89 (s, 3H), 2.36-2.44 (m, 1H), 1.64 (s, 3H), 1.49 (dt, 1H), 1.34 (dt, 1H), 0.79-0.87 (m, 1H).

LC-MS (Method 9): R$_t$=1.04 min; MS (ESIneg): m/z=413 [M−H]$^−$.

Yield: 18.0 mg

Example 204

2-[1-(4-Chlorophenyl)-1-{5-fluoro-7-[(methylsulfonyl)methyl]-1H-indol-3-yl}ethyl]cyclopropane-carbonitrile [trans-diastereomer mixture]

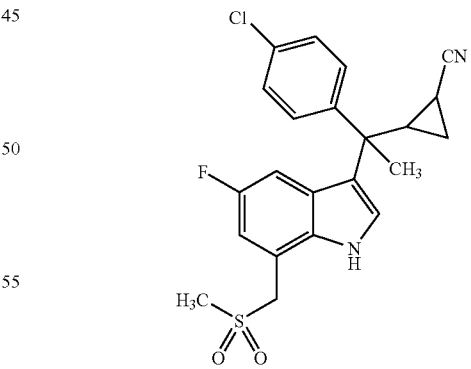

247 mg (1.00 mmol) of 70% pure meta-chloroperbenzoic acid were added to 200 mg (0.50 mmol) of the compound from Example 179 in 6 ml of dichloromethane at 0° C., and the mixture was stirred at RT overnight. 2 ml of methanol were added, and the residue after concentration was purified by preparative HPLC (RP18 column; mobile phase: acetonitrile/water gradient with addition of 0.1% formic acid) to result in 110 mg (48% of theory) of the title compound as mixture of diastereomers.

¹H-NMR (400 MHz, DMSO-d₆): δ=11.3 (s, 1H), 7.53-7.57 (m, 1H), 7.24-7.40 (m, 4H), 6.91-6.99 (m, 1H), 6.40 (dd, 0.5H), 6.31 (dd, 0.5H), 4.70-4.81 (m, 2H), 2.94 (s, 3H), 2.29-2.40 (m, 1H), 1.51-1.60 (m, 3.5H), 1.27-1.43 (m, 1.5H), 0.95-1.03 (m, 0.5H), 0.80-0.87 (m, 0.5H).

LC-MS (Method 5): $R_t$=2.47 min; MS (ESIneg): m/z=429 [M–H]⁻.

Example 205

3-[1-(4-Chlorophenyl)-1-(2,2-difluorocyclopropyl)ethyl]-7-[(methylsulfonyl)methyl]-2,3-dihydro-1H-indole

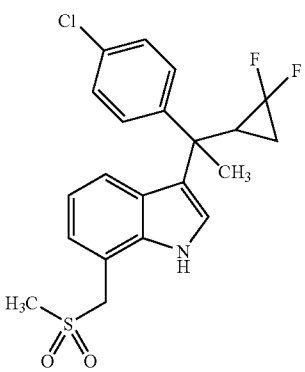

15.1 mg (0.06 mmol) of 70% pure meta-chloroperbenzoic acid were added to 12.0 mg (0.03 mmol) of the compound from Example 180 in 1 ml of dichloromethane, and the mixture was stirred at RT for 2 h. Methanol was added, and the residue after concentration was purified by preparative HPLC (RP18 column; mobile phase: acetonitrile/water gradient with addition of 0.1% formic acid) to result in 6.0 mg (46% of theory) of the title compound as mixture of diastereomers.

¹H-NMR (400 MHz, DMSO-d₆): δ=11.2 (s, 1H), 7.44 (d, 1H), 7.34-7.39 (m, 2H), 7.26-7.32 (m, 2H), 7.07 (d, 1H), 6.76-6.84 (m, 2H), 4.69-4.68 (m, 2H), 2.92 (s, 3H), 2.21-2.27 (m, 0.5H), 2.09-2.16 (m, 0.5H), 1.56-1.69 (m, 3.5H), 1.43-1.55 (m, 1H), 1.32-1.38 (m, 0.5H).

LC-MS (Method 6): $R_t$=2.52 min; MS (ESIneg): m/z=422 [M–H]⁻.

Example 206

3-(1-Ethyl-5-fluoro-2,3-dihydro-1H-inden-1-yl)-7-[(methylsulfonyl)methyl]-1H-indole

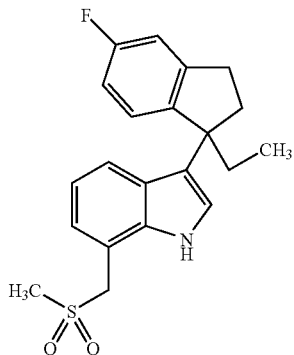

27.5 mg (0.16 mmol) of 70% pure meta-chloroperbenzoic acid were added to 27.0 mg (0.08 mmol) of the compound from Example 181 in 2 ml of dichloromethane, and the mixture was stirred at RT overnight. 2 ml of methanol were added, and the residue after concentration was purified by preparative HPLC (RP18 column; mobile phase: acetonitrile/water gradient with addition of 0.1% formic acid) to result in 3.6 mg (12% of theory) of the title compound as mixture of diastereomers.

¹H-NMR (400 MHz, DMSO-d₆): δ=10.9 (s, 1H), 7.05-7.13 (m, 4H), 7.00-7.05 (m, 1H), 6.84-6.95 (m, 2H), 4.65-4.76 (m, 2H), 2.91-3.02 (m, 2H), 2.89 (s, 3H), 2.47-2.55 (m, 1H), 2.15-2.28 (m, 2H), 1.99-2.10 (m, 1H), 0.79 (t, 3H).

LC-MS (Method 5): $R_t$=2.67 min; MS (ESIneg): m/z=370 [M–H]⁻.

Example 207

3-{1-Cyclopropyl-1-[2-fluoro-4-(trifluoromethyl)phenyl]ethyl}-7-[(methylsulfonyl)methyl]-1H-indole

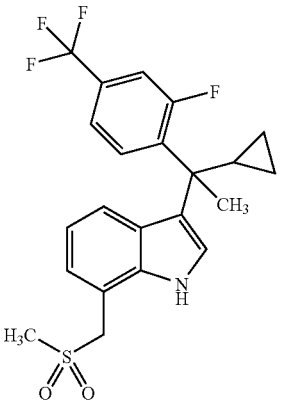

32.3 mg (0.13 mmol) of 70% pure meta-chloroperbenzoic acid were added to 26.0 mg (0.06 mmol) of the compound from Example 182 in 2 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 16 mg (57% of theory) of the title compound as mixture of diastereomers.

¹H-NMR (400 MHz, DMSO-d₆): δ=11.1 (s, 1H), 8.01 (t, 1H), 7.63 (d, 1H), 7.42 (d, 1H), 7.38 (d, 1H), 7.02 (d, 1H), 6.74 (t, 1H), 6.64 (d, 1H), 4.67-4.77 (m, 2H), 2.89 (s, 3H), 1.65-1.75 (m, 1H), 1.60 (s, 3H), 0.47-0.57 (m, 2H), 0.16-0.26 (m, 2H).

LC-MS (Method 9): $R_t$=1.27 min; MS (ESIneg): m/z=438 [M–H]⁻.

Example 208

3-[1-Cyclopropyl-1-(4-methylphenyl)ethyl]-7-[(methylsulfonyl)methyl]-1H-indole

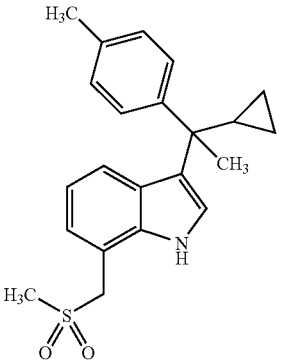

151 mg (0.61 mmol) of 70% pure meta-chloroperbenzoic acid were added to 100 mg (0.30 mmol) of the compound from Example 183 in 2 ml of dichloromethane, and the mixture was stirred at RT overnight. It was diluted with dichloromethane and washed with saturated aqueous sodium bicarbonate solution and water, dried over magnesium sulfate, filtered and concentrated. The residue was purified by preparative HPLC (RP18 column; mobile phase: acetonitrile/water gradient with addition of 0.1% formic acid) to result in 52.9 mg (48% of theory) of the title compound as mixture of diastereomers.

$^1$H-NMR (400 MHz, DMSO-d$_6$): δ=11.0 (s, 1H), 7.42 (s, 1H), 7.13-7.18 (m, 2H), 6.97-7.06 (m, 3H), 6.70-6.74 (m, 2H), 4.66-4.77 (s, 2H), 2.90 (s, 3H), 2.24 (s, 3H), 1.50-1.60 (m, 1H), 1.50 (s, 3H), 0.44-0.52 (m, 1H), 0.35-0.43 (m, 1H), 0.14-0.22 (m, 1H), 0.02-0.10 (m, 1H).

LC-MS (Method 9): R$_t$=1.23 min; MS (ESIneg): m/z=366 [M−H]$^-$.

Example 209

3-[1-(4-Chlorophenyl)-1-cyclopropylethyl]-7-[(methylsulfonyl)methyl]-1H-indole

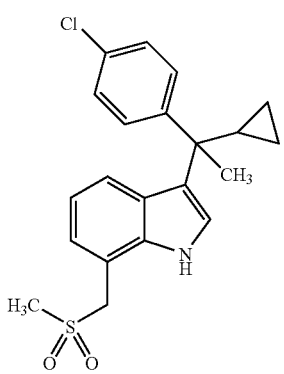

261 mg (0.74 mmol) of the compound from Example 184 were introduced into 50 ml of dichloromethane at 0° C., 361 mg (1.47 mmol) of 70% pure meta-chloroperbenzoic acid were added, and the mixture was stirred at RT for 2 h. 2 ml of methanol were added, and the solution was concentrated. The residue was taken up in ethyl acetate and washed with saturated aqueous sodium bicarbonate solution, water and saturated aqueous sodium chloride solution, and the solvents were removed in a rotary evaporator. The crude product was purified by preparative HPLC (mobile phase: acetonitrile/water gradient) to result in 214 mg (75% of theory) of the title compound.

$^1$H-NMR (400 MHz, DMSO-d$_6$): δ=0.05-0.14 (m, 1H), 0.17-0.26 (m, 1H), 0.38-0.55 (m, 2H), 1.49 (s, 3H), 1.52-1.62 (m, 1H), 2.91 (s, 3H), 4.72 (q, 2H), 6.69-6.79 (m, 2H), 7.03 (d, 1H), 7.26-7.33 (m, 4H), 7.44 (d, 1H), 11.0 (s, 1H).

HPLC (Method 2): R$_t$=4.85 min; MS (ESIneg): m/z=386 [M−H]$^-$.

Example 210

3-{1-Cyclopropyl-1-[4-(trifluoromethyl)phenyl]ethyl}-7-[(methylsulfonyl)methyl]-1H-indole

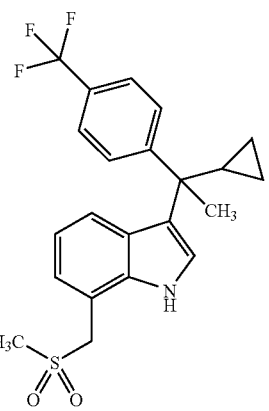

The title compound was prepared starting from 153 mg (0.39 mmol) of the compound from Example 185 in analogy to the synthesis of the compound from Example 209. 63 mg (38% of theory) of the target compound were obtained.

$^1$H-NMR (400 MHz, DMSO-d$_6$): δ=0.10-0.19 (m, 1H), 0.22-0.31 (m, 1H), 0.41-0.58 (m, 2H), 1.51 (s, 3H), 1.58-1.68 (m, 1H), 2.91 (s, 3H), 4.73 (q, 2H), 6.69 (d, 1H), 6.75 (t, 1H), 7.03 (d, 1H), 7.49 (d, 1H), 7.52 (d, 2H), 7.61 (d, 2H), 11.1 (s, 1H).

HPLC (Method 2): R$_t$=4.88 min; MS (ESIneg): m/z=420 [M−H]$^-$.

Example 211

3-[1-Cyclopropyl-1-(3-fluoro-4-methoxyphenyl)ethyl]-7-[(methylsulfonyl)methyl]-1H-indole

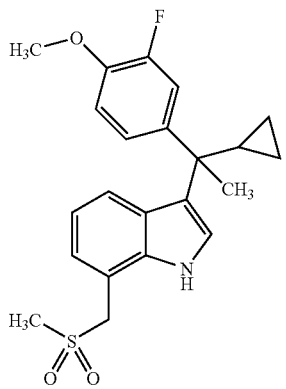

The title compound was prepared starting from 282 mg (0.76 mmol) of the compound from Example 186 in analogy to the synthesis of the compound from Example 209. 215 mg (70% of theory) of the target compound were obtained.

$^1$H-NMR (400 MHz, DMSO-d$_6$): δ=0.05-0.13 (m, 1H), 0.16-0.25 (m, 1H), 0.37-0.54 (m, 2H), 1.48 (s, 3H), 1.51-1.60

(m, 1H), 2.91 (s, 3H), 3.78 (s, 3H), 4.72 (q, 2H), 6.73-6.80 (m, 2H), 6.99-7.07 (m, 4H), 7.42 (d, 1H), 11.0 (s, 1H).

HPLC (Method 1): $R_t$=4.58 min; DCI-MS (ESIpos): m/z=419 [M-NH$_4$]$^-$.

Example 212

3-[1-(1-Benzothiophen-5-yl)-1-cyclopropylethyl]-7-[(methylsulfonyl)methyl]-1H-indole

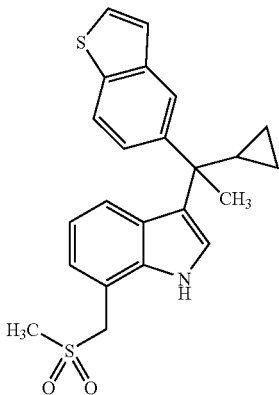

The title compound was prepared starting from 237 mg (0.63 mmol) of the compound from Example 187 in analogy to the synthesis of the compound from Example 209. 144 mg (56% of theory) of the target compound were obtained.

$^1$H-NMR (400 MHz, DMSO-d$_6$): δ=0.08-0.17 (m, 1H), 0.21-0.29 (m, 1H), 0.40-0.58 (m, 2H), 1.58 (s, 3H), 1.62-1.71 (m, 1H), 2.91 (s, 3H), 4.73 (q, 2H), 6.64-6.72 (m, 2H), 7.00 (dd, 1H), 7.23 (dd, 1H), 7.40 (d, 1H), 7.48 (d, 1H), 7.68 (d, 1H), 7.79 (d, 1H), 7.91 (d, 1H), 11.0 (s, 1H).

HPLC (Method 2): $R_t$=4.80 min; MS (ESIne): m/z=408 [M−H]$^-$.

Example 213

3-[1-Cyclopropyl-1-(2,3-dihydro-1,4-benzodioxin-6-yl)ethyl]-7-[(methylsulfonyl)methyl]-1H-indole

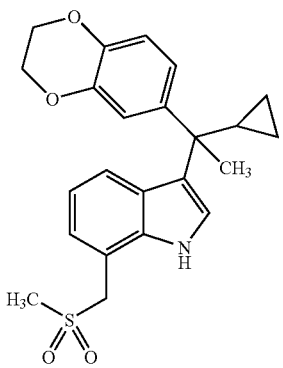

The title compound was prepared starting from 94 mg (0.25 mmol) of the compound from Example 188 in analogy to the synthesis of the compound from Example 209. 56 mg (55% of theory) of the target compound were obtained.

$^1$H-NMR (400 MHz, DMSO-d$_6$): δ=0.03-0.12 (m, 1H), 0.16-0.25 (m, 1H), 0.33-0.43 (m, 1H), 0.43-0.53 (m, 1H), 1.45 (s, 3H), 1.48-1.58 (m, 1H), 2.91 (s, 3H), 4.17 (s, 4H), 4.72 (q, 2H), 6.67-6.84 (m, 5H), 7.02 (d, 1H), 7.39 (s, 1H), 11.0 (s, 1H).

HPLC (Method 1): $R_t$=4.51 min; DCI-MS (ESIpos): m/z=429 [M-NH$_4$]$^-$.

Example 214

3-[1-(1,3-Benzodioxol-5-yl)-1-cyclopropylethyl]-7-[(methylsulfonyl)methyl]-1H-indole

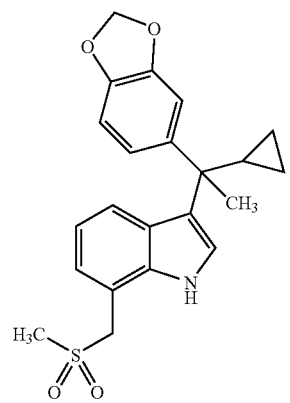

The title compound was prepared starting from 214 mg (0.59 mmol) of the compound from Example 189 in analogy to the synthesis of the compound from Example 209. 162 mg (69% of theory) of the target compound were obtained.

$^1$H-NMR (400 MHz, DMSO-d$_6$): δ=0.05-0.14 (m, 1H), 0.17-0.26 (m, 1H), 0.35-0.54 (m, 2H), 1.47 (s, 3H), 1.50-1.59 (m, 1H), 2.90 (s, 3H), 4.72 (q, 2H), 5.94 (s, 2H), 6.72-6.84 (m, 5H), 7.03 (dd, 1H), 7.40 (d, 1H), 11.0 (s, 1H).

HPLC (Method 1): $R_t$=4.48 min; DCI-MS (ESIpos): m/z=397 [M+H]$^+$.

Example 215

3-[1-Cyclopropyl-1-(2,2-difluoro-1,3-benzodioxol-5-yl)ethyl]-7-[(methylsulfonyl)methyl]-1H-indole

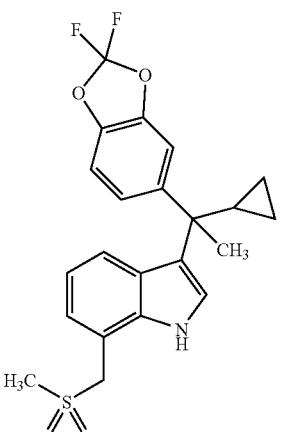

The title compound was prepared starting from 33 mg (0.08 mmol) of the compound from Example 190 in analogy to the synthesis of the compound from Example 209. 27 mg (76% of theory) of the target compound were obtained.

$^1$H-NMR (400 MHz, DMSO-d$_6$): δ=0.10-0.19 (m, 1H), 0.22-0.31 (m, 1H), 0.40-0.57 (m, 2H), 1.49 (s, 3H), 1.54-1.64 (m, 1H), 2.91 (s, 3H), 4.73 (s, 2H), 6.73-6.81 (m, 2H), 7.04 (dd, 1H), 7.12 (dd, 1H), 7.25 (d, 1H), 7.29 (d, 1H), 7.45 (d, 1H), 11.1 (s, 1H).

HPLC (Method 1): R$_t$=4.91 min; DCI-MS (ESIpos): m/z=451 [M+H]$^+$.

Example 216

3-[1-(4-Chlorophenyl)-1-cyclopropylpropyl]-7-[(methylsulfonyl)methyl]-1H-indole

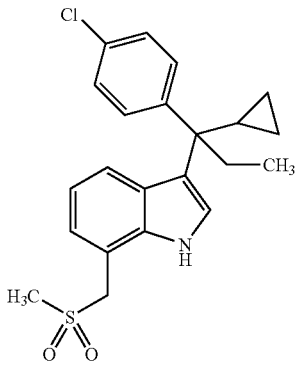

The title compound was prepared starting from 116 mg (0.31 mmol) of the compound from Example 191 in analogy to the synthesis of the compound from Example 209. 98 mg (78% of theory) of the target compound were obtained.

$^1$H-NMR (400 MHz, DMSO-d$_6$): δ=−0.23--0.13 (m, 2H), 0.35-0.48 (m, 2H), 0.68 (t, 3H), 1.62-1.72 (m, 1H), 2.11-2.34 (m, 2H), 2.89 (s, 3H), 4.72 (s, 2H), 6.52 (d, 1H), 6.71 (t, 1H), 7.00 (d, 1H), 7.25 (d, 2H), 7.29 (d, 2H), 7.47 (s, 1H), 11.1 (s, 1H).

HPLC (Method 1): R$_t$=5.02 min; MS (ESIneg): m/z=400 [M−H]$^−$.

Example 217

3-[3-(4-Chloro-2-fluorophenyl)pentan-3-yl]-7-[(methylsulfonyl)methyl]-1H-indole

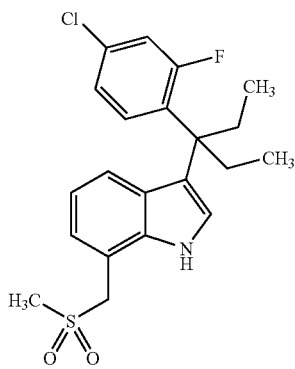

The title compound was prepared starting from 162 mg (0.43 mmol) of the compound from Example 192 in analogy to the synthesis of the compound from Example 209. 164 mg (93% of theory) of the target compound were obtained.

$^1$H-NMR (400 MHz, DMSO-d$_6$): δ=0.59 (t, 6H), 2.11-2.27 (m, 4H), 2.88 (s, 3H), 4.71 (s, 2H), 6.75 (d, 2H), 7.02 (t, 1H), 7.14 (dd, 1H), 7.28 (dd, 1H), 7.34 (d, 1H), 7.56 (d, 1H), 11.0 (s, 1H).

HPLC (Method 1): R$_t$=5.00 min; MS (ESIneg): m/z=406 [M−H]$^−$.

Example 218

3-(5,7-Difluoro-4-methyl-3,4-dihydro-2H-chromen-4-yl)-7-[(methylsulfonyl)methyl]-1H-indole

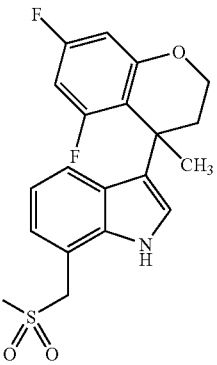

510 mg (1.42 mmol) of the compound from Example 193 were introduced into 50 ml of dichloromethane at 0° C., 700 mg (2.84 mmol) of 70% pure meta-chloroperbenzoic acid were added, and the mixture was stirred at RT for 2 h. 5 ml of methanol were added, and the solution was extracted with saturated aqueous sodium bicarbonate solution. After removal of the solvents in a rotary evaporator, the crude product was purified by preparative HPLC (mobile phase: acetonitrile/water gradient) to result in 386 mg (70% of theory) of the title compound.

$^1$H-NMR (400 MHz, DMSO-d$_6$): δ=1.83-1.93 (m, 4H), 2.36-2.46 (m, 1H), 2.90 (s, 3H), 4.10-4.24 (m, 2H), 4.72 (q, 2H), 6.51-6.59 (m, 1H), 6.63-6.69 (m, 1H), 6.86 (t, 1H), 6.93 (d, 1H), 7.07 (d, 1H), 7.18 (d, 1H), 11.0 (s, 1H).

LC-MS (Method 9): R$_t$=1.13 min; MS (ESIneg): m/z=390 [M−H]$^−$.

Example 219

3-(4-Cyclopropyl-5,7-difluoro-3,4-dihydro-2H-chromen-4-yl)-7-[(methylsulfonyl)methyl]-1H-indole

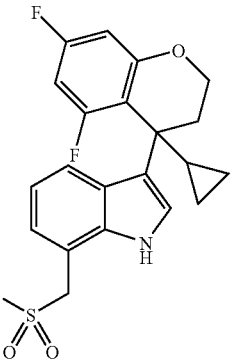

65 mg (0.17 mmol) of the compound from Example 194 were introduced into 10 ml of dichloromethane at 0° C., 83 mg (0.34 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 48 mg (68% of theory) of the title compound.

$^1$H-NMR (400 MHz, DMSO-$d_6$): δ=0.09-0.19 (m, 1H), 0.45-0.57 (m, 2H), 0.68-0.79 (m, 1H), 1.65-1.78 (m, 2H), 2.16-2.26 (m, 1H), 2.90 (s, 3H), 3.98-4.07 (m, 1H), 4.29-4.39 (m, 1H), 4.74 (s, 2H), 6.51-6.66 (m, 2H), 6.90 (t, 1H), 7.10 (d, 1H), 7.13-7.21 (m, 2H), 11.0 (s, 1H).

LC-MS (Method 9): $R_t$=1.17 min; MS (ESIneg): m/z=416 [M−H]$^−$.

Example 220

2-[1-(2,4-Difluorophenyl)-1-{5-fluoro-7-[(methylsulfonyl)methyl]-1H-indol-3-yl}ethyl]cyclopropanecarbonitrile [trans-diastereomer mixture]

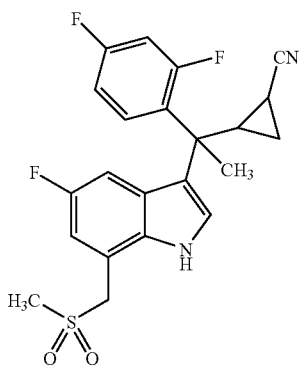

63.1 mg (0.26 mmol) of 70% pure meta-chloroperbenzoic acid were added to 50.0 mg (0.13 mmol) of the compound from Example 195 in 5 ml of dichloromethane, and the mixture was stirred at RT overnight. It was diluted with dichloromethane and washed with saturated aqueous sodium bicarbonate solution and water, dried over magnesium sulfate, filtered and concentrated. The residue was purified by preparative HPLC (RP18 column; mobile phase: acetonitrile/water gradient with addition of 0.1% formic acid) to result in 40.1 mg (74% of theory) of the title compound as mixture of diastereomers.

$^1$H-NMR (400 MHz, DMSO-$d_6$): δ=11.2 (s, 1H), 7.68-7.76 (m, 0.6H), 7.59-7.67 (m, 0.4H), 7.50 (d, 0.6H), 7.45 (d, 0.4H), 7.14-7.22 (m, 1H), 7.04-7.13 (m, 1H), 6.90-6.98 (m, 1H), 6.32 (d, 0.4H), 6.23 (d, 0.6H), 4.69-4.79 (m, 2H), 2.92 (s, 3H), 2.38-2.47 (m, 1H), 1.62 (s, 1.8H), 1.58 (s, 1.2H), 1.47-1.53 (m, 0.6H), 1.40-1.46 (m, 0.4H), 1.32-1.39 (m, 1H), 0.94-1.02 (m, 0.4H), 0.76-0.85 (m, 0.6H).

LC-MS (Method 9): $R_t$=1.17 min; MS (ESIneg): m/z=431 [M−H]$^−$.

Example 221

3-[Cyclopropyl(2,4-dichlorophenyl)methyl]-7-[(methylsulfanyl)methyl]-1H-indole

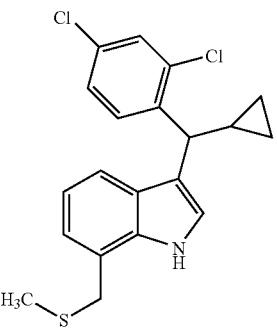

0.2 ml (2.76 mmol) of trifluoroacetic acid was added to 500 mg (2.30 mmol) of the compound from Example 147A and 408 mg (2.30 mmol) of the compound from Example 8A in 32 ml of dichloromethane, and the mixture was stirred at RT for 30 min. It was concentrated and the residue was purified by preparative HPLC (RP18 column; mobile phase: acetonitrile/water gradient with addition of 0.1% formic acid) to result in 342 mg (35% of theory) of the title compound as mixture of diastereomers.

$^1$H-NMR (400 MHz, DMSO-$d_6$): δ=11.0 (s, 1H), 7.57 (d, 1H), 7.45 (d, 1H), 7.37 (d, 1H), 7.33 (dd, 1H), 7.07 (d, 1H), 6.91 (d, 1H), 6.82 (t, 1H), 3.87-3.97 (m, 3H), 1.94 (s, 3H), 1.48-1.58 (m, 1H), 0.64-0.73 (m, 1H), 0.45-0.53 (m, 1H), 0.22-0.35 (m, 2H).

LC-MS (Method 9): $R_t$=1.60 min; MS (ESIneg): m/z=374 [M−H]$^−$.

Example 222

3-{Cyclopropyl[2-fluoro-4-(trifluoromethyl)phenyl]methyl}-7-[(methylsulfanyl)methyl]-1H-indole

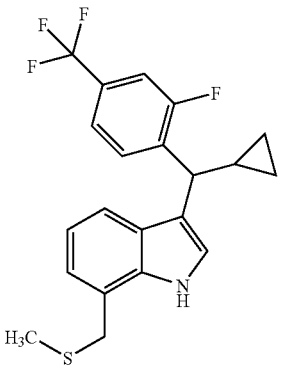

0.66 ml (8.61 mmol) of trifluoroacetic acid was added to 1.68 g (7.18 mmol) of the compound from Example 148A and 1.27 g (7.18 mmol) of the compound from Example 8A in 80 ml of dichloromethane, and the mixture was stirred at RT for 2 h. It was concentrated and the residue was purified by flash chromatography on silica gel (mobile phase: toluene/ethyl acetate 98/2) and preparative HPLC (RP18 column; mobile phase: acetonitrile/water gradient with addition of 0.1% formic acid) to result in 80.0 mg (3% of theory) of the title compound.

¹H-NMR (400 MHz, DMSO-d₆): δ=11.0 (s, 1H), 7.65 (t, 1H), 7.60 (d, 1H), 7.50 (d, 1H), 7.41 (d, 1H), 7.10 (d, 1H), 6.92 (d, 1H), 6.82 (t, 1H), 3.88-3.97 (m, 2H), 3.78 (d, 1H), 1.95 (s, 3H), 1.55-1.66 (m, 1H), 0.65-0.74 (m, 1H), 0.48-0.57 (m, 1H), 0.31-0.38 (m, 1H), 0.21-0.28 (m, 1H).

LC-MS (Method 9): R$_t$=1.43 min; MS (ESIneg): m/z=392 [M−H]⁻.

Example 223

3-{Cyclopropyl[4-(trifluoromethyl)phenyl]methyl}-7-[(methylsulfanyl)methyl]-1H-indole

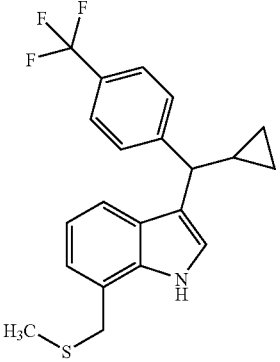

0.76 ml (9.82 mmol) of trifluoroacetic acid was added to 1.77 g (8.19 mmol) of the compound from Example 149A and 1.45 g (8.19 mmol) of the compound from Example 8A in 91 ml of dichloromethane, and the mixture was stirred at RT for 2 h. It was concentrated and the residue was purified by flash chromatography on silica gel (mobile phase: toluene/ethyl acetate 98/2) and preparative HPLC (RP18 column; mobile phase: acetonitrile/water gradient with addition of 0.1% formic acid) to result in 890 mg (29% of theory) of the title compound.

¹H-NMR (400 MHz, DMSO-d₆): δ=11.0 (s, 1H), 7.59-7.64 (m, 2H), 7.52-7.57 (m, 2H), 7.43 (d, 1H), 7.07 (d, 1H), 6.91 (d, 1H), 6.79 (t, 1H), 3.89-3.97 (m, 2H), 3.50 (d, 1H), 1.95 (s, 3H), 1.45-1.58 (m, 1H), 0.62-0.71 (m, 1H), 0.49-0.57 (m, 1H), 0.24-0.36 (m, 2H).

LC-MS (Method 4): R$_t$=1.62 min; MS (ESIneg): m/z=374 [M−H]⁻.

Example 224

3-{[2-Chloro-4-(trifluoromethyl)phenyl](cyclopropyl)methyl}-7-[(methylsulfanyl)methyl]-1H-indole

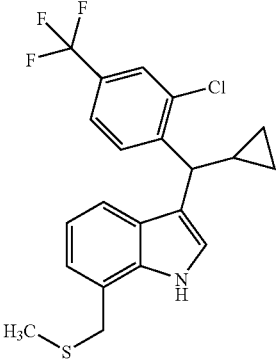

2.6 ml (33.8 mmol) of trifluoroacetic acid were added to 7.07 g (28.2 mmol) of the compound from Example 150A and 5.00 g (28.2 mmol) of the compound from Example 8A in 620 ml of dichloromethane, and the mixture was stirred at RT for 2 h. It was concentrated and the residue was purified by flash chromatography on silica gel (mobile phase: toluene/ethyl acetate 98/2) and preparative HPLC (RP18 column; mobile phase: acetonitrile/water gradient with addition of 0.1% formic acid) to result in 960 mg (7% of theory) of the title compound.

¹H-NMR (400 MHz, DMSO-d₆): δ=11.0 (s, 1H), 7.75 (d, 1H), 7.67 (s, 1H), 7.51 (d, 1H), 7.46 (s, 1H), 7.12 (d, 1H), 6.92 (d, 1H), 6.82 (t, 1H), 3.88-3.98 (m, 2H), 3.52 (d, 1H), 1.95 (s, 3H), 1.49-1.61 (m, 1H), 0.62-0.71 (m, 1H), 0.49-0.59 (m, 1H), 0.24-0.39 (m, 2H).

LC-MS (Method 9): R$_t$=1.45 min; MS (ESIneg): m/z=408 [M−H]⁻.

Example 225

3-[(4-Chloro-2-fluorophenyl)(cyclopropyl)methyl]-7-[(methylsulfanyl)methyl]-1H-indole

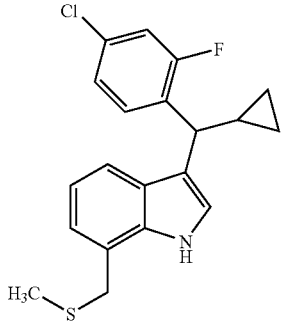

0.13 ml (1.73 mmol) of trifluoroacetic acid was added to 256 mg (1.45 mmol) of the compound from Example 8A and 290 mg (1.45 mmol) of the compound from Example 151A in 20 ml of dichloromethane, and the mixture was stirred at RT for 2 h. It was concentrated and the residue was purified by preparative HPLC (RP18 column; mobile phase: acetonitrile/water gradient with addition of 0.1% formic acid) to result in 273 mg (51% of theory) of the title compound.

¹H-NMR (400 MHz, DMSO-d₆): δ=11.0 (s, 1H), 7.31-7.43 (m, 3H), 7.19 (d, 1H), 7.08 (d, 1H), 6.91 (d, 1H), 6.81 (t, 1H), 3.87-3.97 (m, 2H), 3.69 (d, 1H), 1.95 (s, 3H), 1.49-1.61 (m, 1H), 0.62-0.72 (m, 1H), 0.46-0.55 (m, 1H), 0.27-0.35 (m, 1H), 0.18-0.26 (m, 1H).

LC-MS (Method 9): R$_t$=1.45 min; MS (ESIneg): m/z=358 [M−H]⁻.

Example 226

3-[Cyclopropyl(4-fluorophenyl)methyl]-7-[(methylsulfanyl)methyl]-1H-indole

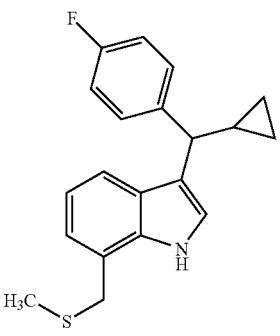

188 mg (1.13 mmol) of cyclopropyl(4-fluorophenyl)methanol and 0.10 ml (1.35 mmol) of trifluoroacetic acid were added to 200 mg (1.13 mmol) of the compound from Example 8A in 13 ml of dichloromethane. The reaction mixture was stirred at RT for 15 min, the solvent was removed in vacuo, and the crude product was then purified by preparative HPLC (mobile phase: acetonitrile/water gradient). 267 mg (73% of theory) of the title compound were obtained.

$^1$H-NMR (400 MHz, DMSO-$d_6$): δ=0.19-0.33 (m, 2H), 0.46-0.56 (m, 1H), 0.58-0.67 (m, 1H), 1.41-1.52 (m, 1H), 1.95 (s, 3H), 3.40 (d, 1H), 3.92 (s, 2H), 6.78 (t, 1H), 6.89 (d, 1H), 7.02-7.09 (m, 3H), 7.30-7.39 (m, 3H), 11.0 (s, 1H).

GC-MS (Method 7): $R_t$=9.72 min; MS (EIpos): m/z=325 [M]$^+$.

Example 227

3-[(4-Chlorophenyl)(cyclopropyl)methyl]-7-[(methylsulfanyl)methyl]-1H-indole

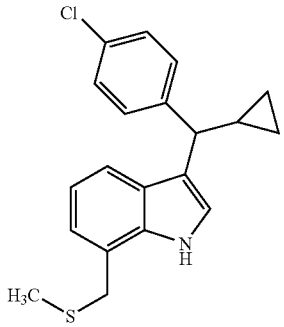

515 mg (2.82 mmol) of the compound from Example 153A and 0.26 ml (3.39 mmol) of trifluoroacetic acid were added to 500 mg (2.82 mmol) of the compound from Example 8A in 20 ml of dichloromethane. The reaction mixture was stirred at RT for 30 min, the solvent was removed in vacuo, and the crude product was then purified by preparative HPLC (mobile phase: acetonitrile/water gradient). 500 mg (50% of theory) of the title compound were obtained.

$^1$H-NMR (400 MHz, DMSO-$d_6$): δ=0.20-0.33 (m, 2H), 0.46-0.56 (m, 1H), 0.59-0.68 (m, 1H), 1.41-1.53 (m, 1H), 1.95 (s, 3H), 3.40 (d, 1H), 3.92 (s, 2H), 6.78 (t, 1H), 6.89 (d, 1H), 7.05 (d, 1H), 7.27-7.36 (m, 4H), 7.38 (d, 1H), 11.0 (s, 1H).

LC-MS (Method 4): $R_t$=1.61 min; MS (ESIneg): m/z=340 [M–H]$^-$.

Example 228

3-[Cyclopropyl(2,4-difluorophenyl)methyl]-7-[(methylsulfanyl)methyl]-1H-indole

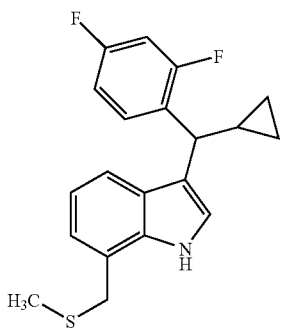

The title compound was prepared starting from 300 mg (1.69 mmol) of the compound from Example 8A and 312 mg (1.69 mmol) of the compound from Example 154A in analogy to the synthesis of the compound from Example 227. 170 mg (29% of theory) of the target compound were obtained.

$^1$H-NMR (400 MHz, DMSO-$d_6$): δ=0.17-0.34 (m, 2H), 0.46-0.55 (m, 1H), 0.62-0.71 (m, 1H), 1.49-1.61 (m, 1H), 1.95 (s, 3H), 3.68 (d, 1H), 3.92 (s, 2H), 6.81 (t, 1H), 6.91 (d, 1H), 7.08 (d, 1H), 7.14 (dt, 1H), 7.35-7.45 (m, 2H), 11.0 (s, 1H).

LC-MS (Method 4): $R_t$=1.56 min; MS (ESIneg): m/z=342 [M–H]$^-$.

Example 229

3-[(2-Chloro-4-fluorophenyl)(cyclopropyl)methyl]-7-[(methylsulfanyl)methyl]-1H-indole

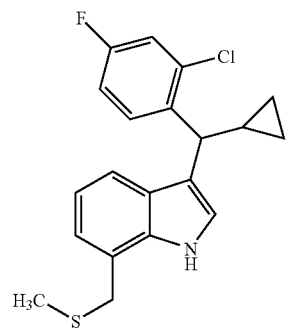

The title compound was prepared starting from 500 mg (2.82 mmol) of the compound from Example 8A and 566 mg (2.82 mmol) of the compound from Example 155A in analogy to the synthesis of the compound from Example 227. 394 mg (39% of theory) of the target compound were obtained.

$^1$H-NMR (400 MHz, DMSO-$d_6$): δ=0.22-0.34 (m, 2H), 0.44-0.53 (m, 1H), 0.63-0.72 (m, 1H), 1.47-1.58 (m, 1H), 1.95 (s, 3H), 3.88-3.97 (m, 3H), 6.81 (t, 1H), 6.91 (d, 1H), 7.07 (d, 1H), 7.12 (dt, 1H), 7.34-7.40 (m, 2H), 7.47 (dd, 1H), 11.0 (s, 1H).

LC-MS (Method 9): $R_t$=1.42 min; MS (ESIneg): m/z=358 [M–H]$^-$.

Example 230

3-[(4-Chloro-2,6-difluorophenyl)(cyclopropyl)methyl]-7-[(methylsulfanyl)methyl]-1H-indole

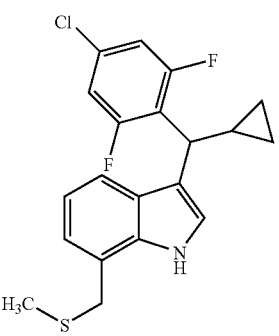

617 mg (2.82 mmol) of the compound from Example 156A and 0.26 ml (3.39 mmol) of trifluoroacetic acid were added to 500 mg (2.82 mmol) of the compound from Example 8A in 20 ml of dichloromethane. The reaction mixture was stirred at RT overnight, the solvent was removed in vacuo, and the crude product was then purified by preparative HPLC (mobile phase: acetonitrile/water gradient). 155 mg (14% of theory) of the title compound were obtained.

$^1$H-NMR (400 MHz, DMSO-d$_6$): δ=0.12-0.21 (m, 1H), 0.34-0.43 (m, 1H), 0.48-0.57 (m, 1H), 0.70-0.80 (m, 1H), 1.71-1.84 (m, 1H), 1.94 (s, 3H), 3.61 (d, 1H), 3.92 (s, 2H), 6.84 (t, 1H), 6.92 (d, 1H), 7.06 (d, 1H), 7.30 (d, 2H), 7.39 (d, 1H), 11.0 (s, 1H).

LC-MS (Method 4): R$_t$=1.66 min; MS (ESIneg): m/z=376 [M−H]$^−$.

Example 231

3-[Cyclopropyl(2,2-difluoro-1,3-benzodioxol-5-yl)methyl]-7-[(methylsulfanyl)methyl]-1H-indole

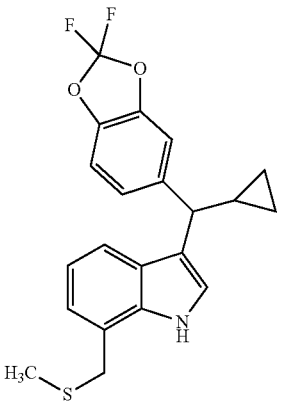

The title compound was prepared starting from 500 mg (2.82 mmol) of the compound from Example 8A and 644 mg (2.82 mmol) of the compound from Example 157A in analogy to the synthesis of the compound from Example 227. A difference was that stirring at RT was for 45 min. 661 mg (60% of theory) of the target compound were obtained.

$^1$H-NMR (400 MHz, DMSO-d$_6$): δ=0.21-0.35 (m, 2H), 0.46-0.56 (m, 1H), 0.60-0.69 (m, 1H), 1.45-1.56 (m, 1H), 1.95 (s, 3H), 3.42 (d, 1H), 3.92 (s, 2H), 6.80 (t, 1H), 6.90 (d, 1H), 7.10 (d, 1H), 7.16 (dd, 1H), 7.26 (d, 1H), 7.35 (d, 1H), 7.42 (d, 1H), 11.0 (s, 1H).

LC-MS (Method 4): R$_t$=1.63 min; MS (ESIneg): m/z=386 [M−H]$^−$.

Example 232

3-[(2-Chloro-4-fluorophenyl)(cyclopropyl)methyl]-5-fluoro-7-[(methylsulfanyl) methyl]-1H-indole

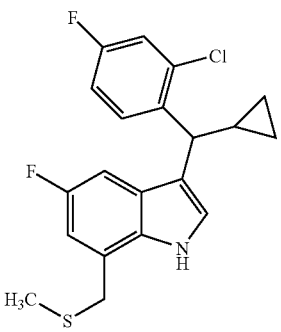

The title compound was prepared starting from 200 mg (1.02 mmol) of the compound from Example 11A and 206 mg (1.02 mmol) of the compound from Example 156A in analogy to the synthesis of the compound from Example 227. 247 mg (64% of theory) of the target compound were obtained.

$^1$H-NMR (400 MHz, DMSO-d$_6$): δ=0.19-0.37 (m, 2H), 0.45-0.54 (m, 1H), 0.63-0.72 (m, 1H), 1.48-1.59 (m, 1H), 1.96 (s, 3H), 3.68 (d, 1H), 3.92 (s, 2H), 6.76 (dd, 1H), 6.82 (dd, 1H), 7.15 (dt, 1H), 7.39 (dt, 1H), 7.42 (d, 1H), 7.51 (dd, 1H), 11.1 (s, 1H).

LC-MS (Method 9): R$_t$=1.41 min; MS (ESIneg): m/z=376 [M−H]$^−$.

Example 233

3-[(2-Chloro-4-fluorophenyl)(cyclopropyl)methyl]-6-fluoro-7-[(methylsulfanyl)methyl]-1H-indole

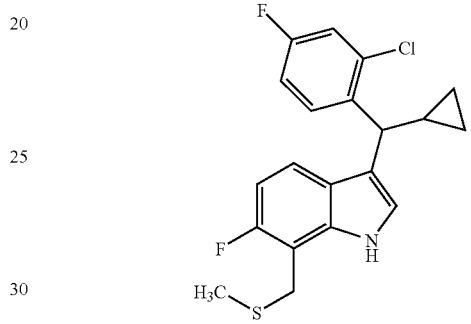

514 mg (2.56 mmol) of the compound from Example 156A and 0.24 ml (3.07 mmol) of trifluoroacetic acid were added to 500 mg (2.56 mmol) of the compound from Example 9A in 4 ml of dichloromethane. The reaction mixture was stirred at RT for 30 min, and the crude product was then purified three times by preparative HPLC (mobile phase: acetonitrile/water gradient) and once by flash chromatography on silica gel (mobile phase: cyclohexane/ethyl acetate 10/1). 404 mg (41% of theory) of the title compound were obtained.

$^1$H-NMR (400 MHz, DMSO-d$_6$): δ=0.21-0.35 (m, 2H), 0.44-0.53 (m, 1H), 0.64-0.74 (m, 1H), 1.46-1.57 (m, 1H), 1.99 (s, 3H), 3.91 (d, 1H), 3.95 (s, 2H), 6.75 (dd, 1H), 7.02 (dd, 1H), 7.14 (dt, 1H), 7.36-7.41 (m, 2H), 7.46 (dd, 1H), 11.1 (s, 1H).

HPLC (Method 1): R$_t$=5.15 min; DCI-MS (ESIpos): m/z=378 [M+H]$^+$.

Example 234

3-[(4-Chlorophenyl)(cyclopropyl)methyl]-6-fluoro-7-[(methylsulfanyl)methyl]-1H-indole

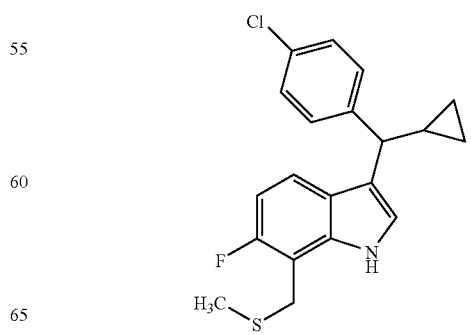

The title compound was prepared starting from 500 mg (2.56 mmol) of the compound from Example 9A and 468 mg (2.56 mmol) of the compound from Example 153A in analogy to the synthesis of the compound from Example 233. 411 mg (44% of theory) of the target compound were obtained.

$^1$H-NMR (400 MHz, DMSO-$d_6$): δ=0.20-0.32 (m, 2H), 0.46-0.55 (m, 1H), 0.60-0.68 (m, 1H), 1.40-1.50 (m, 1H), 1.99 (s, 3H), 3.39 (d, 1H), 3.96 (s, 2H), 6.71 (dd, 1H), 7.01 (dd, 1H), 7.27-7.35 (m, 4H), 7.41 (d, 1H), 11.1 (s, 1H).

HPLC (Method 1): $R_t$=5.09 min; DCI-MS (ESIpos): m/z=360 [M+H]$^+$.

Example 235

3-[(4-Chlorophenyl)(cyclopropyl)methyl]-7-[(methylsulfinyl)methyl]-1H-indole

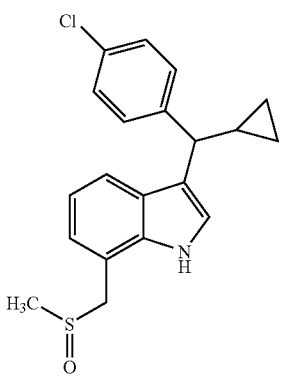

100 mg (0.29 mmol) of the compound from Example 227 were introduced into 15 ml of dichloromethane at 0° C., 72 mg (0.29 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 135 mg of the title compound as mixture of diastereomers.

$^1$H-NMR (400 MHz, DMSO-$d_6$): δ=0.20-0.34 (m, 2H), 0.47-0.56 (m, 1H), 0.59-0.68 (m, 1H), 1.41-1.52 (m, 1H), 2.47-2.53 (s, 3H), 3.41 (d, 1H), 4.23 (dd, 1H), 4.35 (dd, 1H), 6.84 (t, 1H), 6.97 (d, 1H), 7.12 (d, 1H), 7.27-7.36 (m, 4H), 7.45 (s, 1H), 11.1 (s, 1H).

LC-MS (Method 9): $R_t$=1.16 min; MS (ESIneg): m/z=356 [M−H]$^−$.

Example 236

3-[Cyclopropyl(2,4-difluorophenyl)methyl]-7-[(methylsulfinyl)methyl]-1H-indole

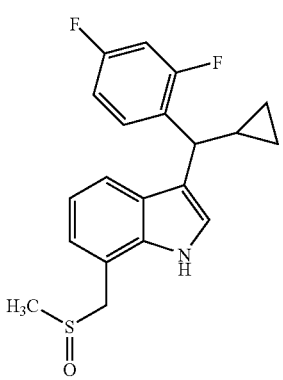

The title compound was prepared starting from 50 mg (0.15 mmol) of the compound from Example 228 in analogy to the synthesis of the compound from Example 235. 43 mg (82% of theory) of the target compound were obtained as mixture of diastereomers.

$^1$H-NMR (400 MHz, DMSO-$d_6$): δ=0.18-0.36 (m, 2H), 0.46-0.56 (m, 1H), 0.62-0.72 (m, 1H), 1.49-1.61 (m, 1H), 2.52 (s, 3H), 3.69 (d, 1H), 4.23 (dd, 1H), 4.35 (dd, 1H), 6.87 (t, 1H), 6.94-7.02 (m, 2H), 7.11-7.19 (m, 2H), 7.36-7.45 (m, 2H), 11.1 (s, 1H).

LC-MS (Method 9): $R_t$=1.12 min; MS (ESIneg): m/z=358 [M−H]$^−$.

Example 237

3-[(2-Chloro-4-fluorophenyl)(cyclopropyl)methyl]-7-[(methylsulfinyl)methyl]-1H-indole

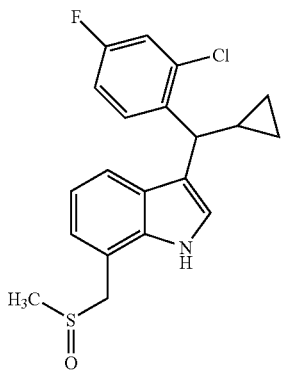

The title compound was prepared starting from 65 mg (0.18 mmol) of the compound from Example 229 in analogy to the synthesis of the compound from Example 235. 68 mg (100% of theory) of the target compound were obtained as mixture of diastereomers.

$^1$H-NMR (400 MHz, DMSO-$d_6$): δ=0.22-0.35 (m, 2H), 0.44-0.54 (m, 1H), 0.63-0.73 (m, 1H), 1.47-1.58 (m, 1H), 2.52 (s, 3H), 3.95 (d, 1H), 4.22 (dd, 1H), 4.35 (t, 1H), 6.87 (t, 1H), 6.98 (d, 1H), 7.09-7.16 (m, 2H), 7.36-7.49 (m, 3H), 11.1 (s, 1H).

LC-MS (Method 9): $R_t$=1.19 min; MS (ESIneg): m/z=374 [M−H]$^−$.

Example 238

3-[(4-Chloro-2,6-difluorophenyl)(cyclopropyl)methyl]-7-[(methylsulfinyl)methyl]-1H-indole

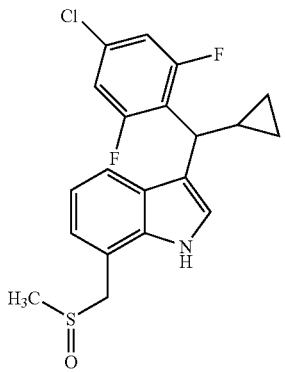

The title compound was prepared starting from 150 mg (0.25 mmol) of the compound from Example 230 in analogy to the synthesis of the compound from Example 235. 75 mg (77% of theory) of the target compound were obtained as mixture of diastereomers.

$^1$H-NMR (400 MHz, DMSO-d$_6$): δ=0.12-0.22 (m, 1H), 0.35-0.44 (m, 1H), 0.48-0.57 (m, 1H), 0.70-0.80 (m, 1H), 1.71-1.83 (m, 1H), 2.51 (s, 3H), 3.62 (d, 1H), 4.23 (dd, 1H), 4.35 (t, 1H), 6.90 (t, 1H), 6.99 (d, 1H), 7.13 (d, 1H), 7.30 (d, 2H), 7.47 (s, 1H), 11.1 (s, 1H).

LC-MS (Method 9): R$_t$=1.21 min; MS (ESIneg): m/z=392 [M−H]$^−$.

Example 239

3-[Cyclopropyl(2,2-difluoro-1,3-benzodioxol-5-yl)methyl]-7-[(methylsulfinyl)methyl]-1H-indole

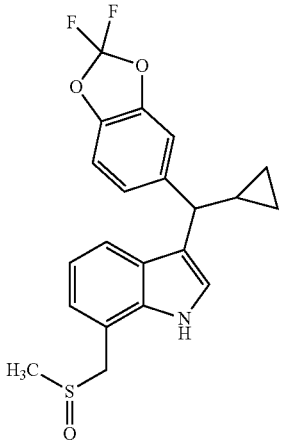

The title compound was prepared starting from 100 mg (0.26 mmol) of the compound from Example 231 in analogy to the synthesis of the compound from Example 235. 92 mg (88% of theory) of the target compound were obtained as mixture of diastereomers.

$^1$H-NMR (400 MHz, DMSO-d$_6$): δ=0.21-0.36 (m, 2H), 0.47-0.56 (m, 1H), 0.60-0.69 (m, 1H), 1.45-1.55 (m, 1H), 2.53 (s, 3H), 3.44 (d, 1H), 4.23 (dd, 1H), 4.35 (t, 1H), 6.85 (t, 1H), 6.98 (d, 1H), 7.17 (t, 2H), 7.26 (d, 1H), 7.35 (d, 1H), 7.48 (s, 1H), 11.1 (s, 1H).

LC-MS (Method 9): R$_t$=1.19 min; MS (ESIneg): m/z=402 [M−H]$^−$.

Example 240

3-[(4-Chlorophenyl)(cyclopropyl)methyl]-6-fluoro-7-[(methylsulfinyl)methyl]-1H-indole

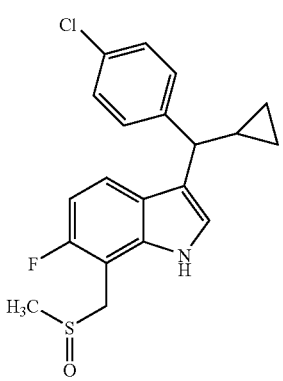

The title compound was prepared starting from 119 mg (0.33 mmol) of the compound from Example 234 in analogy to the synthesis of the compound from Example 196. A difference was that stirring was at 0° C. for 2 h, followed by warming to RT. 92 mg (74% of theory) of the target compound were obtained as mixture of diastereomers.

$^1$H-NMR (400 MHz, DMSO-d$_6$): δ=0.21-0.33 (m, 2H), 0.47-0.56 (m, 1H), 0.59-0.68 (m, 1H), 1.39-1.50 (m, 1H), 2.58 (d, 3H), 3.40 (d, 1H), 4.27-4.37 (m, 2H), 6.77 (dd, 1H), 7.06-7.12 (m, 1H), 7.28-7.35 (m, 4H), 7.44-7.47 (m, 1H), 11.2 (s, 1H).

HPLC (Method 1): R$_t$=4.61 min; MS (ESIpos): m/z=376 [M+H]$^+$.

Example 241

3-[(2-Chloro-4-fluorophenyl)(cyclopropyl)methyl]-6-fluoro-7-[(methylsulfinyl)methyl]-1H-indole

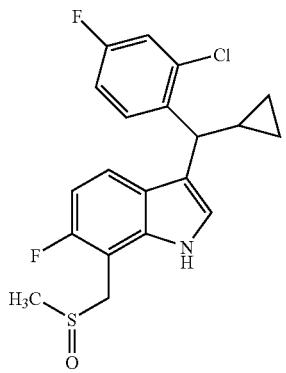

The title compound was prepared starting from 115 mg (0.30 mmol) of the compound from Example 233 in analogy to the synthesis of the compound from Example 196. A difference was that stirring was at 0° C. for 2 h, followed by warming to RT. 85 mg (71% of theory) of the target compound were obtained as mixture of diastereomers.

$^1$H-NMR (400 MHz, DMSO-d$_6$): δ=0.21-0.36 (m, 2H), 0.44-0.54 (m, 1H), 0.63-0.73 (m, 1H), 1.46-1.57 (m, 1H), 2.58 (d, 3H), 3.92 (d, 1H), 4.27-4.37 (m, 2H), 6.81 (dd, 1H), 7.07-7.17 (m, 2H), 7.37-7.49 (m, 3H), 11.2 (s, 1H).

HPLC (Method 1): R$_t$=4.67 min; MS (ESIpos): m/z=394 [M+H]$^+$.

Example 242

3-[Cyclopropyl(2,4-dichlorophenyl)methyl]-7-[(methylsulfonyl)methyl]-1H-indole

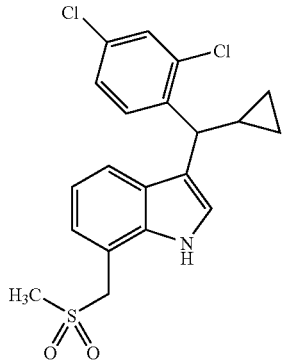

361 mg (1.46 mmol) of 70% pure meta-chloroperbenzoic acid were added to 290 mg (0.77 mmol) of the compound from Example 221 in 43 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 205 mg (65% of theory) of the title compound.

$^1$H-NMR (400 MHz, DMSO-$d_6$): δ=11.1 (s, 1H), 7.57 (d, 1H), 7.43-7.47 (m, 2H), 7.33 (dd, 1H), 7.18 (d, 1H), 7.09 (d, 1H), 6.92 (t, 1H), 4.67-4.77 (m, 2H), 3.95 (d, 1H), 2.88 (s, 3H), 1.47-1.58 (m, 1H), 0.65-0.73 (m, 1H), 0.45-0.54 (m, 1H), 0.22-0.37 (m, 2H).

LC-MS (Method 9): $R_t$=1.37 min; MS (ESIneg): m/z=406 [M−H]$^−$.

Example 243

3-{Cyclopropyl[2-fluoro-4-(trifluoromethyl)phenyl]methyl}-7-[(methylsulfonyl)methyl]-1H-indole

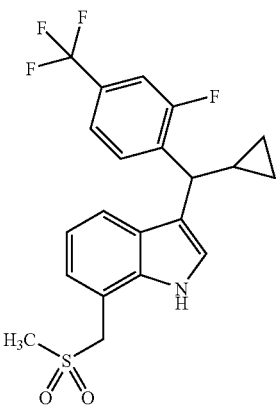

53.6 mg (0.22 mmol) of 70% pure meta-chloroperbenzoic acid were added to 45.0 mg (0.11 mmol) of the compound from Example 222 in 15 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 22.0 mg (45% of theory) of the title compound.

$^1$H-NMR (400 MHz, DMSO-$d_6$): δ=11.1 (s, 1H), 7.65 (t, 1H), 7.60 (d, 1H), 7.48-7.53 (m, 2H), 7.22 (d, 1H), 7.10 (d, 1H), 6.92 (t, 1H), 4.67-4.77 (m, 2H), 3.79 (d, 1H), 2.89 (s, 3H), 1.55-1.67 (m, 1H), 0.65-0.74 (m, 1H), 0.49-0.58 (m, 1H), 0.32-0.40 (m, 1H), 0.21-0.29 (m, 1H).

LC-MS (Method 4): $R_t$=1.44 min; MS (ESIneg): m/z=424 [M−H]$^−$.

Example 244

3-{Cyclopropyl[4-(trifluoromethyl)phenyl]methyl}-7-[(methylsulfonyl)methyl]-1H-indole

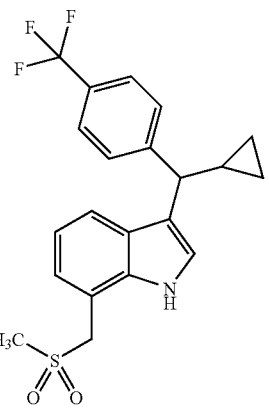

233 mg (0.95 mmol) of 70% pure meta-chloroperbenzoic acid were added to 187 mg (0.50 mmol) of the compound from Example 223 in 50 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 112 mg (55% of theory) of the title compound.

$^1$H-NMR (400 MHz, DMSO-$d_6$): δ=11.1 (s, 1H), 7.60-7.64 (m, 2H), 7.52-7.57 (m, 2H), 7.51 (d, 1H), 7.18 (d, 1H), 7.08 (d, 1H), 6.88 (t, 1H), 4.67-4.77 (m, 2H), 3.52 (d, 1H), 2.89 (s, 3H), 1.47-1.58 (m, 1H), 0.63-0.71 (m, 1H), 0.49-0.57 (m, 1H), 0.25-0.37 (m, 2H).

LC-MS (Method 4): $R_t$=1.41 min; MS (ESIneg): m/z=406 [M−H]$^−$.

Example 245

3-{[2-Chloro-4-(trifluoromethyl)phenyl](cyclopropyl)methyl}-7-[(methylsulfonyl)methyl]-1H-indole

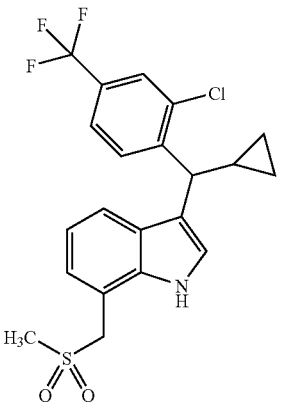

61.8 mg (0.25 mmol) of 70% pure meta-chloroperbenzoic acid were added to 54.1 mg (0.13 mmol) of the compound from Example 224 in 15 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 40.0 mg (69% of theory) of the title compound.

$^1$H-NMR (400 MHz, DMSO-$d_6$): δ=11.1 (s, 1H), 7.83 (s, 1H), 7.70 (d, 1H), 7.64 (d, 1H), 7.48 (d, 1H), 7.20 (d, 1H), 7.10 (d, 1H), 6.92 (t, 1H), 4.67-4.77 (m, 2H), 4.03 (d, 1H), 2.89 (s, 3H), 1.53-1.64 (m, 1H), 0.67-0.76 (m, 1H), 0.47-0.56 (m, 1H), 0.33-0.41 (m, 1H), 0.25-0.33 (m, 1H).

LC-MS (Method 9): $R_t$=1.29 min; MS (ESIneg): m/z=440 [M−H]$^-$.

Example 246

3-[(4-Chloro-2-fluorophenyl)(cyclopropyl)methyl]-7-[(methylsulfonyl)methyl]-1H-indole

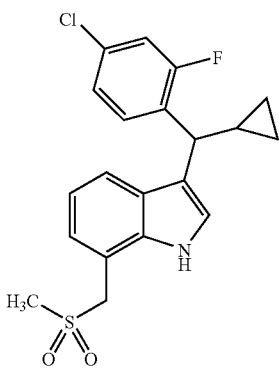

250 mg (1.01 mmol) of 70% pure meta-chloroperbenzoic acid were added to 192 mg (0.53 mmol) of the compound from Example 225 in 30 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 123 mg (56% of theory) of the title compound.

$^1$H-NMR (400 MHz, DMSO-$d_6$): δ=11.1 (s, 1H), 7.45 (d, 1H), 7.40 (t, 1H), 7.35 (dd, 1H), 7.17-7.22 (m, 2H), 7.09 (d, 1H), 6.91 (t, 1H), 4.67-4.77 (m, 2H), 3.71 (d, 1H), 2.89 (s, 3H), 1.50-1.61 (m, 1H), 0.63-0.73 (m, 1H), 0.47-0.56 (m, 1H), 0.28-0.36 (m, 1H), 0.18-0.27 (m, 1H).

LC-MS (Method 9): $R_t$=1.30 min; MS (ESIneg): m/z=390 [M−H]$^-$.

Example 247

3-[(2-Chloro-4-methylphenyl)(cyclopropyl)methyl]-7-[(methylsulfonyl)methyl]-1H-indole

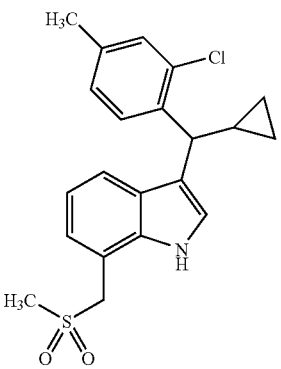

135 mg (0.61 mmol) of indium(III) chloride and 0.07 ml (0.92 mmol) of trifluoroacetic acid were added to 132 mg (0.61 mmol) of the compound from Example 86A and 100 mg (0.51 mmol) of the compound from Example 152A in 5 ml of dichloromethane, and the mixture was stirred at RT overnight. It was concentrated and the residue was purified by preparative HPLC (RP18 column; mobile phase: acetonitrile/water gradient with addition of 0.1% formic acid) to result in 29.0 mg (15% of theory) of the title compound.

$^1$H-NMR (400 MHz, DMSO-$d_6$): δ=11.0 (s, 1H), 7.46 (d, 1H), 7.29 (d, 1H), 7.18-7.23 (m, 2H), 7.08 (d, 1H), 6.99 (dd, 1H), 6.90 (t, 1H), 4.67-4.77 (m, 2H), 3.92 (d, 1H), 2.89 (s, 3H), 2.20 (s, 3H), 1.49-1.59 (m, 1H), 0.63-0.73 (m, 1H), 0.43-0.51 (m, 1H), 0.23-0.34 (m, 2H).

LC-MS (Method 4): $R_t$=1.43 min; MS (ESIneg): m/z=386 [M−H]$^-$.

Example 248

3-[Cyclopropyl(4-fluorophenyl)methyl]-7-[(methylsulfonyl)methyl]-1H-indole

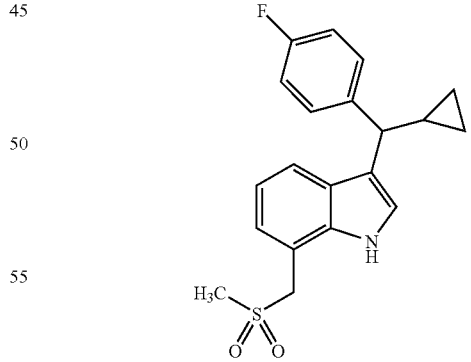

160 mg (0.49 mmol) of the compound from Example 226 were introduced into 33 ml of dichloromethane at 0° C., 242 mg (0.49 mmol) of 70% pure meta-chloroperbenzoic acid were added, and the mixture was stirred at 0° C. for 2 h. 2 ml of methanol were added, and the solution was concentrated. The crude product was purified by preparative HPLC (mobile phase: acetonitrile/water gradient) to result in 118 mg (67% of theory) of the title compound.

¹H-NMR (400 MHz, DMSO-d₆): δ=0.21-0.33 (m, 2H), 0.47-0.56 (m, 1H), 0.59-0.68 (m, 1H), 1.42-1.53 (m, 1H), 2.89 (s, 3H), 3.42 (d, 1H), 4.72 (q, 2H), 6.87 (t, 1H), 7.02-7.10 (m, 2H), 7.17 (d, 1H), 7.30-7.37 (m, 2H), 7.45 (d, 1H), 11.1 (s, 1H).

LC-MS (Method 9): $R_t$=1.15 min; MS (ESIneg): m/z=356 [M−H]⁻.

Example 249

3-[(4-Chlorophenyl)(cyclopropyl)methyl]-7-[(methylsulfonyl)methyl]-1H-indole

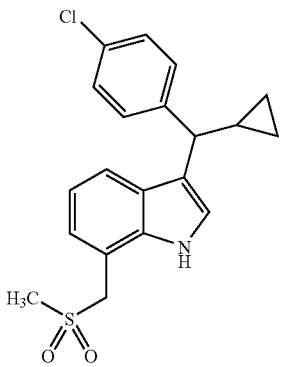

350 mg (1.20 mmol) of the compound from Example 227 were introduced into 40 ml of dichloromethane at 0° C., 505 mg (1.20 mmol) of 70% pure meta-chloroperbenzoic acid were added, and the mixture was stirred at RT for 2 h. 5 ml of methanol were added, and the solution was concentrated. The crude product was purified by preparative HPLC (mobile phase: acetonitrile/water gradient) to result in 243 mg (63% of theory) of the title compound.

¹H-NMR (400 MHz, DMSO-d₆): δ=0.21-0.34 (m, 2H), 0.47-0.56 (m, 1H), 0.60-0.69 (m, 1H), 1.41-1.52 (m, 1H), 2.89 (s, 3H), 3.42 (d, 1H), 4.72 (s, 2H), 6.88 (t, 1H), 7.07 (d, 1H), 7.17 (d, 1H), 7.30 (d, 2H), 7.38 (d, 2H), 7.47 (s, 1H), 11.1 (s, 1H).

LC-MS (Method 9): $R_t$=1.21 min; MS (ESIneg): m/z=372 [M−H]⁻.

Example 250

3-[Cyclopropyl(2,4-difluorophenyl)methyl]-7-[(methylsulfonyl)methyl]-1H-indole

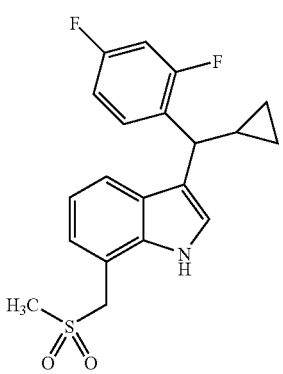

The title compound was prepared starting from 80 mg (0.23 mmol) of the compound from Example 228 in analogy to the synthesis of the compound from Example 249. 62 mg (66% of theory) of the target compound were obtained.

¹H-NMR (400 MHz, DMSO-d₆): δ=0.18-0.35 (m, 2H), 0.47-0.56 (m, 1H), 0.63-0.72 (m, 1H), 1.50-1.621 (m, 1H), 2.89 (s, 3H), 3.69 (d, 1H), 4.72 (q, 1H), 6.91 (t, 1H), 6.98 (dt, 1H), 7.09 (d, 1H), 7.11-7.22 (m, 2H), 7.37-7.47 (m, 2H), 11.1 (s, 1H).

LC-MS (Method 9): $R_t$=1.17 min; MS (ESIneg): m/z=374 [M−H]⁻.

Example 251

3-[(2-Chloro-4-fluorophenyl)(cyclopropyl)methyl]-7-[(methylsulfonyl)methyl]-1H-indole

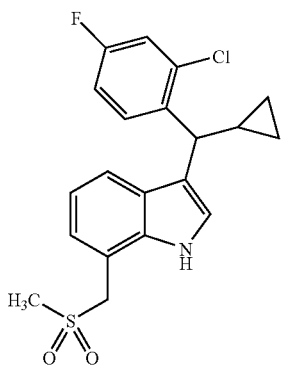

The title compound was prepared starting from 285 mg (0.79 mmol) of the compound from Example 229 in analogy to the synthesis of the compound from Example 249. A difference was that the reaction solution was washed with saturated aqueous sodium bicarbonate solution before purification. 219 mg (71% of theory) of the target compound were obtained.

¹H-NMR (400 MHz, DMSO-d₆): δ=0.22-0.36 (m, 2H), 0.45-0.54 (m, 1H), 0.64-0.73 (m, 1H), 1.48-1.59 (m, 1H), 2.89 (s, 3H), 3.95 (d, 1H), 4.72 (q, 2H), 6.91 (t, 1H), 7.06-7.21 (m, 3H), 7.39 (dd, 1H), 7.42-7.49 (m, 2H), 11.1 (s, 1H).

LC-MS (Method 9): $R_t$=1.23 min; MS (ESIneg): m/z=390 [M−H]⁻.

Example 252

3-[(4-Chloro-2,6-difluorophenyl)(cyclopropyl)methyl]-7-[(methylsulfonyl)methyl]-1H-indole

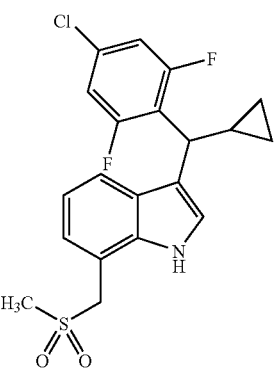

104 mg (0.48 mmol) of the compound from Example 156A and 0.04 ml (0.57 mmol) of trifluoroacetic acid were added to 100 mg (0.48 mmol) of the compound from Example 86A in 4 ml of dichloromethane. The reaction mixture was stirred at RT for 45 min, the solvent was removed in vacuo, and the crude product was then purified by preparative HPLC (mobile phase: acetonitrile/water gradient). 100 mg (51% of theory) of the title compound were obtained.

$^1$H-NMR (400 MHz, DMSO-$d_6$): δ=0.13-0.22 (m, 1H), 0.36-0.44 (m, 1H), 0.48-0.58 (m, 1H), 0.70-0.80 (m, 1H), 1.72-1.83 (m, 1H), 2.88 (s, 3H), 3.62 (d, 1H), 4.73 (q, 2H), 6.94 (t, 1H), 7.10 (d, 1H), 7.18 (d, 1H), 7.30 (d, 2H), 7.48 (d, 1H), 11.1 (s, 1H).

LC-MS (Method 9): $R_t$=1.25 min; MS (ESIneg): m/z=408 [M−H]$^-$.

Example 253

3-[Cyclopropyl(2,2-difluoro-1,3-benzodioxol-5-yl)methyl]-7-[(methylsulfonyl)methyl]-1H-indole

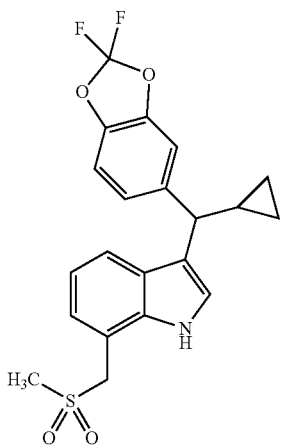

The title compound was prepared starting from 500 mg (1.29 mmol) of the compound from Example 231 in analogy to the synthesis of the compound from Example 249. A difference was that the reaction solution was washed with saturated aqueous sodium bicarbonate solution before purification. 311 mg (57% of theory) of the target compound were obtained.

$^1$H-NMR (400 MHz, DMSO-$d_6$): δ=0.22-0.36 (m, 2H), 0.47-0.56 (m, 1H), 0.61-0.70 (m, 1H), 1.45-1.56 (m, 1H), 2.89 (s, 3H), 3.44 (d, 1H), 4.72 (q, 2H), 6.89 (t, 1H), 7.08 (d, 1H), 7.16 (dd, 1H), 7.22 (d, 1H), 7.26 (d, 1H), 7.36 (d, 1H), 7.49 (d, 1H), 11.1 (s, 1H).

LC-MS (Method 4): $R_t$=1.42 min; MS (ESIneg): m/z=418 [M−H]$^-$.

Example 254

3-[(4-Chlorophenyl)(cyclopropyl)methyl]-5-fluoro-7-[(methylsulfonyl)methyl]-1H-indole

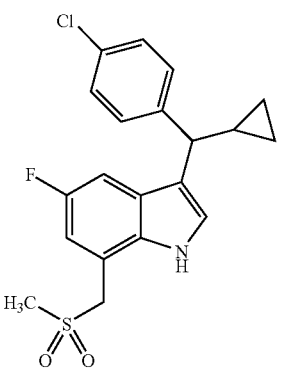

64 mg (0.35 mmol) of the compound from Example 153A and 0.03 ml (0.42 mmol) of trifluoroacetic acid were added to 80 mg (0.35 mmol) of the compound from Example 87A in 2.5 ml of dichloromethane. The reaction mixture was stirred at RT for 45 min, the solvent was removed in vacuo, and the crude product was then purified by preparative HPLC (mobile phase: acetonitrile/water gradient). 110 mg (80% of theory) of the title compound were obtained.

$^1$H-NMR (400 MHz, DMSO-$d_6$): δ=0.21-0.31 (m, 2H), 0.48-0.55 (m, 1H), 0.60-0.68 (m, 1H), 1.42-1.52 (m, 1H), 2.92 (s, 3H), 3.40 (d, 1H), 4.75 (q, 2H), 6.88-6.99 (m, 2H), 7.29-7.37 (m, 4H), 7.55 (d, 1H), 11.2 (s, 1H).

LC-MS (Method 9): $R_t$=1.22 min; MS (ESIneg): m/z=390 [M−H]$^-$.

Example 255

3-[(2-Chloro-4-fluorophenyl)(cyclopropyl)methyl]-5-fluoro-7-[(methylsulfonyl)methyl]-1H-indole

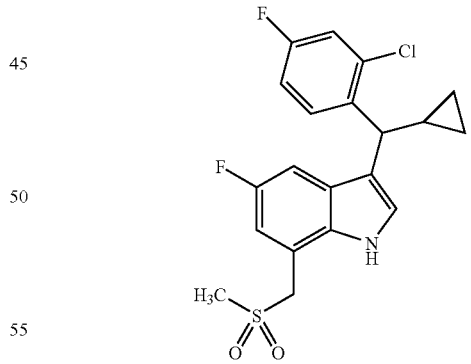

The title compound was prepared starting from 180 mg (0.48 mmol) of the compound from Example 232 in analogy to the synthesis of the compound from Example 249. 145 mg (74% of theory) of the target compound were obtained.

$^1$H-NMR (400 MHz, DMSO-$d_6$): δ=0.19-0.28 (m, 1H), 0.30-0.38 (m, 1H), 0.46-0.54 (m, 1H), 0.64-0.72 (m, 1H), 1.49-1.60 (m, 1H), 2.92 (s, 3H), 3.87 (d, 1H), 4.75 (q, 2H), 6.90 (dd, 1H), 6.98 (dd, 1H), 7.16 (dt, 1H), 7.40 (dd, 1H), 7.48-7.54 (m, 2H), 11.2 (s, 1H).

LC-MS (Method 9): $R_t$=1.24 min; MS (ESIneg): m/z=408 [M−H]$^-$.

Example 256

3-[(4-Chloro-2,6-difluorophenyl)(cyclopropyl)methyl]-5-fluoro-7-[(methylsulfonyl)methyl]-1H-indole

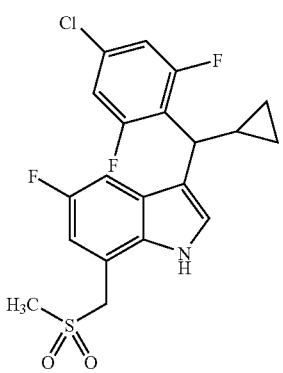

96 mg (0.44 mmol) of the compound from Example 156A and 0.04 ml (0.53 mmol) of trifluoroacetic acid were added to 100 mg (0.44 mmol) of the compound from Example 87A in 3 ml of dichloromethane. The reaction mixture was stirred at RT for 45 min, the solvent was removed in vacuo, and the crude product was then purified by preparative HPLC (mobile phase: acetonitrile/water gradient). 162 mg (86% of theory) of the title compound were obtained.

$^1$H-NMR (400 MHz, DMSO-$d_6$): δ=0.12-0.21 (m, 1H), 0.38-0.48 (m, 1H), 0.48-0.57 (m, 1H), 0.69-0.79 (m, 1H), 1.70-1.83 (m, 1H), 2.91 (s, 3H), 3.59 (d, 1H), 4.75 (q, 2H), 6.89 (dd, 1H), 6.99 (dd, 1H), 7.33 (d, 2H), 7.56 (d, 1H), 11.2 (s, 1H).

LC-MS (Method 4): $R_t$=1.46 min; MS (ESIneg): m/z=426 [M–H]$^-$.

Example 257

3-[Cyclopropyl(2,2-difluoro-1,3-benzodioxol-5-yl)methyl]-5-fluoro-7-[(methylsulfonyl)methyl]-1H-indole

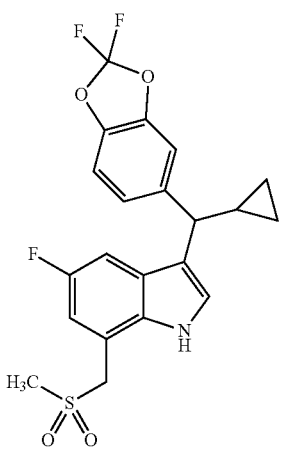

100 mg (0.44 mmol) of the compound from Example 157A and 0.04 ml (0.53 mmol) of trifluoroacetic acid were added to 100 mg (0.44 mmol) of the compound from Example 87A in 5 ml of dichloromethane. The reaction mixture was stirred at RT for 45 min, the solvent was removed in vacuo, and the crude product was then purified by preparative HPLC (mobile phase: acetonitrile/water gradient). 151 mg (78% of theory) of the title compound were obtained.

$^1$H-NMR (400 MHz, DMSO-$d_6$): δ=0.21-0.34 (m, 2H), 0.47-0.55 (m, 1H), 0.60-0.69 (m, 1H), 1.46-1.57 (m, 1H), 2.92 (s, 3H), 3.42 (d, 1H), 4.75 (s, 2H), 6.97 (dd, 1H), 7.01 (dd, 1H), 7.17 (dd, 1H), 7.28 (d, 1H), 7.38 (d, 1H), 7.58 (d, 1H), 11.2 (s, 1H).

LC-MS (Method 9): $R_t$=1.22 min; MS (ESIneg): m/z=436 [M–H]$^-$.

Example 258

3-[(4-Chlorophenyl)(cyclopropyl)methyl]-6-fluoro-7-[(methylsulfonyl)methyl]-1H-indole

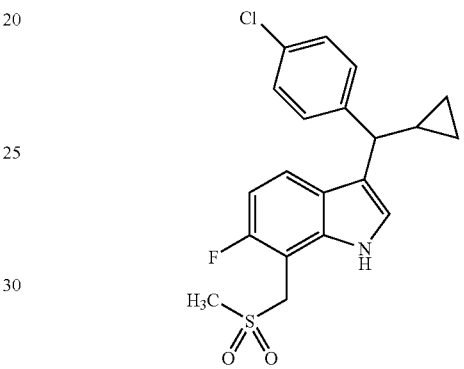

The title compound was prepared starting from 238 mg (0.66 mmol) of the compound from Example 234 in analogy to the synthesis of the compound from Example 209. 144 mg (55% of theory) of the target compound were obtained.

$^1$H-NMR (400 MHz, DMSO-$d_6$): δ=0.22-0.33 (m, 2H), 0.47-0.56 (m, 1H), 0.60-0.68 (m, 1H), 1.40-1.51 (m, 1H), 2.96 (s, 3H), 3.41 (d, 1H), 4.74 (s, 2H), 6.79 (dd, 1H), 7.15 (dd, 1H), 7.28-7.36 (m, 4H), 7.47 (d, 1H), 11.2 (s, 1H).

HPLC (Method 1): $R_t$=4.66 min; MS (ESIpos): m/z=392 [M+H]$^+$.

Example 259

3-[(2-Chloro-4-fluorophenyl)(cyclopropyl)methyl]-6-fluoro-7-[(methylsulfonyl)methyl]-1H-indole

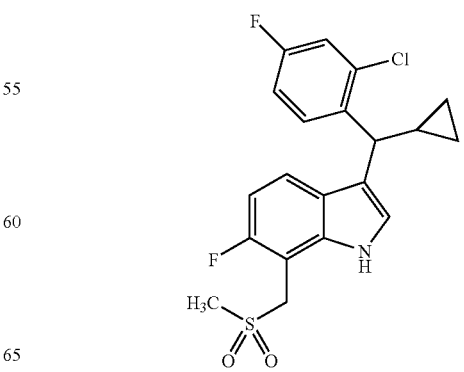

The title compound was prepared starting from 230 mg (0.61 mmol) of the compound from Example 233 in analogy to the synthesis of the compound from Example 249. A difference was that stirring was at 0° C. for 2 h, followed by warming to RT. 166 mg (66% of theory) of the target compound were obtained.

$^1$H-NMR (400 MHz, DMSO-d$_6$): δ=0.21-0.37 (m, 2H), 0.45-0.54 (m, 1H), 0.64-0.73 (m, 1H), 1.47-1.58 (m, 1H), 2.96 (s, 3H), 3.92 (d, 1H), 4.74 (s, 2H), 6.84 (dd, 1H), 7.10-7.19 (m, 2H), 7.39 (dd, 1H), 7.42-7.50 (m, 2H), 11.2 (s, 1H).

HPLC (Method 1): R$_t$=4.71 min; MS (ESIpos): m/z=410 [M+H]$^+$.

Example 260

2-[{5-Fluoro-7-[(methylsulfanyl)methyl]-1H-indol-3-yl}(4-methylphenyl)methyl]cyclopropane-carbonitrile [trans-diastereomer mixture]

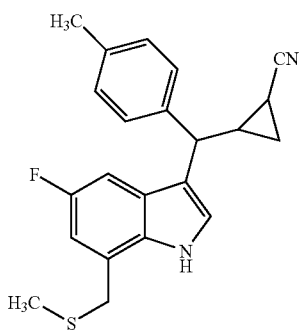

130 mg (0.59 mmol) of indium(III) chloride and 0.05 ml (0.64 mmol) of trifluoroacetic acid were added to 104 mg (0.53 mmol) of the compound from Example 11A and 100 mg (0.53 mmol) of the compound from Example 158A in 6 ml of dichloromethane, and the mixture was stirred under reflux for 1 h. It was diluted with dichloromethane and washed with saturated aqueous sodium bicarbonate solution and water, dried over magnesium sulfate, filtered and concentrated. The residue was purified by preparative HPLC (RP18 column; mobile phase: acetonitrile/water gradient with addition of 0.1% formic acid) to result in 39.6 mg (20% of theory) of the title compound as mixture of diastereomers.

$^1$H-NMR (400 MHz, DMSO-d$_6$): δ=11.1 (s, 1H), 7.21-7.25 (m, 2H), 7.09-7.13 (m, 2H), 6.75-6.83 (m, 2H), 3.87-3.95 (m, 2H), 3.52 (d, 1H), 2.21-2.31 (m, 4H), 1.95 (s, 3H), 1.63-1.69 (m, 1H), 1.35-1.41 (m, 1H), 1.00-1.06 (m, 1H).

LC-MS (Method 9): R$_t$=1.25 min; MS (ESIneg): m/z=363 [M−H]$^-$.

Example 261

3-[(4-Chlorophenyl)(2,2-difluorocyclopropyl)methyl]-7-[(methylsulfonyl)methyl]-1H-indole

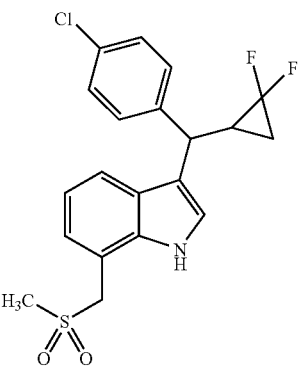

In three parallel batches in each case 3.08 g (13.9 mmol) of indium(III) chloride and 1.6 ml (20.9 mmol) of trifluoroacetic acid were added to in each case 2.54 g (11.6 mmol) of the compound from Example 159A and 2.92 g (13.9 mmol) of the compound from Example 86A in 125 ml of 1,2-dichloroethane, and the mixture was heated under reflux overnight. It was diluted in each case with dichloromethane, and the three batches were combined and washed with saturated aqueous sodium bicarbonate solution, water and saturated aqueous sodium chloride solution, dried over magnesium sulfate, filtered through kieselguhr and concentrated. The residue was purified by preparative SFC (ethylpyridine column; mobile phase: carbon dioxide/methanol gradient; 150 bar; 35° C.) to result in 995 mg (7% of theory) of the title compound as mixture of diastereomers.

The enantiomers were separated by preparative HPLC on a chiral phase [column: chiral silica gel phase based on the selector poly(N-methacryloyl-L-isoleucine 3-pentylamide), 10 μm, 250 mm×20 mm; eluent: linear gradient isohexane/ethyl acetate 9:1→2:8 in 27 minutes; flow rate: 25.0 ml/min; temperature: RT; UV detection: 265 nm]. 173 mg of enantiomer 261-1 and 154 mg of enantiomer 261-2 were obtained.
Enantiomer 261-1:

R$_t$=4.32 min [column: chiral silica gel phase based on the selector poly(N-methacryloyl-L-isoleucine 3-pentylamide), 10 μm, 250 mm×4.6 mm; eluent: isohexane/ethyl acetate 6:4; flow rate: 2.0 ml/min; temperature: RT; UV detection: 265 nm].

1H-NMR (400 MHz, DMSO-d$_6$): δ=11.1 (s, 1H), 7.45 (d, 1H), 7.41-7.45 (m, 2H), 7.31-7.36 (m, 2H), 7.24 (d, 1H), 7.11 (d, 1H), 6.92 (t, 1H), 4.68-4.78 (m, 2H), 3.94 (d, 1H), 2.90 (s, 3H), 2.51-2.65 (m, 1H), 1.56-1.68 (m, 1H), 1.32-1.42 (m, 1H).

LC-MS (Method 9): Rt=1.15 min; MS (ESIneg): m/z=408 [M−H]$^-$.
Enantiomer 261-2:

R$_t$=5.11 min [column: chiral silica gel phase based on the selector poly(N-methacryloyl-L-isoleucine 3-pentylamide), 10 μm, 250 mm×4.6 mm; eluent: isohexane/ethyl acetate 2:8; flow rate: 2.0 ml/min; temperature: RT; UV detection: 265 nm].

1H-NMR (400 MHz, DMSO-d$_6$): δ=11.1 (s, 1H), 7.55 (d, 1H), 7.30-7.38 (m, 4H), 7.26 (d, 1H), 7.10 (d, 1H), 6.91 (t, 1H), 4.67-4.77 (m, 2H), 3.98 (d, 1H), 2.89 (s, 3H), 2.51-2.64 (m, 1H), 1.67-1.78 (m, 1H), 1.25-1.37 (m, 1H).

LC-MS (Method 9): R$_t$=1.16 min; MS (ESIneg): m/z=408 [M−H]$^-$.

Example 262

3-[(4-Chlorophenyl)(2,2-difluorocyclopropyl)methyl]-5-fluoro-7-[(methylsulfonyl)methyl]-1H-indole

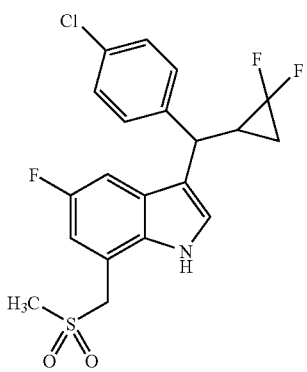

97.1 mg (0.44 mmol) of indium(III) chloride and 0.05 ml (0.07 mmol) of trifluoroacetic acid were added to 80.0 mg (0.37 mmol) of the compound from Example 159A and 100 mg (0.44 mmol) of the compound from Example 87A in 4 ml of 1,2-dichloroethane, and the mixture was heated under reflux overnight. It was concentrated and the residue was taken up in ethyl acetate and washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) to result in 6.0 mg (4% of theory) of the title compound as mixture of diastereomers.

$^1$H-NMR (400 MHz, DMSO-$d_6$): δ=11.3 (s, 1H), 7.64 (d, 0.5H), 7.55 (d, 0.5H), 7.32-7.47 (m, 4H), 6.96-7.09 (m, 2H), 4.70-4.80 (m, 2H), 3.97 (d, 0.5H), 3.92 (d, 0.5H), 2.93 (s, 3H), 2.56-2.66 (m, 1H), 1.56-1.77 (m, 1H), 1.26-1.38 (m, 1H).

LC-MS (Method 9): $R_t$=1.17 min; MS (ESIneg): m/z=426 [M−H]$^-$.

Example 263

2-[{5-Fluoro-7-[(methylsulfonyl)methyl]-1H-indol-3-yl}(4-methylphenyl)methyl]cyclopropane-carbonitrile [trans-diastereomer mixture]

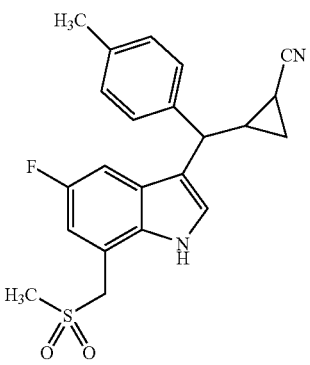

3.63 g (16.4 mmol) of indium(III) chloride and 1.9 ml (24.6 mmol) of trifluoroacetic acid were added to 4.23 g (16.4 mmol) of the compound from Example 87A and 2.56 g (13.7 mmol) of the compound from Example 158A under argon in 300 ml of 1,2-dichloroethane, and the mixture was stirred under reflux for 4 h. It was diluted with dichloromethane and washed with water and saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 3.16 g (49% of theory) of the title compound as mixture of diastereomers.

$^1$H-NMR (400 MHz, DMSO-$d_6$): δ=11.2 (s, 1H), 7.57 (d, 1H), 7.18-7.26 (m, 2H), 7.06-7.14 (m, 2H), 6.89-7.01 (m, 2H), 4.69-4.80 (m, 2H), 3.57 (d, 0.5H), 3.54 (d, 0.5H), 2.92 (d, 1.5H), 2.91 (d, 1.5H), 2.22-2.32 (m, 1H), 2.26 (d, 1.5H), 2.24 (d, 1.5H), 1.61-1.70 (m, 1H), 1.35-1.42 (m, 0.5H), 1.24-1.31 (m, 0.5H), 1.00-1.08 (m, 1H).

LC-MS (Method 9): $R_t$=1.06, 1.08 min; MS (ESIneg): m/z=395 [M−H]$^-$.

Example 264

2-[(4-Methylphenyl){7-[(methylsulfonyl)methyl]-1H-indol-3-yl}methyl]cyclopropanecarbonitrile [trans-diastereomer mixture]

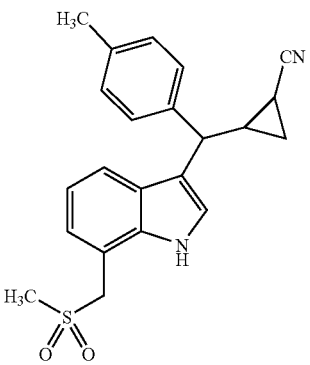

195 mg (0.88 mmol) of indium(III) chloride and 0.11 ml (1.44 mmol) of trifluoroacetic acid were added to 168 mg (0.80 mmol) of the compound from Example 86A and 150 mg (0.80 mmol) of the compound from Example 158A under argon in 9 ml of dichloromethane, and the mixture was heated under reflux for 1 h. It was diluted with dichloromethane and washed with water and saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 100 mg (33% of theory) of the title compound as mixture of diastereomers.

$^1$H-NMR (400 MHz, DMSO-$d_6$): δ=11.11 (s, 0.5H), 11.09 (s, 0.5H), 7.48 (s, 1H), 7.16-7.25 (m, 3H), 7.05-7.12 (m, 3H), 6.89 (t, 0.5H), 6.88 (t, 0.5H), 4.67-4.78 (m, 2H), 3.60 (d, 0.5H), 3.57 (d, 0.5H), 2.89 (d, 1.5H), 2.88 (d, 1.5H), 2.20-2.32 (m, 1H), 2.25 (d, 1.5H), 2.23 (d, 1.5H), 1.70 (dt, 0.5H), 1.64 (dt, 0.5H), 1.39 (dt, 0.5H), 1.27 (dt, 0.5H), 1.01-1.10 (m, 1H).

LC-MS (Method 9): $R_t$=1.04, 1.06 min; MS (ESIneg): m/z=377 [M−H]$^-$.

Example 265

2-({7-[(Methylsulfonyl)methyl]-1H-indol-3-yl}[4-(trifluoromethyl)phenyl]methyl)cyclopropane-carbonitrile [trans-diastereomer mixture]

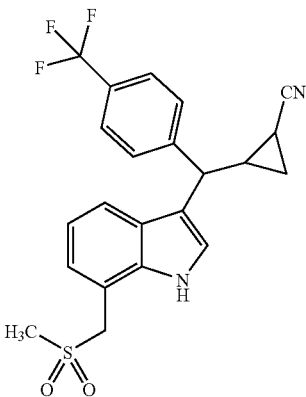

1.05 g (4.75 mmol) of indium(III) chloride and 0.55 ml (7.12 mmol) of trifluoroacetic acid were added to 954 mg (3.96 mmol) of the compound from Example 160A and 1.02 g (4.75 mmol) of the compound from Example 86A in 60 ml of 1,2-dichloroethane, and the mixture was heated under reflux overnight. It was diluted with dichloromethane and washed with water and saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 197 mg (12% of theory) of the title compound as mixture of diastereomers.

$^1$H-NMR (400 MHz, DMSO-$d_6$): δ=11.20 (s, 0.5H), 11.18 (s, 0.5H), 7.54-7.71 (m, 5H), 7.23 (d, 0.5H), 7.21 (d, 0.5H), 7.12 (d, 0.5H), 7.10 (d, 0.5H), 6.92 (t, 0.5H), 6.91 (t, 0.5H), 4.68-4.79 (m, 2H), 3.77 (d, 0.5H), 3.75 (d, 0.5H), 2.90 (s, 1.5H), 2.89 (s, 1.5H), 2.31-2.42 (m, 1H), 1.77-1.84 (m, 0.5H), 1.69-1.76 (m, 0.5H), 1.39-1.46 (m, 0.5H), 1.28-1.34 (m, 0.5H), 1.06-1.18 (m, 1H).

LC-MS (Method 9): $R_t$=1.09, 1.11 min; MS (ESIneg): m/z=431 [M−H]$^-$.

The enantiomers were separated by preparative HPLC initially on a chiral phase [column: Daicel Chiralpak AD-H, 5 µm, 250 mm×20 mm; eluent: isohexane/isopropanol 1:1; flow rate: 20 ml/min; temperature: RT; UV detection: 230 nm] and then by isocratic RP18 separation with acetonitrile/water 1:1.

Enantiomer 265-1:

$R_t$=5.54 min [column: Daicel AD-H, 5 µm, 250 mm×4 mm; eluent: isohexane/isopropanol 1:1; flow rate: 1.0 ml/min; temperature: RT; UV detection: 230 nm].

$R_t$=7.99 min [column: Reprosil C18, 10 µm, 250 mm×4.6 mm; eluent: acetonitrile/water 1:1; flow rate: 1.0 ml/min; temperature: RT; UV detection: 210 nm].

$^1$H-NMR (400 MHz, DMSO-$d_6$): δ=11.2 (s, 1H), 7.66-7.71 (m, 2H), 7.58-7.62 (m, 2H), 7.56 (d, 1H), 7.21 (d, 1H), 7.10 (d, 1H), 6.91 (t, 1H), 4.67-4.77 (m, 2H), 3.75 (d, 1H), 2.89 (s, 3H), 2.31-2.41 (m, 1H), 1.81 (dt, 1H), 1.43 (dt, 1H), 1.10 (ddd, 1H).

Yield: 12.0 mg

Example 266

2-[(2-Chloro-4-fluorophenyl){5-fluoro-7-[(methylsulfonyl)methyl]-1H-indol-3-yl}methyl]cyclopropanecarbonitrile [trans-diastereomer mixture]

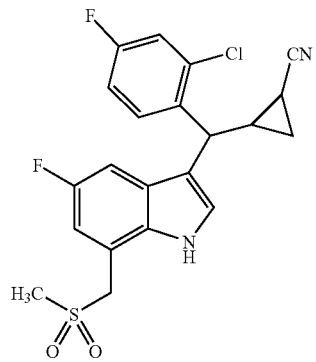

1.62 g (7.31 mmol) of indium(III) chloride and 0.92 ml (12.0 mmol) of trifluoroacetic acid were added to 1.89 g (6.65 mmol) of the compound from Example 87A with a purity of 80% and 1.50 g (6.65 mmol) of the compound from Example 161A under argon in 75 ml of 1,2-dichloroethane, and the mixture was heated under reflux overnight. It was diluted with dichloromethane and washed with water and saturated aqueous sodium bicarbonate solution, dried over magnesium sulfate, filtered and concentrated. The residue was purified by preparative SFC HPLC (RP18 column; mobile phase: acetonitrile/water gradient with addition of 0.1% formic acid) to result in 1.65 g (57% of theory) of the title compound as mixture of diastereomers.

$^1$H-NMR (400 MHz, DMSO-$d_6$): δ=11.30 (s, 0.5H), 11.28 (s, 0.5H), 7.68 (dd, 0.5H), 7.61 (dd, 0.5H), 7.52 (d, 0.5H), 7.46 (d, 0.5H), 7.44 (dd, 0.5H), 7.41 (dd, 0.5H), 7.26 (dt, 0.5H), 7.21 (dt, 0.5H), 6.97-7.07 (m, 2H), 4.70-4.80 (m, 2H), 4.07 (d, 0.5H), 4.04 (d, 0.5H), 2.93 (s, 1.5H), 2.92 (s, 1.5H), 2.36-2.45 (m, 1H), 1.88-1.94 (m, 0.5H), 1.54-1.60 (m, 0.5H), 1.38-1.45 (m, 0.5H), 1.27-1.34 (m, 0.5H), 1.19-1.26 (m, 0.5H), 0.94-1.01 (m, 0.5H).

LC-MS (Method 9): $R_t$=1.08, 1.10 min; MS (ESIneg): m/z=433 [M−H]$^-$.

The enantiomers were separated by preparative HPLC on a chiral phase [column: chiral silica gel phase based on the selector poly(N-methacryloyl-L-isoleucine 3-pentylamide), 10 µm, 250 mm×20 mm; eluent: step gradient isohexane/ethyl acetate 1:9 (15.7 minutes)→0:100 (6 minutes); flow rate: 80.0 ml/min; temperature: RT; UV detection: 265 nm].

Enantiomer 266-1:

$R_t$=3.62 min [column: chiral silica gel phase based on the selector poly(N-methacryloyl-L-isoleucine 3-pentylamide), 10 µm, 250 mm×4.6 mm; eluent: ethyl acetate; flow rate: 2.0 ml/min; temperature: RT; UV detection: 265 nm].

$^1$H-NMR (400 MHz, DMSO-$d_6$): δ=11.3 (s, 1H), 7.68 (dd, 1H), 7.46 (d, 1H), 7.44 (dd, 1H), 7.26 (dt, 1H), 7.05 (dd, 1H), 7.00 (dd, 1H), 4.70-4.80 (m, 2H), 4.04 (d, 1H), 2.92 (s, 3H), 2.36-2.46 (m, 1H), 1.54-1.60 (m, 1H), 1.38-1.45 (m, 1H), 1.19-1.26 (m, 1H).

LC-MS (Method 4): $R_t$=1.26 min; MS (ESIneg): m/z=433 [M−H]$^-$.

Yield: 240 mg

Example 267

2-[(2,4-Difluorophenyl){5-fluoro-7-[(methylsulfonyl)methyl]-1H-indol-3-yl}methyl]cyclopropanecarbonitrile [trans-diastereomer mixture]

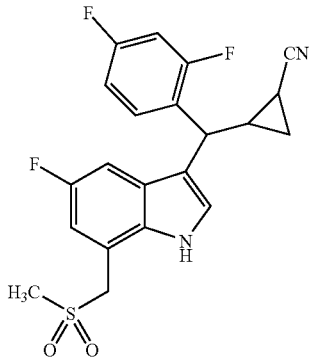

96.9 mg (0.44 mmol) of indium(III) chloride and 0.06 ml (0.72 mmol) of trifluoroacetic acid were added to 113 mg (0.40 mmol) of the compound from Example 87A with a purity of 80% and 100 mg (0.48 mmol) of the compound from Example 162A under argon in 4 ml of dichloromethane, and the mixture was heated under reflux for 1 h. It was diluted with dichloromethane and washed with water and saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 69.0 mg (41% of theory) of the title compound as mixture of diastereomers.

$^1$H-NMR (400 MHz, DMSO-$d_6$): δ=11.28 (s, 0.5H), 11.26 (s, 0.5H), 7.48-7.62 (m, 2H), 7.14-7.23 (m, 1H), 6.97-7.13 (m, 3H), 4.69-4.80 (m, 2H), 3.88 (d, 0.5H), 3.85 (d, 0.5H), 2.93 (s, 1.5H), 2.92 (s, 1.5H), 2.36-2.46 (m, 1H), 1.80-1.87 (m, 0.5H), 1.58-1.64 (m, 0.5H), 1.37-1.44 (m, 0.5H), 1.28-1.35 (m, 0.5H), 1.14-1.21 (m, 0.5H), 0.95-1.02 (m, 0.5H).

LC-MS (Method 6): $R_t$=2.19, 2.22 min; MS (ESIneg): m/z=417 [M–H]$^-$.

Example 268

2-[(4-Chloro-2-methoxyphenyl){5-fluoro-7-[(methylsulfonyl)methyl]-1H-indol-3-yl}methyl]cyclopropanecarbonitrile [trans-diastereomer mixture]

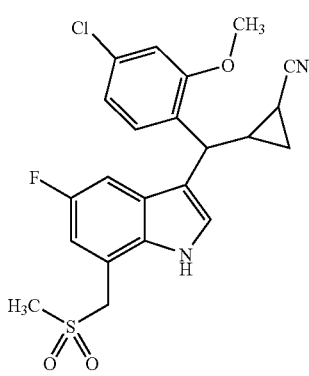

104 mg (0.47 mmol) of indium(III) chloride and 0.05 ml (0.70 mmol) of trifluoroacetic acid were added to 93.0 mg (0.39 mmol) of the compound from Example 163A and 121 mg (0.47 mmol) of the compound from Example 87A with a purity of 88% under argon in 5 ml of 1,2-dichloroethane, and the mixture was heated under reflux for 2 h. Addition of the reaction mixture to saturated aqueous ammonium chloride solution was followed by extraction with dichloromethane, drying over magnesium sulfate, filtration and concentration. The residue was purified by preparative HPLC (RP18 column; mobile phase: acetonitrile/water gradient with addition of 0.1% formic acid) to result in 35.0 mg (20% of theory) of diastereomer 1 and 31.3 mg (18% of theory) of diastereomer 2 of the title compound.

Diastereomer 268-1:

$^1$H-NMR (400 MHz, DMSO-$d_6$): δ=11.2 (s, 1H), 7.50 (d, 1H), 7.31 (d, 1H), 7.08 (d, 1H), 6.93-7.00 (m, 3H), 4.69-4.79 (m, 2H), 3.93 (d, 1H), 3.84 (s, 3H), 2.92 (s, 3H), 2.29-2.36 (m, 1H), 1.51 (dt, 1H), 1.36 (dt, 1H), 1.10 (ddd, 1H).

LC-MS (Method 9): $R_t$=1.09 min; MS (ESIneg): m/z=445 [M–H]$^-$.

Diastereomer 268-2:

$^1$H-NMR (400 MHz, DMSO-$d_6$): δ=11.2 (s, 1H), 7.52 (d, 1H), 7.27 (d, 1H), 7.06 (d, 1H), 6.91-7.02 (m, 3H), 4.70-4.80 (m, 2H), 3.95 (d, 1H), 3.84 (s, 3H), 2.92 (s, 3H), 2.29-2.36 (m, 1H), 1.75 (dt, 1H), 1.25 (dt, 1H), 0.94 (ddd, 1H).

LC-MS (Method 9): $R_t$=1.11 min; MS (ESIneg): m/z=445 [M–H]$^-$.

Example 269

2-[(4-Chloro-2-methoxyphenyl){7-[(methylsulfonyl)methyl]-1H-indol-3-yl}methyl]cyclopropane-carbonitrile [trans-diastereomer mixture

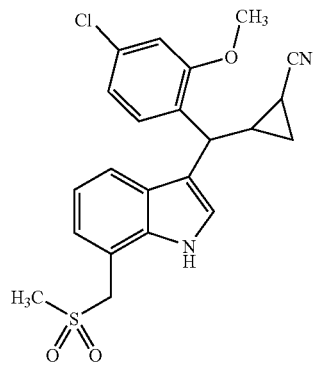

104 mg (0.47 mmol) of indium(III) chloride and 0.05 ml (0.70 mmol) of trifluoroacetic acid were added to 93.0 mg (0.39 mmol) of the compound from Example 163A and 112 mg (0.47 mmol) of the compound from Example 86A with a purity of 88% under argon in 5 ml of 1,2-dichloroethane, and the mixture was heated under reflux for 2 h. Addition of the reaction mixture to saturated aqueous ammonium chloride solution was followed by extraction with dichloromethane, drying over magnesium sulfate, filtration and concentration. The residue was purified by preparative HPLC (RP18 column; mobile phase: acetonitrile/water gradient with addition of 0.1% formic acid) to result in 30.5 mg (18% of theory) of diastereomer 1 and 28.0 mg (17% of theory) of diastereomer 2 of the title compound.

Diastereomer 269-1:

$^1$H-NMR (400 MHz, DMSO-$d_6$): δ=11.1 (s, 1H), 7.43 (d, 1H), 7.24 (d, 1H), 7.19 (d, 1H), 7.07-7.11 (m, 2H), 6.95 (dd,

1H), 6.91 (t, 1H), 4.67-4.76 (m, 2H), 4.01 (d, 1H), 3.85 (s, 3H), 2.89 (s, 3H), 2.25-2.34 (m, 1H), 1.53 (dt, 1H), 1.38 (dt, 1H), 1.06 (ddd, 1H).

LC-MS (Method 9): $R_t$=1.07 min; MS (ESIneg): m/z=427 [M−H]⁻.

Diastereomer 269-2:

¹H-NMR (400 MHz, DMSO-$d_6$): δ=11.1 (s, 1H), 7.44 (d, 1H), 7.21 (d, 1H), 7.19 (d, 1H), 7.10 (d, 1H), 7.06 (d, 1H), 6.88-6.95 (m, 2H), 4.67-4.77 (m, 2H), 4.03 (d, 1H), 3.85 (s, 3H), 2.89 (s, 3H), 2.25-2.34 (m, 1H), 1.72 (dt, 1H), 1.25 (dt, 1H), 0.97 (ddd, 1H).

LC-MS (Method 9): $R_t$=1.10 min; MS (ESIneg): m/z=445 [M−H]⁻.

Example 270

2-[(2,4-Difluorophenyl){7-[(methylsulfonyl)methyl]-1H-indol-3-yl}methyl]cyclopropanecarbonitrile [trans-diastereomer mixture]

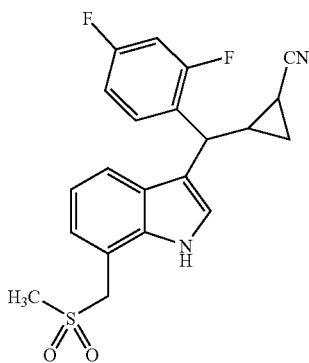

116 mg (0.53 mmol) of indium(III) chloride and 0.07 ml (0.86 mmol) of trifluoroacetic acid were added to 100 mg (0.48 mmol) of the compound from Example 86A and 120 mg (0.57 mmol) of the compound from Example 162A under argon in 5 ml of dichloromethane, and the mixture was stirred under reflux for 1 h. It was diluted with dichloromethane and washed with water and saturated aqueous sodium bicarbonate solution, dried over magnesium sulfate, filtered and concentrated. The residue was purified by preparative HPLC (RP18 column; mobile phase: acetonitrile/water gradient with addition of 0.1% formic acid) to result in 29.0 mg (15% of theory) of the title compound as mixture of diastereomers.

¹H-NMR (400 MHz, DMSO-$d_6$): δ=11.17 (s, 0.5H), 11.15 (s, 0.5H), 7.43-7.57 (m, 2H), 7.15-7.29 (m, 2H), 6.99-7.14 (m, 2H), 6.95 (t, 0.5H), 6.94 (t, 0.5H), 4.67-4.78 (m, 2H), 3.92 (d, 0.5H), 3.89 (d, 0.5H), 2.90 (s, 1.5H), 2.89 (s, 1.5H), 2.34-2.44 (m, 1H), 1.80-1.86 (m, 0.5H), 1.60-1.66 (m, 0.5H), 1.39-1.46 (m, 0.5H), 1.28-1.35 (m, 0.5H), 1.12-1.19 (m, 0.5H), 0.97-1.04 (m, 0.5H).

LC-MS (Method 4): $R_t$=1.18, 1.20 min; MS (ESIneg): m/z=399 [M−H]⁻.

Example 271

2-({5-Fluoro-7-[(methylsulfonyl)methyl]-1H-indol-3-yl}[2-fluoro-4-(trifluoro-methyl)phenyl]methyl)cyclopropanecarbonitrile [trans-diastereomer mixture]

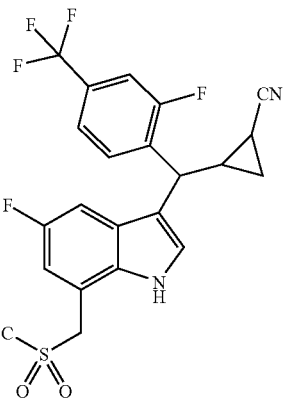

1.63 g (7.35 mmol) of indium(III) chloride and 0.85 ml (11.0 mmol) of trifluoroacetic acid were added to 1.59 g (6.13 mmol) of the compound from Example 164A and 1.90 g (7.35 mmol) of the compound from Example 87A in 100 ml of 1,2-dichloroethane, and the mixture was heated under reflux overnight. It was concentrated and the residue was purified by preparative HPLC (RP18 column; mobile phase: acetonitrile/water gradient with addition of 0.1% formic acid) to result in 763 mg (27% of theory) of the title compound as mixture of diastereomers.

¹H-NMR (400 MHz, DMSO-$d_6$): δ=11.35 (s, 0.5H), 11.32 (s, 0.5H), 7.84 (t, 0.5H), 7.76 (t, 0.5H), 7.53-7.68 (m, 3H), 7.13 (dd, 0.5H), 7.09 (dd, 0.5H), 7.03 (dd, 0.5H), 7.00 (dd, 0.5H), 4.70-4.81 (m, 2H), 3.99 (d, 0.5H), 3.97 (d, 0.5H), 2.93 (s, 1.5H), 2.92 (s, 1.5H), 2.44-2.53 (m, 1H), 1.86-1.93 (m, 0.5H), 1.63-1.70 (m, 0.5H), 1.38-1.45 (m, 0.5H), 1.30-1.37 (m, 0.5H), 1.18-1.25 (m, 0.5H), 0.98-1.06 (m, 0.5H).

LC-MS (Method 6): $R_t$=2.41, 2.46 min; MS (ESIneg): m/z=467 [M−H]⁻.

Separation of the mixture of diastereomers by preparative HPLC (RP18 column; mobile phase: acetonitrile/water gradient with addition of 0.1% formic acid), resulted in 91.9 mg of diastereomer 1 of the title compound.

Diastereomer 271-1:

¹H-NMR (400 MHz, DMSO-$d_6$): δ=11.3 (s, 1H), 7.84 (t, 1H), 7.60-7.67 (m, 2H), 7.55 (d, 1H), 7.13 (dd, 1H), 7.00 (dd, 1H), 4.70-4.79 (m, 2H), 3.97 (d, 1H), 2.92 (s, 3H), 2.44-2.53 (m, 1H), 1.63-1.70 (m, 1H), 1.38-1.45 (m, 1H), 1.18-1.25 (m, 1H).

LC-MS (Method 9): $R_t$=1.10 min; MS (ESIneg): m/z=467 [M−H]⁻.

The enantiomers were separated by preparative HPLC on a chiral phase [column: chiral silica gel phase based on the selector poly(N-methacryloyl-L-isoleucine 3-pentylamide), 10 μm, 250 mm×20 mm; eluent: step gradient isohexane/ethyl acetate 4:6 (30 minutes)→3:7 (30 minutes)→0:100 (15 minutes); flow rate: 80.0 ml/min; temperature: RT; UV detection: 265 nm].

Enantiomer 271-1-1:

$R_t$=7.14 min [column: chiral silica gel phase based on the selector poly(N-methacryloyl-L-isoleucine 3-pentylamide), 10 μm, 250 mm×4.6 mm; eluent: ethyl acetate; flow rate: 2.0 ml/min; temperature: RT; UV detection: 265 nm].

Yield: 40.0 mg

Example 272

2-({5-Fluoro-7-[(methylsulfonyl)methyl]-1H-indol-3-yl}[4-(trifluoromethyl)phenyl]methyl)cyclopropanecarbonitrile [trans-diastereomer mixture]

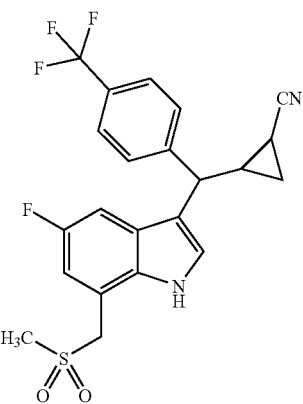

33.0 mg (0.15 mmol) of indium(III) chloride and 0.02 ml (0.22 mmol) of trifluoroacetic acid were added to 30.0 mg (0.12 mmol) of the compound from Example 160A and 41.4 mg (0.15 mmol) of the compound from Example 87A with a purity of 82% under argon in 1 ml of 1,2-dichloroethane, and the mixture was heated under reflux for three days. It was concentrated and the residue was taken up in ethyl acetate, washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) to result in 12.6 mg (23% of theory) of diastereomer 1 and 13.2 mg (24% of theory) of diastereomer 2 of the title compound.

Diastereomer 272-1:

$^1$H-NMR (400 MHz, DMSO-$d_6$): δ=11.3 (s, 1H), 7.67-7.72 (m, 2H), 7.59-7.66 (m, 3H), 6.98-7.05 (m, 2H), 4.70-4.79 (m, 2H), 3.72 (d, 1H), 2.92 (s, 3H), 2.35-2.44 (m, 1H), 1.76 (dt, 1H), 1.41 (dt, 1H), 1.06-1.13 (m, 1H).

LC-MS (Method 9): $R_t$=1.10 min; MS (ESIneg): m/z=449 [M−H]$^−$.

Diastereomer 272-2:

$^1$H-NMR (400 MHz, DMSO-$d_6$): δ=11.3 (s, 1H), 7.63-7.68 (m, 3H), 7.56-7.61 (m, 2H), 6.96-7.03 (m, 2H), 4.71-4.81 (m, 2H), 3.74 (d, 1H), 2.93 (s, 3H), 2.37-2.45 (m, 1H), 1.73 (dt, 1H), 1.31 (dt, 1H), 1.06-1.14 (m, 1H).

LC-MS (Method 9): $R_t$=1.12 min; MS (ESIneg): m/z=449 [M−H]$^−$.

Example 273

2-[(4-Chloro-2-fluorophenyl){5-fluoro-7-[(methylsulfonyl)methyl]-1H-indol-3-yl}methyl]cyclopropanecarbonitrile [trans-diastereomer mixture]

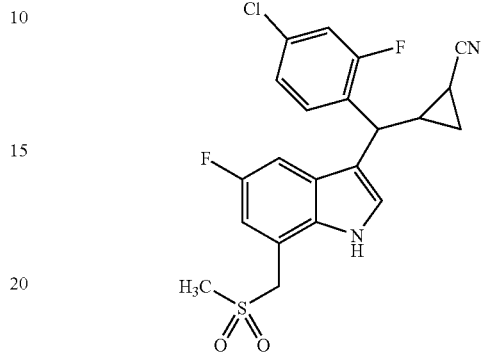

471 mg (2.13 mmol) of indium(III) chloride and 0.25 ml (3.19 mmol) of trifluoroacetic acid were added to 400 mg (1.77 mmol) of the compound from Example 165A and 483 mg (2.13 mmol) of the compound from Example 87A under argon in 18 ml of dichloromethane, and the mixture was heated under reflux for 3 days. It was concentrated and the residue was taken up in ethyl acetate, washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) and another RP18 separation with acetonitrile/water 55:45 to result in 131 mg (17% of theory) of diastereomer 1 and 127 mg (17% of theory) of diastereomer 2 of the title compound.

Diastereomer 273-1:

$^1$H-NMR (400 MHz, DMSO-$d_6$): δ=11.3 (s, 1H), 7.58 (t, 1H), 7.52 (d, 1H), 7.40 (dd, 1H), 7.31 (dd, 1H), 7.07 (dd, 1H), 7.00 (dd, 1H), 4.70-4.79 (m, 2H), 3.87 (d, 1H), 2.92 (s, 3H), 2.38-2.47 (m, 1H), 1.62 (dt, 1H), 1.41 (dt, 1H), 1.18 (ddd, 1H).

LC-MS (Method 9): $R_t$=1.08 min; MS (ESIneg): m/z=433 [M−H]$^−$.

The enantiomers were separated by preparative HPLC on a chiral phase [column: Daicel Chiralpak AD-H, 5 μm, 250 mm×20 mm; eluent: isohexane/(isopropanol/methanol (1:1)) 6:4; flow rate: 20 ml/min; temperature: RT; UV detection: 230 nm].

Enantiomer 273-1-2:

$R_t$=7.90 min [column: Daicel AD-H, 5 μm, 250 mm×4 mm; eluent: isohexane/(ethanol/methanol 1/1) 1:1; flow rate: 1.0 ml/min; temperature: RT; UV detection: 230 nm].

Yield: 44.0 mg

Diastereomer 273-2:

$^1$H-NMR (400 MHz, DMSO-$d_6$): δ=11.3 (s, 1H), 7.55 (d, 1H), 7.51 (t, 1H), 7.38 (dd, 1H), 7.26 (dd, 1H), 6.99-7.07 (m, 2H), 4.70-4.81 (m, 2H), 3.88 (d, 1H), 2.93 (s, 3H), 2.37-2.46 (m, 1H), 1.85 (dt, 1H), 1.32 (dt, 1H), 0.99 (dt, 1H).

LC-MS (Method 9): $R_t$=1.11 min; MS (ESIneg): m/z=433 [M−H]$^−$.

Example 274

2-[(4-Chloro-2-fluorophenyl){7-[(methylsulfonyl)methyl]-1H-indol-3-yl}methyl]cyclopropane-carbonitrile [trans-diastereomer mixture]

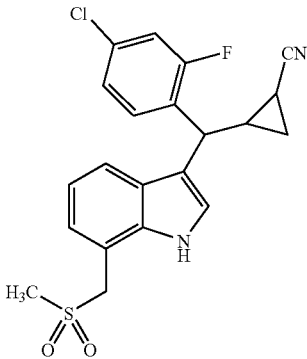

1.76 g (7.98 mmol) of indium(III) chloride and 0.92 ml (12.0 mmol) of trifluoroacetic acid were added to 1.50 g (6.65 mmol) of the compound from Example 165A and 1.67 g (7.98 mmol) of the compound from Example 86A under argon in 69 ml of dichloromethane, and the mixture was heated under reflux for three days. It was concentrated and the residue was taken up in ethyl acetate, washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) and another isocratic RP18 separation with acetonitrile/water 1:1 to result in 283 mg (10% of theory) of diastereomer 1 and 145 mg (5% of theory) of diastereomer 2 of the title compound.

Diastereomer 274-1:
$^1$H-NMR (400 MHz, DMSO-$d_6$): δ=11.2 (s, 1H), 7.52 (t, 1H), 7.45 (d, 1H), 7.40 (dd, 1H), 7.25-7.31 (m, 2H), 7.11 (d, 1H), 6.95 (t, 1H), 4.67-4.77 (m, 2H), 3.91 (d, 1H), 2.88 (s, 3H), 2.35-2.44 (m, 1H), 1.64 (dt, 1H), 1.42 (dt, 1H), 1.17 (dt, 1H).
LC-MS (Method 9): $R_t$=1.09 min; MS (ESIneg): m/z=415 [M−H]$^-$.

Diastereomer 274-2:
$^1$H-NMR (400 MHz, DMSO-$d_6$): δ=11.2 (s, 1H), 7.32-7.51 (m, 3H), 7.20-7.29 (m, 2H), 7.13 (d, 1H), 6.95 (t, 1H), 4.68-4.79 (m, 2H), 3.93 (d, 1H), 2.90 (s, 3H), 2.34-2.44 (m, 1H), 1.84 (dt, 1H), 1.31 (dt, 1H), 0.97-1.05 (m, 1H).
LC-MS (Method 9): $R_t$=1.10 min; MS (ESIneg): m/z=433 [M−H]$^-$.

Example 275

2-[(2-Fluoro-4-methylphenyl){5-fluoro-7-[(methylsulfonyl)methyl]-1H-indol-3-yl}methyl]cyclopropanecarbonitrile [trans-diastereomer mixture]

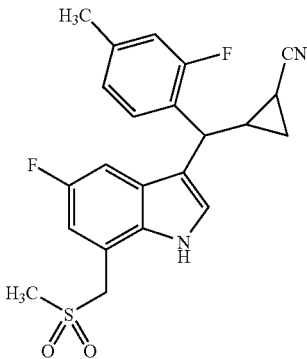

347 mg (1.57 mmol) of indium(III) chloride and 0.18 ml (2.35 mmol) of trifluoroacetic acid were added to 268 mg (1.31 mmol) of the compound from Example 166A and 405 mg (1.57 mmol) of the compound from Example 87A with a purity of 88% under argon in 10 ml of 1,2-dichloroethane, and the mixture was heated under reflux overnight. It was concentrated and the residue was taken up in ethyl acetate, washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) to result in 358 mg (66% of theory) of the title compound as mixture of diastereomers.

$^1$H-NMR (400 MHz, DMSO-$d_6$): δ=11.26 (s, 0.5H), 11.24 (s, 0.5H), 7.53 (d, 0.5H), 7.51 (d, 0.5H), 7.38 (t, 0.5H), 7.32 (t, 0.5H), 6.93-7.04 (m, 4H), 4.69-4.81 (m, 2H), 3.84 (d, 0.5H), 3.81 (d, 0.5H), 2.92 (s, 1.5H), 2.91 (s, 1.5H), 2.32-2.43 (m, 1H), 2.28 (s, 1.5H), 2.26 (s, 1.5H), 1.82 (dt, 0.5H), 1.57 (dt, 0.5H), 1.41 (dt, 0.5H), 1.30 (dt, 0.5H), 1.16 (ddd, 0.5H), 0.97 (dt, 0.5H).
LC-MS (Method 9): $R_t$=1.09, 1.11 min; MS (ESIneg): m/z=413 [M−H]$^-$.

Example 276

2-[(4-Chlorophenyl){7-[(methylsulfonyl)methyl]-1H-indol-3-yl}methyl]cyclopropanecarbonitrile [trans-diastereomer mixture]

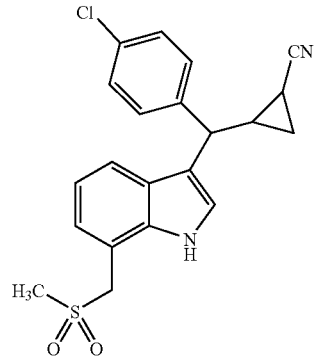

95.7 mg (0.43 mmol) of indium(III) chloride and 0.04 ml (0.49 mmol) of trifluoroacetic acid were added to 83.3 mg (0.40 mmol) of the compound from Example 167A and 100 mg (0.25 mmol) of the compound from Example 86A with a purity of 53% under argon in 5 ml of dichloromethane, and the mixture was heated under reflux for three days. It was concentrated and the residue was purified by preparative HPLC (RP18 column; mobile phase: acetonitrile/water gradient with addition of 0.1% formic acid) to result in 41.0 mg (33% of theory) of the title compound as mixture of diastereomers.

$^1$H-NMR (400 MHz, DMSO-$d_6$): δ=11.16 (s, 0.5H), 11.15 (s, 0.5H), 7.52 (s, 1H), 7.30-7.40 (m, 4H), 7.16-7.23 (m, 1H), 7.07-7.13 (m, 1H), 6.92 (t, 0.5H), 6.90 (t, 0.5H), 4.67-4.78 (m, 2H), 3.67 (d, 0.5H), 3.64 (d, 0.5H), 2.90 (s, 1.5H), 2.89 (s, 1.5H), 2.24-2.35 (m, 1H), 1.73-1.80 (m, 0.5H), 1.64-1.71 (m, 0.5H), 1.38-1.45 (m, 0.5H), 1.26-1.32 (m, 0.5H), 1.03-1.15 (m, 1H).
LC-MS (Method 9): $R_t$=1.05, 1.08 min; MS (ESIneg): m/z=397 [M−H]$^-$.

The enantiomers were separated by preparative HPLC on a chiral phase [column: Daicel Chiralpak OD-H, 5 μm, 250 mm×20 mm; eluent: isohexane/(ethanol/methanol (1:1)) 1:1; flow rate: 20 ml/min; temperature: RT; UV detection: 230 nm].

Enantiomer 276-1:

$R_t$=11.19 min [column: Daicel OD-H, 5 μm, 250 mm×4 mm; eluent: isohexane/(ethanol/methanol (1:1)) 1:1; flow rate: 1.0 ml/min; temperature: RT; UV detection: 230 nm].

$^1$H-NMR (400 MHz, DMSO-$d_6$): δ=11.1 (s, 1H), 7.52 (s, 1H), 7.34-7.41 (m, 4H), 7.18 (d, 1H), 7.09 (d, 1H), 6.90 (d, 1H), 4.67-4.77 (m, 2H), 3.64 (d, 1H), 2.89 (s, 3H), 2.24-2.34 (m, 1H), 1.77 (dt, 1H), 1.41 (dt, 1H), 1.03-1.15 (m, 1H).

LC-MS (Method 6): $R_t$=2.20 min; MS (ESIneg): m/z=397 [M−H]$^-$.

Yield: 45 mg

Example 277

2-[(4-Chlorophenyl){5-fluoro-7-[(methylsulfonyl)methyl]-1H-indol-3-yl}methyl]cyclopropane-carbonitrile [trans-diastereomer mixture]

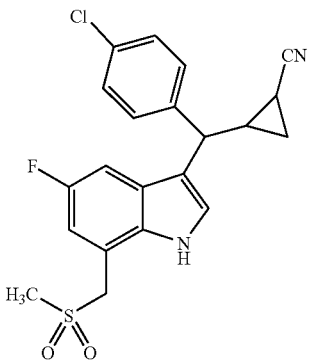

128 mg (0.58 mmol) of indium(III) chloride and 0.07 ml (0.87 mmol) of trifluoroacetic acid were added to 100 mg (0.48 mmol) of the compound from Example 167A and 149 mg (0.58 mmol) of the compound from Example 87A with a purity of 88% under argon in 5 ml of 1,2-dichloroethane, and the mixture was heated under reflux overnight. It was concentrated and the residue was taken up in ethyl acetate, washed with saturated aqueous sodium bicarbonate solution and saturated aqueous sodium chloride solution, dried over sodium sulfate, filtered and concentrated. The residue was purified by preparative HPLC (RP18 column; mobile phase: acetonitrile/water gradient with addition of 0.1% formic acid) to result in 130 mg (65% of theory) of the title compound as mixture of diastereomers.

$^1$H-NMR (400 MHz, DMSO-$d_6$): δ=11.29 (s, 0.5H), 11.27 (s, 0.5H), 7.60 (d, 1H), 7.32-7.42 (m, 4H), 6.94-7.02 (m, 2H), 4.70-4.81 (m, 2H), 3.64 (d, 0.5H), 3.61 (d, 0.5H), 2.93 (d, 1.5H), 2.92 (d, 1.5H), 2.27-2.38 (m, 1H), 1.65-1.76 (m, 1H), 1.36-1.44 (m, 0.5H), 1.26-1.33 (m, 0.5H), 1.03-1.11 (m, 1H).

LC-MS (Method 4): $R_t$=1.24, 1.27 min; MS (ESIneg): m/z=415 [M−H]$^-$.

410 mg of diastereomer 1 of the title compound were obtained in a batch carried out analogously and by separating the mixture of diastereomers by preparative HPLC (RP18 column; mobile phase: acetonitrile/water gradient with addition of 0.1% formic acid).

Diastereomer 277-1:

$^1$H-NMR (400 MHz, DMSO-$d_6$): δ=11.3 (s, 1H), 7.61 (d, 1H), 7.35-7.42 (m, 4H), 6.94-7.01 (m, 2H), 4.70-4.81 (m, 2H), 3.61 (d, 1H), 2.92 (d, 3H), 2.27-2.36 (m, 1H), 1.69-1.76 (m, 1H), 1.36-1.43 (m, 1H), 1.03-1.10 (m, 1H).

LC-MS (Method 9): $R_t$=1.08 min; MS (ESIneg): m/z=415 [M−H]$^-$.

The enantiomers were separated by preparative HPLC on a chiral phase [column: Daicel Chiralpak AD-H, 5 μm, 250 mm×20 mm; eluent: isohexane/(ethanol/methanol (1:1) 1:1; flow rate: 20 ml/min; temperature: RT; UV detection: 230 nm]. The separated enantiomers were purified again by preparative HPLC on an achiral phase (RP18 column; mobile phase: acetonitrile/water gradient with addition of 0.1% formic acid) to result in 17.0 mg of enantiomer 277-1-1.

Enantiomer 277-1-1:

$R_t$=13.48 min [column: Daicel AD-H, 5 μm, 250 mm×4 mm; eluent: isohexane/(ethanol/methanol (1:1)) 1:1; flow rate: 1.0 ml/min; temperature: RT; UV detection: 230 nm].

Example 278

3-[Bis(4-fluorophenyl)methyl]-7-[(methylsulfanyl)methyl]-1H-indole

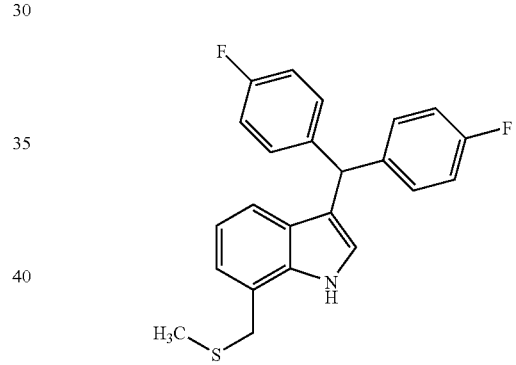

1.24 g (5.64 mmol) of 4,4'-difluorobenzohydrol and 1.25 g (5.64 mmol) of indium(III) chloride were added to 1.00 g (5.64 mmol) of the compound from Example 8A in 30 ml of toluene. The reaction mixture was stirred at 80° C. for 5 h. After cooling to RT, the reaction solution was mixed with ethyl acetate, and the solid was filtered off. The filtrate was mixed with water, the phases were separated, and the aqueous phase was extracted with ethyl acetate. The combined organic phases were dried over sodium sulfate, filtered and concentrated. Purification of the crude product by preparative HPLC (mobile phase: acetonitrile/water gradient) resulted in 0.53 g (25% of theory) of the title compound.

$^1$H-NMR (400 MHz, DMSO-$d_6$): δ=1.96 (s, 3H), 3.93 (s, 2H), 5.72 (s, 1H), 6.68 (s, 1H), 6.82 (t, 1H), 6.94 (d, 1H), 7.01 (d, 1H), 7.08-7.16 (m, 4H), 7.22-7.29 (m, 4H), 11.0 (s, 1H).

LC-MS (Method 4): $R_t$=1.58 min; MS (ESIneg): m/z=378 [M−H]$^-$.

Example 279

3-[Bis(4-chlorophenyl)methyl]-7-[(methylsulfanyl)methyl]-1H-indole

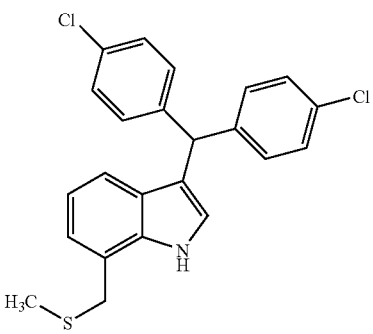

The title compound was prepared starting from 1.50 g (8.46 mmol) of the compound from Example 8A and 2.14 g (8.46 mmol) of 4,4'-dichlorobenzohydrol in analogy to the synthesis of the compound from Example 278. 0.94 g (27% of theory) of the target compound were obtained.

$^1$H-NMR (400 MHz, DMSO-$d_6$): δ=1.96 (s, 3H), 3.94 (s, 2H), 5.73 (s, 1H), 6.71 (s, 1H), 6.83 (t, 1H), 6.95 (d, 1H), 7.02 (d, 1H), 7.24 (d, 4H), 7.36 (d, 4H), 11.0 (s, 1H).

LC-MS (Method 4): $R_t$=1.71 min; MS (ESIneg): m/z=410 [M−H]$^−$.

Example 280

4-[(4-Fluorophenyl){7-[(methylsulfanyl)methyl]-1H-indol-3-yl}methyl]benzonitrile

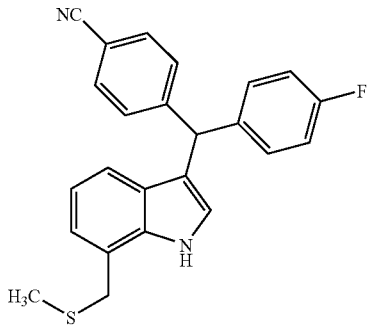

The title compound was prepared starting from 750 mg (4.23 mmol) of the compound from Example 8A and 961 mg (4.23 mmol) of the compound from Example 173A in analogy to the synthesis of the compound from Example 278. 276 mg (17% of theory) of the target compound were obtained.

$^1$H-NMR (400 MHz, DMSO-$d_6$): δ=1.95 (s, 3H), 3.94 (s, 2H), 5.84 (s, 1H), 6.73 (d, 1H), 6.84 (t, 1H), 6.96 (d, 1H), 7.01 (d, 1H), 7.10-7.18 (m, 2H), 7.24-7.31 (m, 2H), 7.43 (d, 2H), 7.77 (d, 2H), 11.1 (s, 1H).

LC-MS (Method 3): $R_t$=2.52 min; MS (ESIneg): m/z=385 [M−H]$^−$.

Example 281

4-[(4-Chlorophenyl){7-[(methylsulfanyl)methyl]-1H-indol-3-yl}methyl]benzonitrile

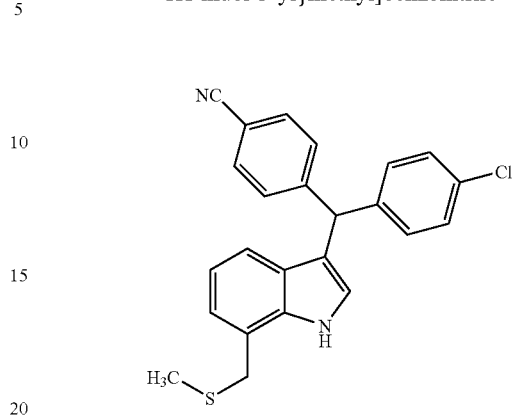

The title compound was prepared starting from 750 mg (4.23 mmol) of the compound from Example 8A and 1.03 g (4.23 mmol) of the compound from Example 174A in analogy to the synthesis of the compound from Example 278. 248 mg (15% of theory) of the target compound were obtained.

$^1$H-NMR (400 MHz, DMSO-$d_6$): δ=1.95 (s, 3H), 3.94 (s, 2H), 5.85 (s, 1H), 6.74 (s, 1H), 6.84 (t, 1H), 6.96 (d, 1H), 7.02 (d, 1H), 7.26 (d, 2H), 7.38 (d, 2H), 7.43 (d, 2H), 7.78 (d, 2H), 11.1 (s, 1H).

LC-MS (Method 5): $R_t$=3.00 min; MS (ESIneg): m/z=401 [M−H]$^−$.

Example 282

3-[(4-Chlorophenyl)(4-methoxyphenyl)methyl]-7-[(methylsulfanyl)methyl]-1H-indole

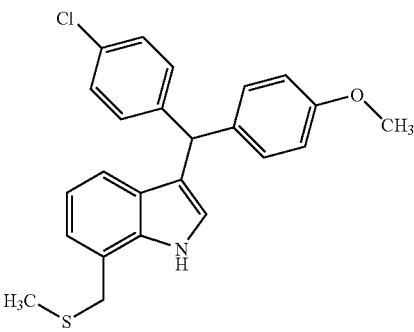

The title compound was prepared starting from 750 mg (4.23 mmol) of the compound from Example 8A and 1.05 g (4.23 mmol) of the compound from Example 175A in analogy to the synthesis of the compound from Example 278. 262 mg (15% of theory) of the target compound were obtained.

$^1$H-NMR (400 MHz, DMSO-$d_6$): δ=1.96 (s, 3H), 3.72 (s, 3H), 3.93 (s, 2H), 5.63 (s, 1H), 6.68 (s, 1H), 6.82 (t, 1H), 6.86 (d, 2H), 6.94 (d, 1H), 7.01 (d, 1H), 7.13 (d, 2H), 7.23 (d, 2H), 7.34 (d, 2H), 11.0 (s, 1H).

LC-MS (Method 9): $R_t$=1.43 min; MS (ESIneg): m/z=406 [M−H]$^−$.

Example 283

3-[(4-Chloro-3-fluorophenyl)(4-fluorophenyl)methyl]-7-[(methylsulfanyl)methyl]-1H-indole

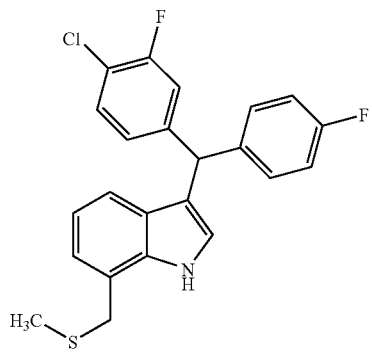

The title compound was prepared starting from 750 mg (4.23 mmol) of the compound from Example 8A and 1.08 g (4.23 mmol) of the compound from Example 176A in analogy to the synthesis of the compound from Example 278. 460 mg (26% of theory) of the target compound were obtained.

$^1$H-NMR (400 MHz, DMSO-d$_6$): δ=1.95 (s, 3H), 3.94 (s, 2H), 5.77 (s, 1H), 6.76 (d, 1H), 6.84 (t, 1H), 6.96 (d, 1H), 7.03 (d, 1H), 7.01-7.17 (m, 3H), 7.20-7.32 (m, 3H), 7.51 (t, 1H), 11.0 (s, 1H).

LC-MS (Method 6): R$_t$=2.94 min; MS (ESIneg): m/z=412 [M−H]$^-$.

Example 284

3-[(3-Chloro-4-fluorophenyl)(4-chlorophenyl)methyl]-7-[(methylsulfanyl)methyl]-1H-indole

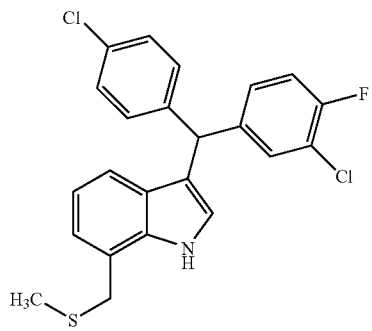

The title compound was prepared starting from 750 mg (4.23 mmol) of the compound from Example 8A and 1.15 g (4.23 mmol) of the compound from Example 177A in analogy to the synthesis of the compound from Example 278. 483 mg (26% of theory) of the target compound were obtained.

$^1$H-NMR (400 MHz, DMSO-d$_6$): δ=1.95 (s, 3H), 3.94 (s, 2H), 5.77 (s, 1H), 6.75 (s, 1H), 6.85 (t, 1H), 6.96 (d, 1H), 7.03 (d, 1H), 7.20-7.28 (m, 3H), 7.32-7.43 (m, 4H), 11.1 (s, 1H).

LC-MS (Method 4): R$_t$=1.71 min; MS (ESIneg): m/z=428 [M−H]$^-$.

Example 285

3-[(4-Chloro-2,6-difluorophenyl)(4-fluorophenyl)methyl]-7-[(methylsulfanyl)methyl]-1H-indole

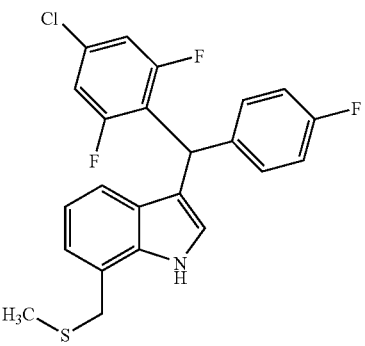

The title compound was prepared starting from 490 mg (2.76 mmol) of the compound from Example 8A and 753 mg (2.76 mmol) of the compound from Example 178A in analogy to the synthesis of the compound from Example 278. 140 mg (12% of theory) of the target compound were obtained.

$^1$H-NMR (400 MHz, DMSO-d$_6$): δ=1.96 (s, 3H), 3.95 (s, 2H), 5.98 (s, 1H), 6.84-6.91 (m, 2H), 6.98 (d, 1H), 7.04 (d, 1H), 7.08-7.15 (m, 2H), 7.21-7.27 (m, 2H), 7.37 (d, 2H), 11.1 (s, 1H).

LC-MS (Method 3): R$_t$=2.84 min; MS (ESIneg): m/z=430 [M−H]$^-$.

Example 286

3-[Bis(4-chloro-2-fluorophenyl)methyl]-7-[(methylsulfanyl)methyl]-1H-indole

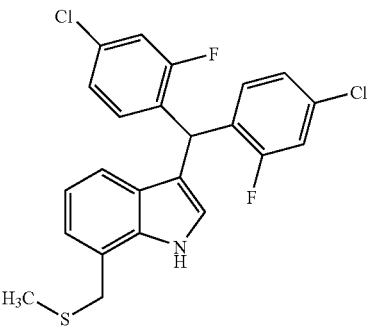

The title compound was prepared starting from 750 mg (4.23 mmol) of the compound from Example 8A and 1.22 g (4.23 mmol) of the compound from Example 179A in analogy to the synthesis of the compound from Example 278. 97 mg (5% of theory) of the target compound were obtained.

$^1$H-NMR (400 MHz, DMSO-d$_6$): δ=1.97 (s, 3H), 3.95 (s, 2H), 6.04 (s, 1H), 6.77 (s, 1H), 6.88 (t, 1H), 6.96-7.08 (m, 4H), 7.23 (dd, 2H), 7.45 (dd, 2H), 11.1 (s, 1H).

LC-MS (Method 4): R$_t$=1.75 min; MS (ESIneg): m/z=446 [M−H]$^-$.

Example 287

3-[(4-Chloro-2-fluorophenyl)(4-fluoro-2-methylphenyl)methyl]-7-[(methylsulfanyl)methyl]-1H-indole

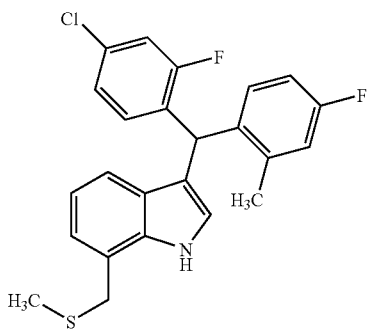

The title compound was prepared starting from 750 mg (4.23 mmol) of the compound from Example 8A and 1.14 g (4.23 mmol) of the compound from Example 180A in analogy to the synthesis of the compound from Example 278. 554 mg (31% of theory) of the target compound were obtained.

$^1$H-NMR (400 MHz, DMSO-$d_6$): δ=1.97 (s, 3H), 2.25 (s, 3H), 3.95 (s, 2H), 5.93 (s, 1H), 6.61 (s, 1H), 6.85 (t, 2H), 6.89-7.00 (m, 3H), 7.04 (d, 1H), 7.09 (dd, 1H), 7.22 (dd, 1H), 7.43 (dd, 1H), 11.1 (s, 1H).

LC-MS (Method 3): $R_t$=2.92 min; MS (ESIneg): m/z=426 [M−H]$^-$.

Example 288

3-[(4-Chloro-2-fluorophenyl)(2,4-difluorophenyl)methyl]-7-[(methylsulfanyl)methyl]-1H-indole

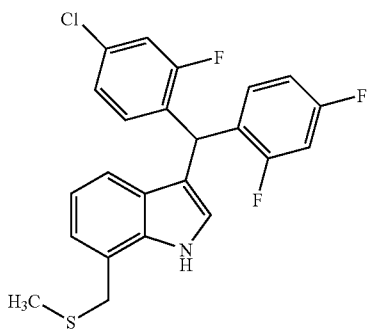

The title compound was prepared starting from 750 mg (4.23 mmol) of the compound from Example 8A and 1.15 g (4.23 mmol) of the compound from Example 181A in analogy to the synthesis of the compound from Example 278. A difference was that stirring at 80° C. for two days was followed by addition of 0.33 ml (4.23 mmol) of trifluoroacetic acid and stirring for an additional 16 h. 65 mg (75% purity, 3% of theory) of the target compound were obtained.

$^1$H-NMR (400 MHz, DMSO-$d_6$): δ=1.97 (s, 3H), 3.96 (s, 2H), 6.13 (s, 1H), 6.86-6.93 (m, 2H), 6.97-7.21 (m, 6H), 7.37-7.44 (m, 2H), 11.2 (s, 1H).

LC-MS (Method 4): $R_t$=1.65 min; MS (ESIneg): m/z=430 [M−H]$^-$.

Example 289

3-[1-(4-Chlorophenyl)-1-(4-fluorophenyl)ethyl]-7-[(methylsulfanyl)methyl]-1H-indole

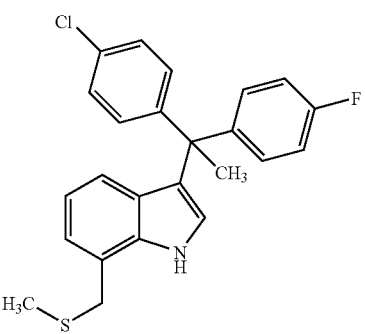

The title compound was prepared starting from 1.00 g (5.64 mmol) of the compound from Example 8A and 1.41 g (5.64 mmol) of the compound from Example 182A in analogy to the synthesis of the compound from Example 278. A difference was that stirring at 80° C. was for only 4 h. 1.31 g (56% of theory) of the target compound were obtained.

$^1$H-NMR (400 MHz, DMSO-$d_6$): δ=1.98 (s, 3H), 2.15 (s, 3H), 3.93 (s, 2H), 6.62 (d, 1H), 6.73-6.79 (m, 2H), 6.92 (dd, 1H), 7.06-7.23 (m, 6H), 7.31-7.36 (m, 2H), 11.0 (s, 1H).

LC-MS (Method 4): $R_t$=1.69 min; MS (ESIneg): m/z=408 [M−H]$^-$.

Example 290

3-[1-(4-Chloro-2-fluorophenyl)-1-(4-fluorophenyl)ethyl]-7-[(methylsulfanyl)methyl]-1H-indole

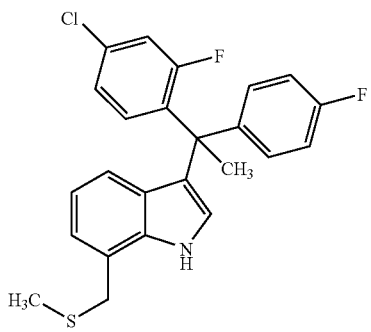

The title compound was prepared starting from 1.00 g (5.64 mmol) of the compound from Example 8A and 1.52 g (5.64 mmol) of the compound from Example 183A in analogy to the synthesis of the compound from Example 278. 0.95 g (39% of theory) of the target compound were obtained.

$^1$H-NMR (400 MHz, DMSO-$d_6$): δ=1.99 (s, 3H), 2.20 (s, 3H), 3.94 (s, 2H), 6.65 (d, 1H), 6.79 (t, 1H), 6.86-6.96 (m, 3H), 7.07-7.24 (m, 5H), 7.36 (dd, 1H), 11.0 (s, 1H).

LC-MS (Method 5): $R_t$=3.23 min; MS (ESIneg): m/z=426 [M−H]$^-$.

Example 291

3-[(4-Chlorophenyl)(4-fluorophenyl)methyl]-5-fluoro-7-[(methylsulfanyl)methyl]-1H-indole

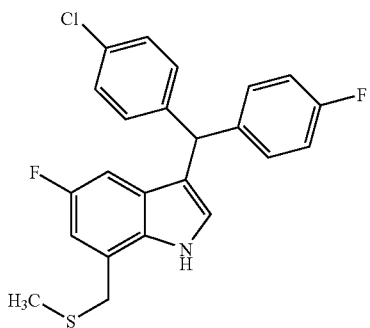

The title compound was prepared starting from 500 mg (2.56 mmol) of the compound from Example 11A and 667 mg (2.56 mmol) of the compound from Example 81A in analogy to the synthesis of the compound from Example 278. A difference was that stirring at 80° C. was for only 4 h. 535 mg (50% of theory) of the target compound were obtained.

$^1$H-NMR (400 MHz, DMSO-$d_6$): δ=1.97 (s, 3H), 3.93 (s, 2H), 5.71 (s, 1H), 6.72 (dd, 1H), 6.81 (s, 1H), 6.85 (dd, 1H), 7.10-7.17 (m, 2H), 7.21-7.29 (m, 4H), 7.34-7.39 (m, 2H), 11.1 (s, 1H).

LC-MS (Method 5): $R_t$=3.14 min; MS (ESIneg): m/z=412 [M−H]$^−$.

Example 292

5-Fluoro-3-[(4-fluoro-2-methylphenyl)(4-fluorophenyl)methyl]-7-[(methylsulfanyl)methyl]-1H-indole

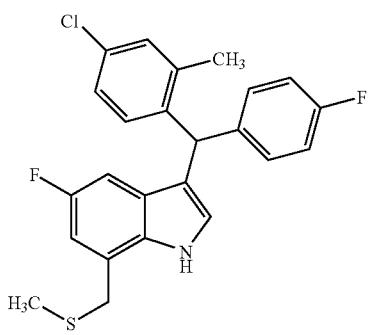

The title compound was prepared starting from 500 mg (2.56 mmol) of the compound from Example 11A and 733 mg (2.56 mmol) of the compound from Example 82A in analogy to the synthesis of the compound from Example 278. A difference was that stirring at 80° C. was for only 4 h. 428 mg (39% of theory) of the target compound were obtained.

$^1$H-NMR (400 MHz, DMSO-$d_6$): δ=1.98 (s, 3H), 2.26 (s, 3H), 3.94 (q, 2H), 5.76 (s, 1H), 6.64 (s, 1H), 6.71 (dd, 2H), 6.82-6.95 (m, 3H), 7.05 (dd, 1H), 7.09-7.22 (m, 4H), 11.1 (s, 1H).

LC-MS (Method 4): $R_t$=1.63 min; MS (ESIneg): m/z=410 [M−H]$^−$.

Example 293

3-[(4-Chloro-2-methylphenyl)(4-fluorophenyl)methyl]-5-fluoro-7-[(methylsulfanyl)methyl]-1H-indole

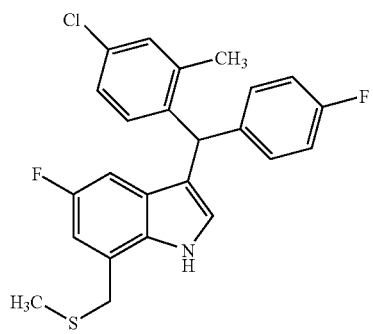

The title compound was prepared starting from 500 mg (2.56 mmol) of the compound from Example 11A and 706 mg (2.56 mmol) of the compound from Example 83A in analogy to the synthesis of the compound from Example 278. A difference was that stirring at 80° C. was for only 4 h. 616 mg (56% of theory) of the target compound were obtained.

$^1$H-NMR (400 MHz, DMSO-$d_6$): δ=1.98 (s, 3H), 2.25 (s, 3H), 3.94 (q, 2H), 5.77 (s, 1H), 6.65 (s, 1H), 6.72 (dd, 2H), 6.82-6.89 (m, 2H), 7.10-7.20 (m, 5H), 7.28 (dd, 1H), 11.1 (s, 1H).

LC-MS (Method 4): $R_t$=1.70 min; MS (ESIneg): m/z=426 [M−H]$^−$.

Example 294 and Example 295

294

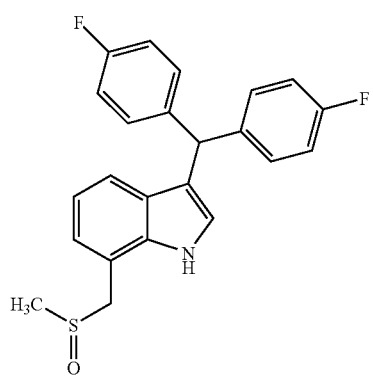

-continued

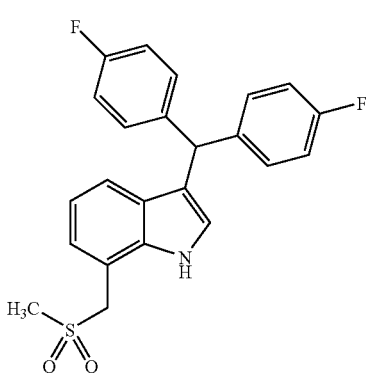

390 mg (1.03 mmol) of the compound from Example 278 were introduced into 40 ml of dichloromethane at 0° C., 507 mg (2.06 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient) to result in 40 mg (10% of theory) of Example 294 as mixture of diastereomers, and 309 mg (73% of theory) of Example 295.

Example 294

3-[Bis(4-fluorophenyl)methyl]-7-[(methylsulfinyl)methyl]-1H-indole $^1$H-NMR (400 MHz, DMSO-d$_6$): δ=2.53 (s, 3H), 4.24 (d, 1H), 4.37 (d, 1H), 5.73 (s, 1H), 6.76 (d, 1H), 6.88 (t, 1H), 7.01 (d, 1H), 7.06-7.16 (m, 5H), 7.22-7.28 (m, 3H), 11.1 (s, 1H).
LC-MS (Method 4): R$_t$=1.32 min; MS (ESIneg): m/z=394 [M−H]$^−$.

Example 295

3-[Bis(4-fluorophenyl)methyl]-7-[(methylsulfonyl)methyl]-1H-indole $^1$H-NMR (400 MHz, DMSO-d$_6$): δ=2.89 (s, 3H), 4.74 (s, 2H), 5.74 (s, 1H), 6.77 (d, 1H), 6.92 (t, 1H), 7.09-7.16 (m, 6H), 7.22-7.28 (m, 4H), 11.1 (s, 1H).
LC-MS (Method 5): R$_t$=2.63 min; MS (ESIneg): m/z=410 [M−H]$^−$.

Example 296

3-[Bis(4-chlorophenyl)methyl]-7-[(methylsulfinyl)methyl]-1H-indole

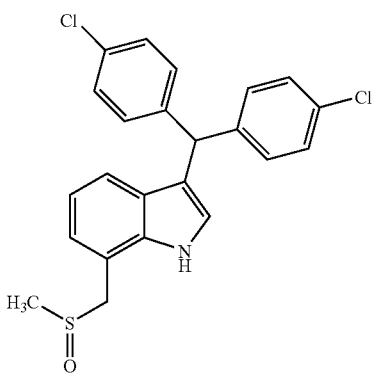

200 mg (0.49 mmol) of the compound from Example 279 were introduced into 20 ml of dichloromethane at 0° C., 120 mg (0.49 mmol) of 70% pure meta-chloroperbenzoic acid were added, and the mixture was stirred at RT for 2 h. 2 ml of methanol were added, and the solution was concentrated. The crude product was purified by preparative HPLC (mobile phase: acetonitrile/water gradient) to result in 134 mg (65% of theory) of the title compound as mixture of diastereomers.
$^1$H-NMR (400 MHz, DMSO-d$_6$): δ=2.53 (s, 3H), 4.24 (d, 1H), 4.37 (d, 1H), 5.74 (s, 1H), 6.79 (d, 1H), 6.89 (t, 1H), 7.02 (d, 1H), 7.09 (d, 1H), 7.23 (d, 4H), 7.36 (d, 4H), 11.1 (s, 1H).
LC-MS (Method 4): R$_t$=1.47 min; MS (ESIneg): m/z=426 [M−H]$^−$.

Example 297

4-[(4-Fluorophenyl){7-[(methylsulfinyl)methyl]-1H-indol-3-yl}methyl]benzonitrile

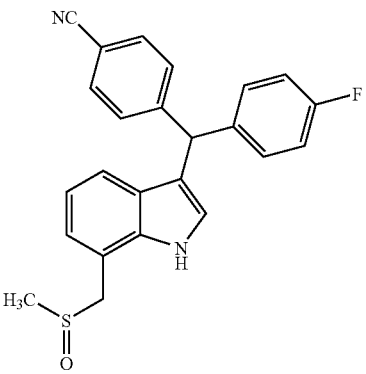

The title compound was prepared starting from 60 mg (0.16 mmol) of the compound from Example 280 in analogy to the synthesis of the compound from Example 296. 61 mg (98% of theory) of the target compound were obtained as mixture of diastereomers.
$^1$H-NMR (400 MHz, DMSO-d$_6$): δ=2.53 (s, 3H), 4.24 (d, 1H), 4.37 (d, 1H), 5.86 (s, 1H), 6.81 (d, 1H), 6.89 (t, 1H), 7.03 (d, 1H), 7.09 (d, 1H), 7.14 (t, 2H), 7.24-7.30 (m, 2H), 7.43 (d, 2H), 7.77 (d, 2H), 11.2 (s, 1H).
LC-MS (Method 4): R$_t$=1.25 min; MS (ESIneg): m/z=401 [M−H]$^−$.

Example 298

4-[(4-Chlorophenyl){7-[(methylsulfinyl)methyl]-1H-indol-3-yl}methyl]benzonitrile

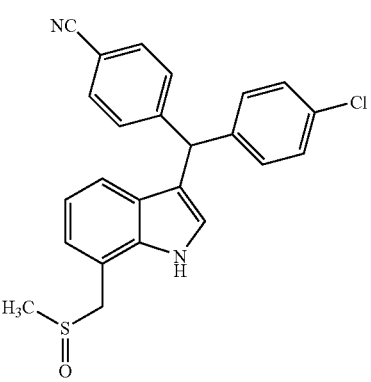

The title compound was prepared starting from 60 mg (0.15 mmol) of the compound from Example 281 in analogy to the synthesis of the compound from Example 296. 62 mg (99% of theory) of the target compound were obtained as mixture of diastereomers.

$^1$H-NMR (400 MHz, DMSO-$d_6$): δ=2.53 (s, 3H), 4.24 (d, 1H), 4.37 (d, 1H), 5.86 (s, 1H), 6.82 (d, 1H), 6.90 (t, 1H), 7.03 (d, 1H), 7.09 (d, 1H), 7.25 (d, 2H), 7.38 (d, 2H), 7.43 (d, 2H), 7.78 (d, 2H), 11.2 (s, 1H).

LC-MS (Method 5): $R_t$=2.47 min; MS (ESIneg): m/z=417 [M−H]$^-$.

Example 299

3-[(4-Chloro-3-fluorophenyl)(4-fluorophenyl)methyl]-7-[(methylsulfinyl)methyl]-1H-indole

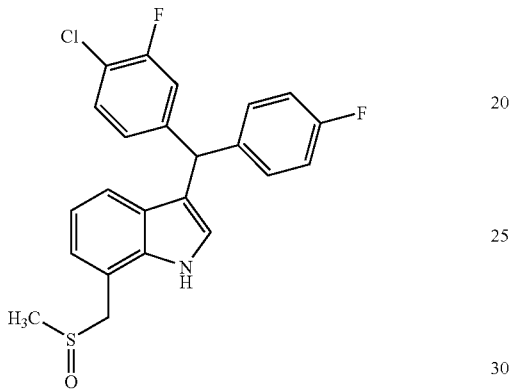

The title compound was prepared starting from 75 mg (0.18 mmol) of the compound from Example 283 in analogy to the synthesis of the compound from Example 296. 76 mg (98% of theory) of the target compound were obtained as mixture of diastereomers.

$^1$H-NMR (400 MHz, DMSO-$d_6$): δ=2.53 (s, 3H), 4.24 (dd, 1H), 4.37 (d, 1H), 5.78 (s, 1H), 6.84 (d, 1H), 6.90 (t, 1H), 7.02 (d, 1H), 7.07-7.17 (m, 4H), 7.20-7.31 (m, 3H), 7.52 (t, 1H), 11.2 (s, 1H).

LC-MS (Method 9): $R_t$=1.24 min; MS (ESIneg): m/z=428 [M−H]$^-$.

Example 300

3-[(3-Chloro-4-fluorophenyl)(4-chlorophenyl)methyl]-7-[(methylsulfinyl)methyl]-1H-indole

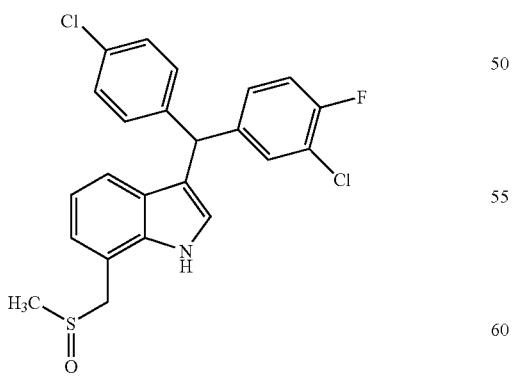

The title compound was prepared starting from 100 mg (0.23 mmol) of the compound from Example 284 in analogy to the synthesis of the compound from Example 296. 102 mg (98% of theory) of the target compound were obtained as mixture of diastereomers.

$^1$H-NMR (400 MHz, DMSO-$d_6$): δ=2.53 (s, 3H), 4.24 (dd, 1H), 4.38 (d, 1H), 5.79 (s, 1H), 6.83 (s, 1H), 6.90 (t, 1H), 7.03 (d, 1H), 7.10 (d, 1H), 7.19-7.23 (m, 3H), 7.32-7.43 (m, 4H), 11.2 (s, 1H).

LC-MS (Method 4): $R_t$=1.47 min; MS (ESIneg): m/z=444 [M−H]$^-$.

Example 301

3-[(4-Chloro-2,6-difluorophenyl)(4-fluorophenyl)methyl]-7-[(methylsulfinyl)methyl]-1H-indole

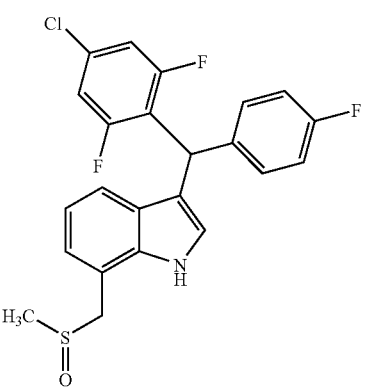

The title compound was prepared starting from 40 mg (0.09 mmol) of the compound from Example 285 in analogy to the synthesis of the compound from Example 296. 38 mg (92% of theory) of the target compound were obtained as mixture of diastereomers.

$^1$H-NMR (400 MHz, DMSO-$d_6$): δ=2.54 (s, 3H), 4.25 (dd, 1H), 4.39 (dd, 1H), 5.99 (s, 1H), 6.93 (t, 1H), 6.97 (s, 1H), 7.05 (d, 1H), 7.08-7.16 (m, 3H), 7.20-7.27 (m, 2H), 7.37 (d, 2H), 11.2 (s, 1H).

LC-MS (Method 3): $R_t$=2.32 min; MS (ESIneg): m/z=446 [M−H]$^-$.

Example 302 and Example 303

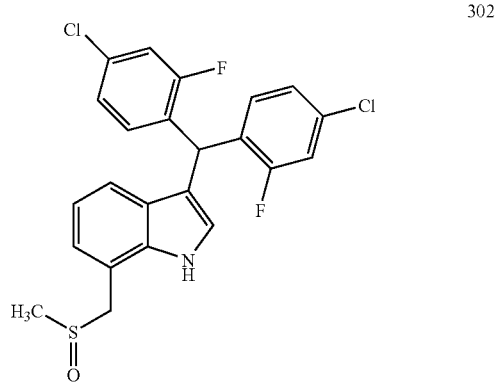

302

-continued

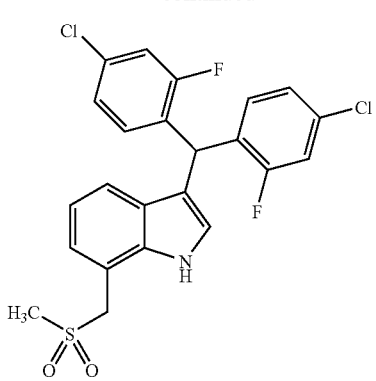

303

89 mg (0.20 mmol) of the compound from Example 286 were introduced into 10 ml of dichloromethane at 0° C., 86 mg (0.35 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient) to result in 46 mg (48% of theory) of Example 302 as mixture of diastereomers, and 31 mg (34% of theory) of Example 303.

Example 302

3-[Bis(4-chloro-2-fluorophenyl)methyl]-7-[(methylsulfinyl)methyl]-1H-indole $^1$H-NMR (400 MHz, DMSO-d$_6$): δ=2.54 (s, 3H), 4.25 (d, 1H), 4.39 (d, 1H), 6.05 (s, 1H), 6.85 (s, 1H), 6.93 (t, 1H), 7.00-7.08 (m, 3H), 7.13 (d, 1H), 7.24 (d, 2H), 7.45 (d, 2H), 11.2 (s, 1H).
LC-MS (Method 3): R$_t$=2.47 min; MS (ESIneg): m/z=462 [M−H]$^−$.

Example 303

3-[Bis(4-chloro-2-fluorophenyl)methyl]-7-[(methylsulfonyl)methyl]-1H-indole $^1$H-NMR (400 MHz, DMSO-d$_6$): δ=2.91 (s, 3H), 4.76 (s, 2H), 6.06 (s, 1H), 6.86 (s, 1H), 6.97 (t, 1H), 7.03 (t, 2H), 7.17 (t, 2H), 7.24 (dd, 2H), 7.46 (dd, 2H), 11.2 (s, 1H).
LC-MS (Method 3): R$_t$=2.59 min; MS (ESIneg): m/z=478 [M−H]$^−$.

Example 304

3-[(4-Chloro-2-fluorophenyl)(4-fluoro-2-methylphenyl)methyl]-7-[(methylsulfinyl)methyl]-1H-indole

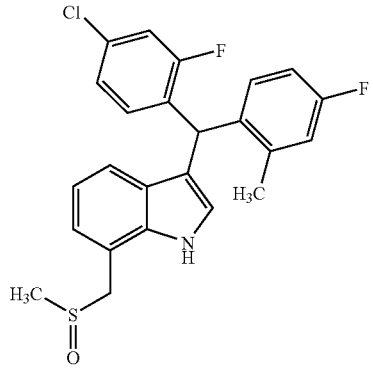

The title compound was prepared starting from 100 mg (0.23 mmol) of the compound from Example 287 in analogy to the synthesis of the compound from Example 296. 99 mg (95% of theory) of the target compound were obtained as mixture of diastereomers.

$^1$H-NMR (400 MHz, DMSO-d$_6$): δ=2.24 (s, 3H), 2.54 (s, 3H), 4.24 (dd, 1H), 4.38 (dd, 1H), 5.94 (s, 1H), 6.69 (d, 1H), 6.82-6.97 (m, 4H), 7.02-7.14 (m, 3H), 7.22 (dd, 1H), 7.43 (dd, 1H), 11.2 (s, 1H).
LC-MS (Method 5): R$_t$=2.76 min; MS (ESIneg): m/z=442 [M−H]$^−$.

Example 305 and Example 306

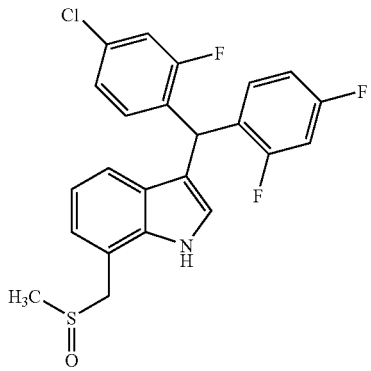

305

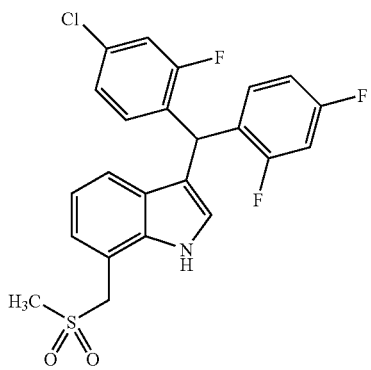

306

60 mg (75% purity, 0.10 mmol) of the compound from Example 288 were introduced into 6 ml of dichloromethane at 0° C., 51 mg (0.21 mmol) of 70% pure meta-chloroperbenzoic acid were added, and the mixture was stirred at RT for 2 h. 2 ml of methanol were added, and the solution was concentrated. The residue was purified by preparative HPLC (mobile phase: acetonitrile/water gradient) to result in 40 mg (83% of theory) of Example 305 as mixture of diastereomers, and 10 mg (63% purity, 13% of theory) of Example 306.

Example 305

3-[(4-Chloro-2-fluorophenyl)(2,4-difluorophenyl)methyl]-7-[(methylsulfinyl)methyl]-1H-indole $^1$H-NMR (400 MHz, DMSO-d$_6$): δ=2.54 (s, 3H), 4.26 (dd, 1H), 4.40 (dd, 1H), 6.14 (s, 1H), 6.94 (t, 1H), 6.99 (s, 1H), 7.01-7.20 (m, 6H), 7.37-7.47 (m, 2H), 11.3 (s, 1H).
LC-MS (Method 4): R$_t$=1.39 min; MS (ESIneg): m/z=446 [M−H]$^−$.

Example 306

3-[(4-Chloro-2-fluorophenyl)(2,4-difluorophenyl)methyl]-7-[(methylsulfinyl)methyl]-1H-indole

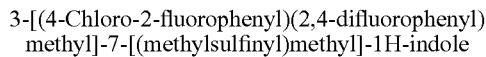

¹H-NMR (400 MHz, DMSO-d₆): δ=2.91 (s, 3H), 4.77 (s, 2H), 6.14 (s, 1H), 6.94-7.07 (m, 3H), 7.09-7.20 (m, 5H), 7.37-7.46 (m, 2H), 11.2 (s, 1H).

LC-MS (Method 4): $R_t$=1.45 min; MS (ESIneg): m/z=462 [M–H]⁻.

Example 307

3-[1-(4-Chlorophenyl)-1-(4-fluorophenyl)ethyl]-7-[(methylsulfinyl)methyl]-1H-indole

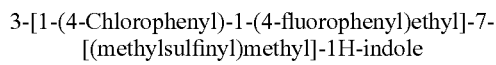

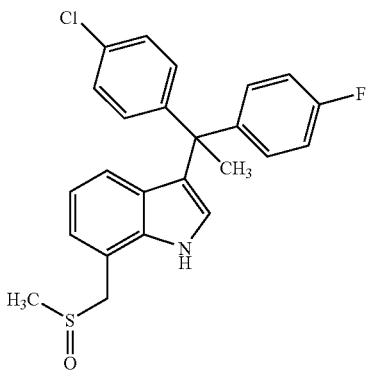

The title compound was prepared starting from 300 mg (0.73 mmol) of the compound from Example 289 in analogy to the synthesis of the compound from Example 296. 193 mg (62% of theory) of the target compound were obtained as mixture of diastereomers.

¹H-NMR (400 MHz, DMSO-d₆): δ=2.16 (s, 3H), 2.55 (s, 3H), 4.23 (d, 1H), 4.37 (d, 1H), 6.72 (d, 1H), 6.78-6.85 (m, 2H), 6.98 (dd, 1H), 7.07-7.14 (m, 2H), 7.15-7.22 (m, 4H), 7.34 (d, 2H), 11.1 (s, 1H).

LC-MS (Method 4): $R_t$=1.45 min; MS (ESIneg): m/z=424 [M–H]⁻.

Example 308

3-[1-(4-Chloro-2-fluorophenyl)-1-(4-fluorophenyl)ethyl]-7-[(methylsulfinyl)methyl]-1H-indole

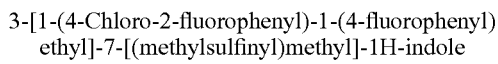

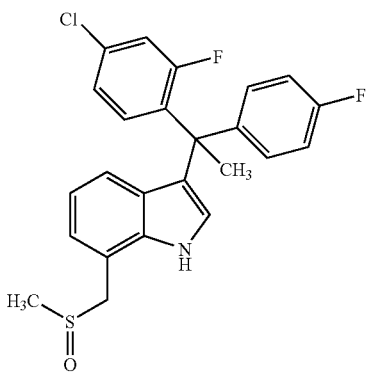

The title compound was prepared starting from 300 mg (0.70 mmol) of the compound from Example 290 in analogy to the synthesis of the compound from Example 296. 258 mg (83% of theory) of the target compound were obtained as mixture of diastereomers.

¹H-NMR (400 MHz, DMSO-d₆): δ=2.20 (s, 3H), 2.56 (s, 3H), 4.23 (s, 1H), 4.38 (s, 1H), 6.76 (dd, 1H), 6.84 (t, 1H), 6.88-6.96 (m, 2H), 7.00 (d, 1H), 7.07-7.25 (m, 5H), 7.36 (dd, 1H), 11.2 (s, 1H).

LC-MS (Method 3): $R_t$=2.38 min; MS (ESIneg): m/z=442 [M–H]⁻.

Example 309

3-[(4-Chlorophenyl)(4-fluorophenyl)methyl]-5-fluoro-7-[(methylsulfinyl)methyl]-1H-indole

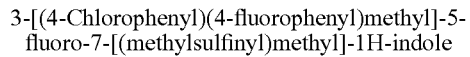

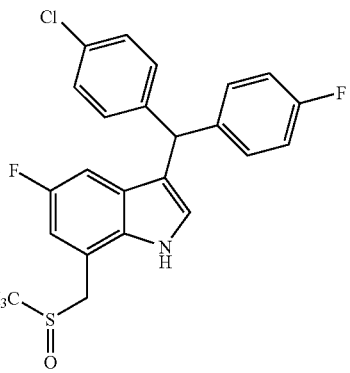

The title compound was prepared starting from 100 mg (0.24 mmol) of the compound from Example 291 in analogy to the synthesis of the compound from Example 296. 102 mg (98% of theory) of the target compound were obtained as mixture of diastereomers.

¹H-NMR (400 MHz, DMSO-d₆): δ=2.54 (s, 3H), 4.23 (d, 1H), 4.38 (d, 1H), 5.72 (s, 1H), 6.81 (dd, 1H), 6.88-6.93 (m, 2H), 6.88-6.96 (m, 2H), 7.13 (t, 2H), 7.21-7.28 (m, 4H), 7.37 (d, 2H), 11.2 (s, 1H).

LC-MS (Method 5): $R_t$=2.66 min; MS (ESIneg): m/z=428 [M–H]⁻.

Example 310

5-Fluoro-3-[(4-fluoro-2-methylphenyl)(4-fluorophenyl)methyl]-7-[(methylsulfinyl)methyl]-1H-indole

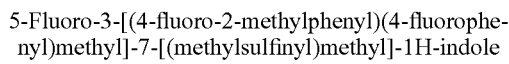

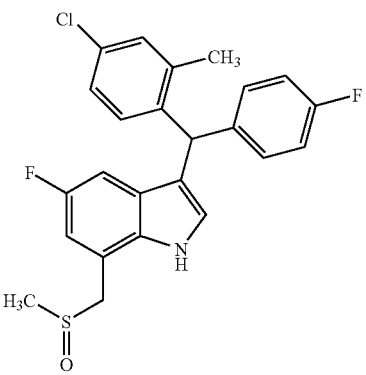

The title compound was prepared starting from 75 mg (0.18 mmol) of the compound from Example 292 in analogy to the synthesis of the compound from Example 296. 75 mg (96% of theory) of the target compound were obtained as mixture of diastereomers.

$^1$H-NMR (400 MHz, DMSO-d$_6$): δ=2.26 (s, 3H), 2.54 (s, 3H), 4.23 (dd, 1H), 4.38 (dd, 1H), 5.78 (s, 1H), 6.72 (s, 1H), 6.77-6.95 (m, 4H), 7.06 (dd, 1H), 7.10-7.21 (m, 4H), 11.2 (s, 1H).

LC-MS (Method 3): R$_t$=2.29 min; MS (ESIneg): m/z=426 [M–H]$^-$.

Example 311

5-Fluoro-3-[(4-fluoro-2-methylphenyl)(4-fluorophenyl)methyl]-7-[(methylsulfinyl)methyl]-1H-indole

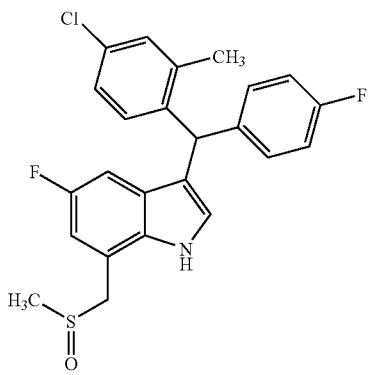

The title compound was prepared starting from 120 mg (0.28 mmol) of the compound from Example 293 in analogy to the synthesis of the compound from Example 296. 114 mg (92% of theory) of the target compound were obtained as mixture of diastereomers.

$^1$H-NMR (400 MHz, DMSO-d$_6$): δ=2.25 (s, 3H), 2.55 (s, 3H), 4.24 (dd, 1H), 4.39 (dd, 1H), 5.79 (s, 1H), 6.74 (d, 1H), 6.79-6.86 (m, 2H), 6.91 (dt, 1H), 7.10-7.21 (m, 5H), 7.28 (d, 1H), 11.2 (s, 1H).

LC-MS (Method 3): R$_t$=2.42 min; MS (ESIneg): m/z=442 [M–H]$^-$.

Example 312

3-[Bis(4-chlorophenyl)methyl]-7-[(methylsulfonyl)methyl]-1H-indole

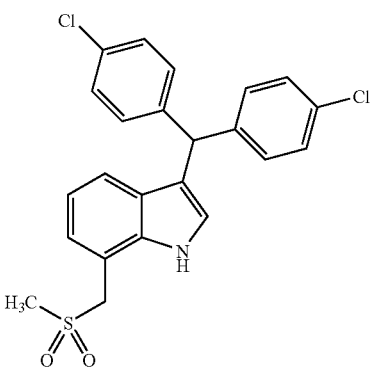

680 mg (1.65 mmol) of the compound from Example 279 were introduced into 40 ml of dichloromethane at 0° C., 813 mg (3.30 mmol) of 70% pure meta-chloroperbenzoic acid were added, and the mixture was stirred at 0° C. for 2 h. 2 ml of methanol were added, and the solution was concentrated. The crude product was purified by preparative HPLC (mobile phase: acetonitrile/water gradient) to result in 529 mg (72% of theory) of the title compound.

$^1$H-NMR (400 MHz, DMSO-d$_6$): δ=2.89 (s, 3H), 4.74 (s, 2H), 5.76 (s, 1H), 6.79 (d, 1H), 6.93 (t, 1H), 7.13 (d, 2H), 7.24 (d, 4H), 7.36 (d, 4H), 11.1 (s, 1H).

LC-MS (Method 4): R$_t$=1.51 min; MS (ESIneg): m/z=442 [M–H]$^-$.

Example 313

4-[(4-Fluorophenyl){7-[(methylsulfonyl)methyl]-1H-indol-3-yl}methyl]benzonitrile

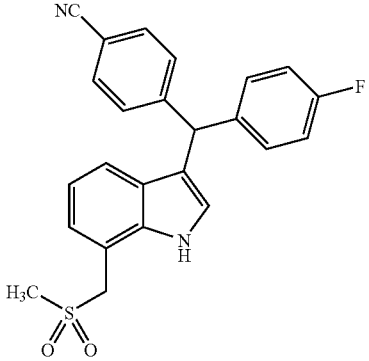

The title compound was prepared starting from 170 mg (0.44 mmol) of the compound from Example 280 in analogy to the synthesis of the compound from Example 312. 155 mg (84% of theory) of the target compound were obtained.

$^1$H-NMR (400 MHz, DMSO-d$_6$): δ=2.89 (s, 3H), 4.74 (s, 2H), 5.87 (s, 1H), 6.82 (d, 1H), 6.93 (t, 1H), 7.10-7.18 (m, 4H), 7.24-7.30 (m, 2H), 7.43 (d, 2H), 7.78 (d, 2H), 11.1 (s, 1H).

LC-MS (Method 9): R$_t$=1.13 min; MS (ESIneg): m/z=417 [M–H]$^-$.

Example 314

3-[(4-Chlorophenyl)(4-methoxyphenyl)methyl]-7-[(methylsulfonyl)methyl]-1H-indole

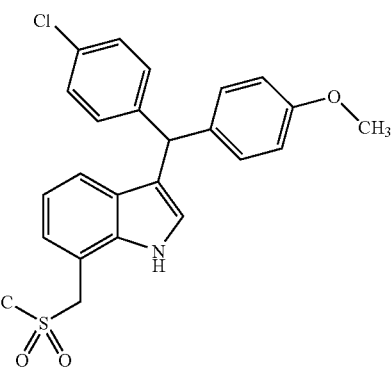

The title compound was prepared starting from 150 mg (0.37 mmol) of the compound from Example 282 in analogy to the synthesis of the compound from Example 312. 130 mg (80% of theory) of the target compound were obtained.

$^1$H-NMR (400 MHz, DMSO-$d_6$): δ=2.89 (s, 3H), 3.72 (s, 3H), 4.73 (s, 2H), 5.65 (s, 1H), 6.76 (s, 1H), 6.84-6.95 (m, 3H), 7.09-7.16 (m, 4H), 7.23 (d, 2H), 7.34 (d, 2H), 11.1 (s, 1H).

LC-MS (Method 5): $R_t$=2.70 min; MS (ESIneg): m/z=438 [M−H]$^−$.

Example 315

3-[(4-Chloro-3-fluorophenyl)(4-fluorophenyl)methyl]-7-[(methylsulfonyl)methyl]-1H-indole

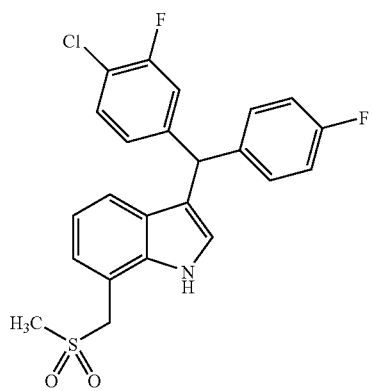

The title compound was prepared starting from 330 mg (0.80 mmol) of the compound from Example 283 in analogy to the synthesis of the compound from Example 312. 323 mg (91% of theory) of the target compound were obtained.

$^1$H-NMR (400 MHz, DMSO-$d_6$): δ=2.89 (s, 3H), 4.75 (s, 2H), 5.79 (s, 1H), 6.85 (d, 1H), 6.94 (t, 1H), 7.07-7.18 (m, 5H), 7.20-7.31 (m, 3H), 7.52 (t, 1H), 11.1 (s, 1H).

LC-MS (Method 9): $R_t$=1.27 min; MS (ESIneg): m/z=444 [M−H]$^−$.

Example 316

3-[(3-Chloro-4-fluorophenyl)(4-chlorophenyl)methyl]-7-[(methylsulfonyl)methyl]-1H-indole

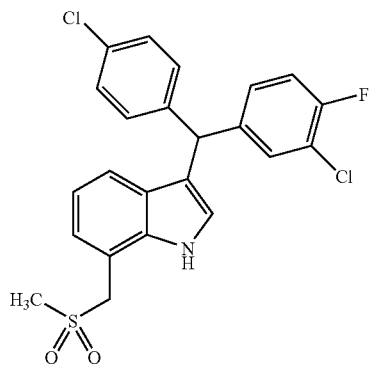

The title compound was prepared starting from 335 mg (0.78 mmol) of the compound from Example 284 in analogy to the synthesis of the compound from Example 312. 295 mg (82% of theory) of the target compound were obtained.

$^1$H-NMR (400 MHz, DMSO-$d_6$): δ=2.89 (s, 3H), 4.75 (s, 2H), 5.79 (s, 1H), 6.84 (s, 1H), 6.94 (t, 1H), 7.14 (dd, 1H), 7.20-7.28 (m, 3H), 7.32-7.43 (m, 4H), 11.1 (s, 1H).

LC-MS (Method 4): $R_t$=1.52 min; MS (ESIneg): m/z=460 [M−H]$^−$.

Example 317

3-[(4-Chloro-2,6-difluorophenyl)(4-fluorophenyl)methyl]-7-[(methylsulfonyl)methyl]-1H-indole

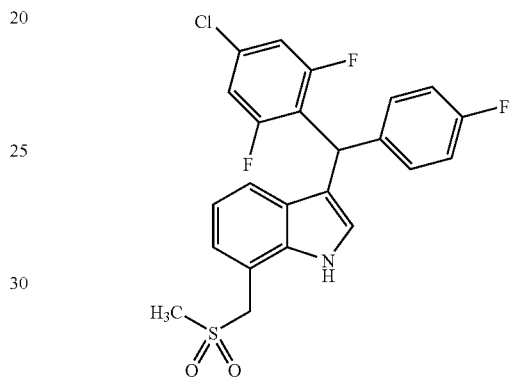

The title compound was prepared starting from 60 mg (0.14 mmol) of the compound from Example 285 in analogy to the synthesis of the compound from Example 312. 58 mg (90% of theory) of the target compound were obtained.

$^1$H-NMR (400 MHz, DMSO-$d_6$): δ=2.90 (s, 3H), 4.76 (s, 2H), 6.00 (s, 1H), 6.94-7.00 (m, 2H), 7.08-7.18 (m, 4H), 7.20-7.26 (m, 2H), 7.37 (d, 2H), 11.2 (s, 1H).

LC-MS (Method 3): $R_t$=2.44 min; MS (ESIneg): m/z=462 [M−H]$^−$.

The enantiomers were separated by preparative HPLC on a chiral phase [column: Daicel Chiralpak AD-H, 5 μm, 250 mm×20 mm; eluent: isohexane/ethanol 6:4; flow rate: 20 ml/min; temperature: 24° C.; UV detection: 230 nm]. The separated enantiomers were purified again by preparative HPLC on an achiral phase (mobile phase: acetonitrile/water gradient):

Enantiomer 317-1:

$R_t$=6.25 min [column: Daicel Chiralpak AD-H, 5 μm, 250 mm×4 mm; eluent: isohexane/ethanol 1:1; flow rate: 1 ml/min; temperature: 24° C.; UV detection: 230 nm];

Yield: 18.0 mg

Enantiomer 317-2:

$R_t$=6.98 min [column: Daicel Chiralpak AD-H, 5 μm, 250 mm×4 mm; eluent: isohexane/ethanol 1:1; flow rate: 1 ml/min; temperature: 24° C.; UV detection: 230 nm].

Yield: 18.0 mg

Example 318

3-[(4-Chloro-2-fluorophenyl)(4-fluoro-2-methylphenyl)methyl]-7-[(methylsulfonyl)methyl]-1H-indole

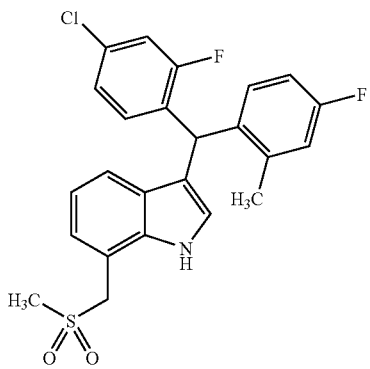

The title compound was prepared starting from 410 mg (0.96 mmol) of the compound from Example 287 in analogy to the synthesis of the compound from Example 312. 427 mg (97% of theory) of the target compound were obtained.

$^1$H-NMR (400 MHz, DMSO-d$_6$): δ=2.25 (s, 3H), 2.91 (s, 3H), 4.75 (s, 2H), 5.94 (s, 1H), 6.70 (d, 1H), 6.85 (dd, 1H), 6.89-6.98 (m, 3H), 7.09 (dd, 1H), 7.15 (dd, 2H), 7.22 (dd, 1H), 7.44 (dd, 1H), 11.1 (s, 1H).

LC-MS (Method 5): R$_t$=2.89 min; MS (ESIneg): m/z=458 [M−H]$^−$.

Example 319

3-[1-(4-Chlorophenyl)-1-(4-fluorophenyl)ethyl]-7-[(methylsulfonyl)methyl]-1H-indole

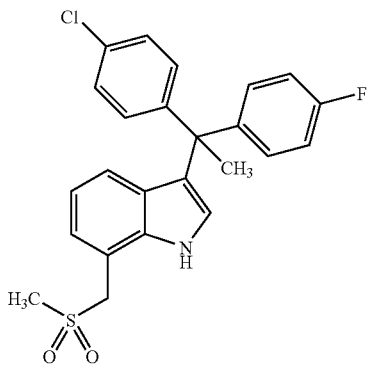

The title compound was prepared starting from 900 mg (2.20 mmol) of the compound from Example 289 in analogy to the synthesis of the compound from Example 312. 939 mg (97% of theory) of the target compound were obtained.

$^1$H-NMR (400 MHz, DMSO-d$_6$): δ=2.16 (s, 3H), 2.92 (s, 3H), 4.74 (s, 2H), 6.72 (d, 1H), 6.82-6.91 (m, 2H), 7.07-7.14 (m, 3H), 7.15-7.22 (m, 4H), 7.34 (d, 2H), 11.1 (s, 1H).

LC-MS (Method 4): R$_t$=1.49 min; MS (ESIneg): m/z=440 [M−H]$^−$.

Example 320

3-[1-(4-Chloro-2-fluorophenyl)-1-(4-fluorophenyl)ethyl]-7-[(methylsulfonyl)methyl]-1H-indole

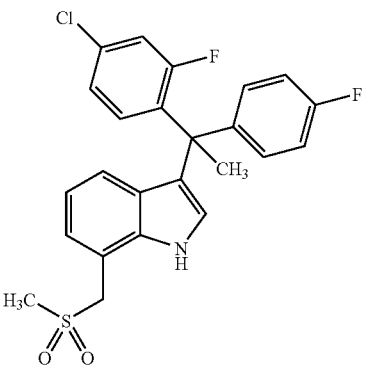

The title compound was prepared starting from 600 mg (1.40 mmol) of the compound from Example 290 in analogy to the synthesis of the compound from Example 312. 589 mg (91% of theory) of the target compound were obtained.

$^1$H-NMR (400 MHz, DMSO-d$_6$): δ=2.21 (s, 3H), 2.92 (s, 3H), 4.75 (s, 2H), 6.76 (d, 1H), 6.85-6.94 (m, 2H), 6.85-6.94 (m, 2H), 6.99 (d, 1H), 7.07-7.15 (m, 3H), 7.15-7.24 (m, 3H), 7.37 (dd, 1H), 11.1 (s, 1H).

LC-MS (Method 3): R$_t$=2.49 min; MS (ESIneg): m/z=458 [M−H]$^−$.

Example 321

3-[(4-Chlorophenyl)(4-fluorophenyl)methyl]-5-fluoro-7-[(methylsulfonyl)methyl]-1H-indole

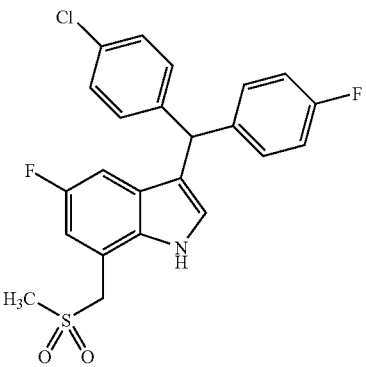

The title compound was prepared starting from 380 mg (0.92 mmol) of the compound from Example 291 in analogy to the synthesis of the compound from Example 312. 364 mg (89% of theory) of the target compound were obtained.

$^1$H-NMR (400 MHz, DMSO-d$_6$): δ=2.92 (s, 3H), 4.77 (s, 2H), 5.73 (s, 1H), 6.87 (dd, 1H), 6.91 (s, 1H), 7.01 (dd, 1H), 7.14 (t, 2H), 7.21-7.28 (m, 4H), 7.37 (d, 2H), 11.2 (s, 1H).

LC-MS (Method 5): R$_t$=2.78 min; MS (ESIneg): m/z=444 [M−H]$^−$.

The enantiomers were separated by preparative HPLC on a chiral phase [column: Daicel Chiralpak AD-H, 5 μm, 250 mm×20 mm; eluent: isohexane/ethanol 8:2; flow rate: 20 ml/min; temperature: 24° C.; UV detection: 230 nm]. The separated enantiomers were purified again by preparative HPLC on an achiral phase (mobile phase: acetonitrile/water gradient):

Enantiomer 321-1:
$R_t$=7.14 min [column: Daicel Chiralpak AD-H, 5 μm, 250 mm×4 mm; eluent: isohexane/ethanol 1:1; flow rate: 1 ml/min; temperature: 24° C.; UV detection: 230 nm];
Yield: 107 mg Enantiomer 321-2:
$R_t$=7.66 min [column: Daicel Chiralpak AD-H, 5 μm, 250 mm×4 mm; eluent: isohexane/ethanol 1:1; flow rate: 1 ml/min; temperature: 24° C.; UV detection: 230 nm].
Yield: 110 mg Example 322

5-Fluoro-3-[(4-fluoro-2-methylphenyl)(4-fluorophenyl)methyl]-7-[(methylsulfonyl)methyl]-1H-indole

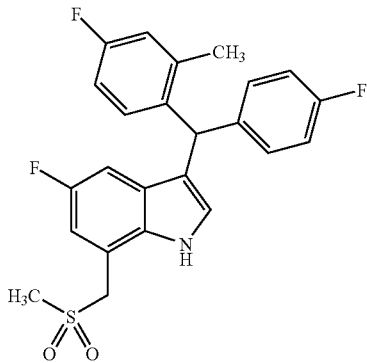

The title compound was prepared starting from 310 mg (0.75 mmol) of the compound from Example 292 in analogy to the synthesis of the compound from Example 312. 269 mg (81% of theory) of the target compound were obtained.

$^1$H-NMR (400 MHz, DMSO-$d_6$): δ=2.26 (s, 3H), 2.93 (s, 3H), 4.77 (s, 2H), 5.79 (s, 1H), 6.74 (s, 1H), 6.81-6.95 (m, 3H), 7.01 (dd, 1H), 7.06 (dd, 1H), 7.10-7.21 (m, 4H), 11.2 (s, 1H).

LC-MS (Method 3): $R_t$=2.42 min; MS (ESIneg): m/z=442 [M−H]$^-$.

Example 323

3-[(4-Chloro-2-methylphenyl)(4-fluorophenyl)methyl]-5-fluoro-7-[(methylsulfonyl)methyl]-1H-indole

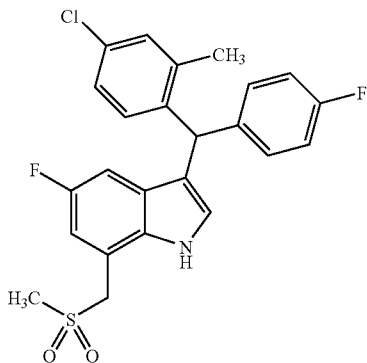

The title compound was prepared starting from 440 mg (1.03 mmol) of the compound from Example 293 in analogy to the synthesis of the compound from Example 312. 400 mg (85% of theory) of the target compound were obtained.

$^1$H-NMR (400 MHz, DMSO-$d_6$): δ=2.25 (s, 3H), 2.93 (s, 3H), 4.78 (s, 2H), 5.79 (s, 1H), 6.75 (d, 1H), 6.83 (d, 1H), 6.87 (dd, 1H), 7.01 (dd, 1H), 7.10-7.21 (m, 5H), 7.28 (d, 1H), 11.2 (s, 1H).

LC-MS (Method 3): $R_t$=2.54 min; MS (ESIneg): m/z=458 [M−H]$^-$.

Example 324

3-{(2,2-Difluorocyclopropyl)[4-(trifluoromethyl)phenyl]methyl}-7-[(methylsulfonyl)methyl]-1H-indole

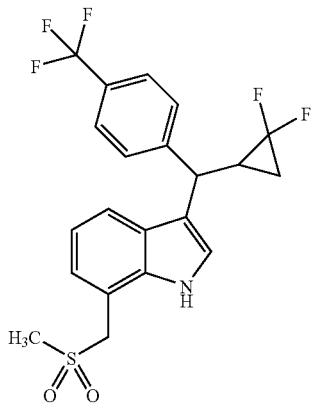

2.05 g (9.27 mmol) of indium(III) chloride were added to 2.50 g (8.50 mmol) of the compound from Example 192A and 1.62 g (7.72 mmol) of the compound from Example 86A in 31 ml of 1,2-dichloroethane under argon and reflux, and the mixture was heated under reflux for 2.5 h. A further 2.00 g (9.04 mmol) of indium(III) chloride were added, and the mixture was heated under reflux for a further 2 h. This was followed by addition of ethyl acetate and saturated aqueous sodium bicarbonate solution, separation of the phases, drying of the organic phase and concentration. The residue was purified by column chromatography on silica gel (mobile phase: cyclohexane/ethyl acetate 1/1) and by preparative HPLC (RP18 column; mobile phase: acetonitrile/water gradient) to result in 13.0 mg (0.3% of theory) of the title compound as mixture of diastereomers.

$^1$H-NMR (400 MHz, DMSO-$d_6$): δ=11.2 (s, 1H), 7.62-7.69 (m, 2.6H), 7.49-7.60 (m, 2.4H), 7.29 (d, 0.7H), 7.26 (d, 0.3H), 7.11 (d, 1H), 6.92 (t, 0.3H), 6.91 (t, 0.7H), 4.68-4.78 (m, 2H), 4.09 (d, 0.7H), 4.06 (d, 0.3H), 2.89 (s, 3H), 2.60-2.74 (m, 1H), 1.70-1.81 (m, 0.7H), 1.59-1.69 (m, 0.3H), 1.30-1.47 (m, 1H).

LC-MS (Method 9): $R_t$=1.19 min; MS (ESIneg): m/z=442 [M−H]$^-$.

Example 325

3-[(2,4-Dichlorophenyl)(2,2-difluorocyclopropyl)methyl]-7-[(methylsulfonyl)methyl]-1H-indole

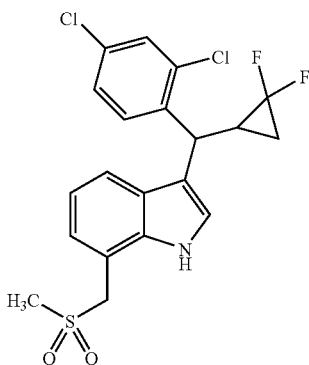

1.64 g (7.39 mmol) of indium(III) chloride were added to 2.00 g (6.78 mmol) of the compound from Example 193A and 1.29 g (6.16 mmol) of the compound from Example 86A in 20 ml of 1,2-dichloroethane under argon and reflux, and the mixture was heated under reflux for 1.5 h. This was followed by addition of ethyl acetate and saturated aqueous sodium bicarbonate solution, separation of the phases, drying of the organic phase and concentration. The residue was purified by column chromatography on silica gel (mobile phase: cyclohexane/ethyl acetate 2/1 and 1/1) and by preparative HPLC (RP18 column; mobile phase: acetonitrile/water gradient) to result in 28.0 mg (1% of theory) of diastereomer 1 and 28.0 mg (1% of theory) of diastereomer 2 of the title compound.

Diastereomer 325-1:

$^1$H-NMR (400 MHz, DMSO-$d_6$): δ=11.2 (s, 1H), 7.62 (d, 1H), 7.58 (d, 1H), 7.37-7.43 (m, 2H), 7.25 (d, 1H), 7.13 (d, 1H), 6.96 (t, 1H), 4.68-4.78 (m, 2H), 4.42 (d, 1H), 2.89 (s, 3H), 2.63-2.76 (m, 1H), 1.62-1.73 (m, 1H), 1.21-1.31 (m, 1H).

LC-MS (Method 9): $R_t$=1.23 min; MS (ESIpos): m/z=444 [M+H]$^+$.

The enantiomers were separated by preparative HPLC on a chiral phase [column: Daicel Chiralpak AS-H, 5 μm, 250 mm×20 mm; eluent: isohexane/isopropanol 1:1; flow rate: 20 ml/min; temperature: RT; UV detection: 230 nm]. 7.0 mg of enantiomer 325-1-1 and 7.0 mg of enantiomer 325-1-2 were obtained.

Enantiomer 325-1-1:

$R_t$=7.58 min [column: Daicel Chiralpak AS, 10 μm, 250 mm×4.6 mm; eluent: isohexane/isopropanol 1:1; flow rate: 1 ml/min; temperature: RT; UV detection: 230 nm].

Enantiomer 325-1-2:

$R_t$=9.55 min [column: Daicel Chiralpak AS, 10 μm, 250 mm×4.6 mm; eluent: isohexane/isopropanol 1:1; flow rate: 1 ml/min; temperature: RT; UV detection: 230 nm].

Diastereomer 325-2:

$^1$H-NMR (400 MHz, DMSO-$d_6$): δ=11.2 (s, 1H), 7.64 (d, 1H), 7.58 (d, 1H), 7.47 (d, 1H), 7.37-7.43 (m, 2H), 7.11 (d, 1H), 6.96 (t, 1H), 4.67-4.76 (m, 2H), 4.37 (d, 1H), 2.88 (s, 3H), 2.65-2.80 (m, 1H), 1.73-1.84 (m, 1H), 1.42-1.52 (m, 1H).

LC-MS (Method 9): $R_t$=1.23 min; MS (ESIpos): m/z=442 [M−H]$^-$.

B. Assessment of the Pharmacological Activity

Abbreviations

DMEM Dulbecco's modified Eagle medium
DNA deoxyribonucleic acid
FCS fetal calf serum
HEPES 4-(2-hydroxyethyl)-1-piperazineethanesulfonic acid
PCR polymerase chain reaction
Tris tris-(hydroxymethyl)methylamine The advantageous pharmacological properties of the compounds of the invention can be shown in the following assays:

1. Cellular In Vitro Assay to Determine the Inhibitory MR Activity and MR Selectivity Compared with Other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, VA 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA-binding domain (amino acids 1-147) from the vector pFC2-dbd (from Stratagene) is cloned with the PCR-amplified ligand-binding domains of the mineralocorticoid receptor (MR, amino acids 734-985), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly luciferase (Photinus pyralis) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, PR and AR cells are plated out in medium (Optimem, 2.5% FCS, 2 mM glutamine, 10 mM HEPES) in 96- (or 384- or 1536-)well microtiter plates on the day before the assay and are kept in a cell incubator (96% humidity, 5% v/v $CO_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

Table A shows the $IC_{50}$ values (MR) of representative exemplary compounds:

TABLE A

| Example No. | MR $IC_{50}$ [μM] | AR $IC_{50}$ [μM] | PR $IC_{50}$ [μM] |
| --- | --- | --- | --- |
| 26 | 0.05 | 2.23 | 2.32 |
| 38-1 | 0.016 | 1.12 | 1.51 |

TABLE A-continued

| Example No. | MR IC$_{50}$ [μM] | AR IC$_{50}$ [μM] | PR IC$_{50}$ [μM] |
|---|---|---|---|
| 43 | 0.078 | 2.92 | 1.98 |
| 56-1 | 0.09 | 5.67 | 4.07 |
| 59-1 | 0.08 | 7.76 | 10 |
| 62 | 0.06 | 7.09 | 12.8 |
| 63 | 0.04 | 3.76 | 4.81 |
| 68 | 0.19 | 5.07 | 3.91 |
| 69 | 0.42 | 5.22 | 6.59 |
| 70 | 0.25 | 9.66 | 7.75 |
| 71 | 0.32 | 3.99 | 4.47 |
| 73 | 0.09 | 5.22 | 6.44 |
| 78-4 | 0.15 | 8.89 | 7.91 |
| 82 | 0.21 | 7.53 | 5.81 |
| 94 | 0.16 | 1.60 | 3.14 |
| 100 | 0.46 | 5.24 | 10 |
| 104 | 0.10 | 5.01 | 8.56 |
| 106 | 0.04 | 5.31 | 11.7 |
| 107 | 0.02 | 3.33 | 4.83 |
| 107-1 | 0.02 | 2.16 | 9.16 |
| 111-1 | 0.03 | 2.52 | 4.5 |
| 113 | 0.13 | 3.22 | 7.24 |
| 114-2 | 0.22 | 1.23 | 6.55 |
| 120 | 0.15 | 10 | 5.51 |
| 124 | 0.12 | 6.94 | 8.13 |
| 130 | 0.1 | 5.74 | 8.88 |
| 140 | 0.27 | 6.60 | 10 |
| 143 | 0.14 | 6.44 | 4.58 |
| 147 | 0.03 | 3.02 | 1.42 |
| 157 | 0.018 | 3.39 | 2.14 |
| 163 | 0.029 | 4.76 | 2.72 |
| 166 | 0.22 | 10 | 10 |
| 169 | 0.11 | 2.28 | 6.57 |
| 171 | 0.03 | 3.20 | 2.23 |
| 172 | 0.02 | 5.28 | 16 |
| 172-1 | 0.007 | 3.80 | 4.31 |
| 177 | 0.077 | 1.94 | 5.78 |
| 179 | 0.1 | 2.03 | 1.93 |
| 219 | 0.042 | 2.73 | 8.12 |
| 238 | 0.19 | 10 | 10 |
| 242 | 0.066 | 1.39 | 3.77 |
| 244 | 0.17 | 10 | |
| 245 | 0.12 | 3.45 | |
| 249 | 0.069 | 3.45 | 9.73 |
| 250 | 0.27 | 1.6 | 10 |
| 252 | 0.071 | 3.03 | 10 |
| 260 | 0.039 | 9.03 | 5.23 |
| 261-1 | 0.033 | 5.64 | 12.3 |
| 261-2 | 0.028 | 6.06 | 5.24 |
| 266-1 | 0.007 | 1.29 | 3.0 |
| 271-1-1 | 0.006 | 0.94 | 10 |
| 273-1-2 | 0.006 | 0.98 | 10 |
| 276 | 0.024 | 10 | 10 |
| 277-1-1 | 0.008 | 3.9 | 10 |
| 296 | 0.21 | 6.57 | 4.81 |
| 324 | 0.40 | 10 | 6.9 |
| 325-1-1 | 0.012 | 0.52 | 7.53 |
| 325-2 | 0.059 | 5.25 | 6.66 |

2. In Vivo Assay for Detecting the Cardiovascular Effect: Diuresis Investigations on Conscious Rats in Metabolism Cages Wistar rats (body weight 250-350 g) are kept with free access to feed (Altromin) and drinking water. From about 72 hours before the start of the test, the animals receive instead of the normal feed exclusively salt-reduced feed with a sodium chloride content of 0.02% (ssniff R/M-H, 10 mm with 0.02% Na, S0602-E081, ssniff Spezialdiäten GmbH, D-59494 Soest). During the test, the animals are housed singly in metabolism cages suitable for rats of this weight class (from Tecniplast Germany GmbH, D-82383 Hohenpeißenberg) with free access to salt-reduced feed and drinking water for about 24 hours. At the start of the test, the substance to be tested is administered into the animals' stomachs by means of gavage in a volume of 0.5 ml/kg of body weight of a suitable solvent. Control animals receive only solvent. Controls and substance tests are carried out in parallel on the same day. Control groups and substance-dose groups each consist of 6 to 8 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

3. DOCA/Salt Model

Administration of deoxycorticosterone acetate (DOCA) in combination with a high-salt diet and unilateral kidney removal in rats induces hypertension which is characterized by relatively low renin levels. As a consequence of this endocrine hypertension (DOCA is a direct precursor of aldosterone), there is, depending on the chosen DOCA concentration, cardiac hypertrophy and further end organ damage, e.g. of the kidney, which is characterized inter alia by proteinuria and glomerulosclerosis. It is thus possible to investigate test substances in this rat model for the presence of an antihypertrophic and end organ-protecting effect.

Approximately 8-week old (body weight between 250 and 300 grams) male Sprague-Dawley (SD) rats undergo left uninephrectomy. For this purpose, the rats are anesthetized with 1.5-2% isoflurane in a mixture of 66% $N_2O$ and 33% $O_2$, and the kidney is removed through a flank incision. So-called sham-operated animals from which no kidney is removed serve as later control animals.

Uninephrectomized SD rats receive 1% sodium chloride in the drinking water and a subcutaneous injection of deoxycorticosterone acetate (dissolved in sesame oil; from Sigma) injected between the shoulder blades once a week (high dose: 100 mg/kg/week s.c.; normal dose: 30 mg/kg/week s.c.).

The substances which are to be investigated for their protective effect in vivo are administered by gavage or via the feed (from Ssniff). One day before the start of the test, the animals are randomized and assigned to groups with an identical number of animals, usually n=10, Throughout the test, drinking water and feed are available ad libitum to the animals. The substances are administered via the feed or once a day by gavage for 4-8 weeks. Animals serving as placebo group are treated in the same way but receive either only the solvent or the feed without test substance.

The effect of the test substances is determined by measuring hemodynamic parameters [blood pressure, heart rate, inotropism (dp/dt), relaxation time (tau), maximum left ventricular pressure, left-ventricular end-diastolic pressure (LVEDP)], determining the weight of the heart, kidney and lung, measuring the protein excretion, and by measuring gene expression of biomarkers (e.g. ANP, atrial natriuretic peptide, and BNP, brain natriuretic peptide) by means of RT/TaqMan PCR after RNA isolation from cardiac tissue.

Statistical analysis takes place using Student's t test after previous examination of the variances for homogeneity.

4. In Vivo Assay for Detecting Anti-Mineralocorticoid Activity on Conscious Dogs The primary aim of the experiment is to investigate the influence of test compounds having antimineralocorticoid receptor activity on the aldosterone-induced sodium retention. The procedure for this is analogous to a published method: Rosenthale, M. E., Schneider F., Kassarich, J. & Datko, L. (1965): Determination of antialdosterone activity in normal dogs, *Proc. Soc. Exp. Biol. Med.*, 118, 806-809.

Male or female beagles with a weight between 8 and 20 kilograms receive a standard diet and have free access to drinking water. On the days of the experiments, the dogs are fasting. A brief aneasthesia is induced with Propofol (4-6 mg/kg intravenously; Propofol 1% Parke-Davis®, Gödecke, Germany) in order to obtain an aliquot of urine (as initial value day 1) with a bladder catheter.

On day 2, all the dogs receive at about 16.00 h 0.3 mg of astonin, a metabolically stable aldosterone derivative (Astonin H, Merck, Germany).

The next morning (day 3), the test substance is administered to the dogs orally in a gelatin capsule. 5 hours later, blood is taken from the dogs to determine the plasma concentration of the substance. Subsequently, again on brief anesthesia, urine is obtained through a bladder catheter.

Treatment with the test substances leads after 5 hours to an increase in the sodium-potassium ratio in the urine (determination of sodium and potassium takes place by flame photometry). Spironolactone, which likewise increases the sodium/potassium ratio in the urine dose-dependently, serves as positive control, and treatment with an empty capsule serves as negative control.

Evaluation takes place by comparing the sodium/potassium ratio in the urine between day 1 and 3. Alternatively, the sodium/potassium ratio can also be compared between placebo and substance on day 3.

5. Chronic Myocardial Infarction Model in Conscious Rats

Male Wistar rats (280-300 g body weight; Harlan-Winkelmann) are anesthetized with 5% isoflurane in an anesthesia cage, intubated connected to a ventilation pump (ugo basile 7025 rodent, 50 strokes/min, 7 ml) and ventilated with 2% isoflurane/$N_2O/O_2$. The body temperature is maintained at 37-38° C. by a heating mat. 0.05 mg/kg Temgesic is given subcutaneously as analgesic. The chest is opened laterally between the third and fourth rib, and the heart is exposed. The coronary artery of the left ventricle (LAD) is permanently ligated with an occlusion thread (Prolene 1 metric 5-0 Ethicon1H) passed underneath shortly below its origin (below the left atrium). The occurrence of a myocardial infarction is monitored by an ECG measurement (Cardioline, Remco, Italy). The thorax is reclosed and the muscle layers are sutured with Ethibond excel 1 metric 5/0 6951H and the epidermis is sutured with Ethibond excel 3/0 6558H. The surgical suture is wetted with a spray dressing (e.g. Nebacetin®N spray dressing, active ingredient: neomycin sulfate) and then the anesthesia is terminated.

One week after the LAD occlusion, the size of the myocardial infarct is estimated by echocardiography (Sequoia 512, Acuson). The animals are randomized and divided into individual treatment groups and a control group without substance treatment. A sham group in which only the surgical procedure, but not the LAD occlusion, was performed is included as further control.

Substance treatment takes place over 8 weeks by gavage or by adding the test compound to the feed or drinking water. The animals are weighed each week, and the water and feed consumption is determined every 14 days.

After treatment for 8 weeks, the animals are again anesthetized (2% isoflurane/$N_2O$/air) and a pressure catheter (Millar SPR-320 2F) is inserted via the carotid artery into the left ventricle. The heart rate, left ventricular pressure (LVP), left-ventricular end-diastolic pressure (LVEDP), contractility (dp/dt) and relaxation rate ($\tau$) are measured there and analyzed with the aid of the Powerlab systems (AD Instruments, ADI-PWLB-4SP) and the Chart 5 software (SN 425-0586). A blood sample is then taken to determine the blood levels of the substance and plasma biomarkers, and the animals are sacrificed. The heart (heart chambers, left ventricle with septum, right ventricle), liver, lung and kidney are removed and weighed.

6. Stroke-Prone Spontaneously Hypertensive Rat Model

Administration of sodium chloride to the so-called stroke-prone spontaneously hypertensive rat (SP-SHR) leads in this model paradoxically to abolition of the physiological salt-induced repression of renin and angiotensin release after a few days. Thus, the hypertension in the SP-SHR animals is characterized by a relatively high renin level. As a consequence of the developing hypertension there is pronounced end-organ damage to the heart and the kidney, which is characterized inter alia by proteinuria and glomerulosclerosis, and general vascular changes. Thus, in particular strokes may develop primarily through cerebrovascular lesions ("stroke-prone") which lead to a high mortality of the untreated animals. It is thus possible to investigate test substances for blood pressure-lowering and end organ-protecting effect in this rat model.

Approximately 10-week old male SP-SH rats (body weight between 190 and 220 g) are randomized and assigned to groups with an equal number of animals, usually n=12-14, one day before the start of the test. Throughout the test, drinking water containing sodium chloride (2% NaCl) and feed are available ad libitum to the animals. The substances are administered once a day by gavage or with the feed (Ssniff, Germany) for 6-8 weeks. Animals treated in the same way but receiving either only the solvent or the feed without test substance serve as placebo group. In the context of a mortality study, the test is terminated when about 50% of the placebo-treated animals have died.

The effect of the test substances is followed by measuring the changes in the systolic blood pressure (via a tail cuff) and the protein excretion in the urine. There are post mortem determinations of the weights of heart, kidney and lung, and histopathological analyses of the heart, kidney and brain with semiquantitative scoring of the histological changes. Various biomarkers (e.g. ANP, atrial natriuretic peptide, and BNP, brain natriuretic peptide, KIM-1, kidney-induced molecule 1, osteopontin-1) are determined by RT/TaqMan PCR following RNA isolation from cardiac and renal tissue or serum or plasma.

Statistical analysis is carried out with Student's t test after previous examination of the variances of homogeneity.

7. CYP Inhibition Assay

Inhibitory properties of an active ingredient on the cytochromes P450 (CYP) of the human body may entail extensive clinical effects (drug interactions) because most of the prescribed medicaments are degraded (metabolized) by these enzymes. The ones involved in this are in particular the CYP isoenzymes of the 1A and 2C families, CYP2D6 and, with a proportion of almost 50%, CYP3A4. In order to preclude or minimize these possible drug interactions (Drug-Drug Interactions, DDI), the ability of substances to be able to inhibit CYP1A2, CYP2C8, CYP2C9, CYP2D6 and CYP3A4 in humans is investigated using human liver microsomes (pool from various individuals). This takes place by measuring CYP isoform-specific metabolites formed from standard substrates such as, for example, phenacetin, amodiaquin, diclofenac, dextromethorphan, midazolam and testosterone. The inhibitory effects are investigated at six different concentrations of the test compounds (1.5, 3.1, 6.3, 12.5, 25 and 50

μM as maximum concentration or 0.6, 1.3, 2.5, 5, 10 and 20 μM as maximum concentration), comparing with the extent of the CYP isoform-specific metabolite formation of the standard substrates in the absence of the test compounds, and calculating the corresponding IC50 values. CYP isoform-specific standard inhibitors such as, for example, fluvoxamine, quercetin, sulfaphenazole, fluoxetine and ketoconazole serve as control of the results obtained. In order to obtain indications of the possible mechanism-based inhibitors (MBI) on CYP3A4, the human liver microsomes are incubated in the presence of the inhibitor to be investigated for 30 minutes before the addition of midazolam or testosterone as standard substrates of CYP3A4. A reduction in the IC50 obtained by comparison with the mixture without preincubation serves as an indicator of a mechanism-based inhibition. Mibefradil serves as positive control.

Procedure:

The incubations of the standard substrates with human liver microsomes (23-233 μg/mL) in the presence of the test compound (as potential inhibitor) are carried out in 96-well plates in a workstation (Tecan, Genesis, Crailsheim, Germany) at 37° C. The incubation times are 15-20 minutes. The test compounds are preferably dissolved in acetonitrile (1.0 or 2.5 mM stock solution). The 96-well plates are produced by sequential addition of a stock solution of NADP+, EDTA, glucose 6-phosphate and glucose-6-phosphate dehydrogenase in phosphate buffer (pH 7.4), the test compound, and a solution of standard substrate and human liver microsomes in phosphate buffer (pH 7.4). The total volume is 200 μl. The corresponding control incubations with and without standard inhibitor also take place on the 96-well plate. The incubations are stopped after the respective incubation time by adding 100 μl of acetonitrile in which there is a suitable internal standard. Precipitated proteins are removed by centrifugation (3000 rpm, 10 minutes, 10° C.). The resulting supernatants of the respective plates are combined on one plate and analyzed by LC-MS/MS. The I050 values are generated from the resulting measured data and used to assess the inhibitory potential of the test compound.

TABLE B

| Example No. | CYP 3A4 Coincubation [μM] | CYP 3A4 Preincubation, 30 min. [μM] |
|---|---|---|
| 59-1 | >20 | 13.1 |
| 73 | >20 | 16.6 |
| 107 | >20 | 12.9 |
| 113 | >20 | >20 |
| 118-1 | >20 | 11.2 |
| 120 | >20 | 14.4 |
| 147 | >20 | 8.8 |
| 166 | >20 | 17.6 |
| 169 | >20 | 17.0 |
| 171 | >20 | 7.8 |
| 172 | >20 | 9.6 |
| 242 | >20 | 15.8 |
| 244 | >20 | >20 |
| 245 | >20 | >20 |
| 249 | >20 | 18.3 |
| 250 | >20 | 19.4 |
| 252 | >20 | >20 |
| 261-1 | >20 | 19.0 |
| 261-2 | >20 | 15.0 |
| 271-1-1 | >40 | 25.6 |

TABLE B-continued

| Example No. | CYP 3A4 Coincubation [μM] | CYP 3A4 Preincubation, 30 min. [μM] |
|---|---|---|
| 273-1-2 | >20 | 13.7 |
| 276 | >20 | 18.2 |

8. Assay to Assess Irreversible CYP3A4 Inhibition

Cytochrom P450 enzyme inhibition, especially irreversible enzyme inhibition, also referred to as mechanism-based inhibition (MBI), is an unwanted metabolic property of a substance which may, on concurrent administration of other medicaments, lead to considerable drug interactions. Criteria for the presence of an irreversible inhibition are a time-, concentration- and cofactor- (nicotinamide adenine dinucleotide phosphate, NADPH) dependent inhibition. To this end, the compounds of the invention are incubated in vitro with human liver microsomes, the influence on the CYP3A4 activity and the metabolic degradation of the novel active ingredient is determined, and the prototypical parameters $k_{inact}$, $K_i$ and the partition ratio r are ascertained therefrom.

Procedure:

The compounds of the invention are incubated with concentrations of 2-20 μM. To this end, stock solutions of the active ingredients with a concentration of 0.2-2 mM are prepared in acetonitrile and then pipetted with a 1:100 dilution into the incubation mixture. The liver microsomes are incubated in 50 mM potassium phosphate buffer (pH 7.4) with and without NADPH-generating system consisting of 1 mM NADP+, 5 mM glucose 6-phosphate and 1 unit of glucose 6-phosphate dehydrogenase, at 37° C. After defined preincubation times of 0-50 min, aliquots are removed from these mixtures, diluted 1:25 in a new incubation, and incubated in the presence of testosterone and new NADPH-generating system again for 20 min. These incubation mixtures are stopped with acetonitrile (final concentration about 30% v/v), and the protein is removed by centrifugation at about 15 000×g. The samples stopped in this way are either analyzed directly or stored at −20° C. until analyzed.

The analysis takes place by high performance liquid chromatography with mass spectrometry detection (LC-MS). The formation of 6β-hydroxytestosterone as measure of CYP3A4 activity, and the test substance still remaining is quantified. The parameters $k_{inact}$, $K_i$ and the partition ratio r are determined therefrom so as to assess the novel active ingredients in relation to MBI.

TABLE C

| Example No. | Partition ratio r |
|---|---|
| 56-1 | 100 |
| 59-1 | 220 |
| 73 | >500 |
| 107 | >400 |
| 113 | >500 |
| 118-1 | 250 |
| 147 | 90 |
| 169 | >500 |
| 172 | 120 |
| 261-1 | >200 |
| 266-1 | >200 |
| 271-1-1 | >200 |
| 273-1-2 | >200 |
| 277-1-1 | >200 |

C. Exemplary Embodiments of Pharmaceutical Compositions

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25)→(from BASF, Ludwigshafen, Germany) and 2 mg of magnesium stearate.

Tablet weight 212 mg, diameter 8 mm, radius of curvature 12 mm.

Production:
The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400. 20 g of oral solution correspond to a single dose of 100 mg of the compound according to the invention.

Production:
The compound of the invention is suspended in the mixture of polyethylene glycol and polysorbate with stirring. The stirring process is continued until the compound according to the invention has completely dissolved.

i.v. Solution:
The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

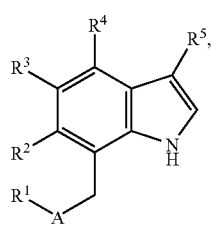

(I)

in which
A is —S—, —S(=O)— or —S(=O)$_2$—,
R$^1$ is (C$_1$-C$_4$)-alkyl or cyclopropyl,
R$^2$ is hydrogen, fluorine or chlorine,
R$^3$ is hydrogen, fluorine, chlorine or methyl,
R$^4$ is hydrogen or fluorine,
R$^5$ is a group of the formula

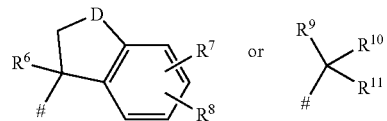

where
# is the point of attachment to the indole,
and
D is —CH$_2$—, —O—, —CH$_2$—CH$_2$— or —CH$_2$—O—,
R$^6$ is (C$_1$-C$_4$)-alkyl or (C$_3$-C$_6$)-cycloalkyl,
in which (C$_1$-C$_4$)-alkyl may be substituted by 1 to 3 substituents independently of one another selected from the group of fluorine, trifluoromethyl, hydroxy and cyano,
and
in which (C$_3$-C$_6$)-cycloalkyl may be substituted by 1 to 3 substituents independently of one another selected from the group of fluorine, hydroxy and cyano,
R$^7$ is hydrogen, halogen, (C$_1$-C$_4$)-alkyl, trifluoromethyl or (C$_1$-C$_4$)-alkoxy,
R$^8$ is hydrogen, halogen, methyl or trifluoromethyl,
R$^9$ is phenyl, naphthyl or 5- to 10-membered heteroaryl,
in which phenyl, naphthyl and 5- to 10-membered heteroaryl may be substituted by 1 to 3 substituents independently of one another selected from the group of halogen, cyano, (C$_1$-C$_4$)-alkyl, fluoromethyl, difluoromethyl, trifluoromethyl, (C$_1$-C$_4$)-alkoxy, fluoromethoxy, difluoromethoxy, trifluoromethoxy and trifluoromethylthio,
or
in which two substituents bonded on adjacent carbon atoms of a phenyl ring together form a group of the formula —O—CH$_2$—O—, —O—CHF—O—, —O—CF$_2$—O—, —O—CH$_2$—CH$_2$—O— or —O—CF$_2$—CF$_2$—O—,
R$^{10}$ is (C$_1$-C$_6$)-alkyl, (C$_3$-C$_7$)-cycloalkyl or phenyl,
in which (C$_1$-C$_6$)-alkyl may be substituted by 1 to 3 substituents independently of one another selected from the group of fluorine, fluoromethyl, difluoromethyl, trifluoromethyl, hydroxy and cyano,
and
in which (C$_3$-C$_7$)-cycloalkyl may be substituted by 1 to 3 substituents independently of one another selected from the group of fluorine, hydroxy and cyano,
and
in which phenyl may be substituted by 1 to 3 substituents independently of one another selected from the group of halogen, cyano, (C$_1$-C$_4$)-alkyl, fluoromethyl, difluoromethyl, trifluoromethyl, (C$_1$-C$_4$)-alkoxy, fluoromethoxy, difluoromethoxy, trifluoromethoxy and trifluoromethylthio,
R$^{11}$ is hydrogen, methyl, ethyl, trifluoromethyl or cyclopropyl,
and the salts thereof.

2. A compound of the formula (I) as claimed in claim 1, in which
A is —S(=O)— or —S(=O)₂—,
R¹ is methyl or ethyl,
R² is hydrogen or fluorine,
R³ is hydrogen or fluorine,
R⁴ is hydrogen,
R⁵ is a group of the formula

where
# is the point of attachment to the indole,
and
R⁹ is phenyl, naphthyl or benzothienyl,
in which phenyl, naphthyl and benzothienyl may be substituted by 1 to 3 substituents independently of one another selected from the group of fluorine, chlorine, cyano, methyl, ethyl, trifluoromethyl and methoxy,
or
in which two substituents bonded to adjacent carbon atoms of a phenyl ring together form a group of the formula —O—CH₂—O— or —O—CF₂—O—,
R¹⁰ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl, 1-hydroxycycloprop-2-yl or phenyl,
in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, cyclopropyl, 1-cyanocycloprop-2-yl and 1-hydroxycycloprop-2-yl may be substituted by 1 or 2 fluorine substituents,
and
in which phenyl may be substituted by 1 or 2 substituents independently of one another selected from the group of fluorine, chlorine, cyano and methyl,
R¹¹ is hydrogen,
and the salts thereof.

3. A compound of the formula (I) as claimed in claim 1, in which
A is —S(=O)— or —S(=O)₂—,
R¹ is methyl or ethyl,
R² is hydrogen or fluorine,
R³ is hydrogen or fluorine,
R⁴ is hydrogen,
R⁵ is a group of the formula

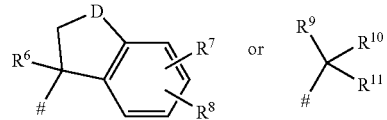

where
# is the point of attachment to the indole,
and
D is —CH₂— or —CH₂—O—,
R⁶ is (C₁-C₄)-alkyl or (C₃-C₆)-cycloalkyl,
in which (C₁-C₄)-alkyl and (C₃-C₆)-cycloalkyl may be substituted by 1 or 2 fluorine substituents,
and
in which (C₁-C₄)-alkyl may be substituted by a substituent selected from the group of hydroxy and cyano,
and
in which (C₃-C₆)-cycloalkyl may be substituted by a substituent selected from the group of hydroxy and cyano,
R⁷ is hydrogen, fluorine, chlorine, methyl or trifluoromethyl,
R⁸ is hydrogen, fluorine, chlorine, methyl or trifluoromethyl,
R⁹ is phenyl, naphthyl or benzothienyl,
in which phenyl, naphthyl and benzothienyl may be substituted by 1 to 3 substituents independently of one another selected from the group of fluorine, chlorine, cyano, methyl, ethyl, trifluoromethyl and methoxy,
or
in which two substituents bonded to adjacent carbon atoms of a phenyl ring together form a group of the formula —O—CH₂—O— or —O—CF₂—O—,
R¹⁰ is 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl, (C₃-C₇)-cycloalkyl or phenyl,
in which 1-cyanoeth-2-yl, 1-cyano-1-methyleth-2-yl, 1-cyano-2-methyleth-2-yl, 1-cyano-1,2-dimethyleth-2-yl, 1-cyano-2,2-dimethyleth-2-yl, 1-cyanoprop-3-yl, 1-cyano-1-methylprop-3-yl, 1-cyano-2-methylprop-3-yl, 1-cyano-3-methylprop-3-yl, 1-cyano-2,3-dimethylprop-3-yl, 1-hydroxyeth-2-yl, 1-hydroxy-1-methyleth-2-yl, 1-hydroxy-2-methyleth-2-yl, 1-hydroxy-1,2-dimethyleth-2-yl, 1-hydroxy-2,2-dimethyleth-2-yl, 1-hydroxyprop-3-yl, 1-hydroxy-1-methylprop-3-yl, 1-hydroxy-2-methylprop-3-yl, 1-hydroxy-3-methylprop-3-yl, 1-hydroxy-2,3-dimethylprop-3-yl and (C₃-C₇)-cycloalkyl may be substituted by 1 or 2 fluorine substituents, and
in which $(C_3-C_7)$-cycloalkyl may be substituted by a substituent selected from the group of hydroxy and cyano,
and
in which phenyl may be substituted by 1 or 2 substituents independently of one another selected from the group of fluorine, chlorine, cyano and methyl,
$R^{11}$ is methyl or ethyl,
and the salts thereof.

4. A compound of the formula (I) as claimed in claim 1, in which
A is $-S(=O)_2-$,
$R^1$ is methyl,
$R^2$ is hydrogen or fluorine,
$R^3$ is hydrogen or fluorine,
$R^4$ is hydrogen,
$R^5$ is a group of the formula

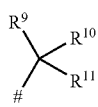

where
# is the point of attachment to the indole,
and
$R^9$ is a group of the formula

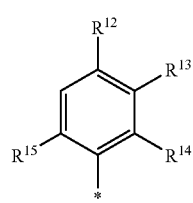

in which
* is the point of attachment to $-CR^{10}R^{11}$,
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is cyclopropyl,
in which cyclopropyl may be substituted by 1 or 2 fluorine substituents,
and
in which cyclopropyl may be substituted by a cyano substituent,
$R^{11}$ is methyl,
and the salts thereof.

5. A compound of the formula (I) as claimed in claim 1, in which
A is $-S(=O)_2-$,
$R^1$ is methyl or ethyl,
$R^2$ is hydrogen or fluorine,
$R^3$ is hydrogen or fluorine,
$R^4$ is hydrogen,
$R^5$ is a group of the formula

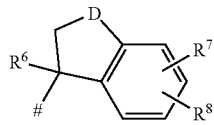

where
# is the point of attachment to the indole,
and
D is $-CH_2-$,
$R^6$ is methyl, ethyl or cyclopropyl,
$R^7$ is hydrogen, fluorine, chlorine or methyl,
$R^8$ is hydrogen, fluorine or chlorine,
and the salts thereof.

6. A compound of the formula (I) as claimed in claim 1, in which
A is $-S(=O)_2-$,
$R^1$ is methyl,
$R^2$ is hydrogen or fluorine,
$R^3$ is hydrogen or fluorine,
$R^4$ is hydrogen,
$R^5$ is a group of the formula

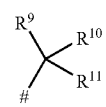

where
# is the point of attachment to the indole,
and
$R^9$ is a group of the formula

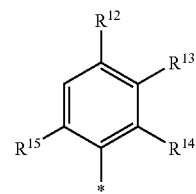

in which
* is the point of attachment to $-CR^{10}R^{11}$,
$R^{12}$ is fluorine, chlorine, methyl and trifluoromethyl,
$R^{13}$ is hydrogen, fluorine or chlorine,
$R^{14}$ is hydrogen, fluorine or chlorine,
$R^{15}$ is hydrogen, fluorine or chlorine,
with the proviso that at least one of the radicals $R^{13}$, $R^{14}$ and $R^{15}$ is hydrogen,
$R^{10}$ is 1-cyanoeth-2-yl, 1-cyano-2-methyleth-2-yl or 1-cyanoprop-3-yl,
$R^{11}$ is methyl or ethyl,
and the salts thereof.

7. A compound of the formula (I) as claimed in claim 1, in which

A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

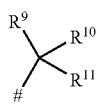

where
# is the point of attachment to the indole,
and
R$^9$ is a group of the formula

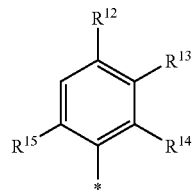

in which
\* is the point of attachment to —CR$^{10}$R$^{11}$,
R$^{12}$ is fluorine, chlorine, methyl and trifluoromethyl,
R$^{13}$ is hydrogen, fluorine or chlorine,
R$^{14}$ is hydrogen, fluorine or chlorine,
R$^{15}$ is hydrogen, fluorine or chlorine,
with the proviso that at least one of the radicals R$^{13}$, R$^{14}$ and R$^{15}$ is hydrogen,
R$^{10}$ is a group of the formula

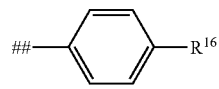

in which
## is the point of attachment to —CR$^9$R$^{11}$,
R$^{16}$ is fluorine or chlorine,
R$^{11}$ is hydrogen,
and the salts thereof.

8. A compound of the formula (I) as claimed in claim 1, in which

A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

where
# is the point of attachment to the indole,
and
R$^9$ is phenyl or benzothienyl,
in which phenyl and benzothienyl may be substituted by 1 or 2 substituents independently of one another selected from the group of fluorine, chlorine, methyl and trifluoromethyl,
R$^{10}$ is 1-cyanoeth-2-yl, 1-cyano-2-methyleth-2-yl or 1-cyanoprop-3-yl,
R$^{11}$ is hydrogen,
and the salts thereof.

9. A compound of the formula (I) as claimed in claim 1, in which

A is —S(=O)$_2$—,
R$^1$ is methyl,
R$^2$ is hydrogen or fluorine,
R$^3$ is hydrogen or fluorine,
R$^4$ is hydrogen,
R$^5$ is a group of the formula

where
# is the point of attachment to the indole,
and
R$^9$ is a group of the formula

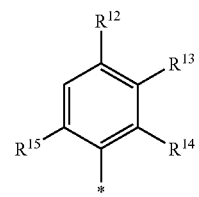

in which
\* is the point of attachment to —CR$^{10}$R$^{11}$,
R$^{12}$ is fluorine, chlorine, methyl and trifluoromethyl,
R$^{13}$ is hydrogen, fluorine or chlorine,
R$^{14}$ is hydrogen, fluorine or chlorine,
R$^{15}$ is hydrogen, fluorine or chlorine,
with the proviso that at least one of the radicals R$^{13}$, R$^{14}$ and R$^{15}$ is hydrogen,
R$^{10}$ is cyclopropyl,
in which cyclopropyl may be substituted by a cyano substituent,
or
in which cyclopropyl may be substituted by 1 or 2 fluorine substituents,
R$^{11}$ is hydrogen,
and the salts thereof.

10. A pharmaceutical composition comprising a compound as defined in claim 1 in combination with a pharmaceutically suitable excipient.

11. A compound of claim 1, wherein the compound is a compound of formula:

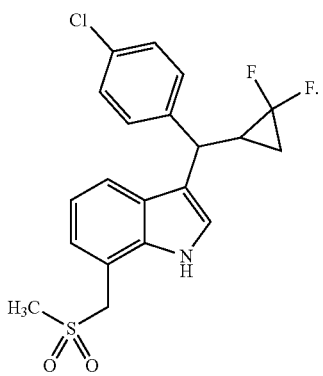

12. A compound of claim 1, wherein the compound is a compound of formula:

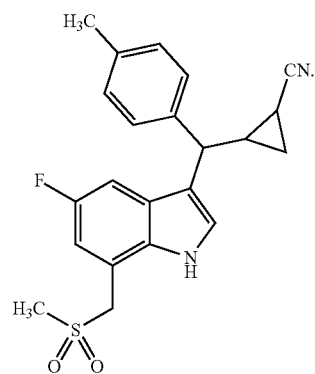

13. A compound claim 1, wherein the compound is a compound of formula:

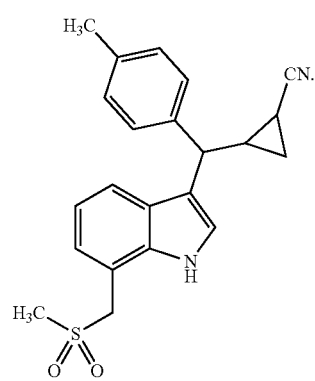

14. A compound of claim 1, wherein the compound is a compound of formula:

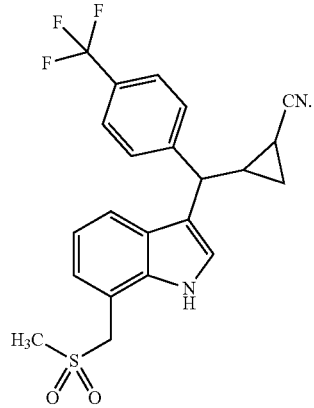

15. A compound of claim 1, wherein the compound is a compound of formula:

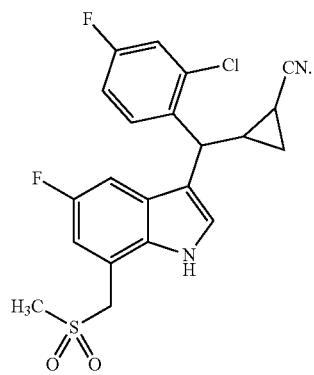

16. A compound of claim 1, wherein the compound is a compound of formula:

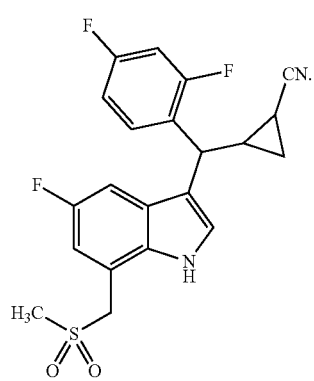

17. A compound of claim 1, wherein the compound is a compound of formula:

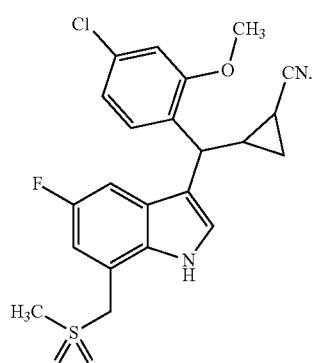

18. A compound of claim 1, wherein the compound is a compound of formula:

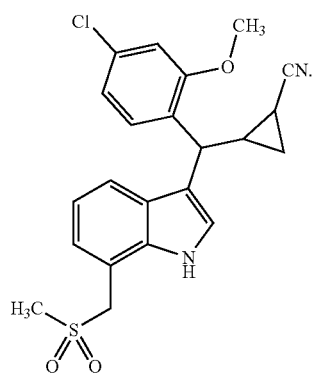

19. A compound of claim 1, wherein the compound is a compound of formula:

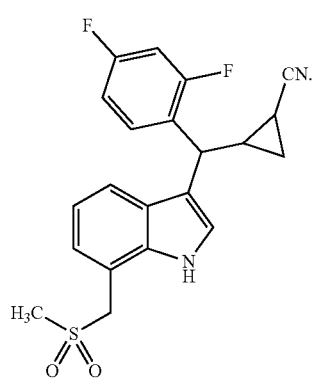

20. A compound of claim 1, wherein the compound is a compound of formula:

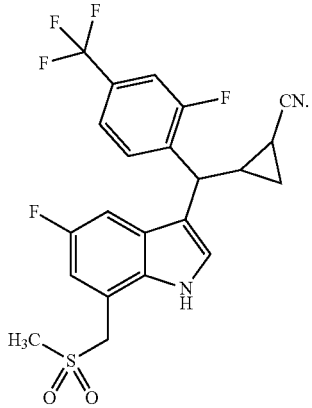

21. A compound of claim 1, wherein the compound is a compound of formula:

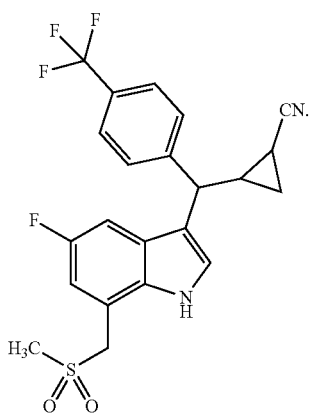

22. A compound of claim 1, wherein the compound is a compound of formula:

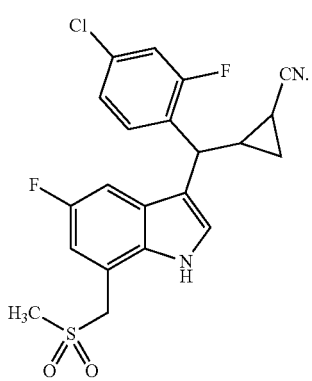

23. A compound of claim 1, wherein the compound is a compound of formula:
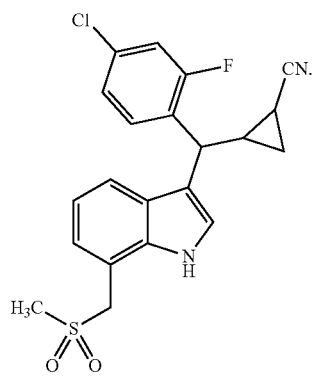
24. A compound claim 1, wherein the compound is a compound of formula:
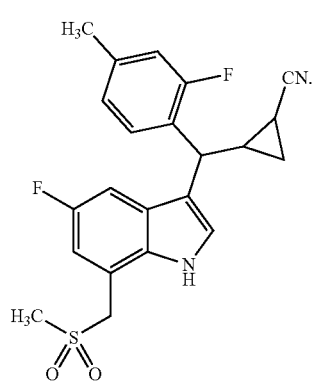
25. A compound of claim 1, wherein the compound is a compound of formula:
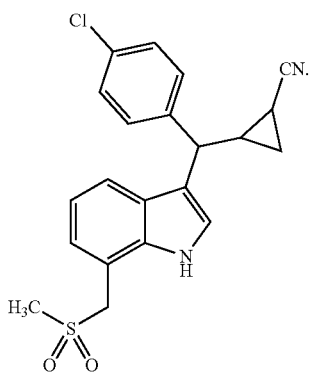
26. A compound claim 1, wherein the compound is a compound of formula:
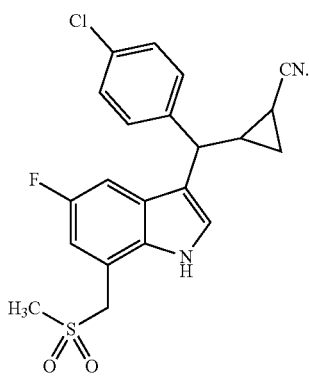
\* \* \* \* \*